US007230076B2

(12) United States Patent
Goddard et al.

(10) Patent No.: US 7,230,076 B2
(45) Date of Patent: Jun. 12, 2007

(54) SECRETED AND TRANSMEMBRANE POLYPEPTIDES AND NUCLEIC ACIDS ENCODING THE SAME

(75) Inventors: Audrey Goddard, San Francisco, CA (US); Paul J. Godowski, Hillsborough, CA (US); J. Christopher Grimaldi, San Francisco, CA (US); Austin L. Gurney, Belmont, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 348 days.

(21) Appl. No.: 10/063,600

(22) Filed: May 3, 2002

(65) Prior Publication Data

US 2003/0181644 A1 Sep. 25, 2003

Related U.S. Application Data

(63) Continuation of application No. 10/006,867, filed on Dec. 6, 2001, which is a continuation of application No. PCT/US00/23328, filed on Aug. 24, 2000, which is a continuation-in-part of application No. 09/403, 297, filed as application No. PCT/US99/20111 on Sep. 1, 1999, now abandoned.

(60) Provisional application No. 60/100,683, filed on Sep. 17, 1998.

(51) Int. Cl.

| | |
|---|---|
| ***C07K 14/00*** | (2006.01) |
| ***C07K 14/52*** | (2006.01) |
| ***C12N 15/00*** | (2006.01) |
| ***A61K 39/00*** | (2006.01) |

(52) U.S. Cl. ...................... 530/350; 530/351; 530/402; 435/69.1; 424/184.1

(58) Field of Classification Search ................ 530/350, 530/402; 536/23.1, 23.5
See application file for complete search history.

(56) References Cited

U.S. PATENT DOCUMENTS

| | | | |
|---|---|---|---|
| 5,536,637 | A | 7/1996 | Jacobs |
| 6,025,156 | A | 2/2000 | Gwynn et al. |
| 6,124,433 | A | 9/2000 | Falb et al. |
| 6,156,500 | A | 12/2000 | Falb |
| 6,162,604 | A | 12/2000 | Jacob |
| 6,228,582 | B1 | 5/2001 | Rodier et al. |
| 6,395,306 | B1 | 5/2002 | Cui et al. |
| 6,414,117 | B1 | 7/2002 | Levinson |
| 6,465,185 | B1 | 10/2002 | Goldfine et al. |
| 6,498,235 | B2 | 12/2002 | Sheppard et al. |
| 6,562,343 | B1 | 5/2003 | Levinson |
| 6,645,499 | B1 | 11/2003 | Lal et al. |
| 6,730,502 | B2 | 5/2004 | Van Hijum et al. |
| 6,737,522 | B2 | 5/2004 | Sundick et al. |

FOREIGN PATENT DOCUMENTS

| | | |
|---|---|---|
| WO | WO 97/38085 | 10/1997 |

OTHER PUBLICATIONS

Haynes et al., 1998, Electrophoresis 19:1862-1872.*
Skolnick et al., 2000, Trends in Biotech. 18:34-39.*
Bork, P., 2000, Genome Research 10:398-400.*
Doerks et al., 1998, Trends in Genetics 14:248-250.*
Hesselgesser, et al, 1997, Methods in Enzymology, 287:59-69.*
Blease, et al, 2000, Resp. Res., 1(1): 54-61.*
Smith et al., 1997, Nature Biotechnology 15: 1222-1223.*
Brenner, S., 1999, Trends in Genetics 15:132-133.*
Strausberg, et al, 2003, Accession No. AAH20905.1.*
Pennica, et al, 1998, Proc. Natl. Acad. Sci., 95: 14717-14722.*
Haynes et al, 1998, Electrophoresis, 19: 1862-1871.*
Hu et al, 2003, Journal of Proteome Research 2: 405-412.*
Klein et al. Selection for Genes Encoding Secreted Proteins and Receptors. *Proc. Natl. Acad. Sci*., 93:7108-7113 (1996).
Database Search, DNA Sequence Alignments [BLASTN 2.2.1[Jul. 12, 2001], NCBI].
Database Search, Protein Sequence Alignments [BLASTN 2.2.1 [Jul. 12, 2001], NCBI].
Alberts, et al. 1994. *Molecular Biology of the Cell, 3rd Edition*, pp. 403-404, 453. New York: Garland Publishing.
Alberts, et al. 2002. *Molecular Biology of the Cell 4th Edition*, pp. 302, 363-364, 379, 435. New York: Garland Publishing.
Grimaldi, et al. 1989. The t(5;14) chromosomal translocation in a case of acute lymphocytic leukemia joins the interleukin-3 gene to the immunoglobulin heavy chain gene. *Blood*, 73(8):2081-2085.
Gygi, et al. Mar. 1999. Correlation between Protein and mRNA Abundance in Yeast. *Molecular and Cellular Biology*, 1720-1730.

(Continued)

*Primary Examiner*—Eileen B. O'Hara
*Assistant Examiner*—Sandra Wegert
(74) *Attorney, Agent, or Firm*—Elizabeth M. Barnes; Mark T. Kresnak; Knobbe, Martens, Olson & Bear LLP

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

12 Claims, 168 Drawing Sheets

OTHER PUBLICATIONS

Hanna, et al. Aug. 1999. HER-2/neu breast cancer predicitive testing. *Pathology Associates Medical Laboratories*.
Hyman et al. Nov. 2002. Impact of DNA Amplification of Gene Expression Patterns. *Cancer Research*, 62:6240-6245.
Lewin, B. 1994. Oncogenes: Gene Expression and Cancer, Chap. 39, pp. 1196-1201. *Genes V*. New York: Oxford University Press.
Lewin, B. 1997. Regulation of Transcription, Chap. 29, pp. 847-848. *Genes VI*. New York: Oxford University Press.
Meeker, et al. 1990. Activation of the interleukin-3 gene by chromosome translocation in acute lymphocytic leukemia with eosinophilia. *Blood*, 76(2):285-289.
Meric, et al. 2002. Translation initiation in cancer: A novel target for therapy. *Molecular Cancer Therapeutics*, 1:971-979.
Ørntoft, et al. 2002. Genome-wide study of gene copy numbers, transcripts, and protein levels in pairs of non-invasive and invasive human transitional cell carcinomas. *Molecular & Cellular Proteomics*, 1:37-45.
Pollack, et al. 2002. Microarray analysis reveals a major direct role of DNA copy number alteration in the transcriptional program of human breast tumors. *PNAS*, 99(20):12963-12968.
Singleton, et al. 1992. Clinical and pathologic significance of the c-*erb*B-2 (*HER-2/neu*) oncogene, *Pathol. Annu*, 1(27)L165-190.
Zhigang, et al. 2004. Prostate stem cell antigen (PSCA) expression in human prostate cancer tissues and its potential role in prostate carcinogenesis and progression of prostate cancer. *World Journal of Surgical Oncology*, 2:13.
Allman, et al. 1996. BCL-6 expression during B-cell activation. *Blood*, 87(12):5257-5268.
Chen, et al. 2002. Discordant Protein and mRNA Expression in Lung Adenocarcinomas. *Molecular & Cellular Proteomics 1.4*, 304-313.
Fu, et al. 1996. Translational regulation of human p53 gene expression. *The EMBO Journal*, vol. 15, No. 16, pp. 4392-4401.
Gökmen-Polar, et al., Feb. 2001, Elevated Protein Kinase C βII Is an Early Promotive Event in Colon Carcinogenesis, *Cancer Research*, vol. 61, pp. 1375-1381.
Hanash, S. 2003. Making sense of microarray data to classify cancer. *The Pharmacogenomics Journal*, 3:308-311.
Hanash, S. Mar. 2005. Integrated global profiling of cancer. *Nature Reviews, Applied Proteomics Collection*, pp. 9-14.
Hancock, W. S. 2004. Do We Have Enough Biomarkers? *Journal of Proteome Research*, 3(4):685.
Jang A. Hill RP, Sep. 1997. An examination of the effects of hypoxia, acidosis, and glucose starvation on the expression of metastasis-associated genes in murine tumor cells. *Clin. Exp. Metastasis 15*(5): pp. 469-483.
Konopka, et al. Jun. 1986. Variable Expression of the Translocated c-abl Oncogene in Philadelphia-Chromosome-Positive B-Lymphoid Cell Lines from Chronic Myelogenous Leukemia Patients, *National Academy of Sciences of the United States of America*, vol. 83, No. 11, pp. 4049-4052.
Ohara, et al. 2001. Directional cDNA library construction assisted by the in vitro recombination reaction. *Nucleic Acids Research*, vol. 29, No. e22, pp. 1-8.
Powell, et al. Oct. 1998. Expression of cytochrome P4502E1 in human liver: assessment by mRNA, genotype and phenotype. *Pharmacogenetics*, vol. 5: pp. 411-421.
Vallejo, et al. Dec. 2000. Evidence of tissue-specific, post-transcriptional regultation of NRF-2 expression. *Biochimie* 82(12): 1129-33.
Wang, et al. 1996. mRNA Differential display: Application in the discovery of novel pharmacological targets. *Trends Pharmacol. Sci*., 17(8):276-279.
Alberts, et al. 1994. *Molecular Biology of the Cell, 3rd Edition*, pp. 1216-1217. New York: Garland Publishing.
Anderson, et al. 1997. A comparison of selected mRNA and protein abundances in human liver. *Electrophoresis*, 18:533-537.
Fessler, et al. 2002. A genomic and proteomic analysis of activation of the human neutrophil by lipopolysaccharide and its mediation by p38 mitogen-activated protein kinase. *The Journal of Biological Chemistry*277(35):31291-31302.
Laird, G., 2001, Accession No. AL445222.
Tokunaga, et al. 2000. Application of quantitative RT-PCR using "TaqMan" technology to evaluate the expression of CK 18 mRNA in various cell lines. *J. Exp. Clin. Cancer Res*., 19(3):375-381.
Abe, et al. "An increased high-mobility group A2 expression level is associated with malignant phenotype in pancreatic exocrine tissue." *Br J Cancer*. Dec. 1, 2003;89(11):2104-9. (Abstract Only).
Ando, et al. "Selective apoptosis of natural killer-cell tumours by I-asparaginase." *Br. J. Haematol*. Sep. 2005;130(6):860-8. (Abstract Only).
Aust, et al. "Human thyroid carcinoma cell lines and normal thyrocytes: expression and regualation of matrix metalloproteinase-1 and tissue matrix metalloproteinase inhibitor-1 messenger-RNA and protein." *Thyroid*Oct. 1997;7(5):713-24. (Abstract Only).
Barnes, et al. "Expression of embryonic fibronectin isoform EIIIA parallels alpha-smooth muscle actin in maturing and diseased kidney." *J Histochem Cytochem*. Jun. 1999;47(6):787-98. (Abstract Only).
Bea, et al. "BMI-1 gene amplification and overexpression in hematological malignancies occur mainly in mantle cell lymphomas." *Cancer Res*. Mar. 15, 2001;61(6):2409-12. (Abstract Only).
Blaschke, et al. "Rapid quantitation of proinflammatory and chemoattractant cytokine expression in small tissue samples and monocyte-derived dendritic cells: validation of a new real-time RT-PCR technology." *J Immunol Methods*. Dec. 1, 2000;246(1-2):79-90. (Abstract Only).
Buckley, et al. "Butyrate-induced reversal of dexamethasone resistance in autonomous rat Nb2 lymphoma cells." Apoptosis. 1997;2(6):518-28. (Abstract Only).
Caberlotto, et al. "Alterations in neuropeptide Y levels and Y1 binding sites in the Flinders Sensitive Line rats, a genetic animal model of depression."*Neurosci Lett*. Apr. 23, 1999;265(3):191-4. (Abstract Only).
Caberlotto, et al. "Neurokinin 1 receptor and relative abundance of the short and long isoforms in the human brain." *Eur J Neurosci*. May 2003;17(9):1736-46. (Abstract Only).
Celis, et al. 2000. Gene expression profiling: monitoring transcription and translation products using DNA microarrays and proteomics. *FEBS Letters*, 480:2-16.
Choi, et al. "Characterization of cyclin D2 expression in human endometrium." 166: *J Soc Gynecol Investig*. Jan.-Feb. 2002;9(1):41-6. (Abstract Only).
Couvelard, et al. "Human chorionic gonadotrophin beta expression in malignant Barrett's oesophagus." *Virchows Arch*. Sep. 2004;445(3):279-84. Epub Aug. 10, 2004. (Abstract Only).
Crick, F. 1970. Central dogma of molecular biology. *Nature*, 227:561-563.
Dagenais, et al. "Downregulation of ENaC activity and expression by TNF-alpha in alveolar epithelial cells." *Am J Physiol Lung Cell Mol Physiol*. Feb. 2004;286(2):L301-11. Epub Sep. 26, 2003. (Abstract Only).
de Boer, et al. "Involvement of the CCND1 gene in hairy cell leukemia." *Ann Oncol*. Mar. 1996;7(3):251-6. (Abstract Only).
Debieve, et al. "Inhibin and activin production and subunit expression in human placental cells cultured in vitro." *Mol Hum Reprod*. Aug. 2000;6(8):743-9. (Abstract Only).
Dong, et al. "Expression of membrane-type matrix metalloproteinases 4, 5, and 6 in mouse corneas infected with *P. aeruginosa." Invest Ophthalmol Vis Sci*. Dec. 2001;42(13):3223-7. (Abstract Only).
Duchrow, et al. "Assessment of proliferative activity in colorectal carcinomas by quantitative reverse transcriptase-polymerase chain reaction (RT-PCR)." *Cancer Invest*. 2001;19(6):588-96. (Abstract Only).
Dyer, et al. "Molecular characterisation of carbohydrate digestion and absorption in equine small intestine." *Equine Vet J*. Jul. 2002;34(4):349-58. (Abstract Only).
Eqwuagu, et al. "Suppressors of cytokine signaling proteins are differentially expressed in Th1 and Th2 cells: implications for Th cell lineage commitment and maintenance." *J Immunol*. Apr. 1, 2002;168(7):3181-7. (Abstract Only).

Eleore, et al. "Modulation of the glutamatergic receptors (AMPA and NMDA) and of glutamate vesicular transporter 2 in the rat facial nucleus after axotomy." *Neuroscience*. 2005;136(1):147-60. Epub Sep. 21, 2005. (Abstract Only).

El-Ghrablv, et al. "Intravitreal invading cells contribute to vitreal cytokine milieu in proliferative vitreoretinopathy." *Br J Ophthalmol*. Apr. 2001;85(4):461-70. (Abstract Only).

Feroze-Merzoug, et al. 2001. Molecular profiling in prostate cancer. *Cancer and Metastasis Reviews*, 20:165-171.

Forsberg, et al. "Altered levels of scavenging enzymes in embryos subjected to a diabetic environment." *Free Radic Res*. Jun. 1996;24(6):451-9. (Abstract Only).

Frevschuss, et al. "Induction of the estrogen receptor by growth hormone and glucocorticoid substitution in primary cultures of rat hepatocytes."*Endocrinology*. Oct. 1993;133(4):1548-54. (Abstract Only).

Fu, et al. "Cyclin D1-negative mantle cell lymphoma: a clinicopathologic study based on gene expression profiling." *Blood*. Dec. 15, 2005; 106(13):4315-21. Epub Aug. 25, 2005. (Abstract Only).

Fuchs, et al. "Oxytocin receptors in bovine cervix: distribution and gene expression during the estrous cycle." *Biol Reprod*. Mar. 1996;54(3):700-8. (Abstract Only).

Furuta, et al. "Silencing of the thrombomodulin gene in human malignant melanoma" *Melanoma Res*. Feb. 2005;15(1):15-20. (Abstract Only).

Futcher, et al. "A sampling of the yeast proteome." *Mol Cell Biol*. Nov. 1999;19(11):7357-68. (Abstract Only).

George, et al. "Pre-translational regulation of cytochrome P450 genes is responsible for disease-specific changes of individual P450 enzymes among patients with cirrhosis." *Biochem Pharmacol*. Mar. 30, 1995;49(7):873-81. (Abstract Only).

Giroux, et al. "Cyclooxygenase-2 expression in macrophages: modulation by protein kinase C-alpha." *J Immunol*. Oct. 1, 2000;165(7):3985-91. (Abstract Only).

Gnatenko, et al. "Transcript profiling of human platelets using microarray and serial analysis of gene expression." *Blood*. Mar. 15, 2003;101(6):2285-93. Epub Nov. 14, 2002. (Abstract Only).

Godbout, et al. "Overexpression of a DEAD box protein (DDX1) in neuroblastoma and retinoblastoma cell lines." *J Biol Chem*. Aug. 14, 1998;273(33):21161-8. (Abstract Only).

Goldenberg, et al. "Modulation of gap junction mediated intercellular communication in TM3 Leydig cells." *J Endocrinol*. May 2003;177(2):327-35. (Abstract Only).

Golebiowski, et al. "Expression level of Ubc9 protein in rat tissues." *Acta Biochim Pol*. 2003;50(4):1065-73. (Abstract Only).

Greenbaum, et al. 2003. Comparing protein abundance and mRNA expression levels on a genomic scale. *Genome Biology*, 4(9):117. 1-117.8.

Grem, et al. "Thymidine kinase, thymidylate synthase, and dihydropyrimidine dehydrogenase profiles of cell lines of the National Cancer Institute's Anticancer Drug Screen." *Clin Cancer Res*. Apr. 2001;7(4):999-1009. (Abstract Only).

Grenback, et al. "Galanin in pituitary adenomas." *Regul Pept*. Feb. 15, 2004;117(2):127-39. (Abstract Only).

Gromova, et al."Protein abundancy and mRNA levels of the adipocyte-type fatty acid binding protein correlate in non-invasive bladder transitional cell carcinomas." *Int J Oncol*. Aug. 1998;13(2):379-83 (Abstract Only).

Guo, et al. "The pathogenic role of macrophage migration inhibitory factor in acute respiratory distress syndrome" *Zhonghua Jie He He Hu Xi Za Zhi*. Jun. 2002;25(6):337-40. (Abstract Only).

Habu, et al. "Restored expression and activity of organic ion transporters rOAT1, rOAT3 and rOCT2 after hyperuricemia in the rat kidney." *Biochem Pharmacol*. Mar. 15, 2005;69(6):993-9. (Abstract Only).

Hahn, et al. "Regulation of cytochrome P4501A1 in teleosts: sustained induction of CYP1A1 mRNA, protein, and catalytic activity by 2,3,7,8-tetrachlorodibenzofuran in the marine fish *Stenotomus chrysops." Toxicol Appl Pharmacol*. Aug. 1994;127(2):187-98. (Abstract Only).

Hahnel, et al. "Expression of the pS2 gene in breast tissues assessed by pS2-mRNA analysis and pS2-protein radioimmunoassay." *Breast Cancer Res Treat*. 1992;24(1):71-4. (Abstract Only).

Hamilton, et al. "The role of the epidermal growth factor receptor in sustaining neutrophil inflammation in severe asthma." *Clin Exp Allergy*. Feb. 2003;33(2):233-40. (Abstract Only).

Hasset, et al. "Human hepatic microsomal epoxide hydrolase: comparative analysis of polymorphic expression." *Arch Biochem Biophys*. Jan. 15, 1997;337(2):275-83. (Abstract Only).

Holten-Andersen, et al. "Localization of tissue inhibitor of metalloproteinases 1 (TIMP-1) in human colorectal adenoma and adenocarcinoma." *Int J Cancer*. Jan. 10, 2005;113(2):198-206. (Abstract Only).

Houghten, et al. 1986. Relative Importance of Position and Individual Amino Acid Residues in Peptide Antigen-Antibody Interactions: Implications in the Mechanism of Antigenic Drift and Antigenic Shift. New Approaches to Immunization, *Vaccines86*, Cold Spring Harbor Laboratory, p. 21-25.

Huang, et al. "Tissue plasminogen activator induced by dengue virus infection of human endothelial cells." *J Med Virol*. Aug. 2003;70(4):610-6. (Abstract Only).

Huettner, et al. "Neu oncogene expression in ovarian tumors: a quantitative study." *Mod Pathol*. May 1992;5(3):250-6. (Abstract Only).

Hui, et al. "Real-time quantitative RT-PCR of cyclin D1 mRNA in mantle cell lymphoma: comparison with FISH and immunohistochemistry." *Leuk Lymphoma*. Aug. 2003;44(8):1385-94. (Abstract Only).

Husain, et al. "Elevation of topoisomerase I messanger RNA, protein, and catalytic activity in human tumors: demonstration of tumor-type specificity and implications for cancer chemotherapy." *Cancer Res*. Jan. 15, 1994;54(2):539-46. (Abstract Only).

Ihmann, et al. "High-level mRNA quantification of proliferation marker pKi-67 is correlated with favorable prognosis in colorectal carcinoma" *J Cancer Res Clin Oncol*. Dec. 2004;130(12):749-56. Epub Sep. 21, 2004. (Abstract Only).

Ikegami, et al. "Modulation of glucagon receptor expression and response is transfected human embryonic kidney cells." *Am J Physiol Cell Physiol*. Oct. 2001;281(4):C1396-402. (Abstract Only).

Irving, et al. 2000. Proteins emerge from disarray *Nature Biotechnology* 18:932-933.

Jacquemin, et al. "Developmental regulation of acidic fibroblast growth factor (aFGF) expression in bovine retina." *Int J Dev Biol*. Sep. 1993;37(3):417-23. (Abstract Only).

Jaime, et al. "The p21(Cip1) protein, a cyclin inhibitor, regulates the levels and the intracellular localization of CDC25A in mice regenerating livers." *Hepatology*, May 2002;35(5):1063-71. (Abstract Only).

Janssens, et al. "Alteration of frizzled expression in renal cell carcinoma." *Tumour Biol*. Jul.-Aug. 2004;25(4):161-71. (Abstract Only).

Jungbluth, et al. "Immunohistochemical analysis of NY-ESO-1 antigen expression in normal and malignant human tissures." *Int J Cancer*. Jun. 15, 2001;92(6):856-60. (Abstract Only).

Kalabis, et al. "Multidrug resistance phosphoglycoprotein (ABCB1) in the mouse placenta: fetal protection" *Biol Reprod*. Oct. 2005;73(4):591-7. Epub May 25, 2005. (Abstract Only).

Kammori, et al. Expression of human telomerase reverse transcriptase gene and protein, and of estrogen and progesterone receptors, in breast tumors: Preliminary data from neo-adjuvant chemotherapy.38 *Int J. Oncol*. Nov. 2005;27(5):1257-63. (Abstract Only).

Khal, et al. "Expression of the ubiquitin-proteasome pathway and muscle loss in experimental cancer cachexia." *Br J Cancer*. Oct. 3, 2005; 93(7):774-80. (Abstract Only).

Khal, et al. "Increased expression of proteasome subunits in skeletal muscle of cancer patients with weight loss." *Int J Biochem Cell Biol*. Oct. 2005;37(10):2196-206. Epub Dec. 2004 (Abstract Only).

Kogo, et al. "Cell type-specific occurrence of caveolin-1alpha and -1beta in the lung caused by expression of distinct mRNAs." *J Biol Chem*. Jun. 11, 2004;279(24):25574-81. Epub Apr. 2, 2004. (Abstract Only).

Kommoss, et al. "Oncogene and growth factor expression in ovarian cancer." *Acta Obstet Gyenecol Scand Suppl.* 1992;155:19-24. (Abstract Only).

Kumar, et al. "Somatostatin receptors in primary human breast cancer: quantitative analysis of mRNA for subtypes 1-5 and correlation with receptor protein expression and tumor pathology." *Breast Cancer Res Treat.* Jul. 2005;92(2):175-86. (Abstract Only).

Kuo, et al. "Atranscriptomic and proteomic analysis of the effect of CpG-ODN on human THP-1 monocytic leukemia cells." *Proteomics.* Mar. 2005;5(4):894-906. (Abstract Only).

Labaer, Joshua. 2003. Letter to the editor: Mining the literature and large datasets. *Nature Biotechnology*, 21(9):976-977.

Landmark, et al. "Cellular location and age-dependent changes of the regulatory subunits of cAMP-dependent protein kinase in rat testis." *J Reprod Fertil.* Nov. 1993;99(2):323-34. (Abstract Only).

Lassmann, et al. "Quantification of CK20 gene and protein expression in colorectal cancer by RT-PCR and immunohistochemistry reveals inter- and intratumour heterogeneity." *J Pathol.* Oct. 2002;198(2):198-206. (Abstract Only).

Legrand, et al. "Expression of the multidrug resistance-associated protein (MRP) mRNA and protein in normal peripheral blood and bone marrow haemopoietic cells." *Br J Haematol.* Jul. 1996;94(1):23-33. (Abstract Only).

Lemstrom, et al. "Vascular endothelial growth factor enhances cardiac allograft arteriosclerosis." *Circulation.* May 28, 2002;105(21):2524-30. (Abstract Only).

Li, et al. "Enhanced expressions of arachidonic acid-sensitive tandem-pore domain potassium channels in rat experimental acute cerebral ischemia." *Biochem Biophys Res Commun.* Feb. 25, 2005;327(4):1163-9. (Abstract Only).

Li, et al. "Retinal preconditioning and the induction of heat-shock protein 27." *Invest Ophthalmol Vis Sci.* Mar. 2003;44(3):1299-304. (Abstract Only).

Lian, et al. 2001. Genomic and proteomic analysis of the myeloid differentiation program. *Blood*, 98(3):513-524.

Lichtinghagen, et al. 2002. Different mRNA and protein expression of matrix metalloproteinases 2 and 9 and tissue inhibitor of metalloproteinases 1 in benign and malignant prostate tissue. *European Urology*, 42:398-406.

Lindberg, et al. "Increasing expression of tissue plasminogen activator and plasminogen activator inhibitor type 2 in dog gingival tissues with progressive inflammation." *Arch Oral Biol.* Jan. 2001;46(1):23-31. (Abstract Only).

Macabeo-Ong, et al. "Effect of duration of fixation on quantitative reverse transcription polymerase chain reaction analyses." *Mod Pathol.* Sep. 2002;15(9):979-87. (Abstract Only).

Madoz-Gurpide, et al. 2003. Molecular analysis of cancer using DNA and protein microarrays. *Adv. Exp. Med. Biol.*, 532:51-58.

Maruyama, et al. "ld-1 and ld-2 are overexpressed in pancreatic cancer and in dysplastic lesions in chronic pancreatitis." *Am J Pathol.* Sep. 1999;155(3):815-22. (Abstract Only).

McGuiness, et al. Mar. 1991, Point mutation in meningococcal *por* A gene associated with increased endemic disease. *The Lancet*, 337:514-517.

McGuiness, et al., Feb. 1993, Class 1 outer membrane protein of *Neisseria meningitides*: epitope analysis of the antigenic diversity between strains, implications for subtype definition and molecular epidemiology. *Mol. Microbiology*, 7:505-514.

Meehan, et al. "Tightly regulated and inducible expression of a yoked hormone-receptor complex in HEK 293 cells." *J Mol Endocrinol.* Feb. 2004;32(1):247-55. (Abstract Only).

Mendoza-Rodriguez, et al. "c-fos and estrogen receptor gene expression pattern in the rat uterine epithelium during the estrous cycle." *Mol Reprod Dev.* Apr. 2003;64(4):379-88. (Abstract Only).

Meoni, et al. "[3H]MK-801 binding and the mRNA for the NMDAR1 subunit of the NMDA receptor are differentially distributed in human and rat forebrain." *Brain Res Mol Brain Res.* Feb. 1998;54(1):13-23. (Abstract Only).

Mezzano, et al. "Overexpression of chemokines, fibrogenic cytokines, and myofibroblasts in human membranous nephropathy." *Kidney Int.* Jan. 2000;57(1):147-58. (Abstract Only).

Mingrone, et al. "Decreased uncoupling protein expression and intramyocytic triglyceride depletion in formerly obese subjects." *Obes. Res.* May 2003;11(5):632-40. (Abstract Only).

Miralles, et al. "Differential expression of the short and long forms of the gamma 2 subunit of GABAA/benzodiazepine receptors." *Brain Res Mol Brain Res.* Jul. 1994;24(1-4):129-39. (Abstract Only).

Mizrachi, et al. "Follicle-stimulating hormone receptor and its messenger ribonucleic acid are present in the bovine cervix and can regulate cervical prostanoid synthesis." *Biol Reprod.* Sep. 1999;61(3):776-84. (Abstract Only).

Monaghan, et al. "The alpha(v)beta6 integrin receptor for Foot-and-mouth disease virus is expressed constitutively on the epithelial cells targeted in cattle." *J Gen Virol.* Oct. 2005;86(Pt 10):2769-80. (Abstract Only).

Montuori, et al. "Urokinase-mediated posttranscriptional regulation of urokinase-receptor expression in non small cell lung carcinoma." *Int J Cancer.* Jun. 20, 2003;105(3):353-60. (Abstract Only).

Munaut, et al. "Vascular endothelial growth factor expression correlates with matrix metalloproteinases MT1-MMP, MMP-2 and MMP-9 in human glioblastomas." *Int J Cancer.* Oct. 10, 2003;106(6):848-55. (Abstract Only).

Nie, et al. "DNA hypermethylation is a mechanism for loss of expression of the HLA class I genes in human esophageal squamous cell carcinomas." *Carcinogenesis.* Oct. 2001;22(10):1615-23. (Abstract Only).

Nuciforo, et al. "Molecular and immunohistochemical analysis of HER2/neu oncogene in synovial sarcoma." *Hum Pathol.* Jul. 2003;34(7):639-45. (Abstract Only).

Oberringer, et al. "Differential expression of heat shock protein 70 in well healing and chronic human wound tissue." *Biochem Biophys Res Commun.* Sep. 25, 1995;214(3):1009-14. (Abstract Only).

Pachmann, et al. "Expression of bcr-abl mRNA in individual chronic myelogenous leukaemia cells as determined by in situ amplification." *Br J Haematol.* Mar. 2001;112(3):749-59. (Abstract Only).

Pairon, et al. "Cell localization and regultion of expression of cytochrome P450 1A1 and 2B1 in rat lung after induction with 3-methylcholanthrene using mRNA hybridization and immunohistochemistry." *Am J Respir Cell Mol Biol.* Oct. 1994;11(4):386-96. (Abstract Only).

Papotti, et al. "Correlative immunohistochemical and reverse transcriptase polymerase chain reaction analysis of somatostatin receptor type 2 in neuroendocrine tumors of the lung." *Diagn Mol Pathol.* Mar. 2000;9(1):47-57. (Abstract Only).

Papotti, et al. "Expression of somatostatin receptor types 1-5 in 81 cases of gastrointestinal and pancreatic endocrine tumors. A correlative immunohistochemical and reverse-transcriptase polymerase chain reaction analysis." *Virchows Arch.* May 2002;440(5):461-75. Epub Mar. 23, 2002. (Abstract Only).

Paredes, et al. "P-cadherin overexpression is an indicator of clinical outcome in invasive breast carcinomas and is associated with CDH3 promoter hypomethylation." *Clin Cancer Res* Aug. 15, 2005;11(16):5869-77. (Abstract Only).

Politis, et al. "Mammary-derived growth inhibitor protein and messenger ribonucleic acid concentrations in different physiological states of the gland." *J Dairy Sci.* Jun. 1992;75(6):1423-9. (Abstract Only).

Powell, et al. Oct. 1998, Expression of cytochrome P4502E1 in human liver: assessment by mRNA, genotype and phenotype. *Pharmacogenetics*, vol. 5: pp. 411-421. (Abstract Only).

Preesman, et al. "T-cell receptor V beta-family usage in primary cutaneous and primary nodal T-cell non-Hodgkin's lymphomas." *J Invest Dermatol.* Nov. 1992;99(5):587-93. (Abstract Only).

Pullig, et al. "Matrilin-3 in human articular cartilage: increased expression in osteoarthritis." *Osteoarthritis Cartilage.* Apr. 2002;10(4):253-63. (abstract Only).

Rey, et al. "Up-regulation of mitochondrial peripheral benzodiazepine receptor expression by tumor necrosis factor alpha in testicular leydig cells. Possible involvement in cell survival." *Biochem Pharmacol.* Dec. 1, 2000;60(11):1639-46. (Abstract Only).

Rudlowski, et al. "GLUT1 messenger RNA and protein induction relates to the malignant transformation of cervical cancer." *Am J Clin Pathol*. Nov. 2003;120(5):691-8. (Abstract Only).
Sasaki, et al. "Expression and distribution of laminin alpha1 and alpha2 chains in embryonic and adult mouse tissues: an immunochemical approach." *Exp Cell Res*. May 1, 2002;275(2):185-99. (Abstract Only).
Sedelies, et al. "Discordant regulation of granzyme H and granzyme B expression in human lymphocytes." *J Biol Chem*. Jun. 18, 2004;279(25):26581-7. Epub Apr. 6, 2004. (Abstract Only).
Shen, et al. "BCL2 protein expression parallels its mRNA level in normal and malignant B cells": *Blood*. Nov. 1, 2004;104(9):2936-9. Epub Jul. 8, 2004. (Abstract Only).
Shinohara, et al. "Quantitative determinations of the steady state transcript levels of hexokinase isozymes and glucose transporter isoforms in normal rat tissues and the malignant tumor cell line AH130." *Biochim Biophys Acta*. Jan. 5, 1998;1368(1):129-36. (Abstract Only).
Silvers, et al. "UVA irradiation-induced activation of activator protein-1 is correlated with induced expression of AP-1 family members in the human keratinocyte cell line HaCaT." *Photochem Photobiol*. Mar. 2002;75(3):302-10. (Abstract Only).
Song, et al. "Rat kidney glutamyl aminopeptidase (aminopeptidase A): molecular identify and cellular localization." *Am J Physiol*. Oct. 1994;267(4 Pt 2):F546-57. (Abstract Only).
Spaziani, et al. "Tumor necrosis factor-alpha upregulates the prostaglandin E2 EP1 receptor subtype and the cyclooxygenase-2 isoform in cultured amnion WISH cells." *J Interferon Cytokine Res*. Dec. 1998;18(12):1039-44. (Abstract Only).
Spika, et al. "Transcriptional activity of potent glucocorticoids: relevance of glucocorticoid receptor isoforms and drug metabolites." *Skin Pharmacol Appl Skin Physiol*. May-Jun. 2003;16(3):143-50. (abstract Only).
Splinter, et al. "Specific inhibition of AQP1 water channels in isolated rat intrahepatic bile duct units by small interfering RNAs." *J Biol Chem*. Feb. 21, 2003;278(8):6268-74. Epub Dec. 4, 2002. (Abstract Only).
Stearns, et al. "Type IV collagenase (M(r) 72,000) expression in human prostate:benign and malignant tissue." *Cancer Res*. Feb. 15, 1993;53(4):878-83. (Abstract Only).
Stein, et al. "The decompensated detrusor III: impact of bladder outlet obstruction on sarcoplasmic endoplasmic reticulum protein and gene expression." *J Urol*. Sep. 2000;164(3 Pt 2):1026-30. (Abstract Only).
Strickland, et al. "TNF-alpha and IL-8 are upregulated in the epidermis of normal human skin after UVB exposure: correlation with neutrophil accumulation and E-selectin expression." *J Invest Dermatol*. May 1997;108(5):763-8. (Abstract Only).
Strutz, et al. "Basic fibroblast growth factor expression is increased in human renal fibrogenesis and may mediate autocrine fibroblast proliferation." *Kidney Int*. Apr. 2000;57(4):1521-38. (Abstract Only).
Takahashi, et al: "Adiposity elevates plasma MCP-1 levels leading to the increased CD11b-positive monocytes in mice.": *J Biol Chem*. Nov. 21, 2003;278(47):46654-60. Epub Sep. 16, 2003. (Abstract Only).
Takimoto, et al. "Augmented expression of neuronal nitric oxide synthase in the atria parasympathetically decreases heart rate during acute myocardial infarction in rats." *Circulation*. Jan. 29, 2002;105(4):490-6. (Abstract Only).
Telek, et al. "Differential upregulation of cellular adhesion molecules at the sites of oxidative stress in experimental acute pancreatitis." *J Surg Res*. Mar. 2001;96(1):56-67. (Abstract Only).
Timchenko, et al. "Myotonic dystrophy: an unstable CTG repeat in a protein kinase gene." *Semin Cell Biol*. Feb. 1995;6(1):13-9. (Abstract Only).
Torronen, et al. "Induction of class 3 aldehyde dehydrogenase in the mouse hepatoma cell line Hepa-1 by various chemicals." *Chem Biol Interact*. Aug. 14, 1992;83(2):107-19. (Abstract Only).
Ullmannova, et al. "Relationship between cyclin D1 and p21(Waf1/Cip1) during differentiation of human myeloid leukemia cell lines." *Leuk Res*. Dec. 2003;27(12):1115-23. (Abstract Only).
Valle, et al. 2003. New approaches for biomarker discovery in lung cancer. *Expert Rev. Mol. Diagn*., 3(1):55-67.
Vallejo, et al. Dec. 2000. Evidence of tissue-specific, post-transcriptional regulation of NRF-2 expression. *Biochimie* 82(12): 1129-33. (Abstract Only).
Van Beers, et al. "Intestinal carbamoyl phosphate synthase I in human and rat. Expression during development shows species differences and mosaic expression in duodenum of both species." *J Histochem Cytochem*. Feb. 1998;46(2):231-40. (Abstract Only).
van der Wilt, et al. "Expression of deoxycytidine kinase in leukaemic cells compared with solid tumour cell lines, liver metastases and normal liver." *Eur J Cancer*. Mar. 2003;39(5):691-7. (Abstract Only).
Waldherr, et al. "Expression of cytokines and growth factors in human glomerulonephritides." *Pediatr Nephrol*. Aug. 1993;7(4):471-8. (Abstract Only).
Walmer, et al. "Malignant transformation of the human endometrium is associated with overexpression of lactoferrin messenger RNA and protein." *Cancer Res*. Mar. 1, 1995;55(5):1168-75. (Abstract Only).
Wang, et al. "Cell proliferation in human soft tissue tumours correlates with platelet-derived growth factor B chain expression: an immunohistochemical and in situ hybridization study." *Cancer Res*. Jan. 15, 1994;54(2):560-4. (Abstract Only).
Wang, et al. "Down-regulation of prostate-specific antigen expression by finasteride through inhibition of complex formation between androgen receptor and steroid receptor-binding consensus in the promoter of the PSA gene in LNCaP cells." *Cancer Res*. Feb. 15, 1997;57(4):714-9. (Abstract Only).
Wang, et al. "Expression of cadherins and catenins in paired tumor and non-neoplastic primary prostate cultures and corresponding prostatectomy specimens." *Urol. Res*. Oct. 2000;28(5):308-15. (Abstract Only).
Wang, et al. 2002. Novel candidate tumor marker genes for lung adenocarcinoma. *Oncogene*, 21:7598-7604.
Weterman, et al. "Expression of calcyclin in human melanocytic lesions." *Cancer Res*. Dec. 15, 1993;53(24):6061-6. (Abstract Only).
Williams, et al. "Estrogen regulation of the cytochrome P450 3A subfamily in humans." *J Pharmacol Exp Ther*. Nov. 2004;311(2):728-35. Epub Jul. 2004. (Abstract Only).
Winstead E.R., 2000. The Evolving Art of Arrays, www.genomenewsnetwork.org, pp. 1-4.
Wojtaszek, et al. "Severely decreased MARCKS expression correlates with ras reversion but not with mitogenic responsiveness." *Oncogene*. Mar. 1993;8(3):755-60. (Abstract Only).
Xi, et al. "Expression of human telomerase reverse transcriptase in cervix cancer and its significance" *Zhonghua Fu Chan Ke Za Zhi*. Jun. 2005;40(6):407-10. (Abstract Only).
Yousef, et al. 2003. Parallel overexpression of seven kallikrein genes in ovarian cancer. *Cancer Research*, 63:2223-2227.
Zhong, et al. "Expression of superoxide dismutases, catalase, and glutathione peroxidase in glioma cells." *Free Radic Biol Med*. Dec. 1999;27(11-12):1334-45. (Abstract Only).
Berner, et al., "Clincopathological association of CD44 mRNA and protein expression expression in primary breast carcinomas" *Histopathology* (2003) 42:546-554.
Brooks, et al., "cDNA array identification of genes regulated in rat renal medulla in response to vasoressin infusion" *Am J Physiol* (2003) 284:F218-F228.
Conrads, et al., "A Combined Proteome and Microarray Investigation of Inorganic Phosphate-induced Pre-osteoblast Cells" *Mol. Cell Proteomics*, 4(9):1284-1296 (2005).
Czupalla, et al., "Comparative study of proteinand mRNA expression during osteoclastogenesis" *Proteomics* 5:3868-3875 (2005).
Ginestier, et al. 2002. "Distinct and Complementary Information Provided by Use of Tissue and DNA Microarrays in the Study of Breast Tumor Markers" *Am. J. Pathol*., 161:1223-1233.
Gronborg, et al. "Biomarker discovery from pancreatic cancer secretome using a differential proteomic approach," *Mol Cell Proteomics*. Jan. 2006:5(1):157-71. Epub Oct. 8, 2005. (Abstract Only).

Kawamoto et al., "Expression Profiles of Active Genes in Human and Mouse Livers," *Gene*, Sep. 26, 1996;174(1):151-8.
King, et al. 2001. "Gene Expression Profile Analysis by DNA Microarrays" JAMA, 286(18):2280-2288.
Kwong, et al., "Synchronous global assessment of gene and protein expression in colorectal cancer progression" *Genomics*, 86:142-158 (2005).
Lederman, et al. 1991. "A single amino acid substitution in a common African allele of the CD4 molecule ablates binding of the monoclonal antibody, OKT4." *Molecular Immunology*28(11):1171-1181.
Lee, et al. "Importance of replication in microarray gene expression studies: Statistical methods and evidence from repetitive cDNA hybridizations" *Proc.Natl.Acad*, USA, 97(18):9834-9839.
Nagaraja, et al. "Gene expression signatures and biomarkers of noninvasive and invasive breast cancer cells: comprehensive profiles by representational difference analysis, microarrays and proteomics." *Oncogene*. (2006) 25:2328-2338.
Oda, et al., "Expression of MDR1/p-glycoprotein and multidrug resistance-associated protein in childhood solid tumours" *Virchows Arch* (1997) 430:99-105.
Sagynaliev, et al. "Web-based data warehouse on gene expression in human colorectal cancer." *Proteomics* 2005, 5:3066-3078.
Saito-Hisaminato et al., Feb. 2002 (Genome-Wide Profiling of Gene Expression in 29 Normal Human Tissues with a cDNA Microarray. *DNA Research 9*, 35-45.
Sugg, et al., "Cytoplasmic staining of *erb*B-2 but not mRNA levels correlates with differentiation in human throid neoplasia" *Clinical Endocrinology* (1998) 49:629-637.
Toler, et al., "Loss of communication in ovarian cancer" *American Journal of Obstertrics and Gynecology*, (2006)194:e27-e31.
Waghray, et al. "Identification of androgen-regulated genes in the prostate cancer cell line LNCaP by serial analysis of gene expression and proteomic analysis." *Proteomics* 2001, 1:1327-1338.
Washburn, et al., "Protein pathway and complex clustering of correlated mRNA and protein expression analyses in *Saccharomyces cerevisiae" Proc. Natl. Acad. Sci*. 100(6): 3107-3112. (2003).
Wildsmith, et al. "Gene Expression Analysis Using Microarrays" *Molecular Biology in Cellular Pathology* Ed. John Crocker and Paul G. Murray, pp. 269-286.

* cited by examiner

FIGURE 1

GGGGCTTCGGCGCCAGCGGCCAGCGCTAGTCGGTCTGGTAAGGATTTACAAAAGGTGCAGGTATG
AGCAGGTCTGAAGACTAACATTTTGTGAAGTTGTAAAACAGAAAACCTGTTAGAAATGTGGTGGT
TTCAGCAAGGCCTCAGTTTCCTTCCTTCAGCCCTTGTAATTTGGACATCTGCTGCTTTCATATTT
TCATACATTACTGCAGTAACACTCCACCATATAGACCCGGCTTTACCTTATATCAGTGACACTGG
TACAGTAGCTCCAGAAAAATGCTTATTTGGGGCAATGCTAAATATTGCGGCAGTTTTATGCATTG
CTACCATTTATGTTCGTTATAAGCAAGTTCATGCTCTGAGTCCTGAAGAGAACGTTATCATCAAA
TTAAACAAGGCTGGCCTTGTACTTGGAATACTGAGTTGTTTAGGACTTTCTATTGTGGCAAACTT
CCAGAAAACAACCCTTTTTGCTGCACATGTAAGTGGAGCTGTGCTTACCTTTGGTATGGGCTCAT
TATATATGTTTGTTCAGACCATCCTTTCCTACCAAATGCAGCCCAAAATCCATGGCAAACAAGTC
TTCTGGATCAGACTGTTGTTGGTTATCTGGTGTGGAGTAAGTGCACTTAGCATGCTGACTTGCTC
ATCAGTTTTGCACAGTGGCAATTTTGGGACTGATTTAGAACAGAAACTCCATTGGAACCCCGAGG
ACAAAGGTTATGTGCTTCACATGATCACTACTGCAGCAGAATGGTCTATGTCATTTTCCTTCTTT
GGTTTTTTCCTGACTTACATTCGTGATTTTCAGAAAATTTCTTTACGGGTGGAAGCCAATTTACA
TGGATTAACCCTCTATGACACTGCACCTTGCCCTATTAACAATGAACGAACACGGCTACTTTCCA
GAGATATTTGATGAAAGGATAAAATATTTCTGTAATGATTATGATTCTCAGGGATTGGGGAAAGG
TTCACAGAAGTTGCTTATTCTTCTCTGAAATTTTCAACCACTTAATCAAGGCTGACAGTAACACT
GATGAATGCTGATAATCAGGAAACATGAAAGAAGCCATTTGATAGATTATTCTAAAGGATATCAT
CAAGAAGACTATTAAAAACACCTATGCCTATACTTTTTTATCTCAGAAAATAAAGTCAAAAGACT
ATG

FIGURE 2

<subunit 1 of 1, 266 aa, 1 stop

<MW: 29766, pI: 8.39, NX(S/T): 0

MWWFQQGLSFLPSALVIWTSAAFIFSYITAVTLHHIDPALPYISDTGTVAPEKCLFGAMLNIAAV
LCIATIYVRYKQVHALSPEENVIIKLNKAGLVLGILSCLGLSIVANFQKTTLFAAHVSGAVLTFG
MGSLYMFVQTILSYQMQPKIHGKQVFWIRLLLVIWCGVSALSMLTCSSVLHSGNFGTDLEQKLHW
NPEDKGYVLHMITTAAEWSMSFSFFGFFLTYIRDFQKISLRVEANLHGLTLYDTAPCPINNERTR
LLSRDI

Important features:

Type II transmembrane domain:

amino acids 13-33

Other Transmembrane domains:

amino acids 54-73, 94-113, 160-180, 122-141

N-myristoylation sites.

amino acids 57-63, 95-101, 99-105, 124-130, 183-189

FIGURE 3

CGGACGCGTGGGCGGACGCGTGGGGGAGAGCCGCAGTCCCGGCTGCAGCACCTGGGAGAAGGCAGACC
GTGTGAGGGGGCCTGTGGCCCCAGCGTGCTGTGGCCTCGGGGAGTGGGAAGTGGAGGCAGGAGCCTTC
CTTACACTTCGCCATGAGTTTCCTCATCGACTCCAGCATCATGATTACCTCCCAGATACTATTTTTG
GATTTGGGTGGCTTTTCTTCATGCGCCAATTGTTTAAAGACTATGAGATACGTCAGTATGTTGTACAG
GTGATCTTCTCCGTGACGTTTGCATTTTCTTGCACCATGTTTGAGCTCATCATCTTTGAAATCTTAGG
AGTATTGAATAGCAGCTCCCGTTATTTTCACTGGAAAATGAACCTGTGTGTAATTCTGCTGATCCTGG
TTTTCATGGTGCCTTTTTACATTGGCTATTTTATTGTGAGCAATATCCGACTACTGCATAAACAACGA
CTGCTTTTTTCCTGTCTCTTATGGCTGACCTTTATGTATTTCTTCTGGAAACTAGGAGATCCCTTTCC
CATTCTCAGCCCAAAACATGGGATCTTATCCATAGAACAGCTCATCAGCCGGGTTGGTGTGATTGGAG
TGACTCTCATGGCTCTTCTTTCTGGATTTGGTGCTGTCAACTGCCCATACACTTACATGTCTTACTTC
CTCAGGAATGTGACTGACACGGATATTCTAGCCCTGGAACGGCGACTGCTGCAAACCATGGATATGAT
CATAAGCAAAAAGAAAAGGATGGCAATGGCACGGAGAACAATGTTCCAGAAGGGGGAAGTGCATAACA
AACCATCAGGTTTCTGGGGAATGATAAAAAGTGTTACCACTTCAGCATCAGGAAGTGAAAATCTTACT
CTTATTCAACAGGAAGTGGATGCTTTGGAAGAATTAAGCAGGCAGCTTTTTCTGGAAACAGCTGATCT
ATATGCTACCAAGGAGAGAATAGAATACTCCAAAACCTTCAAGGGGAAATATTTAATTTTCTTGGTT
ACTTTTTCTCTATTTACTGTGTTTGGAAAATTTTCATGGCTACCATCAATATTGTTTTTGATCGAGTT
GGGAAAACGGATCCTGTCACAAGAGGCATTGAGATCACTGTGAATTATCTGGGAATCCAATTTGATGT
GAAGTTTTGGTCCCAACACATTTCCTTCATTCTTGTTGGAATAATCATCGTCACATCCATCAGAGGAT
TGCTGATCACTCTTACCAAGTTCTTTTATGCCATCTCTAGCAGTAAGTCCTCCAATGTCATTGTCCTG
CTATTAGCACAGATAATGGGCATGTACTTTGTCTCCTCTGTGCTGCTGATCCGAATGAGTATGCCTTT
AGAATACCGCACCATAATCACTGAAGTCCTTGGAGAACTGCAGTTCAACTTCTATCACCGTTGGTTTG
ATGTGATCTTCCTGGTCAGCGCTCTCTCTAGCATACTCTTCCTCTATTTGGCTCACAAACAGGCACCA
GAGAAGCAAATGGCACCTTGAACTTAAGCCTACTACAGACTGTTAGAGGCCAGTGGTTTCAAAATTTA
GATATAAGAGGGGGGAAAAATGGAACCAGGGCCTGACATTTTATAAACAAACAAAATGCTATGGTAGC
ATTTTTCACCTTCATAGCATACTCCTTCCCCGTCAGGTGATACTATGACCATGAGTAGCATCAGCCAG
AACATGAGAGGGAGAACTAACTCAAGACAATACTCAGCAGAGAGCATCCCGTGTGGATATGAGGCTGG
TGTAGAGGCGGAGAGGAGCCAAGAAACTAAAGGTGAAAAATACACTGGAACTCTGGGGCAAGACATGT
CTATGGTAGCTGAGCCAAACACGTAGGATTTCCGTTTTAAGGTTCACATGGAAAAGGTTATAGCTTTG
CCTTGAGATTGACTCATTAAAATCAGAGACTGTAACAAAAAAAAAAAAAAAAAAAAAGGGCGGCCGCG
ACTCTAGAGTCGACCTGCAGAAGCTTGGCCGCCATGGCCCAACTTGTTTATTGCAGCTTATAATG

FIGURE 4

MSFLIDSSIMITSQILFFGFGWLFFMRQLFKDYEIRQYVVQVIFSVTFAFSCTMFELIIFEILGV
LNSSSRYFHWKMNLCVILLILVFMVPFYIGYFIVSNIRLLHKQRLLFSCLLWLTFMYFFWKLGDP
FPILSPKHGILSIEQLISRVGVIGVTLMALLSGFGAVNCPYTYMSYFLRNVTDTDILALERRLLQ
TMDMIISKKKRMAMARRTMFQKGEVHNKPSGFWGMIKSVTTSASGSENLTLIQQEVDALEELSRQ
LFLETADLYATKERIEYSKTFKGKYFNFLGYFFSIYCVWKIFMATINIVFDRVGKTDPVTRGIEI
TVNYLGIQFDVKFWSQHISFILVGIIIVTSIRGLLITLTKFFYAISSSKSSNVIVLLLAQIMGMY
FVSSVLLIRMSMPLEYRTIITEVLGELQFNFYHRWFDVIFLVSALSSILFLYLAHKQAPEKQMAP

Important features:

Signal peptide:

amino acids 1-23

Potential transmembrane domains:

amino acids 37-55, 81-102, 150-168, 288-311, 338-356, 375-398, 425-444

N-glycosylation sites.

amino acids 67-70, 180-183 and 243-246

Eukaryotic cobalamin-binding proteins amino acids 151-160

FIGURE 5

AGCAGGGAAATCCGGATGTCTCGGTTATGAAGTGGAGCAGTGAGTGTGAGCCTCAACATAGTTCC
AGAACTCTCCATCCGGACTAGTTATTGAGCATCTGCCTCTCATATCACCAGTGGCCATCTGAGGT
GTTTCCCTGGCTCTGAAGGGGTAGGCACGATGGCCAGGTGCTTCAGCCTGGTGTTGCTTCTCACT
TCCATCTGGACCACGAGGCTCCTGGTCCAAGGCTCTTTGCGTGCAGAAGAGCTTTCCATCCAGGT
GTCATGCAGAATTATGGGGATCACCCTTGTGAGCAAAAAGGCGAACCAGCAGCTGAATTTCACAG
AAGCTAAGGAGGCCTGTAGGCTGCTGGGACTAAGTTTGGCCGGCAAGGACCAAGTTGAAACAGCC
TTGAAAGCTAGCTTTGAAACTTGCAGCTATGGCTGGGTTGGAGATGGATTCGTGGTCATCTCTAG
GATTAGCCCAAACCCCAAGTGTGGGAAAAATGGGGTGGGTGTCCTGATTTGGAAGGTTCCAGTGA
GCCGACAGTTTGCAGCCTATTGTTACAACTCATCTGATACTTGGACTAACTCGTGCATTCCAGAA
ATTATCACCACCAAAGATCCCATATTCAACACTCAAACTGCAACACAAACAACAGAATTTATTGT
CAGTGACAGTACCTACTCGGTGGCATCCCCTTACTCTACAATACCTGCCCCTACTACTACTCCTC
CTGCTCCAGCTTCCACTTCTATTCCACGGAGAAAAAAATTGATTTGTGTCACAGAAGTTTTTATG
GAAACTAGCACCATGTCTACAGAAACTGAACCATTTGTTGAAAATAAAGCAGCATTCAAGAATGA
AGCTGCTGGGTTTGGAGGTGTCCCCACGGCTCTGCTAGTGCTTGCTCTCCTCTTCTTTGGTGCTG
CAGCTGGTCTTGGATTTTGCTATGTCAAAAGGTATGTGAAGGCCTTCCCTTTTACAAACAAGAAT
CAGCAGAAGGAAATGATCGAAACCAAAGTAGTAAAGGAGGAGAAGGCCAATGATAGCAACCCTAA
TGAGGAATCAAAGAAAACTGATAAAAACCCAGAAGAGTCCAAGAGTCCAAGCAAAACTACCGTGC
GATGCCTGGAAGCTGAAGTTTAGATGAGACAGAAATGAGGAGACACACCTGAGGCTGGTTTCTTT
CATGCTCCTTACCCTGCCCCAGCTGGGGAAATCAAAAGGGCCAAAGAACCAAAGAAGAAAGTCCA
CCCTTGGTTCCTAACTGGAATCAGCTCAGGACTGCCATTGGACTATGGAGTGCACCAAAGAGAAT
GCCCTTCTCCTTATTGTAACCCTGTCTGGATCCTATCCTCCTACCTCCAAAGCTTCCCACGGCCT
TTCTAGCCTGGCTATGTCCTAATAATATCCCACTGGGAGAAAGGAGTTTTGCAAAGTGCAAGGAC
CTAAAACATCTCATCAGTATCCAGTGGTAAAAAGGCCTCCTGGCTGTCTGAGGCTAGGTGGGTTG
AAAGCCAAGGAGTCACTGAGACCAAGGCTTTCTCTACTGATTCCGCAGCTCAGACCCTTTCTTCA
GCTCTGAAAGAGAAACACGTATCCCACCTGACATGTCCTTCTGAGCCCGGTAAGAGCAAAAGAAT
GGCAGAAAAGTTTAGCCCCTGAAAGCCATGGAGATTCTCATAACTTGAGACCTAATCTCTGTAAA
GCTAAAATAAAGAAATAGAACAAGGCTGAGGATACGACAGTACACTGTCAGCAGGGACTGTAAAC
ACAGACAGGGTCAAAGTGTTTTCTCTGAACACATTGAGTTGGAATCACTGTTTAGAACACACACA
CTTACTTTTTCTGGTCTCTACCACTGCTGATATTTTCTCTAGGAAATATACTTTTACAAGTAACA
AAAATAAAAACTCTTATAAATTTCTATTTTTATCTGAGTTACAGAAATGATTACTAAGGAAGATT
ACTCAGTAATTTGTTTAAAAAGTAATAAAATTCAACAAACATTTGCTGAATAGCTACTATATGTC
AAGTGCTGTGCAAGGTATTACACTCTGTAATTGAATATTATTCCTCAAAAAATTGCACATAGTAG
AACGCTATCTGGGAAGCTATTTTTTTCAGTTTTGATATTTCTAGCTTATCTACTTCCAAACTAAT
TTTTATTTTTGCTGAGACTAATCTTATTCATTTTCTCTAATATGGCAACCATTATAACCTTAATT
TATTATTAACATACCTAAGAAGTACATTGTTACCTCTATATACCAAAGCACATTTTAAAGTGCC
ATTAACAAATGTATCACTAGCCCTCCTTTTTCCAACAAGAAGGGACTGAGAGATGCAGAAATATT
TGTGACAAAAAATTAAAGCATTTAGAAAACTT

FIGURE 6

MARCFSLVLLLTSIWTTRLLVQGSLRAEELSIQVSCRIMGITLVSKKANQQLNFTEAKEACRLLG
LSLAGKDQVETALKASFETCSYGWVGDGFVVISRISPNPKCGKNGVGVLIWKVPVSRQFAAYCYN
SSDTWTNSCIPEIITTKDPIFNTQTATQTTEFIVSDSTYSVASPYSTIPAPTTTPPAPASTSIPR
RKKLICVTEVFMETSTMSTETEPFVENKAAFKNEAAGFGGVPTALLVLALLFFGAAAGLGFCYVK
RYVKAFPFTNKNQQKEMIETKVVKEEKANDSNPNEESKKTDKNPEESKSPSKTTVRCLEAEV

Signal sequence:

amino acids 1-16

Transmembrane domain:

amino acids 235-254

N-glycosylation site.

amino acids 53-57, 130-134, 289-293

Casein kinase II phosphorylation site.

amino acids 145-149, 214-218

Tyrosine kinase phosphorylation site.

amino acids 79-88

N-myristoylation site.

amino acids 23-29, 65-71, 234-240, 235-239, 249-255, 253-259

FIGURE 7

CGCCGCGCTCCCGCACCCGCGGCCCGCCCACCGCGCCGCTCCCGCATCTGCACCCGCAGCCCGGC
GGCCTCCCGGCGGGAGCGAGCAGATCCAGTCCGGCCCGCAGCGCAACTCGGTCCAGTCGGGGCGG
CGGCTGCGGGCGCAGAGCGGAGATGCAGCGGCTTGGGGCCACCCTGCTGTGCCTGCTGCTGGCGG
CGGCGGTCCCCACGGCCCCCGCGCCCGCTCCGACGGCGACCTCGGCTCCAGTCAAGCCCGGCCCG
GCTCTCAGCTACCCGCAGGAGGAGGCCACCCTCAATGAGATGTTCCGCGAGGTTGAGGAACTGAT
GGAGGACACGCAGCACAAATTGCGCAGCGCGGTGGAAGAGATGGAGGCAGAAGAAGCTGCTGCTA
AAGCATCATCAGAAGTGAACCTGGCAAACTTACCTCCCAGCTATCACAATGAGACCAACACAGAC
ACGAAGGTTGGAAATAATACCATCCATGTGCACCGAGAAATTCACAAGATAACCAACAACCAGAC
TGGACAAATGGTCTTTTCAGAGACAGTTATCACATCTGTGGGAGACGAAGAAGGCAGAAGGAGCC
ACGAGTGCATCATCGACGAGGACTGTGGGCCCAGCATGTACTGCCAGTTTGCCAGCTTCCAGTAC
ACCTGCCAGCCATGCCGGGGCCAGAGGATGCTCTGCACCCGGGACAGTGAGTGCTGTGGAGACCA
GCTGTGTGTCTGGGGTCACTGCACCAAAATGGCCACCAGGGGCAGCAATGGGACCATCTGTGACA
ACCAGAGGGACTGCCAGCCGGGGCTGTGCTGTGCCTTCCAGAGAGGCCTGCTGTTCCCTGTGTGC
ACACCCCTGCCCGTGGAGGGCGAGCTTTGCCATGACCCCGCCAGCCGGCTTCTGGACCTCATCAC
CTGGGAGCTAGAGCCTGATGGAGCCTTGGACCGATGCCCTTGTGCCAGTGGCCTCCTCTGCCAGC
CCCACAGCCACAGCCTGGTGTATGTGTGCAAGCCGACCTTCGTGGGGAGCCGTGACCAAGATGGG
GAGATCCTGCTGCCCAGAGAGGTCCCCGATGAGTATGAAGTTGGCAGCTTCATGGAGGAGGTGCG
CCAGGAGCTGGAGGACCTGGAGAGGAGCCTGACTGAAGAGATGGCGCTGGGGGAGCCTGCGGCTG
CCGCCGCTGCACTGCTGGGAGGGGAAGAGATTTAGATCTGGACCAGGCTGTGGGTAGATGTGCAA
TAGAAATAGCTAATTTATTTCCCCAGGTGTGTGCTTTAGGCGTGGGCTGACCAGGCTTCTTCCTA
CATCTTCTTCCCAGTAAGTTTCCCCTCTGGCTTGACAGCATGAGGTGTTGTGCATTTGTTCAGCT
CCCCCAGGCTGTTCTCCAGGCTTCACAGTCTGGTGCTTGGGAGAGTCAGGCAGGGTTAAACTGCA
GGAGCAGTTTGCCACCCCTGTCCAGATTATTGGCTGCTTTGCCTCTACCAGTTGGCAGACAGCCG
TTTGTTCTACATGGCTTTGATAATTGTTTGAGGGGAGGAGATGGAAACAATGTGGAGTCTCCCTC
TGATTGGTTTTGGGGAAATGTGGAGAAGAGTGCCCTGCTTTGCAAACATCAACCTGGCAAAAATG
CAACAAATGAATTTTCCACGCAGTTCTTTCCATGGGCATAGGTAAGCTGTGCCTTCAGCTGTTGC
AGATGAAATGTTCTGTTCACCCTGCATTACATGTGTTTATTCATCCAGCAGTGTTGCTCAGCTCC
TACCTCTGTGCCAGGGCAGCATTTTCATATCCAAGATCAATTCCCTCTCTCAGCACAGCCTGGGG
AGGGGGTCATTGTTCTCCTCGTCCATCAGGGATCTCAGAGGCTCAGAGACTGCAAGCTGCTTGCC
CAAGTCACACAGCTAGTGAAGACCAGAGCAGTTTCATCTGGTTGTGACTCTAAGCTCAGTGCTCT
CTCCACTACCCCACACCAGCCTTGGTGCCACCAAAAGTGCTCCCCAAAAGGAAGGAGAATGGGAT
TTTTCTTGAGGCATGCACATCTGGAATTAAGGTCAAACTAATTCTCACATCCCTCTAAAAGTAAA
CTACTGTTAGGAACAGCAGTGTTCTCACAGTGTGGGGCAGCCGTCCTTCTAATGAAGACAATGAT
ATTGACACTGTCCCTCTTTGGCAGTTGCATTAGTAACTTTGAAAGGTATATGACTGAGCGTAGCA
TACAGGTTAACCTGCAGAAACAGTACTTAGGTAATTGTAGGGCGAGGATTATAAATGAAATTTGC
AAAATCACTTAGCAGCAACTGAAGACAATTATCAACCACGTGGAGAAAATCAAACCGAGCAGGGC
TGTGTGAAACATGGTTGTAATATGCGACTGCGAACACTGAACTCTACGCCACTCCACAAATGATG
TTTTCAGGTGTCATGGACTGTTGCCACCATGTATTCATCCAGAGTTCTTAAAGTTTAAAGTTGCA
CATGATTGTATAAGCATGCTTTCTTTGAGTTTTAAATTATGTATAAACATAAGTTGCATTTAGAA
ATCAAGCATAAATCACTTCAACTGCAAAAAAAAAAAAAAAAAAAAAAAAA

FIGURE 8

MQRLGATLLCLLLAAAVPTAPAPAPTATSAPVKPGPALSYPQEEATLNEMFREVEELMEDTQHKL
RSAVEEMEAEEAAAKASSEVNLANLPPSYHNETNTDTKVGNNTIHVHREIHKITNNQTGQMVFSE
TVITSVGDEEGRRSHECIIDEDCGPSMYCQFASFQYTCQPCRGQRMLCTRDSECCGDQLCVWGHC
TKMATRGSNGTICDNQRDCQPGLCCAFQRGLLFPVCTPLPVEGELCHDPASRLLDLITWELEPDG
ALDRCPCASGLLCQPHSHSLVYVCKPTFVGSRDQDGEILLPREVPDEYEVGSFMEEVRQELEDLE
RSLTEEMALGEPAAAAAALLGGEEI

Signal sequence:
amino acids 1-19

N-glycosylation site.
amino acids 96-100, 106-110, 121-125, 204-208

Casein kinase II phosphorylation site.
amino acids 46-50, 67-71, 98-102, 135-139, 206-210, 312-316, 327-331

N-myristoylation site.
amino acids 202-208, 217-223

Amidation site.
amino acids 140-144

FIGURE 9

CGGACGCGTGGGCGGACGCGTGGGGGCTGTGAGAAAGTGCCAATAAATACATCATGCAACCCCAC
GGCCCACCTTGTGAACTCCTCGTGCCCAGGGCTGATGTGCGTCTTCCAGGGCTACTCATCCAAAG
GCCTAATCCAACGTTCTGTCTTCAATCTGCAAATCTATGGGGTCCTGGGGCTCTTCTGGACCCTT
AACTGGGTACTGGCCCTGGGCCAATGCGTCCTCGCTGGAGCCTTTGCCTCCTTCTACTGGGCCTT
CCACAAGCCCCAGGACATCCCTACCTTCCCCTTAATCTCTGCCTTCATCCGCACACTCCGTTACC
ACACTGGGTCATTGGCATTTGGAGCCCTCATCCTGACCCTTGTGCAGATAGCCCGGGTCATCTTG
GAGTATATTGACCACAAGCTCAGAGGAGTGCAGAACCCTGTAGCCCGCTGCATCATGTGCTGTTT
CAAGTGCTGCCTCTGGTGTCTGGAAAAATTTATCAAGTTCCTAAACCGCAATGCATACATCATGA
TCGCCATCTACGGGAAGAATTTCTGTGTCTCAGCCAAAAATGCGTTCATGCTACTCATGCGAAAC
ATTGTCAGGGTGGTCGTCCTGGACAAAGTCACAGACCTGCTGCTGTTCTTTGGGAAGCTGCTGGT
GGTCGGAGGCGTGGGGGTCCTGTCCTTCTTTTTTTTCTCCGGTCGCATCCCGGGGCTGGGTAAAG
ACTTTAAGAGCCCCCACCTCAACTATTACTGGCTGCCCATCATGACCTCCATCCTGGGGGCCTAT
GTCATCGCCAGCGGCTTCTTCAGCGTTTTCGGCATGTGTGTGGACACGCTCTTCCTCTGCTTCCT
GGAAGACCTGGAGCGGAACAACGGCTCCCTGGACCGGCCCTACTACATGTCCAAGAGCCTTCTAA
AGATTCTGGGCAAGAAGAACGAGGCGCCCCCGGACAACAAGAAGAGGAAGAAGTGACAGCTCCGG
CCCTGATCCAGGACTGCACCCCACCCCCACCGTCCAGCCATCCAACCTCACTTCGCCTTACAGGT
CTCCATTTTGTGGTAAAAAAAGGTTTTAGGCCAGGCGCCGTGGCTCACGCCTGTAATCCAACACT
TTGAGAGGCTGAGGCGGGCGGATCACCTGAGTCAGGAGTTCGAGACCAGCCTGGCCAACATGGTG
AAACCTCCGTCTCTATTAAAAATACAAAAATTAGCCGAGAGTGGTGGCATGCACCTGTCATCCCA
GCTACTCGGGAGGCTGAGGCAGGAGAATCGCTTGAACCCGGGAGGCAGAGGTTGCAGTGAGCCGA
GATCGCGCCACTGCACTCCAACCTGGGTGACAGACTCTGTCTCCAAAACAAAACAAACAAACAAA
AAGATTTTATTAAAGATATTTTGTTAACTC

FIGURE 10

RTRGRTRGGCEKVPINTSCNPTAHLVNSSCPGLMCVFQGYSSKGLIQRSVFNLQIYGVLGLFWTL
NWVLALGQCVLAGAFASFYWAFHKPQDIPTFPLISAFIRTLRYHTGSLAFGALILTLVQIARVIL
EYIDHKLRGVQNPVARCIMCCFKCCLWCLEKFIKFLNRNAYIMIAIYGKNFCVSAKNAFMLLMRN
IVRVVVLDKVTDLLLFFGKLLVVGGVGVLSFFFFSGRIPGLGKDFKSPHLNYYWLPIMTSILGAY
VIASGFFSVFGMCVDTLFLCFLEDLERNNGSLDRPYYMSKSLLKILGKKNEAPPDNKKRKK

Important features:

Transmembrane domains:

amino acids 57-80 (type II), 110-126, 215-231, 254-274

N-glycosylation sites.

amino acids 16-20, 27-31, 289-293

Hypothetical YBR002c family proteins.

amino acids 276-288

Ammonium transporters proteins.

amino acids 204-231

N-myristoylation sites.

amino acids 60-66, 78-84

Amidation site.

amino acids 306-310

FIGURE 11

GCCCCGCGCCCGGCGCCGGGCGCCCGAAGCCGGGAGCCACCGCCATGGGGGCCTGCCTGGGAGCCTGC
TCCCTGCTCAGCTGCGCGTCCTGCCTCTGCGGCTCTGCCCCCTGCATCCTGTGCAGCTGCTGCCCCGC
CAGCCGCAACTCCACCGTGAGCCGCCTCATCTTCACGTTCTTCCTCTTCCTGGGGGTGCTGGTGTCCA
TCATTATGCTGAGCCCGGGCGTGGAGAGTCAGCTCTACAAGCTGCCCTGGGTGTGTGAGGAGGGGGCC
GGGATCCCCACCGTCCTGCAGGGCCACATCGACTGTGGCTCCCTGCTTGGCTACCGCGCTGTCTACCG
CATGTGCTTCGCCACGGCGGCCTTCTTCTTCTTCTTTTTCACCCTGCTCATGCTCTGCGTGAGCAGCA
GCCGGGACCCCCGGGCTGCCATCCAGAATGGGTTTTGGTTCTTTAAGTTCCTGATCCTGGTGGGCCTC
ACCGTGGGTGCCTTCTACATCCCTGACGGCTCCTTCACCAACATCTGGTTCTACTTCGGCGTCGTGGG
CTCCTTCCTCTTCATCCTCATCCAGCTGGTGCTGCTCATCGACTTTGCGCACTCCTGGAACCAGCGGT
GGCTGGGCAAGGCCGAGGAGTGCGATTCCCGTGCCTGGTACGCAGGCCTCTTCTTCTTCACTCTCCTC
TTCTACTTGCTGTCGATCGCGGCCGTGGCGCTGATGTTCATGTACTACACTGAGCCCAGCGGCTGCCA
CGAGGGCAAGGTCTTCATCAGCCTCAACCTCACCTTCTGTGTCTGCGTGTCCATCGCTGCTGTCCTGC
CCAAGGTCCAGGACGCCCAGCCCAACTCGGGTCTGCTGCAGGCCTCGGTCATCACCCTCTACACCATG
TTTGTCACCTGGTCAGCCCTATCCAGTATCCCTGAACAGAAATGCAACCCCCATTTGCCAACCCAGCT
GGGCAACGAGACAGTTGTGGCAGGCCCCGAGGGCTATGAGACCCAGTGGTGGGATGCCCCGAGCATTG
TGGGCCTCATCATCTTCCTCCTGTGCACCCTCTTCATCAGTCTGCGCTCCTCAGACCACCGGCAGGTG
AACAGCCTGATGCAGACCGAGGAGTGCCCACCTATGCTAGACGCCACACAGCAGCAGCAGCAGCAGGT
GGCAGCCTGTGAGGGCCGGGCCTTTGACAACGAGCAGGACGGCGTCACCTACAGCTACTCCTTCTTCC
ACTTCTGCCTGGTGCTGGCCTCACTGCACGTCATGATGACGCTCACCAACTGGTACAAGCCCGGTGAG
ACCCGGAAGATGATCAGCACGTGGACCGCCGTGTGGGTGAAGATCTGTGCCAGCTGGGCAGGGCTGCT
CCTCTACCTGTGGACCCTGGTAGCCCCACTCCTCCTGCGCAACCGCGACTTCAGCTGAGGCAGCCTCA
CAGCCTGCCATCTGGTGCCTCCTGCCACCTGGTGCCTCTCGGCTCGGTGACAGCCAACCTGCCCCCTC
CCCACACCAATCAGCCAGGCTGAGCCCCCACCCCTGCCCCAGCTCCAGGACCTGCCCCTGAGCCGGGC
CTTCTAGTCGTAGTGCCTTCAGGGTCCGAGGAGCATCAGGCTCCTGCAGAGCCCCATCCCCCCGCCAC
ACCCACACGGTGGAGCTGCCTCTTCCTTCCCCTCCTCCCTGTTGCCCATACTCAGCATCTCGGATGAA
AGGGCTCCCTTGTCCTCAGGCTCCACGGGAGCGGGGCTGCTGGAGAGAGCGGGGAACTCCCACCACAG
TGGGGCATCCGGCACTGAAGCCCTGGTGTTCCTGGTCACGTCCCCCAGGGGACCCTGCCCCCTTCCTG
GACTTCGTGCCTTACTGAGTCTCTAAGACTTTTTCTAATAAACAAGCCAGTGCGTGTAAAAAAAA

FIGURE 12

MGACLGACSLLSCASCLCGSAPCILCSCCPASRNSTVSRLIFTFFLFLGVLVSIIMLSPGVESQL
YKLPWVCEEGAGIPTVLQGHIDCGSLLGYRAVYRMCFATAAFFFFFFTLLMLCVSSSRDPRAAIQ
NGFWFFKFLILVGLTVGAFYIPDGSFTNIWFYFGVVGSFLFILIQLVLLIDFAHSWNQRWLGKAE
ECDSRAWYAGLFFFTLLFYLLSIAAVALMFMYYTEPSGCHEGKVFISLNLTFCVCVSIAAVLPKV
QDAQPNSGLLQASVITLYTMFVTWSALSSIPEQKCNPHLPTQLGNETVVAGPEGYETQWWDAPSI
VGLIIFLLCTLFISLRSSDHRQVNSLMQTEECPPMLDATQQQQQQVAACEGRAFDNEQDGVTYSY
SFFHFCLVLASLHVMMTLTNWYKPGETRKMISTWTAVWVKICASWAGLLLYLWTLVAPLLLRNRD
FS

Signal sequence:
amino acids 1-20

Transmembrane domains:
amino acids 40-58, 101-116, 134-150, 162-178, 206-223, 240-257,
272-283, 324-340, 391-406, 428-444

FIGURE 13

CGGGCCAGCCTGGGGCGGCCGGCCAGGAACCACCCGTTAAGGTGTCTTCTCTTTAGGGATGGTGA
GGTTGGAAAAAGACTCCTGTAACCCTCCTCCAGGATGAACCACCTGCCAGAAGACATGGAGAACG
CTCTCACCGGGAGCCAGAGCTCCCATGCTTCTCTGCGCAATATCCATTCCATCAACCCCACACAA
CTCATGGCCAGGATTGAGTCCTATGAAGGAAGGGAAAAGAAAGGCATATCTGATGTCAGGAGGAC
TTTCTGTTTGTTTGTCACCTTTGACCTCTTATTCGTAACATTACTGTGGATAATAGAGTTAAATG
TGAATGGAGGCATTGAGAACACATTAGAGAAGGAGGTGATGCAGTATGACTACTATTCTTCATAT
TTTGATATATTTCTTCTGGCAGTTTTTCGATTTAAAGTGTTAATACTTGCATATGCTGTGTGCAG
ACTGCGCCATTGGTGGGCAATAGCGTTGACAACGGCAGTGACCAGTGCCTTTTTACTAGCAAAAG
TGATCCTTTCGAAGCTTTTCTCTCAAGGGGCTTTTGGCTATGTGCTGCCCATCATTTCATTCATC
CTTGCCTGGATTGAGACGTGGTTCCTGGATTTCAAAGTGTTACCTCAAGAAGCAGAAGAAGAAAA
CAGACTCCTGATAGTTCAGGATGCTTCAGAGAGGGCAGCACTTATACCTGGTGGTCTTTCTGATG
GTCAGTTTTATTCCCCTCCTGAATCCGAAGCAGGATCTGAAGAAGCTGAAGAAAAACAGGACAGT
GAGAAACCACTTTTAGAACTATGAGTACTACTTTTGTTAAATGTGAAAAACCCTCACAGAAAGTC
ATCGAGGCAAAAAGAGGCAGGCAGTGGAGTCTCCCTGTCGACAGTAAAGTTGAAATGGTGACGTC
CACTGCTGGCTTTATTGAACAGCTAATAAAGATTTATTTATTGTAATACCTCACAAACGTTGTAC
CATATCCATGCACATTTAGTTGCCTGCCTGTGGCTGGTAAGGTAATGTCATGATTCATCCTCTCT
TCAGTGAGACTGAGCCTGATGTGTTAACAAATAGGTGAAGAAAGTCTTGTGCTGTATTCCTAATC
AAAAGACTTAATATATTGAAGTAACACTTTTTTAGTAAGCAAGATACCTTTTTATTTCAATTCAC
AGAATGGAATTTTTTTGTTTCATGTCTCAGATTTATTTTGTATTTCTTTTTTAACACTCTACATT
TCCCTTGTTTTTTAACTCATGCACATGTGCTCTTTGTACAGTTTTAAAAAGTGTAATAAAATCTG
ACATGTCAATGTGGCTAGTTTTATTTTTCTTGTTTTGCATTATGTGTATGGCCTGAAGTGTTGGA
CTTGCAAAAGGGGAAGAAAGGAATTGCGAATACATGTAAAATGTCACCAGACATTTGTATTATTT
TTATCATGAAATCATGTTTTTCTCTGATTGTTCTGAAATGTTCTAAATACTCTTATTTGAATGC
ACAAAATGACTTAAACCATTCATATCATGTTTCCTTTGCGTTCAGCCAATTTCAATTAAAATGAA
CTAAATTAAAAA

FIGURE 14

MNHLPEDMENALTGSQSSHASLRNIHSINPTQLMARIESYEGREKKGISDVRRTFCLFVTFDLLF

VTLLWIIELNVNGGIENTLEKEVMQYDYYSSYFDIFLLAVFRFKVLILAYAVCRLRHWWAIALTT

AVTSAFLLAKVILSKLFSQGAFGYVLPIISFILAWIETWFLDFKVLPQEAEEENRLLIVQDASER

AALIPGGLSDGQFYSPPESEAGSEEAEEKQDSEKPLLEL

Important features of the protein:

Signal peptide:

amino acids 1-20

Transmembrane domains:

amino acids 54-72, 100-118, 130-144, 146-166

N-myristoylation sites.

amino acids 14-20, 78-84, 79-85, 202-208, 217-223

FIGURE 15

ACTCGAACGCAGTTGCTTCGGGACCCAGGACCCCCTCGGGCCCGACCCGCCAGGAAAGACTGAGG
CCGCGGCCTGCCCCGCCCGGCTCCCTGCGCCGCCGCCTCCCGGGACAGAAG<u>ATG</u>TGCTCCAG
GGTCCCTCTGCTGCTGCCGCTGCTCCTGCTACTGGCCCTGGGGCCTGGGGTGCAGGGCTGCCCAT
CCGGCTGCCAGTGCAGCCAGCCACAGACAGTCTTCTGCACTGCCCGCCAGGGGACCACGGTGCCC
CGAGACGTGCCACCCGACACGGTGGGGCTGTACGTCTTTGAGAACGGCATCACCATGCTCGACGC
AGGCAGCTTTGCCGGCCTGCCGGGCCTGCAGCTCCTGGACCTGTCACAGAACCAGATCGCCAGCC
TGCCCAGCGGGGTCTTCCAGCCACTCGCCAACCTCAGCAACCTGGACCTGACGGCCAACAGGCTG
CATGAAATCACCAATGAGACCTTCCGTGGCCTGCGGCGCCTCGAGCGCCTCTACCTGGGCAAGAA
CCGCATCCGCCACATCCAGCCTGGTGCCTTCGACACGCTCGACCGCCTCCTGGAGCTCAAGCTGC
AGGACAACGAGCTGCGGGCACTGCCCCCGCTGCGCCTGCCCCGCCTGCTGCTGCTGGACCTCAGC
CACAACAGCCTCCTGGCCCTGGAGCCCGGCATCCTGGACACTGCCAACGTGGAGGCGCTGCGGCT
GGCTGGTCTGGGGCTGCAGCAGCTGGACGAGGGGCTCTTCAGCCGCTTGCGCAACCTCCACGACC
TGGATGTGTCCGACAACCAGCTGGAGCGAGTGCCACCTGTGATCCGAGGCCTCCGGGGCCTGACG
CGCCTGCGGCTGGCCGGCAACACCCGCATTGCCCAGCTGCGGCCCGAGGACCTGGCCGGCCTGGC
TGCCCTGCAGGAGCTGGATGTGAGCAACCTAAGCCTGCAGGCCCTGCCTGGCGACCTCTCGGGCC
TCTTCCCCCGCCTGCGGCTGCTGGCAGCTGCCCGCAACCCCTTCAACTGCGTGTGCCCCCTGAGC
TGGTTTGGCCCCTGGGTGCGCGAGAGCCACGTCACACTGGCCAGCCCTGAGGAGACGCGCTGCCA
CTTCCCGCCCAAGAACGCTGGCCGGCTGCTCCTGGAGCTTGACTACGCCGACTTTGGCTGCCCAG
CCACCACCACCACAGCCACAGTGCCCACCACGAGGCCCGTGGTGCGGGAGCCCACAGCCTTGTCT
TCTAGCTTGGCTCCTACCTGGCTTAGCCCCACAGCGCCGGCCACTGAGGCCCCCAGCCCGCCCTC
CACTGCCCCACCGACTGTAGGGCCTGTCCCCCAGCCCCAGGACTGCCCACCGTCCACCTGCCTCA
ATGGGGGCACATGCCACCTGGGGACACGGCACCACCTGGCGTGCTTGTGCCCCGAAGGCTTCACG
GGCCTGTACTGTGAGAGCCAGATGGGGCAGGGGACACGGCCCAGCCCTACACCAGTCACGCCGAG
GCCACCACGGTCCCTGACCCTGGGCATCGAGCCGGTGAGCCCCACCTCCCTGCGCGTGGGGCTGC
AGCGCTACCTCCAGGGGAGCTCCGTGCAGCTCAGGAGCCTCCGTCTCACCTATCGCAACCTATCG
GGCCCTGATAAGCGGCTGGTGACGCTGCGACTGCCTGCCTCGCTCGCTGAGTACACGGTCACCCA
GCTGCGGCCCAACGCCACTTACTCCGTCTGTGTCATGCCTTTGGGGCCCGGGCGGGTGCCGGAGG
GCGAGGAGGCCTGCGGGGAGGCCCATACACCCCCAGCCGTCCACTCCAACCACGCCCCAGTCACC
CAGGCCCGCGAGGGCAACCTGCCGCTCCTCATTGCGCCCGCCCTGGCCGCGGTGCTCCTGGCCGC
GCTGGCTGCGGTGGGGGCAGCCTACTGTGTGCGGCGGGGGCGGGCCATGGCAGCAGCGGCTCAGG
ACAAAGGGCAGGTGGGGCCAGGGGCTGGGCCCCTGGAACTGGAGGGAGTGAAGGTCCCCTTGGAG
CCAGGCCCGAAGGCAACAGAGGGCGGTGGAGAGGCCCTGCCCAGCGGGTCTGAGTGTGAGGTGCC
ACTCATGGGCTTCCCAGGGCCTGGCCTCCAGTCACCCCTCCACGCAAAGCCCTACATC<u>TAA</u>GCCA
GAGAGAGACAGGGCAGCTGGGGCCGGGCTCTCAGCCAGTGAGATGGCCAGCCCCCTCCTGCTGCC
ACACCACGTAAGTTCTCAGTCCCAACCTCGGGGATGTGTGCAGACAGGGCTGTGTGACCACAGCT
GGGCCCTGTTCCCTCTGGACCTCGGTCTCCTCATCTGTGAGATGCTGTGGCCCAGCTGACGAGCC
CTAACGTCCCCAGAACCGAGTGCCTATGAGGACAGTGTCCGCCCTGCCCTCCGCAACGTGCAGTC
CCTGGGCACGGCGGGCCCTGCCATGTGCTGGTAACGCATGCCTGGGTCCTGCTGGGCTCTCCCAC
TCCAGGCGGACCCTGGGGGCCAGTGAAGGAAGCTCCCGGAAAGAGCAGAGGGAGAGCGGGTAGGC
GGCTGTGTGACTCTAGTCTTGGCCCCAGGAAGCGAAGGAACAAAAGAAACTGGAAAGGAAGATGC
TTTAGGAACATGTTTTGCTTTTTTAAAATATATATATTTATAAGAGATCCTTTCCCATTTATTCT
GGGAAGATGTTTTTCAAACTCAGAGACAAGGACTTTGGTTTTTGTAAGACAAACGATGATATGAA
GGCCTTTTGTAAGAAAAAATAAAAGATGAAGTGTGAAA

FIGURE 16

MCSRVPLLLPLLLLLALGPGVQGCPSGCQCSQPQTVFCTARQGTTVPRDVPPDTVGLYVFENGIT
MLDAGSFAGLPGLQLLDLSQNQIASLPSGVFQPLANLSNLDLTANRLHEITNETFRGLRRLERLY
LGKNRIRHIQPGAFDTLDRLLELKLQDNELRALPPLRLPRLLLLDLSHNSLLALEPGILDTANVE
ALRLAGLGLQQLDEGLFSRLRNLHDLDVSDNQLERVPPVIRGLRGLTRLRLAGNTRIAQLRPEDL
AGLAALQELDVSNLSLQALPGDLSGLFPRLRLLAAARNPFNCVCPLSWFGPWVRESHVTLASPEE
TRCHFPPKNAGRLLLELDYADFGCPATTTTATVPTTRPVVREPTALSSSLAPTWLSPTAPATEAP
SPPSTAPPTVGPVPQPQDCPPSTCLNGGTCHLGTRHHLACLCPEGFTGLYCESQMGQGTRPSPTP
VTPRPPRSLTLGIEPVSPTSLRVGLQRYLQGSSVQLRSLRLTYRNLSGPDKRLVTLRLPASLAEY
TVTQLRPNATYSVCVMPLGPGRVPEGEEACGEAHTPPAVHSNHAPVTQAREGNLPLLIAPALAAV
LLAALAAVGAAYCVRRGRAMAAAAQDKGQVGPGAGPLELEGVKVPLEPGPKATEGGGEALPSGSE
CEVPLMGFPGPGLQSPLHAKPYI

Important features:

Signal peptide:

amino acids 1-23

Transmembrane domain:

amino acids 579-599

EGF-like domain cysteine pattern signature.

amino acids 430-442

Leucine zipper pattern.

amino acids 197-219, 269-291

N-glycosylation sites.

amino acids 101-105, 117-121, 273-277, 500-504, 528-532

Tyrosine kinase phosphorylation sites.

amino acids 124-131, 337-345

N-myristoylation sites.

amino acids 23-29, 27-33, 70-76, 142-148, 187-193, 348-354, 594-600, 640-646

FIGURE 17

GCAGCGGCGAGGCGGCGGTGGTGGCTGAGTCCGTGGTGGCAGAGGCGAAGGCGACAGCTCATGCG
GGTCCGGATAGGGCTGACGCTGCTGCTGTGTGCGGTGCTGCTGAGCTTGGCCTCGGCGTCCTCGG
ATGAAGAAGGCAGCCAGGATGAATCCTTAGATTCCAAGACTACTTTGACATCAGATGAGTCAGTA
AAGGACCATACTACTGCAGGCAGAGTAGTTGCTGGTCAAATATTTCTTGATTCAGAAGAATCTGA
ATTAGAATCCTCTATTCAAGAAGAGGAAGACAGCCTCAAGAGCCAAGAGGGGGAAAGTGTCACAG
AAGATATCAGCTTTCTAGAGTCTCCAAATCCAGAAAACAAGGACTATGAAGAGCCAAAGAAAGTA
CGGAAACCAGCTTTGACCGCCATTGAAGGCACAGCACATGGGGAGCCCTGCCACTTCCCTTTTCT
TTTCCTAGATAAGGAGTATGATGAATGTACATCAGATGGGAGGGAAGATGGCAGACTGTGGTGTG
CTACAACCTATGACTACAAAGCAGATGAAAAGTGGGGCTTTTGTGAAACTGAAGAAGAGGCTGCT
AAGAGACGGCAGATGCAGGAAGCAGAAATGATGTATCAAACTGGAATGAAAATCCTTAATGGAAG
CAATAAGAAAAGCCAAAAAAGAGAAGCATATCGGTATCTCCAAAAGGCAGCAAGCATGAACCATA
CCAAAGCCCTGGAGAGAGTGTCATATGCTCTTTTATTTGGTGATTACTTGCCACAGAATATCCAG
GCAGCGAGAGAGATGTTTGAGAAGCTGACTGAGGAAGGCTCTCCCAAGGGACAGACTGCTCTTGG
CTTTCTGTATGCCTCTGGACTTGGTGTTAATTCAAGTCAGGCAAAGGCTCTTGTATATTATACAT
TTGGAGCTCTTGGGGGCAATCTAATAGCCCACATGGTTTTGGTAAGTAGACTTTAGTGGAAGGCT
AATAATATTAACATCAGAAGAATTTGTGGTTTATAGCGGCCACAACTTTTTCAGCTTTCATGATC
CAGATTTGCTTGTATTAAGACCAAATATTCAGTTGAACTTCCTTCAAATTCTTGTTAATGGATAT
AACACATGGAATCTACATGTAAATGAAAGTTGGTGGAGTCCACAATTTTTCTTTAAAATGATTAG
TTTGGCTGATTGCCCCTAAAAAGAGAGATCTGATAAATGGCTCTTTTTAAATTTTCTCTGAGTTG
GAATTGTCAGAATCATTTTTTACATTAGATTATCATAATTTTAAAAATTTTTCTTTAGTTTTTCA
AAATTTTGTAAATGGTGGCTATAGAAAAACAACATGAAATATTATACAATATTTTGCAACAATGC
CCTAAGAATTGTTAAAATTCATGGAGTTATTTGTGCAGAATGACTCCAGAGAGCTCTACTTTCTG
TTTTTTACTTTTCATGATTGGCTGTCTTCCCATTTATTCTGGTCATTTATTGCTAGTGACACTGT
GCCTGCTTCCAGTAGTCTCATTTTCCCTATTTTGCTAATTTGTTACTTTTTCTTTGCTAATTTGG
AAGATTAACTCATTTTTAATAAAATTATGTCTAAGATTAAAAAAAAAAAAAAAAAAAAAAAAAAA
AAAAAAAAAAAAAAAAAAAAAAAAAAAAAAAAAAAAAAAAAAAA

FIGURE 18

MRVRIGLTLLLCAVLLSLASASSDEEGSQDESLDSKTTLTSDESVKDHTTAGRVVAGQIFLDSEESEL
ESSIQEEEDSLKSQEGESVTEDISFLESPNPENKDYEEPKKVRKPALTAIEGTAHGEPCHFPFLFLDK
EYDECTSDGREDGRLWCATTYDYKADEKWGFCETEEEAAKRRQMQEAEMMYQTGMKILNGSNKKSQKR
EAYRYLQKAASMNHTKALERVSYALLFGDYLPQNIQAAREMFEKLTEEGSPKGQTALGFLYASGLGVN
SSQAKALVYYTFGALGGNLIAHMVLVSRL

Important features:

Signal peptide:

amino acids 1-21

N-glycosylation sites.

amino acids 195-199, 217-221, 272-276

Tyrosine kinase phosphorylation site.

amino acids 220-228

N-myristoylation sites.

amino acids 120-126, 253-259, 268-274, 270-274, 285-291, 289-295

Glycosaminoglycan attachment site.

amino acids 267-271

Microbodies C-terminal targeting signal.

amino acids 299-303

Type II fibronectin collagen-binding domain protein.

amino acids 127-169

Fructose-bisphosphate aldolase class-II protein.

amino acids 101-119

FIGURE 19

AATTCAGATTTTAAGCCCATTCTGCAGTGGAATTTCATGAACTAGCAAGAGGACACCATCTTCTT
GTATTATACAAGAAAGGAGTGTACCTATCACACACAGGGGGAAAAATGCTCTTTTGGGTGCTAGG
CCTCCTAATCCTCTGTGGTTTTCTGTGGACTCGTAAAGGAAAACTAAAGATTGAAGACATCACTG
ATAAGTACATTTTTATCACTGGATGTGACTCGGGCTTTGGAAACTTGGCAGCCAGAACTTTTGAT
AAAAAGGGATTTCATGTAATCGCTGCCTGTCTGACTGAATCAGGATCAACAGCTTTAAAGGCAGA
AACCTCAGAGAGACTTCGTACTGTGCTTCTGGATGTGACCGACCCAGAGAATGTCAAGAGGACTG
CCCAGTGGGTGAAGAACCAAGTTGGGGAGAAAGGTCTCTGGGGTCTGATCAATAATGCTGGTGTT
CCCGGCGTGCTGGCTCCCACTGACTGGCTGACACTAGAGGACTACAGAGAACCTATTGAAGTGAA
CCTGTTTGGACTCATCAGTGTGACACTAAATATGCTTCCTTTGGTCAAGAAAGCTCAAGGGAGAG
TTATTAATGTCTCCAGTGTTGGAGGTCGCCTTGCAATCGTTGGAGGGGGCTATACTCCATCCAAA
TATGCAGTGGAAGGTTTCAATGACAGCTTAAGACGGGACATGAAAGCTTTTGGTGTGCACGTCTC
ATGCATTGAACCAGGATTGTTCAAAACAAACTTGGCAGATCCAGTAAAGGTAATTGAAAAAAAC
TCGCCATTTGGGAGCAGCTGTCTCCAGACATCAAACAACAATATGGAGAAGGTTACATTGAAAAA
AGTCTAGACAAACTGAAAGGCAATAAATCCTATGTGAACATGGACCTCTCTCCGGTGGTAGAGTG
CATGGACCACGCTCTAACAAGTCTCTTCCCTAAGACTCATTATGCCGCTGGAAAAGATGCCAAAA
TTTTCTGGATACCTCTGTCTCACATGCCAGCAGCTTTGCAAGACTTTTTATTGTTGAAACAGAAA
GCAGAGCTGGCTAATCCCAAGGCAGTGTGACTCAGCTAACCACAAATGTCTCCTCCAGGCTATGA
AATTGGCCGATTTCAAGAACACATCTCCTTTTCAACCCCATTCCTTATCTGCTCCAACCTGGACT
CATTTAGATCGTGCTTATTTGGATTGCAAAAGGGAGTCCCACCATCGCTGGTGGTATCCCAGGGT
CCCTGCTCAAGTTTTCTTTGAAAAGGAGGGCTGGAATGGTACATCACATAGGCAAGTCCTGCCCT
GTATTTAGGCTTTGCCTGCTTGGTGTGATGTAAGGGAAATTGAAAGACTTGCCCATTCAAAATGA
TCTTTACCGTGGCCTGCCCCATGCTTATGGTCCCCAGCATTTACAGTAACTTGTGAATGTTAAGT
ATCATCTCTTATCTAAATATTAAAAGATAAGTCAACCCAAAAAAAAAAAAAAAAAAAAAAAAAAA
AAAAAAAAAAAAA

FIGURE 20

MLFWVLGLLILCGFLWTRKGKLKIEDITDKYIFITGCDSGFGNLAARTFDKKGFHVIAACLTESG
STALKAETSERLRTVLLDVTDPENVKRTAQWVKNQVGEKGLWGLINNAGVPGVLAPTDWLTLEDY
REPIEVNLFGLISVTLNMLPLVKKAQGRVINVSSVGGRLAIVGGGYTPSKYAVEGFNDSLRRDMK
AFGVHVSCIEPGLFKTNLADPVKVIEKKLAIWEQLSPDIKQQYGEGYIEKSLDKLKGNKSYVNMD
LSPVVECMDHALTSLFPKTHYAAGKDAKIFWIPLSHMPAALQDFLLLKQKAELANPKAV

Important features of the protein:

Signal peptide:

amino acids 1-17

Transmembrane domain:

amino acids 136-152

N-glycosylation sites.

amino acids 161-163, 187-190 and 253-256

Glycosaminoglycan attachment site.

amino acids 39-42

N-myristoylation sites.

amino acids 36-41, 42-47, 108-113, 166-171, 198-203 and 207-212

FIGURE 21

CTGAGGCGGCGGTAGC<u>ATG</u>GAGGGGGAGAGTACGTCGGCGGTGCTCTCGGGCTTTGTGCTCGGCG
CACTCGCTTTCCAGCACCTCAACACGGACTCGGACACGGAAGGTTTTCTTCTTGGGGAAGTAAAA
GGTGAAGCCAAGAACAGCATTACTGATTCCCAAATGGATGATGTTGAAGTTGTTTATACAATTGA
CATTCAGAAATATATTCCATGCTATCAGCTTTTTAGCTTTTATAATTCTTCAGGCGAAGTAAATG
AGCAAGCACTGAAGAAAATATTATCAAATGTCAAAAAGAATGTGGTAGGTTGGTACAAATTCCGT
CGTCATTCAGATCAGATCATGACGTTTAGAGAGAGGCTGCTTCACAAAAACTTGCAGGAGCATTT
TTCAAACCAAGACCTTGTTTTTCTGCTATTAACACCAAGTATAATAACAGAAAGCTGCTCTACTC
ATCGACTGGAACATTCCTTATATAAACCTCAAAAAGGACTTTTTCACAGGGTACCTTTAGTGGTT
GCCAATCTGGGCATGTCTGAACAACTGGGTTATAAAACTGTATCAGGTTCCTGTATGTCCACTGG
TTTTAGCCGAGCAGTACAAACACACAGCTCTAAATTTTTTGAAGAAGATGGATCCTTAAAGGAGG
TACATAAGATAAATGAAATGTATGCTTCATTACAAGAGGAATTAAAGAGTATATGCAAAAAAGTG
GAAGACAGTGAACAAGCAGTAGATAAACTAGTAAAGGATGTAAACAGATTAAAACGAGAAATTGA
GAAAAGGAGAGGAGCACAGATTCAGGCAGCAAGAGAGAAGAACATCCAAAAAGACCCTCAGGAGA
ACATTTTTCTTTGTCAGGCATTACGGACCTTTTTCCAAATTCTGAATTTCTTCATTCATGTGTT
ATGTCTTTAAAAAATAGACATGTTTCTAAAAGTAGCTGTAACTACAACCACCATCTCGATGTAGT
AGACAATCTGACCTTAATGGTAGAACACACTGACATTCCTGAAGCTAGTCCAGCTAGTACACCAC
AAATCATTAAGCATAAAGCCTTAGACTTAGATGACAGATGGCAATTCAAGAGATCTCGGTTGTTA
GATACACAAGACAAACGATCTAAAGCAAATACTGGTAGTAGTAACCAAGATAAAGCATCCAAAAT
GAGCAGCCCAGAAACAGATGAAGAAATTGAAAAGATGAAGGGTTTTGGTGAATATTCACGGTCTC
CTACATTT<u>TGA</u>TCCTTTTAACCTTACAAGGAGATTTTTTTATTTGGCTGATGGGTAAAGCCAAAC
ATTTCTATTGTTTTTACTATGTTGAGCTACTTGCAGTAAGTTCATTTGTTTTTACTATGTTCACC
TGTTTGCAGTAATACACAGATAACTCTTAGTGCATTTACTTCACAAAGTACTTTTTCAAACATCA
GATGCTTTTATTTCCAAACCTTTTTTTCACCTTTCACTAAGTTGTTGAGGGGAAGGCTTACACAG
ACACATTCTTTAGAATTGGAAAAGTGAGACCAGGCACAGTGGCTCACACCTGTAATCCCAGCACT
TAGGGAAGACAAGTCAGGAGGATTGATTGAAGCTAGGAGTTAGAGACCAGCCTGGGCAACGTATT
GAGACCATGTCTATTAAAAAATAAAATGGAAAAGCAAGAATAGCCTTATTTTCAAAATATGGAAA
GAAATTTATATGAAAATTTATCTGAGTCATTAAAATTCTCCTTAAGTGATACTTTTTTAGAAGTA
CATTATGGCTAGAGTTGCCAGATAAAATGCTGGATATCATGCAATAAATTTGCAAAACATCATCT
AAAATTTAAAAAAAAAAAAAAAAAAAAA

FIGURE 22

MEGESTSAVLSGFVLGALAFQHLNTDSDTEGFLLGEVKGEAKNSITDSQMDDVEVVYTIDIQKYI
PCYQLFSFYNSSGEVNEQALKKILSNVKKNVVGWYKFRRHSDQIMTFRERLLHKNLQEHFSNQDL
VFLLLTPSIITESCSTHRLEHSLYKPQKGLFHRVPLVVANLGMSEQLGYKTVSGSCMSTGFSRAV
QTHSSKFFEEDGSLKEVHKINEMYASLQEELKSICKKVEDSEQAVDKLVKDVNRLKREIEKRRGA
QIQAAREKNIQKDPQENIFLCQALRTFFPNSEFLHSCVMSLKNRHVSKSSCNYNHHLDVVDNLTL
MVEHTDIPEASPASTPQIIKHKALDLDDRWQFKRSRLLDTQDKRSKANTGSSNQDKASKMSSPET
DEEIEKMKGFGEYSRSPTF

Important features:

Signal peptide:

amino acids 1-19

N-glycosylation sites.

amino acids 75-79, 322-326

N-myristoylation site.

amino acids 184-154

Growth factor and cytokines receptors family.

amino acids 134-150

FIGURE 23

GGCACAGCCGCGCGGCGGAGGGCAGAGTCAGCCGAGCCGAGTCCAGCCGGACGAGCGGACCAGCGCAGGGCAGCCCAA
GCAGCGCGCAGCGAACGCCCGCCGCCGCCCACACCCTCTGCGGTCCCCGCGGCGCCTGCCACCCTTCCCTCCTTCCCC
GCGTCCCCGCCTCGCCGGCCAGTCAGCTTGCCGGGTTCGCTGCCCCGCGAAACCCCGAGGTCACCAGCCCGCGCCTCT
GCTTCCCTGGGCCGCGCGCCGCCTCCACGCCCTCCTTCTCCCCTGGCCCGGCGCCTGGCACCGGGGACCGTTGCCTGA
CGCGAGGCCCAGCTCTACTTTTCGCCCCGCGTCTCCTCCGCCTGCTCGCCTCTTCCACCAACTCCAACTCCTTCTCCC
TCCAGCTCCACTCGCTAGTCCCCGACTCCGCCAGCCCTCGGCCCGCTGCCGTAGCGCCGCTTCCCGTCCGGTCCCAAA
GGTGGGAACGCGTCCGCCCCGGCCCGCACCATGGCACGGTTCGGCTTGCCCGCGCTTCTCTGCACCCTGGCAGTGCTC
AGCGCCGCGCTGCTGGCTGCCGAGCTCAAGTCGAAAAGTTGCTCGGAAGTGCGACGTCTTTACGTGTCCAAAGGCTTC
AACAAGAACGATGCCCCCCTCCACGAGATCAACGGTGATCATTTGAAGATCTGTCCCCAGGGTTCTACCTGCTGCTCT
CAAGAGATGGAGGAGAAGTACAGCCTGCAAAGTAAAGATGATTTCAAAAGTGTGGTCAGCGAACAGTGCAATCATTTG
CAAGCTGTCTTTGCTTCACGTTACAAGAAGTTTGATGAATTCTTCAAAGAACTACTTGAAAATGCAGAGAAATCCCTG
AATGATATGTTTGTGAAGACATATGGCCATTTATACATGCAAAATTCTGAGCTATTTAAAGATCTCTTCGTAGAGTTG
AAACGTTACTACGTGGTGGGAAATGTGAACCTGGAAGAAATGCTAAATGACTTCTGGGCTCGCCTCCTGGAGCGGATG
TTCCGCCTGGTGAACTCCCAGTACCACTTTACAGATGAGTATCTGGAATGTGTGAGCAAGTATACGGAGCAGCTGAAG
CCCTTCGGAGATGTCCCTCGCAAATTGAAGCTCCAGGTTACTCGTGCTTTTGTAGCAGCCCGTACTTTCGCTCAAGGC
TTAGCGGTTGCGGGAGATGTCGTGAGCAAGGTCTCCGTGGTAAACCCCACAGCCCAGTGTACCCATGCCCTGTTGAAG
ATGATCTACTGCTCCCACTGCCGGGGTCTCGTGACTGTGAAGCCATGTTACAACTACTGCTCAAACATCATGAGAGGC
TGTTTGGCCAACCAAGGGGATCTCGATTTTGAATGGAACAATTTCATAGATGCTATGCTGATGGTGGCAGAGAGGCTA
GAGGGTCCTTTCAACATTGAATCGGTCATGGATCCCATCGATGTGAAGATTTCTGATGCTATTATGAACATGCAGGAT
AATAGTGTTCAAGTGTCTCAGAAGGTTTTCCAGGGATGTGGACCCCCCAAGCCCCTCCCAGCTGGACGAATTTCTCGT
TCCATCTCTGAAAGTGCCTTCAGTGCTCGCTTCAGACCACATCACCCCGAGGAACGCCCAACCACAGCAGCTGGCACT
AGTTTGGACCGACTGGTTACTGATGTCAAGGAGAAACTGAAACAGGCCAAGAAATTCTGGTCCTCCCTTCCGAGCAAC
GTTTGCAACGATGAGAGGATGGCTGCAGGAAACGGCAATGAGGATGACTGTTGGAATGGGAAAGGCAAAAGCAGGTAC
CTGTTTGCAGTGACAGGAAATGGATTAGCCAACCAGGGCAACAACCCAGAGGTCCAGGTTGACACCAGCAAACCAGAC
ATACTGATCCTTCGTCAAATCATGGCTCTTCGAGTGATGACCAGCAAGATGAAGAATGCATACAATGGGAACGACGTG
GACTTCTTTGATATCAGTGATGAAAGTAGTGGAGAAGGAAGTGGAAGTGGCTGTGAGTATCAGCAGTGCCCTTCAGAG
TTTGACTACAATGCCACTGACCATGCTGGGAAGAGTGCCAATGAGAAAGCCGACAGTGCTGGTGTCCGTCCTGGGGCA
CAGGCCTACCTCCTCACTGTCTTCTGCATCTTGTTCCTGGTTATGCAGAGAGAGTGGAGATAATTCTCAAACTCTGAG
AAAAAGTGTTCATCAAAAAGTTAAAAGGCACCAGTTATCACTTTTCTACCATCCTAGTGACTTTGCTTTTTAAATGAA
TGGACAACAATGTACAGTTTTTACTATGTGGCCACTGGTTTAAGAAGTGCTGACTTTGTTTTCTCATTCAGTTTTGGG
AGGAAAAGGGACTGTGCATTGAGTTGGTTCCTGCTCCCCCAAACCATGTTAAACGTGGCTAACAGTGTAGGTACAGAA
CTATAGTTAGTTGTGCATTTGTGATTTTATCACTCTATTATTTGTTTGTATGTTTTTTTCTCATTTCGTTTGTGGGTT
TTTTTTTCCAACTGTGATCTCGCCTTGTTTCTTACAAGCAAACCAGGGTCCCTTCTTGGCACGTAACATGTACGTATT
TCTGAAATATTAAATAGCTGTACAGAAGCAGGTTTTATTTATCATGTTATCTTATTAAAAGAAAAAGCCCAAAAAGC

FIGURE 24

MARFGLPALLCTLAVLSAALLAAELKSKSCSEVRRLYVSKGFNKNDAPLHEINGDHLKICPQGST
CCSQEMEEKYSLQSKDDFKSVVSEQCNHLQAVFASRYKKFDEFFKELLENAEKSLNDMFVKTYGH
LYMQNSELFKDLFVELKRYYVVGNVNLEEMLNDFWARLLERMFRLVNSQYHFTDEYLECVSKYTE
QLKPFGDVPRKLKLQVTRAFVAARTFAQGLAVAGDVVSKVSVVNPTAQCTHALLKMIYCSHCRGL
VTVKPCYNYCSNIMRGCLANQGDLDFEWNNFIDAMLMVAERLEGPFNIESVMDPIDVKISDAIMN
MQDNSVQVSQKVFQGCGPPKPLPAGRISRSISESAFSARFRPHHPEERPTTAAGTSLDRLVTDVK
EKLKQAKKFWSSLPSNVCNDERMAAGNGNEDDCWNGKGKSRYLFAVTGNGLANQGNNPEVQVDTS
KPDILILRQIMALRVMTSKMKNAYNGNDVDFFDISDESSGEGSGSGCEYQQCPSEFDYNATDHAG
KSANEKADSAGVRPGAQAYLLTVFCILFLVMQREWR

Important features:

Signal peptide:

amino acids 1-22

ATP/GTP-binding site motif A (P-loop).

amino acids 515-524

N-glycosylation site.

amino acids 514-518

Glycosaminoglycan attachment sites.

amino acids 494-498, 498-502

N-myristoylation sites.

amino acids 63-69, 224-230, 276-282, 438-444, 497-503, 531-537

Glypicans proteins.

amino acids 54-75, 105-157, 238-280, 309-346, 423-460, 468-506

FIGURE 25

CTCGCCCTCAAATGGGAACGCTGGCCTGGGACTAAAGCATAGACCACCAGGCTGAGTATCCTGAC
CTGAGTCATCCCCAGGGATCAGGAGCCTCCAGCAGGGAACCTTCCATTATATTCTTCAAGCAACT
TACAGCTGCACCGACAGTTGCGATGAAAGTTCTAATCTCTTCCCTCCTCCTGTTGCTGCCACTAA
TGCTGATGTCCATGGTCTCTAGCAGCCTGAATCCAGGGGTCGCCAGAGGCCACAGGGACCGAGGC
CAGGCTTCTAGGAGATGGCTCCAGGAAGGCGGCCAAGAATGTGAGTGCAAAGATTGGTTCCTGAG
AGCCCCGAGAAGAAAATTCATGACAGTGTCTGGGCTGCCAAAGAAGCAGTGCCCCTGTGATCATT
TCAAGGGCAATGTGAAGAAAACAAGACACCAAAGGCACCACAGAAAGCCAAACAAGCATTCCAGA
GCCTGCCAGCAATTTCTCAAACAATGTCAGCTAAGAAGCTTTGCTCTGCCTTTGTAGGAGCTCTG
AGCGCCCACTCTTCCAATTAAACATTCTCAGCCAAGAAGACAGTGAGCACACCTACCAGACACTC
TTCTTCTCCCACCTCACTCTCCCACTGTACCCACCCCTAAATCATTCCAGTGCTCTCAAAAAGCA
TGTTTTTCAAGATCATTTTGTTTGTTGCTCTCTCTAGTGTCTTCTTCTCTCGTCAGTCTTAGCCT
GTGCCCTCCCCTTACCCAGGCTTAGGCTTAATTACCTGAAAGATTCCAGGAAACTGTAGCTTCCT
AGCTAGTGTCATTTAACCTTAAATGCAATCAGGAAAGTAGCAAACAGAAGTCAATAAATATTTTT
AAATGTCAAAAAAAAAAAAAAAA

FIGURE 26

MKVLISSLLLLLPLMLMSMVSSSLNPGVARGHRDRGQASRRWLQEGGQECECKDWFLRAPRRKFM
TVSGLPKKQCPCDHFKGNVKKTRHQRHHRKPNKHSRACQQFLKQCQLRSFALPL

Important features:

Signal peptide:

amino acids 1-22

N-myristoylation sites.

amino acids 27-33, 46-52

FIGURE 27

GGACGCCAGCGCCTGCAGAGGCTGAGCAGGGAAAAAGCCAGTGCCCCAGCGGAAGCACAGCTCAG
AGCTGGTCTGCCATGGACATCCTGGTCCCACTCCTGCAGCTGCTGGTGCTGCTTCTTACCCTGCC
CCTGCACCTCATGGCTCTGCTGGGCTGCTGGCAGCCCCTGTGCAAAAGCTACTTCCCCTACCTGA
TGGCCGTGCTGACTCCCAAGAGCAACCGCAAGATGGAGAGCAAGAAACGGGAGCTCTTCAGCCAG
ATAAAGGGGCTTACAGGAGCCTCCGGGAAAGTGGCCCTACTGGAGCTGGGCTGCGGAACCGGAGC
CAACTTTCAGTTCTACCCACCGGGCTGCAGGGTCACCTGCCTAGACCCAAATCCCCACTTTGAGA
AGTTCCTGACAAAGAGCATGGCTGAGAACAGGCACCTCCAATATGAGCGGTTTGTGGTGGCTCCT
GGAGAGGACATGAGACAGCTGGCTGATGGCTCCATGGATGTGGTGGTCTGCACTCTGGTGCTGTG
CTCTGTGCAGAGCCCAAGGAAGGTCCTGCAGGAGGTCCGGAGAGTACTGAGACCGGGAGGTGTGC
TCTTTTTCTGGGAGCATGTGGCAGAACCATATGGAAGCTGGGCCTTCATGTGGCAGCAAGTTTTC
GAGCCCACCTGGAAACACATTGGGGATGGCTGCTGCCTCACCAGAGAGACCTGGAAGGATCTTGA
GAACGCCCAGTTCTCCGAAATCCAAATGGAACGACAGCCCCCTCCCTTGAAGTGGCTACCTGTTG
GGCCCCACATCATGGGAAAGGCTGTCAAACAATCTTTCCCAAGCTCCAAGGCACTCATTTGCTCC
TTCCCCAGCCTCCAATTAGAACAAGCCACCCACCAGCCTATCTATCTTCCACTGAGAGGGACCTA
GCAGAATGAGAGAAGACATTCATGTACCACCTACTAGTCCCTCTCTCCCCAACCTCTGCCAGGGC
AATCTCTAACTTCAATCCCGCCTTCGACAGTGAAAAAGCTCTACTTCTACGCTGACCCAGGGAGG
AAACACTAGGACCCTGTTGTATCCTCAACTGCAAGTTTCTGGACTAGTCTCCCAACGTTTGCCTC
CCAATGTTGTCCCTTTCCTTCGTTCCCATGGTAAAGCTCCTCTCGCTTTCCTCCTGAGGCTACAC
CCATGCGTCTCTAGGAACTGGTCACAAAAGTCATGGTGCCTGCATCCCTGCCAAGCCCCCCTGAC
CCTCTCTCCCCACTACCACCTTCTTCCTGAGCTGGGGGCACCAGGGAGAATCAGAGATGCTGGGG
ATGCCAGAGCAAGACTCAAAGAGGCAGAGGTTTTGTTCTCAAATATTTTTTAATAAATAGACGAA
ACCACG

FIGURE 28

MDILVPLLQLLVLLLTLPLHLMALLGCWQPLCKSYFPYLMAVLTPKSNRKMESKKRELFSQIKGL
TGASGKVALLELGCGTGANFQFYPPGCRVTCLDPNPHFEKFLTKSMAENRHLQYERFVVAPGEDM
RQLADGSMDVVVCTLVLCSVQSPRKVLQEVRRVLRPGGVLFFWEHVAEPYGSWAFMWQQVFEPTW
KHIGDGCCLTRETWKDLENAQFSEIQMERQPPPLKWLPVGPHIMGKAVKQSFPSSKALICSFPSL
QLEQATHQPIYLPLRGT

Important features:

Signal peptide:

amino acids 1-23

Leucine zipper pattern.

amino acids 10-32

N-myristoylation sites.

amino acids 64-70, 78-84, 80-86, 91-97, 201-207

FIGURE 29

CAATGTTTGCCTATCCACCTCCCCCAAGCCCCTTTACCT<u>ATG</u>CTGCTGCTAACGCTGCTGCTGCT
GCTGCTGCTGCTTAAAGGCTCATGCTTGGAGTGGGGACTGGTCGGTGCCCAGAAAGTCTCTTCTG
CCACTGACGCCCCCATCAGGGATTGGGCCTTCTTTCCCCCTTCCTTTCTGTGTCTCCTGCCTCAT
CGGCCTGCCATGACCTGCAGCCAAGCCCAGCCCCGTGGGGAAGGGGAGAAAGTGGGGGATGGC<u>TA</u>
<u>A</u>GAAAGCTGGGAGATAGGGAACAGAAGAGGGTAGTGGGTGGGCTAGGGGGGCTGCCTTATTTAAA
GTGGTTGTTTATGATTCTTATACTAATTTATACAAAGATATTAAGGCCCTGTTCATTAAGAAATT
GTTCCCTTCCCCTGTGTTCAATGTTTGTAAAGATTGTTCTGTGTAAATATGTCTTTATAATAAAC
AGTTAAAAGCTGAAAAAAAAAAAAAAAAAAAAAAAA

FIGURE 30

MLLLTLLLLLLLLKGSCLEWGLVGAQKVSSATDAPIRDWAFFPPSFLCLLPHRPAMTCSQAQPRG
EGEKVGDG

Important features:

Signal peptide:

amino acids 1-15

Growth factor and cytokines receptors family:

amino acids 3-18

FIGURE 31

GTTTGAATTCCTTCAACTATACCCACAGTCCAAAAGCAGACTCACTGTGTCCCAGGCTACCAGTT
CCTCCAAGCAAGTCATTTCCCTTATTTAACCGATGTGTCCCTCAAACACCTGAGTGCTACTCCCT
ATTTGCATCTGTTTTGATAAATGATGTTGACACCCTCCACCGAATTCTAAGTGGAATCATGTCGG
GAAGAGATACAATCCTTGGCCTGTGTATCCTCGCATTAGCCTTGTCTTTGGCCATGATGTTTACC
TTCAGATTCATCACCACCCTTCTGGTTCACATTTTCATTTCATTGGTTATTTTGGGATTGTTGTT
TGTCTGCGGTGTTTTATGGTGGCTGTATTATGACTATACCAACGACCTCAGCATAGAATTGGACA
CAGAAAGGGAAAATATGAAGTGCGTGCTGGGGTTTGCTATCGTATCCACAGGCATCACGGCAGTG
CTGCTCGTCTTGATTTTTGTTCTCAGAAAGAGAATAAAATTGACAGTTGAGCTTTTCCAAATCAC
AAATAAAGCCATCAGCAGTGCTCCCTTCCTGCTGTTCCAGCCACTGTGGACATTTGCCATCCTCA
TTTTCTTCTGGGTCCTCTGGGTGGCTGTGCTGCTGAGCCTGGGAACTGCAGGAGCTGCCCAGGTT
ATGGAAGGCGGCCAAGTGGAATATAAGCCCCTTTCGGGCATTCGGTACATGTGGTCGTACCATTT
AATTGGCCTCATCTGGACTAGTGAATTCATCCTTGCGTGCCAGCAAATGACTATAGCTGGGGCAG
TGGTTACTTGTTATTTCAACAGAAGTAAAAATGATCCTCCTGATCATCCCATCCTTTCGTCTCTC
TCCATTCTCTTCTTCTACCATCAAGGAACCGTTGTGAAAGGGTCATTTTTAATCTCTGTGGTGAG
GATTCCGAGAATCATTGTCATGTACATGCAAAACGCACTGAAAGAACAGCAGCATGGTGCATTGT
CCAGGTACCTGTTCCGATGCTGCTACTGCTGTTTCTGGTGTCTTGACAAATACCTGCTCCATCTC
AACCAGAATGCATATACTACAACTGCTATTAATGGGACAGATTTCTGTACATCAGCAAAAGATGC
ATTCAAAATCTTGTCCAAGAACTCAAGTCACTTTACATCTATTAACTGCTTTGGAGACTTCATAA
TTTTTCTAGGAAAGGTGTTAGTGGTGTGTTTCACTGTTTTTGGAGGACTCATGGCTTTTAACTAC
AATCGGGCATTCCAGGTGTGGGCAGTCCCTCTGTTATTGGTAGCTTTTTTTGCCTACTTAGTAGC
CCATAGTTTTTTATCTGTGTTTGAAACTGTGCTGGATGCACTTTTCCTGTGTTTTGCTGTTGATC
TGGAAACAAATGATGGATCGTCAGAAAAGCCCTACTTTATGGATCAAGAATTTCTGAGTTTCGTA
AAAAGGAGCAACAAATTAAACAATGCAAGGGCACAGCAGGACAAGCACTCATTAAGGAATGAGGA
GGGAACAGAACTCCAGGCCATTGTGAGATAGATACCCATTTAGGTATCTGTACCTGGAAAACATT
TCCTTCTAAGAGCCATTTACAGAATAGAAGATGAGACCACTAGAGAAAAGTTAGTGAATTTTTTT
TTAAAAGACCTAATAAACCCTATTCTTCCTCAAAA

FIGURE 32

MSGRDTILGLCILALALSLAMMFTFRFITTLLVHIFISLVILGLLFVCGVLWWLYYDYTNDLSIE
LDTERENMKCVLGFAIVSTGITAVLLVLIFVLRKRIKLTVELFQITNKAISSAPFLLFQPLWTFA
ILIFFWVLWVAVLLSLGTAGAAQVMEGGQVEYKPLSGIRYMWSYHLIGLIWTSEFILACQQMTIA
GAVVTCYFNRSKNDPPDHPILSSLSILFFYHQGTVVKGSFLISVVRIPRIIVMYMQNALKEQQHG
ALSRYLFRCCYCCFWCLDKYLLHLNQNAYTTTAINGTDFCTSAKDAFKILSKNSSHFTSINCFGD
FIIFLGKVLVVCFTVFGGLMAFNYNRAFQVWAVPLLLVAFFAYLVAHSFLSVFETVLDALFLCFA
VDLETNDGSSEKPYFMDQEFLSFVKRSNKLNNARAQQDKHSLRNEEGTELQAIVR

Important features:

Signal peptide:

amino acids 1-20

Putative transmembrane domains:

amino acids 35-54, 75-97, 126-146, 185-204, 333-350, 352-371

N-glycosylation sites.

amino acids 204-208, 295-299, 313-317

N-myristoylation sites.

amino acids 147-153, 178-184, 196-202, 296-275, 342-348

FIGURE 33

GTTCGATTAGCTCCTCTGAGAAGAAGAGAAAAGGTTCTTGGACCTCTCCCTGTTTCTTCCTTAGA
ATAATTTGTATGGGATTTGTGATGCAGGAAAGCCTAAGGGAAAAAGAATATTCATTCTGTGTGGT
GAAAATTTTTTGAAAAAAAAATTGCCTTCTTCAAACAAGGGTGTCATTCTGATATTTATGAGGAC
TGTTGTTCTCACTATGAAGGCATCTGTTATTGAAATGTTCCTTGTTTTGCTGGTGACTGGAGTAC
ATTCAAACAAAGAAACGGCAAAGAAGATTAAAAGGCCCAAGTTCACTGTGCCTCAGATCAACTGC
GATGTCAAAGCCGGAAAGATCATCGATCCTGAGTTCATTGTGAAATGTCCAGCAGGATGCCAAGA
CCCCAAATACCATGTTTATGGCACTGACGTGTATGCATCCTACTCCAGTGTGTGTGGCGCTGCCG
TACACAGTGGTGTGCTTGATAATTCAGGAGGGAAAATACTTGTTCGGAAGGTTGCTGGACAGTCT
GGTTACAAAGGGAGTTATTCCAACGGTGTCCAATCGTTATCCCTACCACGATGGAGAGAATCCTT
TATCGTCTTAGAAAGTAAACCCAAAAAGGGTGTAACCTACCCATCAGCTCTTACATACTCATCAT
CGAAAAGTCCAGCTGCCCAAGCAGGTGAGACCACAAAAGCCTATCAGAGGCCACCTATTCCAGGG
ACAACTGCACAGCCGGTCACTCTGATGCAGCTTCTGGCTGTCACTGTAGCTGTGGCCACCCCCAC
CACCTTGCCAAGGCCATCCCCTTCTGCTGCTTCTACCACCAGCATCCCCAGACCACAATCAGTGG
GCCACAGGAGCCAGGAGATGGATCTCTGGTCCACTGCCACCTACACAAGCAGCCAAAACAGGCCC
AGAGCTGATCCAGGTATCCAAAGGCAAGATCCTTCAGGAGCTGCCTTCCAGAAACCTGTTGGAGC
GGATGTCAGCCTGGGACTTGTTCCAAAAGAAGAATTGAGCACACAGTCTTTGGAGCCAGTATCCC
TGGGAGATCCAAACTGCAAAATTGACTTGTCGTTTTTAATTGATGGGAGCACCAGCATTGGCAAA
CGGCGATTCCGAATCCAGAAGCAGCTCCTGGCTGATGTTGCCCAAGCTCTTGACATTGGCCCTGC
CGGTCCACTGATGGGTGTTGTCCAGTATGGAGACAACCCTGCTACTCACTTTAACCTCAAGACAC
ACACGAATTCTCGAGATCTGAAGACAGCCATAGAGAAAATTACTCAGAGAGGAGGACTTTCTAAT
GTAGGTCGGGCCATCTCCTTTGTGACCAAGAACTTCTTTTCCAAAGCCAATGGAAACAGAAGCGG
GGCTCCCAATGTGGTGGTGGTGATGGTGGATGGCTGGCCCACGGACAAAGTGGAGGAGGCTTCAA
GACTTGCGAGAGAGTCAGGAATCAACATTTTCTTCATCACCATTGAAGGTGCTGCTGAAAATGAG
AAGCAGTATGTGGTGGAGCCCAACTTTGCAAACAAGGCCGTGTGCAGAACAAACGGCTTCTACTC
GCTCCACGTGCAGAGCTGGTTTGGCCTCCACAAGACCCTGCAGCCTCTGGTGAAGCGGGTCTGCG
ACACTGACCGCCTGGCCTGCAGCAAGACCTGCTTGAACTCGGCTGACATTGGCTTCGTCATCGAC
GGCTCCAGCAGTGTGGGGACGGGCAACTTCCGCACCGTCCTCCAGTTTGTGACCAACCTCACCAA
AGAGTTTGAGATTTCCGACACGGACACGCGCATCGGGGCCGTGCAGTACACCTACGAACAGCGGC
TGGAGTTTGGGTTCGACAAGTACAGCAGCAAGCCTGACATCCTCAACGCCATCAAGAGGGTGGGC
TACTGGAGTGGTGGCACCAGCACGGGGGCTGCCATCAACTTCGCCCTGGAGCAGCTCTTCAAGAA
GTCCAAGCCCAACAAGAGGAAGTTAATGATCCTCATCACCGACGGGAGGTCCTACGACGACGTCC
GGATCCCAGCCATGGCTGCCCATCTGAAGGGAGTGATCACCTATGCGATAGGCGTTGCCTGGGCT
GCCCAAGAGGAGCTAGAAGTCATTGCCACTCACCCCGCCAGAGACCACTCCTTCTTTGTGGACGA
GTTTGACAACCTCCATCAGTATGTCCCCAGGATCATCCAGAACATTTGTACAGAGTTCAACTCAC
AGCCTCGGAACTGAATTCAGAGCAGGCAGAGCACCAGCAAGTGCTGCTTTACTAACTGACGTGTT
GGACCACCCCACCGCTTAATGGGGCACGCACGGTGCATCAAGTCTTGGGCAGGGCATGGAGAAAC
AAATGTCTTGTTATTATTCTTTGCCATCATGCTTTTTCATATTCCAAAACTTGGAGTTACAAAGA
TGATCACAAACGTATAGAATGAGCCAAAAGGCTACATCATGTTGAGGGTGCTGGAGATTTTACAT
TTTGACAATTGTTTTCAAAATAAATGTTCGGAATACAGTGCAGCCCTTACGACAGGCTTACGTAG
AGCTTTTGTGAGATTTTTAAGTTGTTATTTCTGATTTGAACTCTGTAACCCTCAGCAAGTTTCAT
TTTTGTCATGACAATGTAGGAATTGCTGAATTAAATGTTTAGAAGGATGAAAAATAAAAAAAAAA
AAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAG

FIGURE 34

MRTVVLTMKASVIEMFLVLLVTGVHSNKETAKKIKRPKFTVPQINCDVKAGKIIDPEFIVKCPAG
CQDPKYHVYGTDVYASYSSVCGAAVHSGVLDNSGGKILVRKVAGQSGYKGSYSNGVQSLSLPRWR
ESFIVLESKPKKGVTYPSALTYSSSKSPAAQAGETTKAYQRPPIPGTTAQPVTLMQLLAVTVAVA
TPTTLPRPSPSAASTTSIPRPQSVGHRSQEMDLWSTATYTSSQNRPRADPGIQRQDPSGAAFQKP
VGADVSLGLVPKEELSTQSLEPVSLGDPNCKIDLSFLIDGSTSIGKRRFRIQKQLLADVAQALDI
GPAGPLMGVVQYGDNPATHFNLKTHTNSRDLKTAIEKITQRGGLSNVGRAISFVTKNFFSKANGN
RSGAPNVVVVMVDGWPTDKVEEASRLARESGINIFFITIEGAAENEKQYVVEPNFANKAVCRTNG
FYSLHVQSWFGLHKTLQPLVKRVCDTDRLACSKTCLNSADIGFVIDGSSSVGTGNFRTVLQFVTN
LTKEFEISDTDTRIGAVQYTYEQRLEFGFDKYSSKPDILNAIKRVGYWSGGTSTGAAINFALEQL
FKKSKPNKRKLMILITDGRSYDDVRIPAMAAHLKGVITYAIGVAWAAQEELEVIATHPARDHSFF
VDEFDNLHQYVPRIIQNICTEFNSQPRN

Important features:

Signal peptide:

amino acids 1-26

Transmembrane domain:

amino acids 181-200

N-glycosylation sites.

amino acids 390-394, 520-524

N-myristoylation sites.

amino acids 23-29, 93-99, 115-121, 262-268, 367-373, 389-395, 431-437, 466-472, 509-515, 570-576, 571-577, 575-581, 627-633

Amidation site.

amino acids 304-308

FIGURE 35

CCGAGCACAGGAGATTGCCTGCGTTTAGGAGGTGGCTGCGTTGTGGGAAAAGCTATCAAGGAAGAAATTGC
CAAACCATGTCTTTTTTTCTGTTTTCAGAGTAGTTCACAACAGATCTGAGTGTTTTAATTAAGCATGGAAT
ACAGAAAACAACAAAAAACTTAAGCTTTAATTTCATCTGGAATTCCACAGTTTTCTTAGCTCCCTGGACCC
GGTTGACCTGTTGGCTCTTCCCGCTGGCTGCTCTATCACGTGGTGCTCTCCGACTACTCACCCCGAGTGTA
AAGAACCTTCGGCTCGCGTGCTTCTGAGCTGCTGTGGATGGCCTCGGCTCTCTGGACTGTCCTTCCGAGTA
GGATGTCACTGAGATCCCTCAAATGGAGCCTCCTGCTGCTGTCACTCCTGAGTTTCTTTGTGATGTGGTAC
CTCAGCCTTCCCCACTACAATGTGATAGAACGCGTGAACTGGATGTACTTCTATGAGTATGAGCCGATTTA
CAGACAAGACTTTCACTTCACACTTCGAGAGCATTCAAACTGCTCTCATCAAAATCCATTTCTGGTCATTC
TGGTGACCTCCCACCCTTCAGATGTGAAAGCCAGGCAGGCCATTAGAGTTACTTGGGGTGAAAAAAAGTCT
TGGTGGGGATATGAGGTTCTTACATTTTTCTTATTAGGCCAAGAGGCTGAAAAGGAAGACAAAATGTTGGC
ATTGTCCTTAGAGGATGAACACCTTCTTTATGGTGACATAATCCGACAAGATTTTTTAGACACATATAATA
ACCTGACCTTGAAAACCATTATGGCATTCAGGTGGGTAACTGAGTTTTGCCCCAATGCCAAGTACGTAATG
AAGACAGACACTGATGTTTTCATCAATACTGGCAATTTAGTGAAGTATCTTTTAAACCTAAACCACTCAGA
GAAGTTTTTCACAGGTTATCCTCTAATTGATAATTATTCCTATAGAGGATTTTACCAAAAAACCCATATTT
CTTACCAGGAGTATCCTTTCAAGGTGTTCCCTCCATACTGCAGTGGGTTGGGTTATATAATGTCCAGAGAT
TTGGTGCCAAGGATCTATGAAATGATGGGTCACGTAAAACCCATCAAGTTTGAAGATGTTTATGTCGGGAT
CTGTTTGAATTTATTAAAAGTGAACATTCATATTCCAGAAGACACAAATCTTTTCTTTCTATATAGAATCC
ATTTGGATGTCTGTCAACTGAGACGTGTGATTGCAGCCCATGGCTTTTCTTCCAAGGAGATCATCACTTTT
TGGCAGGTCATGCTAAGGAACACCACATGCCATTATTAACTTCACATTCTACAAAAAGCCTAGAAGGACAG
GATACCTTGTGGAAAGTGTTAAATAAAGTAGGTACTGTGGAAAATTCATGGGGAGGTCAGTGTGCTGGCTT
ACACTGAACTGAAACTCATGAAAAACCCAGACTGGAGACTGGAGGGTTACACTTGTGATTTATTAGTCAGG
CCCTTCAAAGATGATATGTGGAGGAATTAAATATAAAGGAATTGGAGGTTTTTGCTAAAGAAATTAATAGG
ACCAAACAATTTGGACATGTCATTCTGTAGACTAGAATTTCTTAAAAGGGTGTTACTGAGTTATAAGCTCA
CTAGGCTGTAAAAACAAAACAATGTAGAGTTTTATTTATTGAACAATGTAGTCACTTGAAGGTTTTGTGTA
TATCTTATGTGGATTACCAATTTAAAAATATATGTAGTTCTGTGTCAAAAAACTTCTTCACTGAAGTTATA
CTGAACAAAATTTTACCTGTTTTTGGTCATTTATAAAGTACTTCAAGATGTTGCAGTATTTCACAGTTATT
ATTATTTAAAATTACTTCAACTTTGTGTTTTTAAATGTTTTGACGATTTCAATACAAGATAAAAAGGATAG
TGAATCATTCTTTACATGCAAACATTTTCCAGTTACTTAACTGATCAGTTTATTATTGATACATCACTCCA
TTAATGTAAAGTCATAGGTCATTATTGCATATCAGTAATCTCTTGGACTTTGTTAAATATTTTACTGTGGT
AATATAGAGAAGAATTAAAGCAAGAAAATCTGAAAA

FIGURE 36

MASALWTVLPSRMSLRSLKWSLLLLSLLSFFVMWYLSLPHYNVIERVNWMYFYEYEPIYRQDFHF
TLREHSNCSHQNPFLVILVTSHPSDVKARQAIRVTWGEKKSWWGYEVLTFFLLGQEAEKEDKMLA
LSLEDEHLLYGDIIRQDFLDTYNNLTLKTIMAFRWVTEFCPNAKYVMKTDTDVFINTGNLVKYLL
NLNHSEKFFTGYPLIDNYSYRGFYQKTHISYQEYPFKVFPPYCSGLGYIMSRDLVPRIYEMMGHV
KPIKFEDVYVGICLNLLKVNIHIPEDTNLFFLYRIHLDVCQLRRVIAAHGFSSKEIITFWQVMLR
NTTCHY

Important features:

Type II transmembrane domain:

amino acids 20-39

N-glycosylation sites.

amino acids 72-76, 154-158, 198-202, 212-216, 326-330

Glycosaminoglycan attachment site.

amino acids 239-243

Ly-6 / u-PAR domain proteins.

amino acids 23-37

N-myristoylation site.

amino acids 271-277

FIGURE 37

CGCTCGGGCACCAGCCGCGGCAAGGATGGAGCTGGGTTGCTGGACGCAGTTGGGGCTCACTTTTCTTCAGCTCCTTCTCATC
TCGTCCTTGCCAAGAGAGTACACAGTCATTAATGAAGCCTGCCCTGGAGCAGAGTGGAATATCATGTGTCGGGAGTGCTGTG
AATATGATCAGATTGAGTGCGTCTGCCCCGGAAAGAGGGAAGTCGTGGGTTATACCATCCCTTGCTGCAGGAATGAGGAGAA
TGAGTGTGACTCCTGCCTGATCCACCCAGGTTGTACCATCTTTGAAAACTGCAAGAGCTGCCGAAATGGCTCATGGGGGGGT
ACCTTGGATGACTTCTATGTGAAGGGGTTCTACTGTGCAGAGTGCCGAGCAGGCTGGTACGGAGGAGACTGCATGCGATGTG
GCCAGGTTCTGCGAGCCCCAAAGGGTCAGATTTTGTTGGAAAGCTATCCCCTAAATGCTCACTGTGAATGGACCATTCATGC
TAAACCTGGGTTTGTCATCCAACTAAGATTTGTCATGTTGAGTCTGGAGTTTGACTACATGTGCCAGTATGACTATGTTGAG
GTTCGTGATGGAGACAACCGCGATGGCCAGATCATCAAGCGTGTCTGTGGCAACGAGCGGCCAGCTCCTATCCAGAGCATAG
GATCCTCACTCCACGTCCTCTTCCACTCCGATGGCTCCAAGAATTTTGACGGTTTCCATGCCATTTATGAGGAGATCACAGC
ATGCTCCTCATCCCCTTGTTTCCATGACGGCACGTGCGTCCTTGACAAGGCTGGATCTTACAAGTGTGCCTGCTTGGCAGGC
TATACTGGGCAGCGCTGTGAAAATCTCCTTGAAGAAAGAAACTGCTCAGACCCTGGGGGCCCAGTCAATGGGTACCAGAAAA
TAACAGGGGGCCCTGGGCTTATCAACGGACGCCATGCTAAAATTGGCACCGTGGTGTCTTTCTTTTGTAACAACTCCTATGT
TCTTAGTGGCAATGAGAAAAGAACTTGCCAGCAGAATGGAGAGTGGTCAGGGAAACAGCCCATCTGCATAAAAGCCTGCCGA
GAACCAAAGATTTCAGACCTGGTGAGAAGGAGAGTTCTTCCGATGCAGGTTCAGTCAAGGGAGACACCATTACACCAGCTAT
ACTCAGCGGCCTTCAGCAAGCAGAAACTGCAGAGTGCCCCTACCAAGAAGCCAGCCCTTCCCTTTGGAGATCTGCCCATGGG
ATACCAACATCTGCATACCCAGCTCCAGTATGAGTGCATCTCACCCTTCTACCGCCGCCTGGGCAGCAGCAGGAGGACATGT
CTGAGGACTGGGAAGTGGAGTGGGCGGGCACCATCCTGCATCCCTATCTGCGGGAAAATTGAGAACATCACTGCTCCAAAGA
CCCAAGGGTTGCGCTGGCCGTGGCAGGCAGCCATCTACAGGAGGACCAGCGGGGTGCATGACGGCAGCCTACACAAGGGAGC
GTGGTTCCTAGTCTGCAGCGGTGCCCTGGTGAATGAGCGCACTGTGGTGGTGGCTGCCCACTGTGTTACTGACCTGGGGAAG
GTCACCATGATCAAGACAGCAGACCTGAAAGTTGTTTTGGGGAAATTCTACCGGGATGATGACCGGGATGAGAAGACCATCC
AGAGCCTACAGATTTCTGCTATCATTCTGCATCCCAACTATGACCCCATCCTGCTTGATGCTGACATCGCCATCCTGAAGCT
CCTAGACAAGGCCCGTATCAGCACCCGAGTCCAGCCCATCTGCCTCGCTGCCAGTCGGGATCTCAGCACTTCCTTCCAGGAG
TCCCACATCACTGTGGCTGGCTGGAATGTCCTGGCAGACGTGAGGAGCCCTGGCTTCAAGAACGACACACTGCGCTCTGGGG
TGGTCAGTGTGGTGGACTCGCTGCTGTGTGAGGAGCAGCATGAGGACCATGGCATCCCAGTGAGTGTCACTGATAACATGTT
CTGTGCCAGCTGGGAACCCACTGCCCCTTCTGATATCTGCACTGCAGAGACAGGAGGCATCGCGGCTGTGTCCTTCCCGGGA
CGAGCATCTCCTGAGCCACGCTGGCATCTGATGGGACTGGTCAGCTGGAGCTATGATAAAACATGCAGCCACAGGCTCTCCA
CTGCCTTCACCAAGGTGCTGCCTTTTAAAGACTGGATTGAAAGAAATATGAAATGAACCATGCTCATGCACTCCTTGAGAAG
TGTTTCTGTATATCCGTCTGTACGTGTGTCATTGCGTGAAGCAGTGTGGGCCTGAAGTGTGATTTGGCCTGTGAACTTGGCT
GTGCCAGGGCTTCTGACTTCAGGGACAAAACTCAGTGAAGGGTGAGTAGACCTCCATTGCTGGTAGGCTGATGCCGCGTCCA
CTACTAGGACAGCCAATTGGAAGATGCCAGGGCTTGCAAGAAGTAAGTTTCTTCAAAGAAGACCATATACAAAACCTCTCCA
CTCCACTGACCTGGTGGTCTTCCCCAACTTTCAGTTATACGAATGCCATCAGCTTGACCAGGGAAGATCTGGGCTTCATGAG
GCCCCTTTTGAGGCTCTCAAGTTCTAGAGAGCTGCCTGTGGGACAGCCCAGGGCAGCAGAGCTGGGATGTGGTGCATGCCTT
TGTGTACATGGCCACAGTACAGTCTGGTCCTTTTCCTTCCCCATCTCTTGTACACATTTTAATAAAATAAGGGTTGGCTTCT
GAACTACAAAAAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAA

FIGURE 38

MELGCWTQLGLTFLQLLLISSLPREYTVINEACPGAEWNIMCRECCEYDQIECVCPGKREVVGYT
IPCCRNEENECDSCLIHPGCTIFENCKSCRNGSWGGTLDDFYVKGFYCAECRAGWYGGDCMRCGQ
VLRAPKGQILLESYPLNAHCEWTIHAKPGFVIQLRFVMLSLEFDYMCQYDYVEVRDGDNRDGQII
KRVCGNERPAPIQSIGSSLHVLFHSDGSKNFDGFHAIYEEITACSSSPCFHDGTCVLDKAGSYKC
ACLAGYTGQRCENLLEERNCSDPGGPVNGYQKITGGPGLINGRHAKIGTVVSFFCNNSYVLSGNE
KRTCQQNGEWSGKQPICIKACREPKISDLVRRRVLPMQVQSRETPLHQLYSAAFSKQKLQSAPTK
KPALPFGDLPMGYQHLHTQLQYECISPFYRRLGSSRRTCLRTGKWSGRAPSCIPICGKIENITAP
KTQGLRWPWQAAIYRRTSGVHDGSLHKGAWFLVCSGALVNERTVVVAAHCVTDLGKVTMIKTADL
KVVLGKFYRDDDRDEKTIQSLQISAIILHPNYDPILLDADIAILKLLDKARISTRVQPICLAASR
DLSTSFQESHITVAGWNVLADVRSPGFKNDTLRSGVVSVVDSLLCEEQHEDHGIPVSVTDNMFCA
SWEPTAPSDICTAETGGIAAVSFPGRASPEPRWHLMGLVSWSYDKTCSHRLSTAFTKVLPFKDWI
ERNMK

Important features of the protein:

Signal peptide:

amino acids 1-23

EGF-like domain cysteine pattern signature.

amino acids 260-272

N-glycosylation sites.

amino acids 96-100, 279-283, 316-320, 451-455, 614-618

N-myristoylation sites.

amino acids 35-41, 97-103, 256-262, 284-290, 298-304, 308-314, 474-480, 491-497, 638-644, 666-672

Amidation site.

amino acids 56-60

Serine proteases, trypsin family.

amino acids 489-506

CUB domain proteins profile.

amino acids 150-167

FIGURE 39

GGTTCCTACATCCTCTCATCTGAGAATCAGAGAGCATAATCTTCTTACGGGCCCGTGATTTATTAACGTGGCTTAATC
TGAAGGTTCTCAGTCAAATTCTTTGTGATCTACTGATTGTGGGGGCATGGCAAGGTTTGCTTAAAGGAGCTTGGCTGG
TTTGGGCCCTTGTAGCTGACAGAAGGTGGCCAGGGAGAATGCAGCACACTGCTCGGAGAATGAAGGCGCTTCTGTTGC
TGGTCTTGCCTTGGCTCAGTCCTGCTAACTACATTGACAATGTGGGCAACCTGCACTTCCTGTATTCAGAACTCTGTA
AAGGTGCCTCCCACTACGGCCTGACCAAAGATAGGAAGAGGCGCTCACAAGATGGCTGTCCAGACGGCTGTGCGAGCC
TCACAGCCACGGCTCCCTCCCCAGAGGTTTCTGCAGCTGCCACCATCTCCTTAATGACAGACGAGCCTGGCCTAGACA
ACCCTGCCTACGTGTCCTCGGCAGAGGACGGGCAGCCAGCAATCAGCCCAGTGGACTCTGGCCGGAGCAACCGAACTA
GGGCACGGCCCTTTGAGAGATCCACTATTAGAAGCAGATCATTTAAAAAAATAAATCGAGCTTTGAGTGTTCTTCGAA
GGACAAAGAGCGGGAGTGCAGTTGCCAACCATGCCGACCAGGGCAGGGAAAATTCTGAAAACACCACTGCCCCTGAAG
TCTTTCCAAGGTTGTACCACCTGATTCCAGATGGTGAAATTACCAGCATCAAGATCAATCGAGTAGATCCCAGTGAAA
GCCTCTCTATTAGGCTGGTGGGAGGTAGCGAAACCCCACTGGTCCATATCATTATCCAACACATTTATCGTGATGGGG
TGATCGCCAGAGACGGCCGGCTACTGCCAGGAGACATCATTCTAAAGGTCAACGGGATGGACATCAGCAATGTCCCTC
ACAACTACGCTGTGCGTCTCCTGCGGCAGCCCTGCCAGGTGCTGTGGCTGACTGTGATGCGTGAACAGAAGTTCCGCA
GCAGGAACAATGGACAGGCCCCGGATGCCTACAGACCCCGAGATGACAGCTTTCATGTGATTCTCAACAAAAGTAGCC
CCGAGGAGCAGCTTGGAATAAAACTGGTGCGCAAGGTGGATGAGCCTGGGGTTTTCATCTTCAATGTGCTGGATGGCG
GTGTGGCATATCGACATGGTCAGCTTGAGGAGAATGACCGTGTGTTAGCCATCAATGGACATGATCTTCGATATGGCA
GCCCAGAAAGTGCGGCTCATCTGATTCAGGCCAGTGAAAGACGTGTTCACCTCGTCGTGTCCCGCCAGGTTCGGCAGC
GGAGCCCTGACATCTTTCAGGAAGCCGGCTGGAACAGCAATGGCAGCTGGTCCCCAGGGCCAGGGGAGAGGAGCAACA
CTCCCAAGCCCCTCCATCCTACAATTACTTGTCATGAGAAGGTGGTAAATATCCAAAAAGACCCCGGTGAATCTCTCG
GCATGACCGTCGCAGGGGGAGCATCACATAGAGAATGGGATTTGCCTATCTATGTCATCAGTGTTGAGCCCGGAGGAG
TCATAAGCAGAGATGGAAGAATAAAAACAGGTGACATTTTGTTGAATGTGGATGGGGTCGAACTGACAGAGGTCAGCC
GGAGTGAGGCAGTGGCATTATTGAAAAGAACATCATCCTCGATAGTACTCAAAGCTTTGGAAGTCAAAGAGTATGAGC
CCCAGGAAGACTGCAGCAGCCCAGCAGCCCTGGACTCCAACCACAACATGGCCCCACCCAGTGACTGGTCCCCATCCT
GGGTCATGTGGCTGGAATTACCACGGTGCTTGTATAACTGTAAAGATATTGTATTACGAAGAAACACAGCTGGAAGTC
TGGGCTTCTGCATTGTAGGAGGTTATGAAGAATACAATGGAAACAAACCTTTTTTCATCAAATCCATTGTTGAAGGAA
CACCAGCATACAATGATGGAAGAATTAGATGTGGTGATATTCTTCTTGCTGTCAATGGTAGAAGTACATCAGGAATGA
TACATGCTTGCTTGGCAAGACTGCTGAAAGAACTTAAAGGAAGAATTACTCTAACTATTGTTTCTTGGCCTGGCACTT
TTTTATAGAATCAATGATGGGTCAGAGGAAAACAGAAAAATCACAAATAGGCTAAGAAGTTGAAACACTATATTTATC
TTGTCAGTTTTTATATTTAAAGAAAGAATACATTGTAAAAATGTCAGGAAAAGTATGATCATCTAATGAAAGCCAGTT
ACACCTCAGAAAATATGATTCCAAAAAAATTAAAACTACTAGTTTTTTTTCAGTGTGGAGGATTTCTCATTACTCTAC
AACATTGTTTATATTTTTTCTATTCAATAAAAAGCCCTAAAACAACTAAAATGATTGATTTGTATACCCCACTGAATT
CAAGCTGATTTAAATTTAAAATTTGGTATATGCTGAAGTCTGCCAAGGGTACATTATGGCCATTTTTAATTTACAGCT
AAAATATTTTTTAAAATGCATTGCTGAGAAACGTTGCTTTCATCAAACAAGAATAAATATTTTTCAGAAGTTAAA

FIGURE 40

MKALLLLVLPWLSPANYIDNVGNLHFLYSELCKGASHYGLTKDRKRRSQDGCPDGCASLTATAPS
PEVSAAATISLMTDEPGLDNPAYVSSAEDGQPAISPVDSGRSNRTRARPFERSTIRSRSFKKINR
ALSVLRRTKSGSAVANHADQGRENSENTTAPEVFPRLYHLIPDGEITSIKINRVDPSESLSIRLV
GGSETPLVHIIIQHIYRDGVIARDGRLLPGDIILKVNGMDISNVPHNYAVRLLRQPCQVLWLTVM
REQKFRSRNNGQAPDAYRPRDDSFHVILNKSSPEEQLGIKLVRKVDEPGVFIFNVLDGGVAYRHG
QLEENDRVLAINGHDLRYGSPESAAHLIQASERRVHLVVSRQVRQRSPDIFQEAGWNSNGSWSPG
PGERSNTPKPLHPTITCHEKVVNIQKDPGESLGMTVAGGASHREWDLPIYVISVEPGGVISRDGR
IKTGDILLNVDGVELTEVSRSEAVALLKRTSSSIVLKALEVKEYEPQEDCSSPAALDSNHNMAPP
SDWSPSWVMWLELPRCLYNCKDIVLRRNTAGSLGFCIVGGYEEYNGNKPFFIKSIVEGTPAYNDG
RIRCGDILLAVNGRSTSGMIHACLARLLKELKGRITLTIVSWPGTFL

Important features:

Signal peptide:

amino acids 1-15

N-glycosylation sites.

amino acids 108-112, 157-161, 289-293, 384-388

Tyrosine kinase phosphorylation sites.

amino acids 433-441, 492-500

N-myristoylation sites.

amino acids 51-57, 141-147, 233-239, 344-350, 423-429, 447-453, 467-473, 603-609

FIGURE 41

ACCAGGCATTGTATCTTCAGTTGTCATCAAGTTCGCAATCAGATTGGAAAAGCTCAACTTGAAGCTTT
CTTGCCTGCAGTGAAGCAGAGAGATAGATATTATTCACGTAATAAAAAACATGGGCTTCAACCTGACT
TTCCACCTTTCCTACAAATTCCGATTACTGTTGCTGTTGACTTTGTGCCTGACAGTGGTTGGGTGGGC
CACCAGTAACTACTTCGTGGGTGCCATTCAAGAGATTCCTAAAGCAAAGGAGTTCATGGCTAATTTCC
ATAAGACCCTCATTTTGGGGAAGGGAAAAACTCTGACTAATGAAGCATCCACGAAGAAGGTAGAACTT
GACAACTGTCCTTCTGTGTCTCCTTACCTCAGAGGCCAGAGCAAGCTCATTTTCAAACCAGATCTCAC
TTTGGAAGAGGTACAGGCAGAAAATCCCAAAGTGTCCAGAGGCCGGTATCGCCCTCAGGAATGTAAAG
CTTTACAGAGGGTCGCCATCCTCGTTCCCCACCGGAACAGAGAGAAACACCTGATGTACCTGCTGGAA
CATCTGCATCCCTTCCTGCAGAGGCAGCAGCTGGATTATGGCATCTACGTCATCCACCAGGCTGAAGG
TAAAAAGTTTAATCGAGCCAAACTCTTGAATGTGGGCTATCTAGAAGCCCTCAAGGAAGAAAATTGGG
ACTGCTTTATATTCCACGATGTGGACCTGGTACCCGAGAATGACTTTAACCTTTACAAGTGTGAGGAG
CATCCCAAGCATCTGGTGGTTGGCAGGAACAGCACTGGGTACAGGTTACGTTACAGTGGATATTTTGG
GGGTGTTACTGCCCTAAGCAGAGAGCAGTTTTTCAAGGTGAATGGATTCTCTAACAACTACTGGGGAT
GGGGAGGCGAAGACGATGACCTCAGACTCAGGGTTGAGCTCCAAAGAATGAAAATTTCCCGGCCCCTG
CCTGAAGTGGGTAAATATACAATGGTCTTCCACACTAGAGACAAAGGCAATGAGGTGAACGCAGAACG
GATGAAGCTCTTACACCAAGTGTCACGAGTCTGGAGAACAGATGGGTTGAGTAGTTGTTCTTATAAAT
TAGTATCTGTGGAACACAATCCTTTATATATCAACATCACAGTGGATTTCTGGTTTGGTGCATGACCC
TGGATCTTTTGGTGATGTTTGGAAGAACTGATTCTTTGTTTGCAATAATTTTGGCCTAGAGACTTCAA
ATAGTAGCACACATTAAGAACCTGTTACAGCTCATTGTTGAGCTGAATTTTTCCTTTTTGTATTTTCT
TAGCAGAGCTCCTGGTGATGTAGAGTATAAAACAGTTGTAACAAGACAGCTTTCTTAGTCATTTTGAT
CATGAGGGTTAAATATTGTAATATGGATACTTGAAGGACTTTATATAAAAGGATGACTCAAAGGATAA
AATGAACGCTATTTGAGGACTCTGGTTGAAGGAGATTTATTTAAATTTGAAGTAATATATTATGGGAT
AAAAGGCCACAGGAAATAAGACTGCTGAATGTCTGAGAGAACCAGAGTTGTTCTCGTCCAAGGTAGAA
AGGTACGAAGATACAATACTGTTATTCATTTATCCTGTACAATCATCTGTGAAGTGGTGGTGTCAGGT
GAGAAGGCGTCCACAAAAGAGGGGAGAAAAGGCGACGAATCAGGACACAGTGAACTTGGGAATGAAGA
GGTAGCAGGAGGGTGGAGTGTCGGCTGCAAAGGCAGCAGTAGCTGAGCTGGTTGCAGGTGCTGATAGC
CTTCAGGGGAGGACCTGCCCAGGTATGCCTTCCAGTGATGCCCACCAGAGAATACATTCTCTATTAGT
TTTTAAAGAGTTTTTGTAAAATGATTTTGTACAAGTAGGATATGAATTAGCAGTTTACAAGTTTACAT
ATTAACTAATAATAAATATGTCTATCAAATACCTCTGTAGTAAAATGTGAAAAAGCAAAA

FIGURE 42

MGFNLTFHLSYKFRLLLLLTLCLTVVGWATSNYFVGAIQEIPKAKEFMANFHKTLILGKGKTLTN
EASTKKVELDNCPSVSPYLRGQSKLIFKPDLTLEEVQAENPKVSRGRYRPQECKALQRVAILVPH
RNREKHLMYLLEHLHPFLQRQQLDYGIYVIHQAEGKKFNRAKLLNVGYLEALKEENWDCFIFHDV
DLVPENDFNLYKCEEHPKHLVVGRNSTGYRLRYSGYFGGVTALSREQFFKVNGFSNNYWGWGGED
DDLRLRVELQRMKISRPLPEVGKYTMVFHTRDKGNEVNAERMKLLHQVSRVWRTDGLSSCSYKLV
SVEHNPLYINITVDFWFGA

Important features:

Signal peptide:

amino acids 1-27

N-glycosylation sites.

amino acids 4-8, 220-224, 335-339

Xylose isomerase proteins.

amino acids 191-202

FIGURE 43

GCTCAAGACCCAGCAGTGGGACAGCCAGACAGACGGCACGATGGCACTGAGCTCCCAGATCTGGG

CCGCTTGCCTCCTGCTCCTCCTCCTCCTCGCCAGCCTGACCAGTGGCTCTGTTTTCCCACAACAG

ACGGGACAACTTGCAGAGCTGCAACCCCAGGACAGAGCTGGAGCCAGGGCCAGCTGGATGCCCAT

GTTCCAGAGGCGAAGGAGGCGAGACACCCACTTCCCCATCTGCATTTTCTGCTGCGGCTGCTGTC

ATCGATCAAAGTGTGGGATGTGCTGCAAGACGTAGAACCTACCTGCCCTGCCCCGTCCCCTCCC

TTCCTTATTTATTCCTGCTGCCCCAGAACATAGGTCTTGGAATAAAATGGCTGGTTCTTTTGTTT

TCCAAAAAAAAAAAAAAAAAAAAAAAAAAAAAAAAAAAAAAAAAAAAAAAAAAAAAAAAAAAAAA

AAAAAAAAAAAAAAAAAAAAAAAAAAA

FIGURE 44

MALSSQIWAACLLLLLLLASLTSGSVFPQQTGQLAELQPQDRAGARASWMPMFQRRRRRDTHFPI
CIFCCGCCHRSKCGMCCKT

Important features:

Signal peptide:

amino acids 1-24 cAMP- and cGMP-dependent protein kinase phosphorylation site.

amino acids 58-59

N-myristoylation site.

amino acids 44-50

Prokaryotic membrane lipoprotein lipid attachment site.

amino acids 1-12

FIGURE 45

GTGGCTTCATTTCAGTGGCTGACTTCCAGAGAGCAATATGGCTGGTTCCCCAACATGCCTCACCC
TCATCTATATCCTTTGGCAGCTCACAGGGTCAGCAGCCTCTGGACCCGTGAAAGAGCTGGTCGGT
TCCGTTGGTGGGGCCGTGACTTTCCCCCTGAAGTCCAAAGTAAAGCAAGTTGACTCTATTGTCTG
GACCTTCAACACAACCCCTCTTGTCACCATACAGCCAGAAGGGGGCACTATCATAGTGACCCAAA
ATCGTAATAGGGAGAGAGTAGACTTCCCAGATGGAGGCTACTCCCTGAAGCTCAGCAAACTGAAG
AAGAATGACTCAGGGATCTACTATGTGGGGATATACAGCTCATCACTCCAGCAGCCCTCCACCCA
GGAGTACGTGCTGCATGTCTACGAGCACCTGTCAAAGCCTAAAGTCACCATGGGTCTGCAGAGCA
ATAAGAATGGCACCTGTGTGACCAATCTGACATGCTGCATGGAACATGGGGAAGAGGATGTGATT
TATACCTGGAAGGCCCTGGGGCAAGCAGCCAATGAGTCCCATAATGGGTCCATCCTCCCCATCTC
CTGGAGATGGGGAGAAAGTGATATGACCTTCATCTGCGTTGCCAGGAACCCTGTCAGCAGAAACT
TCTCAAGCCCCATCCTTGCCAGGAAGCTCTGTGAAGGTGCTGCTGATGACCCAGATTCCTCCATG
GTCCTCCTGTGTCTCCTGTTGGTGCCCCTCCTGCTCAGTCTCTTTGTACTGGGGCTATTTCTTTG
GTTTCTGAAGAGAGAGAGACAAGAAGAGTACATTGAAGAGAAGAAGAGAGTGGACATTTGTCGGG
AAACTCCTAACATATGCCCCCATTCTGGAGAGAACACAGAGTACGACACAATCCCTCACACTAAT
AGAACAATCCTAAAGGAAGATCCAGCAAATACGGTTTACTCCACTGTGGAAATACCGAAAAAGAT
GGAAAATCCCCACTCACTGCTCACGATGCCAGACACACCAAGGCTATTTGCCTATGAGAATGTTA
TCTAGACAGCAGTGCACTCCCCTAAGTCTCTGCTCA

FIGURE 46

MAGSPTCLTLIYILWQLTGSAASGPVKELVGSVGGAVTFPLKSKVKQVDSIVWTFNTTPLVTIQP
EGGTIIVTQNRNRERVDFPDGGYSLKLSKLKKNDSGIYYVGIYSSSLQQPSTQEYVLHVYEHLSK
PKVTMGLQSNKNGTCVTNLTCCMEHGEEDVIYTWKALGQAANESHNGSILPISWRWGESDMTFIC
VARNPVSRNFSSPILARKLCEGAADDPDSSMVLLCLLLVPLLLSLFVLGLFLWFLKRERQEEYIE
EKKRVDICRETPNICPHSGENTEYDTIPHTNRTILKEDPANTVYSTVEIPKKMENPHSLLTMPDT
PRLFAYENVI

Important features:

Signal peptide:

amino acids 1-22

Transmembrane domain:

amino acids 224-250

Leucine zipper pattern.

amino acids 229-251

N-glycosylation sites.

amino acids 98-102, 142-146, 148-152, 172-176, 176-180, 204-208, 291-295

FIGURE 47

GGCTCGAGCGTTTCTGAGCCAGGGGTGACCATGACCTGCTGCGAAGGATGGACATCCTGCAATGG
ATTCAGCCTGCTGGTTCTACTGCTGTTAGGAGTAGTTCTCAATGCGATACCTCTAATTGTCAGCT
TAGTTGAGGAAGACCAATTTTCTCAAAACCCCATCTCTTGCTTTGAGTGGTGGTTCCCAGGAATT
ATAGGAGCAGGTCTGATGGCCATTCCAGCAACAACAATGTCCTTGACAGCAAGAAAAAGAGCGTG
CTGCAACAACAGAACTGGAATGTTTCTTTCATCATTTTTCAGTGTGATCACAGTCATTGGTGCTC
TGTATTGCATGCTGATATCCATCCAGGCTCTCTTAAAAGGTCCTCTCATGTGTAATTCTCCAAGC
AACAGTAATGCCAATTGTGAATTTTCATTGAAAAACATCAGTGACATTCATCCAGAATCCTTCAA
CTTGCAGTGGTTTTTCAATGACTCTTGTGCACCTCCTACTGGTTTCAATAAACCCACCAGTAACG
ACACCATGGCGAGTGGCTGGAGAGCATCTAGTTTCCACTTCGATTCTGAAGAAAACAAACATAGG
CTTATCCACTTCTCAGTATTTTTAGGTCTATTGCTTGTTGGAATTCTGGAGGTCCTGTTTGGGCT
CAGTCAGATAGTCATCGGTTTCCTTGGCTGTCTGTGTGGAGTCTCTAAGCGAAGAAGTCAAATTG
TGTAGTTTAATGGGAATAAAATGTAAGTATCAGTAGTTTGAAAAAAAAAAA

FIGURE 48

MTCCEGWTSCNGFSLLVLLLLGVVLNAIPLIVSLVEEDQFSQNPISCFEWWFPGIIGAGLMAIPA
TTMSLTARKRACCNNRTGMFLSSFFSVITVIGALYCMLISIQALLKGPLMCNSPSNSNANCEFSL
KNISDIHPESFNLQWFFNDSCAPPTGFNKPTSNDTMASGWRASSFHFDSEENKHRLIHFSVFLGL
LLVGILEVLFGLSQIVIGFLGCLCGVSKRRSQIV

Important features:

Transmembrane domains:

amino acids 10-31 (type II), 50-72, 87-110, 191-213

N-glycosylation sites.

amino acids 80-84, 132-136, 148-152, 163-167 cAMP- and cGMP-dependent protein kinase phosphorylation site.

amino acids 223-227

N-myristoylation sites.

amino acids 22-28, 54-60, 83-89, 97-103, 216-222

Prokaryotic membrane lipoprotein lipid attachment site.

amino acids 207-218

TNFR/NGFR family cysteine-rich region protein.

amino acids 4-12

FIGURE 49

ATCCGTTCTCTGCGCTGCCAGCTCAGGTGAGCCCTCGCCAAGGTGACCTCGCAGGACACTGGTGA
AGGAGCAGTGAGGAACCTGCAGAGTCACACAGTTGCTGACCAATTGAGCTGTGAGCCTGGAGCAG
ATCCGTGGGCTGCAGACCCCCGCCCCAGTGCCTCTCCCCCTGCAGCCCTGCCCCTCGAACTGTGA
CATGGAGAGAGTGACCCTGGCCCTTCTCCTACTGGCAGGCCTGACTGCCTTGGAAGCCAATGACC
CATTTGCCAATAAAGACGATCCCTTCTACTATGACTGGAAAAACCTGCAGCTGAGCGGACTGATC
TGCGGAGGGCTCCTGGCCATTGCTGGGATCGCGGCAGTTCTGAGTGGCAAATGCAAATACAAGAG
CAGCCAGAAGCAGCACAGTCCTGTACCTGAGAAGGCCATCCCACTCATCACTCCAGGCTCTGCCA
CTACTTGCTGAGCACAGGACTGGCCTCCAGGGATGGCCTGAAGCCTAACACTGGCCCCCAGCACC
TCCTCCCCTGGGAGGCCTTATCCTCAAGGAAGGACTTCTCTCCAAGGGCAGGCTGTTAGGCCCCT
TTCTGATCAGGAGGCTTCTTTATGAATTAAACTCGCCCCACCACCCCCTCA

FIGURE 50

MERVTLALLLLAGLTALEANDPFANKDDPFYYDWKNLQLSGLICGGLLAIAGIAAVLSGKCKYKS
SQKQHSPVPEKAIPLITPGSATTC

Important features:

Signal peptide:

amino acids 1-16

Transmembrane domain:

amino acids 36-59

N-myristoylation sites.

amino acids 41-47, 45-51, 84-90

Extracellular proteins SCP/Tpx-1/Ag5/PR-1/Sc7.

amino acids 54-67

FIGURE 51

GTGGACTCTGAGAAGCCCAGGCAGTTGAGGACAGGAGAGAGAAGGCTGCAGACCCAGAGGGAGGG
AGGACAGGGAGTCGGAAGGAGGAGGACAGAGGAGGGCACAGAGACGCAGAGCAAGGGCGGCAAGG
AGGAGACCCTGGTGGGAGGAAGACACTCTGGAGAGAGAGGGGGCTGGGCAGAGATGAAGTTCCAG
GGGCCCCTGGCCTGCCTCCTGCTGGCCCTCTGCCTGGGCAGTGGGGAGGCTGGCCCCCTGCAGAG
CGGAGAGGAAAGCACTGGGACAAATATTGGGGAGGCCCTTGGACATGGCCTGGGAGACGCCCTGA
GCGAAGGGGTGGGAAAGGCCATTGGCAAAGAGGCCGGAGGGGCAGCTGGCTCTAAAGTCAGTGAG
GCCCTTGGCCAAGGGACCAGAGAAGCAGTTGGCACTGGAGTCAGGCAGGTTCCAGGCTTTGGCGC
AGCAGATGCTTTGGGCAACAGGGTCGGGGAAGCAGCCCATGCTCTGGGAAACACTGGGCACGAGA
TTGGCAGACAGGCAGAAGATGTCATTCGACACGGAGCAGATGCTGTCCGCGGCTCCTGGCAGGGG
GTGCCTGGCCACAGTGGTGCTTGGGAAACTTCTGGAGGCCATGGCATCTTTGGCTCTCAAGGTGG
CCTTGGAGGCCAGGGCCAGGGCAATCCTGGAGGTCTGGGGACTCCGTGGGTCCACGGATACCCCG
GAAACTCAGCAGGCAGCTTTGGAATGAATCCTCAGGGAGCTCCCTGGGGTCAAGGAGGCAATGGA
GGGCCACCAAACTTTGGGACCAACACTCAGGGAGCTGTGGCCCAGCCTGGCTATGGTTCAGTGAG
AGCCAGCAACCAGAATGAAGGGTGCACGAATCCCCCACCATCTGGCTCAGGTGGAGGCTCCAGCA
ACTCTGGGGGAGGCAGCGGCTCACAGTCGGGCAGCAGTGGCAGTGGCAGCAATGGTGACAACAAC
AATGGCAGCAGCAGTGGTGGCAGCAGCAGTGGCAGCAGCAGTGGCAGCAGCAGTGGCGGCAGCAG
TGGCGGCAGCAGTGGTGGCAGCAGTGGCAACAGTGGTGGCAGCAGAGGTGACAGCGGCAGTGAGT
CCTCCTGGGGATCCAGCACCGGCTCCTCCTCCGGCAACCACGGTGGGAGCGGCGGAGGAAATGGA
CATAAACCCGGGTGTGAAAAGCCAGGGAATGAAGCCCGCGGGAGCGGGGAATCTGGGATTCAGGG
CTTCAGAGGACAGGGAGTTTCCAGCAACATGAGGGAAATAAGCAAAGAGGGCAATCGCCTCCTTG
GAGGCTCTGGAGACAATTATCGGGGGCAAGGGTCGAGCTGGGGCAGTGGAGGAGGTGACGCTGTT
GGTGGAGTCAATACTGTGAACTCTGAGACGTCTCCTGGGATGTTTAACTTTGACACTTTCTGGAA
GAATTTTAAATCCAAGCTGGGTTTCATCAACTGGGATGCCATAAACAAGGACCAGAGAAGCTCTC
GCATCCCGTGACCTCCAGACAAGGAGCCACCAGATTGGATGGGAGCCCCCACACTCCCTCCTTAA
AACACCACCCTCTCATCACTAATCTCAGCCCTTGCCCTTGAAATAAACCTTAGCTGCCCCACAAA
AAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA

FIGURE 52

MKFQGPLACLLLALCLGSGEAGPLQSGEESTGTNIGEALGHGLGDALSEGVGKAIGKEAGGAAGSKVS
EALGQGTREAVGTGVRQVPGFGAADALGNRVGEAAHALGNTGHEIGRQAEDVIRHGADAVRGSWQGVP
GHSGAWETSGGHGIFGSQGGLGGQGQGNPGGLGTPWVHGYPGNSAGSFGMNPQGAPWGQGGNGGPPNF
GTNTQGAVAQPGYGSVRASNQNEGCTNPPPSGSGGGSSNSGGGSGSQSGSSGSGSNGDNNNGSSSGGS
SSGSSSGSSSGGSSGGSSGGSSGNSGGSRGDSGSESSWGSSTGSSSGNHGGSGGGNGHKPGCEKPGNE
ARGSGESGIQGFRGQGVSSNMREISKEGNRLLGGSGDNYRGQGSSWGSGGGDAVGGVNTVNSETSPGM
FNFDTFWKNFKSKLGFINWDAINKDQRSSRIP

Signal peptide:

amino acids 1-21

N-glycosylation site.

amino acids 265-269

Glycosaminoglycan attachment site.

amino acids 235-239, 237-241, 244-248, 255-259, 324-328, 388-392

Casein kinase II phosphorylation site.

amino acids 26-30, 109-113, 259-263, 300-304, 304-308

N-myristoylation site.

amino acids 17-23, 32-38, 42-48, 50-56, 60-66, 61-67, 64-70, 74-80, 90-96, 96-102, 130-136, 140-146, 149-155, 152-158, 155-161, 159-165, 163-169, 178-184, 190-196, 194-200, 199-205, 218-224, 236-242, 238-244, 239-245, 240-246, 245-251, 246-252, 249-252, 253-259, 256-262, 266-272, 270-276, 271-277, 275-281, 279-285, 283-289, 284-290, 287-293, 288-294, 291-297, 292-298, 295-301, 298-304, 305-311, 311-317, 315-321, 319-325, 322-328, 323-329, 325-331, 343-349, 354-360, 356-362, 374-380, 381-387, 383-389, 387-393, 389-395, 395-401

Cell attachment sequence.

amino acids 301-304

FIGURE 53

GGAGAAGAGGTTGTGTGGGACAAGCTGCTCCCGACAGAAGG<u>ATG</u>TCGCTGCTGAGCCTGCCCTGG
CTGGGCCTCAGACCGGTGGCAATGTCCCCATGGCTACTCCTGCTGCTGGTTGTGGGCTCCTGGCT
ACTCGCCCGCATCCTGGCTTGGACCTATGCCTTCTATAACAACTGCCGCCGGCTCCAGTGTTTCC
CACAGCCCCCAAAACGGAACTGGTTTTGGGGTCACCTGGGCCTGATCACTCCTACAGAGGAGGGC
TTGAAGGACTCGACCCAGATGTCGGCCACCTATTCCCAGGGCTTTACGGTATGGCTGGGTCCCAT
CATCCCCTTCATCGTTTTATGCCACCCTGACACCATCCGGTCTATCACCAATGCCTCAGCTGCCA
TTGCACCCAAGGATAATCTCTTCATCAGGTTCCTGAAGCCCTGGCTGGGAGAAGGGATACTGCTG
AGTGGCGGTGACAAGTGGAGCCGCCACCGTCGGATGCTGACGCCCGCCTTCCATTTCAACATCCT
GAAGTCCTATATAACGATCTTCAACAAGAGTGCAAACATCATGCTTGACAAGTGGCAGCACCTGG
CCTCAGAGGGCAGCAGTCGTCTGGACATGTTTGAGCACATCAGCCTCATGACCTTGGACAGTCTA
CAGAAATGCATCTTCAGCTTTGACAGCCATTGTCAGGAGAGGCCCAGTGAATATATTGCCACCAT
CTTGGAGCTCAGTGCCCTTGTAGAGAAAAGAAGCCAGCATATCCTCCAGCACATGGACTTTCTGT
ATTACCTCTCCCATGACGGGCGGCGCTTCCACAGGGCCTGCCGCCTGGTGCATGACTTCACAGAC
GCTGTCATCCGGGAGCGGCGTCGCACCCTCCCCACTCAGGGTATTGATGATTTTTTCAAAGACAA
AGCCAAGTCCAAGACTTTGGATTTCATTGATGTGCTTCTGCTGAGCAAGGATGAAGATGGGAAGG
CATTGTCAGATGAGGATATAAGAGCAGAGGCTGACACCTTCATGTTTGGAGGCCATGACACCACG
GCCAGTGGCCTCTCCTGGGTCCTGTACAACCTTGCGAGGCACCCAGAATACCAGGAGCGCTGCCG
ACAGGAGGTGCAAGAGCTTCTGAAGGACCGCGATCCTAAAGAGATTGAATGGGACGACCTGGCCC
AGCTGCCCTTCCTGACCATGTGCGTGAAGGAGAGCCTGAGGTTACATCCCCCAGCTCCCTTCATC
TCCCGATGCTGCACCCAGGACATTGTTCTCCCAGATGGCCGAGTCATCCCCAAAGGCATTACCTG
CCTCATCGATATTATAGGGGTCCATCACAACCCAACTGTGTGGCCGGATCCTGAGGTCTACGACC
CCTTCCGCTTTGACCCAGAGAACAGCAAGGGGAGGTCACCTCTGGCTTTTATTCCTTTCTCCGCA
GGGCCCAGGAACTGCATCGGGCAGGCGTTCGCCATGGCGGAGATGAAAGTGGTCCTGGCGTTGAT
GCTGCTGCACTTCCGGTTCCTGCCAGACCACACTGAGCCCCGCAGGAAGCTGGAATTGATCATGC
GCGCCGAGGGCGGGCTTTGGCTGCGGGTGGAGCCCCTGAATGTAGGCTTGCAG<u>TGA</u>CTTTCTGAC
CCATCCACCTGTTTTTTTGCAGATTGTCATGAATAAAACGGTGCTGTCAAA

FIGURE 54

MSLLSLPWLGLRPVAMSPWLLLLLVVGSWLLARILAWTYAFYNNCRRLQCFPQPPKRNWFWGHLG
LITPTEEGLKDSTQMSATYSQGFTVWLGPIIPFIVLCHPDTIRSITNASAAIAPKDNLFIRFLKP
WLGEGILLSGGDKWSRHRRMLTPAFHFNILKSYITIFNKSANIMLDKWQHLASEGSSRLDMFEHI
SLMTLDSLQKCIFSFDSHCQERPSEYIATILELSALVEKRSQHILQHMDFLYYLSHDGRRFHRAC
RLVHDFTDAVIRERRRTLPTQGIDDFFKDKAKSKTLDFIDVLLLSKDEDGKALSDEDIRAEADTF
MFGGHDTTASGLSWVLYNLARHPEYQERCRQEVQELLKDRDPKEIEWDDLAQLPFLTMCVKESLR
LHPPAPFISRCCTQDIVLPDGRVIPKGITCLIDIIGVHHNPTVWPDPEVYDPFRFDPENSKGRSP
LAFIPFSAGPRNCIGQAFAMAEMKVVLALMLLHFRFLPDHTEPRRKLELIMRAEGGLWLRVEPLN
VGLQ

Important features:

Transmembrane domains:

amino acids 13-32 (type II), 77-102

Cytochrome P450 cysteine heme-iron ligand signature.

amino acids 461-471

N-glycosylation sites.

amino acids 112-116, 168-172

FIGURE 55

ATCGCATCAATTGGGAGTACCATCTTCCTCATGGGACCAGTGAAACAGCTGAAGCGAATGTTTGA
GCCTACTCGTTTGATTGCAACTATCATGGTGCTGTTGTGTTTTGCACTTACCCTGTGTTCTGCCT
TTTGGTGGCATAACAAGGGACTTGCACTTATCTTCTGCATTTTGCAGTCTTTGGCATTGACGTGG
TACAGCCTTTCCTTCATACCATTTGCAAGGGATGCTGTGAAGAAGTGTTTTGCCGTGTGTCTTGC
ATAATTCATGGCCAGTTTTATGAAGCTTTGGAAGGCACTATGGACAGAAGCTGGTGGACAGTTTT
GTAACTATCTTCGAAACCTCTGTCTTACAGACATGTGCCTTTTATCTTGCAGCAATGTGTTGCTT
GTGATTCGAACATTTGAGGGTTACTTTTGGAAGCAACAATACATTCTCGAACCTGAATGTCAGTA
GCACAGGATGAGAAGTGGGTTCTGTATCTTGTGGAGTGGAATCTTCCTCATGTACCTGTTTCCTC
TCTGGATGTTGTCCCACTGAATTCCCATGAATACAAACCTATTCAGCAACAGCAAAAAAAAAAAA
AAAAAAAAAAAAAAAAAAAAAAAAAAAAAAAAAAAAAAAAAAAAAAAAAAAAAAAAAAA

FIGURE 56

MGPVKQLKRMFEPTRLIATIMVLLCFALTLCSAFWWHNKGLALIFCILQSLALTWYSLSFIPFAR
DAVKKCFAVCLA

Important features:

Signal peptide:

amino acids 1-33

Type II fibronectin collagen-binding domain protein.

amino acids 30-72

FIGURE 57

CGGCTCGAGCTCGAGCCGAATCGGCTCGAGGGGCAGTGGAGCACCCAGCAGGCCGCCAACATGCTCTGTCTGTGCCTG
TACGTGCCGGTCATCGGGGAAGCCCAGACCGAGTTCCAGTACTTTGAGTCGAAGGGGCTCCCTGCCGAGCTGAAGTCC
ATTTTCAAGCTCAGTGTCTTCATCCCCTCCCAGGAATTCTCCACCTACCGCCAGTGGAAGCAGAAAATTGTACAAGCT
GGAGATAAGGACCTTGATGGGCAGCTAGACTTTGAAGAATTTGTCCATTATCTCCAAGATCATGAGAAGAAGCTGAGG
CTGGTGTTTAAGATTTTGGACAAAAAGAATGATGGACGCATTGACGCGCAGGAGATCATGCAGTCCCTGCGGGACTTG
GGAGTCAAGATATCTGAACAGCAGGCAGAAAAAATTCTCAAGAGCATGGATAAAAACGGCACGATGACCATCGACTGG
AACGAGTGGAGAGACTACCACCTCCTCCACCCCGTGGAAAACATCCCCGAGATCATCCTCTACTGGAAGCATTCCACG
ATCTTTGATGTGGGTGAGAATCTAACGGTCCCGGATGAGTTCACAGTGGAGGAGAGGCAGACGGGGATGTGGTGGAGA
CACCTGGTGGCAGGAGGTGGGGCAGGGGCCGTATCCAGAACCTGCACGGCCCCCCTGGACAGGCTCAAGGTGCTCATG
CAGGTCCATGCCTCCCGCAGCAACAACATGGGCATCGTTGGTGGCTTCACTCAGATGATTCGAGAAGGAGGGGCCAGG
TCACTCTGGCGGGGCAATGGCATCAACGTCCTCAAAATTGCCCCCGAATCAGCCATCAAATTCATGGCCTATGAGCAG
ATCAAGCGCCTTGTTGGTAGTGACCAGGAGACTCTGAGGATTCACGAGAGGCTTGTGGCAGGGTCCTTGGCAGGGGCC
ATCGCCCAGAGCAGCATCTACCCAATGGAGGTCCTGAAGACCCGGATGGCGCTGCGGAAGACAGGCCAGTACTCAGGA
ATGCTGGACTGCGCCAGGAGGATCCTGGCCAGAGAGGGGGTGGCCGCCTTCTACAAAGGCTATGTCCCCAACATGCTG
GGCATCATCCCCTATGCCGGCATCGACCTTGCAGTCTACGAGACGCTCAAGAATGCCTGGCTGCAGCACTATGCAGTG
AACAGCGCGGACCCCGGCGTGTTTGTGCTCCTGGCCTGTGGCACCATGTCCAGTACCTGTGGCCAGCTGGCCAGCTAC
CCCCTGGCCCTAGTCAGGACCCGGATGCAGGCGCAAGCCTCTATTGAGGGCGCTCCGGAGGTGACCATGAGCAGCCTC
TTCAAACATATCCTGCGGACCGAGGGGGCCTTCGGGCTGTACAGGGGGCTGGCCCCCAACTTCATGAAGGTCATCCCA
GCTGTGAGCATCAGCTACGTGGTCTACGAGAACCTGAAGATCACCCTGGGCGTGCAGTCGCGGTGACGGGGGGAGGGC
CGCCCGGCAGTGGACTCGCTGATCCTGGGCCGCAGCCTGGGGTGTGCAGCCATCTCATTCTGTGAATGTGCCAACACT
AAGCTGTCTCGAGCCAAGCTGTGAAAACCCTAGACGCACCCGCAGGGAGGGTGGGGAGAGCTGGCAGGCCCAGGGCTT
GTCCTGCTGACCCCAGCAGACCCTCCTGTTGGTTCCAGCGAAGACCACAGGCATTCCTTAGGGTCCAGGGTCAGCAGG
CTCCGGGCTCACATGTGTAAGGACAGGACATTTTCTGCAGTGCCTGCCAATAGTGAGCTTGGAGCCTGGAGGCCGGCT
TAGTTCTTCCATTTCACCCTTGCAGCCAGCTGTTGGCCACGGCCCCTGCCCTCTGGTCTGCCGTGCATCTCCCTGTGC
CCTCTTGCTGCCTGCCTGTCTGCTGAGGTAAGGTGGGAGGAGGGCTACAGCCCACATCCCACCCCCTCGTCCAATCCC
ATAATCCATGATGAAAGGTGAGGTCACGTGGCCTCCCAGGCCTGACTTCCCAACCTACAGCATTGACGCCAACTTGGC
TGTGAAGGAAGAGGAAAGGATCTGGCCTTGTGGTCACTGGCATCTGAGCCCTGCTGATGGCTGGGGCTCTCGGGCATG
CTTGGGAGTGCAGGGGGCTCGGGCTGCCTGGCCTGGCTGCACAGAAGGCAAGTGCTGGGGCTCATGGTGCTCTGAGCT
GGCCTGGACCCTGTCAGGATGGGCCCCACCTCAGAACCAAACTCACTGTCCCCACTGTGGCATGAGGGCAGTGGAGCA
CCATGTTTGAGGGCGAAGGGCAGAGCGTTTGTGTGTTCTGGGGAGGGAAGGAAAAGGTGTTGGAGGCCTTAATTATGG
ACTGTTGGGAAAAGGGTTTTGTCCAGAAGGACAAGCCGGACAAATGAGCGACTTCTGTGCTTCCAGAGGAAGACGAGG
GAGCAGGAGCTTGGCTGACTGCTCAGAGTCTGTTCTGACGCCCTGGGGGTTCCTGTCCAACCCCAGCAGGGGCGCAGC
GGGACCAGCCCCACATTCCACTTGTGTCACTGCTTGGAACCTATTTATTTTGTATTTATTTGAACAGAGTTATGTCCT
AACTATTTTTATAGATTTGTTTAATTAATAGCTTGTCATTTTCAAGTTCATTTTTTATTCATATTTATGTTCATGGTT
GATTGTACCTTCCCAAGCCCGCCCAGTGGGATGGGAGGAGGAGGAGAAGGGGGGCCTTGGGCCGCTGCAGTCACATCT
GTCCAGAGAAATTCCTTTTGGGACTGGAGGCAGAAAAGCGGCCAGAAGGCAGCAGCCCTGGCTCCTTTCCTTTGGCAG
GTTGGGGAAGGGCTTGCCCCCAGCCTTAGGATTTCAGGGTTTGACTGGGGGCGTGGAGAGAGAGGGAGGAACCTCAAT
AACCTTGAAGGTGGAATCCAGTTATTTCCTGCGCTGCGAGGGTTTCTTTATTTCACTCTTTTCTGAATGTCAAGGCAG
TGAGGTGCCTCTCACTGTGAATTTGTGGTGGGCGGGGGCTGGAGGAGAGGGTGGGGGGCTGGCTCCGTCCCTCCCAGC
CTTCTGCTGCCCTTGCTTAACAATGCCGGCCAACTGGCGACCTCACGGTTGCACTTCCATTCCACCAGAATGACCTGA
TGAGGAAATCTTCAATAGGATGCAAAGATCAATGCAAAAATTGTTATATATGAACATATAACTGGAGTCGTCAAAAAG
CAAATTAAGAAAGAATTGGACGTTAGAAGTTGTCATTTAAAGCAGCCTTCTAATAAAGTTGTTTCAAAGCTGAAAAAA
AAAAAAAAAAAAAAAAAAAAAAAAAAAAAAAAAAAAAAAAAAAAAAAAAAAAAAAAAA

FIGURE 58

MLCLCLYVPVIGEAQTEFQYFESKGLPAELKSIFKLSVFIPSQEFSTYRQWKQKIVQAGDKDLDG
QLDFEEFVHYLQDHEKKLRLVFKILDKKNDGRIDAQEIMQSLRDLGVKISEQQAEKILKSMDKNG
TMTIDWNEWRDYHLLHPVENIPEIILYWKHSTIFDVGENLTVPDEFTVEERQTGMWWRHLVAGGG
AGAVSRTCTAPLDRLKVLMQVHASRSNNMGIVGGFTQMIREGGARSLWRGNGINVLKIAPESAIK
FMAYEQIKRLVGSDQETLRIHERLVAGSLAGAIAQSSIYPMEVLKTRMALRKTGQYSGMLDCARR
ILAREGVAAFYKGYVPNMLGIIPYAGIDLAVYETLKNAWLQHYAVNSADPGVFVLLACGTMSSTC
GQLASYPLALVRTRMQAQASIEGAPEVTMSSLFKHILRTEGAFGLYRGLAPNFMKVIPAVSISYV
VYENLKITLGVQSR

Important features:

Signal peptide:

amino acids 1-16

Putative transmembrane domains:

amino acids 284-304, 339-360, 376-394

Mitochondrial energy transfer proteins signature.

amino acids 206-215, 300-309

N-glycosylation sites.

amino acids 129-133, 169-173

Elongation Factor-hand calcium-binding protein.

amino acids 54-73, 85-104, 121-140

FIGURE 59

GGAAGGCAGCGGCAGCTCCACTCAGCCAGTACCCAGATACGCTGGGAACCTTCCCCAGCCATGGC
TTCCCTGGGGCAGATCCTCTTCTGGAGCATAATTAGCATCATCATTATTCTGGCTGGAGCAATTG
CACTCATCATTGGCTTTGGTATTTCAGGGAGACACTCCATCACAGTCACTACTGTCGCCTCAGCT
GGGAACATTGGGGAGGATGGAATCCTGAGCTGCACTTTTGAACCTGACATCAAACTTTCTGATAT
CGTGATACAATGGCTGAAGGAAGGTGTTTTAGGCTTGGTCCATGAGTTCAAAGAAGGCAAAGATG
AGCTGTCGGAGCAGGATGAAATGTTCAGAGGCCGGACAGCAGTGTTTGCTGATCAAGTGATAGTT
GGCAATGCCTCTTTGCGGCTGAAAAACGTGCAACTCACAGATGCTGGCACCTACAAATGTTATAT
CATCACTTCTAAAGGCAAGGGGAATGCTAACCTTGAGTATAAAACTGGAGCCTTCAGCATGCCGG
AAGTGAATGTGGACTATAATGCCAGCTCAGAGACCTTGCGGTGTGAGGCTCCCCGATGGTTCCCC
CAGCCCACAGTGGTCTGGGCATCCCAAGTTGACCAGGGAGCCAACTTCTCGGAAGTCTCCAATAC
CAGCTTTGAGCTGAACTCTGAGAATGTGACCATGAAGGTTGTGTCTGTGCTCTACAATGTTACGA
TCAACAACACATACTCCTGTATGATTGAAAATGACATTGCCAAAGCAACAGGGGATATCAAAGTG
ACAGAATCGGAGATCAAAAGGCGGAGTCACCTACAGCTGCTAAACTCAAAGGCTTCTCTGTGTGT
CTCTTCTTTCTTTGCCATCAGCTGGGCACTTCTGCCTCTCAGCCCTTACCTGATGCTAAAATAAT
GTGCCTTGGCCACAAAAAAGCATGCAAAGTCATTGTTACAACAGGGATCTACAGAACTATTTCAC
CACCAGATATGACCTAGTTTTATATTTCTGGGAGGAAATGAATTCATATCTAGAAGTCTGGAGTG
AGCAAACAAGAGCAAGAAACAAAAAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGA
GTGATAAGTAAAATGCACGTGGAGACAAGTGCATCCCCAGATCTCAGGGACCTCCCCCTGCCTGT
CACCTGGGGAGTGAGAGGACAGGATAGTGCATGTTCTTTGTCTCTGAATTTTTAGTTATATGTGC
TGTAATGTTGCTCTGAGGAAGCCCCTGGAAAGTCTATCCCAACATATCCACATCTTATATTCCAC
AAATTAAGCTGTAGTATGTACCCTAAGACGCTGCTAATTGACTGCCACTTCGCAACTCAGGGGCG
GCTGCATTTTAGTAATGGGTCAAATGATTCACTTTTTATGATGCTTCCAAAGGTGCCTTGGCTTC
TCTTCCCAACTGACAAATGCCAAAGTTGAGAAAAATGATCATAATTTTAGCATAAACAGAGCAGT
CGGGGACACCGATTTTATAAATAAACTGAGCACCTTCTTTTAAACAAAAAAAAAAAAAAAAAA
AAAAAAAAAAAAAAAAAAAAAAAAAAAAAAAA

FIGURE 60

MASLGQILFWSIISIIIILAGAIALIIGFGISGRHSITVTTVASAGNIGEDGILSCTFEPDIKLS
DIVIQWLKEGVLGLVHEFKEGKDELSEQDEMFRGRTAVFADQVIVGNASLRLKNVQLTDAGTYKC
YIITSKGKGNANLEYKTGAFSMPEVNVDYNASSETLRCEAPRWFPQPTVVWASQVDQGANFSEVS
NTSFELNSENVTMKVVSVLYNVTINNTYSCMIENDIAKATGDIKVTESEIKRRSHLQLLNSKASL
CVSSFFAISWALLPLSPYLMLK

Important features:

Signal peptide:

amino acids 1-28

Transmembrane domain:

amino acids 258-281

N-glycosylation sites.

amino acids 112-116, 160-164, 190-194, 196-200, 205-209, 216-220, 220-224

N-myristoylation sites.

amino acids 52-58, 126-132, 188-194

FIGURE 61

TGACGTCAGAATCACCATGGCCAGCTATCCTTACCGGCAGGGCTGCCCAGGAGCTGCAGGACAAG
CACCAGGAGCCCCTCCGGGTAGCTACTACCCTGGACCCCCCAATAGTGGAGGGCAGTATGGTAGT
GGGCTACCCCCTGGTGGTGGTTATGGGGGTCCTGCCCCTGGAGGGCCTTATGGACCACCAGCTGG
TGGAGGGCCCTATGGACACCCCAATCCTGGGATGTTCCCCTCTGGAACTCCAGGAGGACCATATG
GCGGTGCAGCTCCCGGGGGCCCCTATGGTCAGCCACCTCCAAGTTCCTACGGTGCCCAGCAGCCT
GGGCTTTATGGACAGGGTGGCGCCCCTCCCAATGTGGATCCTGAGGCCTACTCCTGGTTCCAGTC
GGTGGACTCAGATCACAGTGGCTATATCTCCATGAAGGAGCTAAAGCAGGCCCTGGTCAACTGCA
ATTGGTCTTCATTCAATGATGAGACCTGCCTCATGATGATAAACATGTTTGACAAGACCAAGTCA
GGCCGCATCGATGTCTACGGCTTCTCAGCCCTGTGGAAATTCATCCAGCAGTGGAAGAACCTCTT
CCAGCAGTATGACCGGGACCGCTCGGGCTCCATTAGCTACACAGAGCTGCAGCAAGCTCTGTCCC
AAATGGGCTACAACCTGAGCCCCCAGTTCACCCAGCTTCTGGTCTCCCGCTACTGCCCACGCTCT
GCCAATCCTGCCATGCAGCTTGACCGCTTCATCCAGGTGTGCACCCAGCTGCAGGTGCTGACAGA
GGCCTTCCGGGAGAAGGACACAGCTGTACAAGGCAACATCCGGCTCAGCTTCGAGGACTTCGTCA
CCATGACAGCTTCTCGGATGCTATGACCCAACCATCTGTGGAGAGTGGAGTGCACCAGGGACCTT
TCCTGGCTTCTTAGAGTGAGAGAAGTATGTGGACATCTCTTCTTTTCCTGTCCCTCTAGAAGAAC
ATTCTCCCTTGCTTGATGCAACACTGTTCCAAAAGAGGGTGGAGAGTCCTGCATCATAGCCACCA
AATAGTGAGGACCGGGGCTGAGGCCACACAGATAGGGGCCTGATGGAGGAGAGGATAGAAGTTGA
ATGTCCTGATGGCCATGAGCAGTTGAGTGGCACAGCCTGGCACCAGGAGCAGGTCCTTGTAATGG
AGTTAGTGTCCAGTCAGCTGAGCTCCACCCTGATGCCAGTGGTGAGTGTTCATCGGCCTGTTACC
GTTAGTACCTGTGTTCCCTCACCAGGCCATCCTGTCAAACGAGCCCATTTTCTCCAAAGTGGAAT
CTGACCAAGCATGAGAGAGATCTGTCTATGGGACCAGTGGCTTGGATTCTGCCACACCCATAAAT
CCTTGTGTGTTAACTTCTAGCTGCCTGGGGCTGGCCCTGCTCAGACAAATCTGCTCCCTGGGCAT
CTTTGGCCAGGCTTCTGCCCCCTGCAGCTGGGACCCCTCACTTGCCTGCCATGCTCTGCTCGGCT
TCAGTCTCCAGGAGACAGTGGTCACCTCTCCCTGCCAATACTTTTTTAATTTGCATTTTTTTC
ATTTGGGGCCAAAAGTCCAGTGAAATTGTAAGCTTCAATAAAAGGATGAAACTCTGA

FIGURE 62

MASYPYRQGCPGAAGQAPGAPPGSYYPGPPNSGGQYGSGLPPGGGYGGPAPGGPYGPPAGGGPYG
HPNPGMFPSGTPGGPYGGAAPGGPYGQPPPSSYGAQQPGLYGQGGAPPNVDPEAYSWFQSVDSDH
SGYISMKELKQALVNCNWSSFNDETCLMMINMFDKTKSGRIDVYGFSALWKFIQQWKNLFQQYDR
DRSGSISYTELQQALSQMGYNLSPQFTQLLVSRYCPRSANPAMQLDRFIQVCIQLQVLTEAFREK
DTAVQGNIRLSFEDFVTMTASRML

Important features of the protein:

Signal peptide:

amino acids 1-19

N-glycosylation site.

amino acids 147-150

Casein kinase II phosphorylation sites.

amino acids 135-138, 150-153, 202-205, 271-274

N-myristoylation sites.

amino acids 9-14, 15-20, 19-24, 33-38, 34-39, 39-44, 43-48, 61-66, 70-75, 78-83, 83-88, 87-92, 110-115

FIGURE 63

CAGGATGCAGGGCCGCGTGGCAGGGAGCTGCGCTCCTCTGGGCCTGCTCCTGGTCTGTCTTCATC
TCCCAGGCCTCTTTGCCCGGAGCATCGGTGTTGTGGAGGAGAAAGTTTCCCAAAACTTCGGGACC
AACTTGCCTCAGCTCGGACAACCTTCCTCCACTGGCCCCTCTAACTCTGAACATCCGCAGCCCGC
TCTGGACCCTAGGTCTAATGACTTGGCAAGGGTTCCTCTGAAGCTCAGCGTGCCTCCATCAGATG
GCTTCCCACCTGCAGGAGGTTCTGCAGTGCAGAGGTGGCCTCCATCGTGGGGGCTGCCTGCCATG
GATTCCTGGCCCCCTGAGGATCCTTGGCAGATGATGGCTGCTGCGGCTGAGGACCGCCTGGGGGA
AGCGCTGCCTGAAGAACTCTCTTACCTCTCCAGTGCTGCGGCCCTCGCTCCGGGCAGTGGCCCTT
TGCCTGGGGAGTCTTCTCCCGATGCCACAGGCCTCTCACCTGAGGCTTCACTCCTCCACCAGGAC
TCGGAGTCCAGACGACTGCCCCGTTCTAATTCACTGGGAGCCGGGGGAAAAATCCTTTCCCAACG
CCCTCCCTGGTCTCTCATCCACAGGGTTCTGCCTGATCACCCCTGGGGTACCCTGAATCCCAGTG
TGTCCTGGGGAGGTGGAGGCCCTGGGACTGGTTGGGGAACGAGGCCCATGCCACACCCTGAGGGA
ATCTGGGGTATCAATAATCAACCCCCAGGTACCAGCTGGGGAAATATTAATCGGTATCCAGGAGG
CAGCTGGGGAAATATTAATCGGTATCCAGGAGGCAGCTGGGGGAATATTAATCGGTATCCAGGAG
GCAGCTGGGGGAATATTCATCTATACCCAGGTATCAATAACCCATTTCCTCCTGGAGTTCTCCGC
CCTCCTGGCTCTTCTTGGAACATCCCAGCTGGCTTCCCTAATCCTCCAAGCCCTAGGTTGCAGTG
GGGCTAGAGCACGATAGAGGGAAACCCAACATTGGGAGTTAGAGTCCTGCTCCCGCCCCTTGCTG
TGTGGGCTCAATCCAGGCCCTGTTAACATGTTTCCAGCACTATCCCCACTTTTCAGTGCCTCCCC
TGCTCATCTCCAATAAAATAAAAGCACTTATGAAAAAAAAAAAAAAAAAAAAAAAAAAAA
AAAAAAAAAAAAAAAAAAAAAAAAAAAAAAAAAAAAAAAAAAAAAAAAAAAAAAAAAAA

FIGURE 64

MQGRVAGSCAPLGLLLVCLHLPGLFARSIGVVEEKVSQNFGTNLPQLGQPSSTGPSNSEHPQPAL
DPRSNDLARVPLKLSVPPSDGFPPAGGSAVQRWPPSWGLPAMDSWPPEDPWQMMAAAAEDRLGEA
LPEELSYLSSAAALAPGSGPLPGESSPDATGLSPEASLLHQDSESRRLPRSNSLGAGGKILSQRP
PWSLIHRVLPDHPWGTLNPSVSWGGGGPGTGWGTRPMPHPEGIWGINNQPPGTSWGNINRYPGGS
WGNINRYPGGSWGNINRYPGGSWGNIHLYPGINNPFPPGVLRPPGSSWNIPAGFPNPPSPRLQWG

Important features of the protein:

Signal peptide:

amino acids 1-26

Casein kinase II phosphorylation sites.

amino acids 56-59, 155-158

N-myristoylation sites.

amino acids 48-53, 220-225, 221-226, 224-229, 247-252, 258-263, 259-264, 269-274, 270-275, 280-285, 281-286, 305-310

FIGURE 65

AAGGAGAGGCCACCGGGACTTCAGTGTCTCCTCCATCCCAGGAGCGCAGTGGCCACTATGGGGTC
TGGGCTGCCCCTTGTCCTCCTCTTGACCCTCCTTGGCAGCTCACATGGAACAGGGCCGGGTATGA
CTTTGCAACTGAAGCTGAAGGAGTCTTTTCTGACAAATTCCTCCTATGAGTCCAGCTTCCTGGAA
TTGCTTGAAAAGCTCTGCCTCCTCCTCCATCTCCCTTCAGGGACCAGCGTCACCCTCCACCATGC
AAGATCTCAACACCATGTTGTCTGCAACACATGACAGCCATTGAAGCCTGTGTCCTTCTTGGCCC
GGGCTTTTGGGCCGGGGATGCAGGAGGCAGGCCCCGACCCTGTCTTTCAGCAGGCCCCCACCCTC
CTGAGTGGCAATAAATAAAATTCGGTATGCTG

FIGURE 66

MGSGLPLVLLLTLLGSSHGTGPGMTLQLKLKESFLTNSSYESSFLELLEKLCLLLHLPSGTSVTL
HHARSQHHVVCNT

Important features:

Signal peptide:

amino acids 1-19

N-glycosylation site.

amino acids 37-41

N-myristoylation sites.

amino acids 15-21, 19-25, 60-66

FIGURE 67

ACGGACCGAGGGTTCGAGGGAGGGACACGGACCAGGAACCTGAGCTAGGTCAAAGACGCCCGGGC
CAGGTGCCCCGTCGCAGGTGCCCCTGGCCGGAGATGCGGTAGGAGGGGCGAGCGCGAGAAGCCCC
TTCCTCGGCGCTGCCAACCCGCCACCCAGCCCATGGCGAACCCCGGGCTGGGGCTGCTTCTGGCG
CTGGGCCTGCCGTTCCTGCTGGCCCGCTGGGGCCGAGCCTGGGGGCAAATACAGACCACTTCTGC
AAATGAGAATAGCACTGTTTTGCCTTCATCCACCAGCTCCAGCTCCGATGGCAACCTGCGTCCGG
AAGCCATCACTGCTATCATCGTGGTCTTCTCCCTCTTGGCTGCCTTGCTCCTGGCTGTGGGGCTG
GCACTGTTGGTGCGGAAGCTTCGGGAGAAGCGGCAGACGGAGGGCACCTACCGGCCCAGTAGCGA
GGAGCAGTTCTCCCATGCAGCCGAGGCCCGGGCCCCTCAGGACTCCAAGGAGACGGTGCAGGGCT
GCCTGCCCATCTAGGTCCCCTCTCCTGCATCTGTCTCCCTTCATTGCTGTGTGACCTTGGGGAAA
GGCAGTGCCCTCTCTGGGCAGTCAGATCCACCCAGTGCTTAATAGCAGGGAAGAAGGTACTTCAA
AGACTCTGCCCCTGAGGTCAAGAGAGGATGGGGCTATTCACTTTTATATATTTATATAAAATTAG
TAGTGAGATGTAAAAAAAAAAAAAAAAAA

FIGURE 68

MANPGLGLLLALGLPFLLARWGRAWGQIQTTSANENSTVLPSSTSSSSDGNLRPEAITAIIVVFS
LLAALLLAVGLALLVRKLREKRQTEGTYRPSSEEQFSHAAEARAPQDSKETVQGCLPI

Important features:

Signal peptide:

amino acids 1-19

Transmembrane domain:

amino acids 56-80

N-glycosylation site.

amino acids 36-40 cAMP- and cGMP-dependent protein kinase phosphorylation site.

amino acids 86-90

Tyrosine kinase phosphorylation site.

amino acids 86-94

N-myristoylation sites.

amino acids 7-13, 26-32

FIGURE 69

GCCAGGAATAACTAGAGAGGAACAATGGGGTTATTCAGAGGTTTTGTTTTCCTCTTAGTTCTGTGCCTGCTGCACCAG
TCAAATACTTCCTTCATTAAGCTGAATAATAATGGCTTTGAAGATATTGTCATTGTTATAGATCCTAGTGTGCCAGAA
GATGAAAAAATAATTGAACAAATAGAGGATATGGTGACTACAGCTTCTACGTACCTGTTTGAAGCCACAGAAAAAAGA
TTTTTTTTCAAAAATGTATCTATATTAATTCCTGAGAATTGGAAGGAAAATCCTCAGTACAAAAGGCCAAAACATGAA
AACCATAAACATGCTGATGTTATAGTTGCACCACCTACACTCCCAGGTAGAGATGAACCATACACCAAGCAGTTCACA
GAATGTGGAGAGAAAGGCGAATACATTCACTTCACCCCTGACCTTCTACTTGGAAAAAAACAAAATGAATATGGACCA
CCAGGCAAACTGTTTGTCCATGAGTGGGCTCACCTCCGGTGGGGAGTGTTTGATGAGTACAATGAAGATCAGCCTTTC
TACCGTGCTAAGTCAAAAAAAATCGAAGCAACAAGGTGTTCCGCAGGTATCTCTGGTAGAAATAGAGTTTATAAGTGT
CAAGGAGGCAGCTGTCTTAGTAGAGCATGCAGAATTGATTCTACAACAAAACTGTATGGAAAAGATTGTCAATTCTTT
CCTGATAAAGTACAAACAGAAAAAGCATCCATAATGTTTATGCAAAGTATTGATTCTGTTGTTGAATTTTGTAACGAA
AAAACCCATAATCAAGAAGCTCCAAGCCTACAAAACATAAAGTGCAATTTTAGAAGTACATGGGAGGTGATTAGCAAT
TCTGAGGATTTTAAAAACACCATACCCATGGTGACACCACCTCCTCCACCTGTCTTCTCATTGCTGAAGATCAGTCAA
AGAATTGTGTGCTTAGTTCTTGATAAGTCTGGAAGCATGGGGGGTAAGGACCGCCTAAATCGAATGAATCAAGCAGCA
AAACATTTCCTGCTGCAGACTGTTGAAAATGGATCCTGGGTGGGGATGGTTCACTTTGATAGTACTGCCACTATTGTA
AATAAGCTAATCCAAATAAAAAGCAGTGATGAAAGAAACACACTCATGGCAGGATTACCTACATATCCTCTGGGAGGA
ACTTCCATCTGCTCTGGAATTAAATATGCATTTCAGGTGATTGGAGAGCTACATTCCCAACTCGATGGATCCGAAGTA
CTGCTGCTGACTGATGGGGAGGATAACACTGCAAGTTCTTGTATTGATGAAGTGAAACAAAGTGGGGCCATTGTTCAT
TTTATTGCTTTGGGAAGAGCTGCTGATGAAGCAGTAATAGAGATGAGCAAGATAACAGGAGGAAGTCATTTTTATGTT
TCAGATGAAGCTCAGAACAATGGCCTCATTGATGCTTTTGGGGCTCTTACATCAGGAAATACTGATCTCTCCCAGAAG
TCCCTTCAGCTCGAAAGTAAGGGATTAACACTGAATAGTAATGCCTGGATGAACGACACTGTCATAATTGATAGTACA
GTGGGAAAGGACACGTTCTTTCTCATCACATGGAACAGTCTGCCTCCCAGTATTTCTCTCTGGGATCCCAGTGGAACA
ATAATGGAAAATTTCACAGTGGATGCAACTTCCAAAATGGCCTATCTCAGTATTCCAGGAACTGCAAAGGTGGGCACT
TGGGCATACAATCTTCAAGCCAAAGCGAACCCAGAAACATTAACTATTACAGTAACTTCTCGAGCAGCAAATTCTTCT
GTGCCTCCAATCACAGTGAATGCTAAAATGAATAAGGACGTAAACAGTTTCCCCAGCCCAATGATTGTTTACGCAGAA
ATTCTACAAGGATATGTACCTGTTCTTGGAGCCAATGTGACTGCTTTCATTGAATCACAGAATGGACATACAGAAGTT
TTGGAACTTTTGGATAATGGTGCAGGCGCTGATTCTTTCAAGAATGATGGAGTCTACTCCAGGTATTTTACAGCATAT
ACAGAAAATGGCAGATATAGCTTAAAAGTTCGGGCTCATGGAGGAGCAAACACTGCCAGGCTAAAATTACGGCCTCCA
CTGAATAGAGCCGCGTACATACCAGGCTGGGTAGTGAACGGGGAAATTGAAGCAAACCCGCCAAGACCTGAAATTGAT
GAGGATACTCAGACCACCTTGGAGGATTTCAGCCGAACAGCATCCGGAGGTGCATTTGTGGTATCACAAGTCCCAAGC
CTTCCCTTGCCTGACCAATACCCACCAAGTCAAATCACAGACCTTGATGCCACAGTTCATGAGGATAAGATTATTCTT
ACATGGACAGCACCAGGAGATAATTTTGATGTTGGAAAAGTTCAACGTTATATCATAAGAATAAGTGCAAGTATTCTT
GATCTAAGAGACAGTTTTGATGATGCTCTTCAAGTAAATACTACTGATCTGTCACCAAAGGAGGCCAACTCCAAGGAA
AGCTTTGCATTTAAACCAGAAAATATCTCAGAAGAAAATGCAACCCACATATTTATTGCCATTAAAAGTATAGATAAA
AGCAATTTGACATCAAAAGTATCCAACATTGCACAAGTAACTTTGTTTATCCCTCAAGCAAATCCTGATGACATTGAT
CCTACACCTACTCCTACTCCTACTCCTACTCCTGATAAAAGTCATAATTCTGGAGTTAATATTTCTACGCTGGTATTG
TCTGTGATTGGGTCTGTTGTAATTGTTAACTTTATTTTAAGTACCACCATTTGAACCTTAACGAAGAAAAAAATCTTC
AAGTAGACCTAGAAGAGAGTTTTAAAAAACAAAACAATGTAAGTAAAGGATATTTCTGAATCTTAAAATTCATCCCAT
GTGTGATCATAAACTCATAAAAATAATTTTAAGATGTCGGAAAAGGATACTTTGATTAAATAAAAACACTCATGGATA
TGTAAAAACTGTCAAGATTAAAATTTAATAGTTTCATTTATTTGTTATTTTATTTGTAAGAAATAGTGATGAACAAAG
ATCCTTTTTCATACTGATACCTGGTTGTATATTATTTGATGCAACAGTTTTCTGAAATGATATTTCAAATTGCATCAA
GAAATTAAAATCATCTATCTGAGTAGTCAAAATACAAGTAAAGGAGAGCAAATAAACAACATTTGGAAAAAAAAAAAA
AAAAAAAAAAAAAAAAAAAAAAAAAAAAAAAAAAAAAAAAAAAAAAAAAAAAAAAAAAAAAAAA

FIGURE 70

MGLFRGFVFLLVLCLLHQSNTSFIKLNNNGFEDIVIVIDPSVPEDEKIIEQIEDMVTTASTYLFE
ATEKRFFFKNVSILIPENWKENPQYKRPKHENHKHADVIVAPPTLPGRDEPYTKQFTECGEKGEY
IHFTPDLLLGKKQNEYGPPGKLFVHEWAHLRWGVFDEYNEDQPFYRAKSKKIEATRCSAGISGRN
RVYKCQGGSCLSRACRIDSTTKLYGKDCQFFPDKVQTEKASIMFMQSIDSVVEFCNEKTHNQEAP
SLQNIKCNFRSTWEVISNSEDFKNTIPMVTPPPPPVFSLLKISQRIVCLVLDKSGSMGGKDRLNR
MNQAAKHFLLQTVENGSWVGMVHFDSTATIVNKLIQIKSSDERNTLMAGLPTYPLGGTSICSGIK
YAFQVIGELHSQLDGSEVLLLTDGEDNTASSCIDEVKQSGAIVHFIALGRAADEAVIEMSKITGG
SHFYVSDEAQNNGLIDAFGALTSGNTDLSQKSLQLESKGLTLNSNAWMNDTVIIDSTVGKDTFFL
ITWNSLPPSISLWDPSGTIMENFTVDATSKMAYLSIPGTAKVGTWAYNLQAKANPETLTITVTSR
AANSSVPPITVNAKMNKDVNSFPSPMIVYAEILQGYVPVLGANVTAFIESQNGHTEVLELLDNGA
GADSFKNDGVYSRYFTAYTENGRYSLKVRAHGGANTARLKLRPPLNRAAYIPGWVVNGEIEANPP
RPEIDEDTQTTLEDFSRTASGGAFVVSQVPSLPLPDQYPPSQITDLDATVHEDKIILTWTAPGDN
FDVGKVQRYIIRISASILDLRDSFDDALQVNTTDLSPKEANSKESFAFKPENISEENATHIFIAI
KSIDKSNLTSKVSNIAQVTLFIPQANPDDIDPTPTPTPTPTPDKSHNSGVNISTLVLSVIGSVVI
VNFILSTTI

Signal peptide:

amino acids 1-21

Putative transmembrane domains:

amino acids 284-300, 617-633

Leucine zipper pattern.

amino acids 469-491, 476-498

N-glycosylation site.

amino acids 20-24, 75-79, 340-344, 504-508, 542-546, 588-592, 628-632, 811-815, 832-836, 837-841, 852-856, 896-900

FIGURE 71

CTCCTTAGGTGGAAACCCTGGGAGTAGAGTACTGACAGCAAAGACCGGGAAAGACCATACGTCCCCGGGCAGGGGTGA
CAACAGGTGTCATCTTTTTGATCTCGTGTGGCTGCCTTCCTATTTCAAGGAAAGACGCCAAGGTAATTTTGACCCA
GAGGAGCAATGATGTAGCCACCTCCTAACCTTCCCTTCTTGAACCCCCAGTTATGCCAGGATTTACTAGAGAGTGTCA
ACTCAACCAGCAAGCGGCTCCTTCGGCTTAACTTGTGGTTGGAGGAGAGAACCTTTGTGGGGCTGCGTTCTCTTAGCA
GTGCTCAGAAGTGACTTGCCTGAGGGTGGACCAGAAGAAAGGAAAGGTCCCCTCTTGCTGTTGGCTGCACATCAGGAA
GGCTGTGATGGGAATGAAGGTGAAAACTTGGAGATTTCACTTCAGTCATTGCTTCTGCCTGCAAGATCATCCTTTAAA
AGTAGAGAAGCTGCTCTGTGTGGTGGTTAACTCCAAGAGGCAGAACTCGTTCTAGAAGGAAATGGATGCAAGCAGCTC
CGGGGGCCCCAAACGCATGCTTCCTGTGGTCTAGCCCAGGGAAGCCCTTCCGTGGGGGCCCCGGCTTTGAGGGATGCC
ACCGGTTCTGGACGCATGGCTGATTCCTGAATGATGATGGTTCGCCGGGGGCTGCTTGCGTGGATTTCCCGGGTGGTG
GTTTTGCTGGTGCTCCTCTGCTGTGCTATCTCTGTCCTGTACATGTTGGCCTGCACCCCAAAAGGTGACGAGGAGCAG
CTGGCACTGCCCAGGGCCAACAGCCCCACGGGGAAGGAGGGGTACCAGGCCGTCCTTCAGGAGTGGGAGGAGCAGCAC
CGCAACTACGTGAGCAGCCTGAAGCGGCAGATCGCACAGCTCAAGGAGGAGCTGCAGGAGAGGAGTGAGCAGCTCAGG
AATGGGCAGTACCAAGCCAGCGATGCTGCTGGCCTGGGTCTGGACAGGAGCCCCCCAGAGAAAACCCAGGCCGACCTC
CTGGCCTTCCTGCACTCGCAGGTGGACAAGGCAGAGGTGAATGCTGGCGTCAAGCTGGCCACAGAGTATGCAGCAGTG
CCTTTCGATAGCTTTACTCTACAGAAGGTGTACCAGCTGGAGACTGGCCTTACCCGCCACCCCGAGGAGAAGCCTGTG
AGGAAGGACAAGCGGGATGAGTTGGTGGAAGCCATTGAATCAGCCTTGGAGACCCTGAACAATCCTGCAGAGAACAGC
CCCAATCACCGTCCTTACACGGCCTCTGATTTCATAGAAGGGATCTACCGAACAGAAAGGGACAAAGGGACATTGTAT
GAGCTCACCTTCAAAGGGGACCACAAACACGAATTCAAACGGCTCATCTTATTTCGACCATTCAGCCCCATCATGAAA
GTGAAAAATGAAAAGCTCAACATGGCCAACACGCTTATCAATGTTATCGTGCCTCTAGCAAAAAGGGTGGACAAGTTC
CGGCAGTTCATGCAGAATTTCAGGGAGATGTGCATTGAGCAGGATGGGAGAGTCCATCTCACTGTTGTTTACTTTGGG
AAAGAAGAAATAAATGAAGTCAAAGGAATACTTGAAAACACTTCCAAAGCTGCCAACTTCAGGAACTTTACCTTCATC
CAGCTGAATGGAGAATTTTCTCGGGGAAAGGGACTTGATGTTGGAGCCCGCTTCTGGAAGGGAAGCAACGTCCTTCTC
TTTTTCTGTGATGTGGACATCTACTTCACATCTGAATTCCTCAATACGTGTAGGCTGAATACACAGCCAGGGAAGAAG
GTATTTTATCCAGTTCTTTTCAGTCAGTACAATCCTGGCATAATATACGGCCACCATGATGCAGTCCCTCCCTTGGAA
CAGCAGCTGGTCATAAAGAAGGAAACTGGATTTTGGAGAGACTTTGGATTTGGGATGACGTGTCAGTATCGGTCAGAC
TTCATCAATATAGGTGGGTTTGATCTGGACATCAAAGGCTGGGGCGGAGAGGATGTGCACCTTTATCGCAAGTATCTC
CACAGCAACCTCATAGTGGTACGGACGCCTGTGCGAGGACTCTTCCACCTCTGGCATGAGAAGCGCTGCATGGACGAG
CTGACCCCCGAGCAGTACAAGATGTGCATGCAGTCCAAGGCCATGAACGAGGCATCCCACGGCCAGCTGGGCATGCTG
GTGTTCAGGCACGAGATAGAGGCTCACCTTCGCAAACAGAAACAGAAGACAAGTAGCAAAAAAACATGAACTCCCAGA
GAAGGATTGTGGGAGACACTTTTTCTTTCCTTTTGCAATTACTGAAAGTGGCTGCAACAGAGAAAAGACTTCCATAAA
GGACGACAAAAGAATTGGACTGATGGGTCAGAGATGAGAAAGCCTCCGATTTCTCTCTGTTGGGCTTTTTACAACAGA
AATCAAAATCTCCGCTTTGCCTGCAAAAGTAACCCAGTTGCACCCTGTGAAGTGTCTGACAAAGGCAGAATGCTTGTG
AGATTATAAGCCTAATGGTGTGGAGGTTTTGATGGTGTTTACAATACACTGAGACCTGTTGTTTTGTGTGCTCATTGA
AATATTCATGATTTAAGAGCAGTTTTGTAAAAAATTCATTAGCATGAAAGGCAAGCATATTTCTCCTCATATGAATGA
GCCTATCAGCAGGGCTCTAGTTTCTAGGAATGCTAAAATATCAGAAGGCAGGAGAGGAGATAGGCTTATTATGATACT
AGTGAGTACATTAAGTAAAATAAAATGGACCAGAAAAGAAAAGAAACCATAAATATCGTGTCATATTTTCCCCAAGAT
TAACCAAAAATAATCTGCTTATCTTTTTGGTTGTCCTTTTAACTGTCTCCGTTTTTTTCTTTTATTTAAAAATGCACT
TTTTTTCCCTTGTGAGTTATAGTCTGCTTATTTAATTACCACTTTGCAAGCCTTACAAGAGAGCACAAGTTGGCCTAC
ATTTTTATATTTTTTAAGAAGATACTTTGAGATGCATTATGAGAACTTTCAGTTCAAAGCATCAAATTGATGCCATAT
CCAAGGACATGCCAAATGCTGATTCTGTCAGGCACTGAATGTCAGGCATTGAGACATAGGGAAGGAATGGTTTGTACT
AATACAGACGTACAGATACTTTCTCTGAAGAGTATTTTCGAAGAGGAGCAACTGAACACTGGAGGAAAAGAAAATGAC
ACTTTCTGCTTTACAGAAAAGGAAACTCATTCAGACTGGTGATATCGTGATGTACCTAAAAGTCAGAAACCACATTTT
CTCCTCAGAAGTAGGGACCGCTTTCTTACCTGTTTAAATAAACCAAAGTATACCGTGTGAACCAAACAATCTCTTTTC
AAAACAGGGTGCTCCTCCTGGCTTCTGGCTTCCATAAGAAGAAATGGAGAAAAATATATATATATATATATATATTGT
GAAAGATCAATCCATCTGCCAGAATCTAGTGGGATGGAAGTTTTTGCTACATGTTATCCACCCCAGGCCAGGTGGAAG
TAACTGAATTATTTTTTAAATTAAGCAGTTCTACTCAATCACCAAGATGCTTCTGAAAATTGCATTTTATTACCATTT
CAAACTATTTTTTAAAAATAAATACAGTTAACATAGAGTGGTTTCTTCATTCATGTGAAAATTATTAGCCAGCACCAG
ATGCATGAGCTAATTATCTCTTTGAGTCCTTGCTTCTGTTTGCTCACAGTAAACTCATTGTTTAAAAGCTTCAAGAAC
ATTCAAGCTGTTGGTGTGTTAAAAAATGCATTGTATTGATTTGTACTGGTAGTTTATGAAATTTAATTAAAACACAGG
CCATGAATGGAAGGTGGTATTGCACAGCTAATAAAATATGATTTGTGGATATGAA

FIGURE 72

MMMVRRGLLAWISRVVVLLVLLCCAISVLYMLACTPKGDEEQLALPRANSPTGKEGYQAVLQEWE
EQHRNYVSSLKRQIAQLKEELQERSEQLRNGQYQASDAAGLGLDRSPPEKTQADLLAFLHSQVDK
AEVNAGVKLATEYAAVPFDSFTLQKVYQLETGLTRHPEEKPVRKDKRDELVEAIESALETLNNPA
ENSPNHRPYTASDFIEGIYRTERDKGTLYELTFKGDHKHEFKRLILFRPFSPIMKVKNEKLNMAN
TLINVIVPLAKRVDKFRQFMQNFREMCIEQDGRVHLTVVYFGKEEINEVKGILENTSKAANFRNF
TFIQLNGEFSRGKGLDVGARFWKGSNVLLFFCDVDIYFTSEFLNTCRLNTQPGKKVFYPVLFSQY
NPGIIYGHHDAVPPLEQQLVIKKETGFWRDFGFGMTCQYRSDFINIGGFDLDIKGWGGEDVHLYR
KYLHSNLIVVRTPVRGLFHLWHEKRCMDELTPEQYKMCMQSKAMNEASHGQLGMLVFRHEIEAHL
RKQKQKTSSKKT

Important features:

Signal peptide:

amino acids 1-27

N-glycosylation sites.

amino acids 315-319, 324-328

N-myristoylation sites.

amino acids 96-102, 136-142, 212-218, 311-317, 339-345, 393-399

Amidation site.

amino acids 377-381

FIGURE 73

```
GAGACTGCAGAGGGAGATAAAGAGAGAGGGCAAAGAGGCAGCAAGAGATTTGTCCTGGGGATCCA
GAAACCCATGATACCCTACTGAACACCGAATCCCCTGGAAGCCCACAGAGACAGAGACAGCAAGA
GAAGCAGAGATAAATACACTCACGCCAGGAGCTCGCTCGCTCTCTCTCTCTCTCTCACTCCTC
CCTCCCTCTCTCTCTGCCTGTCCTAGTCCTCTAGTCCTCAAATTCCCAGTCCCCTGCACCCCTTC
CTGGGACACTATGTTGTTCTCCGCCCTCCTGCTGGAGGTGATTTGGATCCTGGCTGCAGATGGGG
GTCAACACTGGACGTATGAGGGCCCACATGGTCAGGACCATTGGCCAGCCTCTTACCCTGAGTGT
GGAAACAATGCCCAGTCGCCCATCGATATTCAGACAGACAGTGTGACATTTGACCCTGATTTGCC
TGCTCTGCAGCCCCACGGATATGACCAGCCTGGCACCGAGCCTTTGGACCTGCACAACAATGGCC
ACACAGTGCAACTCTCTCTGCCCTCTACCCTGTATCTGGGTGGACTTCCCCGAAAATATGTAGCT
GCCCAGCTCCACCTGCACTGGGGTCAGAAAGGATCCCCAGGGGGGTCAGAACACCAGATCAACAG
TGAAGCCACATTTGCAGAGCTCCACATTGTACATTATGACTCTGATTCCTATGACAGCTTGAGTG
AGGCTGCTGAGAGGCCTCAGGGCCTGGCTGTCCTGGGCATCCTAATTGAGGTGGGTGAGACTAAG
AATATAGCTTATGAACACATTCTGAGTCACTTGCATGAAGTCAGGCATAAAGATCAGAAGACCTC
AGTGCCTCCCTTCAACCTAAGAGAGCTGCTCCCCAAACAGCTGGGGCAGTACTTCCGCTACAATG
GCTCGCTCACAACTCCCCCTTGCTACCAGAGTGTGCTCTGGACAGTTTTTTATAGAAGGTCCCAG
ATTTCAATGGAACAGCTGGAAAAGCTTCAGGGGACATTGTTCTCCACAGAAGAGGAGCCCTCTAA
GCTTCTGGTACAGAACTACCGAGCCCTTCAGCCTCTCAATCAGCGCATGGTCTTTGCTTCTTTCA
TCCAAGCAGGATCCTCGTATACCACAGGTGAAATGCTGAGTCTAGGTGTAGGAATCTTGGTTGGC
TGTCTCTGCCTTCTCCTGGCTGTTTATTTCATTGCTAGAAAGATTCGGAAGAAGAGGCTGGAAAA
CCGAAAGAGTGTGGTCTTCACCTCAGCACAAGCCACGACTGAGGCATAAATTCCTTCTCAGATAC
CATGGATGTGGATGACTTCCCTTCATGCCTATCAGGAAGCCTCTAAAATGGGGTGTAGGATCTGG
CCAGAAACACTGTAGGAGTAGTAAGCAGATGTCCTCCTTCCCCTGGACATCTCTTAGAGAGGAAT
GGACCCAGGCTGTCATTCCAGGAAGAACTGCAGAGCCTTCAGCCTCTCCAAACATGTAGGAGGAA
ATGAGGAAATCGCTGTGTTGTTAATGCAGAGANCAAACTCTGTTTAGTTGCAGGGGAAGTTTGGG
ATATACCCCAAAGTCCTCTACCCCCTCACTTTTATGGCCCTTTCCCTAGATATACTGCGGGATCT
CTCCTTAGGATAAAGAGTTGCTGTTGAAGTTGTATATTTTTGATCAATATATTTGGAAATTAAAG
TTTCTGACTTT
```

FIGURE 74

MLFSALLLEVIWILAADGGQHWTYEGPHGQDHWPASYPECGNNAQSPIDIQTDSVTFDPDLPALQ
PHGYDQPGTEPLDLHNNGHTVQLSLPSTLYLGGLPRKYVAAQLHLHWGQKGSPGGSEHQINSEAT
FAELHIVHYDSDSYDSLSEAAERPQGLAVLGILIEVGETKNIAYEHILSHLHEVRHKDQKTSVPP
FNLRELLPKQLGQYFRYNGSLTTPPCYQSVLWTVFYRRSQISMEQLEKLQGTLFSTEEEPSKLLV
QNYRALQPLNQRMVFASFIQAGSSYTTGEMLSLGVGILVGCLCLLLAVYFIARKIRKKRLENRKS
VVFTSAQATTEA

Important features of the protein:

Signal peptide:

amino acids 1-15

Transmembrane domain:

amino acids 291-310

N-glycosylation site.

amino acids 213-216

Eukaryotic-type carbonic anhydrases proteins amino acids 197-245, 104-140, 22-69

FIGURE 75

TGCCGCTGCCGCCGCTGCTGCTGTTGCTCCTGGCGGCGCCTTGGGGACGGGCAGTTCCCTGTGTC
TCTGGTGGTTTGCCTAAACCTGCAAACATCACCTTCTTATCCATCAACATGAAGAATGTCCTACA
ATGGACTCCACCAGAGGGTCTTCAAGGAGTTAAAGTTACTTACACTGTGCAGTATTTCATCACAA
ATTGGCCCACCAGAGGTGGCACTGACTACAGATGAGAAGTCCATTTCTGTTGTCCTGACAGCTCC
AGAGAAGTGGAAGAGAAATCCAGAAGACCTTCCTGTTTCCATGCAACAAATATACTCCAATCTGA
AGTATAACGTGTCTGTGTTGAATACTAAATCAAACAGAACGTGGTCCCAGTGTGTGACCAACCAC
ACGCTGGTGCTCACCTGGCTGGAGCCGAACACTCTTTACTGCGTACACGTGGAGTCCTTCGTCCC
AGGGCCCCCTCGCCGTGCTCAGCCTTCTGAGAAGCAGTGTGCCAGGACTTTGAAAGATCAATCAT
CAGAGTTCAAGGCTAAAATCATCTTCTGGTATGTTTTGCCCATATCTATTACCGTGTTTCTTTTT
TCTGTGATGGGCTATTCCATCTACCGATATATCCACGTTGGCAAAGAGAAACACCCAGCAAATTT
GATTTTGATTTATGGAAATGAATTTGACAAAAGATTCTTTGTGCCTGCTGAAAAAATCGTGATTA
ACTTTATCACCCTCAATATCTCGGATGATTCTAAAATTTCTCATCAGGATATGAGTTTACTGGGA
AAAAGCAGTGATGTATCCAGCCTTAATGATCCTCAGCCCAGCGGGAACCTGAGGCCCCCTCAGGA
GGAAGAGGAGGTGAAACATTTAGGGTATGCTTCGCATTTGATGGAAATTTTTTGTGACTCTGAAG
AAAACACGGAAGGTACTTCTCTCACCCAGCAAGAGTCCCTCAGCAGAACAATACCCCCGGATAAA
ACAGTCATTGAATATGAATATGATGTCAGAACCACTGACATTTGTGCGGGGCCTGAAGAGCAGGA
GCTCAGTTTGCAGGAGGAGGTGTCCACACAAGGAACATTATTGGAGTCGCAGGCAGCGTTGGCAG
TCTTGGGCCCGCAAACGTTACAGTACTCATACACCCCTCAGCTCCAAGACTTAGACCCCCTGGCG
CAGGAGCACACAGACTCGGAGGAGGGGCCGGAGGAAGAGCCATCGACGACCCTGGTCGACTGGGA
TCCCCAAACTGGCAGGCTGTGTATTCCTTCGCTGTCCAGCTTCGACCAGGATTCAGAGGGCTGCG
AGCCTTCTGAGGGGGATGGGCTCGGAGAGGAGGGTCTTCTATCTAGACTCTATGAGGAGCCGGCT
CCAGACAGGCCACCAGGAGAAAATGAAACCTATCTCATGCAATTCATGGAGGAATGGGGGTTATA
TGTGCAGATGGAAAACTGATGCCAACACTTCCTTTTGCCTTTTGTTTCCTGTGCAAACAAGTGAG
TCACCCCTTTGATCCCAGCCATAAAGTACCTGGGATGAAAGAAGTTTTTCCAGTTTGTCAGTGT
CTGTGAGAATTACTTATTTCTTTTCTCTATTCTCATAGCACGTGTGTGATTGGTTCATGCATGTA
GGTCTCTTAACAATGATGGTGGGCCTCTGGAGTCCAGGGGCTGGCCGGTTGTTCTATGCAGAGAA
AGCAGTCAATAAATGTTTGCCAGACTGGGTGCAGAATTTATTCAGGTGGGTGT

FIGURE 76

MSYNGLHQRVFKELKLLTLCSISSQIGPPEVALTTDEKSISVVLTAPEKWKRNPEDLPVSMQQIY
SNLKYNVSVLNTKSNRTWSQCVTNHTLVLTWLEPNTLYCVHVESFVPGPPRRAQPSEKQCARTLK
DQSSEFKAKIIFWYVLPISITVFLFSVMGYSIYRYIHVGKEKHPANLILIYGNEFDKRFFVPAEK
IVINFITLNISDDSKISHQDMSLLGKSSDVSSLNDPQPSGNLRPPQEEEEVKHLGYASHLMEIFC
DSEENTEGTSLTQQESLSRTIPPDKTVIEYEYDVRTTDICAGPEEQELSLQEEVSTQGTLLESQA
ALAVLGPQTLQYSYTPQLQDLDPLAQEHTDSEEGPEEEPSTTLVDWDPQTGRLCIPSLSSFDQDS
EGCEPSEGDGLGEEGLLSRLYEEPAPDRPPGENETYLMQFMEEWGLYVQMEN

Important features:

Signal peptide:

amino acids 1-28

Transmembrane domain:

amino acids 140-163

N-glycosylation sites.

amino acids 71-74, 80-83, 89-92, 204-207, 423-426

FIGURE 77

GAGGAGCGGGCCGAGGACTCCAGCGTGCCCAGGTCTGGCATCCTGCACTTGCTGCCCTCTGACAC
CTGGGAAGATGGCCGGCCCGTGGACCTTCACCCTTCTCTGTGGTTTGCTGGCAGCCACCTTGATC
CAAGCCACCCTCAGTCCCACTGCAGTTCTCATCCTCGGCCCAAAAGTCATCAAAGAAAAGCTGAC
ACAGGAGCTGAAGGACCACAACGCCACCAGCATCCTGCAGCAGCTGCCGCTGCTCAGTGCCATGC
GGGAAAAGCCAGCCGGAGGCATCCCTGTGCTGGGCAGCCTGGTGAACACCGTCCTGAAGCACATC
ATCTGGCTGAAGGTCATCACAGCTAACATCCTCCAGCTGCAGGTGAAGCCCTCGGCCAATGACCA
GGAGCTGCTAGTCAAGATCCCCCTGGACATGGTGGCTGGATTCAACACGCCCCTGGTCAAGACCA
TCGTGGAGTTCCACATGACGACTGAGGCCCAAGCCACCATCCGCATGGACACCAGTGCAAGTGGC
CCCACCCGCCTGGTCCTCAGTGACTGTGCCACCAGCCATGGGAGCCTGCGCATCCAACTGCTGTA
TAAGCTCTCCTTCCTGGTGAACGCCTTAGCTAAGCAGGTCATGAACCTCCTAGTGCCATCCCTGC
CCAATCTAGTGAAAAACCAGCTGTGTCCCGTGATCGAGGCTTCCTTCAATGGCATGTATGCAGAC
CTCCTGCAGCTGGTGAAGGTGCCCATTTCCCTCAGCATTGACCGTCTGGAGTTTGACCTTCTGTA
TCCTGCCATCAAGGGTGACACCATTCAGCTCTACCTGGGGGCCAAGTTGTTGGACTCACAGGGAA
AGGTGACCAAGTGGTTCAATAACTCTGCAGCTTCCCTGACAATGCCCACCCTGGACAACATCCCG
TTCAGCCTCATCGTGAGTCAGGACGTGGTGAAAGCTGCAGTGGCTGCTGTGCTCTCTCCAGAAGA
ATTCATGGTCCTGTTGGACTCTGTGCTTCCTGAGAGTGCCCATCGGCTGAAGTCAAGCATCGGGC
TGATCAATGAAAAGGCTGCAGATAAGCTGGGATCTACCCAGATCGTGAAGATCCTAACTCAGGAC
ACTCCCGAGTTTTTTATAGACCAAGGCCATGCCAAGGTGGCCCAACTGATCGTGCTGGAAGTGTT
TCCCTCCAGTGAAGCCCTCCGCCCTTTGTTCACCCTGGGCATCGAAGCCAGCTCGGAAGCTCAGT
TTTACACCAAAGGTGACCAACTTATACTCAACTTGAATAACATCAGCTCTGATCGGATCCAGCTG
ATGAACTCTGGGATTGGCTGGTTCCAACCTGATGTTCTGAAAAACATCATCACTGAGATCATCCA
CTCCATCCTGCTGCCGAACCAGAATGGCAAATTAAGATCTGGGGTCCCAGTGTCATTGGTGAAGG
CCTTGGGATTCGAGGCAGCTGAGTCCTCACTGACCAAGGATGCCCTTGTGCTTACTCCAGCCTCC
TTGTGGAAACCCAGCTCTCCTGTCTCCCAGTGAAGACTTGGATGGCAGCCATCAGGGAAGGCTGG
GTCCCAGCTGGGAGTATGGGTGTGAGCTCTATAGACCATCCCTCTCTGCAATCAATAAACACTTG
CCTGTGAAAAA

FIGURE 78

MAGPWTFTLLCGLLAATLIQATLSPTAVLILGPKVIKEKLTQELKDHNATSILQQLPLLSAMREK
PAGGIPVLGSLVNTVLKHIIWLKVITANILQLQVKPSANDQELLVKIPLDMVAGFNTPLVKTIVE
FHMTTEAQATIRMDTSASGPTRLVLSDCATSHGSLRIQLLYKLSFLVNALAKQVMNLLVPSLPNL
VKNQLCPVIEASFNGMYADLLQLVKVPISLSIDRLEFDLLYPAIKGDTIQLYLGAKLLDSQGKVT
KWFNNSAASLTMPTLDNIPFSLIVSQDVVKAAVAAVLSPEEFMVLLDSVLPESAHRLKSSIGLIN
EKAADKLGSTQIVKILTQDTPEFFIDQGHAKVAQLIVLEVFPSSEALRPLFTLGIEASSEAQFYT
KGDQLILNLNNISSDRIQLMNSGIGWFQPDVLKNIITEIIHSILLPNQNGKLRSGVPVSLVKALG
FEAAESSLTKDALVLTPASLWKPSSPVSQ

Important features of the protein:

Signal peptide:

amino acids 1-21

N-glycosylation sites.

amino acids 48-51, 264-267, 401-404

Glycosaminoglycan attachment site.

amino acids 412-415

LBP / BPI / CETP family proteins.

amino acids 407-457

FIGURE 79

GAGAGAAGTCAGCCTGGCAGAGAGACTCTGAAATGAGGGATTAGAGGTGTTCAAGGAGCAAGAGC
TTCAGCCTGAAGACAAGGGAGCAGTCCCTGAAGACGCTTCTACTGAGAGGTCTGCCATGGCCTCT
CTTGGCCTCCAACTTGTGGGCTACATCCTAGGCCTTCTGGGGCTTTTGGGCACACTGGTTGCCAT
GCTGCTCCCCAGCTGGAAAACAAGTTCTTATGTCGGTGCCAGCATTGTGACAGCAGTTGGCTTCT
CCAAGGGCCTCTGGATGGAATGTGCCACACACAGCACAGGCATCACCCAGTGTGACATCTATAGC
ACCCTTCTGGGCCTGCCCGCTGACATCCAGGCTGCCCAGGCCATGATGGTGACATCCAGTGCAAT
CTCCTCCCTGGCCTGCATTATCTCTGTGGTGGGCATGAGATGCACAGTCTTCTGCCAGGAATCCC
GAGCCAAAGACAGAGTGGCGGTAGCAGGTGGAGTCTTTTTCATCCTTGGAGGCCTCCTGGGATTC
ATTCCTGTTGCCTGGAATCTTCATGGGATCCTACGGGACTTCTACTCACCACTGGTGCCTGACAG
CATGAAATTTGAGATTGGAGAGGCTCTTTACTTGGGCATTATTTCTTCCCTGTTCTCCCTGATAG
CTGGAATCATCCTCTGCTTTTCCTGCTCATCCCAGAGAAATCGCTCCAACTACTACGATGCCTAC
CAAGCCCAACCTCTTGCCACAAGGAGCTCTCCAAGGCCTGGTCAACCTCCCAAAGTCAAGAGTGA
GTTCAATTCCTACAGCCTGACAGGGTATGTGTGAAGAACCAGGGGCCAGAGCTGGGGGGTGGCTG
GGTCTGTGAAAAACAGTGGACAGCACCCCGAGGGCCACAGGTGAGGGACACTACCACTGGATCGT
GTCAGAAGGTGCTGCTGAGGATAGACTGACTTTGGCCATTGGATTGAGCAAAGGCAGAAATGGGG
GCTAGTGTAACAGCATGCAGGTTGAATTGCCAAGGATGCTCGCCATGCCAGCCTTTCTGTTTTCC
TCACCTTGCTGCTCCCCTGCCCTAAGTCCCCAACCCTCAACTTGAAACCCCATTCCCTTAAGCCA
GGACTCAGAGGATCCCTTTGCCCTCTGGTTTACCTGGGACTCCATCCCCAAACCCACTAATCACA
TCCCACTGACTGACCCTCTGTGATCAAAGACCCTCTCTCTGGCTGAGGTTGGCTCTTAGCTCATT
GCTGGGGATGGGAAGGAGAAGCAGTGGCTTTTGTGGGCATTGCTCTAACCTACTTCTCAAGCTTC
CCTCCAAAGAAACTGATTGGCCCTGGAACCTCCATCCCACTCTTGTTATGACTCCACAGTGTCCA
GACTAATTTGTGCATGAACTGAAATAAAACCATCCTACGGTATCCAGGGAACAGAAAGCAGGATG
CAGGATGGGAGGACAGGAAGGCAGCCTGGGACATTTAAAAAAATA

FIGURE 8o

MASLGLQLVGYILGLLGLLGTLVAMLLPSWKTSSYVGASIVTAVGFSKGLWMECATHSTGITQCD
IYSTLLGLPADIQAAQAMMVTSSAISSLACIISVVGMRCTVFCQESRAKDRVAVAGGVFFILGGL
LGFIPVAWNLHGILRDFYSPLVPDSMKFEIGEALYLGIISSLFSLIAGIILCFSCSSQRNRSNYY
DAYQAQPLATRSSPRPGQPPKVKSEFNSYSLTGYV

Important features of the protein:

Signal peptide:

amino acids 1-24

Transmembrane domains:

amino acids 82-102, 117-140, 163-182

N-glycosylation site.

amino acids 190-193

PMP-22 / EMP / MP20 family proteins.

amino acids 46-59

FIGURE 81

CCCACGCGTCCGCGCCTCTCCCTTCTGCTGGACCTTCCTTCGTCTCTCCATCTCTCCCTCCTTTC
CCCGCGTTCTCTTTCCACCTTTCTCTTCTTCCCACCTTAGACCTCCCTTCCTGCCCTCCTTTCCT
GCCCACCGCTGCTTCCTGGCCCTTCTCCGACCCCGCTCTAGCAGCAGACCTCCTGGGGTCTGTGG
GTTGATCTGTGGCCCCTGTGCCTCCGTGTCCTTTTCGTCTCCCTTCCTCCCGACTCCGCTCCCGG
ACCAGCGGCCTGACCCTGGGGAAAGGATGGTTCCCGAGGTGAGGGTCCTCTCCTCCTTGCTGGGA
CTCGCGCTGCTCTGGTTCCCCCTGGACTCCCACGCTCGAGCCCGCCCAGACATGTTCTGCCTTTT
CCATGGGAAGAGATACTCCCCCGGCGAGAGCTGGCACCCCTACTTGGAGCCACAAGGCCTGATGT
ACTGCCTGCGCTGTACCTGCTCAGAGGGCGCCCATGTGAGTTGTTACCGCCTCCACTGTCCGCCT
GTCCACTGCCCCCAGCCTGTGACGGAGCCACAGCAATGCTGTCCCAAGTGTGTGGAACCTCACAC
TCCCTCTGGACTCCGGGCCCCACCAAAGTCCTGCCAGCACAACGGGACCATGTACCAACACGGAG
AGATCTTCAGTGCCCATGAGCTGTTCCCCTCCCGCCTGCCCAACCAGTGTGTCCTCTGCAGCTGC
ACAGAGGGCCAGATCTACTGCGGCCTCACAACCTGCCCCGAACCAGGCTGCCCAGCACCCCTCCC
ACTGCCAGACTCCTGCTGCCAAGCCTGCAAAGATGAGGCAAGTGAGCAATCGGATGAAGAGGACA
GTGTGCAGTCGCTCCATGGGGTGAGACATCCTCAGGATCCATGTTCCAGTGATGCTGGGAGAAAG
AGAGGCCCGGGCACCCCAGCCCCCACTGGCCTCAGCGCCCCTCTGAGCTTCATCCCTCGCCACTT
CAGACCCAAGGGAGCAGGCAGCACAACTGTCAAGATCGTCCTGAAGGAGAAACATAAGAAAGCCT
GTGTGCATGGCGGGAAGACGTACTCCCACGGGGAGGTGTGGCACCCGGCCTTCCGTGCCTTCGGC
CCCTTGCCCTGCATCCTATGCACCTGTGAGGATGGCCGCCAGGACTGCCAGCGTGTGACCTGTCC
CACCGAGTACCCCTGCCGTCACCCCGAGAAAGTGGCTGGGAAGTGCTGCAAGATTTGCCCAGAGG
ACAAAGCAGACCCTGGCCACAGTGAGATCAGTTCTACCAGGTGTCCCAAGGCACCGGGCCGGGTC
CTCGTCCACACATCGGTATCCCCAAGCCCAGACAACCTGCGTCGCTTTGCCCTGGAACACGAGGC
CTCGGACTTGGTGGAGATCTACCTCTGGAAGCTGGTAAAAGATGAGGAAACTGAGGCTCAGAGAG
GTGAAGTACCTGGCCCAAGGCCACACAGCCAGAATCTTCCACTTGACTCAGATCAAGAAAGTCAG
GAAGCAAGACTTCCAGAAAGAGGCACAGCACTTCCGACTGCTCGCTGGCCCCCACGAAGGTCACT
GGAACGTCTTCCTAGCCCAGACCCTGGAGCTGAAGGTCACGGCCAGTCCAGACAAAGTGACCAAG
ACATAACAAAGACCTAACAGTTGCAGATATGAGCTGTATAATTGTTGTTATTATATATTAATAAA
TAAGAAGTTGCATTACCCTCAAAAAAAAAAAAAAAAAAA

FIGURE 82

MVPEVRVLSSLLGLALLWFPLDSHARARPDMFCLFHGKRYSPGESWHPYLEPQGLMYCLRCTCSE
GAHVSCYRLHCPPVHCPQPVTEPQQCCPKCVEPHTPSGLRAPPKSCQHNGTMYQHGEIFSAHELF
PSRLPNQCVLCSCTEGQIYCGLTTCPEPGCPAPLPLPDSCCQACKDEASEQSDEEDSVQSLHGVR
HPQDPCSSDAGRKRGPGTPAPTGLSAPLSFIPRHFRPKGAGSTTVKIVLKEKHKKACVHGGKTYS
HGEVWHPAFRAFGPLPCILCTCEDGRQDCQRVTCPTEYPCRHPEKVAGKCCKICPEDKADPGHSE
ISSTRCPKAPGRVLVHTSVSPSPDNLRRFALEHEASDLVEIYLWKLVKDEETEAQRGEVPGPRPH
SQNLPLDSDQESQEARLPERGTALPTARWPPRRSLERLPSPDPGAEGHGQSRQSDQDITKT

Signal peptide:

amino acids 1-25

FIGURE 83

GACAGCTGTGTCTCGATGGAGTAGACTCTCAGAACAGCGCAGTTTGCCCTCCGCTCACGCAGAGCCTCTCC
GTGGCTTCCGCACCTTGAGCATTAGGCCAGTTCTCCTCTTCTCTCTAATCCATCCGTCACCTCTCCTGTCA
TCCGTTTCCATGCCGTGAGGTCCATTCACAGAACACATCCATGGCTCTCATGCTCAGTTTGGTTCTGAGTC
TCCTCAAGCTGGGATCAGGGCAGTGGCAGGTGTTTGGGCCAGACAAGCCTGTCCAGGCCTTGGTGGGGAG
GACGCAGCATTCTCCTGTTTCCTGTCTCCTAAGACCAATGCAGAGGCCATGGAAGTGCGGTTCTTCAGGGG
CCAGTTCTCTAGCGTGGTCCACCTCTACAGGGACGGGAAGGACCAGCCATTTATGCAGATGCCACAGTATC
AAGGCAGGACAAAACTGGTGAAGGATTCTATTGCGGAGGGGCGCATCTCTCTGAGGCTGGAAAACATTACT
GTGTTGGATGCTGGCCTCTATGGGTGCAGGATTAGTTCCCAGTCTTACTACCAGAAGGCCATCTGGGAGCT
ACAGGTGTCAGCACTGGGCTCAGTTCCTCTCATTTCCATCACGGGATATGTTGATAGAGACATCCAGCTAC
TCTGTCAGTCCTCGGGCTGGTTCCCCCGGCCCACAGCGAAGTGGAAAGGTCCACAAGGACAGGATTTGTCC
ACAGACTCCAGGACAAACAGAGACATGCATGGCCTGTTTGATGTGGAGATCTCTCTGACCGTCCAAGAGAA
CGCCGGGAGCATATCCTGTTCCATGCGGCATGCTCATCTGAGCCGAGAGGTGGAATCCAGGGTACAGATAG
GAGATACCTTTTTCGAGCCTATATCGTGGCACCTGGCTACCAAAGTACTGGGAATACTCTGCTGTGGCCTA
TTTTTTGGCATTGTTGGACTGAAGATTTTCTTCTCCAAATTCCAGTGGAAAATCCAGGCGGAACTGGACTG
GAGAAGAAAGCACGGACAGGCAGAATTGAGAGACGCCCGGAAACACGCAGTGGAGGTGACTCTGGATCCAG
AGACGGCTCACCCGAAGCTCTGCGTTTCTGATCTGAAAACTGTAACCCATAGAAAAGCTCCCCAGGAGGTG
CCTCACTCTGAGAAGAGATTTACAAGGAAGAGTGTGGTGGCTTCTCAGAGTTTCCAAGCAGGGAAACATTA
CTGGGAGGTGGACGGAGGACACAATAAAAGGTGGCGCGTGGGAGTGTGCCGGGATGATGTGGACAGGAGGA
AGGAGTACGTGACTTTGTCTCCCGATCATGGGTACTGGGTCCTCAGACTGAATGGAGAACATTTGTATTTC
ACATTAAATCCCCGTTTTATCAGCGTCTTCCCCAGGACCCCACCTACAAAAATAGGGGTCTTCCTGGACTA
TGAGTGTGGGACCATCTCCTTCTTCAACATAAATGACCAGTCCCTTATTTATACCCTGACATGTCGGTTTG
AAGGCTTATTGAGGCCCTACATTGAGTATCCGTCCTATAATGAGCAAAATGGAACTCCCATAGTCATCTGC
CCAGTCACCCAGGAATCAGAGAAAGAGGCCTCTTGGCAAAGGGCCTCTGCAATCCCAGAGACAAGCAACAG
TGAGTCCTCCTCACAGGCAACCACGCCCTTCCTCCCCAGGGGTGAAATGTAGGATGAATCACATCCCACAT
TCTTCTTTAGGGATATTAAGGTCTCTCTCCCAGATCCAAAGTCCCGCAGCAGCCGGCCAAGGTGGCTTCCA
GATGAAGGGGGACTGGCCTGTCCACATGGGAGTCAGGTGTCATGGCTGCCCTGAGCTGGGAGGGAAGAAGG
CTGACATTACATTTAGTTTGCTCTCACTCCATCTGGCTAAGTGATCTTGAAATACCACCTCTCAGGTGAAG
AACCGTCAGGAATTCCCATCTCACAGGCTGTGGTGTAGATTAAGTAGACAAGGAATGTGAATAATGCTTAG
ATCTTATTGATGACAGAGTGTATCCTAATGGTTTGTTCATTATATTACACTTTCAGTAAAAAAA

FIGURE 84

MALMLSLVLSLLKLGSGQWQVFGPDKPVQALVGEDAAFSCFLSPKTNAEAMEVRFFRGQFSSVVH
LYRDGKDQPFMQMPQYQGRTKLVKDSIAEGRISLRLENITVLDAGLYGCRISSQSYYQKAIWELQ
VSALGSVPLISITGYVDRDIQLLCQSSGWFPRPTAKWKGPQGQDLSTDSRTNRDMHGLFDVEISL
TVQENAGSISCSMRHAHLSREVESRVQIGDTFFEPISWHLATKVLGILCCGLFFGIVGLKIFFSK
FQWKIQAELDWRRKHGQAELRDARKHAVEVTLDPETAHPKLCVSDLKTVTHRKAPQEVPHSEKRF
TRKSVVASQSFQAGKHYWEVDGGHNKRWRVGVCRDDVDRRKEYVTLSPDHGYWVLRLNGEHLYFT
LNPRFISVFPRTPPTKIGVFLDYECGTISFFNINDQSLIYTLTCRFEGLLRPYIEYPSYNEQNGT
PIVICPVTQESEKEASWQRASAIPETSNSESSSQATTPFLPRGEM

Signal peptide:

amino acids 1-17

Transmembrane domain:

amino acids 239-255

FIGURE 85

AACAGACGTTCCCTCGCGGCCCTGGCACCTCTAACCCCAGACATGCTGCTGCTGCTGCCCCT
GCTCTGGGGGAGGGAGAGGGCGGAAGGACAGACAAGTAAACTGCTGACGATGCAGAGTTCCGTGA
CGGTGCAGGAAGGCCTGTGTGTCCATGTGCCCTGCTCCTTCTCCTACCCCTCGCATGGCTGGATT
TACCCTGGCCCAGTAGTTCATGGCTACTGGTTCCGGGAAGGGGCCAATACAGACCAGGATGCTCC
AGTGGCCACAAACAACCCAGCTCGGGCAGTGTGGGAGGAGACTCGGGACCGATTCCACCTCCTTG
GGGACCCACATACCAAGAATTGCACCCTGAGCATCAGAGATGCCAGAAGAAGTGATGCGGGGAGA
TACTTCTTTCGTATGGAGAAAGGAAGTATAAAATGGAATTATAAACATCACCGGCTCTCTGTGAA
TGTGACAGCCTTGACCCACAGGCCCAACATCCTCATCCCAGGCACCCTGGAGTCCGGCTGCCCCC
AGAATCTGACCTGCTCTGTGCCCTGGGCCTGTGAGCAGGGGACACCCCCTATGATCTCCTGGATA
GGGACCTCCGTGTCCCCCCTGGACCCCTCCACCACCCGCTCCTCGGTGCTCACCCTCATCCCACA
GCCCCAGGACCATGGCACCAGCCTCACCTGTCAGGTGACCTTCCCTGGGGCCAGCGTGACCACGA
ACAAGACCGTCCATCTCAACGTGTCCTACCCGCCTCAGAACTTGACCATGACTGTCTTCCAAGGA
GACGGCACAGTATCCACAGTCTTGGGAAATGGCTCATCTCTGTCACTCCCAGAGGGCCAGTCTCT
GCGCCTGGTCTGTGCAGTTGATGCAGTTGACAGCAATCCCCCTGCCAGGCTGAGCCTGAGCTGGA
GAGGCCTGACCCTGTGCCCCTCACAGCCCTCAAACCCGGGGGTGCTGGAGCTGCCTTGGGTGCAC
CTGAGGGATGCAGCTGAATTCACCTGCAGAGCTCAGAACCCTCTCGGCTCTCAGCAGGTCTACCT
GAACGTCTCCCTGCAGAGCAAAGCCACATCAGGAGTGACTCAGGGGGTGGTCGGGGGAGCTGGAG
CCACAGCCCTGGTCTTCCTGTCCTTCTGCGTCATCTTCGTTGTAGTGAGGTCCTGCAGGAAGAAA
TCGGCAAGGCCAGCAGCGGGCGTGGGAGATACGGGCATAGAGGATGCAAACGCTGTCAGGGGTTC
AGCCTCTCAGGGGCCCCTGACTGAACCTTGGGCAGAAGACAGTCCCCCAGACCAGCCTCCCCCAG
CTTCTGCCCGCTCCTCAGTGGGGGAAGGAGAGCTCCAGTATGCATCCCTCAGCTTCCAGATGGTG
AAGCCTTGGGACTCGCGGGGACAGGAGGCCACTGACACCGAGTACTCGGAGATCAAGATCCACAG
ATGAGAAACTGCAGAGACTCACCCTGATTGAGGGATCACAGCCCCTCCAGGCAAGGGAGAAGTCA
GAGGCTGATTCTTGTAGAATTAACAGCCCTCAACGTGATGAGCTATGATAACACTATGAATTATG
TGCAGAGTGAAAAGCACACAGGCTTTAGAGTCAAAGTATCTCAAACCTGAATCCACACTGTGCCC
TCCCTTTTATTTTTTTAACTAAAAGACAGACAAATTCCTA

FIGURE 86

MLLLLLPLLWGRERAEGQTSKLLTMQSSVTVQEGLCVHVPCSFSYPSHGWIYPGPVVHGYWFREG
ANTDQDAPVATNNPARAVWEETRDRFHLLGDPHTKNCTLSIRDARRSDAGRYFFRMEKGSIKWNY
KHHRLSVNVTALTHRPNILIPGTLESGCPQNLTCSVPWACEQGTPPMISWIGTSVSPLDPSTTRS
SVLTLIPQPQDHGTSLTCQVTFPGASVTTNKTVHLNVSYPPQNLTMTVFQGDGTVSTVLGNGSSL
SLPEGQSLRLVCAVDAVDSNPPARLSLSWRGLTLCPSQPSNPGVLELPWVHLRDAAEFTCRAQNP
LGSQQVYLNVSLQSKATSGVTQGVVGGAGATALVFLSFCVIFVVVRSCRKKSARPAAGVGDTGIE
DANAVRGSASQGPLTEPWAEDSPPDQPPPASARSSVGEGELQYASLSFQMVKPWDSRGQEATDTE
YSEIKIHR

Signal peptide:

amino acids 1-15

Transmembrane domain:

amino acids 351-370

FIGURE 87

AGAAAGCTGCACTCTGTTGAGCTCCAGGGCGCAGTGGAGGGAGGGAGTGAAGGAGCTCTCTGTAC
CCAAGGAAAGTGCAGCTGAGACTCAGACAAGATTACAATGAACCAACTCAGCTTCCTGCTGTTTC
TCATAGCGACCACCAGAGGATGGAGTACAGATGAGGCTAATACTTACTTCAAGGAATGGACCTGT
TCTTCGTCTCCATCTCTGCCCAGAAGCTGCAAGGAAATCAAAGACGAATGTCCTAGTGCATTTGA
TGGCCTGTATTTTCTCCGCACTGAGAATGGTGTTATCTACCAGACCTTCTGTGACATGACCTCTG
GGGGTGGCGGCTGGACCCTGGTGGCCAGCGTGCATGAGAATGACATGCGTGGGAAGTGCACGGTG
GGCGATCGCTGGTCCAGTCAGCAGGGCAGCAAAGCAGACTACCCAGAGGGGGACGGCAACTGGGC
CAACTACAACACCTTTGGATCTGCAGAGGCGGCCACGAGCGATGACTACAAGAACCCTGGCTACT
ACGACATCCAGGCCAAGGACCTGGGCATCTGGCACGTGCCCAATAAGTCCCCCATGCAGCACTGG
AGAAACAGCTCCCTGCTGAGGTACCGCACGGACACTGGCTTCCTCCAGACACTGGGACATAATCT
GTTTGGCATCTACCAGAAATATCCAGTGAAATATGGAGAAGGAAAGTGTTGGACTGACAACGGCC
CGGTGATCCCTGTGGTCTATGATTTTGGCGACGCCCAGAAAACAGCATCTTATTACTCACCCTAT
GGCCAGCGGGAATTCACTGCGGGATTTGTTCAGTTCAGGGTATTTAATAACGAGAGAGCAGCCAA
CGCCTTGTGTGCTGGAATGAGGGTCACCGGATGTAACACTGAGCATCACTGCATTGGTGGAGGAG
GATACTTTCCAGAGGCCAGTCCCCAGCAGTGTGGAGATTTTTCTGGTTTTGATTGGAGTGGATAT
GGAACTCATGTTGGTTACAGCAGCAGCCGTGAGATAACTGAGGCAGCTGTGCTTCTATTCTATCG
TTGAGAGTTTTGTGGGAGGGAACCCAGACCTCTCCTCCCAACCATGAGATCCCAAGGATGGAGAA
CAACTTACCCAGTAGCTAGAATGTTAATGGCAGAAGAGAAAACAATAAATCATATTGACTCAAGA
AAAAAA

FIGURE 88

MNQLSFLLFLIATTRGWSTDEANTYFKEWTCSSSPSLPRSCKEIKDECPSAFDGLYFLRTENGVI
YQTFCDMTSGGGGWTLVASVHENDMRGKCTVGDRWSSQQGSKADYPEGDGNWANYNTFGSAEAAT
SDDYKNPGYYDIQAKDLGIWHVPNKSPMQHWRNSSLLRYRTDTGFLQTLGHNLFGIYQKYPVKYG
EGKCWTDNGPVIPVVYDFGDAQKTASYYSPYGQREFTAGFVQFRVFNNERAANALCAGMRVTGCN
TEHHCIGGGGYFPEASPQQCGDFSGFDWSGYGTHVGYSSSREITEAAVLLFYR

Important features:

Signal peptide:

amino acids 1-16

N-glycosylation site.

amino acids 163-167

Glycosaminoglycan attachment sites.

amino acids 74-78, 289-293

N-myristoylation sites.

amino acids 76-82, 115-121, 124-130, 253-259, 292-298

FIGURE 89

CTAGATTTGTCGGCTTGCGGGGAGACTTCAGGAGTCGCTGTCTCTGAACTTCCAGCCTCAGAGAC
CGCCGCCCTTGTCCCCGAGGGCCATGGGCCGGGTCTCAGGGCTTGTGCCCTCTCGCTTCCTGACG
CTCCTGGCGCATCTGGTGGTCGTCATCACCTTATTCTGGTCCCGGGACAGCAACATACAGGCCTG
CCTGCCTCTCACGTTCACCCCCGAGGAGTATGACAAGCAGGACATTCAGCTGGTGGCCGCGCTCT
CTGTCACCCTGGGCCTCTTTGCAGTGGAGCTGGCCGGTTTCCTCTCAGGAGTCTCCATGTTCAAC
AGCACCCAGAGCCTCATCTCCATTGGGGCTCACTGTAGTGCATCCGTGGCCCTGTCCTTCTTCAT
ATTCGAGCGTTGGGAGTGCACTACGTATTGGTACATTTTTGTCTTCTGCAGTGCCCTTCCAGCTG
TCACTGAAATGGCTTTATTCGTCACCGTCTTTGGGCTGAAAAAGAAACCCTTCTGATTACCTTCA
TGACGGGAACCTAAGGACGAAGCCTACAGGGGCAAGGGCCGCTTCGTATTCCTGGAAGAAGGAAG
GCATAGGCTTCGGTTTTCCCCTCGGAAACTGCTTCTGCTGGAGGATATGTGTTGGAATAATTACG
TCTTGAGTCTGGGATTATCCGCATTGTATTTAGTGCTTTGTAATAAAATATGTTTTGTAGTAACA
TTAAGACTTATATACAGTTTTAGGGGACAATTAAAAAAAAAAAA

FIGURE 90

MGRVSGLVPSRFLTLLAHLVVVITLFWSRDSNIQACLPLTFTPEEYDKQDIQLVAALSVTLGLFA
VELAGFLSGVSMFNSTQSLISIGAHCSASVALSFFIFERWECTTYWYIFVFCSALPAVTEMALFV
TVFGLKKKPF

Transmembrane domain:

amino acids 12-28 (type II), 51-66, 107-124

FIGURE 91

CTGGGACCCCGAAAAGAGAAGGGGAGAGCGAGGGGACGAGAGCGGAGGAGGAAGATGCAACTGAC
TCGCTGCTGCTTCGTGTTCCTGGTGCAGGGTAGCCTCTATCTGGTCATCTGTGGCCAGGATGATG
GTCCTCCCGGCTCAGAGGACCCTGAGCGTGATGACCACGAGGGCCAGCCCCGGCCCCGGGTGCCT
CGGAAGCGGGGCCACATCTCACCTAAGTCCCGCCCCATGGCCAATTCCACTCTCCTAGGGCTGCT
GGCCCCGCCTGGGGAGGCTTGGGGCATTCTTGGGCAGCCCCCCAACCGCCCGAACCACAGCCCCC
CACCCTCAGCCAAGGTGAAGAAAATCTTTGGCTGGGGCGACTTCTACTCCAACATCAAGACGGTG
GCCCTGAACCTGCTCGTCACAGGGAAGATTGTGGACCATGGCAATGGGACCTTCAGCGTCCACTT
CCAACACAATGCCACAGGCCAGGGAAACATCTCCATCAGCCTCGTGCCCCCCAGTAAAGCTGTAG
AGTTCCACCAGGAACAGCAGATCTTCATCGAAGCCAAGGCCTCCAAAATCTTCAACTGCCGGATG
GAGTGGGAGAAGGTAGAACGGGGCCGCCGGACCTCGCTTTGCACCCACGACCCAGCCAAGATCTG
CTCCCGAGACCACGCTCAGAGCTCAGCCACCTGGAGCTGCTCCCAGCCCTTCAAAGTCGTCTGTG
TCTACATCGCCTTCTACAGCACGGACTATCGGCTGGTCCAGAAGGTGTGCCCAGATTACAACTAC
CATAGTGATACCCCCTACTACCCATCTGGGTGACCCGGGGCAGGCCACAGAGGCCAGGCCAGGGC
TGGAAGGACAGGCCTGCCCATGCAGGAGACCATCTGGACACCGGGCAGGGAAGGGGTTGGGCCTC
AGGCAGGGAGGGGGGTGGAGACGAGGAGATGCCAAGTGGGGCCAGGGCCAAGTCTCAAGTGGCAG
AGAAAGGGTCCCAAGTGCTGGTCCCAACCTGAAGCTGTGGAGTGACTAGATCACAGGAGCACTGG
AGGAGGAGTGGGCTCTCTGTGCAGCCTCACAGGGCTTTGCCACGGAGCCACAGAGAGATGCTGGG
TCCCCGAGGCCTGTGGGCAGGCCGATCAGTGTGGCCCCAGATCAAGTCATGGGAGGAAGCTAAGC
CCTTGGTTCTTGCCATCCTGAGGAAAGATAGCAACAGGGAGGGGGAGATTTCATCAGTGTGGACA
GCCTGTCAACTTAGGATGGATGGCTGAGAGGGCTTCCTAGGAGCCAGTCAGCAGGGTGGGGTGGG
GCCAGAGGAGCTCTCCAGCCCTGCCTAGTGGGCGCCCTGAGCCCCTTGTCGTGTGCTGAGCATGG
CATGAGGCTGAAGTGGCAACCCTGGGGTCTTTGATGTCTTGACAGATTGACCATCTGTCTCCAGC
CAGGCCACCCCTTTCCAAAATTCCCTCTTCTGCCAGTACTCCCCCTGTACCACCCATTGCTGATG
GCACACCCATCCTTAAGCTAAGACAGGACGATTGTGGTCCTCCCACACTAAGGCCACAGCCCATC
CGCGTGCTGTGTGTCCCTCTTCCACCCCAACCCCTGCTGGCTCCTCTGGGAGCATCCATGTCCCG
GAGAGGGGTCCCTCAACAGTCAGCCTCACCTGTCAGACCGGGGTTCTCCCGGATCTGGATGGCGC
CGCCCTCTCAGCAGCGGGCACGGGTGGGGCGGGGCCGGGCCGCAGAGCATGTGCTGGATCTGTTC
TGTGTGTCTGTCTGTGGGTGGGGGAGGGGAGGGAAGTCTTGTGAAACCGCTGATTGCTGACTTT
TGTGTGAAGAATCGTGTTCTTGGAGCAGGAAATAAAGCTTGCCCCGGGGCA

FIGURE 92

MQLTRCCFVFLVQGSLYLVICGQDDGPPGSEDPERDDHEGQPRPRVPRKRGHISPKSRPMANSTL
LGLLAPPGEAWGILGQPPNRPNHSPPPSAKVKKIFGWGDFYSNIKTVALNLLVTGKIVDHGNGTF
SVHFQHNATGQGNISISLVPPSKAVEFHQEQQIFIEAKASKIFNCRMEWEKVERGRRTSLCTHDP
AKICSRDHAQSSATWSCSQPFKVVCVYIAFYSTDYRLVQKVCPDYNYHSDTPYYPSG

Important features of the protein:

Signal peptide:

amino acids 1-14

N-glycosylation sites.

amino acids 62-65, 127-130, 137-140, 143-146

2-oxo acid dehydrogenases acyltransferase amino acids 61-71

FIGURE 93

CGGTGGCCATGACTGCGGCCGTGTTCTTCGGCTGCGCCTTCATTGCCTTCGGGCCTGCGCTCGCC
CTTTATGTCTTCACCATCGCCATCGAGCCGTTGCGTATCATCTTCCTCATCGCCGGAGCTTTCTT
CTGGTTGGTGTCTCTACTGATTTCGTCCCTTGTTTGGTTCATGGCAAGAGTCATTATTGACAACA
AAGATGGACCAACACAGAAATATCTGCTGATCTTTGGAGCGTTTGTCTCTGTCTATATCCAAGAA
ATGTTCCGATTTGCATATTATAAACTCTTAAAAAAAGCCAGTGAAGGTTTGAAGAGTATAAACCC
AGGTGAGACAGCACCCTCTATGCGACTGCTGGCCTATGTTTCTGGCTTGGGCTTTGGAATCATGA
GTGGAGTATTTTCCTTTGTGAATACCCTATCTGACTCCTTGGGGCCAGGCACAGTGGGCATTCAT
GGAGATTCTCCTCAATTCTTCCTTTATTCAGCTTTCATGACGCTGGTCATTATCTTGCTGCATGT
ATTCTGGGGCATTGTATTTTTTGATGGCTGTGAGAAGAAAAAGTGGGGCATCCTCCTTATCGTTC
TCCTGACCCACCTGCTGGTGTCAGCCCAGACCTTCATAAGTTCTTATTATGGAATAAACCTGGCG
TCAGCATTTATAATCCTGGTGCTCATGGGCACCTGGGCATTCTTAGCTGCGGGAGGCAGCTGCCG
AAGCCTGAAACTCTGCCTGCTCTGCCAAGACAAGAACTTTCTTCTTTACAACCAGCGCTCCAGAT
AACCTCAGGGAACCAGCACTTCCCAAACCGCAGACTACATCTTTAGAGGAAGCACAACTGTGCCT
TTTTCTGAAAATCCCTTTTTCTGGTGGAATTGAGAAAGAAATAAAACTATGCAGATA

FIGURE 94

MTAAVFFGCAFIAFGPALALYVFTIAIEPLRIIFLIAGAFFWLVSLLISSLVWFMARVIIDNKDG
PTQKYLLIFGAFVSVYIQEMFRFAYYKLLKKASEGLKSINPGETAPSMRLLAYVSGLGFGIMSGV
FSFVNTLSDSLGPGTVGIHGDSPQFFLYSAFMTLVIILLHVFWGIVFFDGCEKKKWGILLIVLLT
HLLVSAQTFISSYYGINLASAFIILVLMGTWAFLAAGGSCRSLKLCLLCQDKNFLLYNQRSR

Important features of the protein:

Signal peptide:

amino acids 1-19

Transmembrane domains:

amino acids 32-51, 119-138, 152-169, 216-235

Glycosaminoglycan attachment site.

amino acids 120-123

Sodium:neurotransmitter symporter family protein amino acids 31-65

FIGURE 95

AATTTTTCACCAGAGTAAACTTGAGAAACCAACTGGACCTTGAGTATTGTACATTTTGCCTCGTG
GACCCAAAGGTAGCAATCTGAAAC<u>ATG</u>AGGAGTACGATTCTACTGTTTTGTCTTCTAGGATCAAC
TCGGTCATTACCACAGCTCAAACCTGCTTTGGGACTCCCTCCCACAAAACTGGCTCCGGATCAGG
GAACACTACCAAACCAACAGCAGTCAAATCAGGTCTTTCCTTCTTTAAGTCTGATACCATTAACA
CAGATGCTCACACTGGGGCCAGATCTGCATCTGTTAAATCCTGCTGCAGGAATGACACCTGGTAC
CCAGACCCACCCATTGACCCTGGGAGGGTTGAATGTACAACAGCAACTGCACCCACATGTGTTAC
CAATTTTTGTCACACAACTTGGAGCCCAGGGCACTATCCTAAGCTCAGAGGAATTGCCACAAATC
TTCACGAGCCTCATCATCCATTCCTTGTTCCCGGGAGGCATCCTGCCCACCAGTCAGGCAGGGGC
TAATCCAGATGTCCAGGATGGAAGCCTTCCAGCAGGAGGAGCAGGTGTAAATCCTGCCACCCAGG
GAACCCCAGCAGGCCGCCTCCCAACTCCCAGTGGCACAGATGACGACTTTGCAGTGACCACCCCT
GCAGGCATCCAAAGGAGCACACATGCCATCGAGGAAGCCACCACAGAATCAGCAAATGGAATTCA
G<u>TAA</u>GCTGTTTCAAATTTTTTCAACTAAGCTGCCTCGAATTTGGTGATACATGTGAATCTTTATC
ATTGATTATATTATGGAATAGATTGAGACACATTGGATAGTCTTAGAAGAAATTAATTCTTAATT
TACCTGAAAATATTCTTGAAATTTCAGAAAATATGTTCTATGTAGAGAATCCCAACTTTTAAAAA
CAATAATTCAATGGATAAATCTGTCTTTGAAATATAACATTATGCTGCCTGGATGATATGCATAT
TAAAACATATTTGGAAAACTGGAAAAAAAAAAAAAAAAAAAAAAAAAAAAAAAAAAAAAAAAAAA
AAAAAAAAAAAAAAAAAAAAAAAAAAAAAAAAA

FIGURE 96

MRSTILLFCLLGSTRSLPQLKPALGLPPTKLAPDQGTLPNQQQSNQVFPSLSLIPLTQM
LTLGPDLHLLNPAAGMTPGTQTHPLTLGGLNVQQQLHPHVLPIFVTQLGAQGTILSSEE
LPQIFTSLIIHSLFPGGILPTSQAGANPDVQDGSLPAGGAGVNPATQGTPAGRLPTPSG
TDDDFAVTTPAGIQRSTHAIEEATTESANGIQ

Signal peptide:
amino acids 1-16

FIGURE 97

GCTCAAGTGCCCTGCCTTGCCCCACCCAGCCCAGCCTGGCCAGAGCCCCCTGGAGAAGGAGCTCT
CTTCTTGCTTGGCAGCTGGACCAAGGGAGCCAGTCTTGGGCGCTGGAGGGCCTGTCCTGACCATG
GTCCCTGCCTGGCTGTGGCTGCTTTGTGTCTCCGTCCCCCAGGCTCTCCCCAAGGCCCAGCCTGC
AGAGCTGTCTGTGGAAGTTCCAGAAAACTATGGTGGAAATTTCCCTTTATACCTGACCAAGTTGC
CGCTGCCCCGTGAGGGGGCTGAAGGCCAGATCGTGCTGTCAGGGGACTCAGGCAAGGCAACTGAG
GGCCCATTTGCTATGGATCCAGATTCTGGCTTCCTGCTGGTGACCAGGGCCCTGGACCGAGAGGA
GCAGGCAGAGTACCAGCTACAGGTCACCCTGGAGATGCAGGATGGACATGTCTTGTGGGGTCCAC
AGCCTGTGCTTGTGCACGTGAAGGATGAGAATGACCAGGTGCCCCATTTCTCTCAAGCCATCTAC
AGAGCTCGGCTGAGCCGGGGTACCAGGCCTGGCATCCCCTTCCTCTTCCTTGAGGCTTCAGACCG
GGATGAGCCAGGCACAGCCAACTCGGATCTTCGATTCCACATCCTGAGCCAGGCTCCAGCCCAGC
CTTCCCCAGACATGTTCCAGCTGGAGCCTCGGCTGGGGGCTCTGGCCCTCAGCCCCAAGGGGAGC
ACCAGCCTTGACCACGCCCTGGAGAGGACCTACCAGCTGTTGGTACAGGTCAAGGACATGGGTGA
CCAGGCCTCAGGCCACCAGGCCACTGCCACCGTGGAAGTCTCCATCATAGAGAGCACCTGGGTGT
CCCTAGAGCCTATCCACCTGGCAGAGAATCTCAAAGTCCTATACCCGCACCACATGGCCCAGGTA
CACTGGAGTGGGGGTGATGTGCACTATCACCTGGAGAGCCATCCCCCGGGACCCTTTGAAGTGAA
TGCAGAGGGAAACCTCTACGTGACCAGAGAGCTGGACAGAGAAGCCCAGGCTGAGTACCTGCTCC
AGGTGCGGGCTCAGAATTCCCATGGCGAGGACTATGCGGCCCCTCTGGAGCTGCACGTGCTGGTG
ATGGATGAGAATGACAACGTGCCTATCTGCCCTCCCCGTGACCCCACAGTCAGCATCCCTGAGCT
CAGTCCACCAGGTACTGAAGTGACTAGACTGTCAGCAGAGGATGCAGATGCCCCCGGCTCCCCCA
ATTCCCACGTTGTGTATCAGCTCCTGAGCCCTGAGCCTGAGGATGGGGTAGAGGGGAGAGCCTTC
CAGGTGGACCCCACTTCAGGCAGTGTGACGCTGGGGGTGCTCCCACTCCGAGCAGGCCAGAACAT
CCTGCTTCTGGTGCTGGCCATGGACCTGGCAGGCGCAGAGGGTGGCTTCAGCAGCACGTGTGAAG
TCGAAGTCGCAGTCACAGATATCAATGATCACGCCCCTGAGTTCATCACTTCCCAGATTGGGCCT
ATAAGCCTCCCTGAGGATGTGGAGCCCGGGACTCTGGTGGCCATGCTAACAGCCATTGATGCTGA
CCTCGAGCCCGCCTTCCGCCTCATGGATTTTGCCATTGAGAGGGGAGACACAGAAGGGACTTTTG
GCCTGGATTGGGAGCCAGACTCTGGGCATGTTAGACTCAGACTCTGCAAGAACCTCAGTTATGAG
GCAGCTCCAAGTCATGAGGTGGTGGTGGTGGTGCAGAGTGTGGCGAAGCTGGTGGGGCCAGGCCC
AGGCCCTGGAGCCACCGCCACGGTGACTGTGCTAGTGGAGAGAGTGATGCCACCCCCCAAGTTGG
ACCAGGAGAGCTACGAGGCCAGTGTCCCCATCAGTGCCCCAGCCGGCTCTTTCCTGCTGACCATC
CAGCCCTCCGACCCCATCAGCCGAACCCTCAGGTTCTCCCTAGTCAATGACTCAGAGGGCTGGCT
CTGCATTGAGAAATTCTCCGGGGAGGTGCACACCGCCCAGTCCCTGCAGGGCGCCCAGCCTGGGG
ACACCTACACGGTGCTTGTGGAGGCCCAGGATACAGCCCTGACTCTTGCCCCTGTGCCCTCCCAA
TACCTCTGCACACCCCGCCAAGACCATGGCTTGATCGTGAGTGGACCCAGCAAGGACCCCGATCT
GGCCAGTGGGCACGGTCCCTACAGCTTCACCCTTGGTCCCAACCCCACGGTGCAACGGGATTGGC
GCCTCCAGACTCTCAATGGTTCCCATGCCTACCTCACCTTGGCCCTGCATTGGGTGGAGCCACGT
GAACACATAATCCCCGTGGTGGTCAGCCACAATGCCCAGATGTGGCAGCTCCTGGTTCGAGTGAT
CGTGTGTCGCTGCAACGTGGAGGGGCAGTGCATGCGCAAGGTGGGCCGCATGAAGGGCATGCCCA
CGAAGCTGTCGGCAGTGGGCATCCTTGTAGGCACCCTGGTAGCAATAGGAATCTTCCTCATCCTC
ATTTTCACCCACTGGACCATGTCAAGGAAGAAGGACCCGGATCAACCAGCAGACAGCGTGCCCCT
GAAGGCGACTGTCTGAATGGCCCAGGCAGCTCTAGCTGGGAGCTTGGCCTCTGGCTCCATCTGAG
TCCCCTGGGAGAGAGCCCAGCACCCAAGATCCAGCAGGGGACAGGACAGAGTAGAAGCCCCTCCA
TCTGCCCTGGGGTGGAGGCACCATCACCATCACCAGGCATGTCTGCAGAGCCTGGACACCAACTT
TATGGACTGCCCATGGGAGTGCTCCAAATGTCAGGGTGTTTGCCCAATAATAAAGCCCCAGAGAA
CTGGGCTGGGCCCTATGGGAAAAAAAAAAAAAAAAAAAAAAAAAAAAAAAAAG

FIGURE 98

MVPAWLWLLCVSVPQALPKAQPAELSVEVPENYGGNFPLYLTKLPLPREGAEGQIVLSGDSGKAT
EGPFAMDPDSGFLLVTRALDREEQAEYQLQVTLEMQDGHVLWGPQPVLVHVKDENDQVPHFSQAI
YRARLSRGTRPGIPFLFLEASDRDEPGTANSDLRFHILSQAPAQPSPDMFQLEPRLGALALSPKG
STSLDHALERTYQLLVQVKDMGDQASGHQATATVEVSIIESTWVSLEPIHLAENLKVLYPHHMAQ
VHWSGGDVHYHLESHPPGPFEVNAEGNLYVTRELDREAQAEYLLQVRAQNSHGEDYAAPLELHVL
VMDENDNVPICPPRDPTVSIPELSPPGTEVTRLSAEDADAPGSPNSHVVYQLLSPEPEDGVEGRA
FQVDPTSGSVTLGVLPLRAGQNILLLVLAMDLAGAEGGFSSTCEVEVAVTDINDHAPEFITSQIG
PISLPEDVEPGTLVAMLTAIDADLEPAFRLMDFAIERGDTEGTFGLDWEPDSGHVRLRLCKNLSY
EAAPSHEVVVVVQSVAKLVGPGPGPGATATVTVLVERVMPPPKLDQESYEASVPISAPAGSFLLT
IQPSDPISRTLRFSLVNDSEGWLCIEKFSGEVHTAQSLQGAQPGDTYTVLVEAQDTALTLAPVPS
QYLCTPRQDHGLIVSGPSKDPDLASGHGPYSFTLGPNPTVQRDWRLQTLNGSHAYLTLALHWVEP
REHIIPVVVSHNAQMWQLLVRVIVCRCNVEGQCMRKVGRMKGMPTKLSAVGILVGTLVAIGIFLI
LIFTHWTMSRKKDPDQPADSVPLKATV

Signal peptide:

amino acids 1-18

Transmembrane domain:

amino acids 762-784

FIGURE 99

GGCTGACCGTGCTACATTGCCTGGAGGAAGCCTAAGGAACCCAGGCATCCAGCTGCCCACGCCTG
AGTCCAAGATTCTTCCCAGGAACACAAACGTAGGAGACCCACGCTCCTGGAAGCACCAGCCTTTA
TCTCTTCACCTTCAAGTCCCCTTTCTCAAGAATCCTCTGTTCTTTGCCCTCTAAAGTCTTGGTAC
ATCTAGGACCCAGGCATCTTGCTTTCCAGCCACAAAGAGACAGATGAAGATGCAGAAAGGAAATG
TTCTCCTTATGTTTGGTCTACTATTGCATTTAGAAGCTGCAACAAATTCCAATGAGACTAGCACC
TCTGCCAACACTGGATCCAGTGTGATCTCCAGTGGAGCCAGCACAGCCACCAACTCTGGGTCCAG
TGTGACCTCCAGTGGGGTCAGCACAGCCACCATCTCAGGGTCCAGCGTGACCTCCAATGGGGTCA
GCATAGTCACCAACTCTGAGTTCCATACAACCTCCAGTGGGATCAGCACAGCCACCAACTCTGAG
TTCAGCACAGCGTCCAGTGGGATCAGCATAGCCACCAACTCTGAGTCCAGCACAACCTCCAGTGG
GGCCAGCACAGCCACCAACTCTGAGTCCAGCACACCCTCCAGTGGGGCCAGCACAGTCACCAACT
CTGGGTCCAGTGTGACCTCCAGTGGAGCCAGCACTGCCACCAACTCTGAGTCCAGCACAGTGTCC
AGTAGGGCCAGCACTGCCACCAACTCTGAGTCTAGCACACTCTCCAGTGGGGCCAGCACAGCCAC
CAACTCTGACTCCAGCACAACCTCCAGTGGGGCTAGCACAGCCACCAACTCTGAGTCCAGCACAA
CCTCCAGTGGGGCCAGCACAGCCACCAACTCTGAGTCCAGCACAGTGTCCAGTAGGGCCAGCACT
GCCACCAACTCTGAGTCCAGCACAACCTCCAGTGGGGCCAGCACAGCCACCAACTCTGAGTCCAG
AACGACCTCCAATGGGGCTGGCACAGCCACCAACTCTGAGTCCAGCACGACCTCCAGTGGGGCCA
GCACAGCCACCAACTCTGACTCCAGCACAGTGTCCAGTGGGGCCAGCACTGCCACCAACTCTGAG
TCCAGCACGACCTCCAGTGGGGCCAGCACAGCCACCAACTCTGAGTCCAGCACGACCTCCAGTGG
GGCTAGCACAGCCACCAACTCTGACTCCAGCACAACCTCCAGTGGGGCCGGCACAGCCACCAACT
CTGAGTCCAGCACAGTGTCCAGTGGGATCAGCACAGTCACCAATTCTGAGTCCAGCACACCCTCC
AGTGGGGCCAACACAGCCACCAACTCTGAGTCCAGTACGACCTCCAGTGGGGCCAACACAGCCAC
CAACTCTGAGTCCAGCACAGTGTCCAGTGGGGCCAGCACTGCCACCAACTCTGAGTCCAGCACAA
CCTCCAGTGGGGTCAGCACAGCCACCAACTCTGAGTCCAGCACAACCTCCAGTGGGGCTAGCACA
GCCACCAACTCTGACTCCAGCACAACCTCCAGTGAGGCCAGCACAGCCACCAACTCTGAGTCTAG
CACAGTGTCCAGTGGGATCAGCACAGTCACCAATTCTGAGTCCAGCACAACCTCCAGTGGGGCCA
ACACAGCCACCAACTCTGGGTCCAGTGTGACCTCTGCAGGCTCTGGAACAGCAGCTCTGACTGGA
ATGCACACAACTTCCCATAGTGCATCTACTGCAGTGAGTGAGGCAAAGCCTGGTGGGTCCCTGGT
GCCGTGGGAAATCTTCCTCATCACCCTGGTCTCGGTTGTGGCGGCCGTGGGGCTCTTTGCTGGGC
TCTTCTTCTGTGTGAGAAACAGCCTGTCCCTGAGAAACACCTTTAACACAGCTGTCTACCACCCT
CATGGCCTCAACCATGGCCTTGGTCCAGGCCCTGGAGGGAATCATGGAGCCCCCCACAGGCCCAG
GTGGAGTCCTAACTGGTTCTGGAGGAGACCAGTATCATCGATAGCCATGGAGATGAGCGGGAGGA
ACAGCGGGCCCTGAGCAGCCCCGGAAGCAAGTGCCGCATTCTTCAGGAAGGAAGAGACCTGGGCA
CCCAAGACCTGGTTTCCTTTCATTCATCCCAGGAGACCCCTCCCAGCTTTGTTTGAGATCCTGAA
AATCTTGAAGAAGGTATTCCTCACCTTTCTTGCCTTTACCAGACACTGGAAAGAGAATACTATAT
TGCTCATTTAGCTAAGAAATAAATACATCTCATCTAACACACACGACAAAGAGAAGCTGTGCTTG
CCCCGGGGTGGGTATCTAGCTCTGAGATGAACTCAGTTATAGGAGAAAACCTCCATGCTGGACTC
CATCTGGCATTCAAAATCTCCACAGTAAAATCCAAAGACCTCAAAAAAAAAAAAAAAAAAAAAAA
AAAAAAAAAAAAAAAAAAAAAAAAAAAAAA

FIGURE 100

MKMQKGNVLLMFGLLLHLEAATNSNETSTSANTGSSVISSGASTATNSGSSVTSSGVSTATISGS
SVTSNGVSIVTNSEFHTTSSGISTATNSEFSTASSGISIATNSESSTTSSGASTATNSESSTPSS
GASTVTNSGSSVTSSGASTATNSESSTVSSRASTATNSESSTLSSGASTATNSDSSTTSSGASTA
TNSESSTTSSGASTATNSESSTVSSRASTATNSESSTTSSGASTATNSESRTTSNGAGTATNSES
STTSSGASTATNSDSSTVSSGASTATNSESSTTSSGASTATNSESSTTSSGASTATNSDSSTTSS
GAGTATNSESSTVSSGISTVTNSESSTPSSGANTATNSESSTTSSGANTATNSESSTVSSGASTA
TNSESSTTSSGVSTATNSESSTTSSGASTATNSDSSTTSSEASTATNSESSTVSSGISTVTNSES
STTSSGANTATNSGSSVTSAGSGTAALTGMHTTSHSASTAVSEAKPGGSLVPWEIFLITLVSVVA
AVGLFAGLFFCVRNSLSLRNTFNTAVYHPHGLNHGLGPGPGGNHGAPHRPRWSPNWFWRRPVSSI
AMEMSGRNSGP

Signal peptide:

amino acids 1-20

Transmembrane domain:

amino acids 510-532

FIGURE 101

GGCCGGACGCCTCCGCGTTACGGGATGAATTAACGGCGGGTTCCGCACGGAGGTTGTGACCCCTA
CGGAGCCCCAGCTTGCCCACGCACCCCACTCGGCGTCGCGCGGCGTGCCCTGCTTGTCACAGGTG
GGAGGCTGGAACTATCAGGCTGAAAAACAGAGTGGGTACTCTCTTCTGGGAAGCTGGCAACAAAT
GGATGATGTGATATATGCATTCCAGGGGAAGGGAAATTGTGGTGCTTCTGAACCCATGGTCAATT
AACGAGGCAGTTTCTAGCTACTGCACGTACTTCATAAAGCAGGACTCTAAAAGCTTTGGAATCAT
GGTGTCATGGAAAGGGATTTACTTTATACTGACTCTGTTTTGGGGAAGCTTTTTTGGAAGCATTT
TCATGCTGAGTCCCTTTTTACCTTTGATGTTTGTAAACCCATCTTGGTATCGCTGGATCAACAAC
CGCCTTGTGGCAACATGGCTCACCCTACCTGTGGCATTATTGGAGACCATGTTTGGTGTAAAAGT
GATTATAACTGGGGATGCATTTGTTCCTGGAGAAAGAAGTGTCATTATCATGAACCATCGGACAA
GAATGGACTGGATGTTCCTGTGGAATTGCCTGATGCGATATAGCTACCTCAGATTGGAGAAAATT
TGCCTCAAAGCGAGTCTCAAAGGTGTTCCTGGATTTGGTTGGGCCATGCAGGCTGCTGCCTATAT
CTTCATTCATAGGAAATGGAAGGATGACAAGAGCCATTTCGAAGACATGATTGATTACTTTTGTG
ATATTCACGAACCACTTCAACTCCTCATATTCCCAGAAGGGACTGATCTCACAGAAAACAGCAAG
TCTCGAAGTAATGCATTTGCTGAAAAAAATGGACTTCAGAAATATGAATATGTTTTACATCCAAG
AACTACAGGCTTTACTTTTGTGGTAGACCGTCTAAGAGAAGGTAAGAACCTTGATGCTGTCCATG
ATATCACTGTGGCGTATCCTCACAACATTCCTCAATCAGAGAAGCACCTCCTCCAAGGAGACTTT
CCCAGGGAAATCCACTTTCACGTCCACCGGTATCCAATAGACACCCTCCCCACATCCAAGGAGGA
CCTTCAACTCTGGTGCCACAAACGGTGGGAAGAGAAAGAAGAGAGGCTGCGTTCCTTCTATCAAG
GGGAGAAGAATTTTTATTTACCGGACAGAGTGTCATTCCACCTTGCAAGTCTGAACTCAGGGTC
CTTGTGGTCAAATTGCTCTCTATACTGTATTGGACCCTGTTCAGCCCTGCAATGTGCCTACTCAT
ATATTTGTACAGTCTTGTTAAGTGGTATTTTATAATCACCATTGTAATCTTTGTGCTGCAAGAGA
GAATATTTGGTGGACTGGAGATCATAGAACTTGCATGTTACCGACTTTTACACAAACAGCCACAT
TTAAATTCAAAGAAAAATGAGTAAGATTATAAGGTTTGCCATGTGAAAACCTAGAGCATATTTTG
GAAATGTTCTAAACCTTTCTAAGCTCAGATGCATTTTTGCATGACTATGTCGAATATTTCTTACT
GCCATCATTATTTGTTAAAGATATTTTGCACTTAATTTTGTGGGAAAAATATTGCTACAATTTTT
TTTAATCTCTGAATGTAATTTCGATACTGTGTACATAGCAGGGAGTGATCGGGGTGAAATAACTT
GGGCCAGAATATTATTAAACAATCATCAGGCTTTTAAA

FIGURE 102

MHSRGREIVVLLNPWSINEAVSSYCTYFIKQDSKSFGIMVSWKGIYFILTLFWGSFFGSIFMLSP
FLPLMFVNPSWYRWINNRLVATWLTLPVALLETMFGVKVIITGDAFVPGERSVIIMNHRTRMDWM
FLWNCLMRYSYLRLEKICLKASLKGVPGFGWAMQAAAYIFIHRKWKDDKSHFEDMIDYFCDIHEP
LQLLIFPEGTDLTENSKSRSNAFAEKNGLQKYEYVLHPRTTGFTFVVDRLREGKNLDAVHDITVA
YPHNIPQSEKHLLQGDFPREIHFHVHRYPIDTLPTSKEDLQLWCHKRWEEKEERLRSFYQGEKNF
YFTGQSVIPPCKSELRVLVVKLLSILYWTLFSPAMCLLIYLYSLVKWYFIITIVIFVLQERIFGG
LEIIELACYRLLHKQPHLNSKKNE

Important features of the protein:

Signal peptide:

amino acids 1-22

Transmembrane domains:

amino acids 44-63, 90-108, 354-377

FIGURE 103

CGGCTCGAGCGGCTCGAGTGAAGAGCCTCTCCACGGCTCCTGCGCCTGAGACAGCTGGCCTGACC
TCCAAATCATCCATCCACCCCTGCTGTCATCTGTTTTCATAGTGTGAGATCAACCCACAGGAATA
TCCATGGCTTTTGTGCTCATTTTGGTTCTCAGTTTCTACGAGCTGGTGTCAGGACAGTGGCAAGT
CACTGGACCGGGCAAGTTTGTCCAGGCCTTGGTGGGGGAGGACGCCGTGTTCTCCTGCTCCCTCT
TTCCTGAGACCAGTGCAGAGGCTATGGAAGTGCGGTTCTTCAGGAATCAGTTCCATGCTGTGGTC
CACCTCTACAGAGATGGGGAAGACTGGGAATCTAAGCAGATGCCACAGTATCGAGGGAGAACTGA
GTTTGTGAAGGACTCCATTGCAGGGGGGCGTGTCTCTCTAAGGCTAAAAAACATCACTCCCTCGG
ACATCGGCCTGTATGGGTGCTGGTTCAGTTCCCAGATTTACGATGAGGAGGCCACCTGGGAGCTG
CGGGTGGCAGCACTGGGCTCACTTCCTCTCATTTCCATCGTGGGATATGTTGACGGAGGTATCCA
GTTACTCTGCCTGTCCTCAGGCTGGTTCCCCCAGCCCACAGCCAAGTGGAAAGGTCCACAAGGAC
AGGATTTGTCTTCAGACTCCAGAGCAAATGCAGATGGGTACAGCCTGTATGATGTGGAGATCTCC
ATTATAGTCCAGGAAAATGCTGGGAGCATATTGTGTTCCATCCACCTTGCTGAGCAGAGTCATGA
GGTGGAATCCAAGGTATTGATAGGAGAGACGTTTTTCCAGCCCTCACCTTGGCGCCTGGCTTCTA
TTTTACTCGGGTTACTCTGTGGTGCCCTGTGTGGTGTTGTCATGGGGATGATAATTGTTTTCTTC
AAATCCAAAGGGAAAATCCAGGCGGAACTGGACTGGAGAAGAAAGCACGGACAGGCAGAATTGAG
AGACGCCCGGAAACACGCAGTGGAGGTGACTCTGGATCCAGAGACGGCTCACCCGAAGCTCTGCG
TTTCTGATCTGAAAACTGTAACCCATAGAAAAGCTCCCCAGGAGGTGCCTCACTCTGAGAAGAGA
TTTACAAGGAAGAGTGTGGTGGCTTCTCAGGGTTTCCAAGCAGGGAGACATTACTGGGAGGTGGA
CGTGGGACAAAATGTAGGGTGGTATGTGGAGTGTGTCGGGATGACGTAGACAGGGGGAAGAACA
ATGTGACTTTGTCTCCCAACAATGGGTATTGGGTCCTCAGACTGACAACAGAACATTTGTATTTC
ACATTCAATCCCCATTTTATCAGCCTCCCCCCCAGCACCCCTCCTACACGAGTAGGGGTCTTCCT
GGACTATGAGGGTGGGACCATCTCCTTCTTCAATACAAATGACCAGTCCCTTATTTATACCCTGC
TGACATGTCAGTTTGAAGGCTTGTTGAGACCCTATATCCAGCATGCGATGTATGACGAGGAAAAG
GGGACTCCCATATTCATATGTCCAGTGTCCTGGGGATGAGACAGAGAAGACCCTGCTTAAAGGGC
CCCACACCACAGACCCAGACACAGCCAAGGGAGAGTGCTCCCGACAGGTGGCCCCAGCTTCCTCT
CCGGAGCCTGCGCACAGAGAGTCACGCCCCCCACTCTCCTTTAGGGAGCTGAGGTTCTTCTGCCC
TGAGCCCTGCAGCAGCGGCAGTCACAGCTTCCAGATGAGGGGGGATTGGCCTGACCCTGTGGGAG
TCAGAAGCCATGGCTGCCCTGAAGTGGGGACGGAATAGACTCACATTAGGTTTAGTTTGTGAAAA
CTCCATCCAGCTAAGCGATCTTGAACAAGTCACAACCTCCCAGGCTCCTCATTTGCTAGTCACGG
ACAGTGATTCCTGCCTCACAGGTGAAGATTAAAGAGACAACGAATGTGAATCATGCTTGCAGGTT
TGAGGGCACAGTGTTTGCTAATGATGTGTTTTTATATTATACATTTTCCCACCATAAACTCTGTT
TGCTTATTCCACATTAATTTACTTTTCTCTATACCAAATCACCCATGGAATAGTTATTGAACACC
TGCTTTGTGAGGCTCAAAGAATAAAGAGGAGGTAGGATTTTTCACTGATTCTATAAGCCCAGCAT
TACCTGATACCAAAACCAGGCAAAGAAAACAGAAGAAGAGGAAGGAAAACTACAGGTCCATATCC
CTCATTAACACAGACACAAAAATTCTAAATAAAATTTTAACAAATTAAACTAAACAATATATTTA
AAGATGATATATAACTACTCAGTGTGGTTTGTCCCACAAATGCAGAGTTGGTTTAATATTTAAAT
ATCAACCAGTGTAATTCAGCACATTAATAAAGTAAAAAAGAAAACCATAAAAAAAAAAAAAA

FIGURE 104

MAFVLILVLSFYELVSGQWQVTGPGKFVQALVGEDAVFSCSLFPETSAEAMEVRFFRNQFHAVVH
LYRDGEDWESKQMPQYRGRTEFVKDSIAGGRVSLRLKNITPSDIGLYGCWFSSQIYDEEATWELR
VAALGSLPLISIVGYVDGGIQLLCLSSGWFPQPTAKWKGPQGQDLSSDSRANADGYSLYDVEISI
IVQENAGSILCSIHLAEQSHEVESKVLIGETFFQPSPWRLASILLGLLCGALCGVVMGMIIVFFK
SKGKIQAELDWRRKHGQAELRDARKHAVEVTLDPETAHPKLCVSDLKTVTHRKAPQEVPHSEKRF
TRKSVVASQGFQAGRHYWEVDVGQNVGWYVGVCRDDVDRGKNNVTLSPNNGYWVLRLTTEHLYFT
FNPHFISLPPSTPPTRVGVFLDYEGGTISFFNTNDQSLIYTLLTCQFEGLLRPYIQHAMYDEEKG
TPIFICPVSWG

Signal peptide:

amino acids 1-17

Transmembrane domains:

amino acids 131-150, 235-259

FIGURE 105

CCTTCACAGGACTCTTCATTGCTGGTTGGCAATGATGTATCGGCCAGATGTGGTGAGGGCTAGGAAAAGAG
TTTGTTGGGAACCCTGGGTTATCGGCCTCGTCATCTTCATATCCCTGATTGTCCTGGCAGTGTGCATTGGA
CTCACTGTTCATTATGTGAGATATAATCAAAAGAAGACCTACAATTACTATAGCACATTGTCATTTACAAC
TGACAAACTATATGCTGAGTTTGGCAGAGAGGCTTCTAACAATTTTACAGAAATGAGCCAGAGACTTGAAT
CAATGGTGAAAAATGCATTTTATAAATCTCCATTAAGGGAAGAATTTGTCAAGTCTCAGGTTATCAAGTTC
AGTCAACAGAAGCATGGAGTGTTGGCTCATATGCTGTTGATTTGTAGATTTCACTCTACTGAGGATCCTGA
AACTGTAGATAAAATTGTTCAACTTGTTTTACATGAAAAGCTGCAAGATGCTGTAGGACCCCCTAAAGTAG
ATCCTCACTCAGTTAAAATTAAAAAAATCAACAAGACAGAAACAGACAGCTATCTAAACCATTGCTGCGGA
ACACGAAGAAGTAAAACTCTAGGTCAGAGTCTCAGGATCGTTGGTGGGACAGAAGTAGAAGAGGGTGAATG
GCCCTGGCAGGCTAGCCTGCAGTGGGATGGGAGTCATCGCTGTGGAGCAACCTTAATTAATGCCACATGGC
TTGTGAGTGCTGCTCACTGTTTTACAACATATAAGAACCCTGCCAGATGGACTGCTTCCTTTGGAGTAACA
ATAAAACCTTCGAAAATGAAACGGGGTCTCCGGAGAATAATTGTCCATGAAAAATACAAACACCCATCACA
TGACTATGATATTTCTCTTGCAGAGCTTTCTAGCCCTGTTCCCTACACAAATGCAGTACATAGAGTTTGTC
TCCCTGATGCATCCTATGAGTTTCAACCAGGTGATGTGATGTTTGTGACAGGATTTGGAGCACTGAAAAAT
GATGGTTACAGTCAAAATCATCTTCGACAAGCACAGGTGACTCTCATAGACGCTACAACTTGCAATGAACC
TCAAGCTTACAATGACGCCATAACTCCTAGAATGTTATGTGCTGGCTCCTTAGAAGGAAAAACAGATGCAT
GCCAGGGTGACTCTGGAGGACCACTGGTTAGTTCAGATGCTAGAGATATCTGGTACCTTGCTGGAATAGTG
AGCTGGGGAGATGAATGTGCGAAACCCAACAAGCCTGGTGTTTATACTAGAGTTACGGCCTTGCGGGACTG
GATTACTTCAAAAACTGGTATCTAAGAGACAAAAGCCTCATGGAACAGATAACATTTTTTTTTGTTTTTTG
GGTGTGGAGGCCATTTTTAGAGATACAGAATTGGAGAAGACTTGCAAAACAGCTAGATTTGACTGATCTCA
ATAAACTGTTTGCTTGATGCATGTATTTTCTTCCCAGCTCTGTTCCGCACGTAAGCATCCTGCTTCTGCCA
GATCAACTCTGTCATCTGTGAGCAATAGTTGAAACTTTATGTACATAGAGAAATAGATAATACAATATTAC
ATTACAGCCTGTATTCATTTGTTCTCTAGAAGTTTTGTCAGAATTTTGACTTGTTGACATAAATTTGTAAT
GCATATATACAATTTGAAGCACTCCTTTTCTTCAGTTCCTCAGCTCCTCTCATTTCAGCAAATATCCATTT
TCAAGGTGCAGAACAAGGAGTGAAAGAAAATATAAGAAGAAAAAAATCCCCTACATTTTATTGGCACAGAA
AAGTATTAGGTGTTTTTCTTAGTGGAATATTAGAAATGATCATATTCATTATGAAAGGTCAAGCAAAGACA
GCAGAATACCAATCACTTCATCATTTAGGAAGTATGGGAACTAAGTTAAGGAAGTCCAGAAAGAAGCCAAG
ATATATCCTTATTTTCATTTCCAAACAACTACTATGATAAATGTGAAGAAGATTCTGTTTTTTTGTGACCT
ATAATAATTATACAAACTTCATGCAATGTACTTGTTCTAAGCAAATTAAAGCAAATATTTATTTAACATTG
TTACTGAGGATGTCAACATATAACAATAAAATATAAATCACCCA

FIGURE 106

MMYRPDVVRARKRVCWEPWVIGLVIFISLIVLAVCIGLTVHYVRYNQKKTYNYYSTLSFTTDKLY
AEFGREASNNFTEMSQRLESMVKNAFYKSPLREEFVKSQVIKFSQQKHGVLAHMLLICRFHSTED
PETVDKIVQLVLHEKLQDAVGPPKVDPHSVKIKKINKTETDSYLNHCCGTRRSKTLGQSLRIVGG
TEVEEGEWPWQASLQWDGSHRCGATLINATWLVSAAHCFTTYKNPARWTASFGVTIKPSKMKRGL
RRIIVHEKYKHPSHDYDISLAELSSPVPYTNAVHRVCLPDASYEFQPGDVMFVTGFGALKNDGYS
QNHLRQAQVTLIDATTCNEPQAYNDAITPRMLCAGSLEGKTDACQGDSGGPLVSSDARDIWYLAG
IVSWGDECAKPNKPGVYTRVTALRDWITSKTGI

Transmembrane domain:

amino acids 21-40 (type II)

FIGURE 107

AGAGAAAGAAGCGTCTCCAGCTGAAGCCAATGCAGCCCTCCGGCTCTCCGCGAAGAAGTTCCCTG
CCCCGATGAGCCCCCGCCGTGCGTCCCCGACTATCCCCAGGCGGGCGTGGGCACCGGGCCCAGC
GCCGACGATCGCTGCCGTTTTGCCCTTGGGAGTAGGATGTGGTGAAAGGATGGGGCTTCTCCCTT
ACGGGGCTCACAATGGCCAGAGAAGATTCCGTGAAGTGTCTGCGCTGCCTGCTCTACGCCCTCAA
TCTGCTCTTTTGGTTAATGTCCATCAGTGTGTTGGCAGTTTCTGCTTGGATGAGGGACTACCTAA
ATAATGTTCTCACTTTAACTGCAGAAACGAGGGTAGAGGAAGCAGTCATTTTGACTTACTTTCCT
GTGGTTCATCCGGTCATGATTGCTGTTTGCTGTTTCCTTATCATTGTGGGGATGTTAGGATATTG
TGGAACGGTGAAAAGAAATCTGTTGCTTCTTGCATGGTACTTTGGAAGTTTGCTTGTCATTTTCT
GTGTAGAACTGGCTTGTGGCGTTTGGACATATGAACAGGAACTTATGGTTCCAGTACAATGGTCA
GATATGGTCACTTTGAAAGCCAGGATGACAAATTATGGATTACCTAGATATCGGTGGCTTACTCA
TGCTTGGAATTTTTTTCAGAGAGAGTTTAAGTGCTGTGGAGTAGTATATTTCACTGACTGGTTGG
AAATGACAGAGATGGACTGGCCCCCAGATTCCTGCTGTGTTAGAGAATTCCCAGGATGTTCCAAA
CAGGCCCACCAGGAAGATCTCAGTGACCTTTATCAAGAGGGTTGTGGGAAGAAAATGTATTCCTT
TTTGAGAGGAACCAAACAACTGCAGGTGCTGAGGTTTCTGGGAATCTCCATTGGGGTGACACAAA
TCCTGGCCATGATTCTCACCATTACTCTGCTCTGGGCTCTGTATTATGATAGAAGGGAGCCTGGG
ACAGACCAAATGATGTCCTTGAAGAATGACAACTCTCAGCACCTGTCATGTCCCTCAGTAGAACT
GTTGAAACCAAGCCTGTCAAGAATCTTTGAACACACATCCATGGCAAACAGCTTTAATACACACT
TTGAGATGGAGGAGTTATAAAAAGAAATGTCACAGAAGAAAACCACAAACTTGTTTTATTGGACT
TGTGAATTTTTGAGTACATACTATGTGTTTCAGAAATATGTAGAAATAAAAATGTTGCCATAAAA
TAACACCTAAGCATATACTATTCTATGCTTTAAAATGAGGATGGAAAAGTTTCATGTCATAAGTC
ACCACCTGGACAATAATTGATGCCCTTAAAATGCTGAAGACAGATGTCATACCCACTGTGTAGCC
TGTGTATGACTTTTACTGAACACAGTTATGTTTTGAGGCAGCATGGTTTGATTAGCATTTCCGCA
TCCATGCAAACGAGTCACATATGGTGGGACTGGAGCCATAGTAAAGGTTGATTTACTTCTACCAA
CTAGTATATAAAGTACTAATTAAATGCTAACATAGGAAGTTAGAAAATACTAATAACTTTTATTA
CTCAGCGATCTATTCTTCTGATGCTAAATAAATTATATATCAGAAAACTTTCAATATTGGTGACT
ACCTAAATGTGATTTTTGCTGGTTACTAAAATATTCTTACCACTTAAAAGAGCAAGCTAACACAT
TGTCTTAAGCTGATCAGGGATTTTTTGTATATAAGTCTGTGTTAAATCTGTATAATTCAGTCGAT
TTCAGTTCTGATAATGTTAAGAATAACCATTATGAAAAGGAAAATTTGTCCTGTATAGCATCATT
ATTTTTAGCCTTTCCTGTTAATAAAGCTTTACTATTCTGTCCTGGGCTTATATTACACATATAAC
TGTTATTTAAATACTTAACCACTAATTTTGAAAATTACCAGTGTGATACATAGGAATCATTATTC
AGAATGTAGTCTGGTCTTTAGGAAGTATTAATAAGAAAATTTGCACATAACTTAGTTGATTCAGA
AAGGACTTGTATGCTGTTTTTCTCCCAAATGAAGACTCTTTTTGACACTAAACACTTTTTAAAAA
GCTTATCTTTGCCTTCTCCAAACAAGAAGCAATAGTCTCCAAGTCAATATAAATTCTACAGAAAA
TAGTGTTCTTTTTCTCCAGAAAAATGCTTGTGAGAATCATTAAAACATGTGACAATTTAGAGATT
CTTTGTTTTATTTCACTGATTAATATACTGTGGCAAATTACACAGATTATTAAATTTTTTTACAA
GAGTATAGTATATTTATTTGAAATGGAAAAGTGCATTTTACTGTATTTTGTGTATTTTGTTTAT
TTCTCAGAATATGGAAAGAAAATTAAAATGTGTCAATAAATATTTTCTAGAGAGTAA

FIGURE 108

MAREDSVKCLRCLLYALNLLFWLMSISVLAVSAWMRDYLNNVLTLTAETRVEEAVILTYFPVVHP
VMIAVCCFLIIVGMLGYCGTVKRNLLLLAWYFGSLLVIFCVELACGVWTYEQELMVPVQWSDMVT
LKARMTNYGLPRYRWLTHAWNFFQREFKCCGVVYFTDWLEMTEMDWPPDSCCVREFPGCSKQAHQ
EDLSDLYQEGCGKKMYSFLRGTKQLQVLRFLGISIGVTQILAMILTITLLWALYYDRREPGTDQM
MSLKNDNSQHLSCPSVELLKPSLSRIFEHTSMANSFNTHFEMEEL

Signal peptide:

amino acids 1-33

Transmembrane domains:

amino acids 12-35, 57-86, 94-114, 226-248

FIGURE 109

CCAAGGCCAGAGCTGTGGACACCTTATCCCACTCATCCTCATCCTCTTCCTCTGATAAAGCCCCTACCAGTGCT
GATAAAGTCTTTCTCGTGAGAGCCTAGAGGCCTTAAAAAAAAAAGTGCTTGAAAGAGAAGGGGACAAAGGAACA
CCAGTATTAAGAGGATTTTCCAGTGTTTCTGGCAGTTGGTCCAGAAGGATGCCTCCATTCCTGCTTCTCACCTG
CCTCTTCATCACAGGCACCTCCGTGTCACCCGTGGCCCTAGATCCTTGTTCTGCTTACATCAGCCTGAATGAGC
CCTGGAGGAACACTGACCACCAGTTGGATGAGTCTCAAGGTCCTCCTCTATGTGACAACCATGTGAATGGGGAG
TGGTACCACTTCACGGGCATGGCGGGAGATGCCATGCCTACCTTCTGCATACCAGAAAACCACTGTGGAACCCA
CGCACCTGTCTGGCTCAATGGCAGCCACCCCCTAGAAGGCGACGGCATTGTGCAACGCCAGGCTTGTGCCAGCT
TCAATGGGAACTGCTGTCTCTGGAACACCACGGTGGAAGTCAAGGCTTGCCCTGGAGGCTACTATGTGTATCGT
CTGACCAAGCCCAGCGTCTGCTTCCACGTCTACTGTGGTCATTTTTATGACATCTGCGACGAGGACTGCCATGG
CAGCTGCTCAGATACCAGCGAGTGCACATGCGCTCCAGGAACTGTGCTAGGCCCTGACAGGCAGACATGCTTTG
ATGAAAATGAATGTGAGCAAAACAACGGTGGCTGCAGTGAGATCTGTGTGAACCTCAAAAACTCCTACCGCTGT
GAGTGTGGGGTTGGCCGTGTGCTAAGAAGTGATGGCAAGACTTGTGAAGACGTTGAAGGATGCCACAATAACAA
TGGTGGCTGCAGCCACTCTTGCCTTGGATCTGAGAAAGGCTACCAGTGTGAATGTCCCCGGGGCCTGGTGCTGT
CTGAGGATAACCACACTTGCCAAGTCCCTGTGTTGTGCAAATCAAATGCCATTGAAGTGAACATCCCCAGGGAG
CTGGTTGGTGGCCTGGAGCTCTTCCTGACCAACACCTCCTGCCGAGGAGTGTCCAACGGCACCCATGTCAACAT
CCTCTTCTCTCTCAAGACATGTGGTACAGTGGTCGATGTGGTGAATGACAAGATTGTGGCCAGCAACCTCGTGA
CAGGTCTACCCAAGCAGACCCCGGGGAGCAGCGGGGACTTCATCATCCGAACCAGCAAGCTGCTGATCCCGGTG
ACCTGCGAGTTTCCACGCCTGTACACCATTTCTGAAGGATACGTTCCCAACCTTCGAAACTCCCCACTGGAAAT
CATGAGCCGAAATCATGGGATCTTCCCATTCACTCTGGAGATCTTCAAGGACAATGAGTTTGAAGAGCCTTACC
GGGAAGCTCTGCCCACCCTCAAGCTTCGTGACTCCCTCTACTTTGGCATTGAGCCCGTGGTGCACGTGAGCGGC
TTGGAAAGCTTGGTGGAGAGCTGCTTTGCCACCCCCACCTCCAAGATCGACGAGGTCCTGAAATACTACCTCAT
CCGGGATGGCTGTGTTTCAGATGACTCGGTAAAGCAGTACACATCCCGGGATCACCTAGCAAAGCACTTCCAGG
TCCCTGTCTTCAAGTTTGTGGGCAAAGACCACAAGGAAGTGTTTCTGCACTGCCGGGTTCTTGTCTGTGGAGTG
TTGGACGAGCGTTCCCGCTGTGCCCAGGGTTGCCACCGGCGAATGCGTCGTGGGGCAGGAGGAGAGGACTCAGC
CGGTCTACAGGGCCAGACGCTAACAGGCGGCCCGATCCGCATCGACTGGGAGGACTAGTTCGTAGCCATACCTC
GAGTCCCTGCATTGGACGGCTCTGCTCTTTGGAGCTTCTCCCCCCACCGCCCTCTAAGAACATCTGCCAACAGC
TGGGTTCAGACTTCACACTGTGAGTTCAGACTCCCAGCACCAACTCACTCTGATTCTGGTCCATTCAGTGGGCA
CAGGTCACAGCACTGCTGAACAATGTGGCCTGGGTGGGGTTTCATCTTTCTAGGGTTGAAAACTAAACTGTCCA
CCCAGAAAGACACTCACCCCATTTCCCTCATTTCTTTCCTACACTTAAATACCTCGTGTATGGTGCAATCAGAC
CACAAAATCAGAAGCTGGGTATAATATTTCAAGTTACAAACCCTAGAAAAATTAAACAGTTACTGAAATTATGA
CTTAAATACCCAATGACTCCTTAAATATGTAAATTATAGTTATACCTTGAAATTTCAATTCAAATGCAGACTAA
TTATAGGGAATTTGGAAGTGTATCAATAAAACAGTATATAATTTT

FIGURE 110

MPPFLLLTCLFITGTSVSPVALDPCSAYISLNEPWRNTDHQLDESQGPPLCDNHVNGEWYHFTGMAGDAMP
TFCIPENHCGTHAPVWLNGSHPLEGDGIVQRQACASFNGNCCLWNTTVEVKACPGGYYVYRLTKPSVCFHV
YCGHFYDICDEDCHGSCSDTSECTCAPGTVLGPDRQTCFDENECEQNNGGCSEICVNLKNSYRCECGVGRV
LRSDGKTCEDVEGCHNNNGGCSHSCLGSEKGYQCECPRGLVLSEDNHTCQVPVLCKSNAIEVNIPRELVGG
LELFLTNTSCRGVSNGTHVNILFSLKTCGTVVDVVNDKIVASNLVTGLPKQTPGSSGDFIIRTSKLLIPVT
CEFPRLYTISEGYVPNLRNSPLEIMSRNHGIFPFTLEIFKDNEFEEPYREALPTLKLRDSLYFGIEPVVHV
SGLESLVESCFATPTSKIDEVLKYYLIRDGCVSDDSVKQYTSRDHLAKHFQVPVFKFVGKDHKEVFLHCRV
LVCGVLDERSRCAQGCHRRMRRGAGGEDSAGLQGQTLTGGPIRIDWED

Important features of the protein:

Signal peptide:

amino acids 1-16

N-glycosylation sites.

amino acids 89-93, 116-120, 259-263, 291-295, 299-303

Tyrosine kinase phosphorylation sites.

amino acids 411-418, 443-451

N-myristoylation sites.

amino acids 226-232, 233-239, 240-246, 252-258, 296-302, 300-306, 522-528, 531-537

Aspartic acid and asparagine hydroxylation site.

amino acids 197-209

ZP domain proteins.

amino acids 431-457

Calcium-binding EGF-like proteins.

amino acids 191-212, 232-253

FIGURE 111

```
GAGAGAGGCAGCAGCTTGCTCAGCGGACAAGGATGCTGGGCGTGAGGGACCAAGGCCTGCCCTGCACTCGG
GCCTCCTCCAGCCAGTGCTGACCAGGGACTTCTGACCTGCTGGCCAGCCAGGACCTGTGTGGGGAGGCCCT
CCTGCTGCCTTGGGGTGACAATCTCAGCTCCAGGCTACAGGGAGACCGGGAGGATCACAGAGCCAGC**ATG**T
TACAGGATCCTGACAGTGATCAACCTCTGAACAGCCTCGATGTCAAACCCCTGCGCAAACCCCGTATCCCC
ATGGAGACCTTCAGAAAGGTGGGGATCCCCATCATCATAGCACTACTGAGCCTGGCGAGTATCATCATTGT
GGTTGTCCTCATCAAGGTGATTCTGGATAAATACTACTTCCTCTGCGGGCAGCCTCTCCACTTCATCCCGA
GGAAGCAGCTGTGTGACGGAGAGCTGGACTGTCCCTTGGGGGAGGACGAGGAGCACTGTGTCAAGAGCTTC
CCCGAAGGGCCTGCAGTGGCAGTCCGCCTCTCCAAGGACCGATCCACACTGCAGGTGCTGGACTCGGCCAC
AGGGAACTGGTTCTCTGCCTGTTTCGACAACTTCACAGAAGCTCTCGCTGAGACAGCCTGTAGGCAGATGG
GCTACAGCAGAGCTGTGGAGATTGGCCCAGACCAGGATCTGGATGTTGTTGAAATCACAGAAAACAGCCAG
GAGCTTCGCATGCGGAACTCAAGTGGGCCCTGTCTCTCAGGCTCCCTGGTCTCCCTGCACTGTCTTGCCTG
TGGGAAGAGCCTGAAGACCCCCCGTGTGGTGGGTGGGGAGGAGGCCTCTGTGGATTCTTGGCCTTGGCAGG
TCAGCATCCAGTACGACAAACAGCACGTCTGTGGAGGGAGCATCCTGGACCCCCACTGGGTCCTCACGGCA
GCCCACTGCTTCAGGAAACATACCGATGTGTTCAACTGGAAGGTGCGGGCAGGCTCAGACAAACTGGGCAG
CTTCCCATCCCTGGCTGTGGCCAAGATCATCATCATTGAATTCAACCCCATGTACCCCAAAGACAATGACA
TCGCCCTCATGAAGCTGCAGTTCCCACTCACTTTCTCAGGCACAGTCAGGCCCATCTGTCTGCCCTTCTTT
GATGAGGAGCTCACTCCAGCCACCCCACTCTGGATCATTGGATGGGGCTTTACGAAGCAGAATGGAGGGAA
GATGTCTGACATACTGCTGCAGGCGTCAGTCCAGGTCATTGACAGCACACGGTGCAATGCAGACGATGCGT
ACCAGGGGGAAGTCACCGAGAAGATGATGTGTGCAGGCATCCCGGAAGGGGGTGTGGACACCTGCCAGGGT
GACAGTGGTGGGCCCCTGATGTACCAATCTGACCAGTGGCATGTGGTGGGCATCGTTAGCTGGGGCTATGG
CTGCGGGGGCCCGAGCACCCCAGGAGTATACACCAAGGTCTCAGCCTATCTCAACTGGATCTACAATGTCT
GGAAGGCTGAGCTG**TAA**TGCTGCTGCCCCTTTGCAGTGCTGGGAGCCGCTTCCTTCCTGCCCTGCCCACCT
GGGGATCCCCCAAAGTCAGACACAGAGCAAGAGTCCCCTTGGGTACACCCCTCTGCCCACAGCCTCAGCAT
TTCTTGGAGCAGCAAAGGGCCTCAATTCCTGTAAGAGACCCTCGCAGCCCAGAGGCGCCCAGAGGAAGTCA
GCAGCCCTAGCTCGGCCACACTTGGTGCTCCCAGCATCCCAGGGAGAGACACAGCCCACTGAACAAGGTCT
CAGGGGTATTGCTAAGCCAAGAAGGAACTTTCCCACACTACTGAATGGAAGCAGGCTGTCTTGTAAAAGCC
CAGATCACTGTGGGCTGGAGAGGAGAAGGAAAGGGTCTGCGCCAGCCCTGTCCGTCTTCACCCATCCCCAA
GCCTACTAGAGCAAGAAACCAGTTGTAATATAAAATGCACTGCCCTACTGTTGGTATGACTACCGTTACCT
ACTGTTGTCATTGTTATTACAGCTATGGCCACTATTATTAAAGAGCTGTGTAACATCTCTGGCAAAAAAAA
AAAA
```

FIGURE 112

MLQDPDSDQPLNSLDVKPLRKPRIPMETFRKVGIPIIIALLSLASIIIVVVLIKVILDKYYFLCG
QPLHFIPRKQLCDGELDCPLGEDEEHCVKSFPEGPAVAVRLSKDRSTLQVLDSATGNWFSACFDN
FTEALAETACRQMGYSRAVEIGPDQDLDVVEITENSQELRMRNSSGPCLSGSLVSLHCLACGKSL
KTPRVVGGEEASVDSWPWQVSIQYDKQHVCGGSILDPHWVLTAAHCFRKHTDVFNWKVRAGSDKL
GSFPSLAVAKIIIIEFNPMYPKDNDIALMKLQFPLTFSGTVRPICLPFFDEELTPATPLWIIGWG
FTKQNGGKMSDILLQASVQVIDSTRCNADDAYQGEVTEKMMCAGIPEGGVDTCQGDSGGPLMYQS
DQWHVVGIVSWGYGCGGPSTPGVYTKVSAYLNWIYNVWKAEL

Transmembrane domain:

amino acids 32-53 (typeII)

FIGURE 113

GGCTGGACTGGAACTCCTGGTCCCAAGTGATCCACCCGCCTCAGCCTCCCAAGGTGCTGTGATTA
TAGGTGTAAGCCACCGTGTCTGGCCTCTGAACAACTTTTTCAGCAACTAAAAAAGCCACAGGAGT
TGAACTGCTAGGATTCTGACTATGCTGTGGTGGCTAGTGCTCCTACTCCTACCTACATTAAAATC
TGTTTTTTGTTCTCTTGTAACTAGCCTTTACCTTCCTAACACAGAGGATCTGTCACTGTGGCTCT
GGCCCAAACCTGACCTTCACTCTGGAACGAGAACAGAGGTTTCTACCCACACCGTCCCCTCGAAG
CCGGGGACAGCCTCACCTTGCTGGCCTCTCGCTGGAGCAGTGCCCTCACCAACTGTCTCACGTCT
GGAGGCACTGACTCGGGCAGTGCAGGTAGCTGAGCCTCTTGGTAGCTGCGGCTTTCAAGGTGGGC
CTTGCCCTGGCCGTAGAAGGGATTGACAAGCCCGAAGATTTCATAGGCGATGGCTCCCACTGCCC
AGGCATCAGCCTTGCTGTAGTCAATCACTGCCCTGGGGCCAGGACGGGCCGTGGACACCTGCTCA
GAAGCAGTGGGTGAGACATCACGCTGCCCGCCCATCTAACCTTTTCATGTCCTGCACATCACCTG
ATCCATGGGCTAATCTGAACTCTGTCCCAAGGAACCCAGAGCTTGAGTGAGCTGTGGCTCAGACC
CAGAAGGGGTCTGCTTAGACCACCTGGTTTATGTGACAGGACTTGCATTCTCCTGGAACATGAGG
GAACGCCGGAGGAAAGCAAAGTGGCAGGGAAGGAACTTGTGCCAAATTATGGGTCAGAAAAGATG
GAGGTGTTGGGTTATCACAAGGCATCGAGTCTCCTGCATTCAGTGGACATGTGGGGGAAGGGCTG
CCGATGGCGCATGACACACTCGGGACTCACCTCTGGGGCCATCAGACAGCCGTTTCCGCCCCGAT
CCACGTACCAGCTGCTGAAGGGCAACTGCAGGCCGATGCTCTCATCAGCCAGGCAGCAGCCAAAA
TCTGCGATCACCAGCCAGGGGCAGCCGTCTGGGAAGGAGCAAGCAAAGTGACCATTTCTCCTCCC
CTCCTTCCCTCTGAGAGGCCCTCCTATGTCCCTACTAAAGCCACCAGCAAGACATAGCTGACAGG
GGCTAATGGCTCAGTGTTGGCCCAGGAGGTCAGCAAGGCCTGAGAGCTGATCAGAAGGGCCTGCT
GTGCGAACACGGAAATGCCTCCAGTAAGCACAGGCTGCAAAATCCCCAGGCAAAGGACTGTGTGG
CTCAATTTAAATCATGTTCTAGTAATTGGAGCTGTCCCCAAGACCAAAGGAGCTAGAGCTTGGTT
CAAATGATCTCCAAGGGCCCTTATACCCCAGGAGACTTTGATTTGAATTTGAAACCCCAAATCCA
AACCTAAGAACCAGGTGCATTAAGAATCAGTTATTGCCGGGTGTGGTGGCCTGTAATGCCAACAT
TTTGGGAGGCCGAGGCGGGTAGATCACCTGAGGTCAGGAGTTCAAGACCAGCCTGGCCAACATGG
TGAAACCCCTGTCTCTACTAAAAATACAAAAAAACTAGCCAGGCATGGTGGTGTGTGCCTGTATC
CCAGCTACTCGGGAGGCTGAGACAGGAGAATTACTTGAACCTGGGAGGTGAAGGAGGCTGAGACA
GGAGAATCACTTCAGCCTGAGCAACACAGCGAGACTCTGTCTCAGAAAAAATAAAAAAAGAATTA
TGGTTATTTGTAA

FIGURE 114

MLWWLVLLLLPTLKSVFCSLVTSLYLPNTEDLSLWLWPKPDLHSGTRTEVSTHTVPSKPGTASPC
WPLAGAVPSPTVSRLEALTRAVQVAEPLGSCGFQGGPCPGRRRD

Signal peptide:
amino acids 1-15

FIGURE 115

CAGCAGTGGTCTCTCAGTCCTCTCAAAGCAAGGAAAGAGTACTGTGTGCTGAGAGACCATGGCAA
AGAATCCTCCAGAGAATTGTGAAGACTGTCACATTCTAAATGCAGAAGCTTTTAAATCCAAGAAA
ATATGTAAATCACTTAAGATTTGTGGACTGGTGTTTGGTATCCTGGCCCTAACTCTAATTGTCCT
GTTTTGGGGGAGCAAGCACTTCTGGCCGGAGGTACCCAAAAAAGCCTATGACATGGAGCACACTT
TCTACAGCAATGGAGAGAAGAAGAAGATTTACATGGAAATTGATCCTGTGACCAGAACTGAAATA
TTCAGAAGCGGAAATGGCACTGATGAAACATTGGAAGTGCACGACTTTAAAAACGGATACACTGG
CATCTACTTCGTGGGTCTTCAAAAATGTTTTATCAAAACTCAGATTAAAGTGATTCCTGAATTTT
CTGAACCAGAAGAGGAAATAGATGAGAATGAAGAAATTACCACAACTTTCTTTGAACAGTCAGTG
ATTTGGGTCCCAGCAGAAAAGCCTATTGAAAACCGAGATTTTCTTAAAAATTCCAAAATTCTGGA
GATTTGTGATAACGTGACCATGTATTGGATCAATCCCACTCTAATATCAGTTTCTGAGTTACAAG
ACTTTGAGGAGGAGGGAGAAGATCTTCACTTTCCTGCCAACGAAAAAAAAGGGATTGAACAAAAT
GAACAGTGGGTGGTCCCTCAAGTGAAAGTAGAGAAGACCCGTCACGCCAGACAAGCAAGTGAGGA
AGAACTTCCAATAAATGACTATACTGAAAATGGAATAGAATTTGATCCCATGCTGGATGAGAGAG
GTTATTGTTGTATTTACTGCCGTCGAGGCAACCGCTATTGCCGCCGCGTCTGTGAACCTTTACTA
GGCTACTACCCATATCCATACTGCTACCAAGGAGGACGAGTCATCTGTCGTGTCATCATGCCTTG
TAACTGGTGGGTGGCCCGCATGCTGGGGAGGGTCTAATAGGAGGTTTGAGCTCAAATGCTTAAAC
TGCTGGCAACATATAATAAATGCATGCTATTCAATGAATTTCTGCCTATGAGGCATCTGGCCCCT
GGTAGCCAGCTCTCCAGAATTACTTGTAGGTAATTCCTCTCTTCATGTTCTAATAAACTTCTACA
TTATCACCAAAAAAAAAAAAAAAAAAA

FIGURE 116

MAKNPPENCEDCHILNAEAFKSKKICKSLKICGLVFGILALTLIVLFWGSKHFWPEVPKKAYDME
HTFYSNGEKKKIYMEIDPVTRTEIFRSGNGTDETLEVHDFKNGYTGIYFVGLQKCFIKTQIKVIP
EFSEPEEEIDENEEITTTFFEQSVIWVPAEKPIENRDFLKNSKILEICDNVTMYWINPTLISVSE
LQDFEEEGEDLHFPANEKKGIEQNEQWVVPQVKVEKTRHARQASEEELPINDYTENGIEFDPMLD
ERGYCCIYCRRGNRYCRRVCEPLLGYYPYPYCYQGGRVICRVIMPCNWWVARMLGRV

Important features of the protein:

Signal peptide:

amino acids 1-40

Transmembrane domain:

amino acids 25-47 (type II)

N-glycosylation sites.

amino acids 94-97, 180-183

Glycosaminoglycan attachment sites.

amino acids 92-95, 70-73, 85-88, 133-136, 148-151, 192-195, 239-242

N-myristoylation sites.

amino acids 33-38, 95-100, 116-121, 215-220, 272-277

Microbodies C-terminal targeting signal.

amino acids 315-317

Cytochrome c family heme-binding site signature.

amino acids 9-14

FIGURE 117

GAGCTCCCCTCAGGAGCGCGTTAGCTTCACACCTTCGGCAGCAGGAGGGCGGCAGCTTCTCGCAGGCGGCA
GGGCGGGCGGCCAGGATCATGTCCACCACCACATGCCAAGTGGTGGCGTTCCTCCTGTCCATCCTGGGGCT
GGCCGGCTGCATCGCGGCCACCGGGATGGACATGTGGAGCACCCAGGACCTGTACGACAACCCCGTCACCT
CCGTGTTCCAGTACGAAGGGCTCTGGAGGAGCTGCGTGAGGCAGAGTTCAGGCTTCACCGAATGCAGGCCC
TATTTCACCATCCTGGGACTTCCAGCCATGCTGCAGGCAGTGCGAGCCCTGATGATCGTAGGCATCGTCCT
GGGTGCCATTGGCCTCCTGGTATCCATCTTTGCCCTGAAATGCATCCGCATTGGCAGCATGGAGGACTCTG
CCAAAGCCAACATGACACTGACCTCCGGGATCATGTTCATTGTCTCAGGTCTTTGTGCAATTGCTGGAGTG
TCTGTGTTTGCCAACATGCTGGTGACTAACTTCTGGATGTCCACAGCTAACATGTACACCGGCATGGGTGG
GATGGTGCAGACTGTTCAGACCAGGTACACATTTGGTGCGGCTCTGTTCGTGGGCTGGGTCGCTGGAGGCC
TCACACTAATTGGGGGTGTGATGATGTGCATCGCCTGCCGGGGCCTGGCACCAGAAGAAACCAACTACAAA
GCCGTTTCTTATCATGCCTCAGGCCACAGTGTTGCCTACAAGCCTGGAGGCTTCAAGGCCAGCACTGGCTT
TGGGTCCAACACCAAAAACAAGAAGATATACGATGGAGGTGCCCGCACAGAGGACGAGGTACAATCTTATC
CTTCCAAGCACGACTATGTGTAATGCTCTAAGACCTCTCAGCACGGGCGGAAGAAACTCCCGGAGAGCTCA
CCCAAAAAACAAGGAGATCCCATCTAGATTTCTTCTTGCTTTTGACTCACAGCTGGAAGTTAGAAAAGCCT
CGATTTCATCTTTGGAGAGGCCAAATGGTCTTAGCCTCAGTCTCTGTCTCTAAATATTCCACCATAAAACA
GCTGAGTTATTTATGAATTAGAGGCTATAGCTCACATTTTCAATCCTCTATTTCTTTTTTTAAATATAACT
TTCTACTCTGATGAGAGAATGTGGTTTTAATCTCTCTCTCACATTTTGATGATTTAGACAGACTCCCCCTC
TTCCTCCTAGTCAATAAACCCATTGATGATCTATTTCCCAGCTTATCCCCAAGAAAACTTTTGAAAGGAAA
GAGTAGACCCAAAGATGTTATTTTCTGCTGTTTGAATTTTGTCTCCCCACCCCCAACTTGGCTAGTAATAA
ACACTTACTGAAGAAGAAGCAATAAGAGAAAGATATTTGTAATCTCTCCAGCCCATGATCTCGGTTTTCTT
ACACTGTGATCTTAAAAGTTACCAAACCAAAGTCATTTTCAGTTTGAGGCAACCAAACCTTTCTACTGCTG
TTGACATCTTCTTATTACAGCAACACCATTCTAGGAGTTTCCTGAGCTCTCCACTGGAGTCCTCTTTCTGT
CGCGGGTCAGAAATTGTCCCTAGATGAATGAGAAAATTATTTTTTTTAATTTAAGTCCTAAATATAGTTAA
AATAAATAATGTTTTAGTAAAATGATACACTATCTCTGTGAAATAGCCTCACCCCTACATGTGGATAGAAG
GAAATGAAAAAATAATTGCTTTGACATTGTCTATATGGTACTTTGTAAAGTCATGCTTAAGTACAAATTCC
ATGAAAAGCTCACACCTGTAATCCTAGCACTTTGGGAGGCTGAGGAGGAAGGATCACTTGAGCCCAGAAGT
TCGAGACTAGCCTGGGCAACATGGAGAAGCCCTGTCTCTACAAAATACAGAGAGAAAAAATCAGCCAGTCA
TGGTGGCATACACCTGTAGTCCCAGCATTCCGGGAGGCTGAGGTGGGAGGATCACTTGAGCCCAGGGAGGT
TGGGGCTGCAGTGAGCCATGATCACACCACTGCACTCCAGCCAGGTGACATAGCGAGATCCTGTCTAAAAA
AATAAAAAATAAATAATGGAACACAGCAAGTCCTAGGAAGTAGGTTAAAACTAATTCTTTAA

FIGURE 118

MSTTTCQVVAFLLSILGLAGCIAATGMDMWSTQDLYDNPVTSVFQYEGLWRSCVRQSSGFTECRP
YFTILGLPAMLQAVRALMIVGIVLGAIGLLVSIFALKCIRIGSMEDSAKANMTLTSGIMFIVSGL
CAIAGVSVFANMLVTNFWMSTANMYTGMGGMVQTVQTRYTFGAALFVGWVAGGLTLIGGVMMCIA
CRGLAPEETNYKAVSYHASGHSVAYKPGGFKASTGFGSNTKNKKIYDGGARTEDEVQSYPSKHDY
V

Signal peptide:

amino acids 1-23

Transmembrane domains:

amino acids 81-100, 121-141, 173-194

FIGURE 119

GGAAAAACTGTTCTCTTCTGTGGCACAGAGAACCCTGCTTCAAAGCAGAAGTAGCAGTTCCGGAGTCC
AGCTGGCTAAAACTCATCCCAGAGGATAATGGCAACCCATGCCTTAGAAATCGCTGGGCTGTTTCTTG
GTGGTGTTGGAATGGTGGGCACAGTGGCTGTCACTGTCATGCCTCAGTGGAGAGTGTCGGCCTTCATT
GAAAACAACATCGTGGTTTTTGAAAACTTCTGGGAAGGACTGTGGATGAATTGCGTGAGGCAGGCTAA
CATCAGGATGCAGTGCAAAATCTATGATTCCCTGCTGGCTCTTTCTCCGGACCTACAGGCAGCCAGAG
GACTGATGTGTGCTGCTTCCGTGATGTCCTTCTTGGCTTTCATGATGGCCATCCTTGGCATGAAATGC
ACCAGGTGCACGGGGGACAATGAGAAGGTGAAGGCTCACATTCTGCTGACGGCTGGAATCATCTTCAT
CATCACGGGCATGGTGGTGCTCATCCCTGTGAGCTGGGTTGCCAATGCCATCATCAGAGATTTCTATA
ACTCAATAGTGAATGTTGCCCAAAAACGTGAGCTTGGAGAAGCTCTCTACTTAGGATGGACCACGGCA
CTGGTGCTGATTGTTGGAGGAGCTCTGTTCTGCTGCGTTTTTTGTTGCAACGAAAAGAGCAGTAGCTA
CAGATACTCGATACCTTCCCATCGCACAACCCAAAAAAGTTATCACACCGGAAAGAAGTCACCGAGCG
TCTACTCCAGAAGTCAGTATGTGTAGTTGTGTATGTTTTTTAACTTTACTATAAAGCCATGCAAATG
ACAAAAATCTATATTACTTTCTCAAAATGGACCCCAAAGAAACTTTGATTTACTGTTCTTAACTGCCT
AATCTTAATTACAGGAACTGTGCATCAGCTATTTATGATTCTATAAGCTATTTCAGCAGAATGAGATA
TTAAACCCAATGCTTTGATTGTTCTAGAAAGTATAGTAATTTGTTTTCTAAGGTGGTTCAAGCATCTA
CTCTTTTTATCATTTACTTCAAAATGACATTGCTAAAGACTGCATTATTTTACTACTGTAATTTCTCC
ACGACATAGCATTATGTACATAGATGAGTGTAACATTTATATCTCACATAGAGACATGCTTATATGGT
TTTATTTAAAATGAAATGCCAGTCCATTACACTGAATAAATAGAACTCAACTATTGCTTTTCAGGGAA
ATCATGGATAGGGTTGAAGAAGGTTACTATTAATTGTTTAAAAACAGCTTAGGGATTAATGTCCTCCA
TTTATAATGAAGATTAAAATGAAGGCTTTAATCAGCATTGTAAAGGAAATTGAATGGCTTTCTGATAT
GCTGTTTTTTAGCCTAGGAGTTAGAAATCCTAACTTCTTTATCCTCTTCTCCCAGAGGCTTTTTTTTT
CTTGTGTATTAAATTAACATTTTTAAAACGCAGATATTTTGTCAAGGGGCTTTGCATTCAAACTGCTT
TTCCAGGGCTATACTCAGAAGAAAGATAAAAGTGTGATCTAAGAAAAAGTGATGGTTTTAGGAAAGTG
AAAATATTTTTGTTTTTGTATTTGAAGAAGAATGATGCATTTTGACAAGAAATCATATATGTATGGAT
ATATTTTAATAAGTATTTGAGTACAGACTTTGAGGTTTCATCAATATAAATAAAAGAGCAGAAAAATA
TGTCTTGGTTTTCATTTGCTTACCAAAAAAACAACAACAAAAAAAGTTGTCCTTTGAGAACTTCACCT
GCTCCTATGTGGGTACCTGAGTCAAAATTGTCATTTTTGTTCTGTGAAAAATAAATTTCCTTCTTGTA
CCATTTCTGTTTAGTTTTACTAAAATCTGTAAATACTGTATTTTTCTGTTTATTCCAAATTTGATGAA
ACTGACAATCCAATTTGAAAGTTTGTGTCGACGTCTGTCTAGCTTAAATGAATGTGTTCTATTTGCTT
TATACATTTATATTAATAAATTGTACATTTTTCTAATT

FIGURE 120

MATHALEIAGLFLGGVGMVGTVAVTVMPQWRVSAFIENNIVVFENFWEGLWMNCVRQANIRMQCK
IYDSLLALSPDLQAARGLMCAASVMSFLAFMMAILGMKCTRCTGDNEKVKAHILLTAGIIFIITG
MVVLIPVSWVANAIIRDFYNSIVNVAQKRELGEALYLGWTTALVLIVGGALFCCVFCCNEKSSSY
RYSIPSHRTTQKSYHTGKKSPSVYSRSQYV

Signal peptide:

amino acids 1-17

Transmembrane domains:

amino acids 82-101, 118-145, 164-188

FIGURE 121

GGAGAGAGGCGCGCGGGTGAAAGGCGCATTGATGCAGCCTGCGGCGGCCTCGGAGCGCGGCGGAG
CCAGACGCTGACCACGTTCCTCTCCTCGGTCTCCTCCGCCTCCAGCTCCGCGCTGCCCGGCAGCC
GGGAGCCATGCGACCCCAGGGCCCCGCCGCCTCCCCGCAGCGGCTCCGCGGCCTCCTGCTGCTCC
TGCTGCTGCAGCTGCCCGCGCCGTCGAGCGCCTCTGAGATCCCCAAGGGGAAGCAAAAGGCGCAG
CTCCGGCAGAGGGAGGTGGTGGACCTGTATAATGGAATGTGCTTACAAGGGCCAGCAGGAGTGCC
TGGTCGAGACGGGAGCCCTGGGGCCAATGTTATTCCGGGTACACCTGGGATCCCAGGTCGGGATG
GATTCAAAGGAGAAAAGGGGGAATGTCTGAGGGAAAGCTTTGAGGAGTCCTGGACACCCAACTAC
AAGCAGTGTTCATGGAGTTCATTGAATTATGGCATAGATCTTGGGAAAATTGCGGAGTGTACATT
TACAAAGATGCGTTCAAATAGTGCTCTAAGAGTTTTGTTCAGTGGCTCACTTCGGCTAAAATGCA
GAAATGCATGCTGTCAGCGTTGGTATTTCACATTCAATGGAGCTGAATGTTCAGGACCTCTTCCC
ATTGAAGCTATAATTTATTTGGACCAAGGAAGCCCTGAAATGAATTCAACAATTAATATTCATCG
CACTTCTTCTGTGGAAGGACTTTGTGAAGGAATTGGTGCTGGATTAGTGGATGTTGCTATCTGGG
TTGGCACTTGTTCAGATTACCCAAAAGGAGATGCTTCTACTGGATGGAATTCAGTTTCTCGCATC
ATTATTGAAGAACTACCAAAATAAATGCTTTAATTTTCATTTGCTACCTCTTTTTTTATTATGCC
TTGGAATGGTTCACTTAAATGACATTTTAAATAAGTTTATGTATACATCTGAATGAAAAGCAAAG
CTAAATATGTTTACAGACCAAAGTGTGATTTCACACTGTTTTTAAATCTAGCATTATTCATTTTG
CTTCAATCAAAAGTGGTTTCAATATTTTTTTTAGTTGGTTAGAATACTTTCTTCATAGTCACATT
CTCTCAACCTATAATTTGGAATATTGTTGTGGTCTTTTGTTTTTTCTCTTAGTATAGCATTTTTA
AAAAAATATAAAAGCTACCAATCTTTGTACAATTTGTAAATGTTAAGAATTTTTTTTATATCTGT
TAAATAAAAATTATTTCCAACA

FIGURE 122

MRPQGPAASPQRLRGLLLLLLLQLPAPSSASEIPKGKQKAQLRQREVVDLYNGMCLQGPAGVPGR
DGSPGANVIPGTPGIPGRDGFKGEKGECLRESFEESWTPNYKQCSWSSLNYGIDLGKIAECTFTK
MRSNSALRVLFSGSLRLKCRNACCQRWYFTFNGAECSGPLPIEAIIYLDQGSPEMNSTINIHRTS
SVEGLCEGIGAGLVDVAIWVGTCSDYPKGDASTGWNSVSRIIIEELPK

Signal peptide:

amino acids 1-30

Transmembrane domain:

amino acids 195-217

FIGURE 123

GCTGAGCGTGTGCGCGGTACGGGGCTCTCCTGCCTTCTGGGCTCCAACGCAGCTCTGTGGCTGAA
CTGGGTGCTCATCACGGGAACTGCTGGGCTATGGAATACAGATGTGGCAGCTCAGGTAGCCCCAA
ATTGCCTGGAAGAATACATCATGTTTTTCGATAAGAAGAAATTGTAGGATCCAGTTTTTTTTTA
ACCGCCCCCTCCCCACCCCCCAAAAAAACTGTAAAGATGCAAAAACGTAATATCCATGAAGATCC
TATTACCTAGGAAGATTTTGATGTTTTGCTGCGAATGCGGTGTTGGGATTTATTTGTTCTTGGAG
TGTTCTGCGTGGCTGGCAAAGAATAATGTTCCAAAATCGGTCCATCTCCCAAGGGGTCCAATTTT
TCTTCCTGGGTGTCAGCGAGCCCTGACTCACTACAGTGCAGCTGACAGGGGCTGTCATGCAACTG
GCCCCTAAGCCAAAGCAAAAGACCTAAGGACGACCTTTGAACAATACAAAGG<u>ATG</u>GGTTTCAATG
TAATTAGGCTACTGAGCGGATCAGCTGTAGCACTGGTTATAGCCCCCACTGTCTTACTGACAATG
CTTTCTTCTGCCGAACGAGGATGCCCTAAGGGCTGTAGGTGTGAAGGCAAAATGGTATATTGTGA
ATCTCAGAAATTACAGGAGATACCCTCAAGTATATCTGCTGGTTGCTTAGGTTTGTCCCTTCGCT
ATAACAGCCTTCAAAAACTTAAGTATAATCAATTTAAAGGGCTCAACCAGCTCACCTGGCTATAC
CTTGACCATAACCATATCAGCAATATTGACGAAAATGCTTTTAATGGAATACGCAGACTCAAAGA
GCTGATTCTTAGTTCCAATAGAATCTCCTATTTTCTTAACAATACCTTCAGACCTGTGACAAATT
TACGGAACTTGGATCTGTCCTATAATCAGCTGCATTCTCTGGGATCTGAACAGTTTCGGGGCTTG
CGGAAGCTGCTGAGTTTACATTTACGGTCTAACTCCCTGAGAACCATCCCTGTGCGAATATTCCA
AGACTGCCGCAACCTGGAACTTTTGGACCTGGGATATAACCGGATCCGAAGTTTAGCCAGGAATG
TCTTTGCTGGCATGATCAGACTCAAAGAACTTCACCTGGAGCACAATCAATTTTCCAAGCTCAAC
CTGGCCCTTTTTCCAAGGTTGGTCAGCCTTCAGAACCTTTACTTGCAGTGGAATAAAATCAGTGT
CATAGGACAGACCATGTCCTGGACCTGGAGCTCCTTACAAAGGCTTGATTTATCAGGCAATGAGA
TCGAAGCTTTCAGTGGACCCAGTGTTTTCCAGTGTGTCCCGAATCTGCAGCGCCTCAACCTGGAT
TCCAACAAGCTCACATTTATTGGTCAAGAGATTTTGGATTCTTGGATATCCCTCAATGACATCAG
TCTTGCTGGGAATATATGGGAATGCAGCAGAAATATTTGCTCCCTTGTAAACTGGCTGAAAAGTT
TTAAAGGTCTAAGGGAGAATACAATTATCTGTGCCAGTCCCAAAGAGCTGCAAGGAGTAAATGTG
ATCGATGCAGTGAAGAACTACAGCATCTGTGGCAAAAGTACTACAGAGAGGTTTGATCTGGCCAG
GGCTCTCCCAAAGCCGACGTTTAAGCCCAAGCTCCCCAGGCCGAAGCATGAGAGCAAACCCCCTT
TGCCCCCGACGGTGGGAGCCACAGAGCCCGGCCCAGAGACCGATGCTGACGCCGAGCACATCTCT
TTCCATAAAATCATCGCGGGCAGCGTGGCGCTTTTCCTGTCCGTGCTCGTCATCCTGCTGGTTAT
CTACGTGTCATGGAAGCGGTACCCTGCGAGCATGAAGCAGCTGCAGCAGCGCTCCCTCATGCGAA
GGCACAGGAAAAAGAAAAGACAGTCCCTAAAGCAAATGACTCCCAGCACCCAGGAATTTTATGTA
GATTATAAACCCACCAACACGGAGACCAGCGAGATGCTGCTGAATGGGACGGGACCCTGCACCTA
TAACAAATCGGGCTCCAGGGAGTGTGAGGTA<u>TGA</u>ACCATTGTGATAAAAAGAGCTCTTAAAAGCT
GGGAAATAAGTGGTGCTTTATTGAACTCTGGTGACTATCAAGGGAACGCGATGCCCCCCCTCCCC
TTCCCTCTCCCTCTCACTTTGGTGGCAAGATCCTTCCTTGTCCGTTTTAGTGCATTCATAATACT
GGTCATTTTCCTCTCATACATAATCAACCCATTGAAATTTAAATACCACAATCAATGTGAAGCTT
GAACTCCGGTTTAATATAATACCTATTGTATAAGACCCTTTACTGATTCCATTAATGTCGCATTT
GTTTTAAGATAAAACTTCTTTCATAGGTAAAAAAAAAAA

FIGURE 124

MGFNVIRLLSGSAVALVIAPTVLLTMLSSAERGCPKGCRCEGKMVYCESQKLQEIPSSISAGCLG
LSLRYNSLQKLKYNQFKGLNQLTWLYLDHNHISNIDENAFNGIRRLKELILSSNRISYFLNNTFR
PVTNLRNLDLSYNQLHSLGSEQFRGLRKLLSLHLRSNSLRTIPVRIFQDCRNLELLDLGYNRIRS
LARNVFAGMIRLKELHLEHNQFSKLNLALFPRLVSLQNLYLQWNKISVIGQTMSWTWSSLQRLDL
SGNEIEAFSGPSVFQCVPNLQRLNLDSNKLTFIGQEILDSWISLNDISLAGNIWECSRNICSLVN
WLKSFKGLRENTIICASPKELQGVNVIDAVKNYSICGKSTTERFDLARALPKPTFKPKLPRPKHE
SKPPLPPTVGATEPGPETDADAEHISFHKIIAGSVALFLSVLVILLVIYVSWKRYPASMKQLQQR
SLMRRHRKKKRQSLKQMTPSTQEFYVDYKPTNTETSEMLLNGTGPCTYNKSGSRECEV

Important features of the protein:

Signal peptide:

amino acids 1-33

Transmembrane domain:

amino acids 420-442

N-glycosylation sites.

amino acids 126-129, 357-360, 496-499, 504-507 cAMP- and cGMP-dependent protein kinase phosphorylation site.

amino acids 465-468

Tyrosine kinase phosphorylation site.

amino acids 136-142

N-myristoylation sites.

amino acids 11-16, 33-38, 245-250, 332-337, 497-502, 507-512

FIGURE 125

CCGTTATCGTCTTGCGCTACTGCTGAATGTCCGTCCCGGAGGAGGAGGAGAGGCTTTTGCCGCTG
ACCCAGAGATGGCCCCGAGCGAGCAAATTCCTACTGTCCGGCTGCGCGGCTACCGTGGCCGAGCT
AGCAACCTTTCCCCTGGATCTCACAAAAACTCGACTCCAAATGCAAGGAGAAGCAGCTCTTGCTC
GGTTGGGAGACGGTGCAAGAGAATCTGCCCCCTATAGGGGAATGGTGCGCACAGCCCTAGGGATC
ATTGAAGAGGAAGGCTTTCTAAAGCTTTGGCAAGGAGTGACACCCGCCATTTACAGACACGTAGT
GTATTCTGGAGGTCGAATGGTCACATATGAACATCTCCGAGAGGTTGTGTTTGGCAAAAGTGAAG
ATGAGCATTATCCCCTTTGGAAATCAGTCATTGGAGGGATGATGGCTGGTGTTATTGGCCAGTTT
TTAGCCAATCCAACTGACCTAGTGAAGGTTCAGATGCAAATGGAAGGAAAAAGGAAACTGGAAGG
AAAACCATTGCGATTTCGTGGTGTACATCATGCATTTGCAAAAATCTTAGCTGAAGGAGGAATAC
GAGGGCTTTGGGCAGGCTGGGTACCCAATATACAAAGAGCAGCACTGGTGAATATGGGAGATTTA
ACCACTTATGATACAGTGAAACACTACTTGGTATTGAATACACCACTTGAGGACAATATCATGAC
TCACGGTTTATCAAGTTTATGTTCTGGACTGGTAGCTTCTATTCTGGGAACACCAGCCGATGTCA
TCAAAAGCAGAATAATGAATCAACCACGAGATAAACAAGGAAGGGGACTTTTGTATAAATCATCG
ACTGACTGCTTGATTCAGGCTGTTCAAGGTGAAGGATTCATGAGTCTATATAAAGGCTTTTTACC
ATCTTGGCTGAGAATGACCCCTTGGTCAATGGTGTTCTGGCTTACTTATGAAAAAATCAGAGAGA
TGAGTGGAGTCAGTCCATTTTAA

FIGURE 126

MSVPEEEERLLPLTQRWPRASKFLLSGCAATVAELATFPLDLTKTRLQMQGEAALARLGDGARES
APYRGMVRTALGIIEEEGFLKLWQGVTPAIYRHVVYSGGRMVTYEHLREVVFGKSEDEHYPLWKS
VIGGMMAGVIGQFLANPTDLVKVQMQMEGKRKLEGKPLRFRGVHHAFAKILAEGGIRGLWAGWVP
NIQRAALVNMGDLTTYDTVKHYLVLNTPLEDNIMTHGLSSLCSGLVASILGTPADVIKSRIMNQP
RDKQGRGLLYKSSTDCLIQAVQGEGFMSLYKGFLPSWLRMTPWSMVFWLTYEKIREMSGVSPF

Transmembrane domains:

amino acids 25-38, 130-147, 233-248

FIGURE 127

CGCGGATCGGACCCAAGCAGGTCGGCGGCGGCAGGAGAGCGGCCGGGCGTCAGCTCCTCGAC
CCCCGTGTCGGGCTAGTCCAGCGAGGCGGACGGGCGGCGTGGGCCCATGGCCAGGCCCGGCATGG
AGCGGTGGCGCGACCGGCTGGCGCTGGTGACGGGGGCCTCGGGGGGCATCGGCGCGGCCGTGGCC
CGGGCCCTGGTCCAGCAGGGACTGAAGGTGGTGGGCTGCGCCCGCACTGTGGGCAACATCGAGGA
GCTGGCTGCTGAATGTAAGAGTGCAGGCTACCCCGGGACTTTGATCCCCTACAGATGTGACCTAT
CAAATGAAGAGGACATCCTCTCCATGTTCTCAGCTATCCGTTCTCAGCACAGCGGTGTAGACATC
TGCATCAACAATGCTGGCTTGGCCCGGCCTGACACCCTGCTCTCAGGCAGCACCAGTGGTTGGAA
GGACATGTTCAATGTGAACGTGCTGGCCCTCAGCATCTGCACACGGGAAGCCTACCAGTCCATGA
AGGAGCGGAATGTGGACGATGGGCACATCATTAACATCAATAGCATGTCTGGCCACCGAGTGTTA
CCCCTGTCTGTGACCCACTTCTATAGTGCCACCAAGTATGCCGTCACTGCGCTGACAGAGGGACT
GAGGCAAGAGCTTCGGGAGGCCCAGACCCACATCCGAGCCACGTGCATCTCTCCAGGTGTGGTGG
AGACACAATTCGCCTTCAAACTCCACGACAAGGACCCTGAGAAGGCAGCTGCCACCTATGAGCAA
ATGAAGTGTCTCAAACCCGAGGATGTGGCCGAGGCTGTTATCTACGTCCTCAGCACCCCCGCACA
CATCCAGATTGGAGACATCCAGATGAGGCCCACGGAGCAGGTGACCTAGTGACTGTGGGAGCTCC
TCCTTCCCTCCCCACCCTTCATGGCTTGCCTCCTGCCTCTGGATTTTAGGTGTTGATTTCTGGAT
CACGGGATACCACTTCCTGTCCACACCCCGACCAGGGGCTAGAAAATTTGTTTGAGATTTTTATA
TCATCTTGTCAAATTGCTTCAGTTGTAAATGTGAAAAATGGGCTGGGGAAAGGAGGTGGTGTCCC
TAATTGTTTTACTTGTTAACTTGTTCTTGTGCCCCTGGGCACTTGGCCTTTGTCTGCTCTCAGTG
TCTTCCCTTTGACATGGGAAAGGAGTTGTGGCCAAAATCCCCATCTTCTTGCACCTCAACGTCTG
TGGCTCAGGGCTGGGGTGGCAGAGGGAGGCCTTCACCTTATATCTGTGTTGTTATCCAGGGCTCC
AGACTTCCTCCTCTGCCTGCCCCACTGCACCCTCTCCCCCTTATCTATCTCCTTCTCGGCTCCCC
AGCCCAGTCTTGGCTTCTTGTCCCCTCCTGGGGTCATCCCTCCACTCTGACTCTGACTATGGCAG
CAGAACACCAGGGCCTGGCCCAGTGGATTTCATGGTGATCATTAAAAAAGAAAATCGCAACCAA
AAAAAAAAAA

FIGURE 128

MARPGMERWRDRLALVTGASGGIGAAVARALVQQGLKVVGCARTVGNIEELAAECKSAGYPGTLI
PYRCDLSNEEDILSMFSAIRSQHSGVDICINNAGLARPDTLLSGSTSGWKDMFNVNVLALSICTR
EAYQSMKERNVDDGHIININSMSGHRVLPLSVTHFYSATKYAVTALTEGLRQELREAQTHIRATC
ISPGVVETQFAFKLHDKDPEKAAATYEQMKCLKPEDVAEAVIYVLSTPAHIQIGDIQMRPTEQVT

Important features of the protein:

Signal peptide:

amino acids 1-17

N-myristoylation sites.

amino acids 18-24, 21-27, 22-28, 24-30, 40-46, 90-96, 109-115, 199-205

Short-chain alcohol dehyrogenase.

amino acids 30-42, 104-114

FIGURE 129

AACTTCTACATGGGCCTCCTGCTGCTGGTGCTCTTCCTCAGCCTCCTGCCGGTGGCCTACACCAT
CATGTCCCTCCCACCCTCCTTTGACTGCGGGCCGTTCAGGTGCAGAGTCTCAGTTGCCCGGGAGC
ACCTCCCCTCCCGAGGCAGTCTGCTCAGAGGGCCTCGGCCCAGAATTCCAGTTCTGGTTTCATGC
CAGCCTGTAAAAGGCCATGGAACTTTGGGTGAATCACCGATGCCATTTAAGAGGGTTTTCTGCCA
GGATGGAAATGTTAGGTCGTTCTGTGTCTGCGCTGTTCATTTCAGTAGCCACCAGCCACCTGTGG
CCGTTGAGTGCTTGAAATGAGGAACTGAGAAAATTAATTTCTCATGTATTTTTCTCATTTATTTA
TTAATTTTTAACTGATAGTTGTACATATTTGGGGGTACATGTGATATTTGGATACATGTATACAA
TATATAATGATCAAATCAGGGTAACTGGGATATCCATCACATCAAACATTTATTTTTTATTCTTT
TTAGACAGAGTCTCACTCTGTCACCCAGGCTGGAGTGCAGTGGTGCCATCTCAGCTTACTGCAAC
CTCTGCCTGCCAGGTTCAAGCGATTCTCATGCCTCCACCTCCCAAGTAGCTGGGACTACAGGCAT
GCACCACAATGCCCAACTAATTTTTGTATTTTTAGTAGAGACGGGGTTTTGCCATGTTGCCCAGG
CTGGCCTTGAACTCCTGGCCTCAAACAATCCACTTGCCTCGGCCTCCCAAAGTGTTATGATTACA
GGCGTGAGCCACCGTGCCTGGCCTAAACATTTATCTTTTCTTTGTGTTGGGAACTTTGAAATTAT
ACAATGAATTATTGTTAACTGTCATCTCCCTGCTGTGCTATGGAACACTGGGACTTCTTCCCTCT
ATCTAACTGTATATTTGTACCAGTTAACCAACCGTACTTCATCCCCACTCCTCTCTATCCTTCCC
AACCTCTGATCACCTCATTCTACTCTCTACCTCCATGAGATCCACTTTTTTAGCTCCCACATGTG
AGTAAGAAAATGCAATATTTGTCTTTCTGTGCCTGGCTTATTTCACTTAACATAATGACTTCCTG
TTCCATCCATGTTGCTGCAAATGACAGGATTTCGTTCTTAATTTCAATTAAAATAACCACACATG
GCAAAAA

FIGURE 130

MGLLLLVLFLSLLPVAYTIMSLPPSFDCGPFRCRVSVAREHLPSRGSLLRGPRPRIPVLVSCQPV
KGHGTLGESPMPFKRVFCQDGNVRSFCVCAVHFSSHQPPVAVECLK

Important features of the protein:

Signal peptide:

amino acids 1-18

N-myristoylation site.

amino acids 86-92

Zinc carboxypeptidases, zinc-binding region 2 signature.

amino acids 68-79

FIGURE 131

TTCTGAAGTAACGGAAGCTACCTTGTATAAAGACCTCAACACTGCTGACCATGATCAGCGCAGCCTGGAGC
ATCTTCCTCATCGGGACTAAAATTGGGCTGTTCCTTCAAGTAGCACCTCTATCAGTTATGGCTAAATCCTG
TCCATCTGTGTGTCGCTGCGATGCGGGTTTCATTTACTGTAATGATCGCTTTCTGACATCCATTCCAACAG
GAATACCAGAGGATGCTACAACTCTCTACCTTCAGAACAACCAAATAAATAATGCTGGGATTCCTTCAGAT
TTGAAAAACTTGCTGAAAGTAGAAAGAATATACCTATACCACAACAGTTTAGATGAATTTCCTACCAACCT
CCCAAAGTATGTAAAAGAGTTACATTTGCAAGAAAATAACATAAGGACTATCACTTATGATTCACTTTCAA
AAATTCCCTATCTGGAAGAATTACATTTAGATGACAACTCTGTCTCTGCAGTTAGCATAGAAGAGGGAGCA
TTCCGAGACAGCAACTATCTCCGACTGCTTTTCCTGTCCCGTAATCACCTTAGCACAATTCCCTGGGGTTT
GCCCAGGACTATAGAAGAACTACGCTTGGATGATAATCGCATATCCACTATTTCATCACCATCTCTTCAAG
GTCTCACTAGTCTAAAACGCCTGGTTCTAGATGGAAACCTGTTGAACAATCATGGTTTAGGTGACAAAGTT
TTCTTCAACCTAGTTAATTTGACAGAGCTGTCCCTGGTGCGGAATTCCCTGACTGCTGCACCAGTAAACCT
TCCAGGCACAAACCTGAGGAAGCTTTATCTTCAAGATAACCACATCAATCGGGTGCCCCCAAATGCTTTTT
CTTATCTAAGGCAGCTCTATCGACTGGATATGTCCAATAATAACCTAAGTAATTTACCTCAGGGTATCTTT
GATGATTTGGACAATATAACACAACTGATTCTTCGCAACAATCCCTGGTATTGCGGGTGCAAGATGAAATG
GGTACGTGACTGGTTACAATCACTACCTGTGAAGGTCAACGTGCGTGGGCTCATGTGCCAAGCCCCAGAAA
AGGTTCGTGGGATGGCTATTAAGGATCTCAATGCAGAACTGTTTGATTGTAAGGACAGTGGGATTGTAAGC
ACCATTCAGATAACCACTGCAATACCCAACACAGTGTATCCTGCCCAAGGACAGTGGCCAGCTCCAGTGAC
CAAACAGCCAGATATTAAGAACCCCAAGCTCACTAAGGATCAACAAACCACAGGGAGTCCCTCAAGAAAAA
CAATTACAATTACTGTGAAGTCTGTCACCTCTGATACCATTCATATCTCTTGGAAACTTGCTCTACCTATG
ACTGCTTTGAGACTCAGCTGGCTTAAACTGGGCCATAGCCCGGCATTTGGATCTATAACAGAAACAATTGT
AACAGGGGAACGCAGTGAGTACTTGGTCACAGCCCTGGAGCCTGATTCACCCTATAAAGTATGCATGGTTC
CCATGGAAACCAGCAACCTCTACCTATTTGATGAAACTCCTGTTTGTATTGAGACTGAAACTGCACCCCTT
CGAATGTACAACCCTACAACCACCCTCAATCGAGAGCAAGAGAAAGAACCTTACAAAAACCCCAATTTACC
TTTGGCTGCCATCATTGGTGGGGCTGTGGCCCTGGTTACCATTGCCCTTCTTGCTTTAGTGTGTTGGTATG
TTCATAGGAATGGATCGCTCTTCTCAAGGAACTGTGCATATAGCAAAGGGAGGAGAAGAAAGGATGACTAT
GCAGAAGCTGGCACTAAGAAGGACAACTCTATCCTGGAAATCAGGGAAACTTCTTTTCAGATGTTACCAAT
AAGCAATGAACCCATCTCGAAGGAGGAGTTTGTAATACACACCATATTTCCTCCTAATGGAATGAATCTGT
ACAAAAACAATCACAGTGAAAGCAGTAGTAACCGAAGCTACAGAGACAGTGGTATTCCAGACTCAGATCAC
TCACACTCATGATGCTGAAGGACTCACAGCAGACTTGTGTTTTGGGTTTTTTAAACCTAAGGGAGGTGATG
GT

FIGURE 132

MISAAWSIFLIGTKIGLFLQVAPLSVMAKSCPSVCRCDAGFIYCNDRFLTSIPTGIPEDATTLYL
QNNQINNAGIPSDLKNLLKVERIYLYHNSLDEFPTNLPKYVKELHLQENNIRTITYDSLSKIPYL
EELHLDDNSVSAVSIEEGAFRDSNYLRLLFLSRNHLSTIPWGLPRTIEELRLDDNRISTISSPSL
QGLTSLKRLVLDGNLLNNHGLGDKVFFNLVNLTELSLVRNSLTAAPVNLPGTNLRKLYLQDNHIN
RVPPNAFSYLRQLYRLDMSNNNLSNLPQGIFDDLDNITQLILRNNPWYCGCKMKWVRDWLQSLPV
KVNVRGLMCQAPEKVRGMAIKDLNAELFDCKDSGIVSTIQITTAIPNTVYPAQGQWPAPVTKQPD
IKNPKLTKDQQTTGSPSRKTITITVKSVTSDTIHISWKLALPMTALRLSWLKLGHSPAFGSITET
IVTGERSEYLVTALEPDSPYKVCMVPMETSNLYLFDETPVCIETETAPLRMYNPTTTLNREQEKE
PYKNPNLPLAAIIGGAVALVTIALLALVCWYVHRNGSLFSRNCAYSKGRRRKDDYAEAGTKKDNS
ILEIRETSFQMLPISNEPISKEEFVIHTIFPPNGMNLYKNNHSESSSNRSYRDSGIPDSDHSHS

Important features of the protein:

Signal peptide:

amino acids 1-28

Transmembrane domain:

amino acids 531-552

N-glycosylation sites.

amino acids 226-229, 282-285, 296-299, 555-558, 626-629, 633-636

Tyrosine kinase phosphorylation site.

amino acids 515-522

N-myristoylation sites.

amino acids 12-17, 172-177, 208-213, 359-364, 534-539, 556-561, 640-645

Amidation site.

amino acids 567-570

Leucine zipper pattern.

amino acids 159-180

Phospholipase A2 aspartic acid active site.

amino acids 34-44

FIGURE 133

CCGTCATCCCCCTGCAGCCACCCTTCCCAGAGTCCTTTGCCCAGGCCACCCCAGGCTTCTTGGCA
GCCCTGCCGGGCCACTTGTCTTCATGTCTGCCAGGGGGAGGTGGGAAGGAGGTGGGAGGAGGGCG
TGCAGAGGCAGTCTGGGCTTGGCCAGAGCTCAGGGTGCTGAGCGTGTGACCAGCAGTGAGCAGAG
GCCGGCCATGGCCAGCCTGGGGCTGCTGCTCCTGCTCTTACTGACAGCACTGCCACCGCTGTGGT
CCTCCTCACTGCCTGGGCTGGACACTGCTGAAAGTAAAGCCACCATTGCAGACCTGATCCTGTCT
GCGCTGGAGAGAGCCACCGTCTTCCTAGAACAGAGGCTGCCTGAAATCAACCTGGATGGCATGGT
GGGGGTCCGAGTGCTGGAAGAGCAGCTAAAAAGTGTCCGGGAGAAGTGGGCCCAGGAGCCCCTGC
TGCAGCCGCTGAGCCTGCGCGTGGGGATGCTGGGGGAGAAGCTGGAGGCTGCCATCCAGAGATCC
CTCCACTACCTCAAGCTGAGTGATCCCAAGTACCTAAGAGAGTTCCAGCTGACCCTCCAGCCCGG
GTTTTGGAAGCTCCCACATGCCTGGATCCACACTGATGCCTCCTTGGTGTACCCCACGTTCGGGC
CCCAGGACTCATTCTCAGAGGAGAGAAGTGACGTGTGCCTGGTGCAGCTGCTGGGAACCGGGACG
GACAGCAGCGAGCCCTGCGGCCTCTCAGACCTCTGCAGGAGCCTCATGACCAAGCCCGGCTGCTC
AGGCTACTGCCTGTCCCACCAACTGCTCTTCTTCCTCTGGGCCAGAATGAGGGGATGCACACAGG
GACCACTCCAACAGAGCCAGGACTATATCAACCTCTTCTGCGCCAACATGATGGACTTGAACCGC
AGAGCTGAGGCCATCGGATACGCCTACCCTACCCGGGACATCTTCATGGAAAACATCATGTTCTG
TGGAATGGGCGGCTTCTCCGACTTCTACAAGCTCCGGTGGCTGGAGGCCATTCTCAGCTGGCAGA
AACAGCAGGAAGGATGCTTCGGGGAGCCTGATGCTGAAGATGAAGAATTATCTAAAGCTATTCAA
TATCAGCAGCATTTTTCGAGGAGAGTGAAGAGGCGAGAAAAACAATTTCCAGATTCTCGCTCTGT
TGCTCAGGCTGGAGTACAGTGGCGCAATCTCGGCTCACTGCAACCTTTGCCTCCTGGGTTCAAGC
AATTCTCTTGCCTCATCCTCCCGAGTAGCTGGGACTACAGGAGCGTGCCACCATACCTGGCTAAT
TTTTATATTTTTTTAGTAGAGACAGGGTTTCATCATGTTGCTCATGCTGGTCTCGAACTCCTGAT
CTCAAGAGATCCGCCCACCTCAGGCTCCCAAAGTGTGGGATTATAGGTGTGAGCCACCGTGTCTG
GCTGAAAAGCACTTTCAAAGAGACTGTGTTGAATAAAGGGCCAAGGTTCTTGCCACCCAGCACTC
ATGGGGGCTCTCTCCCCTAGATGGCTGCTCCTCCCACAACACAGCCACAGCAGTGGCAGCCCTGG
GTGGCTTCCTATACATCCTGGCAGAATACCCCCCAGCAAACAGAGAGCCACACCCATCCACACCG
CCACCACCAAGCAGCCGCTGAGACGGACGGTTCCATGCCAGCTGCCTGGAGGAGGAACAGACCCC
TTTAGTCCTCATCCCTTAGATCCTGGAGGGCACGGATCACATCCTGGGAAGAAGGCATCTGGAGG
ATAAGCAAAGCCACCCCGACACCCAATCTTGGAAGCCCTGAGTAGGCAGGGCCAGGGTAGGTGGG
GGCCGGGAGGGACCCAGGTGTGAACGGATGAATAAAGTTCAACTGCAACTGAAAAAAAAAAA

FIGURE 134

MSARGRWEGGGRRACRGSLGLARAQGAERVTSSEQRPAMASLGLLLLLLLTALPPLWSSSLPGLD
TAESKATIADLILSALERATVFLEQRLPEINLDGMVGVRVLEEQLKSVREKWAQEPLLQPLSLRV
GMLGEKLEAAIQRSLHYLKLSDPKYLREFQLTLQPGFWKLPHAWIHTDASLVYPTFGPQDSFSEE
RSDVCLVQLLGTGTDSSEPCGLSDLCRSLMTKPGCSGYCLSHQLLFFLWARMRGCTQGPLQQSQD
YINLFCANMMDLNRRAEAIGYAYPTRDIFMENIMFCGMGGFSDFYKLRWLEAILSWQKQQEGCFG
EPDAEDEELSKAIQYQQHFSRRVKRREKQFPDSRSVAQAGVQWRNLGSLQPLPPGFKQFSCLILP
SSWDYRSVPPYLANFYIFLVETGFHHVAHAGLELLISRDPPTSGSQSVGL

Important features of the protein:

Signal peptide:

amino acids 1-26

Transmembrane domain:

amino acids 39-56

Tyrosine kinase phosphorylation sites.

amino acids 149-156, 274-282

N-myristoylation sites.

amino acids 10-16, 20-26, 63-69, 208-214

Amidation site.

amino acids 10-14

Glycoprotein hormones beta chain signature 1.

amino acids 230-237

FIGURE 135

GGTCTGAGTGCAGAGCTGCTGTCATGGCGGCCGCTCTGTGGGGCTTCTTTCCCGTCCTGCTGCTG
CTGCTGCTATCGGGGGATGTCCAGAGCTCGGAGGTGCCCGGGGCTGCTGCTGAGGGATCGGGAGG
GAGTGGGGTCGGCATAGGAGATCGCTTCAAGATTGAGGGGCGTGCAGTTGTTCCAGGGGTGAAGC
CTCAGGACTGGATCTCGGCGGCCCGAGTGCTGGTAGACGGAGAAGAGCACGTCGGTTTCCTTAAG
ACAGATGGGAGTTTTGTGGTTCATGATATACCTTCTGGATCTTATGTAGTGGAAGTTGTATCTCC
AGCTTACAGATTTGATCCCGTTCGAGTGGATATCACTTCGAAAGGAAAAATGAGAGCAAGATATG
TGAATTACATCAAAACATCAGAGGTTGTCAGACTGCCCTATCCTCTCCAAATGAAATCTTCAGGT
CCACCTTCTTACTTTATTAAAAGGGAATCGTGGGGCTGGACAGACTTTCTAATGAACCCAATGGT
TATGATGATGGTTCTTCCTTTATTGATATTTGTGCTTCTGCCTAAAGTGGTCAACACAAGTGATC
CTGACATGAGACGGGAAATGGAGCAGTCAATGAATATGCTGAATTCCAACCATGAGTTGCCTGAT
GTTTCTGAGTTCATGACAAGACTCTTCTCTTCAAAATCATCTGGCAAATCTAGCAGCGGCAGCAG
TAAAACAGGCAAAAGTGGGGCTGGCAAAAGGAGGTAGTCAGGCCGTCCAGAGCTGGCATTTGCAC
AAACACGGCAACACTGGGTGGCATCCAAGTCTTGGAAAACCGTGTGAAGCAACTACTATAAACTT
GAGTCATCCCGACGTTGATCTCTTACAACTGTGTATGTT
AACTTTTTAGCACATGTTTTGTACTTGGTACACGAGAAAACCCAGCTTTCATCTTTTGTCTGTAT
GAGGTCAATATTGATGTCACTGAATTAATTACAGTGTCCTATAGAAAATGCCATTAATAAATTAT
ATGAACTACTATACATTATGTATATTAATTAAAACATCTTAATCCAGAAATCAAAAAAAAAAAAA
AAAAAAAAAAAAAAA

FIGURE 136

MAAALWGFFPVLLLLLLSGDVQSSEVPGAAAEGSGGSGVGIGDRFKIEGRAVVPGVKPQDWISAA
RVLVDGEEHVGFLKTDGSFVVHDIPSGSYVVEVVSPAYRFDPVRVDITSKGKMRARYVNYIKTSE
VVRLPYPLQMKSSGPPSYFIKRESWGWTDFLMNPMVMMMVLPLLIFVLLPKVVNTSDPDMRREME
QSMNMLNSNHELPDVSEFMTRLFSSKSSGKSSSGSSKTGKSGAGKRR

Important features of the protein:

Signal sequence:

amino acids 1-23

Transmembrane domain:

amino acids 161-182

N-glycosylation site.

amino acids 184-187

Glycosaminoglycan attachment sites.

amino acids 37-40, 236-239 cAMP- and cGMP-dependent protein kinase phosphorylation site.

amino acids 151-154

N-myristoylation sites.

amino acids 33-38, 36-41, 38-44, 229-234

Amidation site.

amino acids 238-241

ATP/GTP-binding site motif A (P-loop).

amino acids 229-236

FIGURE 137

GATGGCGCAGCCACAGCTTCTGTGAGATTCGATTTCTCCCCAGTTCCCCTGTGGGTCTGAGGGGA
CCAGAAGGGTGAGCTACGTTGGCTTTCTGGAAGGGGAGGCTATATGCGTCAATTCCCCAAAACAA
GTTTTGACATTTCCCCTGAAATGTCATTCTCTATCTATTCACTGCAAGTGCCTGCTGTTCCAGGC
CTTACCTGCTGGGCACTAACGGCGGAGCCAGGATGGGGACAGAATAAAGGAGCCACGACCTGTGC
CACCAACTCGCACTCAGACTCTGAACTCAGACCTGAAATCTTCTCTTCACGGGAGGCTTGGCAGT
TTTTCTTACTCCTGTGGTCTCCAGATTTCAGGCCTAAGATGAAAGCCTCTAGTCTTGCCTTCAGC
CTTCTCTCTGCTGCGTTTTATCTCCTATGGACTCCTTCCACTGGACTGAAGACACTCAATTTGGG
AAGCTGTGTGATCGCCACAAACCTTCAGGAAATACGAAATGGATTTTCTGAGATACGGGGCAGTG
TGCAAGCCAAAGATGGAAACATTGACATCAGAATCTTAAGGAGGACTGAGTCTTTGCAAGACACA
AAGCCTGCGAATCGATGCTGCCTCCTGCGCCATTTGCTAAGACTCTATCTGGACAGGGTATTTAA
AAACTACCAGACCCCTGACCATTATACTCTCCGGAAGATCAGCAGCCTCGCCAATTCCTTTCTTA
CCATCAAGAAGGACCTCCGGCTCTCTCATGCCCACATGACATGCCATTGTGGGGAGGAAGCAATG
AAGAAATACAGCCAGATTCTGAGTCACTTTGAAAAGCTGGAACCTCAGGCAGCAGTTGTGAAGGC
TTTGGGGGAACTAGACATTCTTCTGCAATGGATGGAGGAGACAGAATAGGAGGAAAGTGATGCTG
CTGCTAAGAATATTCGAGGTCAAGAGCTCCAGTCTTCAATACCTGCAGAGGAGGCATGACCCCAA
ACCACCATCTCTTTACTGTACTAGTCTTGTGCTGGTCACAGTGTATCTTATTTATGCATTACTTG
CTTCCTTGCATGATTGTCTTTATGCATCCCCAATCTTAATTGAGACCATACTTGTATAAGATTTT
TGTAATATCTTTCTGCTATTGGATATATTTATTAGTTAATATATTTATTTATTTTTTGCTATTTA
ATGTATTTATTTTTTTACTTGGACATGAAACTTTAAAAAAATTCACAGATTATATTTATAACCTG
ACTAGAGCAGGTGATGTATTTTTATACAGTAAAAAAAAAAAACCTTGTAAATTCTAGAAGAGTGG
CTAGGGGGGTTATTCATTTGTATTCAACTAAGGACATATTTACTCATGCTGATGCTCTGTGAGAT
ATTTGAAATTGAACCAATGACTACTTAGGATGGGTTGTGGAATAAGTTTTGATGTGGAATTGCAC
ATCTACCTTACAATTACTGACCATCCCCAGTAGACTCCCCAGTCCCATAATTGTGTATCTTCCAG
CCAGGAATCCTACACGGCCAGCATGTATTTCTACAAATAAAGTTTTCTTTGCATACCAAAAAAAA
AAAAAAAAAAA

FIGURE 138

MRQFPKTSFDISPEMSFSIYSLQVPAVPGLTCWALTAEPGWGQNKGATTCATNSHSDSELRPEIF
SSREAWQFFLLLWSPDFRPKMKASSLAFSLLSAAFYLLWTPSTGLKTLNLGSCVIATNLQEIRNG
FSEIRGSVQAKDGNIDIRILRRTESLQDTKPANRCCLLRHLLRLYLDRVFKNYQTPDHYTLRKIS
SLANSFLTIKKDLRLSHAHMTCHCGEEAMKKYSQILSHFEKLEPQAAVVKALGELDILLQWMEET
E

Important features of the protein:

Signal peptide:

amino acids 1-42 cAMP- and cGMP-dependent protein kinase phosphorylation sites.

amino acids 192-195, 225-228

N-myristoylation sites.

amino acids 42-47, 46-51, 136-141

FIGURE 139

CCTGGAGCCGGAAGCGCGGCTGCAGCAGGGCGAGGCTCCAGGTGGGGTCGGTTCCGCATCCAGCC
TAGCGTGTCCACGATGCGGCTGGGCTCCGGGACTTTCGCTACCTGTTGCGTAGCGATCGAGGTGC
TAGGGATCGCGGTCTTCCTTCGGGGATTCTTCCCGGCTCCCGTTCGTTCCTCTGCCAGAGCGGAA
CACGGAGCGGAGCCCCCAGCGCCCGAACCCTCGGCTGGAGCCAGTTCTAACTGGACCACGCTGCC
ACCACCTCTCTTCAGTAAAGTTGTTATTGTTCTGATAGATGCCTTGAGAGATGATTTTGTGTTTG
GGTCAAAGGGTGTGAAATTTATGCCCTACACAACTTACCTTGTGGAAAAAGGAGCATCTCACAGT
TTTGTGGCTGAAGCAAAGCCACCTACAGTTACTATGCCTCGAATCAAGGCATTGATGACGGGGAG
CCTTCCTGGCTTTGTCGACGTCATCAGGAACCTCAATTCTCCTGCACTGCTGGAAGACAGTGTGA
TAAGACAAGCAAAAGCAGCTGGAAAAAGAATAGTCTTTTATGGAGATGAAACCTGGGTTAAATTA
TTCCCAAAGCATTTTGTGGAATATGATGGAACAACCTCATTTTTCGTGTCAGATTACACAGAGGT
GGATAATAATGTCACGAGGCATTTGGATAAAGTATTAAAAAGAGGAGATTGGGACATATTAATCC
TCCACTACCTGGGGCTGGACCACATTGGCCACATTTCAGGGCCCAACAGCCCCCTGATTGGGCAG
AAGCTGAGCGAGATGGACAGCGTGCTGATGAAGATCCACACCTCACTGCAGTCGAAGGAGAGAGA
GACGCCTTTACCCAATTTGCTGGTTCTTTGTGGTGACCATGGCATGTCTGAAACAGGAAGTCACG
GGGCCTCCTCCACCGAGGAGGTGAATACACCTCTGATTTTAATCAGTTCTGCGTTTGAAAGGAAA
CCCGGTGATATCCGACATCCAAAGCACGTCCAATAGACGGATGTGGCTGCGACACTGGCGATAGC
ACTTGGCTTACCGATTCCAAAAGACAGTGTAGGGAGCCTCCTATTCCCAGTTGTGGAAGGAAGAC
CAATGAGAGAGCAGTTGAGATTTTTACATTTGAATACAGTGCAGCTTAGTAAACTGTTGCAAGAG
AATGTGCCGTCATATGAAAAAGATCCTGGGTTTGAGCAGTTTAAAATGTCAGAAAGATTGCATGG
GAACTGGATCAGACTGTACTTGGAGGAAAAGCATTCAGAAGTCCTATTCAACCTGGGCTCCAAGG
TTCTCAGGCAGTACCTGGATGCTCTGAAGACGCTGAGCTTGTCCCTGAGTGCACAAGTGGCCCAG
TTCTCACCCTGCTCCTGCTCAGCGTCCCACAGGCACTGCACAGAAAGGCTGAGCTGGAAGTCCCA
CTGTCATCTCCTGGGTTTTCTCTGCTCTTTTATTTGGTGATCCTGGTTCTTTCGGCCGTTCACGT
CATTGTGTGCACCTCAGCTGAAAGTTCGTGCTACTTCTGTGGCCTCTCGTGGCTGGCGGCAGGCT
GCCTTTCGTTTACCAGACTCTGGTTGAACACCTGGTGTGTGCCAAGTGCTGGCAGTGCCCTGGAC
AGGGGGCCTCAGGGAAGGACGTGGAGCAGCCTTATCCCAGGCCTCTGGGTGTCCCGACACAGGTG
TTCACATCTGTGCTGTCAGGTCAGATGCCTCAGTTCTTGGAAAGCTAGGTTCCTGCGACTGTTAC
CAAGGTGATTGTAAAGAGCTGGCGGTCACAGAGGAACAAGCCCCCCAGCTGAGGGGGTGTGTGAA
TCGGACAGCCTCCCAGCAGAGGTGTGGGAGCTGCAGCTGAGGGAAGAAGAGACAATCGGCCTGGA
CACTCAGGAGGGTCAAAAGGAGACTTGGTCGCACCACTCATCCTGCCACCCCCAGAATGCATCCT
GCCTCATCAGGTCCAGATTTCTTTCCAAGGCGGACGTTTTCTGTTGGAATTCTTAGTCCTTGGCC
TCGGACACCTTCATTCGTTAGCTGGGGAGTGGTGGTGAGGCAGTGAAGAAGAGGCGGATGGTCAC
ACTCAGATCCACAGAGCCCAGGATCAAGGGACCCACTGCAGTGGCAGCAGGACTGTTGGGCCCCC
ACCCCAACCCTGCACAGCCCTCATCCCCTCTTGGCTTGAGCCGTCAGAGGCCCTGTGCTGAGTGT
CTGACCGAGACACTCACAGCTTTGTCATCAGGGCACAGGCTTCCTCGGAGCCAGGATGATCTGTG
CCACGCTTGCACCTCGGGCCCATCTGGGCTCATGCTCTCTCTCCTGCTATTGAATTAGTACCTAG
CTGCACACAGTATGTAGTTACCAAAAGAATAAACGGCAATAATTGAGAAAAAAAA

FIGURE 140

MRLGSGTFATCCVAIEVLGIAVFLRGFFPAPVRSSARAEHGAEPPAPEPSAGASSNWTTLPPPLF
SKVVIVLIDALRDDFVFGSKGVKFMPYTTYLVEKGASHSFVAEAKPPTVTMPRIKALMTGSLPGF
VDVIRNLNSPALLEDSVIRQAKAAGKRIVFYGDETWVKLFPKHFVEYDGTTSFFVSDYTEVDNNV
TRHLDKVLKRGDWDILILHYLGLDHIGHISGPNSPLIGQKLSEMDSVLMKIHTSLQSKERETPLP
NLLVLCGDHGMSETGSHGASSTEEVNTPLILISSAFERKPGDIRHPKHVQ

Important features of the protein:

Signal peptide:

amino acids 1-34

Transmembrane domain:

amino acids 58-76

N-glycosylation sites.

amino acids 56-60, 194-198

N-myristoylation sites.

amino acids 6-12, 52-58, 100-106, 125-131, 233-239, 270-276, 275-281, 278-284

Amidation site.

amino acids 154-158

Cell attachment sequence.

amino acids 205-208

FIGURE 141

GGCACGAGGCAAGCCTTCCAGGTTATCGTGACGCACCTTGAAAGTCTGAGAGCTACTGCCCTACA
GAAAGTTACTAGTGCCCTAAAGCTGGCGCTGGCACTGATGTTACTGCTGCTGTTGGAGTACAACT
TCCCTATAGAAAACAACTGCCAGCACCTTAAGACCACTCACACCTTCAGAGTGAAGAACTTAAAC
CCGAAGAAATTCAGCATTCATGACCAGGATCACAAAGTACTGGTCCTGGACTCTGGGAATCTCAT
AGCAGTTCCAGATAAAAACTACATACGCCCAGAGATCTTCTTTGCATTAGCCTCATCCTTGAGCT
CAGCCTCTGCGGAGAAAGGAAGTCCGATTCTCCTGGGGGTCTCTAAAGGGGAGTTTTGTCTCTAC
TGTGACAAGGATAAAGGACAAAGTCATCCATCCCTTCAGCTGAAGAAGGAGAAACTGATGAAGCT
GGCTGCCCAAAAGGAATCAGCACGCCGGCCCTTCATCTTTTATAGGGCTCAGGTGGGCTCCTGGA
ACATGCTGGAGTCGGCGGCTCACCCCGGATGGTTCATCTGCACCTCCTGCAATTGTAATGAGCCT
GTTGGGGTGACAGATAAATTTGAGAACAGGAAACACATTGAATTTTCATTTCAACCAGTTTGCAA
AGCTGAAATGAGCCCCAGTGAGGTCAGCGATTAGGAAACTGCCCCATTGAACGCCTTCCTCGCTA
ATTTGAACTAATTGTATAAAAACACCAAACCTGCTCACT

FIGURE 142

MLLLLLEYNFPIENNCQHLKTTHTFRVKNLNPKKFSIHDQDHKVLVLDSGNLIAVPDKNYIRPEI

FFALASSLSSASAEKGSPILLGVSKGEFCLYCDKDKGQSHPSLQLKKEKLMKLAAQKESARRPFI

FYRAQVGSWNMLESAAHPGWFICTSCNCNEPVGVTDKFENRKHIEFSFQPVCKAEMSPSEVSD cAMP- and cGMP-dependent protein kinase phosphorylation site.

amino acids 33-36

N-myristoylation site.

amino acids 50-55, 87-92

Interleukin-1 amino acids 37-182

FIGURE 143

CTAGAGAGTATAGGGCAGAAGGATGGCAGATGAGTGACTCCACATCCAGAGCTGCCTCCCTTTAA
TCCAGGATCCTGTCCTTCCTGTCCTGTAGGAGTGCCTGTTGCCAGTGTGGGGTGAGACAAGTTTG
TCCCACAGGGCTGTCTGAGCAGATAAGATTAAGGGCTGGGTCTGTGCTCAATTAACTCCTGTGGG
CACGGGGGCTGGGAAGAGCAAAGTCAGCGGTGCCTACAGTCAGCACCATGCTGGGCCTGCCGTGG
AAGGGAGGTCTGTCCTGGGCGCTGCTGCTGCTTCTCTTAGGCTCCCAGATCCTGCTGATCTATGC
CTGGCATTTCCACGAGCAAAGGGACTGTGATGAACACAATGTCATGGCTCGTTACCTCCCTGCCA
CAGTGGAGTTTGCTGTCCACACATTCAACCAACAGAGCAAGGACTACTATGCCTACAGACTGGGG
CACATCTTGAATTCCTGGAAGGAGCAGGTGGAGTCCAAGACTGTATTCTCAATGGAGCTACTGCT
GGGGAGAACTAGGTGTGGGAAATTTGAAGACGACATTGACAACTGCCATTTCCAAGAAAGCACAG
AGCTGAACAATACTTTCACCTGCTTCTTCACCATCAGCACCAGGCCCTGGATGACTCAGTTCAGC
CTCCTGAACAAGACCTGCTTGGAGGGATTCCACTGAGTGAAACCCACTCACAGGCTTGTCCATGT
GCTGCTCCCACATTCCGTGGACATCAGCACTACTCTCCTGAGGACTCTTCAGTGGCTGAGCAGCT
TTGGACTTGTTTGTTATCCTATTTTGCATGTGTTTGAGATCTCAGATCAGTGTTTTAGAAAATCC
ACACATCTTGAGCCTAATCATGTAGTGTAGATCATTAAACATCAGCATTTTAAGAAAAAAAAAAA
AAAAAAAAAAAAAAAAAAAAAAAAAAAAAAAAAAAAAAAAAAAAAAAA

FIGURE 144

MLGLPWKGGLSWALLLLLLGSQILLIYAWHFHEQRDCDEHNVMARYLPATVEFAVHTFNQQSKDY
YAYRLGHILNSWKEQVESKTVFSMELLLGRTRCGKFEDDIDNCHFQESTELNNTFTCFFTISTRP
WMTQFSLLNKTCLEGFH

Important features of the protein:

Signal peptide:

amino acids 1-25

N-glycosylation sites.

amino acids 117-121, 139-143

N-myristoylation site.

amino acids 9-15

FIGURE 145

CTGTGCAGCTCGAGGCTCCAGAGGCACACTCCAGAGAGAGCCAAGGTTCTGACGCGATGAGGAAG
CACCTGAGCTGGTGGTGGCTGGCCACTGTCTGCATGCTGCTCTTCAGCCACCTCTCTGCGGTCCA
GACGAGGGGCATCAAGCACAGAATCAAGTGGAACCGGAAGGCCCTGCCCAGCACTGCCCAGATCA
CTGAGGCCCAGGTGGCTGAGAACCGCCCGGGAGCCTTCATCAAGCAAGGCCGCAAGCTCGACATT
GACTTCGGAGCCGAGGGCAACAGGTACTACGAGGCCAACTACTGGCAGTTCCCCGATGGCATCCA
CTACAACGGCTGCTCTGAGGCTAATGTGACCAAGGAGGCATTTGTCACCGGCTGCATCAATGCCA
CCCAGGCGGCGAACCAGGGGGAGTTCCAGAAGCCAGACAACAAGCTCCACCAGCAGGTGCTCTGG
CGGCTGGTCCAGGAGCTCTGCTCCCTCAAGCATTGCGAGTTTTGGTTGGAGAGGGGCGCAGGACT
TCGGGTCACCATGCACCAGCCAGTGCTCCTCTGCCTTCTGGCTTTGATCTGGCTCATGGTGAAAT
AAGCTTGCCAGGAGGCTGGCAGTACAGAGCGCAGCAGCGAGCAAATCCTGGCAAGTGACCCAGCT
CTTCTCCCCCAAACCCACGCGTGTTCTGAAGGTGCCCAGGAGCGGCGATGCACTCGCACTGCAAA
TGCCGCTCCCACGTATGCGCCCTGGTATGTGCCTGCGTTCTGATAGATGGGGGACTGTGGCTTCT
CCGTCACTCCATTCTCAGCCCCTAGCAGAGCGTCTGGCACACTAGATTAGTAGTAAATGCTTGAT
GAGAAGAACACATCAGGCACTGCGCCACCTGCTTCACAGTACTTCCCAACAACTCTTAGAGGTAG
GTGTATTCCCGTTTTACAGATAAGGAAACTGAGGCCCAGAGAGCTGAAGTACTGCACCCAGCATC
ACCAGCTAGAAAGTGGCAGAGCCAGGATTCAACCCTGGCTTGTCTAACCCCAGGTTTTCTGCTCT
GTCCAATTCCAGAGCTGTCTGGTGATCACTTTATGTCTCACAGGGACCCACATCCAAACATGTAT
CTCTAATGAAATTGTGAAAGCTCCATGTTTAGAAATAAATGAAAACACCTGA

FIGURE 146

MRKHLSWWWLATVCMLLFSHLSAVQTRGIKHRIKWNRKALPSTAQITEAQVAENRPGAFIKQGRK
LDIDFGAEGNRYYEANYWQFPDGIHYNGCSEANVTKEAFVTGCINATQAANQGEFQKPDNKLHQQ
VLWRLVQELCSLKHCEFWLERGAGLRVTMHQPVLLCLLALIWLMVK

Important features of the protein:

Signal peptide:

amino acids 1-26

Transmembrane domain:

amino acids 157-171

N-glycosylation sites.

amino acids 98-102, 110-114

Tyrosine kinase phosphorylation site.

amino acids 76-83

N-myristoylation sites.

amino acids 71-77, 88-94, 93-99, 107-113, 154-160

Amidation site.

amino acids 62-66

FIGURE 147

GCCTTGGCCTCCCAAAGGGCTGGGATTATAGGCGTGACCACCATGTCTGGTCCAGAGTCTCATTT
CCTGATGATTTATAGACTCAAAGAAAACTCATGTTCAGAAGCTCTCTTCTCTTCTGGCCTCCTCT
CTGTCTTCTTTCCCTCTTTCTTCTTATTTTAATTAGTAGCATCTACTCAGAGTCATGCAAGCTGG
AAATCTTTCATTTTGCTTGTCAGTGGGGTAGGTCACTGAGTCTTAGTTTTTATTTTTTGAAATTT
CAACTTTCAGATTCAGGGGGTACATGTGAAGGTTTGTTTTATGAGTATATTGCATGATGCTGAGG
TTTGGGGT

FIGURE 148

MFRSSLLFWPPLCLLSLFLLILISSIYSESCKLEIFHFACQWGRSLSLSFYFLKFQLSDSGGTCE
GLFYEYIA

Important features of the protein:

Signal peptide:

amino acids 1-25

N-myristoylation site.

amino acids 62-68

FIGURE 149

GTCTCCGCGTCACAGGAACTTCAGCACCCACAGGGCGGACAGCGCTCCCCTCTACCTGGAGACTTGAC
TCCCGCGCGCCCCAACCCTGCTTATCCCTTGACCGTCGAGTGTCAGAGATCCTGCAGCCGCCCAGTCC
CGGCCCCTCTCCCGCCCCACACCCACCCTCCTGGCTCTTCCTGTTTTTACTCCTCCTTTTCATTCATA
ACAAAAGCTACAGCTCCAGGAGCCCAGCGCCGGGCTGTGACCCAAGCCGAGCGTGGAAGAATGGGGTT
CCTCGGGACCGGCACTTGGATTCTGGTGTTAGTGCTCCCGATTCAAGCTTTCCCCAAACCTGGAGGAA
GCCAAGACAAATCTCTACATAATAGAGAATTAAGTGCAGAAAGACCTTTGAATGAACAGATTGCTGAA
GCAGAAGAAGACAAGATTAAAAAAACATATCCTCCAGAAAACAAGCCAGGTCAGAGCAACTATTCTTT
TGTTGATAACTTGAACCTGCTAAAGGCAATAACAGAAAAGGAAAAAATTGAGAAAGAAAGACAATCTA
TAAGAAGCTCCCCACTTGATAATAAGTTGAATGTGGAAGATGTTGATTCAACCAAGAATCGAAAACTG
ATCGATGATTATGACTCTACTAAGAGTGGATTGGATCATAAATTTCAAGATGATCCAGATGGTCTTCA
TCAACTAGACGGGACTCCTTTAACCGCTGAAGACATTGTCCATAAAATCGCTGCCAGGATTTATGAAG
AAAATGACAGAGCCGTGTTTGACAAGATTGTTTCTAAACTACTTAATCTCGGCCTTATCACAGAAAGC
CAAGCACATACACTGGAAGATGAAGTAGCAGAGGTTTTACAAAAATTAATCTCAAAGGAAGCCAACAA
TTATGAGGAGGATCCCAATAAGCCCACAAGCTGGACTGAGAATCAGGCTGGAAAAATACCAGAGAAAG
TGACTCCAATGGCAGCAATTCAAGATGGTCTTGCTAAGGGAGAAAACGATGAAACAGTATCTAACACA
TTAACCTTGACAAATGGCTTGGAAAGGAGAACTAAAACCTACAGTGAAGACAACTTTGAGGAACTCCA
ATATTTCCCAAATTTCTATGCGCTACTGAAAAGTATTGATTCAGAAAAAGAAGCAAAAGAGAAAGAAA
CACTGATTACTATCATGAAAACACTGATTGACTTTGTGAAGATGATGGTGAAATATGGAACAATATCT
CCAGAAGAAGGTGTTTCCTACCTTGAAAACTTGGATGAAATGATTGCTCTTCAGACCAAAAACAAGCT
AGAAAAAAATGCTACTGACAATATAAGCAAGCTTTTCCCAGCACCATCAGAGAAGAGTCATGAAGAAA
CAGACAGTACCAAGGAAGAAGCAGCTAAGATGGAAAAGGAATATGGAAGCTTGAAGGATTCCACAAAA
GATGATAACTCCAACCCAGGAGGAAAGACAGATGAACCCAAAGGAAAAACAGAAGCCTATTTGGAAGC
CATCAGAAAAAATATTGAATGGTTGAAGAAACATGACAAAAAGGGAAATAAAGAAGATTATGACCTTT
CAAAGATGAGAGACTTCATCAATAAACAAGCTGATGCTTATGTGGAGAAAGGCATCCTTGACAAGGAA
GAAGCCGAGGCCATCAAGCGCATTTATAGCAGCCTGTAAAAATGGCAAAAGATCCAGGAGTCTTTCAA
CTGTTTCAGAAAACATAATATAGCTTAAAACACTTCTAATTCTGTGATTAAAATTTTTTGACCCAAGG
GTTATTAGAAAGTGCTGAATTTACAGTAGTTAACCTTTTACAAGTGGTTAAAACATAGCTTTCTTCCC
GTAAAAACTATCTGAAAGTAAAGTTGTATGTAAGCTGAAAAAAAAAAAAAAAAAAAA

FIGURE 150

MGFLGTGTWILVLVLPIQAFPKPGGSQDKSLHNRELSAERPLNEQIAEAEEDKIKKTYPPENKPG
QSNYSFVDNLNLLKAITEKEKIEKERQSIRSSPLDNKLNVEDVDSTKNRKLIDDYDSTKSGLDHK
FQDDPDGLHQLDGTPLTAEDIVHKIAARIYEENDRAVFDKIVSKLLNLGLITESQAHTLEDEVAE
VLQKLISKEANNYEEDPNKPTSWIENQAGKIPEKVTPMAAIQDGLAKGENDETVSNTLTLTNGLE
RRTKTYSEDNFEELQYFPNFYALLKSIDSEKEAKEKETLITIMKTLIDFVKMMVKYGTISPEEGV
SYLENLDEMIALQTKNKLEKNATDNISKLFPAPSEKSHEETDSTKEEAAKMEKEYGSLKDSTKDD
NSNPGGKTDEPKGKTEAYLEAIRKNIEWLKKHDKKGNKEDYDLSKMRDFINKQADAYVEKGILDK
EEAEAIKRIYSSL

N-glycosylation sites:

amino acids 68-71, 346-349, 350-353

Casein kinase II phosphorylation site:

amino acids 70-73, 82-85, 97-100, 125-128, 147-150, 188-191, 217-220, 265-268, 289-292, 305-308, 320-323, 326-329, 362-365, 368-341, 369-372, 382-385, 386-389, 387-390

N-myristoylation sites:

amino acids 143-148, 239-244

FIGURE 151

CGGCTCGAGGCTCCCGCCAGGAGAAAGGAACATTCTGAGGGGAGTCTACACCCTGTGGAGCTCAA
GATGGTCCTGAGTGGGGCGCTGTGCTTCCGAATGAAGGACTCGGCATTGAAGGTGCTTTATCTGC
ATAATAACCAGCTTCTAGCTGGAGGGCTGCATGCAGGGAAGGTCATTAAAGGTGAAGAGATCAGC
GTGGTCCCCAATCGGTGGCTGGATGCCAGCCTGTCCCCCGTCATCCTGGGTGTCCAGGGTGGAAG
CCAGTGCCTGTCATGTGGGGTGGGGCAGGAGCCGACTCTAACACTAGAGCCAGTGAACATCATGG
AGCTCTATCTTGGTGCCAAGGAATCCAAGAGCTTCACCTTCTACCGGCGGGACATGGGGCTCACC
TCCAGCTTCGAGTCGGCTGCCTACCCGGGCTGGTTCCTGTGCACGGTGCCTGAAGCCGATCAGCC
TGTCAGACTCACCCAGCTTCCCGAGAATGGTGGCTGGAATGCCCCCATCACAGACTTCTACTTCC
AGCAGTGTGACTAGGGCAACGTGCCCCCCAGAACTCCCTGGGCAGAGCCAGCTCGGGTGAGGGGT
GAGTGGAGGAGACCCATGGCGGACAATCACTCTCTCTGCTCTCAGGACCCCCACGTCTGACTTAG
TGGGCACCTGACCACTTTGTCTTCTGGTTCCCAGTTTGGATAAATTCTGAGATTTGGAGCTCAGT
CCACGGTCCTCCCCCACTGGATGGTGCTACTGCTGTGGAACCTTGTAAAAACCATGTGGGGTAAA
CTGGGAATAACATGAAAAGATTTCTGTGGGGGTGGGGTGGGGGAGTGGTGGGAATCATTCCTGCT
TAATGGTAACTGACAAGTGTTACCCTGAGCCCCGCAGGCCAACCCATCCCCAGTTGAGCCTTATA
GGGTCAGTAGCTCTCCACATGAAGTCCTGTCACTCACCACTGTGCAGGAGAGGGAGGTGGTCATA
GAGTCAGGGATCTATGGCCCTTGGCCCAGCCCCACCCCCTTCCCTTTAATCCTGCCACTGTCATA
TGCTACCTTTCCTATCTCTTCCCTCATCATCTTGTTGTGGGCATGAGGAGGTGGTGATGTCAGAA
GAAATGGCTCGAGCTCAGAAGATAAAAGATAAGTAGGGTATGCTGATCCTCTTTTAAAAACCCAA
GATACAATCAAAATCCCAGATGCTGGTCTCTATTCCCATGAAAAAGTGCTCATGACATATTGAGA
AGACCTACTTACAAAGTGGCATATATTGCAATTTATTTTAATTAAAAGATACCTATTTATATATT
TCTTTATAGAAAAAAGTCTGGAAGAGTTTACTTCAATTGTAGCAATGTCAGGGTGGTGGCAGTAT
AGGTGATTTTTCTTTTAATTCTGTTAATTTATCTGTATTTCCTAATTTTTCTACAATGAAGATGA
ATTCCTTGTATAAAAATAAGAAAAGAAATTAATCTTGAGGTAAGCAGAGCAGACATCATCTCTGA
TTGTCCTCAGCCTCCACTTCCCCAGAGTAAATTCAAATTGAATCGAGCTCTGCTGCTCTGGTTGG
TTGTAGTAGTGATCAGGAAACAGATCTCAGCAAAGCCACTGAGGAGGAGGCTGTGCTGAGTTTGT
GTGGCTGGAATCTCTGGGTAAGGAACTTAAAGAACAAAAATCATCTGGTAATTCTTTCCTAGAAG
GATCACAGCCCCTGGGATTCCAAGGCATTGGATCCAGTCTCTAAGAAGGCTGCTGTACTGGTTGA
ATTGTGTCCCCCTCAAATTCACATCCTTCTTGGAATCTCAGTCTGTGAGTTTATTTGGAGATAAG
GTCTCTGCAGATGTAGTTAGTTAAGACAAGGTCATGCTGGATGAAGGTAGACCTAAATTCAATAT
GACTGGTTTCCTTGTATGAAAAGGAGAGGACACAGAGACAGAGGAGACGCGGGGAAGACTATGTA
AAGATGAAGGCAGAGATCGGAGTTTTGCAGCCACAAGCTAAGAAACACCAAGGATTGTGGCAACC
ATCAGAAGCTTGGAAGAGGCAAAGAAGAATTCTTCCCTAGAGGCTTTAGAGGGATAACGGCTCTG
CTGAAACCTTAATCTCAGACTTCCAGCCTCCTGAACGAAGAAAGAATAAATTTCGGCTGTTTTAA
GCCACCAAGGATAATTGGTTACAGCAGCTCTAGGAAACTAATACAGCTGCTAAAATGATCCCTGT
CTCCTCGTGTTTACATTCTGTGTGTGTCCCCTCCCACAATGTACCAAAGTTGTCTTTGTGACCAA
TAGAATATGGCAGAAGTGATGGCATGCCACTTCCAAGATTAGGTTATAAAAGACACTGCAGCTTC
TACTTGAGCCCTCTCTCTCTGCCACCCACCGCCCCCAATCTATCTTGGCTCACTCGCTCTGGGGG
AAGCTAGCTGCCATGCTATGAGCAGGCCTATAAAGAGACTTACGTGGTAAAAAATGAAGTCTCCT
GCCCACAGCCACATTAGTGAACCTAGAAGCAGAGACTCTGTGAGATAATCGATGTTTGTTGTTTT
AAGTTGCTCAGTTTTGGTCTAACTTGTTATGCAGCAATAGATAAATAATATGCAGAGAAAGAG

FIGURE 152

MVLSGALCFRMKDSALKVLYLHNNQLLAGGLHAGKVIKGEEISVVPNRWLDASLSPVILGVQGGS
QCLSCGVGQEPTLTLEPVNIMELYLGAKESKSFTFYRRDMGLTSSFESAAYPGWFLCTVPEADQP
VRLTQLPENGGWNAPITDFYFQQCD

N-myristoylation sites.
amino acids 29-34, 30-35, 60-65, 63-68, 73-78, 91-96, 106-111

Interleukin-1 signature.
amino acids 111-131

Interleukin-1 proteins.
amino acids 8-29, 83-120, 95-134, 64-103

FIGURE 153

CTTCAGAACAGGTTCTCCTTCCCCAGTCACCAGTTGCTCGAGTTAGAATTGTCTGCAATGGCCGC
CCTGCAGAAATCTGTGAGCTCTTTCCTTATGGGGACCCTGGCCACCAGCTGCCTCCTTCTCTTGG
CCCTCTTGGTACAGGGAGGAGCAGCTGCGCCCATCAGCTCCCACTGCAGGCTTGACAAGTCCAAC
TTCCAGCAGCCCTATATCACCAACCGCACCTTCATGCTGGCTAAGGAGGCTAGCTTGGCTGATAA
CAACACAGACGTTCGTCTCATTGGGGAGAAACTGTTCCACGGAGTCAGTATGAGTGAGCGCTGCT
ATCTGATGAAGCAGGTGCTGAACTTCACCCTTGAAGAAGTGCTGTTCCCTCAATCTGATAGGTTC
CAGCCTTATATGCAGGAGGTGGTGCCCTTCCTGGCCAGGCTCAGCAACAGGCTAAGCACATGTCA
TATTGAAGGTGATGACCTGCATATCCAGAGGAATGTGCAAAAGCTGAAGGACACAGTGAAAAAGC
TTGGAGAGAGTGGAGAGATCAAAGCAATTGGAGAACTGGATTTGCTGTTTATGTCTCTGAGAAAT
GCCTGCATTTGACCAGAGCAAAGCTGAAAAATGAATAACTAACCCCCTTTCCCTGCTAGAAATAA
CAATTAGATGCCCCAAAGCGATTTTTTTTAACCAAAAGGAAGATGGGAAGCCAAACTCCATCATG
ATGGGTGGATTCCAAATGAACCCCTGCGTTAGTTACAAAGGAAACCAATGCCACTTTTGTTTATA
AGACCAGAAGGTAGACTTTCTAAGCATAGATATTTATTGATAACATTTCATTGTAACTGGTGTTC
TATACACAGAAAACAATTTATTTTTTAAATAATTGTCTTTTTCCATAAAAAAGATTACTTTCCAT
TCCTTTAGGGGAAAAAACCCCTAAATAGCTTCATGTTTCCATAATCAGTACTTTATATTTATAAA
TGTATTTATTATTATTATAAGACTGCATTTTATTTATATCATTTATTAATATGGATTTATTTAT
AGAAACATCATTCGATATTGCTACTTGAGTGTAAGGCTAATATTGATATTTATGACAATAATTAT
AGAGCTATAACATGTTTATTTGACCTCAATAAACACTTGGATATCCC

FIGURE 154

MAALQKSVSSFLMGTLATSCLLLLALLVQGGAAAPISSHCRLDKSNFQQPYITNRTFMLAKEASL
ADNNTDVRLIGEKLFHGVSMSERCYLMKQVLNFTLEEVLFPQSDRFQPYMQEVVPFLARLSNRLS
TCHIEGDDLHIQRNVQKLKDTVKKLGESGEIKAIGELDLLFMSLRNACI

Important features of the protein:

Signal peptide:

amino acids 1-33

N-glycosylation sites.

amino acids 54-58, 68-72, 97-101

N-myristoylation sites.

amino acids 14-20, 82-88

Prokaryotic membrane lipoprotein lipid attachment site.

amino acids 10-21

FIGURE 155

GGCTTGCTGAAAATAAAATCAGGACTCCTAACCTGCTCCAGTCAGCCTGCTTCCACGAGGCCTGT
CAGTCAGTGCCCGACTTGTGACTGAGTGTGCAGTGCCCAGCATGTACCAGGTCAGTGCAGAGGGC
TGCCTGAGGGCTGTGCTGAGAGGGAGAGGAGCAGAGATGCTGCTGAGGGTGGAGGGAGGCCAAGC
TGCCAGGTTTGGGGCTGGGGGCCAAGTGGAGTGAGAAACTGGGATCCCAGGGGGAGGGTGCAGAT
GAGGGAGCGACCCAGATTAGGTGAGGACAGTTCTCTCATTAGCCTTTTCCTACAGGTGGTTGCAT
TCTTGGCAATGGTCATGGGAACCCACACCTACAGCCACTGGCCCAGCTGCTGCCCCAGCAAAGGG
CAGGACACCTCTGAGGAGCTGCTGAGGTGGAGCACTGTGCCTGTGCCTCCCCTAGAGCCTGCTAG
GCCCAACCGCCACCCAGAGTCCTGTAGGGCCAGTGAAGATGGACCCCTCAACAGCAGGGCCATCT
CCCCCTGGAGATATGAGTTGGACAGAGACTTGAACCGGCTCCCCCAGGACCTGTACCACGCCCGT
TGCCTGTGCCCGCACTGCGTCAGCCTACAGACAGGCTCCCACATGGACCCCCGGGGCAACTCGGA
GCTGCTCTACCACAACCAGACTGTCTTCTACAGGCGGCCATGCCATGGCGAGAAGGGCACCCACA
AGGGCTACTGCCTGGAGCGCAGGCTGTACCGTGTTTCCTTAGCTTGTGTGTGTGTGCGGCCCCGT
GTGATGGGCTAGCCGGACCTGCTGGAGGCTGGTCCCTTTTTGGGAAACCTGGAGCCAGGTGTACA
ACCACTTGCCATGAAGGGCCAGGATGCCCAGATGCTTGGCCCCTGTGAAGTGCTGTCTGGAGCAG
CAGGATCCCGGGACAGGATGGGGGGCTTTGGGGAAAACCTGCACTTCTGCACATTTTGAAAAGAG
CAGCTGCTGCTTAGGGCCGCCGGAAGCTGGTGTCCTGTCATTTTCTCTCAGGAAAGGTTTTCAAA
GTTCTGCCCATTTCTGGAGGCCACCACTCCTGTCTCTTCCTCTTTTCCCATCCCCTGCTACCCTG
GCCCAGCACAGGCACTTTCTAGATATTTCCCCCTTGCTGGAGAAGAAAGAGCCCCTGGTTTTATT
TGTTTGTTTACTCATCACTCAGTGAGCATCTACTTTGGGTGCATTCTAGTGTAGTTACTAGTCTT
TTGACATGGATGATTCTGAGGAGGAAGCTGTTATTGAATGTATAGAGATTTATCCAAATAAATAT
CTTTATTTAAAAATGAAAAA

FIGURE 156

MRERPRLGEDSSLISLFLQVVAFLAMVMGTHTYSHWPSCCPSKGQDTSEELLRWSTVPVPPLEPA
RPNRHPESCRASEDGPLNSRAISPWRYELDRDLNRLPQDLYHARCLCPHCVSLQTGSHMDPRGNS
ELLYHNQTVFYRRPCHGEKGTHKGYCLERRLYRVSLACVCVRPRVMG

Important features of the protein:

Signal peptide:

amino acids 1-32

N-glycosylation site.

amino acids 136-140

Tyrosine kinase phosphorylation site.

amino acids 127-135

N-myristoylation sites.

amino acids 44-50, 150-156

FIGURE 157

CCGGCGATGTCGCTCGTGCTGCTAAGCCTGGCCGCGCTGTGCAGGAGCGCCGTACCCCGAGAGCC
GACCGTTCAATGTGGCTCTGAAACTGGGCCATCTCCAGAGTGGATGCTACAACATGATCTAATCC
CCGGAGACTTGAGGGACCTCCGAGTAGAACCTGTTACAACTAGTGTTGCAACAGGGGACTATTCA
ATTTTGATGAATGTAAGCTGGGTACTCCGGGCAGATGCCAGCATCCGCTTGTTGAAGGCCACCAA
GATTTGTGTGACGGGCAAAAGCAACTTCCAGTCCTACAGCTGTGTGAGGTGCAATTACACAGAGG
CCTTCCAGACTCAGACCAGACCCTCTGGTGGTAAATGGACATTTTCCTACATCGGCTTCCCTGTA
GAGCTGAACACAGTCTATTTCATTGGGGCCCATAATATTCCTAATGCAAATATGAATGAAGATGG
CCCTTCCATGTCTGTGAATTTCACCTCACCAGGCTGCCTAGACCACATAATGAAATATAAAAAA
AGTGTGTCAAGGCCGGAAGCCTGTGGGATCCGAACATCACTGCTTGTAAGAAGAATGAGGAGACA
GTAGAAGTGAACTTCACAACCACTCCCCTGGGAAACAGATACATGGCTCTTATCCAACACAGCAC
TATCATCGGGTTTTCTCAGGTGTTTGAGCCACACCAGAAGAAACAAACGCGAGCTTCAGTGGTGA
TTCCAGTGACTGGGGATAGTGAAGGTGCTACGGTGCAGCTGACTCCATATTTTCCTACTTGTGGC
AGCGACTGCATCCGACATAAAGGAACAGTTGTGCTCTGCCCACAAACAGGCGTCCCTTTCCCTCT
GGATAACAACAAAAGCAAGCCGGGAGGCTGGCTGCCTCTCCTCCTGCTGTCTCTGCTGGTGGCCA
CATGGGTGCTGGTGGCAGGGATCTATCTAATGTGGAGGCACGAAAGGATCAAGAAGACTTCCTTT
TCTACCACCACACTACTGCCCCCCATTAAGGTTCTTGTGGTTTACCCATCTGAAATATGTTTCCA
TCACACAATTTGTTACTTCACTGAATTTCTTCAAAACCATTGCAGAAGTGAGGTCATCCTTGAAA
AGTGGCAGAAAAAGAAAATAGCAGAGATGGGTCCAGTGCAGTGGCTTGCCACTCAAAAGAAGGCA
GCAGACAAAGTCGTCTTCCTTCTTTCCAATGACGTCAACAGTGTGTGCGATGGTACCTGTGGCAA
GAGCGAGGGCAGTCCCAGTGAGAACTCTCAAGACCTCTTCCCCCTTGCCTTTAACCTTTTCTGCA
GTGATCTAAGAAGCCAGATTCATCTGCACAAATACGTGGTGGTCTACTTTAGAGAGATTGATACA
AAAGACGATTACAATGCTCTCAGTGTCTGCCCCAAGTACCACCTCATGAAGGATGCCACTGCTTT
CTGTGCAGAACTTCTCCATGTCAAGCAGCAGGTGTCAGCAGGAAAAAGATCACAAGCCTGCCACG
ATGGCTGCTGCTCCTTGTAG

FIGURE 158

MSLVLLSLAALCRSAVPREPTVQCGSETGPSPEWMLQHDLIPGDLRDLRVEPVTTSVATGDYSILMNVSWV
LRADASIRLLKATKICVTGKSNFQSYSCVRCNYTEAFQTQTRPSGGKWTFSYIGFPVELNTVYFIGAHNIP
NANMNEDGPSMSVNFTSPGCLDHIMKYKKKCVKAGSLWDPNITACKKNEETVEVNFTTTPLGNRYMALIQH
STIIGFSQVFEPHQKKQTRASVVIPVTGDSEGATVQLTPYFPTCGSDCIRHKGTVVLCPQTGVPFPLDNNK
SKPGGWLPLLLLSLLVATWVLVAGIYLMWRHERIKKTSFSTTTLLPPIKVLVVYPSEICFHHTICYFTEFL
QNHCRSEVILEKWQKKKIAEMGPVQWLATQKKAADKVVFLLSNDVNSVCDGTCGKSEGSPSENSQDLFPLA
FNLFCSDLRSQIHLHKYVVVYFREIDTKDDYNALSVCPKYHLMKDATAFCAELLHVKQQVSAGKRSQACHD
GCCSL

Important features of the protein:

Signal peptide:

amino acids 1-14

Transmembrane domain:

amino acids 290-309

N-glycosylation sites.

amino acids 67 - 71, 103 - 107, 156 - 160, 183 - 187, 197 - 201 and 283 - 287 cAMP- and cGMP-dependent protein kinase phosphorylation sites.

amino acids 228 - 232 and 319 - 323

Casein kinase II phosphorylation sites.

amino acids 178 - 182, 402 - 406, 414 - 418 and 453 - 457

N-myristoylation site.

amino acids 116-122

Amidation site.

amino acids 488-452

FIGURE 159

AGCCACCAGCGCAACATGACAGTGAAGACCCTGCATGGCCCAGCCATGGTCAAGTACTTGCTGCT
GTCGATATTGGGGCTTGCCTTTCTGAGTGAGGCGGCAGCTCGGAAAATCCCCAAAGTAGGACATA
CTTTTTTCCAAAAGCCTGAGAGTTGCCCGCCTGTGCCAGGAGGTAGTATGAAGCTTGACATTGGC
ATCATCAATGAAAACCAGCGCGTTTCCATGTCACGTAACATCGAGAGCCGCTCCACCTCCCCCTG
GAATTACACTGTCACTTGGGACCCCAACCGGTACCCCTCGGAAGTTGTACAGGCCCAGTGTAGGA
ACTTGGGCTGCATCAATGCTCAAGGAAAGGAAGACATCTCCATGAATTCCGTTCCCATCCAGCAA
GAGACCCTGGTCGTCCGGAGGAAGCACCAAGGCTGCTCTGTTTCTTTCCAGTTGGAGAAGGTGCT
GGTGACTGTTGGCTGCACCTGCGTCACCCCTGTCATCCACCATGTGCAGTAAGAGGTGCATATCC
ACTCAGCTGAAGAAG

FIGURE 160

MTVKTLHGPAMVKYLLLSILGLAFLSEAAARKIPKVGHTFFQKPESCPPVPGGSMKLDIGIINEN
QRVSMSRNIESRSTSPWNYTVTWDPNRYPSEVVQAQCRNLGCINAQGKEDISMNSVPIQQETLVV
RRKHQGCSVSFQLEKVLVTVGCTCVTPVIHHVQ

Signal sequence:

amino acids 1-30

N-glycosylation site.

amino acids 83-87

N-myristoylation sites.

amino acids 106-111, 136-141

FIGURE 161

ACACTGGCCAAACAAAAACGAAAGCACTCCGTGCTGGAAGTAGGAGGAGAGTCAGGACTCCCAGG
ACAGAGAGTGCACAAACTACCCAGCACAGCCCCCTCCGCCCCCTCTGGAGGCTGAAGAGGGATTC
CAGCCCCTGCCACCCACAGACACGGGCTGACTGGGGTGTCTGCCCCCCTTGGGGGGGGCAGCAC
AGGGCCTCAGGCCTGGGTGCCACCTGGCACCTAGAAGATGCCTGTGCCCTGGTTCTTGCTGTCCT
TGGCACTGGGCCGAAGCCCAGTGGTCCTTTCTCTGGAGAGGCTTGTGGGGCCTCAGGACGCTACC
CACTGCTCTCCGGGCCTCTCCTGCCGCCTCTGGGACAGTGACATACTCTGCCTGCCTGGGGACAT
CGTGCCTGCTCCGGGCCCCGTGCTGGCGCCTACGCACCTGCAGACAGAGCTGGTGCTGAGGTGCC
AGAAGGAGACCGACTGTGACCTCTGTCTGCGTGTGGCTGTCCACTTGGCCGTGCATGGGCACTGG
GAAGAGCCTGAAGATGAGGAAAAGTTTGGAGGAGCAGCTGACTCAGGGGTGGAGGAGCCTAGGAA
TGCCTCTCTCCAGGCCCAAGTCGTGCTCTCCTTCCAGGCCTACCCTACTGCCCGCTGCGTCCTGC
TGGAGGTGCAAGTGCCTGCTGCCCTTGTGCAGTTTGGTCAGTCTGTGGGCTCTGTGGTATATGAC
TGCTTCGAGGCTGCCCTAGGGAGTGAGGTACGAATCTGGTCCTATACTCAGCCCAGGTACGAGAA
GGAACTCAACCACACACAGCAGCTGCCTGCCCTGCCCTGGCTCAACGTGTCAGCAGATGGTGACA
ACGTGCATCTGGTTCTGAATGTCTCTGAGGAGCAGCACTTCGGCCTCTCCCTGTACTGGAATCAG
GTCCAGGGCCCCCCAAAACCCCGGTGGCACAAAAACCTGACTGGACCGCAGATCATTACCTTGAA
CCACACAGACCTGGTTCCCTGCCTCTGTATTCAGGTGTGGCCTCTGGAACCTGACTCCGTTAGGA
CGAACATCTGCCCCTTCAGGGAGGACCCCCGCGCACACCAGAACCTCTGGCAAGCCGCCCGACTG
CGACTGCTGACCCTGCAGAGCTGGCTGCTGGACGCACCGTGCTCGCTGCCCGCAGAAGCGGCACT
GTGCTGGCGGGCTCCGGGTGGGGACCCCTGCCAGCCACTGGTCCCACCGCTTTCCTGGGAGAACG
TCACTGTGGACAAGGTTCTCGAGTTCCCATTGCTGAAAGGCCACCCTAACCTCTGTGTTCAGGTG
AACAGCTCGGAGAAGCTGCAGCTGCAGGAGTGCTTGTGGGCTGACTCCCTGGGGCCTCTCAAAGA
CGATGTGCTACTGTTGGAGACACGAGGCCCCCAGGACAACAGATCCCTCTGTGCCTTGGAACCCA
GTGGCTGTACTTCACTACCCAGCAAAGCCTCCACGAGGGCAGCTCGCCTTGGAGAGTACTTACTA
CAAGACCTGCAGTCAGGCCAGTGTCTGCAGCTATGGGACGATGACTTGGGAGCGCTATGGGCCTG
CCCCATGGACAAATACATCCACAAGCGCTGGGCCCTCGTGTGGCTGGCCTGCCTACTCTTTGCCG
CTGCGCTTTCCCTCATCCTCCTTCTCAAAAAGGATCACGCGAAAGGGTGGCTGAGGCTCTTGAAA
CAGGACGTCCGCTCGGGGGCGGCCGCCAGGGGCCGCGCGGCTCTGCTCCTCTACTCAGCCGATGA
CTCGGGTTTCGAGCGCCTGGTGGGCGCCCTGGCGTCGGCCCTGTGCCAGCTGCCGCTGCGCGTGG
CCGTAGACCTGTGGAGCCGTCGTGAACTGAGCGCGCAGGGGCCCGTGGCTTGGTTTCACGCGCAG
CGGCGCCAGACCCTGCAGGAGGGCGGCGTGGTGGTCTTGCTCTTCTCTCCCGGTGCGGTGGCGCT
GTGCAGCGAGTGGCTACAGGATGGGGTGTCCGGGCCCGGGGCGCACGGCCCGCACGACGCCTTCC
GCGCCTCGCTCAGCTGCGTGCTGCCCGACTTCTTGCAGGGCCGGGCGCCCGGCAGCTACGTGGGG
GCCTGCTTCGACAGGCTGCTCCACCCGGACGCCGTACCCGCCCTTTTCCGCACCGTGCCCGTCTT
CACACTGCCCTCCCAACTGCCAGACTTCCTGGGGGCCCTGCAGCAGCCTCGCGCCCCGCGTTCCG
GGCGGCTCCAAGAGAGAGCGGAGCAAGTGTCCCGGGCCCTTCAGCCAGCCCTGGATAGCTACTTC
CATCCCCCGGGGACTCCCGCGCCGGGACGCGGGGTGGACCAGGGGCGGGACCTGGGGCGGGGGA
CGGGACTTAAATAAAGGCAGACGCTGTTTTTCTAAAAAAA

FIGURE 162

MPVPWFLLSLALGRSPVVLSLERLVGPQDATHCSPGLSCRLWDSDILCLPGDIVPAPGPVLAPTHLQTELV
LRCQKETDCDLCLRVAVHLAVHGHWEEPEDEEKFGGAADSGVEEPRNASLQAQVVLSFQAYPTARCVLLEV
QVPAALVQFGQSVGSVVYDCFEAALGSEVRIWSYTQPRYEKELNHTQQLPALPWLNVSADGDNVHLVLNVS
EEQHFGLSLYWNQVQGPPKPRWHKNLTGPQIITLNHTDLVPCLCIQVWPLEPDSVRTNICPFREDPRAHQN
LWQAARLRLLTLQSWLLDAPCSLPAEAALCWRAPGGDPCQPLVPPLSWENVTVDKVLEFPLLKGHPNLCVQ
VNSSEKLQLQECLWADSLGPLKDDVLLLETRGPQDNRSLCALEPSGCTSLPSKASTRAARLGEYLLQDLQS
GQCLQLWDDDLGALWACPMDKYIHKRWALVWLACLLFAAALSLILLLKKDHAKGWLRLLKQDVRSGAAARG
RAALLLYSADDSGFERLVGALASALCQLPLRVAVDLWSRRELSAQGPVAWFHAQRRQTLQEGGVVVLLFSP
GAVALCSEWLQDGVSGPGAHGPHDAFRASLSCVLPDFLQGRAPGSYVGACFDRLLHPDAVPALFRTVPVFT
LPSQLPDFLGALQQPRAPRSGRLQERAEQVSRALQPALDSYFHPPGTPAPGRGVGPGAGPGAGDGT

Signal sequence:

amino acids 1-20

Transmembrane domain.

amino acids 453-475

N-glycosylation sites.

amino acids 118-121, 186-189, 198-201, 211-214, 238-241, 248-251, 334-337, 357-360, 391-394

Glycosaminoglycan attachment site.

amino acids 583-586 cAMP- and cGMP-dependent protein kinase phosphorylation site.

amino acids 552-555

N-myristoylation sites.

amino acids 107-112, 152-157, 319-324, 438-443, 516-521, 612-617, 692-697, 696-701, 700-705

FIGURE 163

GGGAGGGCTCTGTGCCAGCCCCGATGAGGACGCTGCTGACCATCTTGACTGTGGGATCCCTGGCT
GCTCACGCCCCTGAGGACCCCTCGGATCTGCTCCAGCACGTGAAATTCCAGTCCAGCAACTTTGA
AAACATCCTGACGTGGGACAGCGGGCCAGAGGGCACCCCAGACACGGTCTACAGCATCGAGTATA
AGACGTACGGAGAGAGGGACTGGGTGGCAAAGAAGGGCTGTCAGCGGATCACCCGGAAGTCCTGC
AACCTGACGGTGGAGACGGGCAACCTCACGGAGCTCTACTATGCCAGGGTCACCGCT
GTCAGTGCGGGAGGCCGGTCAGCCACCAAGATGACTGACAGGTTCAGCTCTCTGCAGCACACTAC
CCTCAAGCCACCTGATGTGACCTGTATCTCCAAAGTGAGATCGATTCAGATGATTGTTCATCCTA
CCCCCACGCCAATCCGTGCAGGCGATGGCCACCGGCTAACCCTGGAAGACATCTTCCATGACCTG
TTCTACCACTTAGAGCTCCAGGTCAACCGCACCTACCAAATGCACCTTGGAGGGAAGCAGAGAGA
ATATGAGTTCTTCGGCCTGACCCCTGACACAGAGTTCCTTGGCACCATCATGATTTGCGTTCCCA
CCTGGGCCAAGGAGAGTGCCCCCTACATGTGCCGAGTGAAGACACTGCCAGACCGGACATGGACC
TACTCCTTCTCCGGAGCCTTCCTGTTCTCCATGGGCTTCCTCGTCGCAGTACTCTGCTACCTGAG
CTACAGATATGTCACCAAGCCGCCTGCACCTCCCAACTCCCTGAACGTCCAGCGAGTCCTGACTT
TCCAGCCGCTGCGCTTCATCCAGGAGCACGTCCTGATCCCTGTCTTTGACCTCAGCGGCCCCAGC
AGTCTGGCCCAGCCTGTCCAGTACTCCCAGATCAGGGTGTCTGGACCCAGGGAGCCCGCAGGAGC
TCCACAGCGGCATAGCCTGTCCGAGATCACCTACTTAGGGCAGCCAGACATCTCCATCCTCCAGC
CCTCCAACGTGCCACCTCCCCAGATCCTCTCCCCACTGTCCTATGCCCCAAACGCTGCCCCTGAG
GTCGGGCCCCCATCCTATGCACCTCAGGTGACCCCCGAAGCTCAATTCCCATTCTACGCCCCACA
GGCCATCTCTAAGGTCCAGCCTTCCTCCTATGCCCCTCAAGCCACTCCGGACAGCTGGCCTCCCT
CCTATGGGGTATGCATGGAAGGTTCTGGCAAAGACTCCCCCACTGGGACACTTTCTAGTCCTAAA
CACCTTAGGCCTAAAGGTCAGCTTCAGAAAGAGCCACCAGCTGGAAGCTGCATGTTAGGTGGCCT
TTCTCTGCAGGAGGTGACCTCCTTGGCTATGGAGGAATCCCAAGAAGCAAAATCATTGCACCAGC
CCCTGGGGATTTGCACAGACAGAACATCTGACCCAAATGTGCTACACAGTGGGGAGGAAGGGACA
CCACAGTACCTAAAGGGCCAGCTCCCCCTCCTCTCCTCAGTCCAGATCGAGGGCCACCCCATGTC
CCTCCCTTTGCAACCTCCTTCCGGTCCATGTTCCCCCTCGGACCAAGGTCCAAGTCCCTGGGGCC
TGCTGGAGTCCCTTGTGTGTCCCAAGGATGAAGCCAAGAGCCCAGCCCCTGAGACCTCAGACCTG
GAGCAGCCCACAGAACTGGATTCTCTTTTCAGAGGCCTGGCCCTGACTGTGCAGTGGGAGTCCTG
AGGGGAATGGGAAAGGCTTGGTGCTTCCTCCCTGTCCCTACCCAGTGTCACATCCTTGGCTGTCA
ATCCCATGCCTGCCCATGCCACACACTCTGCGATCTGGCCTCAGACGGGTGCCCTTGAGAGAAGC
AGAGGGAGTGGCATGCAGGGCCCCTGCCATGGGTGCGCTCCTCACCGGAACAAAGCAGCATGATA
AGGACTGCAGCGGGGGAGCTCTGGGGAGCAGCTTGTGTAGACAAGCGCGTGCTCGCTGAGCCCTG
CAAGGCAGAAATGACAGTGCAAGGAGGAAATGCAGGGAAACTCCCGAGGTCCAGAGCCCCACCTC
CTAACACCATGGATTCAAAGTGCTCAGGGAATTTGCCTCTCCTTGCCCCATTCCTGGCCAGTTTC
ACAATCTAGCTCGACAGAGCATGAGGCCCCTGCCTCTTCTGTCATTGTTCAAAGGTGGGAAGAGA
GCCTGGAAAAGAACCAGGCCTGGAAAAGAACCAGAAGGAGGCTGGGCAGAACCAGAACAACCTGC
ACTTCTGCCAAGGCCAGGGCCAGCAGGACGGCAGGACTCTAGGGAGGGGTGTGGCCTGCAGCTCA
TTCCCAGCCAGGGCAACTGCCTGACGTTGCACGATTTCAGCTTCATTCCTCTGATAGAACAAAGC
GAAATGCAGGTCCACCAGGGAGGGAGACACACAAGCCTTTTCTGCAGGCAGGAGTTTCAGACCCT
ATCCTGAGAATGGGGTTTGAAAGGAAGGTGAGGGCTGTGGCCCCTGGACGGGTACAATAACACAC
TGTACTGATGTCACAACTTTGCAAGCTCTGCCTTGGGTTCAGCCCATCTGGGCTCAAATTCCAGC
CTCACCACTCACAAGCTGTGTGACTTCAAACAAATGAAATCAGTGCCCAGAACCTCGGTTTCCTC
ATCTGTAATGTGGGGATCATAACACCTACCTCATGGAGTTGTGGTGAAGATGAAATGAAGTCATG
TCTTTAAAGTGCTTAATAGTGCCTGGTACATGGGCAGTGCCCAATAAACGGTAGCTATTTAAAAA
AAAAAAAA

FIGURE 164

MRTLLTILTVGSLAAHAPEDPSDLLQHVKFQSSNFENILTWDSGPEGTPDTVYSIEYKTYGERDW
VAKKGCQRITRKSCNLTVETGNLTELYYARVTAVSAGGRSATKMTDRFSSLQHTTLKPPDVTCIS
KVRSIQMIVHPTPTPIRAGDGHRLTLEDIFHDLFYHLELQVNRTYQMHLGGKQREYEFFGLTPDT
EFLGTIMICVPTWAKESAPYMCRVKTLPDRTWTYSFSGAFLFSMGFLVAVLCYLSYRYVTKPPAP
PNSLNVQRVLTFQPLRFIQEHVLIPVFDLSGPSSLAQPVQYSQIRVSGPREPAGAPQRHSLSEIT
YLGQPDISILQPSNVPPPQILSPLSYAPNAAPEVGPPSYAPQVTPEAQFPFYAPQAISKVQPSSY
APQATPDSWPPSYGVCMEGSGKDSPTGTLSSPKHLRPKGQLQKEPPAGSCMLGGLSLQEVTSLAM
EESQEAKSLHQPLGICTDRTSDPNVLHSGEEGTPQYLKGQLPLLSSVQIEGHPMSLPLQPPSGPC
SPSDQGPSPWGLLESLVCPKDEAKSPAPETSDLEQPTELDSLFRGLALTVQWES

Signal sequence.

amino acids 1-17

Transmembrane domain.

amino acids 233-250

N-glycosylation sites.

amino acids 80-83, 87-90, 172-175

N-myristoylation sites.

amino acids 11-16, 47-52, 102-107, 531-536, 565-570

FIGURE 165

TGGCCTACTGGAAAAAAAAAAAAAAAAAAAAAAAGTCACCCGGGCCCGCGGTGGCCACAACATGG
CTGCGGCGCCGGGGCTGCTCTTCTGGCTGTTCGTGCTGGGGGCGCTCTGGTGGGTCCCGGGCCAG
TCGGATCTCAGCCACGGACGGCGTTTCTCGGACCTCAAAGTGTGCGGGGACGAAGAGTGCAGCAT
GTTAATGTACCGTGGGAAAGCTCTTGAAGACTTCACGGGCCCTGATTGTCGTTTTGTGAATTTTA
AAAAAGGTGACGATGTATATGTCTACTACAAACTGGCAGGGGGATCCCTTGAACTTTGGGCTGGA
AGTGTTGAACACAGTTTTGGATATTTTCCAAAAGATTTGATCAAGGTACTTCATAAATACACGGA
AGAAGAGCTACATATTCCAGCAGATGAGACAGACTTTGTCTGCTTTGAAGGAGGAAGAGATGATT
TTAATAGTTATAATGTAGAAGAGCTTTTAGGATCTTTGGAACTGGAGGACTCTGTACCTGAAGAG
TCGAAGAAAGCTGAAGAAGTTTCTCAGCACAGAGAGAAATCTCCTGAGGAGTCTCGGGGGCGTGA
ACTTGACCCTGTGCCTGAGCCCGAGGCATTCAGAGCTGATTCAGAGGATGGAGAAGGTGCTTTCT
CAGAGAGCACCGAGGGGCTGCAGGGACAGCCCTCAGCTCAGGAGAGCCACCCTCACACCAGCGGT
CCTGCGGCTAACGCTCAGGGAGTGCAGTCTTCGTTGGACACTTTTGAAGAAATTCTGCACGATAA
ATTGAAAGTGCCGGGAAGCGAAAGCAGAACTGGCAATAGTTCTCCTGCCTCGGTGGAGCGGGAGA
AGACAGATGCTTACAAAGTCCTGAAAACAGAAATGAGTCAGAGAGGAAGTGGACAGTGCGTTATT
CATTACAGCAAAGGATTTCGTTGGCATCAAAATCTAAGTTTGTTTTACAAAGATTGTTTTTAGTA
CTAAGCTGCCTTGGCAGTTTGCATTTTTGAGCCAAACAAAAATATATTATTTTCCCTTCTAAGTA
AAAAAAAAAAAAAAAAAAA

FIGURE 166

MAAAPGLLFWLFVLGALWWVPGQSDLSHGRRFSDLKVCGDEECSMLMYRGKALEDFTGPDCRFVN
FKKGDDVYVYYKLAGGSLELWAGSVEHSFGYFPKDLIKVLHKYTEEELHIPADETDFVCFEGGRD
DFNSYNVEELLGSLELEDSVPEESKKAEEVSQHREKSPEESRGRELDPVPEPEAFRADSEDGEGA
FSESTEGLQGQPSAQESHPHTSGPAANAQGVQSSLDTFEEILHDKLKVPGSESRTGNSSPASVER
EKTDAYKVLKTEMSQRGSGQCVIHYSKGFRWHQNLSLFYKDCF

Important features of the protein:

Signal peptide:

amino acids 1-22

N-glycosylation site.

amino acids 294-298 cAMP- and cGMP-dependent protein kinase phosphorylation site.

amino acids 30-34

Tyrosine kinase phosphorylation site.

amino acids 67-76

N-myristoylation sites.

amino acids 205-211, 225-231, 277-283

Amidation site.

amino acids 28-32

FIGURE 167

CCAGGACCAGGGCGCACCGGCTCAGCCTCTCACTTGTCAGAGGCCGGGGAAGAGAAGCAAAGCGC
AACGGTGTGGTCCAAGCCGGGGCTTCTGCTTCGCCTCTAGGACATACACGGGACCCCCTAACTTC
AGTCCCCCAAACGCGCACCCTCGAAGTCTTGAACTCCAGCCCCGCACATCCACGCGCGGCACAGG
CGCGGCAGGCGGCAGGTCCCGGCCGAAGGCGATGCGCGCAGGGGGTCGGGCAGCTGGGCTCGGGC
GGCGGGAGTAGGGCCCGGCAGGGAGGCAGGGAGGCTGCATATTCAGAGTCGCGGGCTGCGCCCTG
GGCAGAGGCCGCCCTCGCTCCACGCAACACCTGCTGCTGCCACCGCGCCGCGATGAGCCGCGTGG
TCTCGCTGCTGCTGGGCGCCGCGCTGCTCTGCGGCCACGGAGCCTTCTGCCGCCGCGTGGTCAGC
GGCCAAAAGGTGTGTTTTGCTGACTTCAAGCATCCCTGCTACAAAATGGCCTACTTCCATGAACT
GTCCAGCCGAGTGAGCTTTCAGGAGGCACGCCTGGCTTGTGAGAGTGAGGGAGGAGTCCTCCTCA
GCCTTGAGAATGAAGCAGAACAGAAGTTAATAGAGAGCATGTTGCAAAACCTGACAAAACCCGGG
ACAGGGATTTCTGATGGTGATTTCTGGATAGGGCTTTGGAGGAATGGAGATGGGCAAACATCTGG
TGCCTGCCCAGATCTCTACCAGTGGTCTGATGGAAGCAATTCCCAGTACCGAAACTGGTACACAG
ATGAACCTTCCTGCGGAAGTGAAAAGTGTGTTGTGATGTATCACCAACCAACTGCCAATCCTGGC
CTTGGGGGTCCCTACCTTTACCAGTGGAATGATGACAGGTGTAACATGAAGCACAATTATATTTG
CAAGTATGAACCAGAGATTAATCCAACAGCCCCTGTAGAAAAGCCTTATCTTACAAATCAACCAG
GAGACACCCATCAGAATGTGGTTGTTACTGAAGCAGGTATAATTCCCAATCTAATTTATGTTGTT
ATACCAACAATACCCCTGCTCTTACTGATACTGGTTGCTTTTGGAACCTGTTGTTTCCAGATGCT
GCATAAAAGTAAAGGAAGAACAAAAACTAGTCCAAACCAGTCTACACTGTGGATTTCAAAGAGTA
CCAGAAAAGAAAGTGGCATGGAAGTATAATAACTCATTGACTTGGTTCCAGAATTTTGTAATTCT
GGATCTGTATAAGGAATGGCATCAGAACAATAGCTTGGAATGGCTTGAAATCACAAAGGATCTGC
AAGATGAACTGTAAGCTCCCCCTTGAGGCAAATATTAAAGTAATTTTTATATGTCTATTATTTCA
TTTAAAGAATATGCTGTGCTAATAATGGAGTGAGACATGCTTATTTTGCTAAAGGATGCACCCAA
ACTTCAAACTTCAAGCAAATGAAATGGACAATGCAGATAAAGTTGTTATCAACACGTCGGGAGTA
TGTGTGTTAGAAGCAATTCCTTTTATTTCTTTCACCTTTCATAAGTTGTTATCTAGTCAATGTAA
TGTATATTGTATTGAAATTTACAGTGTGCAAAAGTATTTTACCTTTGCATAAGTGTTTGATAAAA
ATGAACTGTTCTAATATTTATTTTTATGGCATCTCATTTTTCAATACATGCTCTTTTGATTAAAG
AAACTTATTACTGTTGTCAACTGAATTCACACACACACAAATATAGTACCATAGAAAAAGTTTGT
TTTCTCGAAATAATTCATCTTTCAGCTTCTCTGCTTTTGGTCAATGTCTAGGAAATCTCTTCAGA
AATAAGAAGCTATTTCATTAAGTGTGATATAAACCTCCTCAAACATTTTACTTAGAGGCAAGGAT
TGTCTAATTTCAATTGTGCAAGACATGTGCCTTATAATTATTTTTAGCTTAAAATTAAACAGATT
TTGTAATAATGTAACTTTGTTAATAGGTGCATAAACACTAATGCAGTCAATTTGAACAAAAGAAG
TGACATACACAATATAAATCATATGTCTTCACACGTTGCCTATATAATGAGAAGCAGCTCTCTGA
GGGTTCTGAAATCAATGTGGTCCCTCTCTTGCCCACTAAACAAAGATGGTTGTTCGGGGTTTGGG
ATTGACACTGGAGGCAGATAGTTGCAAAGTTAGTCTAAGGTTTCCCTAGCTGTATTTAGCCTCTG
ACTATATTAGTATACAAAGAGGTCATGTGGTTGAGACCAGGTGAATAGTCACTATCAGTGTGGAG
ACAAGCACAGCACACAGACATTTTAGGAAGGAAAGGAACTACGAAATCGTGTGAAAATGGGTTGG
AACCCATCAGTGATCGCATATTCATTGATGAGGGTTTGCTTGAGATAGAAAATGGTGGCTCCTTT
CTGTCTTATCTCCTAGTTTCTTCAATGCTTACGCCTTGTTCTTCTCAAGAGAAAGTTGTAACTCT
CTGGTCTTCATATGTCCCTGTGCTCCTTTTAACCAAATAAAGAGTTCTTGTTTCTGGGGGAAAAA
AAAAAAAAAAAAAAAAAAAAAAAAAAAAAAAAA

FIGURE 168

MSRVVSLLLGAALLCGHGAFCRRVVSGQKVCFADFKHPCYKMAYFHELSSRVSFQEARLACESE
GGVLLSLENEAEQKLIESMLQNLTKPGTGISDGDFWIGLWRNGDGQTSGACPDLYQWSDGSNSQ
YRNWYTDEPSCGSEKCVVMYHQPTANPGLGGPYLYQWNDDRCNMKHNYICKYEPEINPTAPVEK
PYLTNQPGDTHQNVVVTEAGIIPNLIYVVIPTIPLLLLILVAFGTCCFQMLHKSKGRTKTSPNQ
STLWISKSTRKESGMEV

Important features of the protein:

Signal peptide:

amino acids 1-21

Transmembrane domain:

amino acids 214-235

N-glycosylation sites.

amino acids 86-89, 255-258 cAMP- and cGMP-dependent protein kinase phosphorylation site.

amino acids 266-269

N-myristoylation sites.

amino acids 27-32, 66-71, 91-96, 93-98, 102-107, 109-114, 140-145, 212-217

SEQUENCE LISTING

<160> NUMBER OF SEQ ID NOS: 170

<210> SEQ ID NO 1
<211> LENGTH: 1173
<212> TYPE: DNA
<213> ORGANISM: Homo Sapien

<400> SEQUENCE: 1

| ggggcttcgg | cgccagcggc | cagcgctagt | cggtctggta | aggatttaca | 50 |
| aaaggtgcag | gtatgagcag | gtctgaagac | taacattttg | tgaagttgta | 100 |
| aaacagaaaa | cctgttagaa | atgtggtggt | ttcagcaagg | cctcagtttc | 150 |
| cttccttcag | cccttgtaat | ttggacatct | gctgctttca | tattttcata | 200 |
| cattactgca | gtaacactcc | accatataga | cccggcttta | ccttatatca | 250 |
| gtgacactgg | tacagtagct | ccagaaaaat | gcttatttgg | ggcaatgcta | 300 |
| aatattgcgg | cagttttatg | cattgctacc | atttatgttc | gttataagca | 350 |
| agttcatgct | ctgagtcctg | aagagaacgt | tatcatcaaa | ttaaacaagg | 400 |
| ctggccttgt | acttggaata | ctgagttgtt | taggactttc | tattgtggca | 450 |
| aacttccaga | aaacaaccct | ttttgctgca | catgtaagtg | gagctgtgct | 500 |
| tacctttggt | atgggctcat | tatatatgtt | tgttcagacc | atcctttcct | 550 |
| accaaatgca | gcccaaaatc | catggcaaac | aagtcttctg | gatcagactg | 600 |
| ttgttggtta | tctggtgtgg | agtaagtgca | cttagcatgc | tgacttgctc | 650 |
| atcagttttg | cacagtggca | attttgggac | tgatttagaa | cagaaactcc | 700 |
| attggaaccc | cgaggacaaa | ggttatgtgc | ttcacatgat | cactactgca | 750 |
| gcagaatggt | ctatgtcatt | ttccttcttt | ggttttttcc | tgacttacat | 800 |
| tcgtgatttt | cagaaaattt | ctttacgggt | ggaagccaat | ttacatggat | 850 |
| taaccctcta | tgacactgca | ccttgcccta | ttaacaatga | acgaacacgg | 900 |
| ctactttcca | gagatatttg | atgaaaggat | aaaatatttc | tgtaatgatt | 950 |
| atgattctca | gggattgggg | aaaggttcac | agaagttgct | tattcttctc | 1000 |
| tgaaattttc | aaccacttaa | tcaaggctga | cagtaacact | gatgaatgct | 1050 |
| gataatcagg | aaacatgaaa | gaagccattt | gatagattat | tctaaaggat | 1100 |
| atcatcaaga | agactattaa | aaacacctat | gcctatactt | ttttatctca | 1150 |
| gaaaataaag | tcaaaagact | atg | | | 1173 |

<210> SEQ ID NO 2
<211> LENGTH: 266
<212> TYPE: PRT
<213> ORGANISM: Homo Sapien

<400> SEQUENCE: 2

Met Trp Trp Phe Gln Gln Gly Leu Ser Phe Leu Pro Ser Ala Leu
 1               5                  10                  15

Val Ile Trp Thr Ser Ala Ala Phe Ile Phe Ser Tyr Ile Thr Ala
                20                  25                  30

Val Thr Leu His His Ile Asp Pro Ala Leu Pro Tyr Ile Ser Asp
                35                  40                  45

Thr Gly Thr Val Ala Pro Glu Lys Cys Leu Phe Gly Ala Met Leu
                50                  55                  60

Asn Ile Ala Ala Val Leu Cys Ile Ala Thr Ile Tyr Val Arg Tyr
65 70 75

Lys Gln Val His Ala Leu Ser Pro Glu Glu Asn Val Ile Ile Lys
80 85 90

Leu Asn Lys Ala Gly Leu Val Leu Gly Ile Leu Ser Cys Leu Gly
95 100 105

Leu Ser Ile Val Ala Asn Phe Gln Lys Thr Thr Leu Phe Ala Ala
110 115 120

His Val Ser Gly Ala Val Leu Thr Phe Gly Met Gly Ser Leu Tyr
125 130 135

Met Phe Val Gln Thr Ile Leu Ser Tyr Gln Met Gln Pro Lys Ile
140 145 150

His Gly Lys Gln Val Phe Trp Ile Arg Leu Leu Leu Val Ile Trp
155 160 165

Cys Gly Val Ser Ala Leu Ser Met Leu Thr Cys Ser Ser Val Leu
170 175 180

His Ser Gly Asn Phe Gly Thr Asp Leu Glu Gln Lys Leu His Trp
185 190 195

Asn Pro Glu Asp Lys Gly Tyr Val Leu His Met Ile Thr Thr Ala
200 205 210

Ala Glu Trp Ser Met Ser Phe Ser Phe Phe Gly Phe Phe Leu Thr
215 220 225

Tyr Ile Arg Asp Phe Gln Lys Ile Ser Leu Arg Val Glu Ala Asn
230 235 240

Leu His Gly Leu Thr Leu Tyr Asp Thr Ala Pro Cys Pro Ile Asn
245 250 255

Asn Glu Arg Thr Arg Leu Leu Ser Arg Asp Ile
260 265

<210> SEQ ID NO 3
<211> LENGTH: 2037
<212> TYPE: DNA
<213> ORGANISM: Homo Sapien

<400> SEQUENCE: 3
cggacgcgtg ggcggacgcg tgggggagag ccgcagtccc ggctgcagca 50
cctgggagaa ggcagaccgt gtgagggggc ctgtggcccc agcgtgctgt 100
ggcctcgggg agtgggaagt ggaggcagga gccttcctta cacttcgcca 150
tgagtttcct catcgactcc agcatcatga ttacctccca gatactattt 200
tttggatttg ggtggctttt cttcatgcgc caattgttta aagactatga 250
gatacgtcag tatgttgtac aggtgatctt ctccgtgacg tttgcatttt 300
cttgcaccat gtttgagctc atcatctttg aaatcttagg agtattgaat 350
agcagctccc gttattttca ctggaaaatg aacctgtgtg taattctgct 400
gatcctggtt ttcatggtgc ctttttacat tggctatttt attgtgagca 450
atatccgact actgcataaa caacgactgc ttttttcctg tctcttatgg 500
ctgaccttta tgtatttctt ctggaaacta ggagatccct ttcccattct 550
cagcccaaaa catgggatct tatccataga acagctcatc agccgggttg 600
gtgtgattgg agtgactctc atggctcttc tttctggatt tggtgctgtc 650
aactgcccat acacttacat gtcttacttc ctcaggaatg tgactgacac 700

-continued

```
ggatattcta gccctggaac ggcgactgct gcaaaccatg gatatgatca        750

taagcaaaaa gaaaaggatg gcaatggcac ggagaacaat gttccagaag        800

ggggaagtgc ataacaaacc atcaggtttc tggggaatga taaaaagtgt        850

taccacttca gcatcaggaa gtgaaaatct tactcttatt caacaggaag        900

tggatgcttt ggaagaatta agcaggcagc tttttctgga aacagctgat        950

ctatatgcta ccaaggagag aatagaatac tccaaaacct tcaaggggaa       1000

atattttaat tttcttggtt actttttctc tatttactgt gtttggaaaa       1050

ttttcatggc taccatcaat attgtttttg atcgagttgg gaaaacggat       1100

cctgtcacaa gaggcattga gatcactgtg aattatctgg gaatccaatt       1150

tgatgtgaag ttttggtccc aacacatttc cttcattctt gttggaataa       1200

tcatcgtcac atccatcaga ggattgctga tcactcttac caagttcttt       1250

tatgccatct ctagcagtaa gtcctccaat gtcattgtcc tgctattagc       1300

acagataatg ggcatgtact ttgtctcctc tgtgctgctg atccgaatga       1350

gtatgccttt agaataccgc accataatca ctgaagtcct tggagaactg       1400

cagttcaact tctatcaccg ttggtttgat gtgatcttcc tggtcagcgc       1450

tctctctagc atactcttcc tctatttggc tcacaaacag gcaccagaga       1500

agcaaatggc accttgaact taagcctact acagactgtt agaggccagt       1550

ggtttcaaaa tttagatata agagggggga aaaatggaac cagggcctga       1600

cattttataa acaaacaaaa tgctatggta gcatttttca ccttcatagc       1650

atactccttc cccgtcaggt gatactatga ccatgagtag catcagccag       1700

aacatgagag ggagaactaa ctcaagacaa tactcagcag agagcatccc       1750

gtgtggatat gaggctggtg tagaggcgga gaggagccaa gaaactaaag       1800

gtgaaaaata cactggaact ctggggcaag acatgtctat ggtagctgag       1850

ccaaacacgt aggatttccg ttttaaggtt cacatggaaa aggttatagc       1900

tttgccttga gattgactca ttaaaatcag agactgtaac aaaaaaaaaa       1950

aaaaaaaaaa agggcggccg cgactctaga gtcgacctgc agaagcttgg       2000

ccgccatggc ccaacttgtt tattgcagct tataatg                     2037
```

```
<210> SEQ ID NO 4
<211> LENGTH: 455
<212> TYPE: PRT
<213> ORGANISM: Homo Sapien

<400> SEQUENCE: 4

Met Ser Phe Leu Ile Asp Ser Ser Ile Met Ile Thr Ser Gln Ile
1               5                   10                  15

Leu Phe Phe Gly Phe Gly Trp Leu Phe Phe Met Arg Gln Leu Phe
                20                  25                  30

Lys Asp Tyr Glu Ile Arg Gln Tyr Val Val Gln Val Ile Phe Ser
                35                  40                  45

Val Thr Phe Ala Phe Ser Cys Thr Met Phe Glu Leu Ile Ile Phe
                50                  55                  60

Glu Ile Leu Gly Val Leu Asn Ser Ser Ser Arg Tyr Phe His Trp
                65                  70                  75

Lys Met Asn Leu Cys Val Ile Leu Leu Ile Leu Val Phe Met Val
                80                  85                  90
```

-continued

```
Pro Phe Tyr Ile Gly Tyr Phe Ile Val Ser Asn Ile Arg Leu Leu
                 95                 100                 105

His Lys Gln Arg Leu Leu Phe Ser Cys Leu Leu Trp Leu Thr Phe
                110                 115                 120

Met Tyr Phe Phe Trp Lys Leu Gly Asp Pro Phe Pro Ile Leu Ser
                125                 130                 135

Pro Lys His Gly Ile Leu Ser Ile Glu Gln Leu Ile Ser Arg Val
                140                 145                 150

Gly Val Ile Gly Val Thr Leu Met Ala Leu Leu Ser Gly Phe Gly
                155                 160                 165

Ala Val Asn Cys Pro Tyr Thr Tyr Met Ser Tyr Phe Leu Arg Asn
                170                 175                 180

Val Thr Asp Thr Asp Ile Leu Ala Leu Glu Arg Arg Leu Leu Gln
                185                 190                 195

Thr Met Asp Met Ile Ile Ser Lys Lys Lys Arg Met Ala Met Ala
                200                 205                 210

Arg Arg Thr Met Phe Gln Lys Gly Glu Val His Asn Lys Pro Ser
                215                 220                 225

Gly Phe Trp Gly Met Ile Lys Ser Val Thr Thr Ser Ala Ser Gly
                230                 235                 240

Ser Glu Asn Leu Thr Leu Ile Gln Gln Glu Val Asp Ala Leu Glu
                245                 250                 255

Glu Leu Ser Arg Gln Leu Phe Leu Glu Thr Ala Asp Leu Tyr Ala
                260                 265                 270

Thr Lys Glu Arg Ile Glu Tyr Ser Lys Thr Phe Lys Gly Lys Tyr
                275                 280                 285

Phe Asn Phe Leu Gly Tyr Phe Phe Ser Ile Tyr Cys Val Trp Lys
                290                 295                 300

Ile Phe Met Ala Thr Ile Asn Ile Val Phe Asp Arg Val Gly Lys
                305                 310                 315

Thr Asp Pro Val Thr Arg Gly Ile Glu Ile Thr Val Asn Tyr Leu
                320                 325                 330

Gly Ile Gln Phe Asp Val Lys Phe Trp Ser Gln His Ile Ser Phe
                335                 340                 345

Ile Leu Val Gly Ile Ile Ile Val Thr Ser Ile Arg Gly Leu Leu
                350                 355                 360

Ile Thr Leu Thr Lys Phe Phe Tyr Ala Ile Ser Ser Ser Lys Ser
                365                 370                 375

Ser Asn Val Ile Val Leu Leu Leu Ala Gln Ile Met Gly Met Tyr
                380                 385                 390

Phe Val Ser Ser Val Leu Leu Ile Arg Met Ser Met Pro Leu Glu
                395                 400                 405

Tyr Arg Thr Ile Ile Thr Glu Val Leu Gly Glu Leu Gln Phe Asn
                410                 415                 420

Phe Tyr His Arg Trp Phe Asp Val Ile Phe Leu Val Ser Ala Leu
                425                 430                 435

Ser Ser Ile Leu Phe Leu Tyr Leu Ala His Lys Gln Ala Pro Glu
                440                 445                 450

Lys Gln Met Ala Pro
                455
```

<210> SEQ ID NO 5
<211> LENGTH: 2372

-continued

<212> TYPE: DNA
<213> ORGANISM: Homo Sapien

<400> SEQUENCE: 5
agcagggaaa tccggatgtc tcggttatga agtggagcag tgagtgtgag 50
cctcaacata gttccagaac tctccatccg gactagttat tgagcatctg 100
cctctcatat caccagtggc catctgaggt gtttccctgg ctctgaaggg 150
gtaggcacga tggccaggtg cttcagcctg gtgttgcttc tcacttccat 200
ctggaccacg aggctcctgg tccaaggctc tttgcgtgca gaagagcttt 250
ccatccaggt gtcatgcaga attatgggga tcacccttgt gagcaaaaag 300
gcgaaccagc agctgaattt cacagaagct aaggaggcct gtaggctgct 350
gggactaagt ttggccggca aggaccaagt tgaaacagcc ttgaaagcta 400
gctttgaaac ttgcagctat ggctgggttg gagatggatt cgtggtcatc 450
tctaggatta gcccaaaccc caagtgtggg aaaaatgggg tgggtgtcct 500
gatttggaag gttccagtga gccgacagtt tgcagcctat tgttacaact 550
catctgatac ttggactaac tcgtgcattc cagaaattat caccaccaaa 600
gatcccatat tcaacactca aactgcaaca caaacaacag aatttattgt 650
cagtgacagt acctactcgg tggcatcccc ttactctaca atacctgccc 700
ctactactac tcctcctgct ccagcttcca cttctattcc acggagaaaa 750
aaattgattt gtgtcacaga agtttttatg gaaactagca ccatgtctac 800
agaaactgaa ccatttgttg aaaataaagc agcattcaag aatgaagctg 850
ctgggtttgg aggtgtcccc acggctctgc tagtgcttgc tctcctcttc 900
tttggtgctg cagctggtct tggattttgc tatgtcaaaa ggtatgtgaa 950
ggccttccct tttacaaaca agaatcagca gaaggaaatg atcgaaacca 1000
aagtagtaaa ggaggagaag gccaatgata gcaaccctaa tgaggaatca 1050
aagaaaactg ataaaaaccc agaagagtcc aagagtccaa gcaaaactac 1100
cgtgcgatgc ctggaagctg aagtttagat gagacagaaa tgaggagaca 1150
cacctgaggc tggtttcttt catgctcctt accctgcccc agctggggaa 1200
atcaaaaggg ccaaagaacc aaagaagaaa gtccaccctt ggttcctaac 1250
tggaatcagc tcaggactgc cattggacta tggagtgcac caaagagaat 1300
gcccttctcc ttattgtaac cctgtctgga tcctatcctc ctacctccaa 1350
agcttcccac ggcctttcta gcctggctat gtcctaataa tatcccactg 1400
ggagaaagga gttttgcaaa gtgcaaggac ctaaaacatc tcatcagtat 1450
ccagtggtaa aaaggcctcc tggctgtctg aggctaggtg ggttgaaagc 1500
caaggagtca ctgagaccaa ggctttctct actgattccg cagctcagac 1550
cctttcttca gctctgaaag agaaacacgt atcccacctg acatgtcctt 1600
ctgagcccgg taagagcaaa agaatggcag aaaagtttag cccctgaaag 1650
ccatggagat tctcataact tgagacctaa tctctgtaaa gctaaaataa 1700
agaaatagaa caaggctgag gatacgacag tacactgtca gcagggactg 1750
taaacacaga cagggtcaaa gtgttttctc tgaacacatt gagttggaat 1800
cactgtttag aacacacaca cttacttttt ctggtctcta ccactgctga 1850

-continued

```
tattttctct aggaaatata cttttacaag taacaaaaat aaaaactctt          1900

ataaatttct atttttatct gagttacaga aatgattact aaggaagatt          1950

actcagtaat ttgtttaaaa agtaataaaa ttcaacaaac atttgctgaa          2000

tagctactat atgtcaagtg ctgtgcaagg tattacactc tgtaattgaa          2050

tattattcct caaaaaattg cacatagtag aacgctatct gggaagctat          2100

ttttttcagt tttgatattt ctagcttatc tacttccaaa ctaattttta          2150

tttttgctga gactaatctt attcattttc tctaatatgg caaccattat          2200

aaccttaatt tattattaac atacctaaga agtacattgt tacctctata          2250

taccaaagca cattttaaaa gtgccattaa caaatgtatc actagccctc          2300

ctttttccaa caagaaggga ctgagagatg cagaaatatt tgtgacaaaa          2350

aattaaagca tttagaaaac tt                                        2372
```

```
<210> SEQ ID NO 6
<211> LENGTH: 322
<212> TYPE: PRT
<213> ORGANISM: Homo Sapien

<400> SEQUENCE: 6

Met Ala Arg Cys Phe Ser Leu Val Leu Leu Leu Thr Ser Ile Trp
  1               5                  10                  15

Thr Thr Arg Leu Leu Val Gln Gly Ser Leu Arg Ala Glu Glu Leu
                 20                  25                  30

Ser Ile Gln Val Ser Cys Arg Ile Met Gly Ile Thr Leu Val Ser
                 35                  40                  45

Lys Lys Ala Asn Gln Gln Leu Asn Phe Thr Glu Ala Lys Glu Ala
                 50                  55                  60

Cys Arg Leu Leu Gly Leu Ser Leu Ala Gly Lys Asp Gln Val Glu
                 65                  70                  75

Thr Ala Leu Lys Ala Ser Phe Glu Thr Cys Ser Tyr Gly Trp Val
                 80                  85                  90

Gly Asp Gly Phe Val Val Ile Ser Arg Ile Ser Pro Asn Pro Lys
                 95                 100                 105

Cys Gly Lys Asn Gly Val Gly Val Leu Ile Trp Lys Val Pro Val
                110                 115                 120

Ser Arg Gln Phe Ala Ala Tyr Cys Tyr Asn Ser Ser Asp Thr Trp
                125                 130                 135

Thr Asn Ser Cys Ile Pro Glu Ile Ile Thr Thr Lys Asp Pro Ile
                140                 145                 150

Phe Asn Thr Gln Thr Ala Thr Gln Thr Thr Glu Phe Ile Val Ser
                155                 160                 165

Asp Ser Thr Tyr Ser Val Ala Ser Pro Tyr Ser Thr Ile Pro Ala
                170                 175                 180

Pro Thr Thr Thr Pro Pro Ala Pro Ala Ser Thr Ser Ile Pro Arg
                185                 190                 195

Arg Lys Lys Leu Ile Cys Val Thr Glu Val Phe Met Glu Thr Ser
                200                 205                 210

Thr Met Ser Thr Glu Thr Glu Pro Phe Val Glu Asn Lys Ala Ala
                215                 220                 225

Phe Lys Asn Glu Ala Ala Gly Phe Gly Gly Val Pro Thr Ala Leu
                230                 235                 240

Leu Val Leu Ala Leu Leu Phe Phe Gly Ala Ala Ala Gly Leu Gly
```

-continued

```
            245                 250                 255

Phe Cys Tyr Val Lys Arg Tyr Val Lys Ala Phe Pro Phe Thr Asn
            260                 265                 270

Lys Asn Gln Gln Lys Glu Met Ile Glu Thr Lys Val Val Lys Glu
            275                 280                 285

Glu Lys Ala Asn Asp Ser Asn Pro Asn Glu Glu Ser Lys Lys Thr
            290                 295                 300

Asp Lys Asn Pro Glu Glu Ser Lys Ser Pro Ser Lys Thr Thr Val
            305                 310                 315

Arg Cys Leu Glu Ala Glu Val
            320


<210> SEQ ID NO 7
<211> LENGTH: 2586
<212> TYPE: DNA
<213> ORGANISM: Homo Sapien

<400> SEQUENCE: 7

cgccgcgctc ccgcacccgc ggcccgccca ccgcgccgct cccgcatctg          50

cacccgcagc ccggcggcct cccggcggga gcgagcagat ccagtccggc         100

ccgcagcgca actcggtcca gtcggggcgg cggctgcggg cgcagagcgg         150

agatgcagcg gcttggggcc accctgctgt gcctgctgct ggcggcggcg         200

gtccccacgg cccccgcgcc cgctccgacg gcgacctcgg ctccagtcaa         250

gcccggcccg gctctcagct acccgcagga ggaggccacc ctcaatgaga         300

tgttccgcga ggttgaggaa ctgatggagg acacgcagca caaattgcgc         350

agcgcggtgg aagagatgga ggcagaagaa gctgctgcta aagcatcatc         400

agaagtgaac ctggcaaact tacctcccag ctatcacaat gagaccaaca         450

cagacacgaa ggttggaaat aataccatcc atgtgcaccg agaaattcac         500

aagataacca acaaccagac tggacaaatg gtcttttcag agacagttat         550

cacatctgtg ggagacgaag aaggcagaag gagccacgag tgcatcatcg         600

acgaggactg tgggcccagc atgtactgcc agtttgccag cttccagtac         650

acctgccagc catgccgggg ccagaggatg ctctgcaccc gggacagtga         700

gtgctgtgga gaccagctgt gtgtctgggg tcactgcacc aaaatggcca         750

ccaggggcag caatgggacc atctgtgaca accagaggga ctgccagccg         800

gggctgtgct gtgccttcca gagaggcctg ctgttccctg tgtgcacacc         850

cctgcccgtg gagggcgagc tttgccatga ccccgccagc cggcttctgg         900

acctcatcac ctgggagcta gagcctgatg gagccttgga ccgatgccct         950

tgtgccagtg gcctcctctg ccagccccac agccacagcc tggtgtatgt        1000

gtgcaagccg accttcgtgg ggagccgtga ccaagatggg gagatcctgc        1050

tgcccagaga ggtccccgat gagtatgaag ttggcagctt catggaggag        1100

gtgcgccagg agctggagga cctggagagg agcctgactg aagagatggc        1150

gctgggggag cctgcggctg ccgccgctgc actgctggga ggggaagaga        1200

tttagatctg gaccaggctg tgggtagatg tgcaatagaa atagctaatt        1250

tatttcccca ggtgtgtgct ttaggcgtgg gctgaccagg cttcttccta        1300

catcttcttc ccagtaagtt tcccctctgg cttgacagca tgaggtgttg        1350
```

-continued

```
tgcatttgtt cagctccccc aggctgttct ccaggcttca cagtctggtg           1400

cttgggagag tcaggcaggg ttaaactgca ggagcagttt gccacccctg           1450

tccagattat tggctgcttt gcctctacca gttggcagac agccgtttgt           1500

tctacatggc tttgataatt gtttgagggg aggagatgga aacaatgtgg           1550

agtctccctc tgattggttt tggggaaatg tggagaagag tgccctgctt           1600

tgcaaacatc aacctggcaa aaatgcaaca aatgaatttt ccacgcagtt           1650

ctttccatgg gcataggtaa gctgtgcctt cagctgttgc agatgaaatg           1700

ttctgttcac cctgcattac atgtgtttat tcatccagca gtgttgctca           1750

gctcctacct ctgtgccagg gcagcatttt catatccaag atcaattccc           1800

tctctcagca cagcctgggg agggggtcat tgttctcctc gtccatcagg           1850

gatctcagag gctcagagac tgcaagctgc ttgcccaagt cacacagcta           1900

gtgaagacca gagcagtttc atctggttgt gactctaagc tcagtgctct           1950

ctccactacc ccacaccagc cttggtgcca ccaaaagtgc tccccaaaag           2000

gaaggagaat gggatttttc ttgaggcatg cacatctgga attaaggtca           2050

aactaattct cacatccctc taaaagtaaa ctactgttag gaacagcagt           2100

gttctcacag tgtggggcag ccgtccttct aatgaagaca atgatattga           2150

cactgtccct ctttggcagt tgcattagta actttgaaag gtatatgact           2200

gagcgtagca tacaggttaa cctgcagaaa cagtacttag gtaattgtag           2250

ggcgaggatt ataaatgaaa tttgcaaaat cacttagcag caactgaaga           2300

caattatcaa ccacgtggag aaaatcaaac cgagcagggc tgtgtgaaac           2350

atggttgtaa tatgcgactg cgaacactga actctacgcc actccacaaa           2400

tgatgttttc aggtgtcatg gactgttgcc accatgtatt catccagagt           2450

tcttaaagtt taaagttgca catgattgta taagcatgct ttctttgagt           2500

tttaaattat gtataaacat aagttgcatt tagaaatcaa gcataaatca           2550

cttcaactgc aaaaaaaaaa aaaaaaaaaa aaaaaa                          2586
```

```
<210> SEQ ID NO 8
<211> LENGTH: 350
<212> TYPE: PRT
<213> ORGANISM: Homo Sapien

<400> SEQUENCE: 8

Met Gln Arg Leu Gly Ala Thr Leu Leu Cys Leu Leu Leu Ala Ala
  1               5                  10                  15

Ala Val Pro Thr Ala Pro Ala Pro Ala Pro Thr Ala Thr Ser Ala
                 20                  25                  30

Pro Val Lys Pro Gly Pro Ala Leu Ser Tyr Pro Gln Glu Glu Ala
                 35                  40                  45

Thr Leu Asn Glu Met Phe Arg Glu Val Glu Glu Leu Met Glu Asp
                 50                  55                  60

Thr Gln His Lys Leu Arg Ser Ala Val Glu Glu Met Glu Ala Glu
                 65                  70                  75

Glu Ala Ala Ala Lys Ala Ser Ser Glu Val Asn Leu Ala Asn Leu
                 80                  85                  90

Pro Pro Ser Tyr His Asn Glu Thr Asn Thr Asp Thr Lys Val Gly
                 95                 100                 105
```

-continued

```
Asn Asn Thr Ile His Val His Arg Glu Ile His Lys Ile Thr Asn
                110                 115                 120

Asn Gln Thr Gly Gln Met Val Phe Ser Glu Thr Val Ile Thr Ser
                125                 130                 135

Val Gly Asp Glu Glu Gly Arg Arg Ser His Glu Cys Ile Ile Asp
                140                 145                 150

Glu Asp Cys Gly Pro Ser Met Tyr Cys Gln Phe Ala Ser Phe Gln
                155                 160                 165

Tyr Thr Cys Gln Pro Cys Arg Gly Gln Arg Met Leu Cys Thr Arg
                170                 175                 180

Asp Ser Glu Cys Cys Gly Asp Gln Leu Cys Val Trp Gly His Cys
                185                 190                 195

Thr Lys Met Ala Thr Arg Gly Ser Asn Gly Thr Ile Cys Asp Asn
                200                 205                 210

Gln Arg Asp Cys Gln Pro Gly Leu Cys Cys Ala Phe Gln Arg Gly
                215                 220                 225

Leu Leu Phe Pro Val Cys Thr Pro Leu Pro Val Glu Gly Glu Leu
                230                 235                 240

Cys His Asp Pro Ala Ser Arg Leu Leu Asp Leu Ile Thr Trp Glu
                245                 250                 255

Leu Glu Pro Asp Gly Ala Leu Asp Arg Cys Pro Cys Ala Ser Gly
                260                 265                 270

Leu Leu Cys Gln Pro His Ser His Ser Leu Val Tyr Val Cys Lys
                275                 280                 285

Pro Thr Phe Val Gly Ser Arg Asp Gln Asp Gly Glu Ile Leu Leu
                290                 295                 300

Pro Arg Glu Val Pro Asp Glu Tyr Glu Val Gly Ser Phe Met Glu
                305                 310                 315

Glu Val Arg Gln Glu Leu Glu Asp Leu Glu Arg Ser Leu Thr Glu
                320                 325                 330

Glu Met Ala Leu Gly Glu Pro Ala Ala Ala Ala Ala Ala Leu Leu
                335                 340                 345

Gly Gly Glu Glu Ile
                350
```

<210> SEQ ID NO 9
<211> LENGTH: 1395
<212> TYPE: DNA
<213> ORGANISM: Homo Sapien

<400> SEQUENCE: 9

```
cggacgcgtg ggcggacgcg tgggggctgt gagaaagtgc caataaatac          50

atcatgcaac cccacggccc accttgtgaa ctcctcgtgc ccagggctga         100

tgtgcgtctt ccagggctac tcatccaaag gcctaatcca acgttctgtc         150

ttcaatctgc aaatctatgg ggtcctgggg ctcttctgga cccttaactg         200

ggtactggcc ctgggccaat gcgtcctcgc tggagccttt gcctccttct         250

actgggcctt ccacaagccc caggacatcc ctaccttccc cttaatctct         300

gccttcatcc gcacactccg ttaccacact gggtcattgg catttggagc         350

cctcatcctg acccttgtgc agatagcccg ggtcatcttg gagtatattg         400

accacaagct cagaggagtg cagaaccctg tagcccgctg catcatgtgc         450

tgtttcaagt gctgcctctg gtgtctggaa aaatttatca agttcctaaa         500
```

-continued

```
ccgcaatgca tacatcatga tcgccatcta cgggaagaat ttctgtgtct          550

cagccaaaaa tgcgttcatg ctactcatgc gaaacattgt cagggtggtc          600

gtcctggaca aagtcacaga cctgctgctg ttctttggga agctgctggt          650

ggtcggaggc gtgggggtcc tgtccttctt ttttttctcc ggtcgcatcc          700

cggggctggg taaagacttt aagagccccc acctcaacta ttactggctg          750

cccatcatga cctccatcct gggggcctat gtcatcgcca gcggcttctt          800

cagcgttttc ggcatgtgtg tggacacgct cttcctctgc ttcctggaag          850

acctggagcg gaacaacggc tccctggacc ggccctacta catgtccaag          900

agccttctaa agattctggg caagaagaac gaggcgcccc cggacaacaa          950

gaagaggaag aagtgacagc tccggccctg atccaggact gcaccccacc         1000

cccaccgtcc agccatccaa cctcacttcg ccttacaggt ctccattttg         1050

tggtaaaaaa aggttttagg ccaggcgccg tggctcacgc ctgtaatcca         1100

acactttgag aggctgaggc gggcggatca cctgagtcag gagttcgaga         1150

ccagcctggc caacatggtg aaacctccgt ctctattaaa aatacaaaaa         1200

ttagccgaga gtggtggcat gcacctgtca tcccagctac tcgggaggct         1250

gaggcaggag aatcgcttga acccgggagg cagaggttgc agtgagccga         1300

gatcgcgcca ctgcactcca acctgggtga cagactctgt ctccaaaaca         1350

aaacaaacaa acaaaaagat tttattaaag atattttgtt aactc              1395
```

<210> SEQ ID NO 10
<211> LENGTH: 321
<212> TYPE: PRT
<213> ORGANISM: Homo Sapien

<400> SEQUENCE: 10

```
Arg Thr Arg Gly Arg Thr Arg Gly Gly Cys Glu Lys Val Pro Ile
  1               5                  10                  15

Asn Thr Ser Cys Asn Pro Thr Ala His Leu Val Asn Ser Ser Cys
                 20                  25                  30

Pro Gly Leu Met Cys Val Phe Gln Gly Tyr Ser Ser Lys Gly Leu
                 35                  40                  45

Ile Gln Arg Ser Val Phe Asn Leu Gln Ile Tyr Gly Val Leu Gly
                 50                  55                  60

Leu Phe Trp Thr Leu Asn Trp Val Leu Ala Leu Gly Gln Cys Val
                 65                  70                  75

Leu Ala Gly Ala Phe Ala Ser Phe Tyr Trp Ala Phe His Lys Pro
                 80                  85                  90

Gln Asp Ile Pro Thr Phe Pro Leu Ile Ser Ala Phe Ile Arg Thr
                 95                 100                 105

Leu Arg Tyr His Thr Gly Ser Leu Ala Phe Gly Ala Leu Ile Leu
                110                 115                 120

Thr Leu Val Gln Ile Ala Arg Val Ile Leu Glu Tyr Ile Asp His
                125                 130                 135

Lys Leu Arg Gly Val Gln Asn Pro Val Ala Arg Cys Ile Met Cys
                140                 145                 150

Cys Phe Lys Cys Cys Leu Trp Cys Leu Glu Lys Phe Ile Lys Phe
                155                 160                 165

Leu Asn Arg Asn Ala Tyr Ile Met Ile Ala Ile Tyr Gly Lys Asn
                170                 175                 180
```

-continued

```
Phe Cys Val Ser Ala Lys Asn Ala Phe Met Leu Leu Met Arg Asn
                185                 190                 195

Ile Val Arg Val Val Val Leu Asp Lys Val Thr Asp Leu Leu Leu
                200                 205                 210

Phe Phe Gly Lys Leu Leu Val Val Gly Gly Val Gly Val Leu Ser
                215                 220                 225

Phe Phe Phe Phe Ser Gly Arg Ile Pro Gly Leu Gly Lys Asp Phe
                230                 235                 240

Lys Ser Pro His Leu Asn Tyr Tyr Trp Leu Pro Ile Met Thr Ser
                245                 250                 255

Ile Leu Gly Ala Tyr Val Ile Ala Ser Gly Phe Phe Ser Val Phe
                260                 265                 270

Gly Met Cys Val Asp Thr Leu Phe Leu Cys Phe Leu Glu Asp Leu
                275                 280                 285

Glu Arg Asn Asn Gly Ser Leu Asp Arg Pro Tyr Tyr Met Ser Lys
                290                 295                 300

Ser Leu Leu Lys Ile Leu Gly Lys Lys Asn Glu Ala Pro Pro Asp
                305                 310                 315

Asn Lys Lys Arg Lys Lys
                320
```

<210> SEQ ID NO 11
<211> LENGTH: 1901
<212> TYPE: DNA
<213> ORGANISM: Homo Sapien

<400> SEQUENCE: 11

```
gccccgcgcc cggcgccggg cgcccgaagc cgggagccac cgccatgggg      50

gcctgcctgg gagcctgctc cctgctcagc tgcgcgtcct gcctctgcgg     100

ctctgccccc tgcatcctgt gcagctgctg ccccgccagc cgcaactcca     150

ccgtgagccg cctcatcttc acgttcttcc tcttcctggg ggtgctggtg     200

tccatcatta tgctgagccc gggcgtggag agtcagctct acaagctgcc     250

ctgggtgtgt gaggaggggg ccgggatccc caccgtcctg cagggccaca     300

tcgactgtgg ctccctgctt ggctaccgcg ctgtctaccg catgtgcttc     350

gccacggcgg ccttcttctt cttctttttc accctgctca tgctctgcgt     400

gagcagcagc cgggaccccc gggctgccat ccagaatggg ttttggttct     450

ttaagttcct gatcctggtg ggcctcaccg tgggtgcctt ctacatccct     500

gacggctcct tcaccaacat ctggttctac ttcggcgtcg tgggctcctt     550

cctcttcatc ctcatccagc tggtgctgct catcgacttt gcgcactcct     600

ggaaccagcg gtggctgggc aaggccgagg agtgcgattc ccgtgcctgg     650

tacgcaggcc tcttcttctt cactctcctc ttctacttgc tgtcgatcgc     700

ggccgtggcg ctgatgttca tgtactacac tgagcccagc ggctgccacg     750

agggcaaggt cttcatcagc ctcaacctca ccttctgtgt ctgcgtgtcc     800

atcgctgctg tcctgcccaa ggtccaggac gcccagccca actcgggtct     850

gctgcaggcc tcggtcatca ccctctacac catgtttgtc acctggtcag     900

ccctatccag tatccctgaa cagaaatgca acccccattt gccaacccag     950

ctgggcaacg agacagttgt ggcaggcccc gagggctatg agacccagtg    1000
```

-continued

```
gtgggatgcc ccgagcattg tgggcctcat catcttcctc ctgtgcaccc          1050

tcttcatcag tctgcgctcc tcagaccacc ggcaggtgaa cagcctgatg          1100

cagaccgagg agtgcccacc tatgctagac gccacacagc agcagcagca          1150

gcaggtggca gcctgtgagg gccgggcctt tgacaacgag caggacggcg          1200

tcacctacag ctactccttc ttccacttct gcctggtgct ggcctcactg          1250

cacgtcatga tgacgctcac caactggtac aagcccggtg agacccggaa          1300

gatgatcagc acgtggaccg ccgtgtgggt gaagatctgt gccagctggg          1350

cagggctgct cctctacctg tggaccctgg tagccccact cctcctgcgc          1400

aaccgcgact tcagctgagg cagcctcaca gcctgccatc tggtgcctcc          1450

tgccacctgg tgcctctcgg ctcggtgaca gccaacctgc cccctcccca          1500

caccaatcag ccaggctgag cccccacccc tgccccagct ccaggacctg          1550

cccctgagcc gggccttcta gtcgtagtgc cttcagggtc cgaggagcat          1600

caggctcctg cagagcccca tccccccgcc acacccacac ggtggagctg          1650

cctcttcctt cccctcctcc ctgttgccca tactcagcat ctcggatgaa          1700

agggctccct tgtcctcagg ctccacggga gcggggctgc tggagagagc          1750

ggggaactcc caccacagtg ggcatccgg cactgaagcc ctggtgttcc           1800

tggtcacgtc ccccagggga ccctgccccc ttcctggact tcgtgcctta          1850

ctgagtctct aagacttttt ctaataaaca agccagtgcg tgtaaaaaaa          1900

a                                                               1901
```

<210> SEQ ID NO 12
<211> LENGTH: 457
<212> TYPE: PRT
<213> ORGANISM: Homo Sapien

<400> SEQUENCE: 12

```
Met Gly Ala Cys Leu Gly Ala Cys Ser Leu Leu Ser Cys Ala Ser
  1               5                  10                  15

Cys Leu Cys Gly Ser Ala Pro Cys Ile Leu Cys Ser Cys Cys Pro
                 20                  25                  30

Ala Ser Arg Asn Ser Thr Val Ser Arg Leu Ile Phe Thr Phe Phe
                 35                  40                  45

Leu Phe Leu Gly Val Leu Val Ser Ile Ile Met Leu Ser Pro Gly
                 50                  55                  60

Val Glu Ser Gln Leu Tyr Lys Leu Pro Trp Val Cys Glu Glu Gly
                 65                  70                  75

Ala Gly Ile Pro Thr Val Leu Gln Gly His Ile Asp Cys Gly Ser
                 80                  85                  90

Leu Leu Gly Tyr Arg Ala Val Tyr Arg Met Cys Phe Ala Thr Ala
                 95                 100                 105

Ala Phe Phe Phe Phe Phe Phe Thr Leu Leu Met Leu Cys Val Ser
                110                 115                 120

Ser Ser Arg Asp Pro Arg Ala Ala Ile Gln Asn Gly Phe Trp Phe
                125                 130                 135

Phe Lys Phe Leu Ile Leu Val Gly Leu Thr Val Gly Ala Phe Tyr
                140                 145                 150

Ile Pro Asp Gly Ser Phe Thr Asn Ile Trp Phe Tyr Phe Gly Val
                155                 160                 165
```

-continued

Val Gly Ser Phe Leu Phe Ile Leu Ile Gln Leu Val Leu Leu Ile
170 175 180

Asp Phe Ala His Ser Trp Asn Gln Arg Trp Leu Gly Lys Ala Glu
185 190 195

Glu Cys Asp Ser Arg Ala Trp Tyr Ala Gly Leu Phe Phe Phe Thr
200 205 210

Leu Leu Phe Tyr Leu Leu Ser Ile Ala Ala Val Ala Leu Met Phe
215 220 225

Met Tyr Tyr Thr Glu Pro Ser Gly Cys His Glu Gly Lys Val Phe
230 235 240

Ile Ser Leu Asn Leu Thr Phe Cys Val Cys Val Ser Ile Ala Ala
245 250 255

Val Leu Pro Lys Val Gln Asp Ala Gln Pro Asn Ser Gly Leu Leu
260 265 270

Gln Ala Ser Val Ile Thr Leu Tyr Thr Met Phe Val Thr Trp Ser
275 280 285

Ala Leu Ser Ser Ile Pro Glu Gln Lys Cys Asn Pro His Leu Pro
290 295 300

Thr Gln Leu Gly Asn Glu Thr Val Val Ala Gly Pro Glu Gly Tyr
305 310 315

Glu Thr Gln Trp Trp Asp Ala Pro Ser Ile Val Gly Leu Ile Ile
320 325 330

Phe Leu Leu Cys Thr Leu Phe Ile Ser Leu Arg Ser Ser Asp His
335 340 345

Arg Gln Val Asn Ser Leu Met Gln Thr Glu Glu Cys Pro Pro Met
350 355 360

Leu Asp Ala Thr Gln Gln Gln Gln Gln Gln Val Ala Ala Cys Glu
365 370 375

Gly Arg Ala Phe Asp Asn Glu Gln Asp Gly Val Thr Tyr Ser Tyr
380 385 390

Ser Phe Phe His Phe Cys Leu Val Leu Ala Ser Leu His Val Met
395 400 405

Met Thr Leu Thr Asn Trp Tyr Lys Pro Gly Glu Thr Arg Lys Met
410 415 420

Ile Ser Thr Trp Thr Ala Val Trp Val Lys Ile Cys Ala Ser Trp
425 430 435

Ala Gly Leu Leu Leu Tyr Leu Trp Thr Leu Val Ala Pro Leu Leu
440 445 450

Leu Arg Asn Arg Asp Phe Ser
455

<210> SEQ ID NO 13
<211> LENGTH: 1572
<212> TYPE: DNA
<213> ORGANISM: Homo Sapien

<400> SEQUENCE: 13
cgggccagcc tggggcggcc ggccaggaac cacccgttaa ggtgtcttct 50
ctttagggat ggtgaggttg gaaaaagact cctgtaaccc tcctccagga 100
tgaaccacct gccagaagac atggagaacg ctctcaccgg gagccagagc 150
tcccatgctt ctctgcgcaa tatccattcc atcaacccca cacaactcat 200
ggccaggatt gagtcctatg aaggaaggga aaagaaaggc atatctgatg 250
tcaggaggac tttctgtttg tttgtcacct ttgacctctt attcgtaaca 300

-continued

```
ttactgtgga taatagagtt aaatgtgaat ggaggcattg agaacacatt          350

agagaaggag gtgatgcagt atgactacta ttcttcatat tttgatatat          400

ttcttctggc agtttttcga tttaaagtgt taatacttgc atatgctgtg          450

tgcagactgc gccattggtg ggcaatagcg ttgacaacgg cagtgaccag          500

tgccttttta ctagcaaaag tgatcctttc gaagcttttc tctcaagggg          550

cttttggcta tgtgctgccc atcatttcat tcatccttgc ctggattgag          600

acgtggttcc tggatttcaa agtgttacct caagaagcag aagaagaaaa          650

cagactcctg atagttcagg atgcttcaga gagggcagca cttatacctg          700

gtggtctttc tgatggtcag ttttattccc ctcctgaatc cgaagcagga          750

tctgaagaag ctgaagaaaa acaggacagt gagaaaccac ttttagaact          800

atgagtacta cttttgttaa atgtgaaaaa ccctcacaga aagtcatcga          850

ggcaaaaaga ggcaggcagt ggagtctccc tgtcgacagt aaagttgaaa          900

tggtgacgtc cactgctggc tttattgaac agctaataaa gatttattta          950

ttgtaatacc tcacaaacgt tgtaccatat ccatgcacat ttagttgcct         1000

gcctgtggct ggtaaggtaa tgtcatgatt catcctctct tcagtgagac         1050

tgagcctgat gtgttaacaa ataggtgaag aaagtcttgt gctgtattcc         1100

taatcaaaag acttaatata ttgaagtaac actttttttag taagcaagat         1150

accttttttat ttcaattcac agaatggaat ttttttgttt catgtctcag         1200

atttattttg tatttctttt ttaacactct acatttccct tgttttttaa         1250

ctcatgcaca tgtgctcttt gtacagtttt aaaaagtgta ataaaatctg         1300

acatgtcaat gtggctagtt ttatttttct tgttttgcat tatgtgtatg         1350

gcctgaagtg ttggacttgc aaaaggggaa gaaaggaatt gcgaatacat         1400

gtaaaatgtc accagacatt tgtattattt ttatcatgaa atcatgtttt         1450

tctctgattg ttctgaaatg ttctaaatac tcttattttg aatgcacaaa         1500

atgacttaaa ccattcatat catgtttcct ttgcgttcag ccaatttcaa         1550

ttaaaatgaa ctaaattaaa aa                                       1572
```

<210> SEQ ID NO 14
<211> LENGTH: 234
<212> TYPE: PRT
<213> ORGANISM: Homo Sapien

<400> SEQUENCE: 14

```
Met Asn His Leu Pro Glu Asp Met Glu Asn Ala Leu Thr Gly Ser
  1               5                  10                  15

Gln Ser Ser His Ala Ser Leu Arg Asn Ile His Ser Ile Asn Pro
                 20                  25                  30

Thr Gln Leu Met Ala Arg Ile Glu Ser Tyr Glu Gly Arg Glu Lys
                 35                  40                  45

Lys Gly Ile Ser Asp Val Arg Arg Thr Phe Cys Leu Phe Val Thr
                 50                  55                  60

Phe Asp Leu Leu Phe Val Thr Leu Leu Trp Ile Ile Glu Leu Asn
                 65                  70                  75

Val Asn Gly Gly Ile Glu Asn Thr Leu Glu Lys Glu Val Met Gln
                 80                  85                  90
```

-continued

Tyr Asp Tyr Tyr Ser Ser Tyr Phe Asp Ile Phe Leu Leu Ala Val
95 100 105

Phe Arg Phe Lys Val Leu Ile Leu Ala Tyr Ala Val Cys Arg Leu
110 115 120

Arg His Trp Trp Ala Ile Ala Leu Thr Thr Ala Val Thr Ser Ala
125 130 135

Phe Leu Leu Ala Lys Val Ile Leu Ser Lys Leu Phe Ser Gln Gly
140 145 150

Ala Phe Gly Tyr Val Leu Pro Ile Ile Ser Phe Ile Leu Ala Trp
155 160 165

Ile Glu Thr Trp Phe Leu Asp Phe Lys Val Leu Pro Gln Glu Ala
170 175 180

Glu Glu Glu Asn Arg Leu Leu Ile Val Gln Asp Ala Ser Glu Arg
185 190 195

Ala Ala Leu Ile Pro Gly Gly Leu Ser Asp Gly Gln Phe Tyr Ser
200 205 210

Pro Pro Glu Ser Glu Ala Gly Ser Glu Glu Ala Glu Glu Lys Gln
215 220 225

Asp Ser Glu Lys Pro Leu Leu Glu Leu
230

<210> SEQ ID NO 15
<211> LENGTH: 2768
<212> TYPE: DNA
<213> ORGANISM: Homo Sapien

<400> SEQUENCE: 15
actcgaacgc agttgcttcg ggacccagga ccccctcggg cccgacccgc 50
caggaaagac tgaggccgcg gcctgccccg cccggctccc tgcgccgccg 100
ccgcctcccg ggacagaaga tgtgctccag ggtccctctg ctgctgccgc 150
tgctcctgct actggccctg gggcctgggg tgcagggctg cccatccggc 200
tgccagtgca gccagccaca gacagtcttc tgcactgccc gccaggggac 250
cacggtgccc cgagacgtgc cacccgacac ggtggggctg tacgtctttg 300
agaacggcat caccatgctc gacgcaggca gctttgccgg cctgccgggc 350
ctgcagctcc tggacctgtc acagaaccag atcgccagcc tgcccagcgg 400
ggtcttccag ccactcgcca acctcagcaa cctggacctg acggccaaca 450
ggctgcatga aatcaccaat gagaccttcc gtggcctgcg gcgcctcgag 500
cgcctctacc tgggcaagaa ccgcatccgc cacatccagc ctggtgcctt 550
cgacacgctc gaccgcctcc tggagctcaa gctgcaggac aacgagctgc 600
gggcactgcc cccgctgcgc ctgccccgcc tgctgctgct ggacctcagc 650
cacaacagcc tcctggccct ggagcccggc atcctggaca ctgccaacgt 700
ggaggcgctg cggctggctg gtctggggct gcagcagctg gacgaggggc 750
tcttcagccg cttgcgcaac ctccacgacc tggatgtgtc cgacaaccag 800
ctggagcgag tgccacctgt gatccgaggc ctccggggcc tgacgcgcct 850
gcggctggcc ggcaacaccc gcattgccca gctgcggccc gaggacctgg 900
ccggcctggc tgccctgcag gagctggatg tgagcaacct aagcctgcag 950
gccctgcctg gcgacctctc gggcctcttc cccgcctgc ggctgctggc 1000 agctgcccgc aacccettca actgcgtgtg ccccctgagc tggtttggcc 1050

-continued

```
cctgggtgcg cgagagccac gtcacactgg ccagccctga ggagacgcgc    1100

tgccacttcc cgcccaagaa cgctggccgg ctgctcctgg agcttgacta    1150

cgccgacttt ggctgcccag ccaccaccac cacagccaca gtgcccacca    1200

cgaggcccgt ggtgcgggag cccacagcct tgtcttctag cttggctcct    1250

acctggctta gccccacagc gccggccact gaggccccca gcccgccctc    1300

cactgcccca ccgactgtag ggcctgtccc ccagccccag gactgcccac    1350

cgtccacctg cctcaatggg ggcacatgcc acctggggac acggcaccac    1400

ctggcgtgct tgtgccccga aggcttcacg ggcctgtact gtgagagcca    1450

gatggggcag gggacacggc ccagccctac accagtcacg ccgaggccac    1500

cacggtccct gaccctgggc atcgagccgg tgagccccac ctccctgcgc    1550

gtggggctgc agcgctacct ccaggggagc tccgtgcagc tcaggagcct    1600

ccgtctcacc tatcgcaacc tatcgggccc tgataagcgg ctggtgacgc    1650

tgcgactgcc tgcctcgctc gctgagtaca cggtcaccca gctgcggccc    1700

aacgccactt actccgtctg tgtcatgcct ttggggcccg ggcgggtgcc    1750

ggagggcgag gaggcctgcg gggaggccca tacaccccca gccgtccact    1800

ccaaccacgc cccagtcacc caggcccgcg agggcaacct gccgctcctc    1850

attgcgcccg ccctggccgc ggtgctcctg gccgcgctgg ctgcggtggg    1900

ggcagcctac tgtgtgcggc gggggcgggc catggcagca gcggctcagg    1950

acaaagggca ggtggggcca ggggctgggc ccctggaact ggagggagtg    2000

aaggtcccct tggagccagg cccgaaggca acagagggcg gtggagaggc    2050

cctgcccagc gggtctgagt gtgaggtgcc actcatgggc ttcccagggc    2100

ctggcctcca gtcacccctc cacgcaaagc cctacatcta agccagagag    2150

agacagggca gctggggccg ggctctcagc cagtgagatg gccagccccc    2200

tcctgctgcc acaccacgta agttctcagt cccaacctcg gggatgtgtg    2250

cagacagggc tgtgtgacca cagctgggcc ctgttccctc tggacctcgg    2300

tctcctcatc tgtgagatgc tgtggcccag ctgacgagcc ctaacgtccc    2350

cagaaccgag tgcctatgag gacagtgtcc gccctgccct ccgcaacgtg    2400

cagtccctgg gcacggcggg ccctgccatg tgctggtaac gcatgcctgg    2450

gtcctgctgg gctctcccac tccaggcgga ccctgggggc cagtgaagga    2500

agctcccgga aagagcagag ggagagcggg taggcggctg tgtgactcta    2550

gtcttggccc caggaagcga aggaacaaaa gaaactggaa aggaagatgc    2600

tttaggaaca tgttttgctt ttttaaaata tatatattta taagagatcc    2650

tttcccattt attctgggaa gatgtttttc aaactcagag acaaggactt    2700

tggtttttgt aagacaaacg atgatatgaa ggccttttgt aagaaaaaat    2750

aaaagatgaa gtgtgaaa                                       2768
```

<210> SEQ ID NO 16
<211> LENGTH: 673
<212> TYPE: PRT
<213> ORGANISM: Homo Sapien

<400> SEQUENCE: 16

-continued

```
Met Cys Ser Arg Val Pro Leu Leu Leu Pro Leu Leu Leu Leu Leu
  1               5                  10                  15

Ala Leu Gly Pro Gly Val Gln Gly Cys Pro Ser Gly Cys Gln Cys
                 20                  25                  30

Ser Gln Pro Gln Thr Val Phe Cys Thr Ala Arg Gln Gly Thr Thr
                 35                  40                  45

Val Pro Arg Asp Val Pro Pro Asp Thr Val Gly Leu Tyr Val Phe
                 50                  55                  60

Glu Asn Gly Ile Thr Met Leu Asp Ala Gly Ser Phe Ala Gly Leu
                 65                  70                  75

Pro Gly Leu Gln Leu Leu Asp Leu Ser Gln Asn Gln Ile Ala Ser
                 80                  85                  90

Leu Pro Ser Gly Val Phe Gln Pro Leu Ala Asn Leu Ser Asn Leu
                 95                 100                 105

Asp Leu Thr Ala Asn Arg Leu His Glu Ile Thr Asn Glu Thr Phe
                110                 115                 120

Arg Gly Leu Arg Arg Leu Glu Arg Leu Tyr Leu Gly Lys Asn Arg
                125                 130                 135

Ile Arg His Ile Gln Pro Gly Ala Phe Asp Thr Leu Asp Arg Leu
                140                 145                 150

Leu Glu Leu Lys Leu Gln Asp Asn Glu Leu Arg Ala Leu Pro Pro
                155                 160                 165

Leu Arg Leu Pro Arg Leu Leu Leu Leu Asp Leu Ser His Asn Ser
                170                 175                 180

Leu Leu Ala Leu Glu Pro Gly Ile Leu Asp Thr Ala Asn Val Glu
                185                 190                 195

Ala Leu Arg Leu Ala Gly Leu Gly Leu Gln Gln Leu Asp Glu Gly
                200                 205                 210

Leu Phe Ser Arg Leu Arg Asn Leu His Asp Leu Asp Val Ser Asp
                215                 220                 225

Asn Gln Leu Glu Arg Val Pro Pro Val Ile Arg Gly Leu Arg Gly
                230                 235                 240

Leu Thr Arg Leu Arg Leu Ala Gly Asn Thr Arg Ile Ala Gln Leu
                245                 250                 255

Arg Pro Glu Asp Leu Ala Gly Leu Ala Ala Leu Gln Glu Leu Asp
                260                 265                 270

Val Ser Asn Leu Ser Leu Gln Ala Leu Pro Gly Asp Leu Ser Gly
                275                 280                 285

Leu Phe Pro Arg Leu Arg Leu Leu Ala Ala Ala Arg Asn Pro Phe
                290                 295                 300

Asn Cys Val Cys Pro Leu Ser Trp Phe Gly Pro Trp Val Arg Glu
                305                 310                 315

Ser His Val Thr Leu Ala Ser Pro Glu Glu Thr Arg Cys His Phe
                320                 325                 330

Pro Pro Lys Asn Ala Gly Arg Leu Leu Leu Glu Leu Asp Tyr Ala
                335                 340                 345

Asp Phe Gly Cys Pro Ala Thr Thr Thr Thr Ala Thr Val Pro Thr
                350                 355                 360

Thr Arg Pro Val Val Arg Glu Pro Thr Ala Leu Ser Ser Ser Leu
                365                 370                 375

Ala Pro Thr Trp Leu Ser Pro Thr Ala Pro Ala Thr Glu Ala Pro
                380                 385                 390

Ser Pro Pro Ser Thr Ala Pro Pro Thr Val Gly Pro Val Pro Gln
```

-continued

```
                395                 400                 405

Pro Gln Asp Cys Pro Pro Ser Thr Cys Leu Asn Gly Gly Thr Cys
                410                 415                 420

His Leu Gly Thr Arg His His Leu Ala Cys Leu Cys Pro Glu Gly
                425                 430                 435

Phe Thr Gly Leu Tyr Cys Glu Ser Gln Met Gly Gln Gly Thr Arg
                440                 445                 450

Pro Ser Pro Thr Pro Val Thr Pro Arg Pro Pro Arg Ser Leu Thr
                455                 460                 465

Leu Gly Ile Glu Pro Val Ser Pro Thr Ser Leu Arg Val Gly Leu
                470                 475                 480

Gln Arg Tyr Leu Gln Gly Ser Ser Val Gln Leu Arg Ser Leu Arg
                485                 490                 495

Leu Thr Tyr Arg Asn Leu Ser Gly Pro Asp Lys Arg Leu Val Thr
                500                 505                 510

Leu Arg Leu Pro Ala Ser Leu Ala Glu Tyr Thr Val Thr Gln Leu
                515                 520                 525

Arg Pro Asn Ala Thr Tyr Ser Val Cys Val Met Pro Leu Gly Pro
                530                 535                 540

Gly Arg Val Pro Glu Gly Glu Glu Ala Cys Gly Glu Ala His Thr
                545                 550                 555

Pro Pro Ala Val His Ser Asn His Ala Pro Val Thr Gln Ala Arg
                560                 565                 570

Glu Gly Asn Leu Pro Leu Leu Ile Ala Pro Ala Leu Ala Ala Val
                575                 580                 585

Leu Leu Ala Ala Leu Ala Ala Val Gly Ala Ala Tyr Cys Val Arg
                590                 595                 600

Arg Gly Arg Ala Met Ala Ala Ala Ala Gln Asp Lys Gly Gln Val
                605                 610                 615

Gly Pro Gly Ala Gly Pro Leu Glu Leu Glu Gly Val Lys Val Pro
                620                 625                 630

Leu Glu Pro Gly Pro Lys Ala Thr Glu Gly Gly Gly Glu Ala Leu
                635                 640                 645

Pro Ser Gly Ser Glu Cys Glu Val Pro Leu Met Gly Phe Pro Gly
                650                 655                 660

Pro Gly Leu Gln Ser Pro Leu His Ala Lys Pro Tyr Ile
                665                 670
```

<210> SEQ ID NO 17
<211> LENGTH: 1672
<212> TYPE: DNA
<213> ORGANISM: Homo Sapien

<400> SEQUENCE: 17

```
gcagcggcga ggcggcggtg gtggctgagt ccgtggtggc agaggcgaag          50

gcgacagctc atgcgggtcc ggatagggct gacgctgctg ctgtgtgcgg         100

tgctgctgag cttggcctcg gcgtcctcgg atgaagaagg cagccaggat         150

gaatccttag attccaagac tactttgaca tcagatgagt cagtaaagga         200

ccatactact gcaggcagag tagttgctgg tcaaatattt cttgattcag         250

aagaatctga attagaatcc tctattcaag aagaggaaga cagcctcaag         300

agccaagagg gggaaagtgt cacagaagat atcagctttc tagagtctcc         350

aaatccagaa aacaaggact atgaagagcc aaagaaagta cggaaaccag         400
```

-continued

```
ctttgaccgc cattgaaggc acagcacatg gggagccctg ccacttccct        450

tttcttttcc tagataagga gtatgatgaa tgtacatcag atgggaggga        500

agatggcaga ctgtggtgtg ctacaaccta tgactacaaa gcagatgaaa        550

agtggggctt ttgtgaaact gaagaagagg ctgctaagag acggcagatg        600

caggaagcag aaatgatgta tcaaactgga atgaaaatcc ttaatggaag        650

caataagaaa agccaaaaaa gagaagcata tcggtatctc caaaaggcag        700

caagcatgaa ccataccaaa gccctggaga gagtgtcata tgctctttta        750

tttggtgatt acttgccaca gaatatccag gcagcgagag agatgtttga        800

gaagctgact gaggaaggct ctcccaaggg acagactgct cttggctttc        850

tgtatgcctc tggacttggt gttaattcaa gtcaggcaaa ggctcttgta        900

tattatacat ttggagctct tgggggcaat ctaatagccc acatggtttt        950

ggtaagtaga ctttagtgga aggctaataa tattaacatc agaagaattt       1000

gtggtttata gcggccacaa ctttttcagc tttcatgatc cagatttgct       1050

tgtattaaga ccaaatattc agttgaactt ccttcaaatt cttgttaatg       1100

gatataacac atggaatcta catgtaaatg aaagttggtg gagtccacaa       1150

tttttcttta aaatgattag tttggctgat tgcccctaaa aagagagatc       1200

tgataaatgg ctctttttaa attttctctg agttggaatt gtcagaatca       1250

ttttttacat tagattatca taattttaaa aatttttctt tagtttttca       1300

aaattttgta aatggtggct atagaaaaac aacatgaaat attatacaat       1350

attttgcaac aatgccctaa gaattgttaa aattcatgga gttatttgtg       1400

cagaatgact ccagagagct ctactttctg ttttttactt ttcatgattg       1450

gctgtcttcc catttattct ggtcatttat tgctagtgac actgtgcctg       1500

cttccagtag tctcattttc cctattttgc taatttgtta ctttttcttt       1550

gctaatttgg aagattaact catttttaat aaaattatgt ctaagattaa       1600

aaaaaaaaaa aaaaaaaaaa aaaaaaaaaa aaaaaaaaaa aaaaaaaaaa       1650

aaaaaaaaaa aaaaaaaaaa aa                                     1672
```

<210> SEQ ID NO 18
<211> LENGTH: 301
<212> TYPE: PRT
<213> ORGANISM: Homo Sapien

<400> SEQUENCE: 18

```
Met Arg Val Arg Ile Gly Leu Thr Leu Leu Leu Cys Ala Val Leu
  1               5                  10                  15

Leu Ser Leu Ala Ser Ala Ser Ser Asp Glu Glu Gly Ser Gln Asp
                 20                  25                  30

Glu Ser Leu Asp Ser Lys Thr Thr Leu Thr Ser Asp Glu Ser Val
                 35                  40                  45

Lys Asp His Thr Thr Ala Gly Arg Val Val Ala Gly Gln Ile Phe
                 50                  55                  60

Leu Asp Ser Glu Glu Ser Glu Leu Glu Ser Ser Ile Gln Glu Glu
                 65                  70                  75

Glu Asp Ser Leu Lys Ser Gln Glu Gly Glu Ser Val Thr Glu Asp
                 80                  85                  90
```

-continued

```
Ile Ser Phe Leu Glu Ser Pro Asn Pro Glu Asn Lys Asp Tyr Glu
                95                  100                 105

Glu Pro Lys Lys Val Arg Lys Pro Ala Leu Thr Ala Ile Glu Gly
                110                 115                 120

Thr Ala His Gly Glu Pro Cys His Phe Pro Phe Leu Phe Leu Asp
                125                 130                 135

Lys Glu Tyr Asp Glu Cys Thr Ser Asp Gly Arg Glu Asp Gly Arg
                140                 145                 150

Leu Trp Cys Ala Thr Thr Tyr Asp Tyr Lys Ala Asp Glu Lys Trp
                155                 160                 165

Gly Phe Cys Glu Thr Glu Glu Glu Ala Ala Lys Arg Arg Gln Met
                170                 175                 180

Gln Glu Ala Glu Met Met Tyr Gln Thr Gly Met Lys Ile Leu Asn
                185                 190                 195

Gly Ser Asn Lys Lys Ser Gln Lys Arg Glu Ala Tyr Arg Tyr Leu
                200                 205                 210

Gln Lys Ala Ala Ser Met Asn His Thr Lys Ala Leu Glu Arg Val
                215                 220                 225

Ser Tyr Ala Leu Leu Phe Gly Asp Tyr Leu Pro Gln Asn Ile Gln
                230                 235                 240

Ala Ala Arg Glu Met Phe Glu Lys Leu Thr Glu Glu Gly Ser Pro
                245                 250                 255

Lys Gly Gln Thr Ala Leu Gly Phe Leu Tyr Ala Ser Gly Leu Gly
                260                 265                 270

Val Asn Ser Ser Gln Ala Lys Ala Leu Val Tyr Tyr Thr Phe Gly
                275                 280                 285

Ala Leu Gly Gly Asn Leu Ile Ala His Met Val Leu Val Ser Arg
                290                 295                 300

Leu


<210> SEQ ID NO 19
<211> LENGTH: 1508
<212> TYPE: DNA
<213> ORGANISM: Homo Sapien

<400> SEQUENCE: 19

aattcagatt ttaagcccat tctgcagtgg aatttcatga actagcaaga           50

ggacaccatc ttcttgtatt atacaagaaa ggagtgtacc tatcacacac          100

agggggaaaa atgctctttt gggtgctagg cctcctaatc ctctgtggtt          150

ttctgtggac tcgtaaagga aaactaaaga ttgaagacat cactgataag          200

tacattttta tcactggatg tgactcgggc tttggaaact tggcagccag          250

aacttttgat aaaaagggat ttcatgtaat cgctgcctgt ctgactgaat          300

caggatcaac agctttaaag gcagaaacct cagagagact tcgtactgtg          350

cttctggatg tgaccgaccc agagaatgtc aagaggactg cccagtgggt          400

gaagaaccaa gttggggaga aaggtctctg ggtctgatc aataatgctg           450

gtgttcccgg cgtgctggct cccactgact ggctgacact agaggactac          500

agagaaccta ttgaagtgaa cctgtttgga ctcatcagtg tgacactaaa          550

tatgcttcct ttggtcaaga aagctcaagg gagagttatt aatgtctcca          600

gtgttggagg tcgccttgca atcgttggag ggggctatac tccatccaaa          650

tatgcagtgg aaggtttcaa tgacagctta agacgggaca tgaaagcttt          700
```

-continued

```
tggtgtgcac gtctcatgca ttgaaccagg attgttcaaa acaaacttgg         750

cagatccagt aaaggtaatt gaaaaaaaac tcgccatttg ggagcagctg         800

tctccagaca tcaaacaaca atatggagaa ggttacattg aaaaaagtct         850

agacaaactg aaaggcaata aatcctatgt gaacatggac ctctctccgg         900

tggtagagtg catggaccac gctctaacaa gtctcttccc taagactcat         950

tatgccgctg gaaaagatgc caaaattttc tggatacctc tgtctcacat        1000

gccagcagct ttgcaagact ttttattgtt gaaacagaaa gcagagctgg        1050

ctaatcccaa ggcagtgtga ctcagctaac cacaaatgtc tcctccaggc        1100

tatgaaattg gccgatttca agaacacatc tccttttcaa ccccattcct        1150

tatctgctcc aacctggact catttagatc gtgcttattt ggattgcaaa        1200

agggagtccc accatcgctg gtggtatccc agggtccctg ctcaagtttt        1250

ctttgaaaag gagggctgga atggtacatc acataggcaa gtcctgccct        1300

gtatttaggc tttgcctgct tggtgtgatg taagggaaat tgaaagactt        1350

gcccattcaa aatgatcttt accgtggcct gccccatgct tatggtcccc        1400

agcatttaca gtaacttgtg aatgttaagt atcatctctt atctaaatat        1450

taaaagataa gtcaacccaa aaaaaaaaaa aaaaaaaaaa aaaaaaaaaa        1500

aaaaaaaa                                                      1508
```

```
<210> SEQ ID NO 20
<211> LENGTH: 319
<212> TYPE: PRT
<213> ORGANISM: Homo Sapien

<400> SEQUENCE: 20

Met Leu Phe Trp Val Leu Gly Leu Leu Ile Leu Cys Gly Phe Leu
  1               5                  10                  15

Trp Thr Arg Lys Gly Lys Leu Lys Ile Glu Asp Ile Thr Asp Lys
                 20                  25                  30

Tyr Ile Phe Ile Thr Gly Cys Asp Ser Gly Phe Gly Asn Leu Ala
                 35                  40                  45

Ala Arg Thr Phe Asp Lys Lys Gly Phe His Val Ile Ala Ala Cys
                 50                  55                  60

Leu Thr Glu Ser Gly Ser Thr Ala Leu Lys Ala Glu Thr Ser Glu
                 65                  70                  75

Arg Leu Arg Thr Val Leu Leu Asp Val Thr Asp Pro Glu Asn Val
                 80                  85                  90

Lys Arg Thr Ala Gln Trp Val Lys Asn Gln Val Gly Glu Lys Gly
                 95                 100                 105

Leu Trp Gly Leu Ile Asn Asn Ala Gly Val Pro Gly Val Leu Ala
                110                 115                 120

Pro Thr Asp Trp Leu Thr Leu Glu Asp Tyr Arg Glu Pro Ile Glu
                125                 130                 135

Val Asn Leu Phe Gly Leu Ile Ser Val Thr Leu Asn Met Leu Pro
                140                 145                 150

Leu Val Lys Lys Ala Gln Gly Arg Val Ile Asn Val Ser Ser Val
                155                 160                 165

Gly Gly Arg Leu Ala Ile Val Gly Gly Gly Tyr Thr Pro Ser Lys
                170                 175                 180
```

-continued

```
Tyr Ala Val Glu Gly Phe Asn Asp Ser Leu Arg Arg Asp Met Lys
                185                 190                 195

Ala Phe Gly Val His Val Ser Cys Ile Glu Pro Gly Leu Phe Lys
                200                 205                 210

Thr Asn Leu Ala Asp Pro Val Lys Val Ile Glu Lys Lys Leu Ala
                215                 220                 225

Ile Trp Glu Gln Leu Ser Pro Asp Ile Lys Gln Gln Tyr Gly Glu
                230                 235                 240

Gly Tyr Ile Glu Lys Ser Leu Asp Lys Leu Lys Gly Asn Lys Ser
                245                 250                 255

Tyr Val Asn Met Asp Leu Ser Pro Val Val Glu Cys Met Asp His
                260                 265                 270

Ala Leu Thr Ser Leu Phe Pro Lys Thr His Tyr Ala Ala Gly Lys
                275                 280                 285

Asp Ala Lys Ile Phe Trp Ile Pro Leu Ser His Met Pro Ala Ala
                290                 295                 300

Leu Gln Asp Phe Leu Leu Leu Lys Gln Lys Ala Glu Leu Ala Asn
                305                 310                 315

Pro Lys Ala Val
```

```
<210> SEQ ID NO 21
<211> LENGTH: 1849
<212> TYPE: DNA
<213> ORGANISM: Homo Sapien

<400> SEQUENCE: 21

ctgaggcggc ggtagcatgg agggggagag tacgtcggcg gtgctctcgg      50

gctttgtgct cggcgcactc gctttccagc acctcaacac ggactcggac     100

acggaaggtt ttcttcttgg ggaagtaaaa ggtgaagcca agaacagcat     150

tactgattcc caaatggatg atgttgaagt tgtttataca attgacattc     200

agaaatatat tccatgctat cagcttttta gcttttataa ttcttcaggc     250

gaagtaaatg agcaagcact gaagaaaata ttatcaaatg tcaaaaagaa     300

tgtggtaggt tggtacaaat tccgtcgtca ttcagatcag atcatgacgt     350

ttagagagag gctgcttcac aaaaacttgc aggagcattt ttcaaaccaa     400

gaccttgttt ttctgctatt aacaccaagt ataataacag aaagctgctc     450

tactcatcga ctggaacatt ccttatataa acctcaaaaa ggactttttc     500

acagggtacc tttagtggtt gccaatctgg gcatgtctga acaactgggt     550

tataaaactg tatcaggttc ctgtatgtcc actggtttta gccgagcagt     600

acaaacacac agctctaaat tttttgaaga agatggatcc ttaaaggagg     650

tacataagat aaatgaaatg tatgcttcat tacaagagga attaaagagt     700

atatgcaaaa aagtggaaga cagtgaacaa gcagtagata aactagtaaa     750

ggatgtaaac agattaaaac gagaaattga gaaaaggaga ggagcacaga     800

ttcaggcagc aagagagaag aacatccaaa aagaccctca ggagaacatt     850

tttctttgtc aggcattacg gaccttttt ccaaattctg aatttcttca     900

ttcatgtgtt atgtctttaa aaaatagaca tgtttctaaa agtagctgta     950

actacaacca ccatctcgat gtagtagaca atctgacctt aatggtagaa    1000

cacactgaca ttcctgaagc tagtccagct agtacaccac aaatcattaa    1050
```

-continued

```
gcataaagcc ttagacttag atgacagatg gcaattcaag agatctcggt          1100

tgttagatac acaagacaaa cgatctaaag caaatactgg tagtagtaac          1150

caagataaag catccaaaat gagcagccca gaaacagatg aagaaattga          1200

aaagatgaag ggttttggtg aatattcacg gtctcctaca ttttgatcct          1250

tttaacctta caaggagatt tttttatttg gctgatgggt aaagccaaac          1300

atttctattg tttttactat gttgagctac ttgcagtaag ttcatttgtt          1350

tttactatgt tcacctgttt gcagtaatac acagataact cttagtgcat          1400

ttacttcaca aagtactttt tcaaacatca gatgctttta tttccaaacc          1450

tttttttcac ctttcactaa gttgttgagg ggaaggctta cacagacaca          1500

ttctttagaa ttggaaaagt gagaccaggc acagtggctc acacctgtaa          1550

tcccagcact tagggaagac aagtcaggag gattgattga agctaggagt          1600

tagagaccag cctgggcaac gtattgagac catgtctatt aaaaaataaa          1650

atggaaaagc aagaatagcc ttattttcaa aatatggaaa gaaatttata          1700

tgaaaattta tctgagtcat taaaattctc cttaagtgat acttttttag          1750

aagtacatta tggctagagt tgccagataa aatgctggat atcatgcaat          1800

aaatttgcaa aacatcatct aaaatttaaa aaaaaaaaaa aaaaaaaaa           1849


<210> SEQ ID NO 22
<211> LENGTH: 409
<212> TYPE: PRT
<213> ORGANISM: Homo Sapien

<400> SEQUENCE: 22

Met Glu Gly Glu Ser Thr Ser Ala Val Leu Ser Gly Phe Val Leu
  1               5                  10                  15

Gly Ala Leu Ala Phe Gln His Leu Asn Thr Asp Ser Asp Thr Glu
                 20                  25                  30

Gly Phe Leu Leu Gly Glu Val Lys Gly Glu Ala Lys Asn Ser Ile
                 35                  40                  45

Thr Asp Ser Gln Met Asp Asp Val Glu Val Val Tyr Thr Ile Asp
                 50                  55                  60

Ile Gln Lys Tyr Ile Pro Cys Tyr Gln Leu Phe Ser Phe Tyr Asn
                 65                  70                  75

Ser Ser Gly Glu Val Asn Glu Gln Ala Leu Lys Lys Ile Leu Ser
                 80                  85                  90

Asn Val Lys Lys Asn Val Val Gly Trp Tyr Lys Phe Arg Arg His
                 95                 100                 105

Ser Asp Gln Ile Met Thr Phe Arg Glu Arg Leu Leu His Lys Asn
                110                 115                 120

Leu Gln Glu His Phe Ser Asn Gln Asp Leu Val Phe Leu Leu Leu
                125                 130                 135

Thr Pro Ser Ile Ile Thr Glu Ser Cys Ser Thr His Arg Leu Glu
                140                 145                 150

His Ser Leu Tyr Lys Pro Gln Lys Gly Leu Phe His Arg Val Pro
                155                 160                 165

Leu Val Val Ala Asn Leu Gly Met Ser Glu Gln Leu Gly Tyr Lys
                170                 175                 180

Thr Val Ser Gly Ser Cys Met Ser Thr Gly Phe Ser Arg Ala Val
                185                 190                 195
```

-continued

Gln Thr His Ser Ser Lys Phe Phe Glu Glu Asp Gly Ser Leu Lys
200 205 210

Glu Val His Lys Ile Asn Glu Met Tyr Ala Ser Leu Gln Glu Glu
215 220 225

Leu Lys Ser Ile Cys Lys Lys Val Glu Asp Ser Glu Gln Ala Val
230 235 240

Asp Lys Leu Val Lys Asp Val Asn Arg Leu Lys Arg Glu Ile Glu
245 250 255

Lys Arg Arg Gly Ala Gln Ile Gln Ala Ala Arg Glu Lys Asn Ile
260 265 270

Gln Lys Asp Pro Gln Glu Asn Ile Phe Leu Cys Gln Ala Leu Arg
275 280 285

Thr Phe Phe Pro Asn Ser Glu Phe Leu His Ser Cys Val Met Ser
290 295 300

Leu Lys Asn Arg His Val Ser Lys Ser Ser Cys Asn Tyr Asn His
305 310 315

His Leu Asp Val Val Asp Asn Leu Thr Leu Met Val Glu His Thr
320 325 330

Asp Ile Pro Glu Ala Ser Pro Ala Ser Thr Pro Gln Ile Ile Lys
335 340 345

His Lys Ala Leu Asp Leu Asp Asp Arg Trp Gln Phe Lys Arg Ser
350 355 360

Arg Leu Leu Asp Thr Gln Asp Lys Arg Ser Lys Ala Asn Thr Gly
365 370 375

Ser Ser Asn Gln Asp Lys Ala Ser Lys Met Ser Ser Pro Glu Thr
380 385 390

Asp Glu Glu Ile Glu Lys Met Lys Gly Phe Gly Glu Tyr Ser Arg
395 400 405

Ser Pro Thr Phe

<210> SEQ ID NO 23
<211> LENGTH: 2651
<212> TYPE: DNA
<213> ORGANISM: Homo Sapien

<400> SEQUENCE: 23
ggcacagccg cgcggcggag ggcagagtca gccgagccga gtccagccgg 50
acgagcggac cagcgcaggg cagcccaagc agcgcgcagc gaacgcccgc 100
cgccgcccac accctctgcg gtccccgcgg cgcctgccac ccttccctcc 150
ttccccgcgt ccccgcctcg ccggccagtc agcttgccgg gttcgctgcc 200
ccgcgaaacc ccgaggtcac cagcccgcgc ctctgcttcc ctgggccgcg 250
cgccgcctcc acgccctcct tctcccctgg cccggcgcct ggcaccgggg 300
accgttgcct gacgcgaggc ccagctctac ttttcgcccc gcgtctcctc 350
cgcctgctcg cctcttccac caactccaac tccttctccc tccagctcca 400
ctcgctagtc cccgactccg ccagccctcg gcccgctgcc gtagcgccgc 450
ttcccgtccg gtcccaaagg tgggaacgcg tccgccccgg cccgcaccat 500
ggcacggttc ggcttgcccg cgcttctctg caccctggca gtgctcagcg 550
ccgcgctgct ggctgccgag ctcaagtcga aaagttgctc ggaagtgcga 600
cgtctttacg tgtccaaagg cttcaacaag aacgatgccc ccctccacga 650
gatcaacggt gatcatttga agatctgtcc ccagggttct acctgctgct 700

-continued

```
ctcaagagat ggaggagaag tacagcctgc aaagtaaaga tgatttcaaa      750
agtgtggtca gcgaacagtg caatcatttg caagctgtct ttgcttcacg      800
ttacaagaag tttgatgaat tcttcaaaga actacttgaa aatgcagaga      850
aatccctgaa tgatatgttt gtgaagacat atggccattt atacatgcaa      900
aattctgagc tatttaaaga tctcttcgta gagttgaaac gttactacgt      950
ggtgggaaat gtgaacctgg aagaaatgct aaatgacttc tgggctcgcc     1000
tcctggagcg gatgttccgc ctggtgaact cccagtacca ctttacagat     1050
gagtatctgg aatgtgtgag caagtatacg gagcagctga agcccttcgg     1100
agatgtccct cgcaaattga agctccaggt tactcgtgct tttgtagcag     1150
cccgtacttt cgctcaaggc ttagcggttg cgggagatgt cgtgagcaag     1200
gtctccgtgg taaaccccac agcccagtgt acccatgccc tgttgaagat     1250
gatctactgc tcccactgcc ggggtctcgt gactgtgaag ccatgttaca     1300
actactgctc aaacatcatg agaggctgtt tggccaacca aggggatctc     1350
gattttgaat ggaacaattt catagatgct atgctgatgg tggcagagag     1400
gctagagggt cctttcaaca ttgaatcggt catggatccc atcgatgtga     1450
agatttctga tgctattatg aacatgcagg ataatagtgt tcaagtgtct     1500
cagaaggttt tccagggatg tggacccccc aagcccctcc cagctggacg     1550
aatttctcgt tccatctctg aaagtgcctt cagtgctcgc ttcagaccac     1600
atcaccccga ggaacgccca accacagcag ctggcactag tttggaccga     1650
ctggttactg atgtcaagga gaaactgaaa caggccaaga aattctggtc     1700
ctcccttccg agcaacgttt gcaacgatga gaggatggct gcaggaaacg     1750
gcaatgagga tgactgttgg aatgggaaag gcaaaagcag gtacctgttt     1800
gcagtgacag gaaatggatt agccaaccag ggcaacaacc cagaggtcca     1850
ggttgacacc agcaaaccag acatactgat ccttcgtcaa atcatggctc     1900
ttcgagtgat gaccagcaag atgaagaatg catacaatgg gaacgacgtg     1950
gacttctttg atatcagtga tgaaagtagt ggagaaggaa gtggaagtgg     2000
ctgtgagtat cagcagtgcc cttcagagtt tgactacaat gccactgacc     2050
atgctgggaa gagtgccaat gagaaagccg acagtgctgg tgtccgtcct     2100
ggggcacagg cctacctcct cactgtcttc tgcatcttgt tcctggttat     2150
gcagagagag tggagataat tctcaaactc tgagaaaaag tgttcatcaa     2200
aaagttaaaa ggcaccagtt atcacttttc taccatccta gtgactttgc     2250
tttttaaatg aatggacaac aatgtacagt ttttactatg tggccactgg     2300
tttaagaagt gctgactttg ttttctcatt cagttttggg aggaaaaggg     2350
actgtgcatt gagttggttc ctgctccccc aaaccatgtt aaacgtggct     2400
aacagtgtag gtacagaact atagttagtt gtgcatttgt gattttatca     2450
ctctattatt tgtttgtatg ttttttttctc atttcgtttg tgggtttttt     2500
tttccaactg tgatctcgcc ttgtttctta caagcaaacc agggtccctt     2550
cttggcacgt aacatgtacg tatttctgaa atattaaata gctgtacaga     2600
agcaggtttt atttatcatg ttatcttatt aaaagaaaaa gcccaaaaag     2650
```

-continued c 2651

<210> SEQ ID NO 24
<211> LENGTH: 556
<212> TYPE: PRT
<213> ORGANISM: Homo Sapien

<400> SEQUENCE: 24

```
Met Ala Arg Phe Gly Leu Pro Ala Leu Leu Cys Thr Leu Ala Val
  1               5                  10                  15

Leu Ser Ala Ala Leu Leu Ala Ala Glu Leu Lys Ser Lys Ser Cys
                 20                  25                  30

Ser Glu Val Arg Arg Leu Tyr Val Ser Lys Gly Phe Asn Lys Asn
                 35                  40                  45

Asp Ala Pro Leu His Glu Ile Asn Gly Asp His Leu Lys Ile Cys
                 50                  55                  60

Pro Gln Gly Ser Thr Cys Cys Ser Gln Glu Met Glu Glu Lys Tyr
                 65                  70                  75

Ser Leu Gln Ser Lys Asp Asp Phe Lys Ser Val Val Ser Glu Gln
                 80                  85                  90

Cys Asn His Leu Gln Ala Val Phe Ala Ser Arg Tyr Lys Lys Phe
                 95                 100                 105

Asp Glu Phe Phe Lys Glu Leu Leu Glu Asn Ala Glu Lys Ser Leu
                110                 115                 120

Asn Asp Met Phe Val Lys Thr Tyr Gly His Leu Tyr Met Gln Asn
                125                 130                 135

Ser Glu Leu Phe Lys Asp Leu Phe Val Glu Leu Lys Arg Tyr Tyr
                140                 145                 150

Val Val Gly Asn Val Asn Leu Glu Glu Met Leu Asn Asp Phe Trp
                155                 160                 165

Ala Arg Leu Leu Glu Arg Met Phe Arg Leu Val Asn Ser Gln Tyr
                170                 175                 180

His Phe Thr Asp Glu Tyr Leu Glu Cys Val Ser Lys Tyr Thr Glu
                185                 190                 195

Gln Leu Lys Pro Phe Gly Asp Val Pro Arg Lys Leu Lys Leu Gln
                200                 205                 210

Val Thr Arg Ala Phe Val Ala Ala Arg Thr Phe Ala Gln Gly Leu
                215                 220                 225

Ala Val Ala Gly Asp Val Val Ser Lys Val Ser Val Val Asn Pro
                230                 235                 240

Thr Ala Gln Cys Thr His Ala Leu Leu Lys Met Ile Tyr Cys Ser
                245                 250                 255

His Cys Arg Gly Leu Val Thr Val Lys Pro Cys Tyr Asn Tyr Cys
                260                 265                 270

Ser Asn Ile Met Arg Gly Cys Leu Ala Asn Gln Gly Asp Leu Asp
                275                 280                 285

Phe Glu Trp Asn Asn Phe Ile Asp Ala Met Leu Met Val Ala Glu
                290                 295                 300

Arg Leu Glu Gly Pro Phe Asn Ile Glu Ser Val Met Asp Pro Ile
                305                 310                 315

Asp Val Lys Ile Ser Asp Ala Ile Met Asn Met Gln Asp Asn Ser
                320                 325                 330

Val Gln Val Ser Gln Lys Val Phe Gln Gly Cys Gly Pro Pro Lys
                335                 340                 345
```

-continued

```
Pro Leu Pro Ala Gly Arg Ile Ser Arg Ser Ile Ser Glu Ser Ala
                350                 355                 360

Phe Ser Ala Arg Phe Arg Pro His His Pro Glu Glu Arg Pro Thr
                365                 370                 375

Thr Ala Ala Gly Thr Ser Leu Asp Arg Leu Val Thr Asp Val Lys
                380                 385                 390

Glu Lys Leu Lys Gln Ala Lys Lys Phe Trp Ser Ser Leu Pro Ser
                395                 400                 405

Asn Val Cys Asn Asp Glu Arg Met Ala Ala Gly Asn Gly Asn Glu
                410                 415                 420

Asp Asp Cys Trp Asn Gly Lys Gly Lys Ser Arg Tyr Leu Phe Ala
                425                 430                 435

Val Thr Gly Asn Gly Leu Ala Asn Gln Gly Asn Asn Pro Glu Val
                440                 445                 450

Gln Val Asp Thr Ser Lys Pro Asp Ile Leu Ile Leu Arg Gln Ile
                455                 460                 465

Met Ala Leu Arg Val Met Thr Ser Lys Met Lys Asn Ala Tyr Asn
                470                 475                 480

Gly Asn Asp Val Asp Phe Phe Asp Ile Ser Asp Glu Ser Ser Gly
                485                 490                 495

Glu Gly Ser Gly Ser Gly Cys Glu Tyr Gln Gln Cys Pro Ser Glu
                500                 505                 510

Phe Asp Tyr Asn Ala Thr Asp His Ala Gly Lys Ser Ala Asn Glu
                515                 520                 525

Lys Ala Asp Ser Ala Gly Val Arg Pro Gly Ala Gln Ala Tyr Leu
                530                 535                 540

Leu Thr Val Phe Cys Ile Leu Phe Leu Val Met Gln Arg Glu Trp
                545                 550                 555

Arg


<210> SEQ ID NO 25
<211> LENGTH: 870
<212> TYPE: DNA
<213> ORGANISM: Homo Sapien

<400> SEQUENCE: 25

ctcgccctca aatgggaacg ctggcctggg actaaagcat agaccaccag        50

gctgagtatc ctgacctgag tcatccccag ggatcaggag cctccagcag       100

ggaaccttcc attatattct tcaagcaact tacagctgca ccgacagttg       150

cgatgaaagt tctaatctct tccctcctcc tgttgctgcc actaatgctg       200

atgtccatgg tctctagcag cctgaatcca ggggtcgcca gaggccacag       250

ggaccgaggc caggcttcta ggagatggct ccaggaaggc ggccaagaat       300

gtgagtgcaa agattggttc ctgagagccc cgagaagaaa attcatgaca       350

gtgtctgggc tgccaaagaa gcagtgcccc tgtgatcatt tcaagggcaa       400

tgtgaagaaa acaagacacc aaaggcacca cagaaagcca aacaagcatt       450

ccagagcctg ccagcaattt ctcaaacaat gtcagctaag aagctttgct       500

ctgcctttgt aggagctctg agcgcccact cttccaatta aacattctca       550

gccaagaaga cagtgagcac acctaccaga cactcttctt ctcccacctc       600

actctcccac tgtacccacc cctaaatcat tccagtgctc tcaaaaagca       650

tgtttttcaa gatcattttg tttgttgctc tctctagtgt cttcttctct       700
```

-continued

```
cgtcagtctt agcctgtgcc ctccccttac ccaggcttag gcttaattac           750

ctgaaagatt ccaggaaact gtagcttcct agctagtgtc atttaacctt           800

aaatgcaatc aggaaagtag caaacagaag tcaataaata tttttaaatg           850

tcaaaaaaaa aaaaaaaaaa                                            870


<210> SEQ ID NO 26
<211> LENGTH: 119
<212> TYPE: PRT
<213> ORGANISM: Homo Sapien

<400> SEQUENCE: 26

Met Lys Val Leu Ile Ser Ser Leu Leu Leu Leu Leu Pro Leu Met
  1               5                  10                  15

Leu Met Ser Met Val Ser Ser Ser Leu Asn Pro Gly Val Ala Arg
                 20                  25                  30

Gly His Arg Asp Arg Gly Gln Ala Ser Arg Arg Trp Leu Gln Glu
                 35                  40                  45

Gly Gly Gln Glu Cys Glu Cys Lys Asp Trp Phe Leu Arg Ala Pro
                 50                  55                  60

Arg Arg Lys Phe Met Thr Val Ser Gly Leu Pro Lys Lys Gln Cys
                 65                  70                  75

Pro Cys Asp His Phe Lys Gly Asn Val Lys Lys Thr Arg His Gln
                 80                  85                  90

Arg His His Arg Lys Pro Asn Lys His Ser Arg Ala Cys Gln Gln
                 95                 100                 105

Phe Leu Lys Gln Cys Gln Leu Arg Ser Phe Ala Leu Pro Leu
                110                 115


<210> SEQ ID NO 27
<211> LENGTH: 1371
<212> TYPE: DNA
<213> ORGANISM: Homo Sapien

<400> SEQUENCE: 27

ggacgccagc gcctgcagag gctgagcagg gaaaaagcca gtgccccagc            50

ggaagcacag ctcagagctg gtctgccatg gacatcctgg tcccactcct           100

gcagctgctg gtgctgcttc ttaccctgcc cctgcacctc atggctctgc           150

tgggctgctg gcagcccctg tgcaaaagct acttccccta cctgatggcc           200

gtgctgactc ccaagagcaa ccgcaagatg gagagcaaga aacgggagct           250

cttcagccag ataaaggggc ttacaggagc ctccgggaaa gtggccctac           300

tggagctggg ctgcggaacc ggagccaact ttcagttcta cccaccgggc           350

tgcagggtca cctgcctaga cccaaatccc cactttgaga agttcctgac           400

aaagagcatg gctgagaaca ggcacctcca atatgagcgg tttgtggtgg           450

ctcctggaga ggacatgaga cagctggctg atggctccat ggatgtggtg           500

gtctgcactc tggtgctgtg ctctgtgcag agcccaagga aggtcctgca           550

ggaggtccgg agagtactga gaccgggagg tgtgctcttt ttctgggagc           600

atgtggcaga accatatgga agctgggcct tcatgtggca gcaagttttc           650

gagcccacct ggaaacacat tggggatggc tgctgcctca ccagagagac           700

ctggaaggat cttgagaacg cccagttctc cgaaatccaa atggaacgac           750
```

-continued

```
agccccctcc cttgaagtgg ctacctgttg ggccccacat catgggaaag          800

gctgtcaaac aatctttccc aagctccaag gcactcattt gctccttccc          850

cagcctccaa ttagaacaag ccacccacca gcctatctat cttccactga          900

gagggaccta gcagaatgag agaagacatt catgtaccac ctactagtcc          950

ctctctcccc aacctctgcc agggcaatct ctaacttcaa tcccgccttc         1000

gacagtgaaa aagctctact tctacgctga cccagggagg aaacactagg         1050

accctgttgt atcctcaact gcaagtttct ggactagtct cccaacgttt         1100

gcctcccaat gttgtccctt tccttcgttc ccatggtaaa gctcctctcg         1150

ctttcctcct gaggctacac ccatgcgtct ctaggaactg gtcacaaaag         1200

tcatggtgcc tgcatccctg ccaagccccc ctgaccctct ctccccacta         1250

ccaccttctt cctgagctgg gggcaccagg gagaatcaga gatgctgggg         1300

atgccagagc aagactcaaa gaggcagagg ttttgttctc aaatattttt         1350

taataaatag acgaaaccac g                                        1371
```

```
<210> SEQ ID NO 28
<211> LENGTH: 277
<212> TYPE: PRT
<213> ORGANISM: Homo Sapien

<400> SEQUENCE: 28

Met Asp Ile Leu Val Pro Leu Leu Gln Leu Leu Val Leu Leu Leu
  1               5                  10                  15

Thr Leu Pro Leu His Leu Met Ala Leu Leu Gly Cys Trp Gln Pro
                 20                  25                  30

Leu Cys Lys Ser Tyr Phe Pro Tyr Leu Met Ala Val Leu Thr Pro
                 35                  40                  45

Lys Ser Asn Arg Lys Met Glu Ser Lys Lys Arg Glu Leu Phe Ser
                 50                  55                  60

Gln Ile Lys Gly Leu Thr Gly Ala Ser Gly Lys Val Ala Leu Leu
                 65                  70                  75

Glu Leu Gly Cys Gly Thr Gly Ala Asn Phe Gln Phe Tyr Pro Pro
                 80                  85                  90

Gly Cys Arg Val Thr Cys Leu Asp Pro Asn Pro His Phe Glu Lys
                 95                 100                 105

Phe Leu Thr Lys Ser Met Ala Glu Asn Arg His Leu Gln Tyr Glu
                110                 115                 120

Arg Phe Val Val Ala Pro Gly Glu Asp Met Arg Gln Leu Ala Asp
                125                 130                 135

Gly Ser Met Asp Val Val Val Cys Thr Leu Val Leu Cys Ser Val
                140                 145                 150

Gln Ser Pro Arg Lys Val Leu Gln Glu Val Arg Arg Val Leu Arg
                155                 160                 165

Pro Gly Gly Val Leu Phe Phe Trp Glu His Val Ala Glu Pro Tyr
                170                 175                 180

Gly Ser Trp Ala Phe Met Trp Gln Gln Val Phe Glu Pro Thr Trp
                185                 190                 195

Lys His Ile Gly Asp Gly Cys Cys Leu Thr Arg Glu Thr Trp Lys
                200                 205                 210

Asp Leu Glu Asn Ala Gln Phe Ser Glu Ile Gln Met Glu Arg Gln
                215                 220                 225
```

-continued

```
Pro Pro Pro Leu Lys Trp Leu Pro Val Gly Pro His Ile Met Gly
                230                 235                 240

Lys Ala Val Lys Gln Ser Phe Pro Ser Ser Lys Ala Leu Ile Cys
                245                 250                 255

Ser Phe Pro Ser Leu Gln Leu Glu Gln Ala Thr His Gln Pro Ile
                260                 265                 270

Tyr Leu Pro Leu Arg Gly Thr
                275
```

<210> SEQ ID NO 29
<211> LENGTH: 494
<212> TYPE: DNA
<213> ORGANISM: Homo Sapien

<400> SEQUENCE: 29

```
caatgtttgc ctatccacct cccccaagcc cctttaccta tgctgctgct                50

aacgctgctg ctgctgctgc tgctgcttaa aggctcatgc ttggagtggg               100

gactggtcgg tgcccagaaa gtctcttctg ccactgacgc ccccatcagg               150

gattgggcct tctttccccc ttcctttctg tgtctcctgc ctcatcggcc               200

tgccatgacc tgcagccaag cccagccccg tggggaaggg gagaaagtgg               250

gggatggcta agaaagctgg gagataggga acagaagagg gtagtgggtg               300

ggctaggggg gctgccttat ttaaagtggt tgtttatgat tcttatacta               350

atttatacaa agatattaag gccctgttca ttaagaaatt gttcccttcc               400

cctgtgttca atgtttgtaa agattgttct gtgtaaatat gtctttataa               450

taaacagtta aaagctgaaa aaaaaaaaaa aaaaaaaaaa aaaa                     494
```

<210> SEQ ID NO 30
<211> LENGTH: 73
<212> TYPE: PRT
<213> ORGANISM: Homo Sapien

<400> SEQUENCE: 30

```
Met Leu Leu Leu Thr Leu Leu Leu Leu Leu Leu Leu Leu Lys Gly
  1               5                  10                  15

Ser Cys Leu Glu Trp Gly Leu Val Gly Ala Gln Lys Val Ser Ser
                 20                  25                  30

Ala Thr Asp Ala Pro Ile Arg Asp Trp Ala Phe Phe Pro Pro Ser
                 35                  40                  45

Phe Leu Cys Leu Leu Pro His Arg Pro Ala Met Thr Cys Ser Gln
                 50                  55                  60

Ala Gln Pro Arg Gly Glu Gly Glu Lys Val Gly Asp Gly
                 65                  70
```

<210> SEQ ID NO 31
<211> LENGTH: 1660
<212> TYPE: DNA
<213> ORGANISM: Homo Sapien

<400> SEQUENCE: 31

```
gtttgaattc cttcaactat acccacagtc caaaagcaga ctcactgtgt                50

cccaggctac cagttcctcc aagcaagtca tttcccttat ttaaccgatg               100

tgtccctcaa acacctgagt gctactccct atttgcatct gttttgataa               150

atgatgttga caccctccac cgaattctaa gtggaatcat gtcgggaaga               200
```

-continued

```
gatacaatcc ttggcctgtg tatcctcgca ttagccttgt ctttggccat        250
gatgtttacc ttcagattca tcaccaccct tctggttcac attttcattt        300
cattggttat tttgggattg ttgtttgtct gcggtgtttt atggtggctg        350
tattatgact ataccaacga cctcagcata gaattggaca cagaaaggga        400
aaatatgaag tgcgtgctgg ggtttgctat cgtatccaca ggcatcacgg        450
cagtgctgct cgtcttgatt tttgttctca gaaagagaat aaaattgaca        500
gttgagcttt tccaaatcac aaataaagcc atcagcagtg ctcccttcct        550
gctgttccag ccactgtgga catttgccat cctcattttc ttctgggtcc        600
tctgggtggc tgtgctgctg agcctgggaa ctgcaggagc tgcccaggtt        650
atggaaggcg gccaagtgga atataagccc ctttcgggca ttcggtacat        700
gtggtcgtac catttaattg gcctcatctg gactagtgaa ttcatccttg        750
cgtgccagca aatgactata gctggggcag tggttacttg ttatttcaac        800
agaagtaaaa atgatcctcc tgatcatccc atcctttcgt ctctctccat        850
tctcttcttc taccatcaag gaaccgttgt gaaagggtca tttttaatct        900
ctgtggtgag gattccgaga atcattgtca tgtacatgca aaacgcactg        950
aaagaacagc agcatggtgc attgtccagg tacctgttcc gatgctgcta       1000
ctgctgtttc tggtgtcttg acaaatacct gctccatctc aaccagaatg       1050
catatactac aactgctatt aatgggacag atttctgtac atcagcaaaa       1100
gatgcattca aaatcttgtc caagaactca agtcacttta catctattaa       1150
ctgctttgga gacttcataa tttttctagg aaaggtgtta gtggtgtgtt       1200
tcactgtttt tggaggactc atggctttta actacaatcg ggcattccag       1250
gtgtgggcag tccctctgtt attggtagct ttttttgcct acttagtagc       1300
ccatagtttt ttatctgtgt ttgaaactgt gctggatgca cttttcctgt       1350
gttttgctgt tgatctggaa acaaatgatg gatcgtcaga aaagccctac       1400
tttatggatc aagaatttct gagtttcgta aaaaggagca acaaattaaa       1450
caatgcaagg gcacagcagg acaagcactc attaaggaat gaggagggaa       1500
cagaactcca ggccattgtg agatagatac ccatttaggt atctgtacct       1550
ggaaaacatt tccttctaag agccatttac agaatagaag atgagaccac       1600
tagagaaaag ttagtgaatt ttttttaaa agacctaata aaccctattc        1650
ttcctcaaaa                                                    1660
```

<210> SEQ ID NO 32
<211> LENGTH: 445
<212> TYPE: PRT
<213> ORGANISM: Homo Sapien

<400> SEQUENCE: 32

```
Met Ser Gly Arg Asp Thr Ile Leu Gly Leu Cys Ile Leu Ala Leu
  1               5                  10                  15

Ala Leu Ser Leu Ala Met Met Phe Thr Phe Arg Phe Ile Thr Thr
                 20                  25                  30

Leu Leu Val His Ile Phe Ile Ser Leu Val Ile Leu Gly Leu Leu
                 35                  40                  45

Phe Val Cys Gly Val Leu Trp Trp Leu Tyr Tyr Asp Tyr Thr Asn
                 50                  55                  60
```

-continued

```
Asp Leu Ser Ile Glu Leu Asp Thr Glu Arg Glu Asn Met Lys Cys
                65                  70                  75

Val Leu Gly Phe Ala Ile Val Ser Thr Gly Ile Thr Ala Val Leu
                80                  85                  90

Leu Val Leu Ile Phe Val Leu Arg Lys Arg Ile Lys Leu Thr Val
                95                  100                 105

Glu Leu Phe Gln Ile Thr Asn Lys Ala Ile Ser Ser Ala Pro Phe
                110                 115                 120

Leu Leu Phe Gln Pro Leu Trp Thr Phe Ala Ile Leu Ile Phe Phe
                125                 130                 135

Trp Val Leu Trp Val Ala Val Leu Leu Ser Leu Gly Thr Ala Gly
                140                 145                 150

Ala Ala Gln Val Met Glu Gly Gly Gln Val Glu Tyr Lys Pro Leu
                155                 160                 165

Ser Gly Ile Arg Tyr Met Trp Ser Tyr His Leu Ile Gly Leu Ile
                170                 175                 180

Trp Thr Ser Glu Phe Ile Leu Ala Cys Gln Gln Met Thr Ile Ala
                185                 190                 195

Gly Ala Val Val Thr Cys Tyr Phe Asn Arg Ser Lys Asn Asp Pro
                200                 205                 210

Pro Asp His Pro Ile Leu Ser Ser Leu Ser Ile Leu Phe Phe Tyr
                215                 220                 225

His Gln Gly Thr Val Val Lys Gly Ser Phe Leu Ile Ser Val Val
                230                 235                 240

Arg Ile Pro Arg Ile Ile Val Met Tyr Met Gln Asn Ala Leu Lys
                245                 250                 255

Glu Gln Gln His Gly Ala Leu Ser Arg Tyr Leu Phe Arg Cys Cys
                260                 265                 270

Tyr Cys Cys Phe Trp Cys Leu Asp Lys Tyr Leu Leu His Leu Asn
                275                 280                 285

Gln Asn Ala Tyr Thr Thr Thr Ala Ile Asn Gly Thr Asp Phe Cys
                290                 295                 300

Thr Ser Ala Lys Asp Ala Phe Lys Ile Leu Ser Lys Asn Ser Ser
                305                 310                 315

His Phe Thr Ser Ile Asn Cys Phe Gly Asp Phe Ile Ile Phe Leu
                320                 325                 330

Gly Lys Val Leu Val Val Cys Phe Thr Val Phe Gly Gly Leu Met
                335                 340                 345

Ala Phe Asn Tyr Asn Arg Ala Phe Gln Val Trp Ala Val Pro Leu
                350                 355                 360

Leu Leu Val Ala Phe Phe Ala Tyr Leu Val Ala His Ser Phe Leu
                365                 370                 375

Ser Val Phe Glu Thr Val Leu Asp Ala Leu Phe Leu Cys Phe Ala
                380                 385                 390

Val Asp Leu Glu Thr Asn Asp Gly Ser Ser Glu Lys Pro Tyr Phe
                395                 400                 405

Met Asp Gln Glu Phe Leu Ser Phe Val Lys Arg Ser Asn Lys Leu
                410                 415                 420

Asn Asn Ala Arg Ala Gln Gln Asp Lys His Ser Leu Arg Asn Glu
                425                 430                 435

Glu Gly Thr Glu Leu Gln Ala Ile Val Arg
                440                 445
```

-continued

<210> SEQ ID NO 33
<211> LENGTH: 2773
<212> TYPE: DNA
<213> ORGANISM: Homo Sapien

<400> SEQUENCE: 33

```
gttcgattag ctcctctgag aagaagagaa aaggttcttg gacctctccc      50
tgtttcttcc ttagaataat ttgtatggga tttgtgatgc aggaaagcct     100
aagggaaaaa gaatattcat tctgtgtggt gaaaattttt tgaaaaaaaa     150
attgccttct tcaaacaagg gtgtcattct gatatttatg aggactgttg     200
ttctcactat gaaggcatct gttattgaaa tgttccttgt tttgctggtg     250
actggagtac attcaaacaa agaaacggca aagaagatta aaaggcccaa     300
gttcactgtg cctcagatca actgcgatgt caaagccgga aagatcatcg     350
atcctgagtt cattgtgaaa tgtccagcag gatgccaaga ccccaaatac     400
catgtttatg gcactgacgt gtatgcatcc tactccagtg tgtgtggcgc     450
tgccgtacac agtggtgtgc ttgataattc aggagggaaa atacttgttc     500
ggaaggttgc tggacagtct ggttacaaag ggagttattc caacggtgtc     550
caatcgttat ccctaccacg atggagagaa tcctttatcg tcttagaaag     600
taaacccaaa aagggtgtaa cctacccatc agctcttaca tactcatcat     650
cgaaaagtcc agctgcccaa gcaggtgaga ccacaaaagc ctatcagagg     700
ccacctattc cagggacaac tgcacagccg gtcactctga tgcagcttct     750
ggctgtcact gtagctgtgg ccacccccac caccttgcca aggccatccc     800
cttctgctgc ttctaccacc agcatcccca gaccacaatc agtgggccac     850
aggagccagg agatggatct ctggtccact gccacctaca caagcagcca     900
aaacaggccc agagctgatc caggtatcca aaggcaagat ccttcaggag     950
ctgccttcca gaaacctgtt ggagcggatg tcagcctggg acttgttcca    1000
aaagaagaat tgagcacaca gtctttggag ccagtatccc tgggagatcc    1050
aaactgcaaa attgacttgt cgtttttaat tgatgggagc accagcattg    1100
gcaaacggcg attccgaatc cagaagcagc tcctggctga tgttgcccaa    1150
gctcttgaca ttggccctgc cggtccactg atgggtgttg tccagtatgg    1200
agacaaccct gctactcact ttaacctcaa gacacacacg aattctcgag    1250
atctgaagac agccatagag aaaattactc agagaggagg actttctaat    1300
gtaggtcggg ccatctcctt tgtgaccaag aacttctttt ccaaagccaa    1350
tggaaacaga agcggggctc ccaatgtggt ggtggtgatg gtggatggct    1400
ggcccacgga caaagtggag gaggcttcaa gacttgcgag agagtcagga    1450
atcaacattt tcttcatcac cattgaaggt gctgctgaaa atgagaagca    1500
gtatgtggtg gagcccaact ttgcaaacaa ggccgtgtgc agaacaaacg    1550
gcttctactc gctccacgtg cagagctggt ttggcctcca caagaccctg    1600
cagcctctgg tgaagcgggt ctgcgacact gaccgcctgg cctgcagcaa    1650
gacctgcttg aactcggctg acattggctt cgtcatcgac ggctccagca    1700
gtgtggggac gggcaacttc cgcaccgtcc tccagtttgt gaccaacctc    1750
accaaagagt ttgagatttc cgacacggac acgcgcatcg ggccgtgca     1800
```

-continued

```
gtacacctac gaacagcggc tggagtttgg gttcgacaag tacagcagca          1850

agcctgacat cctcaacgcc atcaagaggg tgggctactg gagtggtggc          1900

accagcacgg gggctgccat caacttcgcc ctggagcagc tcttcaagaa          1950

gtccaagccc aacaagagga agttaatgat cctcatcacc gacgggaggt          2000

cctacgacga cgtccggatc ccagccatgg ctgcccatct gaagggagtg          2050

atcacctatg cgataggcgt tgcctgggct gcccaagagg agctagaagt          2100

cattgccact caccccgcca gagaccactc cttctttgtg gacgagtttg          2150

acaacctcca tcagtatgtc cccaggatca tccagaacat ttgtacagag          2200

ttcaactcac agcctcggaa ctgaattcag agcaggcaga gcaccagcaa          2250

gtgctgcttt actaactgac gtgttggacc accccaccgc ttaatggggc          2300

acgcacggtg catcaagtct tgggcagggc atggagaaac aaatgtcttg          2350

ttattattct ttgccatcat gctttttcat attccaaaac ttggagttac          2400

aaagatgatc acaaacgtat agaatgagcc aaaaggctac atcatgttga          2450

gggtgctgga gattttacat tttgacaatt gttttcaaaa taaatgttcg          2500

gaatacagtg cagcccttac gacaggctta cgtagagctt ttgtgagatt          2550

tttaagttgt tatttctgat ttgaactctg taaccctcag caagtttcat          2600

ttttgtcatg acaatgtagg aattgctgaa ttaaatgttt agaaggatga          2650

aaaataaaaa aaaaaaaaaa aaaaaaaaaa aaaaaaaaaa aaaaaaaaaa          2700

aaaaaaaaaa aaaaaaaaaa aaaaaaaaaa aaaaaaaaaa aaaaaaaaaa          2750

aaaaaaaaaa aaaaaaaaaa aag                                       2773
```

<210> SEQ ID NO 34
<211> LENGTH: 678
<212> TYPE: PRT
<213> ORGANISM: Homo Sapien

<400> SEQUENCE: 34

```
Met Arg Thr Val Val Leu Thr Met Lys Ala Ser Val Ile Glu Met
  1               5                  10                  15

Phe Leu Val Leu Leu Val Thr Gly Val His Ser Asn Lys Glu Thr
                 20                  25                  30

Ala Lys Lys Ile Lys Arg Pro Lys Phe Thr Val Pro Gln Ile Asn
                 35                  40                  45

Cys Asp Val Lys Ala Gly Lys Ile Ile Asp Pro Glu Phe Ile Val
                 50                  55                  60

Lys Cys Pro Ala Gly Cys Gln Asp Pro Lys Tyr His Val Tyr Gly
                 65                  70                  75

Thr Asp Val Tyr Ala Ser Tyr Ser Ser Val Cys Gly Ala Ala Val
                 80                  85                  90

His Ser Gly Val Leu Asp Asn Ser Gly Gly Lys Ile Leu Val Arg
                 95                 100                 105

Lys Val Ala Gly Gln Ser Gly Tyr Lys Gly Ser Tyr Ser Asn Gly
                110                 115                 120

Val Gln Ser Leu Ser Leu Pro Arg Trp Arg Glu Ser Phe Ile Val
                125                 130                 135

Leu Glu Ser Lys Pro Lys Lys Gly Val Thr Tyr Pro Ser Ala Leu
                140                 145                 150
```

-continued

```
Thr Tyr Ser Ser Ser Lys Ser Pro Ala Ala Gln Ala Gly Glu Thr
                155                 160                 165

Thr Lys Ala Tyr Gln Arg Pro Pro Ile Pro Gly Thr Thr Ala Gln
                170                 175                 180

Pro Val Thr Leu Met Gln Leu Leu Ala Val Thr Val Ala Val Ala
                185                 190                 195

Thr Pro Thr Thr Leu Pro Arg Pro Ser Pro Ser Ala Ala Ser Thr
                200                 205                 210

Thr Ser Ile Pro Arg Pro Gln Ser Val Gly His Arg Ser Gln Glu
                215                 220                 225

Met Asp Leu Trp Ser Thr Ala Thr Tyr Thr Ser Ser Gln Asn Arg
                230                 235                 240

Pro Arg Ala Asp Pro Gly Ile Gln Arg Gln Asp Pro Ser Gly Ala
                245                 250                 255

Ala Phe Gln Lys Pro Val Gly Ala Asp Val Ser Leu Gly Leu Val
                260                 265                 270

Pro Lys Glu Glu Leu Ser Thr Gln Ser Leu Glu Pro Val Ser Leu
                275                 280                 285

Gly Asp Pro Asn Cys Lys Ile Asp Leu Ser Phe Leu Ile Asp Gly
                290                 295                 300

Ser Thr Ser Ile Gly Lys Arg Arg Phe Arg Ile Gln Lys Gln Leu
                305                 310                 315

Leu Ala Asp Val Ala Gln Ala Leu Asp Ile Gly Pro Ala Gly Pro
                320                 325                 330

Leu Met Gly Val Val Gln Tyr Gly Asp Asn Pro Ala Thr His Phe
                335                 340                 345

Asn Leu Lys Thr His Thr Asn Ser Arg Asp Leu Lys Thr Ala Ile
                350                 355                 360

Glu Lys Ile Thr Gln Arg Gly Gly Leu Ser Asn Val Gly Arg Ala
                365                 370                 375

Ile Ser Phe Val Thr Lys Asn Phe Phe Ser Lys Ala Asn Gly Asn
                380                 385                 390

Arg Ser Gly Ala Pro Asn Val Val Val Val Met Val Asp Gly Trp
                395                 400                 405

Pro Thr Asp Lys Val Glu Glu Ala Ser Arg Leu Ala Arg Glu Ser
                410                 415                 420

Gly Ile Asn Ile Phe Phe Ile Thr Ile Glu Gly Ala Ala Glu Asn
                425                 430                 435

Glu Lys Gln Tyr Val Val Glu Pro Asn Phe Ala Asn Lys Ala Val
                440                 445                 450

Cys Arg Thr Asn Gly Phe Tyr Ser Leu His Val Gln Ser Trp Phe
                455                 460                 465

Gly Leu His Lys Thr Leu Gln Pro Leu Val Lys Arg Val Cys Asp
                470                 475                 480

Thr Asp Arg Leu Ala Cys Ser Lys Thr Cys Leu Asn Ser Ala Asp
                485                 490                 495

Ile Gly Phe Val Ile Asp Gly Ser Ser Ser Val Gly Thr Gly Asn
                500                 505                 510

Phe Arg Thr Val Leu Gln Phe Val Thr Asn Leu Thr Lys Glu Phe
                515                 520                 525

Glu Ile Ser Asp Thr Asp Thr Arg Ile Gly Ala Val Gln Tyr Thr
                530                 535                 540

Tyr Glu Gln Arg Leu Glu Phe Gly Phe Asp Lys Tyr Ser Ser Lys
```

-continued

```
                545                 550                 555

Pro Asp Ile Leu Asn Ala Ile Lys Arg Val Gly Tyr Trp Ser Gly
                560                 565                 570

Gly Thr Ser Thr Gly Ala Ala Ile Asn Phe Ala Leu Glu Gln Leu
                575                 580                 585

Phe Lys Lys Ser Lys Pro Asn Lys Arg Lys Leu Met Ile Leu Ile
                590                 595                 600

Thr Asp Gly Arg Ser Tyr Asp Asp Val Arg Ile Pro Ala Met Ala
                605                 610                 615

Ala His Leu Lys Gly Val Ile Thr Tyr Ala Ile Gly Val Ala Trp
                620                 625                 630

Ala Ala Gln Glu Glu Leu Glu Val Ile Ala Thr His Pro Ala Arg
                635                 640                 645

Asp His Ser Phe Phe Val Asp Glu Phe Asp Asn Leu His Gln Tyr
                650                 655                 660

Val Pro Arg Ile Ile Gln Asn Ile Cys Thr Glu Phe Asn Ser Gln
                665                 670                 675

Pro Arg Asn


<210> SEQ ID NO 35
<211> LENGTH: 2095
<212> TYPE: DNA
<213> ORGANISM: Homo Sapien

<400> SEQUENCE: 35

ccgagcacag gagattgcct gcgtttagga ggtggctgcg ttgtgggaaa        50

agctatcaag gaagaaattg ccaaaccatg tcttttttc tgttttcaga        100

gtagttcaca acagatctga gtgttttaat taagcatgga atacagaaaa       150

caacaaaaaa cttaagcttt aatttcatct ggaattccac agttttctta       200

gctccctgga cccggttgac ctgttggctc ttcccgctgg ctgctctatc       250

acgtggtgct ctccgactac tcaccccgag tgtaaagaac cttcggctcg       300

cgtgcttctg agctgctgtg gatggcctcg gctctctgga ctgtccttcc       350

gagtaggatg tcactgagat ccctcaaatg gagcctcctg ctgctgtcac       400

tcctgagttt ctttgtgatg tggtacctca gccttcccca ctacaatgtg       450

atagaacgcg tgaactggat gtacttctat gagtatgagc cgatttacag       500

acaagacttt cacttcacac ttcgagagca ttcaaactgc tctcatcaaa       550

atccatttct ggtcattctg gtgacctccc acccttcaga tgtgaaagcc       600

aggcaggcca ttagagttac ttggggtgaa aaaaagtctt ggtggggata       650

tgaggttctt acatttttct tattaggcca agaggctgaa aaggaagaca       700

aaatgttggc attgtcctta gaggatgaac accttcttta tggtgacata       750

atccgacaag attttttaga cacatataat aacctgacct tgaaaaccat       800

tatggcattc aggtgggtaa ctgagttttg ccccaatgcc aagtacgtaa       850

tgaagacaga cactgatgtt ttcatcaata ctggcaattt agtgaagtat       900

cttttaaacc taaaccactc agagaagttt ttcacaggtt atcctctaat       950

tgataattat tcctatagag gattttacca aaaaacccat atttcttacc      1000

aggagtatcc tttcaaggtg ttccctccat actgcagtgg gttgggttat      1050

ataatgtcca gagatttggt gccaaggatc tatgaaatga tgggtcacgt      1100
```

-continued

```
aaaacccatc aagtttgaag atgtttatgt cgggatctgt ttgaatttat 1150

taaaagtgaa cattcatatt ccagaagaca caaatctttt ctttctatat 1200

agaatccatt tggatgtctg tcaactgaga cgtgtgattg cagcccatgg 1250

cttttcttcc aaggagatca tcactttttg gcaggtcatg ctaaggaaca 1300

ccacatgcca ttattaactt cacattctac aaaaagccta gaaggacagg 1350

ataccttgtg gaaagtgtta aataaagtag gtactgtgga aaattcatgg 1400

ggaggtcagt gtgctggctt acactgaact gaaactcatg aaaaacccag 1450

actggagact ggagggttac acttgtgatt tattagtcag gcccttcaaa 1500

gatgatatgt ggaggaatta aatataaagg aattggaggt ttttgctaaa 1550

gaaattaata ggaccaaaca atttggacat gtcattctgt agactagaat 1600

ttcttaaaag ggtgttactg agttataagc tcactaggct gtaaaaacaa 1650

aacaatgtag agttttattt attgaacaat gtagtcactt gaaggttttg 1700

tgtatatctt atgtggatta ccaatttaaa aatatatgta gttctgtgtc 1750

aaaaaacttc ttcactgaag ttatactgaa caaaatttta cctgtttttg 1800

gtcatttata aagtacttca agatgttgca gtatttcaca gttattatta 1850

tttaaaatta cttcaacttt gtgtttttaa atgttttgac gatttcaata 1900

caagataaaa aggatagtga atcattcttt acatgcaaac attttccagt 1950

tacttaactg atcagtttat tattgataca tcactccatt aatgtaaagt 2000

cataggtcat tattgcatat cagtaatctc ttggactttg ttaaatattt 2050

tactgtggta atatagagaa gaattaaagc aagaaaatct gaaaa 2095
```

<210> SEQ ID NO 36
<211> LENGTH: 331
<212> TYPE: PRT
<213> ORGANISM: Homo Sapien

<400> SEQUENCE: 36

```
Met Ala Ser Ala Leu Trp Thr Val Leu Pro Ser Arg Met Ser Leu
  1               5                  10                  15

Arg Ser Leu Lys Trp Ser Leu Leu Leu Leu Ser Leu Leu Ser Phe
                 20                  25                  30

Phe Val Met Trp Tyr Leu Ser Leu Pro His Tyr Asn Val Ile Glu
                 35                  40                  45

Arg Val Asn Trp Met Tyr Phe Tyr Glu Tyr Glu Pro Ile Tyr Arg
                 50                  55                  60

Gln Asp Phe His Phe Thr Leu Arg Glu His Ser Asn Cys Ser His
                 65                  70                  75

Gln Asn Pro Phe Leu Val Ile Leu Val Thr Ser His Pro Ser Asp
                 80                  85                  90

Val Lys Ala Arg Gln Ala Ile Arg Val Thr Trp Gly Glu Lys Lys
                 95                 100                 105

Ser Trp Trp Gly Tyr Glu Val Leu Thr Phe Phe Leu Leu Gly Gln
                110                 115                 120

Glu Ala Glu Lys Glu Asp Lys Met Leu Ala Leu Ser Leu Glu Asp
                125                 130                 135

Glu His Leu Leu Tyr Gly Asp Ile Ile Arg Gln Asp Phe Leu Asp
                140                 145                 150
```

-continued

```
Thr Tyr Asn Asn Leu Thr Leu Lys Thr Ile Met Ala Phe Arg Trp
                155                 160                 165

Val Thr Glu Phe Cys Pro Asn Ala Lys Tyr Val Met Lys Thr Asp
                170                 175                 180

Thr Asp Val Phe Ile Asn Thr Gly Asn Leu Val Lys Tyr Leu Leu
                185                 190                 195

Asn Leu Asn His Ser Glu Lys Phe Phe Thr Gly Tyr Pro Leu Ile
                200                 205                 210

Asp Asn Tyr Ser Tyr Arg Gly Phe Tyr Gln Lys Thr His Ile Ser
                215                 220                 225

Tyr Gln Glu Tyr Pro Phe Lys Val Phe Pro Pro Tyr Cys Ser Gly
                230                 235                 240

Leu Gly Tyr Ile Met Ser Arg Asp Leu Val Pro Arg Ile Tyr Glu
                245                 250                 255

Met Met Gly His Val Lys Pro Ile Lys Phe Glu Asp Val Tyr Val
                260                 265                 270

Gly Ile Cys Leu Asn Leu Leu Lys Val Asn Ile His Ile Pro Glu
                275                 280                 285

Asp Thr Asn Leu Phe Phe Leu Tyr Arg Ile His Leu Asp Val Cys
                290                 295                 300

Gln Leu Arg Arg Val Ile Ala Ala His Gly Phe Ser Ser Lys Glu
                305                 310                 315

Ile Ile Thr Phe Trp Gln Val Met Leu Arg Asn Thr Thr Cys His
                320                 325                 330

Tyr
```

<210> SEQ ID NO 37
<211> LENGTH: 2846
<212> TYPE: DNA
<213> ORGANISM: Homo Sapien

<400> SEQUENCE: 37

```
cgctcgggca ccagccgcgg caaggatgga gctgggttgc tggacgcagt           50

tggggctcac ttttcttcag ctccttctca tctcgtcctt gccaagagag          100

tacacagtca ttaatgaagc ctgccctgga gcagagtgga atatcatgtg          150

tcgggagtgc tgtgaatatg atcagattga gtgcgtctgc cccggaaaga          200

gggaagtcgt gggttatacc atcccttgct gcaggaatga ggagaatgag          250

tgtgactcct gcctgatcca cccaggttgt accatctttg aaaactgcaa          300

gagctgccga aatggctcat ggggggtac cttggatgac ttctatgtga            350

aggggttcta ctgtgcagag tgccgagcag gctggtacgg aggagactgc          400

atgcgatgtg gccaggttct gcgagcccca aagggtcaga ttttgttgga          450

aagctatccc ctaaatgctc actgtgaatg gaccattcat gctaaacctg          500

ggtttgtcat ccaactaaga tttgtcatgt tgagtctgga gtttgactac          550

atgtgccagt atgactatgt tgaggttcgt gatggagaca accgcgatgg          600

ccagatcatc aagcgtgtct gtggcaacga gcggccagct cctatccaga          650

gcataggatc ctcactccac gtcctcttcc actccgatgg ctccaagaat          700

tttgacggtt tccatgccat ttatgaggag atcacagcat gctcctcatc          750

cccttgtttc catgacggca cgtgcgtcct tgacaaggct ggatcttaca          800

agtgtgcctg cttggcaggc tatactgggc agcgctgtga aaatctcctt          850
```

-continued

```
gaagaaagaa actgctcaga ccctgggggc ccagtcaatg ggtaccagaa        900
aataacaggg ggccctgggc ttatcaacgg acgccatgct aaaattggca        950
ccgtggtgtc tttcttttgt aacaactcct atgttcttag tggcaatgag       1000
aaaagaactt gccagcagaa tggagagtgg tcagggaaac agcccatctg       1050
cataaaagcc tgccgagaac caaagatttc agacctggtg agaaggagag       1100
ttcttccgat gcaggttcag tcaagggaga caccattaca ccagctatac       1150
tcagcggcct tcagcaagca gaaactgcag agtgccccta ccaagaagcc       1200
agcccttccc tttggagatc tgcccatggg ataccaacat ctgcataccc       1250
agctccagta tgagtgcatc tcacccttct accgccgcct gggcagcagc       1300
aggaggacat gtctgaggac tgggaagtgg agtgggcggg caccatcctg       1350
catccctatc tgcgggaaaa ttgagaacat cactgctcca aagacccaag       1400
ggttgcgctg gccgtggcag gcagccatct acaggaggac cagcggggtg       1450
catgacggca gcctacacaa gggagcgtgg ttcctagtct gcagcggtgc       1500
cctggtgaat gagcgcactg tggtggtggc tgcccactgt gttactgacc       1550
tggggaaggt caccatgatc aagacagcag acctgaaagt tgttttgggg       1600
aaattctacc gggatgatga ccgggatgag aagaccatcc agagcctaca       1650
gatttctgct atcattctgc atcccaacta tgaccccatc ctgcttgatg       1700
ctgacatcgc catcctgaag ctcctagaca aggcccgtat cagcacccga       1750
gtccagccca tctgcctcgc tgccagtcgg gatctcagca cttccttcca       1800
ggagtcccac atcactgtgg ctggctggaa tgtcctggca gacgtgagga       1850
gccctggctt caagaacgac acactgcgct ctggggtggt cagtgtggtg       1900
gactcgctgc tgtgtgagga gcagcatgag gaccatggca tcccagtgag       1950
tgtcactgat aacatgttct gtgccagctg ggaacccact gccccttctg       2000
atatctgcac tgcagagaca ggaggcatcg cggctgtgtc cttcccggga       2050
cgagcatctc ctgagccacg ctggcatctg atgggactgg tcagctggag       2100
ctatgataaa acatgcagcc acaggctctc cactgccttc accaaggtgc       2150
tgccttttaa agactggatt gaaagaaata tgaaatgaac catgctcatg       2200
cactccttga gaagtgtttc tgtatatccg tctgtacgtg tgtcattgcg       2250
tgaagcagtg tgggcctgaa gtgtgatttg gcctgtgaac ttggctgtgc       2300
cagggcttct gacttcaggg acaaaactca gtgaagggtg agtagacctc       2350
cattgctggt aggctgatgc cgcgtccact actaggacag ccaattggaa       2400
gatgccaggg cttgcaagaa gtaagtttct tcaaagaaga ccatatacaa       2450
aacctctcca ctccactgac ctggtggtct tccccaactt tcagttatac       2500
gaatgccatc agcttgacca gggaagatct gggcttcatg aggccccttt       2550
tgaggctctc aagttctaga gagctgcctg tgggacagcc cagggcagca       2600
gagctgggat gtggtgcatg cctttgtgta catggccaca gtacagtctg       2650
gtccttttcc ttccccatct cttgtacaca ttttaataaa ataagggttg       2700
gcttctgaac tacaaaaaaa aaaaaaaaaa aaaaaaaaaa aaaaaaaaaa       2750
aaaaaaaaaa aaaaaaaaaa aaaaaaaaaa aaaaaaaaaa aaaaaaaaaa       2800
```

-continued aaaaaaaaaa aaaaaaaaaa aaaaaaaaaa aaaaaaaaaa aaaaaa 2846

<210> SEQ ID NO 38
<211> LENGTH: 720
<212> TYPE: PRT
<213> ORGANISM: Homo Sapien

<400> SEQUENCE: 38

Met Glu Leu Gly Cys Trp Thr Gln Leu Gly Leu Thr Phe Leu Gln
1 5 10 15

Leu Leu Leu Ile Ser Ser Leu Pro Arg Glu Tyr Thr Val Ile Asn
20 25 30

Glu Ala Cys Pro Gly Ala Glu Trp Asn Ile Met Cys Arg Glu Cys
35 40 45

Cys Glu Tyr Asp Gln Ile Glu Cys Val Cys Pro Gly Lys Arg Glu
50 55 60

Val Val Gly Tyr Thr Ile Pro Cys Cys Arg Asn Glu Glu Asn Glu
65 70 75

Cys Asp Ser Cys Leu Ile His Pro Gly Cys Thr Ile Phe Glu Asn
80 85 90

Cys Lys Ser Cys Arg Asn Gly Ser Trp Gly Gly Thr Leu Asp Asp
95 100 105

Phe Tyr Val Lys Gly Phe Tyr Cys Ala Glu Cys Arg Ala Gly Trp
110 115 120

Tyr Gly Gly Asp Cys Met Arg Cys Gly Gln Val Leu Arg Ala Pro
125 130 135

Lys Gly Gln Ile Leu Leu Glu Ser Tyr Pro Leu Asn Ala His Cys
140 145 150

Glu Trp Thr Ile His Ala Lys Pro Gly Phe Val Ile Gln Leu Arg
155 160 165

Phe Val Met Leu Ser Leu Glu Phe Asp Tyr Met Cys Gln Tyr Asp
170 175 180

Tyr Val Glu Val Arg Asp Gly Asp Asn Arg Asp Gly Gln Ile Ile
185 190 195

Lys Arg Val Cys Gly Asn Glu Arg Pro Ala Pro Ile Gln Ser Ile
200 205 210

Gly Ser Ser Leu His Val Leu Phe His Ser Asp Gly Ser Lys Asn
215 220 225

Phe Asp Gly Phe His Ala Ile Tyr Glu Glu Ile Thr Ala Cys Ser
230 235 240

Ser Ser Pro Cys Phe His Asp Gly Thr Cys Val Leu Asp Lys Ala
245 250 255

Gly Ser Tyr Lys Cys Ala Cys Leu Ala Gly Tyr Thr Gly Gln Arg
260 265 270

Cys Glu Asn Leu Leu Glu Glu Arg Asn Cys Ser Asp Pro Gly Gly
275 280 285

Pro Val Asn Gly Tyr Gln Lys Ile Thr Gly Gly Pro Gly Leu Ile
290 295 300

Asn Gly Arg His Ala Lys Ile Gly Thr Val Val Ser Phe Phe Cys
305 310 315

Asn Asn Ser Tyr Val Leu Ser Gly Asn Glu Lys Arg Thr Cys Gln
320 325 330

Gln Asn Gly Glu Trp Ser Gly Lys Gln Pro Ile Cys Ile Lys Ala
335 340 345

-continued

```
Cys Arg Glu Pro Lys Ile Ser Asp Leu Val Arg Arg Arg Val Leu
                350                 355                 360

Pro Met Gln Val Gln Ser Arg Glu Thr Pro Leu His Gln Leu Tyr
                365                 370                 375

Ser Ala Ala Phe Ser Lys Gln Lys Leu Gln Ser Ala Pro Thr Lys
                380                 385                 390

Lys Pro Ala Leu Pro Phe Gly Asp Leu Pro Met Gly Tyr Gln His
                395                 400                 405

Leu His Thr Gln Leu Gln Tyr Glu Cys Ile Ser Pro Phe Tyr Arg
                410                 415                 420

Arg Leu Gly Ser Ser Arg Arg Thr Cys Leu Arg Thr Gly Lys Trp
                425                 430                 435

Ser Gly Arg Ala Pro Ser Cys Ile Pro Ile Cys Gly Lys Ile Glu
                440                 445                 450

Asn Ile Thr Ala Pro Lys Thr Gln Gly Leu Arg Trp Pro Trp Gln
                455                 460                 465

Ala Ala Ile Tyr Arg Arg Thr Ser Gly Val His Asp Gly Ser Leu
                470                 475                 480

His Lys Gly Ala Trp Phe Leu Val Cys Ser Gly Ala Leu Val Asn
                485                 490                 495

Glu Arg Thr Val Val Val Ala Ala His Cys Val Thr Asp Leu Gly
                500                 505                 510

Lys Val Thr Met Ile Lys Thr Ala Asp Leu Lys Val Val Leu Gly
                515                 520                 525

Lys Phe Tyr Arg Asp Asp Asp Arg Asp Glu Lys Thr Ile Gln Ser
                530                 535                 540

Leu Gln Ile Ser Ala Ile Ile Leu His Pro Asn Tyr Asp Pro Ile
                545                 550                 555

Leu Leu Asp Ala Asp Ile Ala Ile Leu Lys Leu Leu Asp Lys Ala
                560                 565                 570

Arg Ile Ser Thr Arg Val Gln Pro Ile Cys Leu Ala Ala Ser Arg
                575                 580                 585

Asp Leu Ser Thr Ser Phe Gln Glu Ser His Ile Thr Val Ala Gly
                590                 595                 600

Trp Asn Val Leu Ala Asp Val Arg Ser Pro Gly Phe Lys Asn Asp
                605                 610                 615

Thr Leu Arg Ser Gly Val Val Ser Val Val Asp Ser Leu Leu Cys
                620                 625                 630

Glu Glu Gln His Glu Asp His Gly Ile Pro Val Ser Val Thr Asp
                635                 640                 645

Asn Met Phe Cys Ala Ser Trp Glu Pro Thr Ala Pro Ser Asp Ile
                650                 655                 660

Cys Thr Ala Glu Thr Gly Gly Ile Ala Ala Val Ser Phe Pro Gly
                665                 670                 675

Arg Ala Ser Pro Glu Pro Arg Trp His Leu Met Gly Leu Val Ser
                680                 685                 690

Trp Ser Tyr Asp Lys Thr Cys Ser His Arg Leu Ser Thr Ala Phe
                695                 700                 705

Thr Lys Val Leu Pro Phe Lys Asp Trp Ile Glu Arg Asn Met Lys
                710                 715                 720
```

<210> SEQ ID NO 39
<211> LENGTH: 2571
<212> TYPE: DNA

-continued

<213> ORGANISM: Homo Sapien

<400> SEQUENCE: 39

```
ggttcctaca tcctctcatc tgagaatcag agagcataat cttcttacgg        50
gcccgtgatt tattaacgtg gcttaatctg aaggttctca gtcaaattct       100
ttgtgatcta ctgattgtgg gggcatggca aggtttgctt aaaggagctt       150
ggctggtttg ggcccttgta gctgacagaa ggtggccagg gagaatgcag       200
cacactgctc ggagaatgaa ggcgcttctg ttgctggtct tgccttggct       250
cagtcctgct aactacattg acaatgtggg caacctgcac ttcctgtatt       300
cagaactctg taaaggtgcc tcccactacg gcctgaccaa agataggaag       350
aggcgctcac aagatggctg tccagacggc tgtgcgagcc tcacagccac       400
ggctccctcc ccagaggttt ctgcagctgc caccatctcc ttaatgacag       450
acgagcctgg cctagacaac cctgcctacg tgtcctcggc agaggacggg       500
cagccagcaa tcagcccagt ggactctggc cggagcaacc gaactagggc       550
acggcccttt gagagatcca ctattagaag cagatcattt aaaaaaataa       600
atcgagcttt gagtgttctt cgaaggacaa agagcgggag tgcagttgcc       650
aaccatgccg accagggcag ggaaaattct gaaaacacca ctgcccctga       700
agtctttcca aggttgtacc acctgattcc agatggtgaa attaccagca       750
tcaagatcaa tcgagtagat cccagtgaaa gcctctctat taggctggtg       800
ggaggtagcg aaaccccact ggtccatatc attatccaac acatttatcg       850
tgatggggtg atcgccagag acggccggct actgccagga gacatcattc       900
taaaggtcaa cgggatggac atcagcaatg tccctcacaa ctacgctgtg       950
cgtctcctgc ggcagccctg ccaggtgctg tggctgactg tgatgcgtga      1000
acagaagttc cgcagcagga acaatggaca ggccccggat gcctacagac      1050
cccgagatga cagctttcat gtgattctca acaaaagtag ccccgaggag      1100
cagcttggaa taaaactggt gcgcaaggtg gatgagcctg ggtttttcat      1150
cttcaatgtg ctggatggcg gtgtggcata tcgacatggt cagcttgagg      1200
agaatgaccg tgtgttagcc atcaatggac atgatcttcg atatggcagc      1250
ccagaaagtg cggctcatct gattcaggcc agtgaaagac gtgttcacct      1300
cgtcgtgtcc cgccaggttc ggcagcggag ccctgacatc tttcaggaag      1350
ccggctggaa cagcaatggc agctggtccc cagggccagg ggagaggagc      1400
aacactccca agcccctcca tcctacaatt acttgtcatg agaaggtggt      1450
aaatatccaa aaagaccccg gtgaatctct cggcatgacc gtcgcagggg      1500
gagcatcaca tagagaatgg gatttgccta tctatgtcat cagtgttgag      1550
cccggaggag tcataagcag agatggaaga ataaaaacag gtgacatttt      1600
gttgaatgtg gatggggtcg aactgacaga ggtcagccgg agtgaggcag      1650
tggcattatt gaaaagaaca tcatcctcga tagtactcaa agctttggaa      1700
gtcaaagagt atgagcccca ggaagactgc agcagcccag cagccctgga      1750
ctccaaccac aacatggccc cacccagtga ctggtcccca tcctgggtca      1800
tgtggctgga attaccacgg tgcttgtata actgtaaaga tattgtatta      1850
cgaagaaaca cagctggaag tctgggcttc tgcattgtag gaggttatga      1900
```

-continued

```
agaatacaat ggaaacaaac ctttttttcat caaatccatt gttgaaggaa    1950

caccagcata caatgatgga agaattagat gtggtgatat tcttcttgct    2000

gtcaatggta gaagtacatc aggaatgata catgcttgct tggcaagact    2050

gctgaaagaa cttaaaggaa gaattactct aactattgtt tcttggcctg    2100

gcactttttt atagaatcaa tgatgggtca gaggaaaaca gaaaaatcac    2150

aaataggcta agaagttgaa acactatatt tatcttgtca gtttttatat    2200

ttaaagaaag aatacattgt aaaaatgtca ggaaaagtat gatcatctaa    2250

tgaaagccag ttacacctca gaaaatatga ttccaaaaaa attaaaacta    2300

ctagtttttt ttcagtgtgg aggatttctc attactctac aacattgttt    2350

atatttttc tattcaataa aaagccctaa aacaactaaa atgattgatt    2400

tgtatacccc actgaattca agctgattta aatttaaaat ttggtatatg    2450

ctgaagtctg ccaagggtac attatggcca tttttaattt acagctaaaa    2500

tattttttaa aatgcattgc tgagaaacgt tgctttcatc aaacaagaat    2550

aaatattttt cagaagttaa a                                    2571
```

```
<210> SEQ ID NO 40
<211> LENGTH: 632
<212> TYPE: PRT
<213> ORGANISM: Homo Sapien

<400> SEQUENCE: 40

Met Lys Ala Leu Leu Leu Leu Val Leu Pro Trp Leu Ser Pro Ala
  1               5                  10                  15

Asn Tyr Ile Asp Asn Val Gly Asn Leu His Phe Leu Tyr Ser Glu
                 20                  25                  30

Leu Cys Lys Gly Ala Ser His Tyr Gly Leu Thr Lys Asp Arg Lys
                 35                  40                  45

Arg Arg Ser Gln Asp Gly Cys Pro Asp Gly Cys Ala Ser Leu Thr
                 50                  55                  60

Ala Thr Ala Pro Ser Pro Glu Val Ser Ala Ala Ala Thr Ile Ser
                 65                  70                  75

Leu Met Thr Asp Glu Pro Gly Leu Asp Asn Pro Ala Tyr Val Ser
                 80                  85                  90

Ser Ala Glu Asp Gly Gln Pro Ala Ile Ser Pro Val Asp Ser Gly
                 95                 100                 105

Arg Ser Asn Arg Thr Arg Ala Arg Pro Phe Glu Arg Ser Thr Ile
                110                 115                 120

Arg Ser Arg Ser Phe Lys Lys Ile Asn Arg Ala Leu Ser Val Leu
                125                 130                 135

Arg Arg Thr Lys Ser Gly Ser Ala Val Ala Asn His Ala Asp Gln
                140                 145                 150

Gly Arg Glu Asn Ser Glu Asn Thr Thr Ala Pro Glu Val Phe Pro
                155                 160                 165

Arg Leu Tyr His Leu Ile Pro Asp Gly Glu Ile Thr Ser Ile Lys
                170                 175                 180

Ile Asn Arg Val Asp Pro Ser Glu Ser Leu Ser Ile Arg Leu Val
                185                 190                 195

Gly Gly Ser Glu Thr Pro Leu Val His Ile Ile Ile Gln His Ile
                200                 205                 210
```

-continued

```
Tyr Arg Asp Gly Val Ile Ala Arg Asp Gly Arg Leu Leu Pro Gly
                215                 220                 225

Asp Ile Ile Leu Lys Val Asn Gly Met Asp Ile Ser Asn Val Pro
                230                 235                 240

His Asn Tyr Ala Val Arg Leu Leu Arg Gln Pro Cys Gln Val Leu
                245                 250                 255

Trp Leu Thr Val Met Arg Glu Gln Lys Phe Arg Ser Arg Asn Asn
                260                 265                 270

Gly Gln Ala Pro Asp Ala Tyr Arg Pro Arg Asp Asp Ser Phe His
                275                 280                 285

Val Ile Leu Asn Lys Ser Ser Pro Glu Glu Gln Leu Gly Ile Lys
                290                 295                 300

Leu Val Arg Lys Val Asp Glu Pro Gly Val Phe Ile Phe Asn Val
                305                 310                 315

Leu Asp Gly Gly Val Ala Tyr Arg His Gly Gln Leu Glu Glu Asn
                320                 325                 330

Asp Arg Val Leu Ala Ile Asn Gly His Asp Leu Arg Tyr Gly Ser
                335                 340                 345

Pro Glu Ser Ala Ala His Leu Ile Gln Ala Ser Glu Arg Arg Val
                350                 355                 360

His Leu Val Val Ser Arg Gln Val Arg Gln Arg Ser Pro Asp Ile
                365                 370                 375

Phe Gln Glu Ala Gly Trp Asn Ser Asn Gly Ser Trp Ser Pro Gly
                380                 385                 390

Pro Gly Glu Arg Ser Asn Thr Pro Lys Pro Leu His Pro Thr Ile
                395                 400                 405

Thr Cys His Glu Lys Val Val Asn Ile Gln Lys Asp Pro Gly Glu
                410                 415                 420

Ser Leu Gly Met Thr Val Ala Gly Gly Ala Ser His Arg Glu Trp
                425                 430                 435

Asp Leu Pro Ile Tyr Val Ile Ser Val Glu Pro Gly Gly Val Ile
                440                 445                 450

Ser Arg Asp Gly Arg Ile Lys Thr Gly Asp Ile Leu Leu Asn Val
                455                 460                 465

Asp Gly Val Glu Leu Thr Glu Val Ser Arg Ser Glu Ala Val Ala
                470                 475                 480

Leu Leu Lys Arg Thr Ser Ser Ser Ile Val Leu Lys Ala Leu Glu
                485                 490                 495

Val Lys Glu Tyr Glu Pro Gln Glu Asp Cys Ser Ser Pro Ala Ala
                500                 505                 510

Leu Asp Ser Asn His Asn Met Ala Pro Pro Ser Asp Trp Ser Pro
                515                 520                 525

Ser Trp Val Met Trp Leu Glu Leu Pro Arg Cys Leu Tyr Asn Cys
                530                 535                 540

Lys Asp Ile Val Leu Arg Arg Asn Thr Ala Gly Ser Leu Gly Phe
                545                 550                 555

Cys Ile Val Gly Gly Tyr Glu Glu Tyr Asn Gly Asn Lys Pro Phe
                560                 565                 570

Phe Ile Lys Ser Ile Val Glu Gly Thr Pro Ala Tyr Asn Asp Gly
                575                 580                 585

Arg Ile Arg Cys Gly Asp Ile Leu Leu Ala Val Asn Gly Arg Ser
                590                 595                 600

Thr Ser Gly Met Ile His Ala Cys Leu Ala Arg Leu Leu Lys Glu
```

-continued

```
             605                 610                 615

Leu Lys Gly Arg Ile Thr Leu Thr Ile Val Ser Trp Pro Gly Thr
             620                 625                 630

Phe Leu


<210> SEQ ID NO 41
<211> LENGTH: 1964
<212> TYPE: DNA
<213> ORGANISM: Homo Sapien

<400> SEQUENCE: 41

accaggcatt gtatcttcag ttgtcatcaa gttcgcaatc agattggaaa        50

agctcaactt gaagctttct tgcctgcagt gaagcagaga gatagatatt       100

attcacgtaa taaaaaacat gggcttcaac ctgactttcc acctttccta       150

caaattccga ttactgttgc tgttgacttt gtgcctgaca gtggttgggt       200

gggccaccag taactacttc gtgggtgcca ttcaagagat tcctaaagca       250

aaggagttca tggctaattt ccataagacc ctcattttgg ggaagggaaa       300

aactctgact aatgaagcat ccacgaagaa ggtagaactt gacaactgtc       350

cttctgtgtc tccttacctc agaggccaga gcaagctcat tttcaaacca       400

gatctcactt tggaagaggt acaggcagaa aatcccaaag tgtccagagg       450

ccggtatcgc cctcaggaat gtaaagcttt acagagggtc gccatcctcg       500

ttccccaccg gaacagagag aaacacctga tgtacctgct ggaacatctg       550

catcccttcc tgcagaggca gcagctggat tatggcatct acgtcatcca       600

ccaggctgaa ggtaaaaagt ttaatcgagc caaactcttg aatgtgggct       650

atctagaagc cctcaaggaa gaaaattggg actgctttat attccacgat       700

gtggacctgg tacccgagaa tgactttaac ctttacaagt gtgaggagca       750

tcccaagcat ctggtggttg gcaggaacag cactgggtac aggttacgtt       800

acagtggata ttttgggggt gttactgccc taagcagaga gcagtttttc       850

aaggtgaatg gattctctaa caactactgg ggatggggag gcgaagacga       900

tgacctcaga ctcagggttg agctccaaag aatgaaaatt tcccggcccc       950

tgcctgaagt gggtaaatat acaatggtct tccacactag agacaaaggc      1000

aatgaggtga acgcagaacg gatgaagctc ttacaccaag tgtcacgagt      1050

ctggagaaca gatgggttga gtagttgttc ttataaatta gtatctgtgg      1100

aacacaatcc tttatatatc aacatcacag tggatttctg gtttggtgca      1150

tgaccctgga tcttttggtg atgtttggaa gaactgattc tttgtttgca      1200

ataattttgg cctagagact tcaaatagta gcacacatta agaacctgtt      1250

acagctcatt gttgagctga atttttcctt tttgtatttt cttagcagag      1300

ctcctggtga tgtagagtat aaaacagttg taacaagaca gctttcttag      1350

tcattttgat catgagggtt aaatattgta atatggatac ttgaaggact      1400

ttatataaaa ggatgactca aaggataaaa tgaacgctat ttgaggactc      1450

tggttgaagg agatttattt aaatttgaag taatatatta tgggataaaa      1500

ggccacagga aataagactg ctgaatgtct gagagaacca gagttgttct      1550

cgtccaaggt agaaaggtac gaagatacaa tactgttatt catttatcct      1600
```

-continued

```
gtacaatcat ctgtgaagtg gtggtgtcag gtgagaaggc gtccacaaaa             1650

gaggggagaa aaggcgacga atcaggacac agtgaacttg ggaatgaaga             1700

ggtagcagga gggtggagtg tcggctgcaa aggcagcagt agctgagctg             1750

gttgcaggtg ctgatagcct tcaggggagg acctgcccag gtatgccttc             1800

cagtgatgcc caccagagaa tacattctct attagttttt aaagagtttt             1850

tgtaaaatga ttttgtacaa gtaggatatg aattagcagt ttacaagttt             1900

acatattaac taataataaa tatgtctatc aaatacctct gtagtaaaat             1950

gtgaaaaagc aaaa                                                    1964


<210> SEQ ID NO 42
<211> LENGTH: 344
<212> TYPE: PRT
<213> ORGANISM: Homo Sapien

<400> SEQUENCE: 42

Met Gly Phe Asn Leu Thr Phe His Leu Ser Tyr Lys Phe Arg Leu
  1               5                  10                  15

Leu Leu Leu Leu Thr Leu Cys Leu Thr Val Val Gly Trp Ala Thr
                 20                  25                  30

Ser Asn Tyr Phe Val Gly Ala Ile Gln Glu Ile Pro Lys Ala Lys
                 35                  40                  45

Glu Phe Met Ala Asn Phe His Lys Thr Leu Ile Leu Gly Lys Gly
                 50                  55                  60

Lys Thr Leu Thr Asn Glu Ala Ser Thr Lys Lys Val Glu Leu Asp
                 65                  70                  75

Asn Cys Pro Ser Val Ser Pro Tyr Leu Arg Gly Gln Ser Lys Leu
                 80                  85                  90

Ile Phe Lys Pro Asp Leu Thr Leu Glu Glu Val Gln Ala Glu Asn
                 95                 100                 105

Pro Lys Val Ser Arg Gly Arg Tyr Arg Pro Gln Glu Cys Lys Ala
                110                 115                 120

Leu Gln Arg Val Ala Ile Leu Val Pro His Arg Asn Arg Glu Lys
                125                 130                 135

His Leu Met Tyr Leu Leu Glu His Leu His Pro Phe Leu Gln Arg
                140                 145                 150

Gln Gln Leu Asp Tyr Gly Ile Tyr Val Ile His Gln Ala Glu Gly
                155                 160                 165

Lys Lys Phe Asn Arg Ala Lys Leu Leu Asn Val Gly Tyr Leu Glu
                170                 175                 180

Ala Leu Lys Glu Glu Asn Trp Asp Cys Phe Ile Phe His Asp Val
                185                 190                 195

Asp Leu Val Pro Glu Asn Asp Phe Asn Leu Tyr Lys Cys Glu Glu
                200                 205                 210

His Pro Lys His Leu Val Val Gly Arg Asn Ser Thr Gly Tyr Arg
                215                 220                 225

Leu Arg Tyr Ser Gly Tyr Phe Gly Gly Val Thr Ala Leu Ser Arg
                230                 235                 240

Glu Gln Phe Phe Lys Val Asn Gly Phe Ser Asn Asn Tyr Trp Gly
                245                 250                 255

Trp Gly Gly Glu Asp Asp Asp Leu Arg Leu Arg Val Glu Leu Gln
                260                 265                 270

Arg Met Lys Ile Ser Arg Pro Leu Pro Glu Val Gly Lys Tyr Thr
```

-continued

```
            275                 280                 285

Met Val Phe His Thr Arg Asp Lys Gly Asn Glu Val Asn Ala Glu
                290                 295                 300

Arg Met Lys Leu Leu His Gln Val Ser Arg Val Trp Arg Thr Asp
                305                 310                 315

Gly Leu Ser Ser Cys Ser Tyr Lys Leu Val Ser Val Glu His Asn
                320                 325                 330

Pro Leu Tyr Ile Asn Ile Thr Val Asp Phe Trp Phe Gly Ala
                335                 340


<210> SEQ ID NO 43
<211> LENGTH: 485
<212> TYPE: DNA
<213> ORGANISM: Homo Sapien

<400> SEQUENCE: 43

gctcaagacc cagcagtggg acagccagac agacggcacg atggcactga        50

gctcccagat ctgggccgct tgcctcctgc tcctcctcct cctcgccagc       100

ctgaccagtg gctctgtttt cccacaacag acgggacaac ttgcagagct       150

gcaaccccag gacagagctg gagccagggc cagctggatg cccatgttcc       200

agaggcgaag gaggcgagac acccacttcc ccatctgcat tttctgctgc       250

ggctgctgtc atcgatcaaa gtgtgggatg tgctgcaaga cgtagaacct       300

acctgccctg cccccgtccc ctcccttcct tatttattcc tgctgcccca       350

gaacataggt cttggaataa aatggctggt tcttttgttt tccaaaaaaa       400

aaaaaaaaaa aaaaaaaaaa aaaaaaaaaa aaaaaaaaaa aaaaaaaaaa       450

aaaaaaaaaa aaaaaaaaaa aaaaaaaaaa aaaaa                       485


<210> SEQ ID NO 44
<211> LENGTH: 84
<212> TYPE: PRT
<213> ORGANISM: Homo Sapien

<400> SEQUENCE: 44

Met Ala Leu Ser Ser Gln Ile Trp Ala Ala Cys Leu Leu Leu Leu
  1               5                  10                  15

Leu Leu Leu Ala Ser Leu Thr Ser Gly Ser Val Phe Pro Gln Gln
                 20                  25                  30

Thr Gly Gln Leu Ala Glu Leu Gln Pro Gln Asp Arg Ala Gly Ala
                 35                  40                  45

Arg Ala Ser Trp Met Pro Met Phe Gln Arg Arg Arg Arg Arg Asp
                 50                  55                  60

Thr His Phe Pro Ile Cys Ile Phe Cys Cys Gly Cys Cys His Arg
                 65                  70                  75

Ser Lys Cys Gly Met Cys Cys Lys Thr
                 80


<210> SEQ ID NO 45
<211> LENGTH: 1076
<212> TYPE: DNA
<213> ORGANISM: Homo Sapien

<400> SEQUENCE: 45

gtggcttcat ttcagtggct gacttccaga gagcaatatg gctggttccc        50

caacatgcct caccctcatc tatatccttt ggcagctcac agggtcagca       100
```

-continued

```
gcctctggac ccgtgaaaga gctggtcggt tccgttggtg gggccgtgac          150

tttccccctg aagtccaaag taaagcaagt tgactctatt gtctggacct          200

tcaacacaac ccctcttgtc accatacagc cagaaggggg cactatcata          250

gtgacccaaa atcgtaatag ggagagagta gacttcccag atggaggcta          300

ctccctgaag ctcagcaaac tgaagaagaa tgactcaggg atctactatg          350

tggggatata cagctcatca ctccagcagc cctccaccca ggagtacgtg          400

ctgcatgtct acgagcacct gtcaaagcct aaagtcacca tgggtctgca          450

gagcaataag aatggcacct gtgtgaccaa tctgacatgc tgcatggaac          500

atggggaaga ggatgtgatt tatacctgga aggccctggg gcaagcagcc          550

aatgagtccc ataatgggtc catcctcccc atctcctgga gatggggaga          600

aagtgatatg accttcatct gcgttgccag gaaccctgtc agcagaaact          650

tctcaagccc catccttgcc aggaagctct gtgaaggtgc tgctgatgac          700

ccagattcct ccatggtcct cctgtgtctc ctgttggtgc cctcctgct          750

cagtctcttt gtactggggc tatttctttg gtttctgaag agagagagac          800

aagaagagta cattgaagag aagaagagag tggacatttg tcgggaaact          850

cctaacatat gcccccattc tggagagaac acagagtacg acacaatccc          900

tcacactaat agaacaatcc taaaggaaga tccagcaaat acggtttact          950

ccactgtgga aataccgaaa aagatggaaa atccccactc actgctcacg         1000

atgccagaca caccaaggct atttgcctat gagaatgtta tctagacagc         1050

agtgcactcc cctaagtctc tgctca                                   1076
```

```
<210> SEQ ID NO 46
<211> LENGTH: 335
<212> TYPE: PRT
<213> ORGANISM: Homo Sapien

<400> SEQUENCE: 46

Met Ala Gly Ser Pro Thr Cys Leu Thr Leu Ile Tyr Ile Leu Trp
1               5                   10                  15

Gln Leu Thr Gly Ser Ala Ala Ser Gly Pro Val Lys Glu Leu Val
                20                  25                  30

Gly Ser Val Gly Gly Ala Val Thr Phe Pro Leu Lys Ser Lys Val
                35                  40                  45

Lys Gln Val Asp Ser Ile Val Trp Thr Phe Asn Thr Thr Pro Leu
                50                  55                  60

Val Thr Ile Gln Pro Glu Gly Gly Thr Ile Ile Val Thr Gln Asn
                65                  70                  75

Arg Asn Arg Glu Arg Val Asp Phe Pro Asp Gly Gly Tyr Ser Leu
                80                  85                  90

Lys Leu Ser Lys Leu Lys Lys Asn Asp Ser Gly Ile Tyr Tyr Val
                95                  100                 105

Gly Ile Tyr Ser Ser Ser Leu Gln Gln Pro Ser Thr Gln Glu Tyr
                110                 115                 120

Val Leu His Val Tyr Glu His Leu Ser Lys Pro Lys Val Thr Met
                125                 130                 135

Gly Leu Gln Ser Asn Lys Asn Gly Thr Cys Val Thr Asn Leu Thr
                140                 145                 150
```

-continued

```
Cys Cys Met Glu His Gly Glu Glu Asp Val Ile Tyr Thr Trp Lys
                155                 160                 165

Ala Leu Gly Gln Ala Ala Asn Glu Ser His Asn Gly Ser Ile Leu
                170                 175                 180

Pro Ile Ser Trp Arg Trp Gly Glu Ser Asp Met Thr Phe Ile Cys
                185                 190                 195

Val Ala Arg Asn Pro Val Ser Arg Asn Phe Ser Ser Pro Ile Leu
                200                 205                 210

Ala Arg Lys Leu Cys Glu Gly Ala Ala Asp Asp Pro Asp Ser Ser
                215                 220                 225

Met Val Leu Leu Cys Leu Leu Leu Val Pro Leu Leu Leu Ser Leu
                230                 235                 240

Phe Val Leu Gly Leu Phe Leu Trp Phe Leu Lys Arg Glu Arg Gln
                245                 250                 255

Glu Glu Tyr Ile Glu Glu Lys Lys Arg Val Asp Ile Cys Arg Glu
                260                 265                 270

Thr Pro Asn Ile Cys Pro His Ser Gly Glu Asn Thr Glu Tyr Asp
                275                 280                 285

Thr Ile Pro His Thr Asn Arg Thr Ile Leu Lys Glu Asp Pro Ala
                290                 295                 300

Asn Thr Val Tyr Ser Thr Val Glu Ile Pro Lys Lys Met Glu Asn
                305                 310                 315

Pro His Ser Leu Leu Thr Met Pro Asp Thr Pro Arg Leu Phe Ala
                320                 325                 330

Tyr Glu Asn Val Ile
                335
```

<210> SEQ ID NO 47
<211> LENGTH: 766
<212> TYPE: DNA
<213> ORGANISM: Homo Sapien

<400> SEQUENCE: 47

```
ggctcgagcg tttctgagcc aggggtgacc atgacctgct gcgaaggatg      50

gacatcctgc aatggattca gcctgctggt tctactgctg ttaggagtag     100

ttctcaatgc gatacctcta attgtcagct tagttgagga agaccaattt     150

tctcaaaacc ccatctcttg ctttgagtgg tggttcccag gaattatagg     200

agcaggtctg atggccattc cagcaacaac aatgtccttg acagcaagaa     250

aaagagcgtg ctgcaacaac agaactggaa tgtttctttc atcatttttc     300

agtgtgatca cagtcattgg tgctctgtat tgcatgctga tatccatcca     350

ggctctctta aaaggtcctc tcatgtgtaa ttctccaagc aacagtaatg     400

ccaattgtga attttcattg aaaaacatca gtgacattca tccagaatcc     450

ttcaacttgc agtggttttt caatgactct tgtgcacctc ctactggttt     500

caataaaccc accagtaacg acaccatggc gagtggctgg agagcatcta     550

gtttccactt cgattctgaa gaaaacaaac ataggcttat ccacttctca     600

gtatttttag gtctattgct tgttggaatt ctggaggtcc tgtttgggct     650

cagtcagata gtcatcggtt tccttggctg tctgtgtgga gtctctaagc     700

gaagaagtca aattgtgtag tttaatggga ataaaatgta agtatcagta     750

gtttgaaaaa aaaaaa                                          766
```

-continued

<210> SEQ ID NO 48
<211> LENGTH: 229
<212> TYPE: PRT
<213> ORGANISM: Homo Sapien

<400> SEQUENCE: 48

```
Met Thr Cys Cys Glu Gly Trp Thr Ser Cys Asn Gly Phe Ser Leu
  1               5                  10                  15

Leu Val Leu Leu Leu Leu Gly Val Val Leu Asn Ala Ile Pro Leu
                 20                  25                  30

Ile Val Ser Leu Val Glu Glu Asp Gln Phe Ser Gln Asn Pro Ile
                 35                  40                  45

Ser Cys Phe Glu Trp Trp Phe Pro Gly Ile Ile Gly Ala Gly Leu
                 50                  55                  60

Met Ala Ile Pro Ala Thr Thr Met Ser Leu Thr Ala Arg Lys Arg
                 65                  70                  75

Ala Cys Cys Asn Asn Arg Thr Gly Met Phe Leu Ser Ser Phe Phe
                 80                  85                  90

Ser Val Ile Thr Val Ile Gly Ala Leu Tyr Cys Met Leu Ile Ser
                 95                 100                 105

Ile Gln Ala Leu Leu Lys Gly Pro Leu Met Cys Asn Ser Pro Ser
                110                 115                 120

Asn Ser Asn Ala Asn Cys Glu Phe Ser Leu Lys Asn Ile Ser Asp
                125                 130                 135

Ile His Pro Glu Ser Phe Asn Leu Gln Trp Phe Phe Asn Asp Ser
                140                 145                 150

Cys Ala Pro Pro Thr Gly Phe Asn Lys Pro Thr Ser Asn Asp Thr
                155                 160                 165

Met Ala Ser Gly Trp Arg Ala Ser Ser Phe His Phe Asp Ser Glu
                170                 175                 180

Glu Asn Lys His Arg Leu Ile His Phe Ser Val Phe Leu Gly Leu
                185                 190                 195

Leu Leu Val Gly Ile Leu Glu Val Leu Phe Gly Leu Ser Gln Ile
                200                 205                 210

Val Ile Gly Phe Leu Gly Cys Leu Cys Gly Val Ser Lys Arg Arg
                215                 220                 225

Ser Gln Ile Val
```

<210> SEQ ID NO 49
<211> LENGTH: 636
<212> TYPE: DNA
<213> ORGANISM: Homo Sapien

<400> SEQUENCE: 49

```
atccgttctc tgcgctgcca gctcaggtga gccctcgcca aggtgacctc         50

gcaggacact ggtgaaggag cagtgaggaa cctgcagagt cacacagttg        100

ctgaccaatt gagctgtgag cctggagcag atccgtgggc tgcagacccc        150

cgccccagtg cctctccccc tgcagccctg cccctcgaac tgtgacatgg        200

agagagtgac cctggccctt ctcctactgg caggcctgac tgccttggaa        250

gccaatgacc catttgccaa taaagacgat cccttctact atgactggaa        300

aaacctgcag ctgagcggac tgatctgcgg agggctcctg gccattgctg        350

ggatcgcggc agttctgagt ggcaaatgca aatacaagag cagccagaag        400
```

-continued

```
cagcacagtc ctgtacctga gaaggccatc ccactcatca ctccaggctc      450

tgccactact tgctgagcac aggactggcc tccagggatg gcctgaagcc      500

taacactggc ccccagcacc tcctcccctg ggaggcctta tcctcaagga      550

aggacttctc tccaagggca ggctgttagg cccctttctg atcaggaggc      600

ttctttatga attaaactcg ccccaccacc ccctca                     636


<210> SEQ ID NO 50
<211> LENGTH: 89
<212> TYPE: PRT
<213> ORGANISM: Homo Sapien

<400> SEQUENCE: 50

Met Glu Arg Val Thr Leu Ala Leu Leu Leu Leu Ala Gly Leu Thr
  1               5                  10                  15

Ala Leu Glu Ala Asn Asp Pro Phe Ala Asn Lys Asp Asp Pro Phe
                 20                  25                  30

Tyr Tyr Asp Trp Lys Asn Leu Gln Leu Ser Gly Leu Ile Cys Gly
                 35                  40                  45

Gly Leu Leu Ala Ile Ala Gly Ile Ala Ala Val Leu Ser Gly Lys
                 50                  55                  60

Cys Lys Tyr Lys Ser Ser Gln Lys Gln His Ser Pro Val Pro Glu
                 65                  70                  75

Lys Ala Ile Pro Leu Ile Thr Pro Gly Ser Ala Thr Thr Cys
                 80                  85


<210> SEQ ID NO 51
<211> LENGTH: 1734
<212> TYPE: DNA
<213> ORGANISM: Homo Sapien

<400> SEQUENCE: 51

gtggactctg agaagcccag gcagttgagg acaggagaga gaaggctgca       50

gacccagagg gagggaggac agggagtcgg aaggaggagg acagaggagg      100

gcacagagac gcagagcaag ggcggcaagg aggagaccct ggtgggagga      150

agacactctg gagagagagg gggctgggca gagatgaagt tccaggggcc      200

cctggcctgc ctcctgctgg ccctctgcct gggcagtggg gaggctggcc      250

ccctgcagag cggagaggaa agcactggga caaatattgg ggaggccctt      300

ggacatggcc tgggagacgc cctgagcgaa ggggtgggaa aggccattgg      350

caaagaggcc ggaggggcag ctggctctaa agtcagtgag gcccttggcc      400

aagggaccag agaagcagtt ggcactggag tcaggcaggt tccaggcttt      450

ggcgcagcag atgctttggg caacagggtc ggggaagcag cccatgctct      500

gggaaacact gggcacgaga ttggcagaca ggcagaagat gtcattcgac      550

acggagcaga tgctgtccgc ggctcctggc agggggtgcc tggccacagt      600

ggtgcttggg aaacttctgg aggccatggc atctttggct ctcaaggtgg      650

ccttggaggc cagggccagg gcaatcctgg aggtctgggg actccgtggg      700

tccacggata ccccggaaac tcagcaggca gctttggaat gaatcctcag      750

ggagctccct ggggtcaagg aggcaatgga gggccaccaa actttgggac      800

caacactcag ggagctgtgg cccagcctgg ctatggttca gtgagagcca      850

gcaaccagaa tgaagggtgc acgaatcccc caccatctgg ctcaggtgga      900
```

-continued

```
ggctccagca actctggggg aggcagcggc tcacagtcgg gcagcagtgg            950
cagtggcagc aatggtgaca acaacaatgg cagcagcagt ggtggcagca           1000
gcagtggcag cagcagtggc agcagcagtg gcggcagcag tggcggcagc           1050
agtggtggca gcagtggcaa cagtggtggc agcagaggtg acagcggcag           1100
tgagtcctcc tggggatcca gcaccggctc ctcctccggc aaccacggtg           1150
ggagcggcgg aggaaatgga cataaacccg ggtgtgaaaa gccagggaat           1200
gaagcccgcg ggagcgggga atctgggatt cagggcttca gaggacaggg           1250
agtttccagc aacatgaggg aaataagcaa agagggcaat cgcctccttg           1300
gaggctctgg agacaattat cgggggcaag ggtcgagctg ggcagtgga            1350
ggaggtgacg ctgttggtgg agtcaatact gtgaactctg agacgtctcc           1400
tgggatgttt aactttgaca ctttctggaa gaattttaaa tccaagctgg           1450
gtttcatcaa ctgggatgcc ataaacaagg accagagaag ctctcgcatc           1500
ccgtgacctc cagacaagga gccaccagat tggatgggag cccccacact           1550
ccctccttaa aacaccaccc tctcatcact aatctcagcc cttgcccttg           1600
aaataaacct tagctgcccc acaaaaaaaa aaaaaaaaaa aaaaaaaaaa           1650
aaaaaaaaaa aaaaaaaaaa aaaaaaaaaa aaaaaaaaaa aaaaaaaaaa           1700
aaaaaaaaaa aaaaaaaaaa aaaaaaaaaa aaaa                            1734
```

```
<210> SEQ ID NO 52
<211> LENGTH: 440
<212> TYPE: PRT
<213> ORGANISM: Homo Sapien

<400> SEQUENCE: 52

Met Lys Phe Gln Gly Pro Leu Ala Cys Leu Leu Leu Ala Leu Cys
  1               5                  10                  15

Leu Gly Ser Gly Glu Ala Gly Pro Leu Gln Ser Gly Glu Glu Ser
                 20                  25                  30

Thr Gly Thr Asn Ile Gly Glu Ala Leu Gly His Gly Leu Gly Asp
                 35                  40                  45

Ala Leu Ser Glu Gly Val Gly Lys Ala Ile Gly Lys Glu Ala Gly
                 50                  55                  60

Gly Ala Ala Gly Ser Lys Val Ser Glu Ala Leu Gly Gln Gly Thr
                 65                  70                  75

Arg Glu Ala Val Gly Thr Gly Val Arg Gln Val Pro Gly Phe Gly
                 80                  85                  90

Ala Ala Asp Ala Leu Gly Asn Arg Val Gly Glu Ala Ala His Ala
                 95                 100                 105

Leu Gly Asn Thr Gly His Glu Ile Gly Arg Gln Ala Glu Asp Val
                110                 115                 120

Ile Arg His Gly Ala Asp Ala Val Arg Gly Ser Trp Gln Gly Val
                125                 130                 135

Pro Gly His Ser Gly Ala Trp Glu Thr Ser Gly Gly His Gly Ile
                140                 145                 150

Phe Gly Ser Gln Gly Gly Leu Gly Gly Gln Gly Gln Gly Asn Pro
                155                 160                 165

Gly Gly Leu Gly Thr Pro Trp Val His Gly Tyr Pro Gly Asn Ser
                170                 175                 180
```

-continued

```
Ala Gly Ser Phe Gly Met Asn Pro Gln Gly Ala Pro Trp Gly Gln
                185                 190                 195

Gly Gly Asn Gly Gly Pro Pro Asn Phe Gly Thr Asn Thr Gln Gly
                200                 205                 210

Ala Val Ala Gln Pro Gly Tyr Gly Ser Val Arg Ala Ser Asn Gln
                215                 220                 225

Asn Glu Gly Cys Thr Asn Pro Pro Pro Ser Gly Ser Gly Gly Gly
                230                 235                 240

Ser Ser Asn Ser Gly Gly Gly Ser Gly Ser Gln Ser Gly Ser Ser
                245                 250                 255

Gly Ser Gly Ser Asn Gly Asp Asn Asn Asn Gly Ser Ser Ser Gly
                260                 265                 270

Gly Ser Ser Ser Gly Ser Ser Ser Gly Ser Ser Ser Gly Gly Ser
                275                 280                 285

Ser Gly Gly Ser Ser Gly Gly Ser Ser Gly Asn Ser Gly Gly Ser
                290                 295                 300

Arg Gly Asp Ser Gly Ser Glu Ser Ser Trp Gly Ser Ser Thr Gly
                305                 310                 315

Ser Ser Ser Gly Asn His Gly Gly Ser Gly Gly Gly Asn Gly His
                320                 325                 330

Lys Pro Gly Cys Glu Lys Pro Gly Asn Glu Ala Arg Gly Ser Gly
                335                 340                 345

Glu Ser Gly Ile Gln Gly Phe Arg Gly Gln Gly Val Ser Ser Asn
                350                 355                 360

Met Arg Glu Ile Ser Lys Glu Gly Asn Arg Leu Leu Gly Gly Ser
                365                 370                 375

Gly Asp Asn Tyr Arg Gly Gln Gly Ser Ser Trp Gly Ser Gly Gly
                380                 385                 390

Gly Asp Ala Val Gly Gly Val Asn Thr Val Asn Ser Glu Thr Ser
                395                 400                 405

Pro Gly Met Phe Asn Phe Asp Thr Phe Trp Lys Asn Phe Lys Ser
                410                 415                 420

Lys Leu Gly Phe Ile Asn Trp Asp Ala Ile Asn Lys Asp Gln Arg
                425                 430                 435

Ser Ser Arg Ile Pro
                440
```

<210> SEQ ID NO 53
<211> LENGTH: 1676
<212> TYPE: DNA
<213> ORGANISM: Homo Sapien

<400> SEQUENCE: 53

```
ggagaagagg ttgtgtggga caagctgctc ccgacagaag gatgtcgctg         50

ctgagcctgc cctggctggg cctcagaccg gtggcaatgt ccccatggct        100

actcctgctg ctggttgtgg gctcctggct actcgcccgc atcctggctt        150

ggacctatgc cttctataac aactgccgcc ggctccagtg tttcccacag        200

cccccaaaac ggaactggtt ttggggtcac ctgggcctga tcactcctac        250

agaggagggc ttgaaggact cgacccagat gtcggccacc tattcccagg        300

gctttacggt atggctgggt cccatcatcc ccttcatcgt tttatgccac        350

cctgacacca tccggtctat caccaatgcc tcagctgcca ttgcacccaa        400

ggataatctc ttcatcaggt tcctgaagcc ctggctggga gaagggatac        450
```

-continued

```
tgctgagtgg cggtgacaag tggagccgcc accgtcggat gctgacgccc    500

gccttccatt tcaacatcct gaagtcctat ataacgatct tcaacaagag    550

tgcaaacatc atgcttgaca agtggcagca cctggcctca gagggcagca    600

gtcgtctgga catgtttgag cacatcagcc tcatgacctt ggacagtcta    650

cagaaatgca tcttcagctt tgacagccat tgtcaggaga ggcccagtga    700

atatattgcc accatcttgg agctcagtgc ccttgtagag aaaagaagcc    750

agcatatcct ccagcacatg gactttctgt attacctctc ccatgacggg    800

cggcgcttcc acagggcctg ccgcctggtg catgacttca cagacgctgt    850

catccgggag cggcgtcgca ccctccccac tcagggtatt gatgattttt    900

tcaaagacaa agccaagtcc aagactttgg atttcattga tgtgcttctg    950

ctgagcaagg atgaagatgg gaaggcattg tcagatgagg atataagagc   1000

agaggctgac accttcatgt ttggaggcca tgacaccacg gccagtggcc   1050

tctcctgggt cctgtacaac cttgcgaggc acccagaata ccaggagcgc   1100

tgccgacagg aggtgcaaga gcttctgaag gaccgcgatc ctaaagagat   1150

tgaatgggac gacctggccc agctgccctt cctgaccatg tgcgtgaagg   1200

agagcctgag gttacatccc ccagctccct tcatctcccg atgctgcacc   1250

caggacattg ttctcccaga tggccgagtc atccccaaag gcattacctg   1300

cctcatcgat attatagggg tccatcacaa cccaactgtg tggccggatc   1350

ctgaggtcta cgaccccttc cgctttgacc cagagaacag caaggggagg   1400

tcacctctgg cttttattcc tttctccgca gggcccagga actgcatcgg   1450

gcaggcgttc gccatggcgg agatgaaagt ggtcctggcg ttgatgctgc   1500

tgcacttccg gttcctgcca gaccacactg agccccgcag gaagctggaa   1550

ttgatcatgc gcgccgaggg cgggctttgg ctgcgggtgg agcccctgaa   1600

tgtaggcttg cagtgacttt ctgacccatc cacctgtttt tttgcagatt   1650

gtcatgaata aaacggtgct gtcaaa                             1676
```

```
<210> SEQ ID NO 54
<211> LENGTH: 524
<212> TYPE: PRT
<213> ORGANISM: Homo Sapien

<400> SEQUENCE: 54

Met Ser Leu Leu Ser Leu Pro Trp Leu Gly Leu Arg Pro Val Ala
  1               5                  10                  15

Met Ser Pro Trp Leu Leu Leu Leu Leu Val Val Gly Ser Trp Leu
                 20                  25                  30

Leu Ala Arg Ile Leu Ala Trp Thr Tyr Ala Phe Tyr Asn Asn Cys
                 35                  40                  45

Arg Arg Leu Gln Cys Phe Pro Gln Pro Pro Lys Arg Asn Trp Phe
                 50                  55                  60

Trp Gly His Leu Gly Leu Ile Thr Pro Thr Glu Glu Gly Leu Lys
                 65                  70                  75

Asp Ser Thr Gln Met Ser Ala Thr Tyr Ser Gln Gly Phe Thr Val
                 80                  85                  90

Trp Leu Gly Pro Ile Ile Pro Phe Ile Val Leu Cys His Pro Asp
                 95                 100                 105
```

-continued

```
Thr Ile Arg Ser Ile Thr Asn Ala Ser Ala Ala Ile Ala Pro Lys
                110                 115                 120

Asp Asn Leu Phe Ile Arg Phe Leu Lys Pro Trp Leu Gly Glu Gly
                125                 130                 135

Ile Leu Leu Ser Gly Gly Asp Lys Trp Ser Arg His Arg Arg Met
                140                 145                 150

Leu Thr Pro Ala Phe His Phe Asn Ile Leu Lys Ser Tyr Ile Thr
                155                 160                 165

Ile Phe Asn Lys Ser Ala Asn Ile Met Leu Asp Lys Trp Gln His
                170                 175                 180

Leu Ala Ser Glu Gly Ser Ser Arg Leu Asp Met Phe Glu His Ile
                185                 190                 195

Ser Leu Met Thr Leu Asp Ser Leu Gln Lys Cys Ile Phe Ser Phe
                200                 205                 210

Asp Ser His Cys Gln Glu Arg Pro Ser Glu Tyr Ile Ala Thr Ile
                215                 220                 225

Leu Glu Leu Ser Ala Leu Val Glu Lys Arg Ser Gln His Ile Leu
                230                 235                 240

Gln His Met Asp Phe Leu Tyr Tyr Leu Ser His Asp Gly Arg Arg
                245                 250                 255

Phe His Arg Ala Cys Arg Leu Val His Asp Phe Thr Asp Ala Val
                260                 265                 270

Ile Arg Glu Arg Arg Arg Thr Leu Pro Thr Gln Gly Ile Asp Asp
                275                 280                 285

Phe Phe Lys Asp Lys Ala Lys Ser Lys Thr Leu Asp Phe Ile Asp
                290                 295                 300

Val Leu Leu Leu Ser Lys Asp Glu Asp Gly Lys Ala Leu Ser Asp
                305                 310                 315

Glu Asp Ile Arg Ala Glu Ala Asp Thr Phe Met Phe Gly Gly His
                320                 325                 330

Asp Thr Thr Ala Ser Gly Leu Ser Trp Val Leu Tyr Asn Leu Ala
                335                 340                 345

Arg His Pro Glu Tyr Gln Glu Arg Cys Arg Gln Glu Val Gln Glu
                350                 355                 360

Leu Leu Lys Asp Arg Asp Pro Lys Glu Ile Glu Trp Asp Asp Leu
                365                 370                 375

Ala Gln Leu Pro Phe Leu Thr Met Cys Val Lys Glu Ser Leu Arg
                380                 385                 390

Leu His Pro Pro Ala Pro Phe Ile Ser Arg Cys Cys Thr Gln Asp
                395                 400                 405

Ile Val Leu Pro Asp Gly Arg Val Ile Pro Lys Gly Ile Thr Cys
                410                 415                 420

Leu Ile Asp Ile Ile Gly Val His His Asn Pro Thr Val Trp Pro
                425                 430                 435

Asp Pro Glu Val Tyr Asp Pro Phe Arg Phe Asp Pro Glu Asn Ser
                440                 445                 450

Lys Gly Arg Ser Pro Leu Ala Phe Ile Pro Phe Ser Ala Gly Pro
                455                 460                 465

Arg Asn Cys Ile Gly Gln Ala Phe Ala Met Ala Glu Met Lys Val
                470                 475                 480

Val Leu Ala Leu Met Leu Leu His Phe Arg Phe Leu Pro Asp His
                485                 490                 495
```

-continued

```
Thr Glu Pro Arg Arg Lys Leu Glu Leu Ile Met Arg Ala Glu Gly
                500                 505                 510

Gly Leu Trp Leu Arg Val Glu Pro Leu Asn Val Gly Leu Gln
                515                 520
```

<210> SEQ ID NO 55
<211> LENGTH: 644
<212> TYPE: DNA
<213> ORGANISM: Homo Sapien

<400> SEQUENCE: 55

```
atcgcatcaa ttgggagtac catcttcctc atgggaccag tgaaacagct      50

gaagcgaatg tttgagccta ctcgtttgat tgcaactatc atggtgctgt     100

tgtgttttgc acttaccctg tgttctgcct tttggtggca taacaaggga     150

cttgcactta tcttctgcat tttgcagtct ttggcattga cgtggtacag     200

cctttccttc ataccatttg caagggatgc tgtgaagaag tgttttgccg     250

tgtgtcttgc ataattcatg gccagtttta tgaagctttg gaaggcacta     300

tggacagaag ctggtggaca gttttgtaac tatcttcgaa acctctgtct     350

tacagacatg tgccttttat cttgcagcaa tgtgttgctt gtgattcgaa     400

catttgaggg ttacttttgg aagcaacaat acattctcga acctgaatgt     450

cagtagcaca ggatgagaag tgggttctgt atcttgtgga gtggaatctt     500

cctcatgtac ctgtttcctc tctggatgtt gtcccactga attcccatga     550

atacaaacct attcagcaac agcaaaaaaa aaaaaaaaaa aaaaaaaaaa     600

aaaaaaaaaa aaaaaaaaaa aaaaaaaaaa aaaaaaaaaa aaaa           644
```

<210> SEQ ID NO 56
<211> LENGTH: 77
<212> TYPE: PRT
<213> ORGANISM: Homo Sapien

<400> SEQUENCE: 56

```
Met Gly Pro Val Lys Gln Leu Lys Arg Met Phe Glu Pro Thr Arg
  1               5                  10                  15

Leu Ile Ala Thr Ile Met Val Leu Leu Cys Phe Ala Leu Thr Leu
                 20                  25                  30

Cys Ser Ala Phe Trp Trp His Asn Lys Gly Leu Ala Leu Ile Phe
                 35                  40                  45

Cys Ile Leu Gln Ser Leu Ala Leu Thr Trp Tyr Ser Leu Ser Phe
                 50                  55                  60

Ile Pro Phe Ala Arg Asp Ala Val Lys Lys Cys Phe Ala Val Cys
                 65                  70                  75

Leu Ala
```

<210> SEQ ID NO 57
<211> LENGTH: 3334
<212> TYPE: DNA
<213> ORGANISM: Homo Sapien

<400> SEQUENCE: 57

```
cggctcgagc tcgagccgaa tcggctcgag gggcagtgga gcacccagca      50

ggccgccaac atgctctgtc tgtgcctgta cgtgccggtc atcggggaag     100

cccagaccga gttccagtac tttgagtcga aggggctccc tgccgagctg     150
```

-continued

```
aagtccattt tcaagctcag tgtcttcatc ccctcccagg aattctccac          200
ctaccgccag tggaagcaga aaattgtaca agctggagat aaggaccttg          250
atgggcagct agactttgaa gaatttgtcc attatctcca agatcatgag          300
aagaagctga ggctggtgtt taagattttg gacaaaaaga atgatggacg          350
cattgacgcg caggagatca tgcagtccct gcgggacttg ggagtcaaga          400
tatctgaaca gcaggcagaa aaaattctca agagcatgga taaaaacggc          450
acgatgacca tcgactggaa cgagtggaga gactaccacc tcctccaccc          500
cgtggaaaac atccccgaga tcatcctcta ctggaagcat tccacgatct          550
ttgatgtggg tgagaatcta acggtcccgg atgagttcac agtggaggag          600
aggcagacgg ggatgtggtg gagacacctg gtggcaggag gtggggcagg          650
ggccgtatcc agaacctgca cggccccct ggacaggctc aaggtgctca           700
tgcaggtcca tgcctcccgc agcaacaaca tgggcatcgt tggtggcttc          750
actcagatga ttcgagaagg aggggccagg tcactctggc ggggcaatgg          800
catcaacgtc ctcaaaattg cccccgaatc agccatcaaa ttcatggcct          850
atgagcagat caagcgcctt gttggtagtg accaggagac tctgaggatt          900
cacgagaggc ttgtggcagg gtccttggca ggggccatcg cccagagcag          950
catctaccca atggaggtcc tgaagacccg gatggcgctg cggaagacag         1000
gccagtactc aggaatgctg gactgcgcca ggaggatcct ggccagagag         1050
ggggtggccg ccttctacaa aggctatgtc cccaacatgc tgggcatcat         1100
cccctatgcc ggcatcgacc ttgcagtcta cgagacgctc aagaatgcct         1150
ggctgcagca ctatgcagtg aacagcgcgg accccggcgt gtttgtgctc         1200
ctggcctgtg gcaccatgtc cagtacctgt ggccagctgg ccagctaccc         1250
cctggcccta gtcaggaccc ggatgcaggc gcaagcctct attgagggcg         1300
ctccggaggt gaccatgagc agcctcttca aacatatcct gcggaccgag         1350
ggggccttcg ggctgtacag ggggctggcc cccaacttca tgaaggtcat         1400
cccagctgtg agcatcagct acgtggtcta cgagaacctg aagatcaccc         1450
tgggcgtgca gtcgcggtga cgggggggagg gccgcccggc agtggactcg         1500
ctgatcctgg gccgcagcct ggggtgtgca gccatctcat tctgtgaatg         1550
tgccaacact aagctgtctc gagccaagct gtgaaaaccc tagacgcacc         1600
cgcagggagg gtggggagag ctggcaggcc cagggcttgt cctgctgacc         1650
ccagcagacc ctcctgttgg ttccagcgaa gaccacaggc attccttagg         1700
gtccagggtc agcaggctcc gggctcacat gtgtaaggac aggacatttt         1750
ctgcagtgcc tgccaatagt gagcttggag cctggaggcc ggcttagttc         1800
ttccatttca cccttgcagc cagctgttgg ccacggcccc tgccctctgg         1850
tctgccgtgc atctccctgt gccctcttgc tgcctgcctg tctgctgagg         1900
taaggtggga ggagggctac agcccacatc ccaccccctc gtccaatccc         1950
ataatccatg atgaaaggtg aggtcacgtg gcctcccagg cctgacttcc         2000
caacctacag cattgacgcc aacttggctg tgaaggaaga ggaaaggatc         2050
tggccttgtg gtcactggca tctgagccct gctgatggct ggggctctcg         2100
ggcatgcttg ggagtgcagg gggctcgggc tgcctggcct ggctgcacag         2150
```

-continued

```
aaggcaagtg ctggggctca tggtgctctg agctggcctg gaccctgtca        2200

ggatgggccc cacctcagaa ccaaactcac tgtccccact gtggcatgag        2250

ggcagtggag caccatgttt gagggcgaag ggcagagcgt ttgtgtgttc        2300

tggggaggga aggaaaaggt gttggaggcc ttaattatgg actgttggga        2350

aaagggtttt gtccagaagg acaagccgga caaatgagcg acttctgtgc        2400

ttccagagga agacgaggga gcaggagctt ggctgactgc tcagagtctg        2450

ttctgacgcc ctgggggttc ctgtccaacc ccagcagggg cgcagcggga        2500

ccagccccac attccacttg tgtcactgct tggaacctat ttattttgta        2550

tttatttgaa cagagttatg tcctaactat ttttatagat ttgtttaatt        2600

aatagcttgt cattttcaag ttcatttttt attcatattt atgttcatgg        2650

ttgattgtac cttcccaagc ccgcccagtg ggatgggagg aggaggagaa        2700

ggggggcctt gggccgctgc agtcacatct gtccagagaa attccttttg        2750

ggactggagg cagaaaagcg gccagaaggc agcagccctg gctcctttcc        2800

tttggcaggt tggggaaggg cttgccccca gccttaggat ttcagggttt        2850

gactgggggc gtggagagag agggaggaac ctcaataacc ttgaaggtgg        2900

aatccagtta tttcctgcgc tgcgagggtt tctttatttc actcttttct        2950

gaatgtcaag gcagtgaggt gcctctcact gtgaatttgt ggtgggcggg        3000

ggctggagga gagggtgggg ggctggctcc gtccctccca gccttctgct        3050

gcccttgctt aacaatgccg gccaactggc gacctcacgg ttgcacttcc        3100

attccaccag aatgacctga tgaggaaatc ttcaatagga tgcaaagatc        3150

aatgcaaaaa ttgttatata tgaacatata actggagtcg tcaaaaagca        3200

aattaagaaa gaattggacg ttagaagttg tcatttaaag cagccttcta        3250

ataaagttgt ttcaaagctg aaaaaaaaaa aaaaaaaaaa aaaaaaaaaa        3300

aaaaaaaaaa aaaaaaaaaa aaaaaaaaaa aaaa                         3334


<210> SEQ ID NO 58
<211> LENGTH: 469
<212> TYPE: PRT
<213> ORGANISM: Homo Sapien

<400> SEQUENCE: 58

Met Leu Cys Leu Cys Leu Tyr Val Pro Val Ile Gly Glu Ala Gln
  1               5                  10                  15

Thr Glu Phe Gln Tyr Phe Glu Ser Lys Gly Leu Pro Ala Glu Leu
                 20                  25                  30

Lys Ser Ile Phe Lys Leu Ser Val Phe Ile Pro Ser Gln Glu Phe
                 35                  40                  45

Ser Thr Tyr Arg Gln Trp Lys Gln Lys Ile Val Gln Ala Gly Asp
                 50                  55                  60

Lys Asp Leu Asp Gly Gln Leu Asp Phe Glu Glu Phe Val His Tyr
                 65                  70                  75

Leu Gln Asp His Glu Lys Lys Leu Arg Leu Val Phe Lys Ile Leu
                 80                  85                  90

Asp Lys Lys Asn Asp Gly Arg Ile Asp Ala Gln Glu Ile Met Gln
                 95                 100                 105

Ser Leu Arg Asp Leu Gly Val Lys Ile Ser Glu Gln Gln Ala Glu
```

-continued

```
                110                 115                 120

Lys Ile Leu Lys Ser Met Asp Lys Asn Gly Thr Met Thr Ile Asp
                125                 130                 135

Trp Asn Glu Trp Arg Asp Tyr His Leu Leu His Pro Val Glu Asn
                140                 145                 150

Ile Pro Glu Ile Ile Leu Tyr Trp Lys His Ser Thr Ile Phe Asp
                155                 160                 165

Val Gly Glu Asn Leu Thr Val Pro Asp Glu Phe Thr Val Glu Glu
                170                 175                 180

Arg Gln Thr Gly Met Trp Trp Arg His Leu Val Ala Gly Gly Gly
                185                 190                 195

Ala Gly Ala Val Ser Arg Thr Cys Thr Ala Pro Leu Asp Arg Leu
                200                 205                 210

Lys Val Leu Met Gln Val His Ala Ser Arg Ser Asn Asn Met Gly
                215                 220                 225

Ile Val Gly Gly Phe Thr Gln Met Ile Arg Glu Gly Gly Ala Arg
                230                 235                 240

Ser Leu Trp Arg Gly Asn Gly Ile Asn Val Leu Lys Ile Ala Pro
                245                 250                 255

Glu Ser Ala Ile Lys Phe Met Ala Tyr Glu Gln Ile Lys Arg Leu
                260                 265                 270

Val Gly Ser Asp Gln Glu Thr Leu Arg Ile His Glu Arg Leu Val
                275                 280                 285

Ala Gly Ser Leu Ala Gly Ala Ile Ala Gln Ser Ser Ile Tyr Pro
                290                 295                 300

Met Glu Val Leu Lys Thr Arg Met Ala Leu Arg Lys Thr Gly Gln
                305                 310                 315

Tyr Ser Gly Met Leu Asp Cys Ala Arg Arg Ile Leu Ala Arg Glu
                320                 325                 330

Gly Val Ala Ala Phe Tyr Lys Gly Tyr Val Pro Asn Met Leu Gly
                335                 340                 345

Ile Ile Pro Tyr Ala Gly Ile Asp Leu Ala Val Tyr Glu Thr Leu
                350                 355                 360

Lys Asn Ala Trp Leu Gln His Tyr Ala Val Asn Ser Ala Asp Pro
                365                 370                 375

Gly Val Phe Val Leu Leu Ala Cys Gly Thr Met Ser Ser Thr Cys
                380                 385                 390

Gly Gln Leu Ala Ser Tyr Pro Leu Ala Leu Val Arg Thr Arg Met
                395                 400                 405

Gln Ala Gln Ala Ser Ile Glu Gly Ala Pro Glu Val Thr Met Ser
                410                 415                 420

Ser Leu Phe Lys His Ile Leu Arg Thr Glu Gly Ala Phe Gly Leu
                425                 430                 435

Tyr Arg Gly Leu Ala Pro Asn Phe Met Lys Val Ile Pro Ala Val
                440                 445                 450

Ser Ile Ser Tyr Val Val Tyr Glu Asn Leu Lys Ile Thr Leu Gly
                455                 460                 465

Val Gln Ser Arg
```

```
<210> SEQ ID NO 59
<211> LENGTH: 1658
<212> TYPE: DNA
<213> ORGANISM: Homo Sapien
```

<400> SEQUENCE: 59
ggaaggcagc ggcagctcca ctcagccagt acccagatac gctgggaacc 50
ttccccagcc atggcttccc tggggcagat cctcttctgg agcataatta 100
gcatcatcat tattctggct ggagcaattg cactcatcat tggctttggt 150
atttcaggga gacactccat cacagtcact actgtcgcct cagctgggaa 200
cattggggag gatggaatcc tgagctgcac ttttgaacct gacatcaaac 250
tttctgatat cgtgatacaa tggctgaagg aaggtgtttt aggcttggtc 300
catgagttca aagaaggcaa agatgagctg tcggagcagg atgaaatgtt 350
cagaggccgg acagcagtgt ttgctgatca agtgatagtt ggcaatgcct 400
ctttgcggct gaaaaacgtg caactcacag atgctggcac ctacaaatgt 450
tatatcatca cttctaaagg caaggggaat gctaaccttg agtataaaac 500
tggagccttc agcatgccgg aagtgaatgt ggactataat gccagctcag 550
agaccttgcg gtgtgaggct ccccgatggt tcccccagcc cacagtggtc 600
tgggcatccc aagttgacca gggagccaac ttctcggaag tctccaatac 650
cagctttgag ctgaactctg agaatgtgac catgaaggtt gtgtctgtgc 700
tctacaatgt tacgatcaac aacacatact cctgtatgat tgaaaatgac 750
attgccaaag caacagggga tatcaaagtg acagaatcgg agatcaaaag 800
gcggagtcac ctacagctgc taaactcaaa ggcttctctg tgtgtctctt 850
ctttctttgc catcagctgg gcacttctgc ctctcagccc ttacctgatg 900
ctaaaataat gtgccttggc cacaaaaaag catgcaaagt cattgttaca 950
acagggatct acagaactat ttcaccacca gatatgacct agttttatat 1000
ttctgggagg aaatgaattc atatctagaa gtctggagtg agcaaacaag 1050
agcaagaaac aaaaagaagc caaaagcaga aggctccaat atgaacaaga 1100
taaatctatc ttcaaagaca tattagaagt tgggaaaata attcatgtga 1150
actagacaag tgtgttaaga gtgataagta aaatgcacgt ggagacaagt 1200
gcatccccag atctcaggga cctccccctg cctgtcacct ggggagtgag 1250
aggacaggat agtgcatgtt ctttgtctct gaatttttag ttatatgtgc 1300
tgtaatgttg ctctgaggaa gcccctggaa agtctatccc aacatatcca 1350
catcttatat tccacaaatt aagctgtagt atgtacccta agacgctgct 1400
aattgactgc cacttcgcaa ctcaggggcg gctgcatttt agtaatgggt 1450
caaatgattc actttttatg atgcttccaa aggtgccttg gcttctcttc 1500
ccaactgaca aatgccaaag ttgagaaaaa tgatcataat tttagcataa 1550
acagagcagt cggggacacc gattttataa ataaactgag caccttcttt 1600
ttaaacaaaa aaaaaaaaaa aaaaaaaaaa aaaaaaaaaa aaaaaaaaaa 1650
aaaaaaaa 1658

<210> SEQ ID NO 60
<211> LENGTH: 282
<212> TYPE: PRT
<213> ORGANISM: Homo Sapien

<400> SEQUENCE: 60

Met Ala Ser Leu Gly Gln Ile Leu Phe Trp Ser Ile Ile Ser Ile

-continued

```
1               5                   10                  15

Ile Ile Ile Leu Ala Gly Ala Ile Ala Leu Ile Ile Gly Phe Gly
                20                  25                  30

Ile Ser Gly Arg His Ser Ile Thr Val Thr Thr Val Ala Ser Ala
                35                  40                  45

Gly Asn Ile Gly Glu Asp Gly Ile Leu Ser Cys Thr Phe Glu Pro
                50                  55                  60

Asp Ile Lys Leu Ser Asp Ile Val Ile Gln Trp Leu Lys Glu Gly
                65                  70                  75

Val Leu Gly Leu Val His Glu Phe Lys Glu Gly Lys Asp Glu Leu
                80                  85                  90

Ser Glu Gln Asp Glu Met Phe Arg Gly Arg Thr Ala Val Phe Ala
                95                  100                 105

Asp Gln Val Ile Val Gly Asn Ala Ser Leu Arg Leu Lys Asn Val
                110                 115                 120

Gln Leu Thr Asp Ala Gly Thr Tyr Lys Cys Tyr Ile Ile Thr Ser
                125                 130                 135

Lys Gly Lys Gly Asn Ala Asn Leu Glu Tyr Lys Thr Gly Ala Phe
                140                 145                 150

Ser Met Pro Glu Val Asn Val Asp Tyr Asn Ala Ser Ser Glu Thr
                155                 160                 165

Leu Arg Cys Glu Ala Pro Arg Trp Phe Pro Gln Pro Thr Val Val
                170                 175                 180

Trp Ala Ser Gln Val Asp Gln Gly Ala Asn Phe Ser Glu Val Ser
                185                 190                 195

Asn Thr Ser Phe Glu Leu Asn Ser Glu Asn Val Thr Met Lys Val
                200                 205                 210

Val Ser Val Leu Tyr Asn Val Thr Ile Asn Asn Thr Tyr Ser Cys
                215                 220                 225

Met Ile Glu Asn Asp Ile Ala Lys Ala Thr Gly Asp Ile Lys Val
                230                 235                 240

Thr Glu Ser Glu Ile Lys Arg Arg Ser His Leu Gln Leu Leu Asn
                245                 250                 255

Ser Lys Ala Ser Leu Cys Val Ser Ser Phe Phe Ala Ile Ser Trp
                260                 265                 270

Ala Leu Leu Pro Leu Ser Pro Tyr Leu Met Leu Lys
                275                 280
```

<210> SEQ ID NO 61
<211> LENGTH: 1617
<212> TYPE: DNA
<213> ORGANISM: Homo Sapien

<400> SEQUENCE: 61

```
tgacgtcaga atcaccatgg ccagctatcc ttaccggcag ggctgcccag        50

gagctgcagg acaagcacca ggagcccctc cgggtagcta ctaccctgga       100

ccccccaata gtggagggca gtatggtagt gggctacccc ctggtggtgg       150

ttatgggggt cctgcccctg gagggcctta tggaccacca gctggtggag       200

ggccctatgg acaccccaat cctgggatgt tcccctctgg aactccagga       250

ggaccatatg gcggtgcagc tcccgggggc ccctatggtc agccacctcc       300

aagttcctac ggtgcccagc agcctgggct ttatggacag ggtggcgccc       350

ctcccaatgt ggatcctgag gcctactcct ggttccagtc ggtggactca       400
```

-continued

```
gatcacagtg gctatatctc catgaaggag ctaaagcagg ccctggtcaa              450

ctgcaattgg tcttcattca atgatgagac ctgcctcatg atgataaaca              500

tgtttgacaa gaccaagtca ggccgcatcg atgtctacgg cttctcagcc              550

ctgtggaaat tcatccagca gtggaagaac ctcttccagc agtatgaccg              600

ggaccgctcg ggctccatta gctacacaga gctgcagcaa gctctgtccc              650

aaatgggcta caacctgagc cccagttca cccagcttct ggtctcccgc               700

tactgcccac gctctgccaa tcctgccatg cagcttgacc gcttcatcca              750

ggtgtgcacc cagctgcagg tgctgacaga ggccttccgg gagaaggaca              800

cagctgtaca aggcaacatc cggctcagct tcgaggactt cgtcaccatg              850

acagcttctc ggatgctatg acccaaccat ctgtggagag tggagtgcac              900

cagggacctt tcctggcttc ttagagtgag agaagtatgt ggacatctct              950

tcttttcctg tccctctaga agaacattct cccttgcttg atgcaacact             1000

gttccaaaag agggtggaga gtcctgcatc atagccacca aatagtgagg             1050

accggggctg aggccacaca gataggggcc tgatggagga gaggatagaa             1100

gttgaatgtc ctgatggcca tgagcagttg agtggcacag cctggcacca             1150

ggagcaggtc cttgtaatgg agttagtgtc cagtcagctg agctccaccc             1200

tgatgccagt ggtgagtgtt catcggcctg ttaccgttag tacctgtgtt             1250

ccctcaccag gccatcctgt caaacgagcc cattttctcc aaagtggaat             1300

ctgaccaagc atgagagaga tctgtctatg ggaccagtgg cttggattct             1350

gccacaccca taaatccttg tgtgttaact tctagctgcc tggggctggc             1400

cctgctcaga caaatctgct ccctgggcat ctttggccag gcttctgccc             1450

cctgcagctg ggacccctca cttgcctgcc atgctctgct cggcttcagt             1500

ctccaggaga cagtggtcac ctctccctgc caatactttt tttaatttgc             1550

atttttttc atttggggcc aaaagtccag tgaaattgta agcttcaata              1600

aaaggatgaa actctga                                                 1617
```

```
<210> SEQ ID NO 62
<211> LENGTH: 284
<212> TYPE: PRT
<213> ORGANISM: Homo Sapien

<400> SEQUENCE: 62

Met Ala Ser Tyr Pro Tyr Arg Gln Gly Cys Pro Gly Ala Ala Gly
  1               5                  10                  15

Gln Ala Pro Gly Ala Pro Pro Gly Ser Tyr Tyr Pro Gly Pro Pro
                 20                  25                  30

Asn Ser Gly Gly Gln Tyr Gly Ser Gly Leu Pro Pro Gly Gly Gly
                 35                  40                  45

Tyr Gly Gly Pro Ala Pro Gly Gly Pro Tyr Gly Pro Pro Ala Gly
                 50                  55                  60

Gly Gly Pro Tyr Gly His Pro Asn Pro Gly Met Phe Pro Ser Gly
                 65                  70                  75

Thr Pro Gly Gly Pro Tyr Gly Gly Ala Ala Pro Gly Gly Pro Tyr
                 80                  85                  90

Gly Gln Pro Pro Pro Ser Ser Tyr Gly Ala Gln Gln Pro Gly Leu
                 95                 100                 105
```

-continued

```
Tyr Gly Gln Gly Gly Ala Pro Pro Asn Val Asp Pro Glu Ala Tyr
                110                 115                 120

Ser Trp Phe Gln Ser Val Asp Ser Asp His Ser Gly Tyr Ile Ser
                125                 130                 135

Met Lys Glu Leu Lys Gln Ala Leu Val Asn Cys Asn Trp Ser Ser
                140                 145                 150

Phe Asn Asp Glu Thr Cys Leu Met Met Ile Asn Met Phe Asp Lys
                155                 160                 165

Thr Lys Ser Gly Arg Ile Asp Val Tyr Gly Phe Ser Ala Leu Trp
                170                 175                 180

Lys Phe Ile Gln Gln Trp Lys Asn Leu Phe Gln Gln Tyr Asp Arg
                185                 190                 195

Asp Arg Ser Gly Ser Ile Ser Tyr Thr Glu Leu Gln Gln Ala Leu
                200                 205                 210

Ser Gln Met Gly Tyr Asn Leu Ser Pro Gln Phe Thr Gln Leu Leu
                215                 220                 225

Val Ser Arg Tyr Cys Pro Arg Ser Ala Asn Pro Ala Met Gln Leu
                230                 235                 240

Asp Arg Phe Ile Gln Val Cys Thr Gln Leu Gln Val Leu Thr Glu
                245                 250                 255

Ala Phe Arg Glu Lys Asp Thr Ala Val Gln Gly Asn Ile Arg Leu
                260                 265                 270

Ser Phe Glu Asp Phe Val Thr Met Thr Ala Ser Arg Met Leu
                275                 280
```

<210> SEQ ID NO 63
<211> LENGTH: 1234
<212> TYPE: DNA
<213> ORGANISM: Homo Sapien

<400> SEQUENCE: 63

```
caggatgcag ggccgcgtgg cagggagctg cgctcctctg ggcctgctcc      50

tggtctgtct tcatctccca ggcctctttg cccggagcat cggtgttgtg     100

gaggagaaag tttcccaaaa cttcgggacc aacttgcctc agctcggaca     150

accttcctcc actggcccct ctaactctga acatccgcag cccgctctgg     200

accctaggtc taatgacttg gcaagggttc ctctgaagct cagcgtgcct     250

ccatcagatg gcttcccacc tgcaggaggt tctgcagtgc agaggtggcc     300

tccatcgtgg gggctgcctg ccatggattc ctggcccccct gaggatcctt     350

ggcagatgat ggctgctgcg gctgaggacc gcctggggga agcgctgcct     400

gaagaactct cttacctctc cagtgctgcg gccctcgctc cgggcagtgg     450

ccctttgcct ggggagtctt ctcccgatgc cacaggcctc tcacctgagg     500

cttcactcct ccaccaggac tcggagtcca gacgactgcc ccgttctaat     550

tcactgggag ccgggggaaa aatcctttcc caacgccctc cctggtctct     600

catccacagg gttctgcctg atcacccctg gggtaccctg aatcccagtg     650

tgtcctgggg aggtggaggc cctgggactg gttggggaac gaggcccatg     700

ccacaccctg agggaatctg ggtatcaat aatcaacccc caggtaccag     750

ctggggaaat attaatcggt atccaggagg cagctgggga aatattaatc     800

ggtatccagg aggcagctgg gggaatatta atcggtatcc aggaggcagc     850
```

-continued

```
tgggggaata ttcatctata cccaggtatc aataacccat ttcctcctgg          900

agttctccgc cctcctggct cttcttggaa catcccagct ggcttcccta          950

atcctccaag ccctaggttg cagtggggct agagcacgat agagggaaac         1000

ccaacattgg gagttagagt cctgctcccg ccccttgctg tgtgggctca         1050

atccaggccc tgttaacatg tttccagcac tatccccact tttcagtgcc         1100

tcccctgctc atctccaata aaataaaagc acttatgaaa aaaaaaaaaa         1150

aaaaaaaaaa aaaaaaaaaa aaaaaaaaaa aaaaaaaaaa aaaaaaaaaa         1200

aaaaaaaaaa aaaaaaaaaa aaaaaaaaaa aaaa                          1234
```

<210> SEQ ID NO 64
<211> LENGTH: 325
<212> TYPE: PRT
<213> ORGANISM: Homo Sapien

<400> SEQUENCE: 64

```
Met Gln Gly Arg Val Ala Gly Ser Cys Ala Pro Leu Gly Leu Leu
  1               5                  10                  15

Leu Val Cys Leu His Leu Pro Gly Leu Phe Ala Arg Ser Ile Gly
                 20                  25                  30

Val Val Glu Glu Lys Val Ser Gln Asn Phe Gly Thr Asn Leu Pro
                 35                  40                  45

Gln Leu Gly Gln Pro Ser Ser Thr Gly Pro Ser Asn Ser Glu His
                 50                  55                  60

Pro Gln Pro Ala Leu Asp Pro Arg Ser Asn Asp Leu Ala Arg Val
                 65                  70                  75

Pro Leu Lys Leu Ser Val Pro Pro Ser Asp Gly Phe Pro Pro Ala
                 80                  85                  90

Gly Gly Ser Ala Val Gln Arg Trp Pro Pro Ser Trp Gly Leu Pro
                 95                 100                 105

Ala Met Asp Ser Trp Pro Pro Glu Asp Pro Trp Gln Met Met Ala
                110                 115                 120

Ala Ala Ala Glu Asp Arg Leu Gly Glu Ala Leu Pro Glu Glu Leu
                125                 130                 135

Ser Tyr Leu Ser Ser Ala Ala Ala Leu Ala Pro Gly Ser Gly Pro
                140                 145                 150

Leu Pro Gly Glu Ser Ser Pro Asp Ala Thr Gly Leu Ser Pro Glu
                155                 160                 165

Ala Ser Leu Leu His Gln Asp Ser Glu Ser Arg Arg Leu Pro Arg
                170                 175                 180

Ser Asn Ser Leu Gly Ala Gly Gly Lys Ile Leu Ser Gln Arg Pro
                185                 190                 195

Pro Trp Ser Leu Ile His Arg Val Leu Pro Asp His Pro Trp Gly
                200                 205                 210

Thr Leu Asn Pro Ser Val Ser Trp Gly Gly Gly Gly Pro Gly Thr
                215                 220                 225

Gly Trp Gly Thr Arg Pro Met Pro His Pro Glu Gly Ile Trp Gly
                230                 235                 240

Ile Asn Asn Gln Pro Pro Gly Thr Ser Trp Gly Asn Ile Asn Arg
                245                 250                 255

Tyr Pro Gly Gly Ser Trp Gly Asn Ile Asn Arg Tyr Pro Gly Gly
                260                 265                 270

Ser Trp Gly Asn Ile Asn Arg Tyr Pro Gly Gly Ser Trp Gly Asn
```

-continued 275 280 285

Ile His Leu Tyr Pro Gly Ile Asn Asn Pro Phe Pro Pro Gly Val
290 295 300

Leu Arg Pro Pro Gly Ser Ser Trp Asn Ile Pro Ala Gly Phe Pro
305 310 315

Asn Pro Pro Ser Pro Arg Leu Gln Trp Gly
320 325

<210> SEQ ID NO 65
<211> LENGTH: 422
<212> TYPE: DNA
<213> ORGANISM: Homo Sapien

<400> SEQUENCE: 65
aaggagaggc caccgggact tcagtgtctc ctccatccca ggagcgcagt 50
ggccactatg gggtctgggc tgccccttgt cctcctcttg accctccttg 100
gcagctcaca tggaacaggg ccgggtatga ctttgcaact gaagctgaag 150
gagtcttttc tgacaaattc ctcctatgag tccagcttcc tggaattgct 200
tgaaaagctc tgcctcctcc tccatctccc ttcagggacc agcgtcaccc 250
tccaccatgc aagatctcaa caccatgttg tctgcaacac atgacagcca 300
ttgaagcctg tgtccttctt ggcccgggct tttgggccgg ggatgcagga 350
ggcaggcccc gaccctgtct ttcagcaggc ccccaccctc ctgagtggca 400
ataaataaaa ttcggtatgc tg 422

<210> SEQ ID NO 66
<211> LENGTH: 78
<212> TYPE: PRT
<213> ORGANISM: Homo Sapien

<400> SEQUENCE: 66

Met Gly Ser Gly Leu Pro Leu Val Leu Leu Leu Thr Leu Leu Gly
1 5 10 15

Ser Ser His Gly Thr Gly Pro Gly Met Thr Leu Gln Leu Lys Leu
20 25 30

Lys Glu Ser Phe Leu Thr Asn Ser Ser Tyr Glu Ser Ser Phe Leu
35 40 45

Glu Leu Leu Glu Lys Leu Cys Leu Leu Leu His Leu Pro Ser Gly
50 55 60

Thr Ser Val Thr Leu His His Ala Arg Ser Gln His His Val Val
65 70 75

Cys Asn Thr

<210> SEQ ID NO 67
<211> LENGTH: 744
<212> TYPE: DNA
<213> ORGANISM: Homo Sapien

<400> SEQUENCE: 67
acggaccgag ggttcgaggg agggacacgg accaggaacc tgagctaggt 50
caaagacgcc cgggccaggt gccccgtcgc aggtgcccct ggccggagat 100
gcggtaggag gggcgagcgc gagaagcccc ttcctcggcg ctgccaaccc 150
gccacccagc ccatggcgaa ccccgggctg gggctgcttc tggcgctggg 200
cctgccgttc ctgctggccc gctggggccg agcctggggg caaatacaga 250

-continued

```
ccacttctgc aaatgagaat agcactgttt tgccttcatc caccagctcc         300

agctccgatg gcaacctgcg tccggaagcc atcactgcta tcatcgtggt         350

cttctccctc ttggctgcct tgctcctggc tgtggggctg gcactgttgg         400

tgcggaagct tcgggagaag cggcagacgg agggcaccta ccggcccagt         450

agcgaggagc agttctccca tgcagccgag gcccgggccc ctcaggactc         500

caaggagacg gtgcagggct gcctgcccat ctaggtcccc tctcctgcat         550

ctgtctccct tcattgctgt gtgaccttgg ggaaaggcag tgccctctct         600

gggcagtcag atccacccag tgcttaatag cagggaagaa ggtacttcaa         650

agactctgcc cctgaggtca agagaggatg ggctattca cttttatata          700

tttatataaa attagtagtg agatgtaaaa aaaaaaaaaa aaaa               744
```

```
<210> SEQ ID NO 68
<211> LENGTH: 123
<212> TYPE: PRT
<213> ORGANISM: Homo Sapien

<400> SEQUENCE: 68

Met Ala Asn Pro Gly Leu Gly Leu Leu Leu Ala Leu Gly Leu Pro
  1               5                  10                  15

Phe Leu Leu Ala Arg Trp Gly Arg Ala Trp Gly Gln Ile Gln Thr
                 20                  25                  30

Thr Ser Ala Asn Glu Asn Ser Thr Val Leu Pro Ser Ser Thr Ser
                 35                  40                  45

Ser Ser Ser Asp Gly Asn Leu Arg Pro Glu Ala Ile Thr Ala Ile
                 50                  55                  60

Ile Val Val Phe Ser Leu Leu Ala Ala Leu Leu Leu Ala Val Gly
                 65                  70                  75

Leu Ala Leu Leu Val Arg Lys Leu Arg Glu Lys Arg Gln Thr Glu
                 80                  85                  90

Gly Thr Tyr Arg Pro Ser Ser Glu Glu Gln Phe Ser His Ala Ala
                 95                 100                 105

Glu Ala Arg Ala Pro Gln Asp Ser Lys Glu Thr Val Gln Gly Cys
                110                 115                 120

Leu Pro Ile
```

```
<210> SEQ ID NO 69
<211> LENGTH: 3265
<212> TYPE: DNA
<213> ORGANISM: Homo Sapien

<400> SEQUENCE: 69

gccaggaata actagagagg aacaatgggg ttattcagag gttttgtttt          50

cctcttagtt ctgtgcctgc tgcaccagtc aaatacttcc ttcattaagc         100

tgaataataa tggctttgaa gatattgtca ttgttataga tcctagtgtg         150

ccagaagatg aaaaaataat tgaacaaata gaggatatgg tgactacagc         200

ttctacgtac ctgtttgaag ccacagaaaa aagatttttt ttcaaaaatg         250

tatctatatt aattcctgag aattggaagg aaaatcctca gtacaaaagg         300

ccaaaacatg aaaaccataa acatgctgat gttatagttg caccacctac         350

actcccaggt agagatgaac catacaccaa gcagttcaca gaatgtggag         400
```

-continued

```
agaaaggcga atacattcac ttcacccctg accttctact tggaaaaaaa       450
caaaatgaat atggaccacc aggcaaactg tttgtccatg agtgggctca       500
cctccggtgg ggagtgtttg atgagtacaa tgaagatcag cctttctacc       550
gtgctaagtc aaaaaaaatc gaagcaacaa ggtgttccgc aggtatctct       600
ggtagaaata gagtttataa gtgtcaagga ggcagctgtc ttagtagagc       650
atgcagaatt gattctacaa caaaactgta tggaaaagat tgtcaattct       700
ttcctgataa agtacaaaca gaaaaagcat ccataatgtt tatgcaaagt       750
attgattctg ttgttgaatt ttgtaacgaa aaaacccata atcaagaagc       800
tccaagccta caaaacataa agtgcaattt tagaagtaca tgggaggtga       850
ttagcaattc tgaggatttt aaaaacacca tacccatggt gacaccacct       900
cctccacctg tcttctcatt gctgaagatc agtcaaagaa ttgtgtgctt       950
agttcttgat aagtctggaa gcatgggggg taaggaccgc ctaaatcgaa      1000
tgaatcaagc agcaaaacat ttcctgctgc agactgttga aaatggatcc      1050
tgggtgggga tggttcactt tgatagtact gccactattg taaataagct      1100
aatccaaata aaaagcagtg atgaaagaaa cacactcatg gcaggattac      1150
ctacatatcc tctgggagga acttccatct gctctggaat taaatatgca      1200
tttcaggtga ttggagagct acattcccaa ctcgatggat ccgaagtact      1250
gctgctgact gatggggagg ataacactgc aagttcttgt attgatgaag      1300
tgaaacaaag tggggccatt gttcatttta ttgctttggg aagagctgct      1350
gatgaagcag taatagagat gagcaagata acaggaggaa gtcattttta      1400
tgtttcagat gaagctcaga acaatggcct cattgatgct tttggggctc      1450
ttacatcagg aaatactgat ctctcccaga agtcccttca gctcgaaagt      1500
aagggattaa cactgaatag taatgcctgg atgaacgaca ctgtcataat      1550
tgatagtaca gtgggaaagg acacgttctt tctcatcaca tggaacagtc      1600
tgcctcccag tatttctctc tgggatccca gtggaacaat aatggaaaat      1650
ttcacagtgg atgcaacttc caaaatggcc tatctcagta ttccaggaac      1700
tgcaaaggtg ggcacttggg catacaatct tcaagccaaa gcgaacccag      1750
aaacattaac tattacagta acttctcgag cagcaaattc ttctgtgcct      1800
ccaatcacag tgaatgctaa aatgaataag gacgtaaaca gtttccccag      1850
cccaatgatt gtttacgcag aaattctaca aggatatgta cctgttcttg      1900
gagccaatgt gactgctttc attgaatcac agaatggaca tacagaagtt      1950
ttggaacttt tggataatgg tgcaggcgct gattctttca agaatgatgg      2000
agtctactcc aggtatttta cagcatatac agaaaatggc agatatagct      2050
taaaagttcg ggctcatgga ggagcaaaca ctgccaggct aaaattacgg      2100
cctccactga atagagccgc gtacatacca ggctgggtag tgaacgggga      2150
aattgaagca aacccgccaa gacctgaaat tgatgaggat actcagacca      2200
ccttggagga tttcagccga acagcatccg gaggtgcatt tgtggtatca      2250
caagtcccaa gccttccctt gcctgaccaa tacccaccaa gtcaaatcac      2300
agaccttgat gccacagttc atgaggataa gattattctt acatggacag      2350
caccaggaga taattttgat gttggaaaag ttcaacgtta tatcataaga      2400
```

-continued

```
ataagtgcaa gtattcttga tctaagagac agttttgatg atgctcttca        2450

agtaaatact actgatctgt caccaaagga ggccaactcc aaggaaagct        2500

ttgcatttaa accagaaaat atctcagaag aaaatgcaac ccacatattt        2550

attgccatta aaagtataga taaaagcaat ttgacatcaa aagtatccaa        2600

cattgcacaa gtaactttgt ttatccctca agcaaatcct gatgacattg        2650

atcctacacc tactcctact cctactccta ctcctgataa aagtcataat        2700

tctggagtta atatttctac gctggtattg tctgtgattg ggtctgttgt        2750

aattgttaac tttattttaa gtaccaccat ttgaacctta acgaagaaaa        2800

aaatcttcaa gtagacctag aagagagttt taaaaaacaa aacaatgtaa        2850

gtaaaggata tttctgaatc ttaaaattca tcccatgtgt gatcataaac        2900

tcataaaaat aattttaaga tgtcggaaaa ggatactttg attaaataaa        2950

aacactcatg gatatgtaaa aactgtcaag attaaaattt aatagtttca        3000

tttatttgtt attttatttg taagaaatag tgatgaacaa agatcctttt        3050

tcatactgat acctggttgt atattatttg atgcaacagt tttctgaaat        3100

gatatttcaa attgcatcaa gaaattaaaa tcatctatct gagtagtcaa        3150

aatacaagta aaggagagca aataaacaac atttggaaaa aaaaaaaaaa        3200

aaaaaaaaaa aaaaaaaaaa aaaaaaaaaa aaaaaaaaaa aaaaaaaaaa        3250

aaaaaaaaaa aaaaa                                              3265
```

<210> SEQ ID NO 70
<211> LENGTH: 919
<212> TYPE: PRT
<213> ORGANISM: Homo Sapien

<400> SEQUENCE: 70

```
Met Gly Leu Phe Arg Gly Phe Val Phe Leu Leu Val Leu Cys Leu
  1               5                  10                  15

Leu His Gln Ser Asn Thr Ser Phe Ile Lys Leu Asn Asn Asn Gly
                 20                  25                  30

Phe Glu Asp Ile Val Ile Val Ile Asp Pro Ser Val Pro Glu Asp
                 35                  40                  45

Glu Lys Ile Ile Glu Gln Ile Glu Asp Met Val Thr Thr Ala Ser
                 50                  55                  60

Thr Tyr Leu Phe Glu Ala Thr Glu Lys Arg Phe Phe Phe Lys Asn
                 65                  70                  75

Val Ser Ile Leu Ile Pro Glu Asn Trp Lys Glu Asn Pro Gln Tyr
                 80                  85                  90

Lys Arg Pro Lys His Glu Asn His Lys His Ala Asp Val Ile Val
                 95                 100                 105

Ala Pro Pro Thr Leu Pro Gly Arg Asp Glu Pro Tyr Thr Lys Gln
                110                 115                 120

Phe Thr Glu Cys Gly Glu Lys Gly Glu Tyr Ile His Phe Thr Pro
                125                 130                 135

Asp Leu Leu Leu Gly Lys Lys Gln Asn Glu Tyr Gly Pro Pro Gly
                140                 145                 150

Lys Leu Phe Val His Glu Trp Ala His Leu Arg Trp Gly Val Phe
                155                 160                 165

Asp Glu Tyr Asn Glu Asp Gln Pro Phe Tyr Arg Ala Lys Ser Lys
```

-continued

```
                170                 175                 180

Lys Ile Glu Ala Thr Arg Cys Ser Ala Gly Ile Ser Gly Arg Asn
                185                 190                 195

Arg Val Tyr Lys Cys Gln Gly Gly Ser Cys Leu Ser Arg Ala Cys
                200                 205                 210

Arg Ile Asp Ser Thr Thr Lys Leu Tyr Gly Lys Asp Cys Gln Phe
                215                 220                 225

Phe Pro Asp Lys Val Gln Thr Glu Lys Ala Ser Ile Met Phe Met
                230                 235                 240

Gln Ser Ile Asp Ser Val Val Glu Phe Cys Asn Glu Lys Thr His
                245                 250                 255

Asn Gln Glu Ala Pro Ser Leu Gln Asn Ile Lys Cys Asn Phe Arg
                260                 265                 270

Ser Thr Trp Glu Val Ile Ser Asn Ser Glu Asp Phe Lys Asn Thr
                275                 280                 285

Ile Pro Met Val Thr Pro Pro Pro Pro Pro Val Phe Ser Leu Leu
                290                 295                 300

Lys Ile Ser Gln Arg Ile Val Cys Leu Val Leu Asp Lys Ser Gly
                305                 310                 315

Ser Met Gly Gly Lys Asp Arg Leu Asn Arg Met Asn Gln Ala Ala
                320                 325                 330

Lys His Phe Leu Leu Gln Thr Val Glu Asn Gly Ser Trp Val Gly
                335                 340                 345

Met Val His Phe Asp Ser Thr Ala Thr Ile Val Asn Lys Leu Ile
                350                 355                 360

Gln Ile Lys Ser Ser Asp Glu Arg Asn Thr Leu Met Ala Gly Leu
                365                 370                 375

Pro Thr Tyr Pro Leu Gly Gly Thr Ser Ile Cys Ser Gly Ile Lys
                380                 385                 390

Tyr Ala Phe Gln Val Ile Gly Glu Leu His Ser Gln Leu Asp Gly
                395                 400                 405

Ser Glu Val Leu Leu Leu Thr Asp Gly Glu Asp Asn Thr Ala Ser
                410                 415                 420

Ser Cys Ile Asp Glu Val Lys Gln Ser Gly Ala Ile Val His Phe
                425                 430                 435

Ile Ala Leu Gly Arg Ala Ala Asp Glu Ala Val Ile Glu Met Ser
                440                 445                 450

Lys Ile Thr Gly Gly Ser His Phe Tyr Val Ser Asp Glu Ala Gln
                455                 460                 465

Asn Asn Gly Leu Ile Asp Ala Phe Gly Ala Leu Thr Ser Gly Asn
                470                 475                 480

Thr Asp Leu Ser Gln Lys Ser Leu Gln Leu Glu Ser Lys Gly Leu
                485                 490                 495

Thr Leu Asn Ser Asn Ala Trp Met Asn Asp Thr Val Ile Ile Asp
                500                 505                 510

Ser Thr Val Gly Lys Asp Thr Phe Phe Leu Ile Thr Trp Asn Ser
                515                 520                 525

Leu Pro Pro Ser Ile Ser Leu Trp Asp Pro Ser Gly Thr Ile Met
                530                 535                 540

Glu Asn Phe Thr Val Asp Ala Thr Ser Lys Met Ala Tyr Leu Ser
                545                 550                 555

Ile Pro Gly Thr Ala Lys Val Gly Thr Trp Ala Tyr Asn Leu Gln
                560                 565                 570
```

-continued

```
Ala Lys Ala Asn Pro Glu Thr Leu Thr Ile Thr Val Thr Ser Arg
                575                 580                 585

Ala Ala Asn Ser Ser Val Pro Pro Ile Thr Val Asn Ala Lys Met
                590                 595                 600

Asn Lys Asp Val Asn Ser Phe Pro Ser Pro Met Ile Val Tyr Ala
                605                 610                 615

Glu Ile Leu Gln Gly Tyr Val Pro Val Leu Gly Ala Asn Val Thr
                620                 625                 630

Ala Phe Ile Glu Ser Gln Asn Gly His Thr Glu Val Leu Glu Leu
                635                 640                 645

Leu Asp Asn Gly Ala Gly Ala Asp Ser Phe Lys Asn Asp Gly Val
                650                 655                 660

Tyr Ser Arg Tyr Phe Thr Ala Tyr Thr Glu Asn Gly Arg Tyr Ser
                665                 670                 675

Leu Lys Val Arg Ala His Gly Gly Ala Asn Thr Ala Arg Leu Lys
                680                 685                 690

Leu Arg Pro Pro Leu Asn Arg Ala Ala Tyr Ile Pro Gly Trp Val
                695                 700                 705

Val Asn Gly Glu Ile Glu Ala Asn Pro Pro Arg Pro Glu Ile Asp
                710                 715                 720

Glu Asp Thr Gln Thr Thr Leu Glu Asp Phe Ser Arg Thr Ala Ser
                725                 730                 735

Gly Gly Ala Phe Val Val Ser Gln Val Pro Ser Leu Pro Leu Pro
                740                 745                 750

Asp Gln Tyr Pro Pro Ser Gln Ile Thr Asp Leu Asp Ala Thr Val
                755                 760                 765

His Glu Asp Lys Ile Ile Leu Thr Trp Thr Ala Pro Gly Asp Asn
                770                 775                 780

Phe Asp Val Gly Lys Val Gln Arg Tyr Ile Ile Arg Ile Ser Ala
                785                 790                 795

Ser Ile Leu Asp Leu Arg Asp Ser Phe Asp Asp Ala Leu Gln Val
                800                 805                 810

Asn Thr Thr Asp Leu Ser Pro Lys Glu Ala Asn Ser Lys Glu Ser
                815                 820                 825

Phe Ala Phe Lys Pro Glu Asn Ile Ser Glu Glu Asn Ala Thr His
                830                 835                 840

Ile Phe Ile Ala Ile Lys Ser Ile Asp Lys Ser Asn Leu Thr Ser
                845                 850                 855

Lys Val Ser Asn Ile Ala Gln Val Thr Leu Phe Ile Pro Gln Ala
                860                 865                 870

Asn Pro Asp Asp Ile Asp Pro Thr Pro Thr Pro Thr Pro Thr Pro
                875                 880                 885

Thr Pro Asp Lys Ser His Asn Ser Gly Val Asn Ile Ser Thr Leu
                890                 895                 900

Val Leu Ser Val Ile Gly Ser Val Val Ile Val Asn Phe Ile Leu
                905                 910                 915

Ser Thr Thr Ile
```

<210> SEQ ID NO 71
<211> LENGTH: 3877
<212> TYPE: DNA
<213> ORGANISM: Homo Sapien

<400> SEQUENCE: 71

-continued

```
ctccttaggt ggaaaccctg ggagtagagt actgacagca aagaccggga      50
aagaccatac gtccccgggc aggggtgaca acaggtgtca tctttttgat     100
ctcgtgtgtg gctgccttcc tatttcaagg aaagacgcca aggtaatttt     150
gacccagagg agcaatgatg tagccacctc ctaaccttcc cttcttgaac     200
ccccagttat gccaggattt actagagagt gtcaactcaa ccagcaagcg     250
gctccttcgg cttaacttgt ggttggagga gagaaccttt gtggggctgc     300
gttctcttag cagtgctcag aagtgacttg cctgagggtg gaccagaaga     350
aaggaaaggt cccctcttgc tgttggctgc acatcaggaa ggctgtgatg     400
ggaatgaagg tgaaaacttg gagatttcac ttcagtcatt gcttctgcct     450
gcaagatcat cctttaaaag tagagaagct gctctgtgtg gtggttaact     500
ccaagaggca gaactcgttc tagaaggaaa tggatgcaag cagctccggg     550
ggccccaaac gcatgcttcc tgtggtctag cccagggaag cccttccgtg     600
ggggccccgg ctttgaggga tgccaccggt tctggacgca tggctgattc     650
ctgaatgatg atggttcgcc gggggctgct tgcgtggatt tcccgggtgg     700
tggttttgct ggtgctcctc tgctgtgcta tctctgtcct gtacatgttg     750
gcctgcaccc caaaaggtga cgaggagcag ctggcactgc ccagggccaa     800
cagccccacg gggaaggagg ggtaccaggc cgtccttcag gagtgggagg     850
agcagcaccg caactacgtg agcagcctga agcggcagat cgcacagctc     900
aaggaggagc tgcaggagag gagtgagcag ctcaggaatg ggcagtacca     950
agccagcgat gctgctggcc tgggtctgga caggagcccc ccagagaaaa    1000
cccaggccga cctcctggcc ttcctgcact cgcaggtgga caaggcagag    1050
gtgaatgctg gcgtcaagct ggccacagag tatgcagcag tgcctttcga    1100
tagctttact ctacagaagg tgtaccagct ggagactggc cttacccgcc    1150
accccgagga gaagcctgtg aggaaggaca agcgggatga gttggtggaa    1200
gccattgaat cagccttgga gaccctgaac aatcctgcag agaacagccc    1250
caatcaccgt ccttacacgg cctctgattt catagaaggg atctaccgaa    1300
cagaaaggga caaagggaca ttgtatgagc tcaccttcaa aggggaccac    1350
aaacacgaat tcaaacggct catcttattt cgaccattca gccccatcat    1400
gaaagtgaaa aatgaaaagc tcaacatggc caacacgctt atcaatgtta    1450
tcgtgcctct agcaaaaagg gtggacaagt tccggcagtt catgcagaat    1500
ttcagggaga tgtgcattga gcaggatggg agagtccatc tcactgttgt    1550
ttactttggg aaagaagaaa taaatgaagt caaaggaata cttgaaaaca    1600
cttccaaagc tgccaacttc aggaacttta ccttcatcca gctgaatgga    1650
gaattttctc ggggaaaggg acttgatgtt ggagcccgct tctggaaggg    1700
aagcaacgtc cttctctttt tctgtgatgt ggacatctac ttcacatctg    1750
aattcctcaa tacgtgtagg ctgaatacac agccagggaa gaaggtattt    1800
tatccagttc ttttcagtca gtacaatcct ggcataatat acggccacca    1850
tgatgcagtc cctcccttgg aacagcagct ggtcataaag aaggaaactg    1900
gattttggag agactttgga tttgggatga cgtgtcagta tcggtcagac    1950
```

-continued

```
ttcatcaata taggtgggtt tgatctggac atcaaaggct ggggcggaga          2000
ggatgtgcac ctttatcgca agtatctcca cagcaacctc atagtggtac          2050
ggacgcctgt gcgaggactc ttccacctct ggcatgagaa gcgctgcatg          2100
gacgagctga cccccgagca gtacaagatg tgcatgcagt ccaaggccat          2150
gaacgaggca tcccacggcc agctgggcat gctggtgttc aggcacgaga          2200
tagaggctca ccttcgcaaa cagaaacaga agacaagtag caaaaaaaca          2250
tgaactccca gagaaggatt gtgggagaca ctttttcttt ccttttgcaa          2300
ttactgaaag tggctgcaac agagaaaaga cttccataaa ggacgacaaa          2350
agaattggac tgatgggtca gagatgagaa agcctccgat ttctctctgt          2400
tgggcttttt acaacagaaa tcaaaatctc cgctttgcct gcaaaagtaa          2450
cccagttgca ccctgtgaag tgtctgacaa aggcagaatg cttgtgagat          2500
tataagccta atggtgtgga ggttttgatg gtgtttacaa tacactgaga          2550
cctgttgttt tgtgtgctca ttgaaatatt catgatttaa gagcagtttt          2600
gtaaaaaatt cattagcatg aaaggcaagc atatttctcc tcatatgaat          2650
gagcctatca gcagggctct agtttctagg aatgctaaaa tatcagaagg          2700
caggagagga gataggctta ttatgatact agtgagtaca ttaagtaaaa          2750
taaaatggac cagaaaagaa aagaaaccat aaatatcgtg tcatattttc          2800
cccaagatta accaaaaata atctgcttat ctttttggtt gtccttttaa          2850
ctgtctccgt ttttttcttt tatttaaaaa tgcacttttt ttcccttgtg          2900
agttatagtc tgcttattta attaccactt tgcaagcctt acaagagagc          2950
acaagttggc ctacattttt atattttta agaagatact ttgagatgca          3000
ttatgagaac tttcagttca aagcatcaaa ttgatgccat atccaaggac          3050
atgccaaatg ctgattctgt caggcactga atgtcaggca ttgagacata          3100
gggaaggaat ggtttgtact aatacagacg tacagatact ttctctgaag          3150
agtattttcg aagaggagca actgaacact ggaggaaaag aaaatgacac          3200
tttctgcttt acagaaaagg aaactcattc agactggtga tatcgtgatg          3250
tacctaaaag tcagaaacca cattttctcc tcagaagtag ggaccgcttt          3300
cttacctgtt taaataaacc aaagtatacc gtgtgaacca aacaatctct          3350
tttcaaaaca gggtgctcct cctggcttct ggcttccata agaagaaatg          3400
gagaaaaata tatatatata tatatatatt gtgaaagatc aatccatctg          3450
ccagaatcta gtgggatgga agtttttgct acatgttatc caccccaggc          3500
caggtggaag taactgaatt attttttaaa ttaagcagtt ctactcaatc          3550
accaagatgc ttctgaaaat tgcattttat taccatttca aactattttt          3600
taaaaataaa tacagttaac atagagtggt ttcttcattc atgtgaaaat          3650
tattagccag caccagatgc atgagctaat tatctctttg agtccttgct          3700
tctgtttgct cacagtaaac tcattgttta aaagcttcaa gaacattcaa          3750
gctgttggtg tgttaaaaaa tgcattgtat tgatttgtac tggtagttta          3800
tgaaatttaa ttaaaacaca ggccatgaat ggaaggtggt attgcacagc          3850
taataaaata tgatttgtgg atatgaa                                   3877
```

-continued

<210> SEQ ID NO 72
<211> LENGTH: 532
<212> TYPE: PRT
<213> ORGANISM: Homo Sapien

<400> SEQUENCE: 72

```
Met Met Met Val Arg Arg Gly Leu Leu Ala Trp Ile Ser Arg Val
  1               5                  10                  15

Val Val Leu Leu Val Leu Leu Cys Cys Ala Ile Ser Val Leu Tyr
                 20                  25                  30

Met Leu Ala Cys Thr Pro Lys Gly Asp Glu Glu Gln Leu Ala Leu
                 35                  40                  45

Pro Arg Ala Asn Ser Pro Thr Gly Lys Glu Gly Tyr Gln Ala Val
                 50                  55                  60

Leu Gln Glu Trp Glu Glu Gln His Arg Asn Tyr Val Ser Ser Leu
                 65                  70                  75

Lys Arg Gln Ile Ala Gln Leu Lys Glu Glu Leu Gln Glu Arg Ser
                 80                  85                  90

Glu Gln Leu Arg Asn Gly Gln Tyr Gln Ala Ser Asp Ala Ala Gly
                 95                 100                 105

Leu Gly Leu Asp Arg Ser Pro Pro Glu Lys Thr Gln Ala Asp Leu
                110                 115                 120

Leu Ala Phe Leu His Ser Gln Val Asp Lys Ala Glu Val Asn Ala
                125                 130                 135

Gly Val Lys Leu Ala Thr Glu Tyr Ala Ala Val Pro Phe Asp Ser
                140                 145                 150

Phe Thr Leu Gln Lys Val Tyr Gln Leu Glu Thr Gly Leu Thr Arg
                155                 160                 165

His Pro Glu Glu Lys Pro Val Arg Lys Asp Lys Arg Asp Glu Leu
                170                 175                 180

Val Glu Ala Ile Glu Ser Ala Leu Glu Thr Leu Asn Asn Pro Ala
                185                 190                 195

Glu Asn Ser Pro Asn His Arg Pro Tyr Thr Ala Ser Asp Phe Ile
                200                 205                 210

Glu Gly Ile Tyr Arg Thr Glu Arg Asp Lys Gly Thr Leu Tyr Glu
                215                 220                 225

Leu Thr Phe Lys Gly Asp His Lys His Glu Phe Lys Arg Leu Ile
                230                 235                 240

Leu Phe Arg Pro Phe Ser Pro Ile Met Lys Val Lys Asn Glu Lys
                245                 250                 255

Leu Asn Met Ala Asn Thr Leu Ile Asn Val Ile Val Pro Leu Ala
                260                 265                 270

Lys Arg Val Asp Lys Phe Arg Gln Phe Met Gln Asn Phe Arg Glu
                275                 280                 285

Met Cys Ile Glu Gln Asp Gly Arg Val His Leu Thr Val Val Tyr
                290                 295                 300

Phe Gly Lys Glu Glu Ile Asn Glu Val Lys Gly Ile Leu Glu Asn
                305                 310                 315

Thr Ser Lys Ala Ala Asn Phe Arg Asn Phe Thr Phe Ile Gln Leu
                320                 325                 330

Asn Gly Glu Phe Ser Arg Gly Lys Gly Leu Asp Val Gly Ala Arg
                335                 340                 345

Phe Trp Lys Gly Ser Asn Val Leu Leu Phe Phe Cys Asp Val Asp
                350                 355                 360
```

-continued

```
Ile Tyr Phe Thr Ser Glu Phe Leu Asn Thr Cys Arg Leu Asn Thr
                365                 370                 375

Gln Pro Gly Lys Lys Val Phe Tyr Pro Val Leu Phe Ser Gln Tyr
                380                 385                 390

Asn Pro Gly Ile Ile Tyr Gly His His Asp Ala Val Pro Pro Leu
                395                 400                 405

Glu Gln Gln Leu Val Ile Lys Lys Glu Thr Gly Phe Trp Arg Asp
                410                 415                 420

Phe Gly Phe Gly Met Thr Cys Gln Tyr Arg Ser Asp Phe Ile Asn
                425                 430                 435

Ile Gly Gly Phe Asp Leu Asp Ile Lys Gly Trp Gly Gly Glu Asp
                440                 445                 450

Val His Leu Tyr Arg Lys Tyr Leu His Ser Asn Leu Ile Val Val
                455                 460                 465

Arg Thr Pro Val Arg Gly Leu Phe His Leu Trp His Glu Lys Arg
                470                 475                 480

Cys Met Asp Glu Leu Thr Pro Glu Gln Tyr Lys Met Cys Met Gln
                485                 490                 495

Ser Lys Ala Met Asn Glu Ala Ser His Gly Gln Leu Gly Met Leu
                500                 505                 510

Val Phe Arg His Glu Ile Glu Ala His Leu Arg Lys Gln Lys Gln
                515                 520                 525

Lys Thr Ser Ser Lys Lys Thr
                530
```

<210> SEQ ID NO 73
<211> LENGTH: 1701
<212> TYPE: DNA
<213> ORGANISM: Homo Sapien
<220> FEATURE:
<221> NAME/KEY: unsure
<222> LOCATION: 1528
<223> OTHER INFORMATION: unknown base

<400> SEQUENCE: 73

```
gagactgcag agggagataa agagagaggg caaagaggca gcaagagatt      50

tgtcctgggg atccagaaac ccatgatacc ctactgaaca ccgaatcccc     100

tggaagccca cagagacaga gacagcaaga gaagcagaga taaatacact     150

cacgccagga gctcgctcgc tctctctctc tctctctcac tcctccctcc     200

ctctctctct gcctgtccta gtcctctagt cctcaaattc ccagtcccct     250

gcaccccttc ctgggacact atgttgttct ccgccctcct gctggaggtg     300

atttggatcc tggctgcaga tgggggtcaa cactggacgt atgagggccc     350

acatggtcag gaccattggc cagcctctta ccctgagtgt ggaaacaatg     400

cccagtcgcc catcgatatt cagacagaca gtgtgacatt tgaccctgat     450

ttgcctgctc tgcagcccca cggatatgac cagcctggca ccgagccttt     500

ggacctgcac aacaatggcc acacagtgca actctctctg ccctctaccc     550

tgtatctggg tggacttccc cgaaaatatg tagctgccca gctccacctg     600

cactggggtc agaaaggatc cccagggggg tcagaacacc agatcaacag     650

tgaagccaca tttgcagagc tccacattgt acattatgac tctgattcct     700

atgacagctt gagtgaggct gctgagaggc ctcagggcct ggctgtcctg     750

ggcatcctaa ttgaggtggg tgagactaag aatatagctt atgaacacat     800
```

-continued

```
tctgagtcac ttgcatgaag tcaggcataa agatcagaag acctcagtgc       850
ctcccttcaa cctaagagag ctgctcccca aacagctggg gcagtacttc       900
cgctacaatg gctcgctcac aactccccct tgctaccaga gtgtgctctg       950
gacagttttt tatagaaggt cccagatttc aatggaacag ctggaaaagc      1000
ttcaggggac attgttctcc acagaagagg agccctctaa gcttctggta      1050
cagaactacc gagcccttca gcctctcaat cagcgcatgg tctttgcttc      1100
tttcatccaa gcaggatcct cgtataccac aggtgaaatg ctgagtctag      1150
gtgtaggaat cttggttggc tgtctctgcc ttctcctggc tgtttatttc      1200
attgctagaa agattcggaa gaagaggctg gaaaaccgaa agagtgtggt      1250
cttcacctca gcacaagcca cgactgaggc ataaattcct tctcagatac      1300
catggatgtg gatgacttcc cttcatgcct atcaggaagc ctctaaaatg      1350
gggtgtagga tctggccaga aacactgtag gagtagtaag cagatgtcct      1400
ccttcccctg gacatctctt agagaggaat ggacccaggc tgtcattcca      1450
ggaagaactg cagagccttc agcctctcca aacatgtagg aggaaatgag      1500
gaaatcgctg tgttgttaat gcagaganca aactctgttt agttgcaggg      1550
gaagtttggg atataccca aagtcctcta ccccctcact tttatggccc      1600
tttccctaga tatactgcgg gatctctcct taggataaag agttgctgtt      1650
gaagttgtat atttttgatc aatatatttg gaaattaaag tttctgactt      1700
t                                                           1701
```

<210> SEQ ID NO 74
<211> LENGTH: 337
<212> TYPE: PRT
<213> ORGANISM: Homo Sapien

<400> SEQUENCE: 74

```
Met Leu Phe Ser Ala Leu Leu Leu Glu Val Ile Trp Ile Leu Ala
  1               5                  10                  15

Ala Asp Gly Gly Gln His Trp Thr Tyr Glu Gly Pro His Gly Gln
                 20                  25                  30

Asp His Trp Pro Ala Ser Tyr Pro Glu Cys Gly Asn Asn Ala Gln
                 35                  40                  45

Ser Pro Ile Asp Ile Gln Thr Asp Ser Val Thr Phe Asp Pro Asp
                 50                  55                  60

Leu Pro Ala Leu Gln Pro His Gly Tyr Asp Gln Pro Gly Thr Glu
                 65                  70                  75

Pro Leu Asp Leu His Asn Asn Gly His Thr Val Gln Leu Ser Leu
                 80                  85                  90

Pro Ser Thr Leu Tyr Leu Gly Gly Leu Pro Arg Lys Tyr Val Ala
                 95                 100                 105

Ala Gln Leu His Leu His Trp Gly Gln Lys Gly Ser Pro Gly Gly
                110                 115                 120

Ser Glu His Gln Ile Asn Ser Glu Ala Thr Phe Ala Glu Leu His
                125                 130                 135

Ile Val His Tyr Asp Ser Asp Ser Tyr Asp Ser Leu Ser Glu Ala
                140                 145                 150

Ala Glu Arg Pro Gln Gly Leu Ala Val Leu Gly Ile Leu Ile Glu
                155                 160                 165
```

-continued

```
Val Gly Glu Thr Lys Asn Ile Ala Tyr Glu His Ile Leu Ser His
                170                 175                 180

Leu His Glu Val Arg His Lys Asp Gln Lys Thr Ser Val Pro Pro
                185                 190                 195

Phe Asn Leu Arg Glu Leu Leu Pro Lys Gln Leu Gly Gln Tyr Phe
                200                 205                 210

Arg Tyr Asn Gly Ser Leu Thr Thr Pro Pro Cys Tyr Gln Ser Val
                215                 220                 225

Leu Trp Thr Val Phe Tyr Arg Arg Ser Gln Ile Ser Met Glu Gln
                230                 235                 240

Leu Glu Lys Leu Gln Gly Thr Leu Phe Ser Thr Glu Glu Glu Pro
                245                 250                 255

Ser Lys Leu Leu Val Gln Asn Tyr Arg Ala Leu Gln Pro Leu Asn
                260                 265                 270

Gln Arg Met Val Phe Ala Ser Phe Ile Gln Ala Gly Ser Ser Tyr
                275                 280                 285

Thr Thr Gly Glu Met Leu Ser Leu Gly Val Gly Ile Leu Val Gly
                290                 295                 300

Cys Leu Cys Leu Leu Leu Ala Val Tyr Phe Ile Ala Arg Lys Ile
                305                 310                 315

Arg Lys Lys Arg Leu Glu Asn Arg Lys Ser Val Val Phe Thr Ser
                320                 325                 330

Ala Gln Ala Thr Thr Glu Ala
                335
```

<210> SEQ ID NO 75
<211> LENGTH: 1743
<212> TYPE: DNA
<213> ORGANISM: Homo Sapien

<400> SEQUENCE: 75

```
tgccgctgcc gccgctgctg ctgttgctcc tggcggcgcc ttggggacgg        50

gcagttccct gtgtctctgg tggtttgcct aaacctgcaa acatcacctt       100

cttatccatc aacatgaaga atgtcctaca atggactcca ccagagggtc       150

ttcaaggagt taaagttact tacactgtgc agtatttcat cacaaattgg       200

cccaccagag gtggcactga ctacagatga gaagtccatt tctgttgtcc       250

tgacagctcc agagaagtgg aagagaaatc cagaagacct tcctgtttcc       300

atgcaacaaa tatactccaa tctgaagtat aacgtgtctg tgttgaatac       350

taaatcaaac agaacgtggt cccagtgtgt gaccaaccac acgctggtgc       400

tcacctggct ggagccgaac actctttact gcgtacacgt ggagtccttc       450

gtcccagggc cccctcgccg tgctcagcct tctgagaagc agtgtgccag       500

gactttgaaa gatcaatcat cagagttcaa ggctaaaatc atcttctggt       550

atgttttgcc catatctatt accgtgtttc ttttttctgt gatgggctat       600

tccatctacc gatatatcca cgttggcaaa gagaaacacc cagcaaattt       650

gattttgatt tatggaaatg aatttgacaa aagattcttt gtgcctgctg       700

aaaaaatcgt gattaacttt atcaccctca atatctcgga tgattctaaa       750

atttctcatc aggatatgag tttactggga aaaagcagtg atgtatccag       800

ccttaatgat cctcagccca gcgggaacct gaggccccct caggaggaag       850
```

-continued

```
aggaggtgaa acatttaggg tatgcttcgc atttgatgga aattttttgt       900

gactctgaag aaaacacgga aggtacttct ctcacccagc aagagtccct       950

cagcagaaca atacccccgg ataaaacagt cattgaatat gaatatgatg      1000

tcagaaccac tgacatttgt gcggggcctg aagagcagga gctcagtttg      1050

caggaggagg tgtccacaca aggaacatta ttggagtcgc aggcagcgtt      1100

ggcagtcttg ggcccgcaaa cgttacagta ctcatacacc cctcagctcc      1150

aagacttaga ccccctggcg caggagcaca cagactcgga ggaggggccg      1200

gaggaagagc catcgacgac cctggtcgac tgggatcccc aaactggcag      1250

gctgtgtatt ccttcgctgt ccagcttcga ccaggattca gagggctgcg      1300

agccttctga gggggatggg ctcggagagg agggtcttct atctagactc      1350

tatgaggagc cggctccaga caggccacca ggagaaaatg aaacctatct      1400

catgcaattc atggaggaat gggggttata tgtgcagatg gaaaactgat      1450

gccaacactt ccttttgcct tttgtttcct gtgcaaacaa gtgagtcacc      1500

cctttgatcc cagccataaa gtacctggga tgaaagaagt tttttccagt      1550

ttgtcagtgt ctgtgagaat tacttatttc ttttctctat tctcatagca      1600

cgtgtgtgat tggttcatgc atgtaggtct cttaacaatg atggtgggcc      1650

tctggagtcc aggggctggc cggttgttct atgcagagaa agcagtcaat      1700

aaatgtttgc cagactgggt gcagaattta ttcaggtggg tgt             1743
```

```
<210> SEQ ID NO 76
<211> LENGTH: 442
<212> TYPE: PRT
<213> ORGANISM: Homo Sapien

<400> SEQUENCE: 76

Met Ser Tyr Asn Gly Leu His Gln Arg Val Phe Lys Glu Leu Lys
  1               5                  10                  15

Leu Leu Thr Leu Cys Ser Ile Ser Ser Gln Ile Gly Pro Pro Glu
                 20                  25                  30

Val Ala Leu Thr Thr Asp Glu Lys Ser Ile Ser Val Val Leu Thr
                 35                  40                  45

Ala Pro Glu Lys Trp Lys Arg Asn Pro Glu Asp Leu Pro Val Ser
                 50                  55                  60

Met Gln Gln Ile Tyr Ser Asn Leu Lys Tyr Asn Val Ser Val Leu
                 65                  70                  75

Asn Thr Lys Ser Asn Arg Thr Trp Ser Gln Cys Val Thr Asn His
                 80                  85                  90

Thr Leu Val Leu Thr Trp Leu Glu Pro Asn Thr Leu Tyr Cys Val
                 95                 100                 105

His Val Glu Ser Phe Val Pro Gly Pro Pro Arg Arg Ala Gln Pro
                110                 115                 120

Ser Glu Lys Gln Cys Ala Arg Thr Leu Lys Asp Gln Ser Ser Glu
                125                 130                 135

Phe Lys Ala Lys Ile Ile Phe Trp Tyr Val Leu Pro Ile Ser Ile
                140                 145                 150

Thr Val Phe Leu Phe Ser Val Met Gly Tyr Ser Ile Tyr Arg Tyr
                155                 160                 165

Ile His Val Gly Lys Glu Lys His Pro Ala Asn Leu Ile Leu Ile
                170                 175                 180
```

Tyr Gly Asn Glu Phe Asp Lys Arg Phe Phe Val Pro Ala Glu Lys
185 190 195

Ile Val Ile Asn Phe Ile Thr Leu Asn Ile Ser Asp Asp Ser Lys
200 205 210

Ile Ser His Gln Asp Met Ser Leu Leu Gly Lys Ser Ser Asp Val
215 220 225

Ser Ser Leu Asn Asp Pro Gln Pro Ser Gly Asn Leu Arg Pro Pro
230 235 240

Gln Glu Glu Glu Glu Val Lys His Leu Gly Tyr Ala Ser His Leu
245 250 255

Met Glu Ile Phe Cys Asp Ser Glu Glu Asn Thr Glu Gly Thr Ser
260 265 270

Leu Thr Gln Gln Glu Ser Leu Ser Arg Thr Ile Pro Pro Asp Lys
275 280 285

Thr Val Ile Glu Tyr Glu Tyr Asp Val Arg Thr Thr Asp Ile Cys
290 295 300

Ala Gly Pro Glu Glu Gln Glu Leu Ser Leu Gln Glu Glu Val Ser
305 310 315

Thr Gln Gly Thr Leu Leu Glu Ser Gln Ala Ala Leu Ala Val Leu
320 325 330

Gly Pro Gln Thr Leu Gln Tyr Ser Tyr Thr Pro Gln Leu Gln Asp
335 340 345

Leu Asp Pro Leu Ala Gln Glu His Thr Asp Ser Glu Glu Gly Pro
350 355 360

Glu Glu Glu Pro Ser Thr Thr Leu Val Asp Trp Asp Pro Gln Thr
365 370 375

Gly Arg Leu Cys Ile Pro Ser Leu Ser Ser Phe Asp Gln Asp Ser
380 385 390

Glu Gly Cys Glu Pro Ser Glu Gly Asp Gly Leu Gly Glu Glu Gly
395 400 405

Leu Leu Ser Arg Leu Tyr Glu Glu Pro Ala Pro Asp Arg Pro Pro
410 415 420

Gly Glu Asn Glu Thr Tyr Leu Met Gln Phe Met Glu Glu Trp Gly
425 430 435

Leu Tyr Val Gln Met Glu Asn
440

<210> SEQ ID NO 77
<211> LENGTH: 1636
<212> TYPE: DNA
<213> ORGANISM: Homo Sapien

<400> SEQUENCE: 77
gaggagcggg ccgaggactc cagcgtgccc aggtctggca tcctgcactt 50
gctgccctct gacacctggg aagatggccg gcccgtggac cttcaccctt 100
ctctgtggtt tgctggcagc caccttgatc caagccaccc tcagtcccac 150
tgcagttctc atcctcggcc caaaagtcat caaagaaaag ctgacacagg 200
agctgaagga ccacaacgcc accagcatcc tgcagcagct gccgctgctc 250
agtgccatgc gggaaaagcc agccggaggc atccctgtgc tgggcagcct 300
ggtgaacacc gtcctgaagc acatcatctg gctgaaggtc atcacagcta 350
acatcctcca gctgcaggtg aagccctcgg ccaatgacca ggagctgcta 400

-continued

```
gtcaagatcc ccctggacat ggtggctgga ttcaacacgc ccctggtcaa            450

gaccatcgtg gagttccaca tgacgactga ggcccaagcc accatccgca            500

tggacaccag tgcaagtggc cccacccgcc tggtcctcag tgactgtgcc            550

accagccatg ggagcctgcg catccaactg ctgtataagc tctccttcct            600

ggtgaacgcc ttagctaagc aggtcatgaa cctcctagtg ccatccctgc            650

ccaatctagt gaaaaaccag ctgtgtcccg tgatcgaggc ttccttcaat            700

ggcatgtatg cagacctcct gcagctggtg aaggtgccca tttccctcag            750

cattgaccgt ctggagtttg accttctgta tcctgccatc aagggtgaca            800

ccattcagct ctacctgggg gccaagttgt tggactcaca gggaaaggtg            850

accaagtggt tcaataactc tgcagcttcc ctgacaatgc ccaccctgga            900

caacatcccg ttcagcctca tcgtgagtca ggacgtggtg aaagctgcag            950

tggctgctgt gctctctcca gaagaattca tggtcctgtt ggactctgtg           1000

cttcctgaga gtgcccatcg gctgaagtca agcatcgggc tgatcaatga           1050

aaaggctgca gataagctgg gatctaccca gatcgtgaag atcctaactc           1100

aggacactcc cgagtttttt atagaccaag gccatgccaa ggtggcccaa           1150

ctgatcgtgc tggaagtgtt tccctccagt gaagccctcc gccctttgtt           1200

caccctgggc atcgaagcca gctcggaagc tcagttttac accaaaggtg           1250

accaacttat actcaacttg aataacatca gctctgatcg gatccagctg           1300

atgaactctg ggattggctg gttccaacct gatgttctga aaaacatcat           1350

cactgagatc atccactcca tcctgctgcc gaaccagaat ggcaaattaa           1400

gatctggggt cccagtgtca ttggtgaagg ccttgggatt cgaggcagct           1450

gagtcctcac tgaccaagga tgcccttgtg cttactccag cctccttgtg           1500

gaaacccagc tctcctgtct cccagtgaag acttggatgg cagccatcag           1550

ggaaggctgg gtcccagctg ggagtatggg tgtgagctct atagaccatc           1600

cctctctgca atcaataaac acttgcctgt gaaaaa                          1636
```

```
<210> SEQ ID NO 78
<211> LENGTH: 484
<212> TYPE: PRT
<213> ORGANISM: Homo Sapien

<400> SEQUENCE: 78

Met Ala Gly Pro Trp Thr Phe Thr Leu Leu Cys Gly Leu Leu Ala
  1               5                  10                  15

Ala Thr Leu Ile Gln Ala Thr Leu Ser Pro Thr Ala Val Leu Ile
                 20                  25                  30

Leu Gly Pro Lys Val Ile Lys Glu Lys Leu Thr Gln Glu Leu Lys
                 35                  40                  45

Asp His Asn Ala Thr Ser Ile Leu Gln Gln Leu Pro Leu Leu Ser
                 50                  55                  60

Ala Met Arg Glu Lys Pro Ala Gly Gly Ile Pro Val Leu Gly Ser
                 65                  70                  75

Leu Val Asn Thr Val Leu Lys His Ile Ile Trp Leu Lys Val Ile
                 80                  85                  90

Thr Ala Asn Ile Leu Gln Leu Gln Val Lys Pro Ser Ala Asn Asp
                 95                 100                 105
```

-continued

```
Gln Glu Leu Leu Val Lys Ile Pro Leu Asp Met Val Ala Gly Phe
                110                 115                 120

Asn Thr Pro Leu Val Lys Thr Ile Val Glu Phe His Met Thr Thr
                125                 130                 135

Glu Ala Gln Ala Thr Ile Arg Met Asp Thr Ser Ala Ser Gly Pro
                140                 145                 150

Thr Arg Leu Val Leu Ser Asp Cys Ala Thr Ser His Gly Ser Leu
                155                 160                 165

Arg Ile Gln Leu Leu Tyr Lys Leu Ser Phe Leu Val Asn Ala Leu
                170                 175                 180

Ala Lys Gln Val Met Asn Leu Leu Val Pro Ser Leu Pro Asn Leu
                185                 190                 195

Val Lys Asn Gln Leu Cys Pro Val Ile Glu Ala Ser Phe Asn Gly
                200                 205                 210

Met Tyr Ala Asp Leu Leu Gln Leu Val Lys Val Pro Ile Ser Leu
                215                 220                 225

Ser Ile Asp Arg Leu Glu Phe Asp Leu Leu Tyr Pro Ala Ile Lys
                230                 235                 240

Gly Asp Thr Ile Gln Leu Tyr Leu Gly Ala Lys Leu Leu Asp Ser
                245                 250                 255

Gln Gly Lys Val Thr Lys Trp Phe Asn Asn Ser Ala Ala Ser Leu
                260                 265                 270

Thr Met Pro Thr Leu Asp Asn Ile Pro Phe Ser Leu Ile Val Ser
                275                 280                 285

Gln Asp Val Val Lys Ala Ala Val Ala Ala Val Leu Ser Pro Glu
                290                 295                 300

Glu Phe Met Val Leu Leu Asp Ser Val Leu Pro Glu Ser Ala His
                305                 310                 315

Arg Leu Lys Ser Ser Ile Gly Leu Ile Asn Glu Lys Ala Ala Asp
                320                 325                 330

Lys Leu Gly Ser Thr Gln Ile Val Lys Ile Leu Thr Gln Asp Thr
                335                 340                 345

Pro Glu Phe Phe Ile Asp Gln Gly His Ala Lys Val Ala Gln Leu
                350                 355                 360

Ile Val Leu Glu Val Phe Pro Ser Ser Glu Ala Leu Arg Pro Leu
                365                 370                 375

Phe Thr Leu Gly Ile Glu Ala Ser Ser Glu Ala Gln Phe Tyr Thr
                380                 385                 390

Lys Gly Asp Gln Leu Ile Leu Asn Leu Asn Asn Ile Ser Ser Asp
                395                 400                 405

Arg Ile Gln Leu Met Asn Ser Gly Ile Gly Trp Phe Gln Pro Asp
                410                 415                 420

Val Leu Lys Asn Ile Ile Thr Glu Ile Ile His Ser Ile Leu Leu
                425                 430                 435

Pro Asn Gln Asn Gly Lys Leu Arg Ser Gly Val Pro Val Ser Leu
                440                 445                 450

Val Lys Ala Leu Gly Phe Glu Ala Ala Glu Ser Ser Leu Thr Lys
                455                 460                 465

Asp Ala Leu Val Leu Thr Pro Ala Ser Leu Trp Lys Pro Ser Ser
                470                 475                 480

Pro Val Ser Gln
```

<210> SEQ ID NO 79

-continued

<211> LENGTH: 1475
<212> TYPE: DNA
<213> ORGANISM: Homo Sapien

<400> SEQUENCE: 79

```
gagagaagtc agcctggcag agagactctg aaatgaggga ttagaggtgt      50

tcaaggagca agagcttcag cctgaagaca agggagcagt ccctgaagac     100

gcttctactg agaggtctgc catggcctct cttggcctcc aacttgtggg     150

ctacatccta ggccttctgg ggcttttggg cacactggtt gccatgctgc     200

tccccagctg gaaaacaagt tcttatgtcg gtgccagcat tgtgacagca     250

gttggcttct ccaagggcct ctggatggaa tgtgccacac acagcacagg     300

catcacccag tgtgacatct atagcaccct tctgggcctg cccgctgaca     350

tccaggctgc ccaggccatg atggtgacat ccagtgcaat ctcctccctg     400

gcctgcatta tctctgtggt gggcatgaga tgcacagtct tctgccagga     450

atcccgagcc aaagacagag tggcggtagc aggtggagtc tttttcatcc     500

ttggaggcct cctgggattc attcctgttg cctggaatct tcatgggatc     550

ctacgggact tctactcacc actggtgcct gacagcatga aatttgagat     600

tggagaggct ctttacttgg gcattatttc ttccctgttc tccctgatag     650

ctggaatcat cctctgcttt tcctgctcat cccagagaaa tcgctccaac     700

tactacgatg cctaccaagc ccaacctctt gccacaagga gctctccaag     750

gcctggtcaa cctcccaaag tcaagagtga gttcaattcc tacagcctga     800

cagggtatgt gtgaagaacc aggggccaga gctggggggt ggctgggtct     850

gtgaaaaaca gtggacagca ccccgagggc cacaggtgag ggacactacc     900

actggatcgt gtcagaaggt gctgctgagg atagactgac tttggccatt     950

ggattgagca aaggcagaaa tgggggctag tgtaacagca tgcaggttga    1000

attgccaagg atgctcgcca tgccagcctt tctgttttcc tcaccttgct    1050

gctcccctgc cctaagtccc caaccctcaa cttgaaaccc cattccctta    1100

agccaggact cagaggatcc ctttgccctc tggtttacct gggactccat    1150

ccccaaaccc actaatcaca tcccactgac tgaccctctg tgatcaaaga    1200

ccctctctct ggctgaggtt ggctcttagc tcattgctgg ggatgggaag    1250

gagaagcagt ggcttttgtg ggcattgctc taacctactt ctcaagcttc    1300

cctccaaaga aactgattgg ccctggaacc tccatcccac tcttgttatg    1350

actccacagt gtccagacta atttgtgcat gaactgaaat aaaaccatcc    1400

tacggtatcc agggaacaga aagcaggatg caggatggga ggacaggaag    1450

gcagcctggg acatttaaaa aaata                               1475
```

<210> SEQ ID NO 80
<211> LENGTH: 230
<212> TYPE: PRT
<213> ORGANISM: Homo Sapien

<400> SEQUENCE: 80

```
Met Ala Ser Leu Gly Leu Gln Leu Val Gly Tyr Ile Leu Gly Leu
  1               5                  10                  15

Leu Gly Leu Leu Gly Thr Leu Val Ala Met Leu Leu Pro Ser Trp
                 20                  25                  30
```

-continued

```
Lys Thr Ser Ser Tyr Val Gly Ala Ser Ile Val Thr Ala Val Gly
                35                  40                  45

Phe Ser Lys Gly Leu Trp Met Glu Cys Ala Thr His Ser Thr Gly
                50                  55                  60

Ile Thr Gln Cys Asp Ile Tyr Ser Thr Leu Leu Gly Leu Pro Ala
                65                  70                  75

Asp Ile Gln Ala Ala Gln Ala Met Met Val Thr Ser Ser Ala Ile
                80                  85                  90

Ser Ser Leu Ala Cys Ile Ile Ser Val Val Gly Met Arg Cys Thr
                95                  100                 105

Val Phe Cys Gln Glu Ser Arg Ala Lys Asp Arg Val Ala Val Ala
                110                 115                 120

Gly Gly Val Phe Phe Ile Leu Gly Gly Leu Leu Gly Phe Ile Pro
                125                 130                 135

Val Ala Trp Asn Leu His Gly Ile Leu Arg Asp Phe Tyr Ser Pro
                140                 145                 150

Leu Val Pro Asp Ser Met Lys Phe Glu Ile Gly Glu Ala Leu Tyr
                155                 160                 165

Leu Gly Ile Ile Ser Ser Leu Phe Ser Leu Ile Ala Gly Ile Ile
                170                 175                 180

Leu Cys Phe Ser Cys Ser Ser Gln Arg Asn Arg Ser Asn Tyr Tyr
                185                 190                 195

Asp Ala Tyr Gln Ala Gln Pro Leu Ala Thr Arg Ser Ser Pro Arg
                200                 205                 210

Pro Gly Gln Pro Pro Lys Val Lys Ser Glu Phe Asn Ser Tyr Ser
                215                 220                 225

Leu Thr Gly Tyr Val
                230
```

<210> SEQ ID NO 81
<211> LENGTH: 1732
<212> TYPE: DNA
<213> ORGANISM: Homo Sapien

<400> SEQUENCE: 81

```
cccacgcgtc cgcgcctctc ccttctgctg gaccttcctt cgtctctcca         50

tctctccctc ctttccccgc gttctctttc cacctttctc ttcttcccac        100

cttagacctc ccttcctgcc ctcctttcct gcccaccgct gcttcctggc        150

ccttctccga ccccgctcta gcagcagacc tcctggggtc tgtgggttga        200

tctgtggccc ctgtgcctcc gtgtcctttt cgtctccctt cctcccgact        250

ccgctcccgg accagcggcc tgaccctggg gaaaggatgg ttcccgaggt        300

gagggtcctc tcctccttgc tgggactcgc gctgctctgg ttccccctgg        350

actcccacgc tcgagcccgc ccagacatgt tctgcctttt ccatgggaag        400

agatactccc ccggcgagag ctggcacccc tacttggagc cacaaggcct        450

gatgtactgc ctgcgctgta cctgctcaga gggcgcccat gtgagttgtt        500

accgcctcca ctgtccgcct gtccactgcc cccagcctgt gacggagcca        550

cagcaatgct gtcccaagtg tgtggaacct cacactccct ctggactccg        600

ggccccacca aagtcctgcc agcacaacgg gaccatgtac caacacggag        650

agatcttcag tgcccatgag ctgttcccct cccgcctgcc caaccagtgt        700
```

-continued

```
gtcctctgca gctgcacaga gggccagatc tactgcggcc tcacaacctg         750

ccccgaacca ggctgcccag cacccctccc actgccagac tcctgctgcc         800

aagcctgcaa agatgaggca agtgagcaat cggatgaaga ggacagtgtg         850

cagtcgctcc atggggtgag acatcctcag gatccatgtt ccagtgatgc         900

tgggagaaag agaggcccgg gcaccccagc cccactggc ctcagcgccc         950

ctctgagctt catccctcgc cacttcagac ccaagggagc aggcagcaca        1000

actgtcaaga tcgtcctgaa ggagaaacat aagaaagcct gtgtgcatgg        1050

cgggaagacg tactcccacg gggaggtgtg gcacccggcc ttccgtgcct        1100

tcggcccctt gccctgcatc ctatgcacct gtgaggatgg ccgccaggac        1150

tgccagcgtg tgacctgtcc caccgagtac ccctgccgtc accccgagaa        1200

agtggctggg aagtgctgca agatttgccc agaggacaaa gcagaccctg        1250

gccacagtga gatcagttct accaggtgtc ccaaggcacc gggccgggtc        1300

ctcgtccaca catcggtatc cccaagccca gacaacctgc gtcgctttgc        1350

cctggaacac gaggcctcgg acttggtgga gatctacctc tggaagctgg        1400

taaaagatga ggaaactgag gctcagagag gtgaagtacc tggcccaagg        1450

ccacacagcc agaatcttcc acttgactca gatcaagaaa gtcaggaagc        1500

aagacttcca gaaagaggca cagcacttcc gactgctcgc tggcccccac        1550

gaaggtcact ggaacgtctt cctagcccag accctggagc tgaaggtcac        1600

ggccagtcca gacaaagtga ccaagacata acaaagacct aacagttgca        1650

gatatgagct gtataattgt tgttattata tattaataaa taagaagttg        1700

cattaccctc aaaaaaaaaa aaaaaaaaaa aa                           1732
```

<210> SEQ ID NO 82
<211> LENGTH: 451
<212> TYPE: PRT
<213> ORGANISM: Homo Sapien

<400> SEQUENCE: 82

```
Met Val Pro Glu Val Arg Val Leu Ser Ser Leu Leu Gly Leu Ala
  1               5                  10                  15

Leu Leu Trp Phe Pro Leu Asp Ser His Ala Arg Ala Arg Pro Asp
                 20                  25                  30

Met Phe Cys Leu Phe His Gly Lys Arg Tyr Ser Pro Gly Glu Ser
                 35                  40                  45

Trp His Pro Tyr Leu Glu Pro Gln Gly Leu Met Tyr Cys Leu Arg
                 50                  55                  60

Cys Thr Cys Ser Glu Gly Ala His Val Ser Cys Tyr Arg Leu His
                 65                  70                  75

Cys Pro Pro Val His Cys Pro Gln Pro Val Thr Glu Pro Gln Gln
                 80                  85                  90

Cys Cys Pro Lys Cys Val Glu Pro His Thr Pro Ser Gly Leu Arg
                 95                 100                 105

Ala Pro Pro Lys Ser Cys Gln His Asn Gly Thr Met Tyr Gln His
                110                 115                 120

Gly Glu Ile Phe Ser Ala His Glu Leu Phe Pro Ser Arg Leu Pro
                125                 130                 135

Asn Gln Cys Val Leu Cys Ser Cys Thr Glu Gly Gln Ile Tyr Cys
                140                 145                 150
```

-continued

Gly Leu Thr Thr Cys Pro Glu Pro Gly Cys Pro Ala Pro Leu Pro
155 160 165

Leu Pro Asp Ser Cys Cys Gln Ala Cys Lys Asp Glu Ala Ser Glu
170 175 180

Gln Ser Asp Glu Glu Asp Ser Val Gln Ser Leu His Gly Val Arg
185 190 195

His Pro Gln Asp Pro Cys Ser Ser Asp Ala Gly Arg Lys Arg Gly
200 205 210

Pro Gly Thr Pro Ala Pro Thr Gly Leu Ser Ala Pro Leu Ser Phe
215 220 225

Ile Pro Arg His Phe Arg Pro Lys Gly Ala Gly Ser Thr Thr Val
230 235 240

Lys Ile Val Leu Lys Glu Lys His Lys Lys Ala Cys Val His Gly
245 250 255

Gly Lys Thr Tyr Ser His Gly Glu Val Trp His Pro Ala Phe Arg
260 265 270

Ala Phe Gly Pro Leu Pro Cys Ile Leu Cys Thr Cys Glu Asp Gly
275 280 285

Arg Gln Asp Cys Gln Arg Val Thr Cys Pro Thr Glu Tyr Pro Cys
290 295 300

Arg His Pro Glu Lys Val Ala Gly Lys Cys Cys Lys Ile Cys Pro
305 310 315

Glu Asp Lys Ala Asp Pro Gly His Ser Glu Ile Ser Ser Thr Arg
320 325 330

Cys Pro Lys Ala Pro Gly Arg Val Leu Val His Thr Ser Val Ser
335 340 345

Pro Ser Pro Asp Asn Leu Arg Arg Phe Ala Leu Glu His Glu Ala
350 355 360

Ser Asp Leu Val Glu Ile Tyr Leu Trp Lys Leu Val Lys Asp Glu
365 370 375

Glu Thr Glu Ala Gln Arg Gly Glu Val Pro Gly Pro Arg Pro His
380 385 390

Ser Gln Asn Leu Pro Leu Asp Ser Asp Gln Glu Ser Gln Glu Ala
395 400 405

Arg Leu Pro Glu Arg Gly Thr Ala Leu Pro Thr Ala Arg Trp Pro
410 415 420

Pro Arg Arg Ser Leu Glu Arg Leu Pro Ser Pro Asp Pro Gly Ala
425 430 435

Glu Gly His Gly Gln Ser Arg Gln Ser Asp Gln Asp Ile Thr Lys
440 445 450

Thr

<210> SEQ ID NO 83
<211> LENGTH: 2052
<212> TYPE: DNA
<213> ORGANISM: Homo Sapien

<400> SEQUENCE: 83
gacagctgtg tctcgatgga gtagactctc agaacagcgc agtttgccct 50
ccgctcacgc agagcctctc cgtggcttcc gcaccttgag cattaggcca 100
gttctcctct tctctctaat ccatccgtca cctctcctgt catccgtttc 150
catgccgtga ggtccattca cagaacacat ccatggctct catgctcagt 200

-continued

```
ttggttctga gtctcctcaa gctgggatca gggcagtggc aggtgtttgg      250
gccagacaag cctgtccagg ccttggtggg ggaggacgca gcattctcct      300
gtttcctgtc tcctaagacc aatgcagagg ccatggaagt gcggttcttc      350
aggggccagt tctctagcgt ggtccacctc tacagggacg ggaaggacca      400
gccatttatg cagatgccac agtatcaagg caggacaaaa ctggtgaagg      450
attctattgc ggaggggcgc atctctctga ggctggaaaa cattactgtg      500
ttggatgctg gcctctatgg gtgcaggatt agttcccagt cttactacca      550
gaaggccatc tgggagctac aggtgtcagc actgggctca gttcctctca      600
tttccatcac gggatatgtt gatagagaca tccagctact ctgtcagtcc      650
tcgggctggt tcccccggcc cacagcgaag tggaaaggtc cacaaggaca      700
ggatttgtcc acagactcca ggacaaacag agacatgcat ggcctgtttg      750
atgtggagat ctctctgacc gtccaagaga acgccgggag catatcctgt      800
tccatgcggc atgctcatct gagccgagag gtggaatcca gggtacagat      850
aggagatacc tttttcgagc ctatatcgtg gcacctggct accaaagtac      900
tgggaatact ctgctgtggc ctattttttg gcattgttgg actgaagatt      950
ttcttctcca aattccagtg gaaaatccag gcggaactgg actggagaag     1000
aaagcacgga caggcagaat tgagagacgc ccggaaacac gcagtggagg     1050
tgactctgga tccagagacg gctcacccga agctctgcgt ttctgatctg     1100
aaaactgtaa cccatagaaa agctccccag gaggtgcctc actctgagaa     1150
gagatttaca aggaagagtg tggtggcttc tcagagtttc caagcaggga     1200
aacattactg ggaggtggac ggaggacaca ataaaaggtg gcgcgtggga     1250
gtgtgccggg atgatgtgga caggaggaag gagtacgtga ctttgtctcc     1300
cgatcatggg tactgggtcc tcagactgaa tggagaacat ttgtatttca     1350
cattaaatcc ccgttttatc agcgtcttcc ccaggacccc acctacaaaa     1400
ataggggtct tcctggacta tgagtgtggg accatctcct tcttcaacat     1450
aaatgaccag tcccttattt ataccctgac atgtcggttt gaaggcttat     1500
tgaggcccta cattgagtat ccgtcctata atgagcaaaa tggaactccc     1550
atagtcatct gcccagtcac ccaggaatca gagaaagagg cctcttggca     1600
aagggcctct gcaatcccag agacaagcaa cagtgagtcc tcctcacagg     1650
caaccacgcc cttcctcccc aggggtgaaa tgtaggatga atcacatccc     1700
acattcttct ttagggatat taaggtctct ctcccagatc caaagtcccg     1750
cagcagccgg ccaaggtggc ttccagatga agggggactg gcctgtccac     1800
atgggagtca ggtgtcatgg ctgccctgag ctgggaggga agaaggctga     1850
cattacattt agtttgctct cactccatct ggctaagtga tcttgaaata     1900
ccacctctca ggtgaagaac cgtcaggaat tcccatctca caggctgtgg     1950
tgtagattaa gtagacaagg aatgtgaata atgcttagat cttattgatg     2000
acagagtgta tcctaatggt ttgttcatta tattacactt tcagtaaaaa     2050
aa                                                         2052
```

<210> SEQ ID NO 84
<211> LENGTH: 500

-continued

<212> TYPE: PRT
<213> ORGANISM: Homo Sapien

<400> SEQUENCE: 84

```
Met Ala Leu Met Leu Ser Leu Val Leu Ser Leu Leu Lys Leu Gly
  1               5                  10                  15

Ser Gly Gln Trp Gln Val Phe Gly Pro Asp Lys Pro Val Gln Ala
                 20                  25                  30

Leu Val Gly Glu Asp Ala Ala Phe Ser Cys Phe Leu Ser Pro Lys
                 35                  40                  45

Thr Asn Ala Glu Ala Met Glu Val Arg Phe Phe Arg Gly Gln Phe
                 50                  55                  60

Ser Ser Val Val His Leu Tyr Arg Asp Gly Lys Asp Gln Pro Phe
                 65                  70                  75

Met Gln Met Pro Gln Tyr Gln Gly Arg Thr Lys Leu Val Lys Asp
                 80                  85                  90

Ser Ile Ala Glu Gly Arg Ile Ser Leu Arg Leu Glu Asn Ile Thr
                 95                 100                 105

Val Leu Asp Ala Gly Leu Tyr Gly Cys Arg Ile Ser Ser Gln Ser
                110                 115                 120

Tyr Tyr Gln Lys Ala Ile Trp Glu Leu Gln Val Ser Ala Leu Gly
                125                 130                 135

Ser Val Pro Leu Ile Ser Ile Thr Gly Tyr Val Asp Arg Asp Ile
                140                 145                 150

Gln Leu Leu Cys Gln Ser Ser Gly Trp Phe Pro Arg Pro Thr Ala
                155                 160                 165

Lys Trp Lys Gly Pro Gln Gly Gln Asp Leu Ser Thr Asp Ser Arg
                170                 175                 180

Thr Asn Arg Asp Met His Gly Leu Phe Asp Val Glu Ile Ser Leu
                185                 190                 195

Thr Val Gln Glu Asn Ala Gly Ser Ile Ser Cys Ser Met Arg His
                200                 205                 210

Ala His Leu Ser Arg Glu Val Glu Ser Arg Val Gln Ile Gly Asp
                215                 220                 225

Thr Phe Phe Glu Pro Ile Ser Trp His Leu Ala Thr Lys Val Leu
                230                 235                 240

Gly Ile Leu Cys Cys Gly Leu Phe Phe Gly Ile Val Gly Leu Lys
                245                 250                 255

Ile Phe Phe Ser Lys Phe Gln Trp Lys Ile Gln Ala Glu Leu Asp
                260                 265                 270

Trp Arg Arg Lys His Gly Gln Ala Glu Leu Arg Asp Ala Arg Lys
                275                 280                 285

His Ala Val Glu Val Thr Leu Asp Pro Glu Thr Ala His Pro Lys
                290                 295                 300

Leu Cys Val Ser Asp Leu Lys Thr Val Thr His Arg Lys Ala Pro
                305                 310                 315

Gln Glu Val Pro His Ser Glu Lys Arg Phe Thr Arg Lys Ser Val
                320                 325                 330

Val Ala Ser Gln Ser Phe Gln Ala Gly Lys His Tyr Trp Glu Val
                335                 340                 345

Asp Gly Gly His Asn Lys Arg Trp Arg Val Gly Val Cys Arg Asp
                350                 355                 360

Asp Val Asp Arg Arg Lys Glu Tyr Val Thr Leu Ser Pro Asp His
                365                 370                 375
```

-continued

Gly Tyr Trp Val Leu Arg Leu Asn Gly Glu His Leu Tyr Phe Thr
380 385 390

Leu Asn Pro Arg Phe Ile Ser Val Phe Pro Arg Thr Pro Pro Thr
395 400 405

Lys Ile Gly Val Phe Leu Asp Tyr Glu Cys Gly Thr Ile Ser Phe
410 415 420

Phe Asn Ile Asn Asp Gln Ser Leu Ile Tyr Thr Leu Thr Cys Arg
425 430 435

Phe Glu Gly Leu Leu Arg Pro Tyr Ile Glu Tyr Pro Ser Tyr Asn
440 445 450

Glu Gln Asn Gly Thr Pro Ile Val Ile Cys Pro Val Thr Gln Glu
455 460 465

Ser Glu Lys Glu Ala Ser Trp Gln Arg Ala Ser Ala Ile Pro Glu
470 475 480

Thr Ser Asn Ser Glu Ser Ser Ser Gln Ala Thr Thr Pro Phe Leu
485 490 495

Pro Arg Gly Glu Met
500

<210> SEQ ID NO 85
<211> LENGTH: 1665
<212> TYPE: DNA
<213> ORGANISM: Homo Sapien

<400> SEQUENCE: 85
aacagacgtt ccctcgcggc cctggcacct ctaaccccag acatgctgct 50
gctgctgctg cccctgctct gggggaggga gagggcggaa ggacagacaa 100
gtaaactgct gacgatgcag agttccgtga cggtgcagga aggcctgtgt 150
gtccatgtgc cctgctcctt ctcctacccc tcgcatggct ggatttaccc 200
tggcccagta gttcatggct actggttccg ggaaggggcc aatacagacc 250
aggatgctcc agtggccaca aacaacccag ctcgggcagt gtgggaggag 300
actcgggacc gattccacct ccttggggac ccacatacca agaattgcac 350
cctgagcatc agagatgcca gaagaagtga tgcggggaga tacttctttc 400
gtatggagaa aggaagtata aaatggaatt ataaacatca ccggctctct 450
gtgaatgtga cagccttgac ccacaggccc aacatcctca tcccaggcac 500
cctggagtcc ggctgccccc agaatctgac ctgctctgtg ccctgggcct 550
gtgagcaggg gacacccccct atgatctcct ggatagggac ctccgtgtcc 600
cccctggacc cctccaccac ccgctcctcg gtgctcaccc tcatcccaca 650
gccccaggac catggcacca gcctcacctg tcaggtgacc ttccctgggg 700
ccagcgtgac cacgaacaag accgtccatc tcaacgtgtc ctacccgcct 750
cagaacttga ccatgactgt cttccaagga gacggcacag tatccacagt 800
cttgggaaat ggctcatctc tgtcactccc agagggccag tctctgcgcc 850
tggtctgtgc agttgatgca gttgacagca atcccccctgc caggctgagc 900 ctgagctgga gaggcctgac cctgtgcccc tcacagccct caaacccggg 950
ggtgctggag ctgccttggg tgcacctgag ggatgcagct gaattcacct 1000
gcagagctca gaaccctctc ggctctcagc aggtctacct gaacgtctcc 1050
ctgcagagca aagccacatc aggagtgact caggggggtgg tcgggggagc 1100

-continued

```
tggagccaca gccctggtct tcctgtcctt ctgcgtcatc ttcgttgtag      1150

tgaggtcctg caggaagaaa tcggcaaggc cagcagcggg cgtgggagat      1200

acgggcatag aggatgcaaa cgctgtcagg ggttcagcct ctcaggggcc      1250

cctgactgaa ccttgggcag aagacagtcc cccagaccag cctcccccag      1300

cttctgcccg ctcctcagtg ggggaaggag agctccagta tgcatccctc      1350

agcttccaga tggtgaagcc ttgggactcg cggggacagg aggccactga      1400

caccgagtac tcggagatca agatccacag atgagaaact gcagagactc      1450

accctgattg agggatcaca gcccctccag gcaagggaga agtcagaggc      1500

tgattcttgt agaattaaca gccctcaacg tgatgagcta tgataacact      1550

atgaattatg tgcagagtga aaagcacaca ggctttagag tcaaagtatc      1600

tcaaacctga atccacactg tgccctccct tttatttttt taactaaaag      1650

acagacaaat tccta                                            1665
```

```
<210> SEQ ID NO 86
<211> LENGTH: 463
<212> TYPE: PRT
<213> ORGANISM: Homo Sapien

<400> SEQUENCE: 86

Met Leu Leu Leu Leu Leu Pro Leu Leu Trp Gly Arg Glu Arg Ala
  1               5                  10                  15

Glu Gly Gln Thr Ser Lys Leu Leu Thr Met Gln Ser Ser Val Thr
                 20                  25                  30

Val Gln Glu Gly Leu Cys Val His Val Pro Cys Ser Phe Ser Tyr
                 35                  40                  45

Pro Ser His Gly Trp Ile Tyr Pro Gly Pro Val Val His Gly Tyr
                 50                  55                  60

Trp Phe Arg Glu Gly Ala Asn Thr Asp Gln Asp Ala Pro Val Ala
                 65                  70                  75

Thr Asn Asn Pro Ala Arg Ala Val Trp Glu Glu Thr Arg Asp Arg
                 80                  85                  90

Phe His Leu Leu Gly Asp Pro His Thr Lys Asn Cys Thr Leu Ser
                 95                 100                 105

Ile Arg Asp Ala Arg Arg Ser Asp Ala Gly Arg Tyr Phe Phe Arg
                110                 115                 120

Met Glu Lys Gly Ser Ile Lys Trp Asn Tyr Lys His His Arg Leu
                125                 130                 135

Ser Val Asn Val Thr Ala Leu Thr His Arg Pro Asn Ile Leu Ile
                140                 145                 150

Pro Gly Thr Leu Glu Ser Gly Cys Pro Gln Asn Leu Thr Cys Ser
                155                 160                 165

Val Pro Trp Ala Cys Glu Gln Gly Thr Pro Pro Met Ile Ser Trp
                170                 175                 180

Ile Gly Thr Ser Val Ser Pro Leu Asp Pro Ser Thr Thr Arg Ser
                185                 190                 195

Ser Val Leu Thr Leu Ile Pro Gln Pro Gln Asp His Gly Thr Ser
                200                 205                 210

Leu Thr Cys Gln Val Thr Phe Pro Gly Ala Ser Val Thr Thr Asn
                215                 220                 225

Lys Thr Val His Leu Asn Val Ser Tyr Pro Pro Gln Asn Leu Thr
```

-continued

```
                230                 235                 240

Met Thr Val Phe Gln Gly Asp Gly Thr Val Ser Thr Val Leu Gly
                245                 250                 255

Asn Gly Ser Ser Leu Ser Leu Pro Glu Gly Gln Ser Leu Arg Leu
                260                 265                 270

Val Cys Ala Val Asp Ala Val Asp Ser Asn Pro Pro Ala Arg Leu
                275                 280                 285

Ser Leu Ser Trp Arg Gly Leu Thr Leu Cys Pro Ser Gln Pro Ser
                290                 295                 300

Asn Pro Gly Val Leu Glu Leu Pro Trp Val His Leu Arg Asp Ala
                305                 310                 315

Ala Glu Phe Thr Cys Arg Ala Gln Asn Pro Leu Gly Ser Gln Gln
                320                 325                 330

Val Tyr Leu Asn Val Ser Leu Gln Ser Lys Ala Thr Ser Gly Val
                335                 340                 345

Thr Gln Gly Val Val Gly Gly Ala Gly Ala Thr Ala Leu Val Phe
                350                 355                 360

Leu Ser Phe Cys Val Ile Phe Val Val Val Arg Ser Cys Arg Lys
                365                 370                 375

Lys Ser Ala Arg Pro Ala Ala Gly Val Gly Asp Thr Gly Ile Glu
                380                 385                 390

Asp Ala Asn Ala Val Arg Gly Ser Ala Ser Gln Gly Pro Leu Thr
                395                 400                 405

Glu Pro Trp Ala Glu Asp Ser Pro Pro Asp Gln Pro Pro Pro Ala
                410                 415                 420

Ser Ala Arg Ser Ser Val Gly Glu Gly Glu Leu Gln Tyr Ala Ser
                425                 430                 435

Leu Ser Phe Gln Met Val Lys Pro Trp Asp Ser Arg Gly Gln Glu
                440                 445                 450

Ala Thr Asp Thr Glu Tyr Ser Glu Ile Lys Ile His Arg
                455                 460
```

<210> SEQ ID NO 87
<211> LENGTH: 1176
<212> TYPE: DNA
<213> ORGANISM: Homo Sapien

<400> SEQUENCE: 87

```
agaaagctgc actctgttga gctccagggc gcagtggagg gagggagtga              50

aggagctctc tgtacccaag gaaagtgcag ctgagactca gacaagatta             100

caatgaacca actcagcttc ctgctgtttc tcatagcgac caccagagga             150

tggagtacag atgaggctaa tacttacttc aaggaatgga cctgttcttc             200

gtctccatct ctgcccagaa gctgcaagga aatcaaagac gaatgtccta             250

gtgcatttga tggcctgtat tttctccgca ctgagaatgg tgttatctac             300

cagaccttct gtgacatgac ctctgggggt ggcggctgga ccctggtggc             350

cagcgtgcat gagaatgaca tgcgtgggaa gtgcacggtg ggcgatcgct             400

ggtccagtca gcagggcagc aaagcagact acccagaggg ggacggcaac             450

tgggccaact acaacacctt tggatctgca gaggcggcca cgagcgatga             500

ctacaagaac cctggctact acgacatcca ggccaaggac ctgggcatct             550

ggcacgtgcc caataagtcc cccatgcagc actggagaaa cagctccctg             600
```

-continued

```
ctgaggtacc gcacggacac tggcttcctc cagacactgg gacataatct        650

gtttggcatc taccagaaat atccagtgaa atatggagaa ggaaagtgtt        700

ggactgacaa cggcccggtg atccctgtgg tctatgattt tggcgacgcc        750

cagaaaacag catcttatta ctcaccctat ggccagcggg aattcactgc        800

gggatttgtt cagttcaggg tatttaataa cgagagagca gccaacgcct        850

tgtgtgctgg aatgagggtc accggatgta acactgagca tcactgcatt        900

ggtggaggag gatactttcc agaggccagt ccccagcagt gtggagattt        950

ttctggtttt gattggagtg gatatggaac tcatgttggt tacagcagca       1000

gccgtgagat aactgaggca gctgtgcttc tattctatcg ttgagagttt       1050

tgtgggaggg aacccagacc tctcctccca accatgagat cccaaggatg       1100

gagaacaact tacccagtag ctagaatgtt aatggcagaa gagaaaacaa       1150

taaatcatat tgactcaaga aaaaaa                                 1176
```

```
<210> SEQ ID NO 88
<211> LENGTH: 313
<212> TYPE: PRT
<213> ORGANISM: Homo Sapien

<400> SEQUENCE: 88

Met Asn Gln Leu Ser Phe Leu Leu Phe Leu Ile Ala Thr Thr Arg
  1               5                  10                  15

Gly Trp Ser Thr Asp Glu Ala Asn Thr Tyr Phe Lys Glu Trp Thr
                 20                  25                  30

Cys Ser Ser Ser Pro Ser Leu Pro Arg Ser Cys Lys Glu Ile Lys
                 35                  40                  45

Asp Glu Cys Pro Ser Ala Phe Asp Gly Leu Tyr Phe Leu Arg Thr
                 50                  55                  60

Glu Asn Gly Val Ile Tyr Gln Thr Phe Cys Asp Met Thr Ser Gly
                 65                  70                  75

Gly Gly Gly Trp Thr Leu Val Ala Ser Val His Glu Asn Asp Met
                 80                  85                  90

Arg Gly Lys Cys Thr Val Gly Asp Arg Trp Ser Ser Gln Gln Gly
                 95                 100                 105

Ser Lys Ala Asp Tyr Pro Glu Gly Asp Gly Asn Trp Ala Asn Tyr
                110                 115                 120

Asn Thr Phe Gly Ser Ala Glu Ala Ala Thr Ser Asp Asp Tyr Lys
                125                 130                 135

Asn Pro Gly Tyr Tyr Asp Ile Gln Ala Lys Asp Leu Gly Ile Trp
                140                 145                 150

His Val Pro Asn Lys Ser Pro Met Gln His Trp Arg Asn Ser Ser
                155                 160                 165

Leu Leu Arg Tyr Arg Thr Asp Thr Gly Phe Leu Gln Thr Leu Gly
                170                 175                 180

His Asn Leu Phe Gly Ile Tyr Gln Lys Tyr Pro Val Lys Tyr Gly
                185                 190                 195

Glu Gly Lys Cys Trp Thr Asp Asn Gly Pro Val Ile Pro Val Val
                200                 205                 210

Tyr Asp Phe Gly Asp Ala Gln Lys Thr Ala Ser Tyr Tyr Ser Pro
                215                 220                 225

Tyr Gly Gln Arg Glu Phe Thr Ala Gly Phe Val Gln Phe Arg Val
                230                 235                 240
```

-continued

```
Phe Asn Asn Glu Arg Ala Ala Asn Ala Leu Cys Ala Gly Met Arg
                245                 250                 255

Val Thr Gly Cys Asn Thr Glu His His Cys Ile Gly Gly Gly Gly
                260                 265                 270

Tyr Phe Pro Glu Ala Ser Pro Gln Gln Cys Gly Asp Phe Ser Gly
                275                 280                 285

Phe Asp Trp Ser Gly Tyr Gly Thr His Val Gly Tyr Ser Ser Ser
                290                 295                 300

Arg Glu Ile Thr Glu Ala Ala Val Leu Leu Phe Tyr Arg
                305                 310
```

<210> SEQ ID NO 89
<211> LENGTH: 759
<212> TYPE: DNA
<213> ORGANISM: Homo Sapien

<400> SEQUENCE: 89

```
ctagatttgt cggcttgcgg ggagacttca ggagtcgctg tctctgaact              50

tccagcctca gagaccgccg cccttgtccc cgagggccat gggccgggtc             100

tcagggcttg tgccctctcg cttcctgacg ctcctggcgc atctggtggt             150

cgtcatcacc ttattctggt cccgggacag caacatacag gcctgcctgc             200

ctctcacgtt cacccccgag gagtatgaca agcaggacat tcagctggtg             250

gccgcgctct ctgtcaccct gggcctcttt gcagtggagc tggccggttt             300

cctctcagga gtctccatgt tcaacagcac ccagagcctc atctccattg             350

gggctcactg tagtgcatcc gtggccctgt ccttcttcat attcgagcgt             400

tgggagtgca ctacgtattg gtacattttt gtcttctgca gtgcccttcc             450

agctgtcact gaaatggctt tattcgtcac cgtctttggg ctgaaaaaga             500

aacccttctg attaccttca tgacgggaac ctaaggacga agcctacagg             550

ggcaagggcc gcttcgtatt cctggaagaa ggaaggcata ggcttcggtt             600

ttcccctcgg aaactgcttc tgctggagga tatgtgttgg aataattacg             650

tcttgagtct gggattatcc gcattgtatt tagtgctttg taataaaata             700

tgttttgtag taacattaag acttatatac agttttaggg gacaattaaa             750

aaaaaaaaa                                                          759
```

<210> SEQ ID NO 90
<211> LENGTH: 140
<212> TYPE: PRT
<213> ORGANISM: Homo Sapien

<400> SEQUENCE: 90

```
Met Gly Arg Val Ser Gly Leu Val Pro Ser Arg Phe Leu Thr Leu
  1               5                  10                  15

Leu Ala His Leu Val Val Val Ile Thr Leu Phe Trp Ser Arg Asp
                 20                  25                  30

Ser Asn Ile Gln Ala Cys Leu Pro Leu Thr Phe Thr Pro Glu Glu
                 35                  40                  45

Tyr Asp Lys Gln Asp Ile Gln Leu Val Ala Ala Leu Ser Val Thr
                 50                  55                  60

Leu Gly Leu Phe Ala Val Glu Leu Ala Gly Phe Leu Ser Gly Val
                 65                  70                  75
```

-continued

```
Ser Met Phe Asn Ser Thr Gln Ser Leu Ile Ser Ile Gly Ala His
                80                  85                  90

Cys Ser Ala Ser Val Ala Leu Ser Phe Phe Ile Phe Glu Arg Trp
                95                  100                 105

Glu Cys Thr Thr Tyr Trp Tyr Ile Phe Val Phe Cys Ser Ala Leu
                110                 115                 120

Pro Ala Val Thr Glu Met Ala Leu Phe Val Thr Val Phe Gly Leu
                125                 130                 135

Lys Lys Lys Pro Phe
                140
```

<210> SEQ ID NO 91
<211> LENGTH: 1871
<212> TYPE: DNA
<213> ORGANISM: Homo Sapien

<400> SEQUENCE: 91

```
ctgggacccc gaaaagagaa ggggagagcg aggggacgag agcggaggag      50

gaagatgcaa ctgactcgct gctgcttcgt gttcctggtg cagggtagcc     100

tctatctggt catctgtggc caggatgatg gtcctcccgg ctcagaggac     150

cctgagcgtg atgaccacga gggccagccc cggccccggg tgcctcggaa     200

gcggggccac atctcaccta agtcccgccc catggccaat tccactctcc     250

tagggctgct ggccccgcct ggggaggctt ggggcattct tgggcagccc     300

cccaaccgcc cgaaccacag ccccccaccc tcagccaagg tgaagaaaat     350

ctttggctgg ggcgacttct actccaacat caagacggtg gccctgaacc     400

tgctcgtcac agggaagatt gtggaccatg gcaatgggac cttcagcgtc     450

cacttccaac acaatgccac aggccaggga aacatctcca tcagcctcgt     500

gcccccccagt aaagctgtag agttccacca ggaacagcag atcttcatcg     550

aagccaaggc ctccaaaatc ttcaactgcc ggatggagtg ggagaaggta     600

gaacggggcc gccggacctc gctttgcacc cacgacccag ccaagatctg     650

ctcccgagac cacgctcaga gctcagccac ctggagctgc tcccagccct     700

tcaaagtcgt ctgtgtctac atcgccttct acagcacgga ctatcggctg     750

gtccagaagg tgtgcccaga ttacaactac catagtgata ccccctacta     800

cccatctggg tgacccgggg caggccacag aggccaggcc agggctggaa     850

ggacaggcct gcccatgcag gagaccatct ggacaccggg cagggaaggg     900

gttgggcctc aggcagggag gggggtggag acgaggagat gccaagtggg     950

gccagggcca agtctcaagt ggcagagaaa gggtcccaag tgctggtccc    1000

aacctgaagc tgtggagtga ctagatcaca ggagcactgg aggaggagtg    1050

ggctctctgt gcagcctcac agggctttgc cacggagcca cagagagatg    1100

ctgggtcccc gaggcctgtg ggcaggccga tcagtgtggc cccagatcaa    1150

gtcatgggag gaagctaagc ccttggttct tgccatcctg aggaaagata    1200

gcaacaggga gggggagatt tcatcagtgt ggacagcctg tcaacttagg    1250

atggatggct gagagggctt cctaggagcc agtcagcagg gtggggtggg    1300

gccagaggag ctctccagcc ctgcctagtg ggcgccctga gccccttgtc    1350

gtgtgctgag catggcatga ggctgaagtg gcaaccctgg ggtctttgat    1400
```

-continued

```
gtcttgacag attgaccatc tgtctccagc caggccaccc ctttccaaaa          1450

ttccctcttc tgccagtact ccccctgtac cacccattgc tgatggcaca          1500

cccatcctta agctaagaca ggacgattgt ggtcctccca cactaaggcc          1550

acagcccatc cgcgtgctgt gtgtccctct tccaccccaa cccctgctgg          1600

ctcctctggg agcatccatg tcccggagag ggtccctcca acagtcagcc          1650

tcacctgtca gaccggggtt ctcccggatc tggatggcgc cgccctctca          1700

gcagcgggca cgggtggggc ggggccgggc cgcagagcat gtgctggatc          1750

tgttctgtgt gtctgtctgt gggtgggggg aggggaggga agtcttgtga          1800

aaccgctgat tgctgacttt tgtgtgaaga atcgtgttct tggagcagga          1850

aataaagctt gccccggggc a                                         1871


<210> SEQ ID NO 92
<211> LENGTH: 252
<212> TYPE: PRT
<213> ORGANISM: Homo Sapien

<400> SEQUENCE: 92

Met Gln Leu Thr Arg Cys Cys Phe Val Phe Leu Val Gln Gly Ser
  1               5                  10                  15

Leu Tyr Leu Val Ile Cys Gly Gln Asp Asp Gly Pro Pro Gly Ser
                 20                  25                  30

Glu Asp Pro Glu Arg Asp Asp His Glu Gly Gln Pro Arg Pro Arg
                 35                  40                  45

Val Pro Arg Lys Arg Gly His Ile Ser Pro Lys Ser Arg Pro Met
                 50                  55                  60

Ala Asn Ser Thr Leu Leu Gly Leu Leu Ala Pro Pro Gly Glu Ala
                 65                  70                  75

Trp Gly Ile Leu Gly Gln Pro Pro Asn Arg Pro Asn His Ser Pro
                 80                  85                  90

Pro Pro Ser Ala Lys Val Lys Lys Ile Phe Gly Trp Gly Asp Phe
                 95                 100                 105

Tyr Ser Asn Ile Lys Thr Val Ala Leu Asn Leu Leu Val Thr Gly
                110                 115                 120

Lys Ile Val Asp His Gly Asn Gly Thr Phe Ser Val His Phe Gln
                125                 130                 135

His Asn Ala Thr Gly Gln Gly Asn Ile Ser Ile Ser Leu Val Pro
                140                 145                 150

Pro Ser Lys Ala Val Glu Phe His Gln Glu Gln Gln Ile Phe Ile
                155                 160                 165

Glu Ala Lys Ala Ser Lys Ile Phe Asn Cys Arg Met Glu Trp Glu
                170                 175                 180

Lys Val Glu Arg Gly Arg Arg Thr Ser Leu Cys Thr His Asp Pro
                185                 190                 195

Ala Lys Ile Cys Ser Arg Asp His Ala Gln Ser Ser Ala Thr Trp
                200                 205                 210

Ser Cys Ser Gln Pro Phe Lys Val Val Cys Val Tyr Ile Ala Phe
                215                 220                 225

Tyr Ser Thr Asp Tyr Arg Leu Val Gln Lys Val Cys Pro Asp Tyr
                230                 235                 240

Asn Tyr His Ser Asp Thr Pro Tyr Tyr Pro Ser Gly
                245                 250
```

-continued

<210> SEQ ID NO 93
<211> LENGTH: 902
<212> TYPE: DNA
<213> ORGANISM: Homo Sapien

<400> SEQUENCE: 93
cggtggccat gactgcggcc gtgttcttcg gctgcgcctt cattgccttc 50
gggcctgcgc tcgcccttta tgtcttcacc atcgccatcg agccgttgcg 100
tatcatcttc ctcatcgccg gagctttctt ctggttggtg tctctactga 150
tttcgtccct tgtttggttc atggcaagag tcattattga caacaaagat 200
ggaccaacac agaaatatct gctgatcttt ggagcgtttg tctctgtcta 250
tatccaagaa atgttccgat ttgcatatta taaactctta aaaaaagcca 300
gtgaaggttt gaagagtata aacccaggtg agacagcacc ctctatgcga 350
ctgctggcct atgtttctgg cttgggcttt ggaatcatga gtggagtatt 400
ttcctttgtg aataccctat ctgactcctt ggggccaggc acagtgggca 450
ttcatggaga ttctcctcaa ttcttccttt attcagcttt catgacgctg 500
gtcattatct tgctgcatgt attctggggc attgtatttt ttgatggctg 550
tgagaagaaa aagtggggca tcctccttat cgttctcctg acccacctgc 600
tggtgtcagc ccagaccttc ataagttctt attatggaat aaacctggcg 650
tcagcattta taatcctggt gctcatgggc acctgggcat tcttagctgc 700
gggaggcagc tgccgaagcc tgaaactctg cctgctctgc caagacaaga 750
actttcttct ttacaaccag cgctccagat aacctcaggg aaccagcact 800
tcccaaaccg cagactacat ctttagagga agcacaactg tgcctttttc 850
tgaaaatccc tttttctggt ggaattgaga aagaaataaa actatgcaga 900
ta 902

<210> SEQ ID NO 94
<211> LENGTH: 257
<212> TYPE: PRT
<213> ORGANISM: Homo Sapien

<400> SEQUENCE: 94

Met Thr Ala Ala Val Phe Phe Gly Cys Ala Phe Ile Ala Phe Gly
1 5 10 15

Pro Ala Leu Ala Leu Tyr Val Phe Thr Ile Ala Ile Glu Pro Leu
20 25 30

Arg Ile Ile Phe Leu Ile Ala Gly Ala Phe Phe Trp Leu Val Ser
35 40 45

Leu Leu Ile Ser Ser Leu Val Trp Phe Met Ala Arg Val Ile Ile
50 55 60

Asp Asn Lys Asp Gly Pro Thr Gln Lys Tyr Leu Leu Ile Phe Gly
65 70 75

Ala Phe Val Ser Val Tyr Ile Gln Glu Met Phe Arg Phe Ala Tyr
80 85 90

Tyr Lys Leu Leu Lys Lys Ala Ser Glu Gly Leu Lys Ser Ile Asn
95 100 105

Pro Gly Glu Thr Ala Pro Ser Met Arg Leu Leu Ala Tyr Val Ser
110 115 120

Gly Leu Gly Phe Gly Ile Met Ser Gly Val Phe Ser Phe Val Asn

-continued 125 130 135

Thr Leu Ser Asp Ser Leu Gly Pro Gly Thr Val Gly Ile His Gly
140 145 150

Asp Ser Pro Gln Phe Phe Leu Tyr Ser Ala Phe Met Thr Leu Val
155 160 165

Ile Ile Leu Leu His Val Phe Trp Gly Ile Val Phe Phe Asp Gly
170 175 180

Cys Glu Lys Lys Lys Trp Gly Ile Leu Leu Ile Val Leu Leu Thr
185 190 195

His Leu Leu Val Ser Ala Gln Thr Phe Ile Ser Ser Tyr Tyr Gly
200 205 210

Ile Asn Leu Ala Ser Ala Phe Ile Ile Leu Val Leu Met Gly Thr
215 220 225

Trp Ala Phe Leu Ala Ala Gly Gly Ser Cys Arg Ser Leu Lys Leu
230 235 240

Cys Leu Leu Cys Gln Asp Lys Asn Phe Leu Leu Tyr Asn Gln Arg
245 250 255

Ser Arg

<210> SEQ ID NO 95
<211> LENGTH: 1073
<212> TYPE: DNA
<213> ORGANISM: Homo Sapien

<400> SEQUENCE: 95
aatttttcac cagagtaaac ttgagaaacc aactggacct tgagtattgt 50
acattttgcc tcgtggaccc aaaggtagca atctgaaaca tgaggagtac 100
gattctactg ttttgtcttc taggatcaac tcggtcatta ccacagctca 150
aacctgcttt gggactccct cccacaaaac tggctccgga tcagggaaca 200
ctaccaaacc aacagcagtc aaatcaggtc tttccttctt taagtctgat 250
accattaaca cagatgctca cactggggcc agatctgcat ctgttaaatc 300
ctgctgcagg aatgacacct ggtacccaga cccacccatt gaccctggga 350
gggttgaatg tacaacagca actgcaccca catgtgttac caatttttgt 400
cacacaactt ggagcccagg gcactatcct aagctcagag gaattgccac 450
aaatcttcac gagcctcatc atccattcct tgttcccggg aggcatcctg 500
cccaccagtc aggcaggggc taatccagat gtccaggatg gaagccttcc 550
agcaggagga gcaggtgtaa atcctgccac ccagggaacc ccagcaggcc 600
gcctcccaac tcccagtggc acagatgacg actttgcagt gaccacccct 650
gcaggcatcc aaaggagcac acatgccatc gaggaagcca ccacagaatc 700
agcaaatgga attcagtaag ctgtttcaaa ttttttcaac taagctgcct 750
cgaatttggt gatacatgtg aatctttatc attgattata ttatggaata 800
gattgagaca cattggatag tcttagaaga aattaattct taatttacct 850
gaaaatattc ttgaaatttc agaaaatatg ttctatgtag agaatcccaa 900
cttttaaaaa caataattca atggataaat ctgtctttga aatataacat 950
tatgctgcct ggatgatatg catattaaaa catatttgga aaactggaaa 1000
aaaaaaaaaa aaaaaaaaaa aaaaaaaaaa aaaaaaaaaa aaaaaaaaaa 1050
aaaaaaaaaa aaaaaaaaaa aaa 1073

-continued

<210> SEQ ID NO 96
<211> LENGTH: 209
<212> TYPE: PRT
<213> ORGANISM: Homo Sapien

<400> SEQUENCE: 96

```
Met Arg Ser Thr Ile Leu Leu Phe Cys Leu Leu Gly Ser Thr Arg
  1               5                  10                  15

Ser Leu Pro Gln Leu Lys Pro Ala Leu Gly Leu Pro Pro Thr Lys
                 20                  25                  30

Leu Ala Pro Asp Gln Gly Thr Leu Pro Asn Gln Gln Gln Ser Asn
                 35                  40                  45

Gln Val Phe Pro Ser Leu Ser Leu Ile Pro Leu Thr Gln Met Leu
                 50                  55                  60

Thr Leu Gly Pro Asp Leu His Leu Leu Asn Pro Ala Ala Gly Met
                 65                  70                  75

Thr Pro Gly Thr Gln Thr His Pro Leu Thr Leu Gly Gly Leu Asn
                 80                  85                  90

Val Gln Gln Gln Leu His Pro His Val Leu Pro Ile Phe Val Thr
                 95                 100                 105

Gln Leu Gly Ala Gln Gly Thr Ile Leu Ser Ser Glu Glu Leu Pro
                110                 115                 120

Gln Ile Phe Thr Ser Leu Ile Ile His Ser Leu Phe Pro Gly Gly
                125                 130                 135

Ile Leu Pro Thr Ser Gln Ala Gly Ala Asn Pro Asp Val Gln Asp
                140                 145                 150

Gly Ser Leu Pro Ala Gly Gly Ala Gly Val Asn Pro Ala Thr Gln
                155                 160                 165

Gly Thr Pro Ala Gly Arg Leu Pro Thr Pro Ser Gly Thr Asp Asp
                170                 175                 180

Asp Phe Ala Val Thr Thr Pro Ala Gly Ile Gln Arg Ser Thr His
                185                 190                 195

Ala Ile Glu Glu Ala Thr Thr Glu Ser Ala Asn Gly Ile Gln
                200                 205
```

<210> SEQ ID NO 97
<211> LENGTH: 2848
<212> TYPE: DNA
<213> ORGANISM: Homo Sapien

<400> SEQUENCE: 97

```
gctcaagtgc cctgccttgc cccacccagc ccagcctggc cagagccccc        50

tggagaagga gctctcttct tgcttggcag ctggaccaag ggagccagtc       100

ttgggcgctg gagggcctgt cctgaccatg gtccctgcct ggctgtggct       150

gctttgtgtc tccgtccccc aggctctccc caaggcccag cctgcagagc       200

tgtctgtgga agttccagaa aactatggtg gaaatttccc tttatacctg       250

accaagttgc cgctgccccg tgagggggct gaaggccaga tcgtgctgtc       300

aggggactca ggcaaggcaa ctgagggccc atttgctatg gatccagatt       350

ctggcttcct gctggtgacc agggccctgg accgagagga gcaggcagag       400

taccagctac aggtcaccct ggagatgcag gatggacatg tcttgtgggg       450

tccacagcct gtgcttgtgc acgtgaagga tgagaatgac caggtgcccc       500
```

-continued

```
atttctctca agccatctac agagctcggc tgagccgggg taccaggcct 550
ggcatcccct tcctcttcct tgaggcttca gaccgggatg agccaggcac 600
agccaactcg gatcttcgat tccacatcct gagccaggct ccagcccagc 650
cttccccaga catgttccag ctggagcctc ggctgggggc tctggccctc 700
agccccaagg ggagcaccag ccttgaccac gccctggaga ggacctacca 750
gctgttggta caggtcaagg acatgggtga ccaggcctca ggccaccagg 800
ccactgccac cgtggaagtc tccatcatag agagcacctg ggtgtcccta 850
gagcctatcc acctggcaga gaatctcaaa gtcctatacc cgcaccacat 900
ggcccaggta cactggagtg ggggtgatgt gcactatcac ctggagagcc 950
atcccccggg accctttgaa gtgaatgcag agggaaacct ctacgtgacc 1000
agagagctgg acagagaagc ccaggctgag tacctgctcc aggtgcgggc 1050
tcagaattcc catggcgagg actatgcggc ccctctggag ctgcacgtgc 1100
tggtgatgga tgagaatgac aacgtgccta tctgccctcc ccgtgacccc 1150
acagtcagca tccctgagct cagtccacca ggtactgaag tgactagact 1200
gtcagcagag gatgcagatg cccccggctc ccccaattcc cacgttgtgt 1250
atcagctcct gagccctgag cctgaggatg gggtagaggg gagagccttc 1300
caggtggacc ccacttcagg cagtgtgacg ctgggggtgc tcccactccg 1350
agcaggccag aacatcctgc ttctggtgct ggccatggac ctggcaggcg 1400
cagagggtgg cttcagcagc acgtgtgaag tcgaagtcgc agtcacagat 1450
atcaatgatc acgcccctga gttcatcact tcccagattg ggcctataag 1500
cctccctgag gatgtggagc ccgggactct ggtggccatg ctaacagcca 1550
ttgatgctga cctcgagccc gccttccgcc tcatggattt tgccattgag 1600
aggggagaca cagaagggac ttttggcctg gattgggagc cagactctgg 1650
gcatgttaga ctcagactct gcaagaacct cagttatgag gcagctccaa 1700
gtcatgaggt ggtggtggtg gtgcagagtg tggcgaagct ggtggggcca 1750
ggcccaggcc ctggagccac cgccacggtg actgtgctag tggagagagt 1800
gatgccaccc cccaagttgg accaggagag ctacgaggcc agtgtcccca 1850
tcagtgcccc agccggctct ttcctgctga ccatccagcc ctccgacccc 1900
atcagccgaa ccctcaggtt ctccctagtc aatgactcag agggctggct 1950
ctgcattgag aaattctccg gggaggtgca caccgcccag tccctgcagg 2000
gcgcccagcc tggggacacc tacacggtgc ttgtggaggc ccaggataca 2050
gccctgactc ttgcccctgt gccctcccaa tacctctgca caccccgcca 2100
agaccatggc ttgatcgtga gtggacccag caaggacccc gatctggcca 2150
gtgggcacgg tccctacagc ttcacccttg gtcccaaccc cacggtgcaa 2200
cgggattggc gcctccagac tctcaatggt tcccatgcct acctcacctt 2250
ggccctgcat tgggtggagc cacgtgaaca cataatcccc gtggtggtca 2300
gccacaatgc ccagatgtgg cagctcctgg ttcgagtgat cgtgtgtcgc 2350
tgcaacgtgg aggggcagtg catgcgcaag gtgggccgca tgaagggcat 2400
gcccacgaag ctgtcggcag tgggcatcct tgtaggcacc ctggtagcaa 2450
taggaatctt cctcatcctc attttcaccc actggaccat gtcaaggaag 2500
```

-continued

```
aaggacccgg atcaaccagc agacagcgtg cccctgaagg cgactgtctg           2550

aatggcccag gcagctctag ctgggagctt ggcctctggc tccatctgag           2600

tcccctggga gagagcccag cacccaagat ccagcagggg acaggacaga           2650

gtagaagccc ctccatctgc cctggggtgg aggcaccatc accatcacca           2700

ggcatgtctg cagagcctgg acaccaactt tatggactgc ccatgggagt           2750

gctccaaatg tcagggtgtt tgcccaataa taaagcccca gagaactggg           2800

ctgggcccta tgggaaaaaa aaaaaaaaaa aaaaaaaaaa aaaaaaag             2848
```

```
<210> SEQ ID NO 98
<211> LENGTH: 807
<212> TYPE: PRT
<213> ORGANISM: Homo Sapien

<400> SEQUENCE: 98

Met Val Pro Ala Trp Leu Trp Leu Leu Cys Val Ser Val Pro Gln
  1               5                  10                  15

Ala Leu Pro Lys Ala Gln Pro Ala Glu Leu Ser Val Glu Val Pro
                 20                  25                  30

Glu Asn Tyr Gly Gly Asn Phe Pro Leu Tyr Leu Thr Lys Leu Pro
                 35                  40                  45

Leu Pro Arg Glu Gly Ala Glu Gly Gln Ile Val Leu Ser Gly Asp
                 50                  55                  60

Ser Gly Lys Ala Thr Glu Gly Pro Phe Ala Met Asp Pro Asp Ser
                 65                  70                  75

Gly Phe Leu Leu Val Thr Arg Ala Leu Asp Arg Glu Glu Gln Ala
                 80                  85                  90

Glu Tyr Gln Leu Gln Val Thr Leu Glu Met Gln Asp Gly His Val
                 95                 100                 105

Leu Trp Gly Pro Gln Pro Val Leu Val His Val Lys Asp Glu Asn
                110                 115                 120

Asp Gln Val Pro His Phe Ser Gln Ala Ile Tyr Arg Ala Arg Leu
                125                 130                 135

Ser Arg Gly Thr Arg Pro Gly Ile Pro Phe Leu Phe Leu Glu Ala
                140                 145                 150

Ser Asp Arg Asp Glu Pro Gly Thr Ala Asn Ser Asp Leu Arg Phe
                155                 160                 165

His Ile Leu Ser Gln Ala Pro Ala Gln Pro Ser Pro Asp Met Phe
                170                 175                 180

Gln Leu Glu Pro Arg Leu Gly Ala Leu Ala Leu Ser Pro Lys Gly
                185                 190                 195

Ser Thr Ser Leu Asp His Ala Leu Glu Arg Thr Tyr Gln Leu Leu
                200                 205                 210

Val Gln Val Lys Asp Met Gly Asp Gln Ala Ser Gly His Gln Ala
                215                 220                 225

Thr Ala Thr Val Glu Val Ser Ile Ile Glu Ser Thr Trp Val Ser
                230                 235                 240

Leu Glu Pro Ile His Leu Ala Glu Asn Leu Lys Val Leu Tyr Pro
                245                 250                 255

His His Met Ala Gln Val His Trp Ser Gly Gly Asp Val His Tyr
                260                 265                 270

His Leu Glu Ser His Pro Pro Gly Pro Phe Glu Val Asn Ala Glu
                275                 280                 285
```

-continued

```
Gly Asn Leu Tyr Val Thr Arg Glu Leu Asp Arg Glu Ala Gln Ala
                290                 295                 300

Glu Tyr Leu Leu Gln Val Arg Ala Gln Asn Ser His Gly Glu Asp
                305                 310                 315

Tyr Ala Ala Pro Leu Glu Leu His Val Leu Val Met Asp Glu Asn
                320                 325                 330

Asp Asn Val Pro Ile Cys Pro Pro Arg Asp Pro Thr Val Ser Ile
                335                 340                 345

Pro Glu Leu Ser Pro Pro Gly Thr Glu Val Thr Arg Leu Ser Ala
                350                 355                 360

Glu Asp Ala Asp Ala Pro Gly Ser Pro Asn Ser His Val Val Tyr
                365                 370                 375

Gln Leu Leu Ser Pro Glu Pro Glu Asp Gly Val Glu Gly Arg Ala
                380                 385                 390

Phe Gln Val Asp Pro Thr Ser Gly Ser Val Thr Leu Gly Val Leu
                395                 400                 405

Pro Leu Arg Ala Gly Gln Asn Ile Leu Leu Leu Val Leu Ala Met
                410                 415                 420

Asp Leu Ala Gly Ala Glu Gly Gly Phe Ser Ser Thr Cys Glu Val
                425                 430                 435

Glu Val Ala Val Thr Asp Ile Asn Asp His Ala Pro Glu Phe Ile
                440                 445                 450

Thr Ser Gln Ile Gly Pro Ile Ser Leu Pro Glu Asp Val Glu Pro
                455                 460                 465

Gly Thr Leu Val Ala Met Leu Thr Ala Ile Asp Ala Asp Leu Glu
                470                 475                 480

Pro Ala Phe Arg Leu Met Asp Phe Ala Ile Glu Arg Gly Asp Thr
                485                 490                 495

Glu Gly Thr Phe Gly Leu Asp Trp Glu Pro Asp Ser Gly His Val
                500                 505                 510

Arg Leu Arg Leu Cys Lys Asn Leu Ser Tyr Glu Ala Ala Pro Ser
                515                 520                 525

His Glu Val Val Val Val Val Gln Ser Val Ala Lys Leu Val Gly
                530                 535                 540

Pro Gly Pro Gly Pro Gly Ala Thr Ala Thr Val Thr Val Leu Val
                545                 550                 555

Glu Arg Val Met Pro Pro Pro Lys Leu Asp Gln Glu Ser Tyr Glu
                560                 565                 570

Ala Ser Val Pro Ile Ser Ala Pro Ala Gly Ser Phe Leu Leu Thr
                575                 580                 585

Ile Gln Pro Ser Asp Pro Ile Ser Arg Thr Leu Arg Phe Ser Leu
                590                 595                 600

Val Asn Asp Ser Glu Gly Trp Leu Cys Ile Glu Lys Phe Ser Gly
                605                 610                 615

Glu Val His Thr Ala Gln Ser Leu Gln Gly Ala Gln Pro Gly Asp
                620                 625                 630

Thr Tyr Thr Val Leu Val Glu Ala Gln Asp Thr Ala Leu Thr Leu
                635                 640                 645

Ala Pro Val Pro Ser Gln Tyr Leu Cys Thr Pro Arg Gln Asp His
                650                 655                 660

Gly Leu Ile Val Ser Gly Pro Ser Lys Asp Pro Asp Leu Ala Ser
                665                 670                 675
```

-continued

```
Gly His Gly Pro Tyr Ser Phe Thr Leu Gly Pro Asn Pro Thr Val
                680                 685                 690

Gln Arg Asp Trp Arg Leu Gln Thr Leu Asn Gly Ser His Ala Tyr
                695                 700                 705

Leu Thr Leu Ala Leu His Trp Val Glu Pro Arg Glu His Ile Ile
                710                 715                 720

Pro Val Val Val Ser His Asn Ala Gln Met Trp Gln Leu Leu Val
                725                 730                 735

Arg Val Ile Val Cys Arg Cys Asn Val Glu Gly Gln Cys Met Arg
                740                 745                 750

Lys Val Gly Arg Met Lys Gly Met Pro Thr Lys Leu Ser Ala Val
                755                 760                 765

Gly Ile Leu Val Gly Thr Leu Val Ala Ile Gly Ile Phe Leu Ile
                770                 775                 780

Leu Ile Phe Thr His Trp Thr Met Ser Arg Lys Lys Asp Pro Asp
                785                 790                 795

Gln Pro Ala Asp Ser Val Pro Leu Lys Ala Thr Val
                800                 805
```

<210> SEQ ID NO 99
<211> LENGTH: 2436
<212> TYPE: DNA
<213> ORGANISM: Homo Sapien

<400> SEQUENCE: 99

```
ggctgaccgt gctacattgc ctggaggaag cctaaggaac ccaggcatcc      50

agctgcccac gcctgagtcc aagattcttc ccaggaacac aaacgtagga     100

gacccacgct cctggaagca ccagccttta tctcttcacc ttcaagtccc     150

ctttctcaag aatcctctgt tctttgccct ctaaagtctt ggtacatcta     200

ggacccaggc atcttgcttt ccagccacaa agagacagat gaagatgcag     250

aaaggaaatg ttctccttat gtttggtcta ctattgcatt tagaagctgc     300

aacaaattcc aatgagacta gcacctctgc caacactgga tccagtgtga     350

tctccagtgg agccagcaca gccaccaact ctgggtccag tgtgacctcc     400

agtggggtca gcacagccac catctcaggg tccagcgtga cctccaatgg     450

ggtcagcata gtcaccaact ctgagttcca tacaacctcc agtgggatca     500

gcacagccac caactctgag ttcagcacag cgtccagtgg gatcagcata     550

gccaccaact ctgagtccag cacaacctcc agtggggcca gcacagccac     600

caactctgag tccagcacac cctccagtgg ggccagcaca gtcaccaact     650

ctgggtccag tgtgacctcc agtggagcca gcactgccac caactctgag     700

tccagcacag tgtccagtag ggccagcact gccaccaact ctgagtctag     750

cacactctcc agtggggcca gcacagccac caactctgac tccagcacaa     800

cctccagtgg ggctagcaca gccaccaact ctgagtccag cacaacctcc     850

agtggggcca gcacagccac caactctgag tccagcacag tgtccagtag     900

ggccagcact gccaccaact ctgagtccag cacaacctcc agtggggcca     950

gcacagccac caactctgag tccagaacga cctccaatgg ggctggcaca    1000

gccaccaact ctgagtccag cacgacctcc agtggggcca gcacagccac    1050

caactctgac tccagcacag tgtccagtgg ggccagcact gccaccaact    1100
```

-continued

```
ctgagtccag cacgacctcc agtggggcca gcacagccac caactctgag          1150
tccagcacga cctccagtgg ggctagcaca gccaccaact ctgactccag          1200
cacaacctcc agtggggccg gcacagccac caactctgag tccagcacag          1250
tgtccagtgg gatcagcaca gtcaccaatt ctgagtccag cacaccctcc          1300
agtggggcca acacagccac caactctgag tccagtacga cctccagtgg          1350
ggccaacaca gccaccaact ctgagtccag cacagtgtcc agtggggcca          1400
gcactgccac caactctgag tccagcacaa cctccagtgg ggtcagcaca          1450
gccaccaact ctgagtccag cacaacctcc agtggggcta gcacagccac          1500
caactctgac tccagcacaa cctccagtga ggccagcaca gccaccaact          1550
ctgagtctag cacagtgtcc agtgggatca gcacagtcac caattctgag          1600
tccagcacaa cctccagtgg ggccaacaca gccaccaact ctgggtccag          1650
tgtgacctct gcaggctctg gaacagcagc tctgactgga atgcacacaa          1700
cttcccatag tgcatctact gcagtgagtg aggcaaagcc tggtgggtcc          1750
ctggtgccgt gggaaatctt cctcatcacc ctggtctcgg ttgtggcggc          1800
cgtggggctc tttgctgggc tcttcttctg tgtgagaaac agcctgtccc          1850
tgagaaacac ctttaacaca gctgtctacc accctcatgg cctcaaccat          1900
ggccttggtc caggccctgg agggaatcat ggagcccccc acaggcccag          1950
gtggagtcct aactggttct ggaggagacc agtatcatcg atagccatgg          2000
agatgagcgg gaggaacagc gggccctgag cagccccgga agcaagtgcc          2050
gcattcttca ggaaggaaga gacctgggca cccaagacct ggtttccttt          2100
cattcatccc aggagacccc tcccagcttt gtttgagatc ctgaaaatct          2150
tgaagaaggt attcctcacc tttcttgcct ttaccagaca ctggaaagag          2200
aatactatat tgctcattta gctaagaaat aaatacatct catctaacac          2250
acacgacaaa gagaagctgt gcttgccccg gggtgggtat ctagctctga          2300
gatgaactca gttataggag aaaacctcca tgctggactc catctggcat          2350
tcaaaatctc cacagtaaaa tccaaagacc tcaaaaaaaa aaaaaaaaaa          2400
aaaaaaaaaa aaaaaaaaaa aaaaaaaaaa aaaaaa                          2436

<210> SEQ ID NO 100
<211> LENGTH: 596
<212> TYPE: PRT
<213> ORGANISM: Homo Sapien

<400> SEQUENCE: 100

Met Lys Met Gln Lys Gly Asn Val Leu Leu Met Phe Gly Leu Leu
  1               5                  10                  15

Leu His Leu Glu Ala Ala Thr Asn Ser Asn Glu Thr Ser Thr Ser
                 20                  25                  30

Ala Asn Thr Gly Ser Ser Val Ile Ser Ser Gly Ala Ser Thr Ala
                 35                  40                  45

Thr Asn Ser Gly Ser Ser Val Thr Ser Ser Gly Val Ser Thr Ala
                 50                  55                  60

Thr Ile Ser Gly Ser Ser Val Thr Ser Asn Gly Val Ser Ile Val
                 65                  70                  75

Thr Asn Ser Glu Phe His Thr Thr Ser Ser Gly Ile Ser Thr Ala
                 80                  85                  90
```

-continued

```
Thr Asn Ser Glu Phe Ser Thr Ala Ser Ser Gly Ile Ser Ile Ala
                 95                 100                 105

Thr Asn Ser Glu Ser Ser Thr Thr Ser Ser Gly Ala Ser Thr Ala
                110                 115                 120

Thr Asn Ser Glu Ser Ser Thr Pro Ser Ser Gly Ala Ser Thr Val
                125                 130                 135

Thr Asn Ser Gly Ser Ser Val Thr Ser Ser Gly Ala Ser Thr Ala
                140                 145                 150

Thr Asn Ser Glu Ser Ser Thr Val Ser Ser Arg Ala Ser Thr Ala
                155                 160                 165

Thr Asn Ser Glu Ser Ser Thr Leu Ser Ser Gly Ala Ser Thr Ala
                170                 175                 180

Thr Asn Ser Asp Ser Ser Thr Thr Ser Ser Gly Ala Ser Thr Ala
                185                 190                 195

Thr Asn Ser Glu Ser Ser Thr Thr Ser Ser Gly Ala Ser Thr Ala
                200                 205                 210

Thr Asn Ser Glu Ser Ser Thr Val Ser Ser Arg Ala Ser Thr Ala
                215                 220                 225

Thr Asn Ser Glu Ser Ser Thr Thr Ser Ser Gly Ala Ser Thr Ala
                230                 235                 240

Thr Asn Ser Glu Ser Arg Thr Thr Ser Asn Gly Ala Gly Thr Ala
                245                 250                 255

Thr Asn Ser Glu Ser Ser Thr Thr Ser Ser Gly Ala Ser Thr Ala
                260                 265                 270

Thr Asn Ser Asp Ser Ser Thr Val Ser Ser Gly Ala Ser Thr Ala
                275                 280                 285

Thr Asn Ser Glu Ser Ser Thr Thr Ser Ser Gly Ala Ser Thr Ala
                290                 295                 300

Thr Asn Ser Glu Ser Ser Thr Thr Ser Ser Gly Ala Ser Thr Ala
                305                 310                 315

Thr Asn Ser Asp Ser Ser Thr Thr Ser Ser Gly Ala Gly Thr Ala
                320                 325                 330

Thr Asn Ser Glu Ser Ser Thr Val Ser Ser Gly Ile Ser Thr Val
                335                 340                 345

Thr Asn Ser Glu Ser Ser Thr Pro Ser Ser Gly Ala Asn Thr Ala
                350                 355                 360

Thr Asn Ser Glu Ser Ser Thr Thr Ser Ser Gly Ala Asn Thr Ala
                365                 370                 375

Thr Asn Ser Glu Ser Ser Thr Val Ser Ser Gly Ala Ser Thr Ala
                380                 385                 390

Thr Asn Ser Glu Ser Ser Thr Thr Ser Ser Gly Val Ser Thr Ala
                395                 400                 405

Thr Asn Ser Glu Ser Ser Thr Thr Ser Ser Gly Ala Ser Thr Ala
                410                 415                 420

Thr Asn Ser Asp Ser Ser Thr Thr Ser Ser Glu Ala Ser Thr Ala
                425                 430                 435

Thr Asn Ser Glu Ser Ser Thr Val Ser Ser Gly Ile Ser Thr Val
                440                 445                 450

Thr Asn Ser Glu Ser Ser Thr Thr Ser Ser Gly Ala Asn Thr Ala
                455                 460                 465

Thr Asn Ser Gly Ser Ser Val Thr Ser Ala Gly Ser Gly Thr Ala
                470                 475                 480
```

-continued

```
Ala Leu Thr Gly Met His Thr Thr Ser His Ser Ala Ser Thr Ala
                485                 490                 495

Val Ser Glu Ala Lys Pro Gly Gly Ser Leu Val Pro Trp Glu Ile
                500                 505                 510

Phe Leu Ile Thr Leu Val Ser Val Val Ala Ala Val Gly Leu Phe
                515                 520                 525

Ala Gly Leu Phe Phe Cys Val Arg Asn Ser Leu Ser Leu Arg Asn
                530                 535                 540

Thr Phe Asn Thr Ala Val Tyr His Pro His Gly Leu Asn His Gly
                545                 550                 555

Leu Gly Pro Gly Pro Gly Gly Asn His Gly Ala Pro His Arg Pro
                560                 565                 570

Arg Trp Ser Pro Asn Trp Phe Trp Arg Arg Pro Val Ser Ser Ile
                575                 580                 585

Ala Met Glu Met Ser Gly Arg Asn Ser Gly Pro
                590                 595


<210> SEQ ID NO 101
<211> LENGTH: 1728
<212> TYPE: DNA
<213> ORGANISM: Homo Sapien

<400> SEQUENCE: 101

ggccggacgc ctccgcgtta cgggatgaat taacggcggg ttccgcacgg             50

aggttgtgac ccctacggag ccccagcttg cccacgcacc ccactcggcg            100

tcgcgcggcg tgccctgctt gtcacaggtg ggaggctgga actatcaggc            150

tgaaaaacag agtgggtact ctcttctggg aagctggcaa caaatggatg            200

atgtgatata tgcattccag gggaagggaa attgtggtgc ttctgaaccc            250

atggtcaatt aacgaggcag tttctagcta ctgcacgtac ttcataaagc            300

aggactctaa aagctttgga atcatggtgt catggaaagg gatttacttt            350

atactgactc tgttttgggg aagctttttt ggaagcattt tcatgctgag            400

tcccttttta cctttgatgt ttgtaaaccc atcttggtat cgctggatca            450

acaaccgcct tgtggcaaca tggctcaccc tacctgtggc attattggag            500

accatgtttg gtgtaaaagt gattataact ggggatgcat ttgttcctgg            550

agaaagaagt gtcattatca tgaaccatcg gacaagaatg gactggatgt            600

tcctgtggaa ttgcctgatg cgatatagct acctcagatt ggagaaaatt            650

tgcctcaaag cgagtctcaa aggtgttcct ggatttggtt gggccatgca            700

ggctgctgcc tatatcttca ttcataggaa atggaaggat gacaagagcc            750

atttcgaaga catgattgat tacttttgtg atattcacga accacttcaa            800

ctcctcatat tcccagaagg gactgatctc acagaaaaca gcaagtctcg            850

aagtaatgca tttgctgaaa aaaatggact tcagaaatat gaatatgttt            900

tacatccaag aactacaggc tttacttttg tggtagaccg tctaagagaa            950

ggtaagaacc ttgatgctgt ccatgatatc actgtggcgt atcctcacaa           1000

cattcctcaa tcagagaagc acctcctcca aggagacttt cccagggaaa           1050

tccactttca cgtccaccgg tatccaatag acaccctccc cacatccaag           1100

gaggaccttc aactctggtg ccacaaacgg tgggaagaga aagaagagag           1150

gctgcgttcc ttctatcaag ggagaagaa tttttatttt accggacaga            1200
```

-continued

```
gtgtcattcc accttgcaag tctgaactca gggtccttgt ggtcaaattg          1250

ctctctatac tgtattggac cctgttcagc cctgcaatgt gcctactcat          1300

atatttgtac agtcttgtta agtggtattt tataatcacc attgtaatct          1350

ttgtgctgca agagagaata tttggtggac tggagatcat agaacttgca          1400

tgttaccgac ttttacacaa acagccacat ttaaattcaa agaaaaatga          1450

gtaagattat aaggtttgcc atgtgaaaac ctagagcata ttttggaaat          1500

gttctaaacc tttctaagct cagatgcatt tttgcatgac tatgtcgaat          1550

atttcttact gccatcatta tttgttaaag atattttgca cttaattttg          1600

tgggaaaaat attgctacaa tttttttaa tctctgaatg taatttcgat          1650

actgtgtaca tagcagggag tgatcggggt gaaataactt gggccagaat          1700

attattaaac aatcatcagg cttttaaa                                 1728


<210> SEQ ID NO 102
<211> LENGTH: 414
<212> TYPE: PRT
<213> ORGANISM: Homo Sapien

<400> SEQUENCE: 102

Met His Ser Arg Gly Arg Glu Ile Val Val Leu Leu Asn Pro Trp
1               5                   10                  15

Ser Ile Asn Glu Ala Val Ser Ser Tyr Cys Thr Tyr Phe Ile Lys
                20                  25                  30

Gln Asp Ser Lys Ser Phe Gly Ile Met Val Ser Trp Lys Gly Ile
                35                  40                  45

Tyr Phe Ile Leu Thr Leu Phe Trp Gly Ser Phe Phe Gly Ser Ile
                50                  55                  60

Phe Met Leu Ser Pro Phe Leu Pro Leu Met Phe Val Asn Pro Ser
                65                  70                  75

Trp Tyr Arg Trp Ile Asn Asn Arg Leu Val Ala Thr Trp Leu Thr
                80                  85                  90

Leu Pro Val Ala Leu Leu Glu Thr Met Phe Gly Val Lys Val Ile
                95                  100                 105

Ile Thr Gly Asp Ala Phe Val Pro Gly Glu Arg Ser Val Ile Ile
                110                 115                 120

Met Asn His Arg Thr Arg Met Asp Trp Met Phe Leu Trp Asn Cys
                125                 130                 135

Leu Met Arg Tyr Ser Tyr Leu Arg Leu Glu Lys Ile Cys Leu Lys
                140                 145                 150

Ala Ser Leu Lys Gly Val Pro Gly Phe Gly Trp Ala Met Gln Ala
                155                 160                 165

Ala Ala Tyr Ile Phe Ile His Arg Lys Trp Lys Asp Asp Lys Ser
                170                 175                 180

His Phe Glu Asp Met Ile Asp Tyr Phe Cys Asp Ile His Glu Pro
                185                 190                 195

Leu Gln Leu Leu Ile Phe Pro Glu Gly Thr Asp Leu Thr Glu Asn
                200                 205                 210

Ser Lys Ser Arg Ser Asn Ala Phe Ala Glu Lys Asn Gly Leu Gln
                215                 220                 225

Lys Tyr Glu Tyr Val Leu His Pro Arg Thr Thr Gly Phe Thr Phe
                230                 235                 240
```

-continued

```
Val Val Asp Arg Leu Arg Glu Gly Lys Asn Leu Asp Ala Val His
                245                 250                 255

Asp Ile Thr Val Ala Tyr Pro His Asn Ile Pro Gln Ser Glu Lys
                260                 265                 270

His Leu Leu Gln Gly Asp Phe Pro Arg Glu Ile His Phe His Val
                275                 280                 285

His Arg Tyr Pro Ile Asp Thr Leu Pro Thr Ser Lys Glu Asp Leu
                290                 295                 300

Gln Leu Trp Cys His Lys Arg Trp Glu Glu Lys Glu Glu Arg Leu
                305                 310                 315

Arg Ser Phe Tyr Gln Gly Glu Lys Asn Phe Tyr Phe Thr Gly Gln
                320                 325                 330

Ser Val Ile Pro Pro Cys Lys Ser Glu Leu Arg Val Leu Val Val
                335                 340                 345

Lys Leu Leu Ser Ile Leu Tyr Trp Thr Leu Phe Ser Pro Ala Met
                350                 355                 360

Cys Leu Leu Ile Tyr Leu Tyr Ser Leu Val Lys Trp Tyr Phe Ile
                365                 370                 375

Ile Thr Ile Val Ile Phe Val Leu Gln Glu Arg Ile Phe Gly Gly
                380                 385                 390

Leu Glu Ile Ile Glu Leu Ala Cys Tyr Arg Leu Leu His Lys Gln
                395                 400                 405

Pro His Leu Asn Ser Lys Lys Asn Glu
                410
```

<210> SEQ ID NO 103
<211> LENGTH: 2403
<212> TYPE: DNA
<213> ORGANISM: Homo Sapien

<400> SEQUENCE: 103

```
cggctcgagc ggctcgagtg aagagcctct ccacggctcc tgcgcctgag          50

acagctggcc tgacctccaa atcatccatc cacccctgct gtcatctgtt         100

ttcatagtgt gagatcaacc cacaggaata tccatggctt ttgtgctcat         150

tttggttctc agtttctacg agctggtgtc aggacagtgg caagtcactg         200

gaccgggcaa gtttgtccag gccttggtgg gggaggacgc cgtgttctcc         250

tgctccctct ttcctgagac cagtgcagag gctatggaag tgcggttctt         300

caggaatcag ttccatgctg tggtccacct ctacagagat ggggaagact         350

gggaatctaa gcagatgcca cagtatcgag ggagaactga gtttgtgaag         400

gactccattg cagggggggcg tgtctctcta aggctaaaaa acatcactcc         450

ctcggacatc ggcctgtatg ggtgctggtt cagttcccag atttacgatg         500

aggaggccac ctgggagctg cgggtggcag cactgggctc acttcctctc         550

atttccatcg tgggatatgt tgacggaggt atccagttac tctgcctgtc         600

ctcaggctgg ttcccccagc ccacagccaa gtggaaaggt ccacaaggac         650

aggatttgtc ttcagactcc agagcaaatg cagatgggta cagcctgtat         700

gatgtggaga tctccattat agtccaggaa aatgctggga gcatattgtg         750

ttccatccac cttgctgagc agagtcatga ggtggaatcc aaggtattga         800

taggagagac gtttttccag ccctcacctt ggcgcctggc ttctatttta         850

ctcgggttac tctgtggtgc cctgtgtggt gttgtcatgg ggatgataat         900
```

-continued

```
tgttttcttc aaatccaaag ggaaaatcca ggcggaactg gactggagaa        950

gaaagcacgg acaggcagaa ttgagagacg cccggaaaca cgcagtggag       1000

gtgactctgg atccagagac ggctcacccg aagctctgcg tttctgatct       1050

gaaaactgta acccatagaa aagctcccca ggaggtgcct cactctgaga       1100

agagatttac aaggaagagt gtggtggctt ctcagggttt ccaagcaggg       1150

agacattact gggaggtgga cgtgggacaa aatgtagggt ggtatgtggg       1200

agtgtgtcgg gatgacgtag acagggggaa gaacaatgtg actttgtctc       1250

ccaacaatgg gtattgggtc ctcagactga caacagaaca tttgtatttc       1300

acattcaatc cccattttat cagcctcccc cccagcaccc ctcctacacg       1350

agtaggggtc ttcctggact atgagggtgg gaccatctcc ttcttcaata       1400

caaatgacca gtcccttatt tataccctgc tgacatgtca gtttgaaggc       1450

ttgttgagac cctatatcca gcatgcgatg tatgacgagg aaaaggggac       1500

tcccatattc atatgtccag tgtcctgggg atgagacaga gaagaccctg       1550

cttaaagggc cccacaccac agacccagac acagccaagg gagagtgctc       1600

ccgacaggtg gccccagctt cctctccgga gcctgcgcac agagagtcac       1650

gccccccact ctcctttagg gagctgaggt tcttctgccc tgagccctgc       1700

agcagcggca gtcacagctt ccagatgagg ggggattggc ctgaccctgt       1750

gggagtcaga agccatggct gccctgaagt ggggacggaa tagactcaca       1800

ttaggtttag tttgtgaaaa ctccatccag ctaagcgatc ttgaacaagt       1850

cacaacctcc caggctcctc atttgctagt cacggacagt gattcctgcc       1900

tcacaggtga agattaaaga gacaacgaat gtgaatcatg cttgcaggtt       1950

tgagggcaca gtgtttgcta atgatgtgtt tttatattat acattttccc       2000

accataaact ctgtttgctt attccacatt aatttacttt tctctatacc       2050

aaatcaccca tggaatagtt attgaacacc tgctttgtga ggctcaaaga       2100

ataaagagga ggtaggattt ttcactgatt ctataagccc agcattacct       2150

gataccaaaa ccaggcaaag aaaacagaag aagaggaagg aaaactacag       2200

gtccatatcc ctcattaaca cagacacaaa aattctaaat aaaattttaa       2250

caaattaaac taaacaatat atttaaagat gatatataac tactcagtgt       2300

ggtttgtccc acaaatgcag agttggttta atatttaaat atcaaccagt       2350

gtaattcagc acattaataa agtaaaaaag aaaaccataa aaaaaaaaaa       2400

aaa 2403

<210> SEQ ID NO 104
<211> LENGTH: 466
<212> TYPE: PRT
<213> ORGANISM: Homo Sapien

<400> SEQUENCE: 104

Met Ala Phe Val Leu Ile Leu Val Leu Ser Phe Tyr Glu Leu Val
  1               5                  10                  15

Ser Gly Gln Trp Gln Val Thr Gly Pro Gly Lys Phe Val Gln Ala
                 20                  25                  30

Leu Val Gly Glu Asp Ala Val Phe Ser Cys Ser Leu Phe Pro Glu
                 35                  40                  45
```

-continued

```
Thr Ser Ala Glu Ala Met Glu Val Arg Phe Phe Arg Asn Gln Phe
                50                  55                  60

His Ala Val Val His Leu Tyr Arg Asp Gly Glu Asp Trp Glu Ser
                65                  70                  75

Lys Gln Met Pro Gln Tyr Arg Gly Arg Thr Glu Phe Val Lys Asp
                80                  85                  90

Ser Ile Ala Gly Gly Arg Val Ser Leu Arg Leu Lys Asn Ile Thr
                95                 100                 105

Pro Ser Asp Ile Gly Leu Tyr Gly Cys Trp Phe Ser Ser Gln Ile
               110                 115                 120

Tyr Asp Glu Glu Ala Thr Trp Glu Leu Arg Val Ala Ala Leu Gly
               125                 130                 135

Ser Leu Pro Leu Ile Ser Ile Val Gly Tyr Val Asp Gly Gly Ile
               140                 145                 150

Gln Leu Leu Cys Leu Ser Ser Gly Trp Phe Pro Gln Pro Thr Ala
               155                 160                 165

Lys Trp Lys Gly Pro Gln Gly Gln Asp Leu Ser Ser Asp Ser Arg
               170                 175                 180

Ala Asn Ala Asp Gly Tyr Ser Leu Tyr Asp Val Glu Ile Ser Ile
               185                 190                 195

Ile Val Gln Glu Asn Ala Gly Ser Ile Leu Cys Ser Ile His Leu
               200                 205                 210

Ala Glu Gln Ser His Glu Val Glu Ser Lys Val Leu Ile Gly Glu
               215                 220                 225

Thr Phe Phe Gln Pro Ser Pro Trp Arg Leu Ala Ser Ile Leu Leu
               230                 235                 240

Gly Leu Leu Cys Gly Ala Leu Cys Gly Val Val Met Gly Met Ile
               245                 250                 255

Ile Val Phe Phe Lys Ser Lys Gly Lys Ile Gln Ala Glu Leu Asp
               260                 265                 270

Trp Arg Arg Lys His Gly Gln Ala Glu Leu Arg Asp Ala Arg Lys
               275                 280                 285

His Ala Val Glu Val Thr Leu Asp Pro Glu Thr Ala His Pro Lys
               290                 295                 300

Leu Cys Val Ser Asp Leu Lys Thr Val Thr His Arg Lys Ala Pro
               305                 310                 315

Gln Glu Val Pro His Ser Glu Lys Arg Phe Thr Arg Lys Ser Val
               320                 325                 330

Val Ala Ser Gln Gly Phe Gln Ala Gly Arg His Tyr Trp Glu Val
               335                 340                 345

Asp Val Gly Gln Asn Val Gly Trp Tyr Val Gly Val Cys Arg Asp
               350                 355                 360

Asp Val Asp Arg Gly Lys Asn Asn Val Thr Leu Ser Pro Asn Asn
               365                 370                 375

Gly Tyr Trp Val Leu Arg Leu Thr Thr Glu His Leu Tyr Phe Thr
               380                 385                 390

Phe Asn Pro His Phe Ile Ser Leu Pro Pro Ser Thr Pro Pro Thr
               395                 400                 405

Arg Val Gly Val Phe Leu Asp Tyr Glu Gly Gly Thr Ile Ser Phe
               410                 415                 420

Phe Asn Thr Asn Asp Gln Ser Leu Ile Tyr Thr Leu Leu Thr Cys
               425                 430                 435
```

-continued

```
Gln Phe Glu Gly Leu Leu Arg Pro Tyr Ile Gln His Ala Met Tyr
                440                 445                 450

Asp Glu Glu Lys Gly Thr Pro Ile Phe Ile Cys Pro Val Ser Trp
                455                 460                 465

Gly
```

<210> SEQ ID NO 105
<211> LENGTH: 2103
<212> TYPE: DNA
<213> ORGANISM: Homo Sapien

<400> SEQUENCE: 105

```
ccttcacagg actcttcatt gctggttggc aatgatgtat cggccagatg      50

tggtgagggc taggaaaaga gtttgttggg aaccctgggt tatcggcctc     100

gtcatcttca tatccctgat tgtcctggca gtgtgcattg gactcactgt     150

tcattatgtg agatataatc aaaagaagac ctacaattac tatagcacat     200

tgtcatttac aactgacaaa ctatatgctg agtttggcag agaggcttct     250

aacaatttta cagaaatgag ccagagactt gaatcaatgg tgaaaaatgc     300

attttataaa tctccattaa gggaagaatt tgtcaagtct caggttatca     350

agttcagtca acagaagcat ggagtgttgg ctcatatgct gttgatttgt     400

agatttcact ctactgagga tcctgaaact gtagataaaa ttgttcaact     450

tgttttacat gaaaagctgc aagatgctgt aggacccccc aaagtagatc     500

ctcactcagt taaaattaaa aaaatcaaca agacagaaac agacagctat     550

ctaaaccatt gctgcggaac acgaagaagt aaaactctag gtcagagtct     600

caggatcgtt ggtgggacag aagtagaaga gggtgaatgg ccctggcagg     650

ctagcctgca gtgggatggg agtcatcgct gtggagcaac cttaattaat     700

gccacatggc ttgtgagtgc tgctcactgt tttacaacat ataagaaccc     750

tgccagatgg actgcttcct ttggagtaac aataaaacct tcgaaaatga     800

aacggggtct ccggagaata attgtccatg aaaaatacaa acacccatca     850

catgactatg atatttctct tgcagagctt tctagccctg ttccctacac     900

aaatgcagta catagagttt gtctccctga tgcatcctat gagtttcaac     950

caggtgatgt gatgtttgtg acaggatttg gagcactgaa aaatgatggt    1000

tacagtcaaa atcatcttcg acaagcacag gtgactctca tagacgctac    1050

aacttgcaat gaacctcaag cttacaatga cgccataact cctagaatgt    1100

tatgtgctgg ctccttagaa ggaaaaacag atgcatgcca gggtgactct    1150

ggaggaccac tggttagttc agatgctaga gatatctggt accttgctgg    1200

aatagtgagc tggggagatg aatgtgcgaa acccaacaag cctggtgttt    1250

atactagagt tacggccttg cgggactgga ttacttcaaa aactggtatc    1300

taagagacaa aagcctcatg gaacagataa cattttttttt tgttttttgg    1350

gtgtggaggc catttttaga gatacagaat tggagaagac ttgcaaaaca    1400

gctagatttg actgatctca ataaactgtt tgcttgatgc atgtattttc    1450

ttcccagctc tgttccgcac gtaagcatcc tgcttctgcc agatcaactc    1500

tgtcatctgt gagcaatagt tgaaacttta tgtacataga gaaatagata    1550

atacaatatt acattacagc ctgtattcat ttgttctcta gaagttttgt    1600
```

cagaattttg acttgttgac ataaatttgt aatgcatata tacaatttga 1650
agcactcctt ttcttcagtt cctcagctcc tctcatttca gcaaatatcc 1700
attttcaagg tgcagaacaa ggagtgaaag aaaatataag aagaaaaaaa 1750
tcccctacat tttattggca cagaaaagta ttaggtgttt ttcttagtgg 1800
aatattagaa atgatcatat tcattatgaa aggtcaagca aagacagcag 1850
aataccaatc acttcatcat ttaggaagta tgggaactaa gttaaggaag 1900
tccagaaaga agccaagata tatccttatt ttcatttcca aacaactact 1950
atgataaatg tgaagaagat tctgtttttt tgtgacctat aataattata 2000
caaacttcat gcaatgtact tgttctaagc aaattaaagc aaatatttat 2050
ttaacattgt tactgaggat gtcaacatat aacaataaaa tataaatcac 2100
cca 2103

<210> SEQ ID NO 106
<211> LENGTH: 423
<212> TYPE: PRT
<213> ORGANISM: Homo Sapien

<400> SEQUENCE: 106

Met Met Tyr Arg Pro Asp Val Val Arg Ala Arg Lys Arg Val Cys
1 5 10 15

Trp Glu Pro Trp Val Ile Gly Leu Val Ile Phe Ile Ser Leu Ile
20 25 30

Val Leu Ala Val Cys Ile Gly Leu Thr Val His Tyr Val Arg Tyr
35 40 45

Asn Gln Lys Lys Thr Tyr Asn Tyr Tyr Ser Thr Leu Ser Phe Thr
50 55 60

Thr Asp Lys Leu Tyr Ala Glu Phe Gly Arg Glu Ala Ser Asn Asn
65 70 75

Phe Thr Glu Met Ser Gln Arg Leu Glu Ser Met Val Lys Asn Ala
80 85 90

Phe Tyr Lys Ser Pro Leu Arg Glu Glu Phe Val Lys Ser Gln Val
95 100 105

Ile Lys Phe Ser Gln Gln Lys His Gly Val Leu Ala His Met Leu
110 115 120

Leu Ile Cys Arg Phe His Ser Thr Glu Asp Pro Glu Thr Val Asp
125 130 135

Lys Ile Val Gln Leu Val Leu His Glu Lys Leu Gln Asp Ala Val
140 145 150

Gly Pro Pro Lys Val Asp Pro His Ser Val Lys Ile Lys Lys Ile
155 160 165

Asn Lys Thr Glu Thr Asp Ser Tyr Leu Asn His Cys Cys Gly Thr
170 175 180

Arg Arg Ser Lys Thr Leu Gly Gln Ser Leu Arg Ile Val Gly Gly
185 190 195

Thr Glu Val Glu Glu Gly Glu Trp Pro Trp Gln Ala Ser Leu Gln
200 205 210

Trp Asp Gly Ser His Arg Cys Gly Ala Thr Leu Ile Asn Ala Thr
215 220 225

Trp Leu Val Ser Ala Ala His Cys Phe Thr Thr Tyr Lys Asn Pro
230 235 240

-continued

Ala Arg Trp Thr Ala Ser Phe Gly Val Thr Ile Lys Pro Ser Lys
245 250 255

Met Lys Arg Gly Leu Arg Arg Ile Ile Val His Glu Lys Tyr Lys
260 265 270

His Pro Ser His Asp Tyr Asp Ile Ser Leu Ala Glu Leu Ser Ser
275 280 285

Pro Val Pro Tyr Thr Asn Ala Val His Arg Val Cys Leu Pro Asp
290 295 300

Ala Ser Tyr Glu Phe Gln Pro Gly Asp Val Met Phe Val Thr Gly
305 310 315

Phe Gly Ala Leu Lys Asn Asp Gly Tyr Ser Gln Asn His Leu Arg
320 325 330

Gln Ala Gln Val Thr Leu Ile Asp Ala Thr Thr Cys Asn Glu Pro
335 340 345

Gln Ala Tyr Asn Asp Ala Ile Thr Pro Arg Met Leu Cys Ala Gly
350 355 360

Ser Leu Glu Gly Lys Thr Asp Ala Cys Gln Gly Asp Ser Gly Gly
365 370 375

Pro Leu Val Ser Ser Asp Ala Arg Asp Ile Trp Tyr Leu Ala Gly
380 385 390

Ile Val Ser Trp Gly Asp Glu Cys Ala Lys Pro Asn Lys Pro Gly
395 400 405

Val Tyr Thr Arg Val Thr Ala Leu Arg Asp Trp Ile Thr Ser Lys
410 415 420

Thr Gly Ile

<210> SEQ ID NO 107
<211> LENGTH: 2397
<212> TYPE: DNA
<213> ORGANISM: Homo Sapien

<400> SEQUENCE: 107
agagaaagaa gcgtctccag ctgaagccaa tgcagccctc cggctctccg 50
cgaagaagtt ccctgccccg atgagccccc gccgtgcgtc cccgactatc 100
cccaggcggg cgtggggcac cgggcccagc gccgacgatc gctgccgttt 150
tgcccttggg agtaggatgt ggtgaaagga tggggcttct cccttacggg 200
gctcacaatg gccagagaag attccgtgaa gtgtctgcgc tgcctgctct 250
acgccctcaa tctgctcttt tggttaatgt ccatcagtgt gttggcagtt 300
tctgcttgga tgagggacta cctaaataat gttctcactt taactgcaga 350
aacgagggta gaggaagcag tcattttgac ttactttcct gtggttcatc 400
cggtcatgat tgctgtttgc tgtttcctta tcattgtggg gatgttagga 450
tattgtggaa cggtgaaaag aaatctgttg cttcttgcat ggtactttgg 500
aagtttgctt gtcattttct gtgtagaact ggcttgtggc gtttggacat 550
atgaacagga acttatggtt ccagtacaat ggtcagatat ggtcactttg 600
aaagccagga tgacaaatta tggattacct agatatcggt ggcttactca 650
tgcttggaat ttttttcaga gagagtttaa gtgctgtgga gtagtatatt 700
tcactgactg gttggaaatg acagagatgg actggccccc agattcctgc 750
tgtgttagag aattcccagg atgttccaaa caggcccacc aggaagatct 800
cagtgacctt tatcaagagg gttgtgggaa gaaaatgtat tcctttttga 850

-continued

```
gaggaaccaa acaactgcag gtgctgaggt ttctgggaat ctccattggg        900
gtgacacaaa tcctggccat gattctcacc attactctgc tctgggctct        950
gtattatgat agaagggagc ctgggacaga ccaaatgatg tccttgaaga       1000
atgacaactc tcagcacctg tcatgtccct cagtagaact gttgaaacca       1050
agcctgtcaa gaatctttga acacacatcc atggcaaaca gctttaatac       1100
acactttgag atggaggagt tataaaaaga aatgtcacag aagaaaacca       1150
caaacttgtt ttattggact tgtgaatttt tgagtacata ctatgtgttt       1200
cagaaatatg tagaaataaa aatgttgcca taaaataaca cctaagcata       1250
tactattcta tgctttaaaa tgaggatgga aaagtttcat gtcataagtc       1300
accacctgga caataattga tgcccttaaa atgctgaaga cagatgtcat       1350
acccactgtg tagcctgtgt atgactttta ctgaacacag ttatgttttg       1400
aggcagcatg gtttgattag catttccgca tccatgcaaa cgagtcacat       1450
atggtgggac tggagccata gtaaaggttg atttacttct accaactagt       1500
atataaagta ctaattaaat gctaacatag gaagttagaa aatactaata       1550
acttttatta ctcagcgatc tattcttctg atgctaaata aattatatat       1600
cagaaaactt tcaatattgg tgactaccta aatgtgattt ttgctggtta       1650
ctaaaatatt cttaccactt aaaagagcaa gctaacacat tgtcttaagc       1700
tgatcaggga ttttttgtat ataagtctgt gttaaatctg tataattcag       1750
tcgatttcag ttctgataat gttaagaata accattatga aaaggaaaat       1800
ttgtcctgta tagcatcatt atttttagcc tttcctgtta ataaagcttt       1850
actattctgt cctgggctta tattacacat ataactgtta tttaaatact       1900
taaccactaa ttttgaaaat taccagtgtg atacatagga atcattattc       1950
agaatgtagt ctggtcttta ggaagtatta ataagaaaat ttgcacataa       2000
cttagttgat tcagaaagga cttgtatgct gtttttctcc caaatgaaga       2050
ctctttttga cactaaacac tttttaaaaa gcttatcttt gccttctcca       2100
aacaagaagc aatagtctcc aagtcaatat aaattctaca gaaaatagtg       2150
ttctttttct ccagaaaaat gcttgtgaga atcattaaaa catgtgacaa       2200
tttagagatt ctttgtttta tttcactgat taatatactg tggcaaatta       2250
cacagattat taaatttttt tacaagagta tagtatattt atttgaaatg       2300
ggaaaagtgc attttactgt attttgtgta ttttgtttat ttctcagaat       2350
atggaaagaa aattaaaatg tgtcaataaa tattttctag agagtaa          2397
```

<210> SEQ ID NO 108
<211> LENGTH: 305
<212> TYPE: PRT
<213> ORGANISM: Homo Sapien

<400> SEQUENCE: 108

```
Met Ala Arg Glu Asp Ser Val Lys Cys Leu Arg Cys Leu Leu Tyr
  1               5                  10                  15

Ala Leu Asn Leu Leu Phe Trp Leu Met Ser Ile Ser Val Leu Ala
                 20                  25                  30

Val Ser Ala Trp Met Arg Asp Tyr Leu Asn Asn Val Leu Thr Leu
                 35                  40                  45
```

-continued

```
Thr Ala Glu Thr Arg Val Glu Glu Ala Val Ile Leu Thr Tyr Phe
                50                  55                  60

Pro Val Val His Pro Val Met Ile Ala Val Cys Cys Phe Leu Ile
                65                  70                  75

Ile Val Gly Met Leu Gly Tyr Cys Gly Thr Val Lys Arg Asn Leu
                80                  85                  90

Leu Leu Leu Ala Trp Tyr Phe Gly Ser Leu Leu Val Ile Phe Cys
                95                  100                 105

Val Glu Leu Ala Cys Gly Val Trp Thr Tyr Glu Gln Glu Leu Met
                110                 115                 120

Val Pro Val Gln Trp Ser Asp Met Val Thr Leu Lys Ala Arg Met
                125                 130                 135

Thr Asn Tyr Gly Leu Pro Arg Tyr Arg Trp Leu Thr His Ala Trp
                140                 145                 150

Asn Phe Phe Gln Arg Glu Phe Lys Cys Cys Gly Val Val Tyr Phe
                155                 160                 165

Thr Asp Trp Leu Glu Met Thr Glu Met Asp Trp Pro Pro Asp Ser
                170                 175                 180

Cys Cys Val Arg Glu Phe Pro Gly Cys Ser Lys Gln Ala His Gln
                185                 190                 195

Glu Asp Leu Ser Asp Leu Tyr Gln Glu Gly Cys Gly Lys Lys Met
                200                 205                 210

Tyr Ser Phe Leu Arg Gly Thr Lys Gln Leu Gln Val Leu Arg Phe
                215                 220                 225

Leu Gly Ile Ser Ile Gly Val Thr Gln Ile Leu Ala Met Ile Leu
                230                 235                 240

Thr Ile Thr Leu Leu Trp Ala Leu Tyr Tyr Asp Arg Arg Glu Pro
                245                 250                 255

Gly Thr Asp Gln Met Met Ser Leu Lys Asn Asp Asn Ser Gln His
                260                 265                 270

Leu Ser Cys Pro Ser Val Glu Leu Leu Lys Pro Ser Leu Ser Arg
                275                 280                 285

Ile Phe Glu His Thr Ser Met Ala Asn Ser Phe Asn Thr His Phe
                290                 295                 300

Glu Met Glu Glu Leu
                305
```

<210> SEQ ID NO 109
<211> LENGTH: 2339
<212> TYPE: DNA
<213> ORGANISM: Homo Sapien

<400> SEQUENCE: 109

```
ccaaggccag agctgtggac accttatccc actcatcctc atcctcttcc        50

tctgataaag cccctaccag tgctgataaa gtctttctcg tgagagccta       100

gaggccttaa aaaaaaaagt gcttgaaaga gaaggggaca aaggaacacc       150

agtattaaga ggattttcca gtgtttctgg cagttggtcc agaaggatgc       200

ctccattcct gcttctcacc tgcctcttca tcacaggcac ctccgtgtca       250

cccgtggccc tagatccttg ttctgcttac atcagcctga atgagccctg       300

gaggaacact gaccaccagt tggatgagtc tcaaggtcct cctctatgtg       350

acaaccatgt gaatggggag tggtaccact tcacgggcat ggcgggagat       400
```

-continued

```
gccatgccta ccttctgcat accagaaaac cactgtggaa cccacgcacc          450
tgtctggctc aatggcagcc accccctaga aggcgacggc attgtgcaac          500
gccaggcttg tgccagcttc aatgggaact gctgtctctg gaacaccacg          550
gtggaagtca aggcttgccc tggaggctac tatgtgtatc gtctgaccaa          600
gcccagcgtc tgcttccacg tctactgtgg tcatttttat gacatctgcg          650
acgaggactg ccatggcagc tgctcagata ccagcgagtg cacatgcgct          700
ccaggaactg tgctaggccc tgacaggcag acatgctttg atgaaaatga          750
atgtgagcaa aacaacggtg gctgcagtga gatctgtgtg aacctcaaaa          800
actcctaccg ctgtgagtgt ggggttggcc gtgtgctaag aagtgatggc          850
aagacttgtg aagacgttga aggatgccac aataacaatg gtggctgcag          900
ccactcttgc cttggatctg agaaaggcta ccagtgtgaa tgtccccggg          950
gcctggtgct gtctgaggat aaccacactt gccaagtccc tgtgttgtgc         1000
aaatcaaatg ccattgaagt gaacatcccc agggagctgg ttggtggcct         1050
ggagctcttc ctgaccaaca cctcctgccg aggagtgtcc aacggcaccc         1100
atgtcaacat cctcttctct ctcaagacat gtggtacagt ggtcgatgtg         1150
gtgaatgaca agattgtggc cagcaacctc gtgacaggtc tacccaagca         1200
gaccccgggg agcagcgggg acttcatcat ccgaaccagc aagctgctga         1250
tcccggtgac ctgcgagttt ccacgcctgt acaccatttc tgaaggatac         1300
gttcccaacc ttcgaaactc cccactggaa atcatgagcc gaaatcatgg         1350
gatcttccca ttcactctgg agatcttcaa ggacaatgag tttgaagagc         1400
cttaccggga agctctgccc accctcaagc ttcgtgactc cctctacttt         1450
ggcattgagc ccgtggtgca cgtgagcggc ttggaaagct tggtggagag         1500
ctgctttgcc acccccacct ccaagatcga cgaggtcctg aaatactacc         1550
tcatccggga tggctgtgtt tcagatgact cggtaaagca gtacacatcc         1600
cgggatcacc tagcaaagca cttccaggtc cctgtcttca agtttgtggg         1650
caaagaccac aaggaagtgt ttctgcactg ccgggttctt gtctgtggag         1700
tgttggacga gcgttcccgc tgtgcccagg gttgccaccg gcgaatgcgt         1750
cgtggggcag gaggagagga ctcagccggt ctacagggcc agacgctaac         1800
aggcggcccg atccgcatcg actgggagga ctagttcgta gccatacctc         1850
gagtccctgc attggacggc tctgctcttt ggagcttctc cccccaccgc         1900
cctctaagaa catctgccaa cagctgggtt cagacttcac actgtgagtt         1950
cagactccca gcaccaactc actctgattc tggtccattc agtgggcaca         2000
ggtcacagca ctgctgaaca atgtggcctg ggtggggttt catctttcta         2050
gggttgaaaa ctaaactgtc cacccagaaa gacactcacc ccatttccct         2100
catttctttc ctacacttaa atacctcgtg tatggtgcaa tcagaccaca         2150
aaatcagaag ctgggtataa tatttcaagt tacaaaccct agaaaaatta         2200
aacagttact gaaattatga cttaaatacc caatgactcc ttaaatatgt         2250
aaattatagt tataccttga aatttcaatt caaatgcaga ctaattatag         2300
ggaatttgga agtgtatcaa taaaacagta tataatttt                     2339
```

-continued

<210> SEQ ID NO 110
<211> LENGTH: 545
<212> TYPE: PRT
<213> ORGANISM: Homo Sapien

<400> SEQUENCE: 110

```
Met Pro Pro Phe Leu Leu Leu Thr Cys Leu Phe Ile Thr Gly Thr
  1               5                  10                  15

Ser Val Ser Pro Val Ala Leu Asp Pro Cys Ser Ala Tyr Ile Ser
                 20                  25                  30

Leu Asn Glu Pro Trp Arg Asn Thr Asp His Gln Leu Asp Glu Ser
                 35                  40                  45

Gln Gly Pro Pro Leu Cys Asp Asn His Val Asn Gly Glu Trp Tyr
                 50                  55                  60

His Phe Thr Gly Met Ala Gly Asp Ala Met Pro Thr Phe Cys Ile
                 65                  70                  75

Pro Glu Asn His Cys Gly Thr His Ala Pro Val Trp Leu Asn Gly
                 80                  85                  90

Ser His Pro Leu Glu Gly Asp Gly Ile Val Gln Arg Gln Ala Cys
                 95                 100                 105

Ala Ser Phe Asn Gly Asn Cys Cys Leu Trp Asn Thr Thr Val Glu
                110                 115                 120

Val Lys Ala Cys Pro Gly Gly Tyr Tyr Val Tyr Arg Leu Thr Lys
                125                 130                 135

Pro Ser Val Cys Phe His Val Tyr Cys Gly His Phe Tyr Asp Ile
                140                 145                 150

Cys Asp Glu Asp Cys His Gly Ser Cys Ser Asp Thr Ser Glu Cys
                155                 160                 165

Thr Cys Ala Pro Gly Thr Val Leu Gly Pro Asp Arg Gln Thr Cys
                170                 175                 180

Phe Asp Glu Asn Glu Cys Glu Gln Asn Asn Gly Gly Cys Ser Glu
                185                 190                 195

Ile Cys Val Asn Leu Lys Asn Ser Tyr Arg Cys Glu Cys Gly Val
                200                 205                 210

Gly Arg Val Leu Arg Ser Asp Gly Lys Thr Cys Glu Asp Val Glu
                215                 220                 225

Gly Cys His Asn Asn Asn Gly Gly Cys Ser His Ser Cys Leu Gly
                230                 235                 240

Ser Glu Lys Gly Tyr Gln Cys Glu Cys Pro Arg Gly Leu Val Leu
                245                 250                 255

Ser Glu Asp Asn His Thr Cys Gln Val Pro Val Leu Cys Lys Ser
                260                 265                 270

Asn Ala Ile Glu Val Asn Ile Pro Arg Glu Leu Val Gly Gly Leu
                275                 280                 285

Glu Leu Phe Leu Thr Asn Thr Ser Cys Arg Gly Val Ser Asn Gly
                290                 295                 300

Thr His Val Asn Ile Leu Phe Ser Leu Lys Thr Cys Gly Thr Val
                305                 310                 315

Val Asp Val Val Asn Asp Lys Ile Val Ala Ser Asn Leu Val Thr
                320                 325                 330

Gly Leu Pro Lys Gln Thr Pro Gly Ser Ser Gly Asp Phe Ile Ile
                335                 340                 345

Arg Thr Ser Lys Leu Leu Ile Pro Val Thr Cys Glu Phe Pro Arg
                350                 355                 360
```

-continued

```
Leu Tyr Thr Ile Ser Glu Gly Tyr Val Pro Asn Leu Arg Asn Ser
                365                 370                 375

Pro Leu Glu Ile Met Ser Arg Asn His Gly Ile Phe Pro Phe Thr
                380                 385                 390

Leu Glu Ile Phe Lys Asp Asn Glu Phe Glu Glu Pro Tyr Arg Glu
                395                 400                 405

Ala Leu Pro Thr Leu Lys Leu Arg Asp Ser Leu Tyr Phe Gly Ile
                410                 415                 420

Glu Pro Val Val His Val Ser Gly Leu Glu Ser Leu Val Glu Ser
                425                 430                 435

Cys Phe Ala Thr Pro Thr Ser Lys Ile Asp Glu Val Leu Lys Tyr
                440                 445                 450

Tyr Leu Ile Arg Asp Gly Cys Val Ser Asp Asp Ser Val Lys Gln
                455                 460                 465

Tyr Thr Ser Arg Asp His Leu Ala Lys His Phe Gln Val Pro Val
                470                 475                 480

Phe Lys Phe Val Gly Lys Asp His Lys Glu Val Phe Leu His Cys
                485                 490                 495

Arg Val Leu Val Cys Gly Val Leu Asp Glu Arg Ser Arg Cys Ala
                500                 505                 510

Gln Gly Cys His Arg Arg Met Arg Arg Gly Ala Gly Gly Glu Asp
                515                 520                 525

Ser Ala Gly Leu Gln Gly Gln Thr Leu Thr Gly Gly Pro Ile Arg
                530                 535                 540

Ile Asp Trp Glu Asp
                545


<210> SEQ ID NO 111
<211> LENGTH: 2063
<212> TYPE: DNA
<213> ORGANISM: Homo Sapien

<400> SEQUENCE: 111

gagagaggca gcagcttgct cagcggacaa ggatgctggg cgtgagggac                50

caaggcctgc cctgcactcg ggcctcctcc agccagtgct gaccagggac               100

ttctgacctg ctggccagcc aggacctgtg tggggaggcc ctcctgctgc               150

cttggggtga caatctcagc tccaggctac agggagaccg ggaggatcac               200

agagccagca tgttacagga tcctgacagt gatcaacctc tgaacagcct               250

cgatgtcaaa cccctgcgca aaccccgtat ccccatggag accttcagaa               300

aggtggggat ccccatcatc atagcactac tgagcctggc gagtatcatc               350

attgtggttg tcctcatcaa ggtgattctg gataaatact acttcctctg               400

cgggcagcct ctccacttca tcccgaggaa gcagctgtgt gacggagagc               450

tggactgtcc cttgggggag gacgaggagc actgtgtcaa gagcttcccc               500

gaagggcctg cagtggcagt ccgcctctcc aaggaccgat ccacactgca               550

ggtgctggac tcggccacag ggaactggtt ctctgcctgt ttcgacaact               600

tcacagaagc tctcgctgag acagcctgta ggcagatggg ctacagcaga               650

gctgtggaga ttggcccaga ccaggatctg gatgttgttg aaatcacaga               700

aaacagccag gagcttcgca tgcggaactc aagtgggccc tgtctctcag               750

gctccctggt ctccctgcac tgtcttgcct gtgggaagag cctgaagacc               800
```

-continued

```
ccccgtgtgg tgggtgggga ggaggcctct gtggattctt ggccttggca        850

ggtcagcatc cagtacgaca aacagcacgt ctgtggaggg agcatcctgg        900

acccccactg ggtcctcacg gcagcccact gcttcaggaa acataccgat        950

gtgttcaact ggaaggtgcg ggcaggctca gacaaactgg gcagcttccc       1000

atccctggct gtggccaaga tcatcatcat tgaattcaac cccatgtacc       1050

ccaaagacaa tgacatcgcc ctcatgaagc tgcagttccc actcactttc       1100

tcaggcacag tcaggcccat ctgtctgccc ttctttgatg aggagctcac       1150

tccagccacc ccactctgga tcattggatg gggctttacg aagcagaatg       1200

gagggaagat gtctgacata ctgctgcagg cgtcagtcca ggtcattgac       1250

agcacacggt gcaatgcaga cgatgcgtac caggggggaag tcaccgagaa      1300

gatgatgtgt gcaggcatcc cggaaggggg tgtggacacc tgccagggtg       1350

acagtggtgg gcccctgatg taccaatctg accagtggca tgtggtgggc       1400

atcgttagct ggggctatgg ctgcgggggc ccgagcaccc caggagtata       1450

caccaaggtc tcagcctatc tcaactggat ctacaatgtc tggaaggctg       1500

agctgtaatg ctgctgcccc tttgcagtgc tgggagccgc ttccttcctg       1550

ccctgcccac ctggggatcc cccaaagtca gacacagagc aagagtcccc       1600

ttgggtacac ccctctgccc acagcctcag catttcttgg agcagcaaag       1650

ggcctcaatt cctgtaagag accctcgcag cccagaggcg cccagaggaa       1700

gtcagcagcc ctagctcggc cacacttggt gctcccagca tcccagggag       1750

agacacagcc cactgaacaa ggtctcaggg gtattgctaa gccaagaagg       1800

aactttccca cactactgaa tggaagcagg ctgtcttgta aaagcccaga       1850

tcactgtggg ctggagagga gaaggaaagg gtctgcgcca gccctgtccg       1900

tcttcaccca tccccaagcc tactagagca agaaaccagt tgtaatataa       1950

aatgcactgc cctactgttg gtatgactac cgttacctac tgttgtcatt       2000

gttattacag ctatggccac tattattaaa gagctgtgta acatctctgg       2050

caaaaaaaaa aaa                                               2063


<210> SEQ ID NO 112
<211> LENGTH: 432
<212> TYPE: PRT
<213> ORGANISM: Homo Sapien

<400> SEQUENCE: 112

Met Leu Gln Asp Pro Asp Ser Asp Gln Pro Leu Asn Ser Leu Asp
  1               5                  10                  15

Val Lys Pro Leu Arg Lys Pro Arg Ile Pro Met Glu Thr Phe Arg
                 20                  25                  30

Lys Val Gly Ile Pro Ile Ile Ile Ala Leu Leu Ser Leu Ala Ser
                 35                  40                  45

Ile Ile Ile Val Val Val Leu Ile Lys Val Ile Leu Asp Lys Tyr
                 50                  55                  60

Tyr Phe Leu Cys Gly Gln Pro Leu His Phe Ile Pro Arg Lys Gln
                 65                  70                  75

Leu Cys Asp Gly Glu Leu Asp Cys Pro Leu Gly Glu Asp Glu Glu
                 80                  85                  90

His Cys Val Lys Ser Phe Pro Glu Gly Pro Ala Val Ala Val Arg
```

-continued

```
                95                  100                 105

Leu Ser Lys Asp Arg Ser Thr Leu Gln Val Leu Asp Ser Ala Thr
                110                 115                 120

Gly Asn Trp Phe Ser Ala Cys Phe Asp Asn Phe Thr Glu Ala Leu
                125                 130                 135

Ala Glu Thr Ala Cys Arg Gln Met Gly Tyr Ser Arg Ala Val Glu
                140                 145                 150

Ile Gly Pro Asp Gln Asp Leu Asp Val Val Glu Ile Thr Glu Asn
                155                 160                 165

Ser Gln Glu Leu Arg Met Arg Asn Ser Ser Gly Pro Cys Leu Ser
                170                 175                 180

Gly Ser Leu Val Ser Leu His Cys Leu Ala Cys Gly Lys Ser Leu
                185                 190                 195

Lys Thr Pro Arg Val Val Gly Gly Glu Glu Ala Ser Val Asp Ser
                200                 205                 210

Trp Pro Trp Gln Val Ser Ile Gln Tyr Asp Lys Gln His Val Cys
                215                 220                 225

Gly Gly Ser Ile Leu Asp Pro His Trp Val Leu Thr Ala Ala His
                230                 235                 240

Cys Phe Arg Lys His Thr Asp Val Phe Asn Trp Lys Val Arg Ala
                245                 250                 255

Gly Ser Asp Lys Leu Gly Ser Phe Pro Ser Leu Ala Val Ala Lys
                260                 265                 270

Ile Ile Ile Ile Glu Phe Asn Pro Met Tyr Pro Lys Asp Asn Asp
                275                 280                 285

Ile Ala Leu Met Lys Leu Gln Phe Pro Leu Thr Phe Ser Gly Thr
                290                 295                 300

Val Arg Pro Ile Cys Leu Pro Phe Phe Asp Glu Glu Leu Thr Pro
                305                 310                 315

Ala Thr Pro Leu Trp Ile Ile Gly Trp Gly Phe Thr Lys Gln Asn
                320                 325                 330

Gly Gly Lys Met Ser Asp Ile Leu Leu Gln Ala Ser Val Gln Val
                335                 340                 345

Ile Asp Ser Thr Arg Cys Asn Ala Asp Asp Ala Tyr Gln Gly Glu
                350                 355                 360

Val Thr Glu Lys Met Met Cys Ala Gly Ile Pro Glu Gly Gly Val
                365                 370                 375

Asp Thr Cys Gln Gly Asp Ser Gly Gly Pro Leu Met Tyr Gln Ser
                380                 385                 390

Asp Gln Trp His Val Val Gly Ile Val Ser Trp Gly Tyr Gly Cys
                395                 400                 405

Gly Gly Pro Ser Thr Pro Gly Val Tyr Thr Lys Val Ser Ala Tyr
                410                 415                 420

Leu Asn Trp Ile Tyr Asn Val Trp Lys Ala Glu Leu
                425                 430
```

<210> SEQ ID NO 113
<211> LENGTH: 1768
<212> TYPE: DNA
<213> ORGANISM: Homo Sapien

<400> SEQUENCE: 113

```
ggctggactg gaactcctgg tcccaagtga tccacccgcc tcagcctccc              50

aaggtgctgt gattataggt gtaagccacc gtgtctggcc tctgaacaac             100
```

-continued

```
tttttcagca actaaaaaag ccacaggagt tgaactgcta ggattctgac        150

tatgctgtgg tggctagtgc tcctactcct acctacatta aaatctgttt        200

tttgttctct tgtaactagc ctttaccttc ctaacacaga ggatctgtca        250

ctgtggctct ggcccaaacc tgaccttcac tctggaacga gaacagaggt        300

ttctacccac accgtcccct cgaagccggg gacagcctca ccttgctggc        350

ctctcgctgg agcagtgccc tcaccaactg tctcacgtct ggaggcactg        400

actcgggcag tgcaggtagc tgagcctctt ggtagctgcg gctttcaagg        450

tgggccttgc cctggccgta gaagggattg acaagcccga agatttcata        500

ggcgatggct cccactgccc aggcatcagc cttgctgtag tcaatcactg        550

ccctggggcc aggacgggcc gtggacacct gctcagaagc agtgggtgag        600

acatcacgct gcccgcccat ctaacctttt catgtcctgc acatcacctg        650

atccatgggc taatctgaac tctgtcccaa ggaacccaga gcttgagtga        700

gctgtggctc agacccagaa ggggtctgct tagaccacct ggtttatgtg        750

acaggacttg cattctcctg gaacatgagg gaacgccgga ggaaagcaaa        800

gtggcaggga aggaacttgt gccaaattat gggtcagaaa agatggaggt        850

gttgggttat cacaaggcat cgagtctcct gcattcagtg gacatgtggg        900

ggaagggctg ccgatggcgc atgacacact cgggactcac ctctggggcc        950

atcagacagc cgtttccgcc ccgatccacg taccagctgc tgaagggcaa       1000

ctgcaggccg atgctctcat cagccaggca gcagccaaaa tctgcgatca       1050

ccagccaggg gcagccgtct gggaaggagc aagcaaagtg accatttctc       1100

ctcccctcct tccctctgag aggccctcct atgtccctac taaagccacc       1150

agcaagacat agctgacagg ggctaatggc tcagtgttgg cccaggaggt       1200

cagcaaggcc tgagagctga tcagaagggc ctgctgtgcg aacacggaaa       1250

tgcctccagt aagcacaggc tgcaaaatcc ccaggcaaag gactgtgtgg       1300

ctcaatttaa atcatgttct agtaattgga gctgtcccca agaccaaagg       1350

agctagagct tggttcaaat gatctccaag ggcccttata ccccaggaga       1400

ctttgatttg aatttgaaac cccaaatcca aacctaagaa ccaggtgcat       1450

taagaatcag ttattgccgg gtgtggtggc ctgtaatgcc aacattttgg       1500

gaggccgagg cgggtagatc acctgaggtc aggagttcaa gaccagcctg       1550

gccaacatgg tgaaacccct gtctctacta aaaatacaaa aaaactagcc       1600

aggcatggtg gtgtgtgcct gtatcccagc tactcgggag gctgagacag       1650

gagaattact tgaacctggg aggtgaagga ggctgagaca ggagaatcac       1700

ttcagcctga gcaacacagc gagactctgt ctcagaaaaa ataaaaaaag       1750

aattatggtt atttgtaa                                          1768


<210> SEQ ID NO 114
<211> LENGTH: 109
<212> TYPE: PRT
<213> ORGANISM: Homo Sapien

<400> SEQUENCE: 114

Met Leu Trp Trp Leu Val Leu Leu Leu Leu Pro Thr Leu Lys Ser
  1               5                  10                  15
```

-continued

```
Val Phe Cys Ser Leu Val Thr Ser Leu Tyr Leu Pro Asn Thr Glu
                20                  25                  30

Asp Leu Ser Leu Trp Leu Trp Pro Lys Pro Asp Leu His Ser Gly
                35                  40                  45

Thr Arg Thr Glu Val Ser Thr His Thr Val Pro Ser Lys Pro Gly
                50                  55                  60

Thr Ala Ser Pro Cys Trp Pro Leu Ala Gly Ala Val Pro Ser Pro
                65                  70                  75

Thr Val Ser Arg Leu Glu Ala Leu Thr Arg Ala Val Gln Val Ala
                80                  85                  90

Glu Pro Leu Gly Ser Cys Gly Phe Gln Gly Gly Pro Cys Pro Gly
                95                 100                 105

Arg Arg Arg Asp
```

<210> SEQ ID NO 115
<211> LENGTH: 1197
<212> TYPE: DNA
<213> ORGANISM: Homo Sapien

<400> SEQUENCE: 115

```
cagcagtggt ctctcagtcc tctcaaagca aggaaagagt actgtgtgct        50
gagagaccat ggcaaagaat cctccagaga attgtgaaga ctgtcacatt       100
ctaaatgcag aagcttttaa atccaagaaa atatgtaaat cacttaagat       150
ttgtggactg gtgtttggta tcctggccct aactctaatt gtcctgtttt       200
gggggagcaa gcacttctgg ccggaggtac ccaaaaaagc ctatgacatg       250
gagcacactt tctacagcaa tggagagaag aagaagattt acatggaaat       300
tgatcctgtg accagaactg aaatattcag aagcggaaat ggcactgatg       350
aaacattgga agtgcacgac tttaaaaacg gatacactgg catctacttc       400
gtgggtcttc aaaaatgttt tatcaaaact cagattaaag tgattcctga       450
attttctgaa ccagaagagg aaatagatga gaatgaagaa attaccacaa       500
ctttctttga acagtcagtg atttgggtcc cagcagaaaa gcctattgaa       550
aaccgagatt ttcttaaaaa ttccaaaatt ctggagattt gtgataacgt       600
gaccatgtat tggatcaatc ccactctaat atcagtttct gagttacaag       650
actttgagga ggagggagaa gatcttcact ttcctgccaa cgaaaaaaaa       700
gggattgaac aaaatgaaca gtgggtggtc cctcaagtga aagtagagaa       750
gacccgtcac gccagacaag caagtgagga agaacttcca ataaatgact       800
atactgaaaa tggaatagaa tttgatccca tgctggatga gagaggttat       850
tgttgtattt actgccgtcg aggcaaccgc tattgccgcc gcgtctgtga       900
acctttacta ggctactacc catatccata ctgctaccaa ggaggacgag       950
tcatctgtcg tgtcatcatg ccttgtaact ggtgggtggc ccgcatgctg      1000
gggagggtct aataggaggt ttgagctcaa atgcttaaac tgctggcaac      1050
atataataaa tgcatgctat tcaatgaatt tctgcctatg aggcatctgg      1100
cccctggtag ccagctctcc agaattactt gtaggtaatt cctctcttca      1150
tgttctaata aacttctaca ttatcaccaa aaaaaaaaaa aaaaaaa         1197
```

<210> SEQ ID NO 116

-continued

<211> LENGTH: 317
<212> TYPE: PRT
<213> ORGANISM: Homo Sapien

<400> SEQUENCE: 116

```
Met Ala Lys Asn Pro Pro Glu Asn Cys Glu Asp Cys His Ile Leu
  1               5                  10                  15

Asn Ala Glu Ala Phe Lys Ser Lys Lys Ile Cys Lys Ser Leu Lys
                 20                  25                  30

Ile Cys Gly Leu Val Phe Gly Ile Leu Ala Leu Thr Leu Ile Val
                 35                  40                  45

Leu Phe Trp Gly Ser Lys His Phe Trp Pro Glu Val Pro Lys Lys
                 50                  55                  60

Ala Tyr Asp Met Glu His Thr Phe Tyr Ser Asn Gly Glu Lys Lys
                 65                  70                  75

Lys Ile Tyr Met Glu Ile Asp Pro Val Thr Arg Thr Glu Ile Phe
                 80                  85                  90

Arg Ser Gly Asn Gly Thr Asp Glu Thr Leu Glu Val His Asp Phe
                 95                 100                 105

Lys Asn Gly Tyr Thr Gly Ile Tyr Phe Val Gly Leu Gln Lys Cys
                110                 115                 120

Phe Ile Lys Thr Gln Ile Lys Val Ile Pro Glu Phe Ser Glu Pro
                125                 130                 135

Glu Glu Glu Ile Asp Glu Asn Glu Glu Ile Thr Thr Thr Phe Phe
                140                 145                 150

Glu Gln Ser Val Ile Trp Val Pro Ala Glu Lys Pro Ile Glu Asn
                155                 160                 165

Arg Asp Phe Leu Lys Asn Ser Lys Ile Leu Glu Ile Cys Asp Asn
                170                 175                 180

Val Thr Met Tyr Trp Ile Asn Pro Thr Leu Ile Ser Val Ser Glu
                185                 190                 195

Leu Gln Asp Phe Glu Glu Glu Gly Glu Asp Leu His Phe Pro Ala
                200                 205                 210

Asn Glu Lys Lys Gly Ile Glu Gln Asn Glu Gln Trp Val Val Pro
                215                 220                 225

Gln Val Lys Val Glu Lys Thr Arg His Ala Arg Gln Ala Ser Glu
                230                 235                 240

Glu Glu Leu Pro Ile Asn Asp Tyr Thr Glu Asn Gly Ile Glu Phe
                245                 250                 255

Asp Pro Met Leu Asp Glu Arg Gly Tyr Cys Cys Ile Tyr Cys Arg
                260                 265                 270

Arg Gly Asn Arg Tyr Cys Arg Arg Val Cys Glu Pro Leu Leu Gly
                275                 280                 285

Tyr Tyr Pro Tyr Pro Tyr Cys Tyr Gln Gly Gly Arg Val Ile Cys
                290                 295                 300

Arg Val Ile Met Pro Cys Asn Trp Trp Val Ala Arg Met Leu Gly
                305                 310                 315

Arg Val
```

<210> SEQ ID NO 117
<211> LENGTH: 2121
<212> TYPE: DNA
<213> ORGANISM: Homo Sapien

<400> SEQUENCE: 117

-continued

```
gagctcccct caggagcgcg ttagcttcac accttcggca gcaggagggc        50
ggcagcttct cgcaggcggc agggcgggcg gccaggatca tgtccaccac       100
cacatgccaa gtggtggcgt tcctcctgtc catcctgggg ctggccggct       150
gcatcgcggc caccgggatg gacatgtgga gcacccagga cctgtacgac       200
aaccccgtca cctccgtgtt ccagtacgaa gggctctgga ggagctgcgt       250
gaggcagagt tcaggcttca ccgaatgcag gccctatttc accatcctgg       300
gacttccagc catgctgcag gcagtgcgag ccctgatgat cgtaggcatc       350
gtcctgggtg ccattggcct cctggtatcc atctttgccc tgaaatgcat       400
ccgcattggc agcatggagg actctgccaa agccaacatg acactgacct       450
ccgggatcat gttcattgtc tcaggtcttt gtgcaattgc tggagtgtct       500
gtgtttgcca acatgctggt gactaacttc tggatgtcca cagctaacat       550
gtacaccggc atgggtggga tggtgcagac tgttcagacc aggtacacat       600
ttggtgcggc tctgttcgtg ggctgggtcg ctggaggcct cacactaatt       650
gggggtgtga tgatgtgcat cgcctgccgg ggcctggcac cagaagaaac       700
caactacaaa gccgtttctt atcatgcctc aggccacagt gttgcctaca       750
agcctggagg cttcaaggcc agcactggct ttgggtccaa caccaaaaac       800
aagaagatat acgatggagg tgcccgcaca gaggacgagg tacaatctta       850
tccttccaag cacgactatg tgtaatgctc taagacctct cagcacgggc       900
ggaagaaact cccggagagc tcacccaaaa aacaaggaga tcccatctag       950
atttcttctt gcttttgact cacagctgga agttagaaaa gcctcgattt      1000
catctttgga gaggccaaat ggtcttagcc tcagtctctg tctctaaata      1050
ttccaccata aaacagctga gttatttatg aattagaggc tatagctcac      1100
attttcaatc ctctatttct ttttttaaat ataactttct actctgatga      1150
gagaatgtgg ttttaatctc tctctcacat tttgatgatt tagacagact      1200
ccccctcttc ctcctagtca ataaacccat tgatgatcta tttcccagct      1250
tatccccaag aaaacttttg aaaggaaaga gtagacccaa agatgttatt      1300
ttctgctgtt tgaattttgt ctccccaccc ccaacttggc tagtaataaa      1350
cacttactga agaagaagca ataagagaaa gatatttgta atctctccag      1400
cccatgatct cggttttctt acactgtgat cttaaaagtt accaaaccaa      1450
agtcattttc agtttgaggc aaccaaacct ttctactgct gttgacatct      1500
tcttattaca gcaacaccat tctaggagtt tcctgagctc tccactggag      1550
tcctctttct gtcgcgggtc agaaattgtc cctagatgaa tgagaaaatt      1600
attttttta atttaagtcc taaatatagt taaaataaat aatgttttag       1650
taaaatgata cactatctct gtgaaatagc ctcaccccta catgtggata      1700
gaaggaaatg aaaaaataat tgctttgaca ttgtctatat ggtactttgt      1750
aaagtcatgc ttaagtacaa attccatgaa aagctcacac ctgtaatcct      1800
agcactttgg gaggctgagg aggaaggatc acttgagccc agaagttcga      1850
gactagcctg ggcaacatgg agaagccctg tctctacaaa atacagagag      1900
aaaaaatcag ccagtcatgg tggcatacac ctgtagtccc agcattccgg      1950
gaggctgagg tgggaggatc acttgagccc agggaggttg gggctgcagt      2000
```

-continued

```
gagccatgat cacaccactg cactccagcc aggtgacata gcgagatcct           2050

gtctaaaaaa ataaaaaata aataatggaa cacagcaagt cctaggaagt           2100

aggttaaaac taattcttta a                                          2121
```

<210> SEQ ID NO 118
<211> LENGTH: 261
<212> TYPE: PRT
<213> ORGANISM: Homo Sapien

<400> SEQUENCE: 118

```
Met Ser Thr Thr Thr Cys Gln Val Val Ala Phe Leu Leu Ser Ile
  1               5                  10                  15

Leu Gly Leu Ala Gly Cys Ile Ala Ala Thr Gly Met Asp Met Trp
                 20                  25                  30

Ser Thr Gln Asp Leu Tyr Asp Asn Pro Val Thr Ser Val Phe Gln
                 35                  40                  45

Tyr Glu Gly Leu Trp Arg Ser Cys Val Arg Gln Ser Ser Gly Phe
                 50                  55                  60

Thr Glu Cys Arg Pro Tyr Phe Thr Ile Leu Gly Leu Pro Ala Met
                 65                  70                  75

Leu Gln Ala Val Arg Ala Leu Met Ile Val Gly Ile Val Leu Gly
                 80                  85                  90

Ala Ile Gly Leu Leu Val Ser Ile Phe Ala Leu Lys Cys Ile Arg
                 95                 100                 105

Ile Gly Ser Met Glu Asp Ser Ala Lys Ala Asn Met Thr Leu Thr
                110                 115                 120

Ser Gly Ile Met Phe Ile Val Ser Gly Leu Cys Ala Ile Ala Gly
                125                 130                 135

Val Ser Val Phe Ala Asn Met Leu Val Thr Asn Phe Trp Met Ser
                140                 145                 150

Thr Ala Asn Met Tyr Thr Gly Met Gly Gly Met Val Gln Thr Val
                155                 160                 165

Gln Thr Arg Tyr Thr Phe Gly Ala Ala Leu Phe Val Gly Trp Val
                170                 175                 180

Ala Gly Gly Leu Thr Leu Ile Gly Gly Val Met Met Cys Ile Ala
                185                 190                 195

Cys Arg Gly Leu Ala Pro Glu Glu Thr Asn Tyr Lys Ala Val Ser
                200                 205                 210

Tyr His Ala Ser Gly His Ser Val Ala Tyr Lys Pro Gly Gly Phe
                215                 220                 225

Lys Ala Ser Thr Gly Phe Gly Ser Asn Thr Lys Asn Lys Lys Ile
                230                 235                 240

Tyr Asp Gly Gly Ala Arg Thr Glu Asp Glu Val Gln Ser Tyr Pro
                245                 250                 255

Ser Lys His Asp Tyr Val
                260
```

<210> SEQ ID NO 119
<211> LENGTH: 2010
<212> TYPE: DNA
<213> ORGANISM: Homo Sapien

<400> SEQUENCE: 119

```
ggaaaaactg ttctcttctg tggcacagag aaccctgctt caaagcagaa             50
```

-continued

```
gtagcagttc cggagtccag ctggctaaaa ctcatcccag aggataatgg      100
caacccatgc cttagaaatc gctgggctgt ttcttggtgg tgttggaatg      150
gtgggcacag tggctgtcac tgtcatgcct cagtggagag tgtcggcctt      200
cattgaaaac aacatcgtgg tttttgaaaa cttctgggaa ggactgtgga      250
tgaattgcgt gaggcaggct aacatcagga tgcagtgcaa aatctatgat      300
tccctgctgg ctctttctcc ggacctacag gcagccagag gactgatgtg      350
tgctgcttcc gtgatgtcct tcttggcttt catgatggcc atccttggca      400
tgaaatgcac caggtgcacg ggggacaatg agaaggtgaa ggctcacatt      450
ctgctgacgg ctggaatcat cttcatcatc acgggcatgg tggtgctcat      500
ccctgtgagc tgggttgcca atgccatcat cagagatttc tataactcaa      550
tagtgaatgt tgcccaaaaa cgtgagcttg gagaagctct ctacttagga      600
tggaccacgg cactggtgct gattgttgga ggagctctgt tctgctgcgt      650
tttttgttgc aacgaaaaga gcagtagcta cagatactcg ataccttccc      700
atcgcacaac ccaaaaaagt tatcacaccg gaaagaagtc accgagcgtc      750
tactccagaa gtcagtatgt gtagttgtgt atgttttttt aactttacta      800
taaagccatg caaatgacaa aaatctatat tactttctca aaatggaccc      850
caaagaaact ttgatttact gttcttaact gcctaatctt aattacagga      900
actgtgcatc agctatttat gattctataa gctatttcag cagaatgaga      950
tattaaaccc aatgctttga ttgttctaga aagtatagta atttgttttc     1000
taaggtggtt caagcatcta ctctttttat catttacttc aaaatgacat     1050
tgctaaagac tgcattattt tactactgta atttctccac gacatagcat     1100
tatgtacata gatgagtgta acatttatat ctcacataga gacatgctta     1150
tatggtttta tttaaaatga aatgccagtc cattacactg aataaataga     1200
actcaactat tgcttttcag ggaaatcatg gatagggttg aagaaggtta     1250
ctattaattg tttaaaaaca gcttagggat taatgtcctc catttataat     1300
gaagattaaa atgaaggctt taatcagcat tgtaaaggaa attgaatggc     1350
tttctgatat gctgtttttt agcctaggag ttagaaatcc taacttcttt     1400
atcctcttct cccagaggct tttttttct tgtgtattaa attaacattt     1450
ttaaaacgca gatattttgt caaggggctt tgcattcaaa ctgcttttcc     1500
agggctatac tcagaagaaa gataaaagtg tgatctaaga aaaagtgatg     1550
gttttaggaa agtgaaaata tttttgtttt tgtatttgaa gaagaatgat     1600
gcattttgac aagaaatcat atatgtatgg atatatttta ataagtattt     1650
gagtacagac tttgaggttt catcaatata aataaaagag cagaaaaata     1700
tgtcttggtt ttcatttgct taccaaaaaa acaacaacaa aaaaagttgt     1750
cctttgagaa cttcacctgc tcctatgtgg gtacctgagt caaaattgtc     1800
atttttgttc tgtgaaaaat aaatttcctt cttgtaccat ttctgtttag     1850
ttttactaaa atctgtaaat actgtatttt tctgtttatt ccaaatttga     1900
tgaaactgac aatccaattt gaaagtttgt gtcgacgtct gtctagctta     1950
aatgaatgtg ttctatttgc tttatacatt tatattaata aattgtacat     2000
ttttctaatt                                                 2010
```

<210> SEQ ID NO 120
<211> LENGTH: 225
<212> TYPE: PRT
<213> ORGANISM: Homo Sapien

<400> SEQUENCE: 120

Met Ala Thr His Ala Leu Glu Ile Ala Gly Leu Phe Leu Gly Gly
1 5 10 15

Val Gly Met Val Gly Thr Val Ala Val Thr Val Met Pro Gln Trp
20 25 30

Arg Val Ser Ala Phe Ile Glu Asn Asn Ile Val Val Phe Glu Asn
35 40 45

Phe Trp Glu Gly Leu Trp Met Asn Cys Val Arg Gln Ala Asn Ile
50 55 60

Arg Met Gln Cys Lys Ile Tyr Asp Ser Leu Leu Ala Leu Ser Pro
65 70 75

Asp Leu Gln Ala Ala Arg Gly Leu Met Cys Ala Ala Ser Val Met
80 85 90

Ser Phe Leu Ala Phe Met Met Ala Ile Leu Gly Met Lys Cys Thr
95 100 105

Arg Cys Thr Gly Asp Asn Glu Lys Val Lys Ala His Ile Leu Leu
110 115 120

Thr Ala Gly Ile Ile Phe Ile Ile Thr Gly Met Val Val Leu Ile
125 130 135

Pro Val Ser Trp Val Ala Asn Ala Ile Ile Arg Asp Phe Tyr Asn
140 145 150

Ser Ile Val Asn Val Ala Gln Lys Arg Glu Leu Gly Glu Ala Leu
155 160 165

Tyr Leu Gly Trp Thr Thr Ala Leu Val Leu Ile Val Gly Gly Ala
170 175 180

Leu Phe Cys Cys Val Phe Cys Cys Asn Glu Lys Ser Ser Ser Tyr
185 190 195

Arg Tyr Ser Ile Pro Ser His Arg Thr Thr Gln Lys Ser Tyr His
200 205 210

Thr Gly Lys Lys Ser Pro Ser Val Tyr Ser Arg Ser Gln Tyr Val
215 220 225

<210> SEQ ID NO 121
<211> LENGTH: 1257
<212> TYPE: DNA
<213> ORGANISM: Homo Sapien

<400> SEQUENCE: 121
ggagagaggc gcgcgggtga aaggcgcatt gatgcagcct gcggcggcct 50
cggagcgcgg cggagccaga cgctgaccac gttcctctcc tcggtctcct 100
ccgcctccag ctccgcgctg cccggcagcc gggagccatg cgaccccagg 150
gccccgccgc ctccccgcag cggctccgcg gcctcctgct gctcctgctg 200
ctgcagctgc ccgcgccgtc gagcgcctct gagatcccca aggggaagca 250
aaaggcgcag ctccggcaga gggaggtggt ggacctgtat aatggaatgt 300
gcttacaagg gccagcagga gtgcctggtc gagacgggag ccctggggcc 350
aatgttattc cgggtacacc tgggatccca ggtcgggatg gattcaaagg 400
agaaaagggg gaatgtctga gggaaagctt tgaggagtcc tggacaccca 450

-continued

```
actacaagca gtgttcatgg agttcattga attatggcat agatcttggg          500

aaaattgcgg agtgtacatt tacaaagatg cgttcaaata gtgctctaag          550

agttttgttc agtggctcac ttcggctaaa atgcagaaat gcatgctgtc          600

agcgttggta tttcacattc aatggagctg aatgttcagg acctcttccc          650

attgaagcta taatttattt ggaccaagga agccctgaaa tgaattcaac          700

aattaatatt catcgcactt cttctgtgga aggactttgt gaaggaattg          750

gtgctggatt agtggatgtt gctatctggg ttggcacttg ttcagattac          800

ccaaaaggag atgcttctac tggatggaat tcagtttctc gcatcattat          850

tgaagaacta ccaaaataaa tgctttaatt ttcatttgct acctcttttt          900

ttattatgcc ttggaatggt tcacttaaat gacattttaa ataagtttat          950

gtatacatct gaatgaaaag caaagctaaa tatgtttaca gaccaaagtg         1000

tgatttcaca ctgtttttaa atctagcatt attcattttg cttcaatcaa         1050

aagtggtttc aatattttttt ttagttggtt agaatacttt cttcatagtc         1100

acattctctc aacctataat ttggaatatt gttgtggtct tttgtttttt         1150

ctcttagtat agcattttta aaaaaatata aaagctacca atctttgtac         1200

aatttgtaaa tgttaagaat ttttttata tctgttaaat aaaaattatt          1250

tccaaca                                                        1257
```

<210> SEQ ID NO 122
<211> LENGTH: 243
<212> TYPE: PRT
<213> ORGANISM: Homo Sapien

<400> SEQUENCE: 122

```
Met Arg Pro Gln Gly Pro Ala Ala Ser Pro Gln Arg Leu Arg Gly
  1               5                  10                  15

Leu Leu Leu Leu Leu Leu Leu Gln Leu Pro Ala Pro Ser Ser Ala
                 20                  25                  30

Ser Glu Ile Pro Lys Gly Lys Gln Lys Ala Gln Leu Arg Gln Arg
                 35                  40                  45

Glu Val Val Asp Leu Tyr Asn Gly Met Cys Leu Gln Gly Pro Ala
                 50                  55                  60

Gly Val Pro Gly Arg Asp Gly Ser Pro Gly Ala Asn Val Ile Pro
                 65                  70                  75

Gly Thr Pro Gly Ile Pro Gly Arg Asp Gly Phe Lys Gly Glu Lys
                 80                  85                  90

Gly Glu Cys Leu Arg Glu Ser Phe Glu Glu Ser Trp Thr Pro Asn
                 95                 100                 105

Tyr Lys Gln Cys Ser Trp Ser Ser Leu Asn Tyr Gly Ile Asp Leu
                110                 115                 120

Gly Lys Ile Ala Glu Cys Thr Phe Thr Lys Met Arg Ser Asn Ser
                125                 130                 135

Ala Leu Arg Val Leu Phe Ser Gly Ser Leu Arg Leu Lys Cys Arg
                140                 145                 150

Asn Ala Cys Cys Gln Arg Trp Tyr Phe Thr Phe Asn Gly Ala Glu
                155                 160                 165

Cys Ser Gly Pro Leu Pro Ile Glu Ala Ile Ile Tyr Leu Asp Gln
                170                 175                 180
```

-continued

```
Gly Ser Pro Glu Met Asn Ser Thr Ile Asn Ile His Arg Thr Ser
                185                 190                 195

Ser Val Glu Gly Leu Cys Glu Gly Ile Gly Ala Gly Leu Val Asp
                200                 205                 210

Val Ala Ile Trp Val Gly Thr Cys Ser Asp Tyr Pro Lys Gly Asp
                215                 220                 225

Ala Ser Thr Gly Trp Asn Ser Val Ser Arg Ile Ile Ile Glu Glu
                230                 235                 240

Leu Pro Lys


<210> SEQ ID NO 123
<211> LENGTH: 2379
<212> TYPE: DNA
<213> ORGANISM: Homo Sapien

<400> SEQUENCE: 123

gctgagcgtg tgcgcggtac ggggctctcc tgccttctgg gctccaacgc              50

agctctgtgg ctgaactggg tgctcatcac gggaactgct gggctatgga             100

atacagatgt ggcagctcag gtagccccaa attgcctgga agaatacatc             150

atgtttttcg ataagaagaa attgtaggat ccagtttttt ttttaaccgc             200

cccctcccca ccccccaaaa aaactgtaaa gatgcaaaaa cgtaatatcc             250

atgaagatcc tattacctag gaagattttg atgttttgct gcgaatgcgg             300

tgttgggatt tatttgttct tggagtgttc tgcgtggctg gcaaagaata             350

atgttccaaa atcggtccat ctcccaaggg gtccaatttt tcttcctggg             400

tgtcagcgag ccctgactca ctacagtgca gctgacaggg gctgtcatgc             450

aactggcccc taagccaaag caaaagacct aaggacgacc tttgaacaat             500

acaaaggatg ggtttcaatg taattaggct actgagcgga tcagctgtag             550

cactggttat agcccccact gtcttactga caatgctttc ttctgccgaa             600

cgaggatgcc ctaagggctg taggtgtgaa ggcaaaatgg tatattgtga             650

atctcagaaa ttacaggaga taccctcaag tatatctgct ggttgcttag             700

gtttgtccct tcgctataac agccttcaaa aacttaagta taatcaattt             750

aaagggctca accagctcac ctggctatac cttgaccata accatatcag             800

caatattgac gaaaatgctt ttaatggaat acgcagactc aaagagctga             850

ttcttagttc caatagaatc tcctattttc ttaacaatac cttcagacct             900

gtgacaaatt tacggaactt ggatctgtcc tataatcagc tgcattctct             950

gggatctgaa cagtttcggg gcttgcggaa gctgctgagt ttacatttac            1000

ggtctaactc cctgagaacc atccctgtgc gaatattcca agactgccgc            1050

aacctggaac ttttggacct gggatataac cggatccgaa gtttagccag            1100

gaatgtcttt gctggcatga tcagactcaa agaacttcac ctggagcaca            1150

atcaattttc caagctcaac ctggcccttt ttccaaggtt ggtcagcctt            1200

cagaaccttt acttgcagtg gaataaaatc agtgtcatag gacagaccat            1250

gtcctggacc tggagctcct tacaaaggct tgatttatca ggcaatgaga            1300

tcgaagcttt cagtggaccc agtgttttcc agtgtgtccc gaatctgcag            1350

cgcctcaacc tggattccaa caagctcaca tttattggtc aagagatttt            1400

ggattcttgg atatccctca atgacatcag tcttgctggg aatatatggg            1450
```

```
aatgcagcag aaatatttgc tcccttgtaa actggctgaa aagttttaaa        1500

ggtctaaggg agaatacaat tatctgtgcc agtcccaaag agctgcaagg        1550

agtaaatgtg atcgatgcag tgaagaacta cagcatctgt ggcaaaagta        1600

ctacagagag gtttgatctg gccagggctc tcccaaagcc gacgtttaag        1650

cccaagctcc ccaggccgaa gcatgagagc aaaccccctt tgcccccgac        1700

ggtgggagcc acagagcccg gcccagagac cgatgctgac gccgagcaca        1750

tctctttcca taaaatcatc gcgggcagcg tggcgctttt cctgtccgtg        1800

ctcgtcatcc tgctggttat ctacgtgtca tggaagcggt accctgcgag        1850

catgaagcag ctgcagcagc gctccctcat gcgaaggcac aggaaaaaga        1900

aaagacagtc cctaaagcaa atgactccca gcacccagga attttatgta        1950

gattataaac ccaccaacac ggagaccagc gagatgctgc tgaatgggac        2000

gggaccctgc acctataaca aatcgggctc cagggagtgt gaggtatgaa        2050

ccattgtgat aaaagagct cttaaaagct gggaaataag tggtgcttta         2100

ttgaactctg gtgactatca agggaacgcg atgccccccc tccccttccc        2150

tctccctctc actttggtgg caagatcctt ccttgtccgt tttagtgcat        2200

tcataatact ggtcattttc ctctcataca taatcaaccc attgaaattt        2250

aaataccaca atcaatgtga agcttgaact ccggtttaat ataataccta        2300

ttgtataaga ccctttactg attccattaa tgtcgcattt gttttaagat        2350

aaaacttctt tcataggtaa aaaaaaaaa                               2379
```

<210> SEQ ID NO 124
<211> LENGTH: 513
<212> TYPE: PRT
<213> ORGANISM: Homo Sapien

<400> SEQUENCE: 124

```
Met Gly Phe Asn Val Ile Arg Leu Leu Ser Gly Ser Ala Val Ala
 1               5                  10                  15

Leu Val Ile Ala Pro Thr Val Leu Thr Met Leu Ser Ser Ala
            20                  25                  30

Glu Arg Gly Cys Pro Lys Gly Cys Arg Cys Glu Gly Lys Met Val
            35                  40                  45

Tyr Cys Glu Ser Gln Lys Leu Gln Glu Ile Pro Ser Ser Ile Ser
            50                  55                  60

Ala Gly Cys Leu Gly Leu Ser Leu Arg Tyr Asn Ser Leu Gln Lys
            65                  70                  75

Leu Lys Tyr Asn Gln Phe Lys Gly Leu Asn Gln Leu Thr Trp Leu
            80                  85                  90

Tyr Leu Asp His Asn His Ile Ser Asn Ile Asp Glu Asn Ala Phe
            95                 100                 105

Asn Gly Ile Arg Arg Leu Lys Glu Leu Ile Leu Ser Ser Asn Arg
           110                 115                 120

Ile Ser Tyr Phe Leu Asn Asn Thr Phe Arg Pro Val Thr Asn Leu
           125                 130                 135

Arg Asn Leu Asp Leu Ser Tyr Asn Gln Leu His Ser Leu Gly Ser
           140                 145                 150

Glu Gln Phe Arg Gly Leu Arg Lys Leu Leu Ser Leu His Leu Arg
           155                 160                 165
```

-continued

Ser Asn Ser Leu Arg Thr Ile Pro Val Arg Ile Phe Gln Asp Cys
170 175 180

Arg Asn Leu Glu Leu Leu Asp Leu Gly Tyr Asn Arg Ile Arg Ser
185 190 195

Leu Ala Arg Asn Val Phe Ala Gly Met Ile Arg Leu Lys Glu Leu
200 205 210

His Leu Glu His Asn Gln Phe Ser Lys Leu Asn Leu Ala Leu Phe
215 220 225

Pro Arg Leu Val Ser Leu Gln Asn Leu Tyr Leu Gln Trp Asn Lys
230 235 240

Ile Ser Val Ile Gly Gln Thr Met Ser Trp Thr Trp Ser Ser Leu
245 250 255

Gln Arg Leu Asp Leu Ser Gly Asn Glu Ile Glu Ala Phe Ser Gly
260 265 270

Pro Ser Val Phe Gln Cys Val Pro Asn Leu Gln Arg Leu Asn Leu
275 280 285

Asp Ser Asn Lys Leu Thr Phe Ile Gly Gln Glu Ile Leu Asp Ser
290 295 300

Trp Ile Ser Leu Asn Asp Ile Ser Leu Ala Gly Asn Ile Trp Glu
305 310 315

Cys Ser Arg Asn Ile Cys Ser Leu Val Asn Trp Leu Lys Ser Phe
320 325 330

Lys Gly Leu Arg Glu Asn Thr Ile Ile Cys Ala Ser Pro Lys Glu
335 340 345

Leu Gln Gly Val Asn Val Ile Asp Ala Val Lys Asn Tyr Ser Ile
350 355 360

Cys Gly Lys Ser Thr Thr Glu Arg Phe Asp Leu Ala Arg Ala Leu
365 370 375

Pro Lys Pro Thr Phe Lys Pro Lys Leu Pro Arg Pro Lys His Glu
380 385 390

Ser Lys Pro Pro Leu Pro Pro Thr Val Gly Ala Thr Glu Pro Gly
395 400 405

Pro Glu Thr Asp Ala Asp Ala Glu His Ile Ser Phe His Lys Ile
410 415 420

Ile Ala Gly Ser Val Ala Leu Phe Leu Ser Val Leu Val Ile Leu
425 430 435

Leu Val Ile Tyr Val Ser Trp Lys Arg Tyr Pro Ala Ser Met Lys
440 445 450

Gln Leu Gln Gln Arg Ser Leu Met Arg Arg His Arg Lys Lys Lys
455 460 465

Arg Gln Ser Leu Lys Gln Met Thr Pro Ser Thr Gln Glu Phe Tyr
470 475 480

Val Asp Tyr Lys Pro Thr Asn Thr Glu Thr Ser Glu Met Leu Leu
485 490 495

Asn Gly Thr Gly Pro Cys Thr Tyr Asn Lys Ser Gly Ser Arg Glu
500 505 510

Cys Glu Val

<210> SEQ ID NO 125
<211> LENGTH: 998
<212> TYPE: DNA
<213> ORGANISM: Homo Sapien

<400> SEQUENCE: 125

-continued

```
ccgttatcgt cttgcgctac tgctgaatgt ccgtcccgga ggaggaggag      50
aggcttttgc cgctgaccca gagatggccc cgagcgagca aattcctact     100
gtccggctgc gcggctaccg tggccgagct agcaaccttt cccctggatc     150
tcacaaaaac tcgactccaa atgcaaggag aagcagctct tgctcggttg     200
ggagacggtg caagagaatc tgccccctat aggggaatgg tgcgcacagc     250
cctagggatc attgaagagg aaggctttct aaagctttgg caaggagtga     300
cacccgccat ttacagacac gtagtgtatt ctggaggtcg aatggtcaca     350
tatgaacatc tccgagaggt tgtgtttggc aaaagtgaag atgagcatta     400
tcccctttgg aaatcagtca ttggagggat gatggctggt gttattggcc     450
agtttttagc caatccaact gacctagtga aggttcagat gcaaatggaa     500
ggaaaaagga aactggaagg aaaaccattg cgatttcgtg gtgtacatca     550
tgcatttgca aaaatcttag ctgaaggagg aatacgaggg ctttgggcag     600
gctgggtacc caatatacaa agagcagcac tggtgaatat gggagattta     650
accacttatg atacagtgaa acactacttg gtattgaata caccacttga     700
ggacaatatc atgactcacg gtttatcaag tttatgttct ggactggtag     750
cttctattct gggaacacca gccgatgtca tcaaaagcag aataatgaat     800
caaccacgag ataaacaagg aaggggactt ttgtataaat catcgactga     850
ctgcttgatt caggctgttc aaggtgaagg attcatgagt ctatataaag     900
gctttttacc atcttggctg agaatgaccc cttggtcaat ggtgttctgg     950
cttacttatg aaaaaatcag agagatgagt ggagtcagtc cattttaa       998
```

<210> SEQ ID NO 126
<211> LENGTH: 323
<212> TYPE: PRT
<213> ORGANISM: Homo Sapien

<400> SEQUENCE: 126

```
Met Ser Val Pro Glu Glu Glu Glu Arg Leu Leu Pro Leu Thr Gln
  1               5                  10                  15

Arg Trp Pro Arg Ala Ser Lys Phe Leu Leu Ser Gly Cys Ala Ala
                 20                  25                  30

Thr Val Ala Glu Leu Ala Thr Phe Pro Leu Asp Leu Thr Lys Thr
                 35                  40                  45

Arg Leu Gln Met Gln Gly Glu Ala Ala Leu Ala Arg Leu Gly Asp
                 50                  55                  60

Gly Ala Arg Glu Ser Ala Pro Tyr Arg Gly Met Val Arg Thr Ala
                 65                  70                  75

Leu Gly Ile Ile Glu Glu Glu Gly Phe Leu Lys Leu Trp Gln Gly
                 80                  85                  90

Val Thr Pro Ala Ile Tyr Arg His Val Val Tyr Ser Gly Gly Arg
                 95                 100                 105

Met Val Thr Tyr Glu His Leu Arg Glu Val Val Phe Gly Lys Ser
                110                 115                 120

Glu Asp Glu His Tyr Pro Leu Trp Lys Ser Val Ile Gly Gly Met
                125                 130                 135

Met Ala Gly Val Ile Gly Gln Phe Leu Ala Asn Pro Thr Asp Leu
                140                 145                 150
```

-continued

```
Val Lys Val Gln Met Gln Met Glu Gly Lys Arg Lys Leu Glu Gly
                155                 160                 165

Lys Pro Leu Arg Phe Arg Gly Val His His Ala Phe Ala Lys Ile
                170                 175                 180

Leu Ala Glu Gly Gly Ile Arg Gly Leu Trp Ala Gly Trp Val Pro
                185                 190                 195

Asn Ile Gln Arg Ala Ala Leu Val Asn Met Gly Asp Leu Thr Thr
                200                 205                 210

Tyr Asp Thr Val Lys His Tyr Leu Val Leu Asn Thr Pro Leu Glu
                215                 220                 225

Asp Asn Ile Met Thr His Gly Leu Ser Ser Leu Cys Ser Gly Leu
                230                 235                 240

Val Ala Ser Ile Leu Gly Thr Pro Ala Asp Val Ile Lys Ser Arg
                245                 250                 255

Ile Met Asn Gln Pro Arg Asp Lys Gln Gly Arg Gly Leu Leu Tyr
                260                 265                 270

Lys Ser Ser Thr Asp Cys Leu Ile Gln Ala Val Gln Gly Glu Gly
                275                 280                 285

Phe Met Ser Leu Tyr Lys Gly Phe Leu Pro Ser Trp Leu Arg Met
                290                 295                 300

Thr Pro Trp Ser Met Val Phe Trp Leu Thr Tyr Glu Lys Ile Arg
                305                 310                 315

Glu Met Ser Gly Val Ser Pro Phe
                320
```

<210> SEQ ID NO 127
<211> LENGTH: 1505
<212> TYPE: DNA
<213> ORGANISM: Homo Sapien

<400> SEQUENCE: 127

```
cgcggatcgg acccaagcag gtcggcggcg gcggcaggag agcggccggg     50

cgtcagctcc tcgacccccg tgtcgggcta gtccagcgag gcggacgggc    100

ggcgtgggcc catggccagg cccggcatgg agcggtggcg cgaccggctg    150

gcgctggtga cgggggcctc gggggcatc ggcgcggccg tggcccgggc    200

cctggtccag cagggactga aggtggtggg ctgcgcccgc actgtgggca    250

acatcgagga gctggctgct gaatgtaaga gtgcaggcta ccccgggact    300

ttgatcccct acagatgtga cctatcaaat gaagaggaca tcctctccat    350

gttctcagct atccgttctc agcacagcgg tgtagacatc tgcatcaaca    400

atgctggctt ggcccggcct gacaccctgc tctcaggcag caccagtggt    450

tggaaggaca tgttcaatgt gaacgtgctg gccctcagca tctgcacacg    500

ggaagcctac cagtccatga aggagcggaa tgtggacgat gggcacatca    550

ttaacatcaa tagcatgtct ggccaccgag tgttacccct gtctgtgacc    600

cacttctata gtgccaccaa gtatgccgtc actgcgctga cagagggact    650

gaggcaagag cttcgggagg cccagaccca catccgagcc acgtgcatct    700

ctccaggtgt ggtggagaca caattcgcct tcaaactcca cgacaaggac    750

cctgagaagg cagctgccac ctatgagcaa atgaagtgtc tcaaacccga    800

ggatgtggcc gaggctgtta tctacgtcct cagcaccccc gcacacatcc    850

agattggaga catccagatg aggcccacgg agcaggtgac ctagtgactg    900
```

-continued

```
tgggagctcc tccttccctc cccacccttc atggcttgcc tcctgcctct        950
ggattttagg tgttgatttc tggatcacgg gataccactt cctgtccaca       1000
ccccgaccag gggctagaaa atttgtttga gatttttata tcatcttgtc       1050
aaattgcttc agttgtaaat gtgaaaaatg ggctggggaa aggaggtggt       1100
gtccctaatt gttttacttg ttaacttgtt cttgtgcccc tgggcacttg       1150
gcctttgtct gctctcagtg tcttcccttt gacatgggaa aggagttgtg       1200
gccaaaatcc ccatcttctt gcacctcaac gtctgtggct cagggctggg       1250
gtggcagagg gaggccttca ccttatatct gtgttgttat ccagggctcc       1300
agacttcctc ctctgcctgc cccactgcac cctctccccc ttatctatct       1350
ccttctcggc tccccagccc agtcttggct tcttgtcccc tcctggggtc       1400
atccctccac tctgactctg actatggcag cagaacacca gggcctggcc       1450
cagtggattt catggtgatc attaaaaaag aaaaatcgca accaaaaaaa       1500
aaaaa                                                        1505
```

```
<210> SEQ ID NO 128
<211> LENGTH: 260
<212> TYPE: PRT
<213> ORGANISM: Homo Sapien

<400> SEQUENCE: 128

Met Ala Arg Pro Gly Met Glu Arg Trp Arg Asp Arg Leu Ala Leu
  1               5                  10                  15

Val Thr Gly Ala Ser Gly Gly Ile Gly Ala Ala Val Ala Arg Ala
                 20                  25                  30

Leu Val Gln Gln Gly Leu Lys Val Val Gly Cys Ala Arg Thr Val
                 35                  40                  45

Gly Asn Ile Glu Glu Leu Ala Ala Glu Cys Lys Ser Ala Gly Tyr
                 50                  55                  60

Pro Gly Thr Leu Ile Pro Tyr Arg Cys Asp Leu Ser Asn Glu Glu
                 65                  70                  75

Asp Ile Leu Ser Met Phe Ser Ala Ile Arg Ser Gln His Ser Gly
                 80                  85                  90

Val Asp Ile Cys Ile Asn Asn Ala Gly Leu Ala Arg Pro Asp Thr
                 95                 100                 105

Leu Leu Ser Gly Ser Thr Ser Gly Trp Lys Asp Met Phe Asn Val
                110                 115                 120

Asn Val Leu Ala Leu Ser Ile Cys Thr Arg Glu Ala Tyr Gln Ser
                125                 130                 135

Met Lys Glu Arg Asn Val Asp Asp Gly His Ile Ile Asn Ile Asn
                140                 145                 150

Ser Met Ser Gly His Arg Val Leu Pro Leu Ser Val Thr His Phe
                155                 160                 165

Tyr Ser Ala Thr Lys Tyr Ala Val Thr Ala Leu Thr Glu Gly Leu
                170                 175                 180

Arg Gln Glu Leu Arg Glu Ala Gln Thr His Ile Arg Ala Thr Cys
                185                 190                 195

Ile Ser Pro Gly Val Val Glu Thr Gln Phe Ala Phe Lys Leu His
                200                 205                 210

Asp Lys Asp Pro Glu Lys Ala Ala Ala Thr Tyr Glu Gln Met Lys
                215                 220                 225
```

-continued

Cys Leu Lys Pro Glu Asp Val Ala Glu Ala Val Ile Tyr Val Leu
                230                 235                 240

Ser Thr Pro Ala His Ile Gln Ile Gly Asp Ile Gln Met Arg Pro
                245                 250                 255

Thr Glu Gln Val Thr
                260

<210> SEQ ID NO 129
<211> LENGTH: 1177
<212> TYPE: DNA
<213> ORGANISM: Homo Sapien

<400> SEQUENCE: 129
aacttctaca tgggcctcct gctgctggtg ctcttcctca gcctcctgcc 50
ggtggcctac accatcatgt ccctcccacc ctcctttgac tgcgggccgt 100
tcaggtgcag agtctcagtt gcccgggagc acctcccctc ccgaggcagt 150
ctgctcagag ggcctcggcc cagaattcca gttctggttt catgccagcc 200
tgtaaaaggc catggaactt tgggtgaatc accgatgcca tttaagaggg 250
ttttctgcca ggatggaaat gttaggtcgt tctgtgtctg cgctgttcat 300
ttcagtagcc accagccacc tgtggccgtt gagtgcttga aatgaggaac 350
tgagaaaatt aatttctcat gtatttttct catttattta ttaattttta 400
actgatagtt gtacatattt gggggtacat gtgatatttg gatacatgta 450
tacaatatat aatgatcaaa tcagggtaac tgggatatcc atcacatcaa 500
acatttattt tttattcttt ttagacagag tctcactctg tcacccaggc 550
tggagtgcag tggtgccatc tcagcttact gcaacctctg cctgccaggt 600
tcaagcgatt ctcatgcctc cacctcccaa gtagctggga ctacaggcat 650
gcaccacaat gcccaactaa tttttgtatt tttagtagag acggggtttt 700
gccatgttgc ccaggctggc cttgaactcc tggcctcaaa caatccactt 750
gcctcggcct cccaaagtgt tatgattaca ggcgtgagcc accgtgcctg 800
gcctaaacat ttatcttttc tttgtgttgg gaactttgaa attatacaat 850
gaattattgt taactgtcat ctccctgctg tgctatggaa cactgggact 900
tcttccctct atctaactgt atatttgtac cagttaacca accgtacttc 950
atccccactc ctctctatcc ttcccaacct ctgatcacct cattctactc 1000
tctacctcca tgagatccac ttttttagct cccacatgtg agtaagaaaa 1050
tgcaatattt gtctttctgt gcctggctta tttcacttaa cataatgact 1100
tcctgttcca tccatgttgc tgcaaatgac aggatttcgt tcttaatttc 1150
aattaaaata accacacatg gcaaaaa 1177

<210> SEQ ID NO 130
<211> LENGTH: 111
<212> TYPE: PRT
<213> ORGANISM: Homo Sapien

<400> SEQUENCE: 130

Met Gly Leu Leu Leu Leu Val Leu Phe Leu Ser Leu Leu Pro Val
  1               5                  10                  15

Ala Tyr Thr Ile Met Ser Leu Pro Pro Ser Phe Asp Cys Gly Pro
                 20                  25                  30

-continued

```
Phe Arg Cys Arg Val Ser Val Ala Arg Glu His Leu Pro Ser Arg
                35                  40                  45

Gly Ser Leu Leu Arg Gly Pro Arg Pro Arg Ile Pro Val Leu Val
                50                  55                  60

Ser Cys Gln Pro Val Lys Gly His Gly Thr Leu Gly Glu Ser Pro
                65                  70                  75

Met Pro Phe Lys Arg Val Phe Cys Gln Asp Gly Asn Val Arg Ser
                80                  85                  90

Phe Cys Val Cys Ala Val His Phe Ser Ser His Gln Pro Pro Val
                95                  100                 105

Ala Val Glu Cys Leu Lys
                110


<210> SEQ ID NO 131
<211> LENGTH: 2061
<212> TYPE: DNA
<213> ORGANISM: Homo Sapien

<400> SEQUENCE: 131

ttctgaagta acggaagcta ccttgtataa agacctcaac actgctgacc      50

atgatcagcg cagcctggag catcttcctc atcgggacta aaattgggct     100

gttccttcaa gtagcacctc tatcagttat ggctaaatcc tgtccatctg     150

tgtgtcgctg cgatgcgggt ttcatttact gtaatgatcg ctttctgaca     200

tccattccaa caggaatacc agaggatgct acaactctct accttcagaa     250

caaccaaata aataatgctg ggattccttc agatttgaaa aacttgctga     300

aagtagaaag aatataccta taccacaaca gtttagatga atttcctacc     350

aacctcccaa agtatgtaaa agagttacat ttgcaagaaa ataacataag     400

gactatcact tatgattcac tttcaaaaat tccctatctg gaagaattac     450

atttagatga caactctgtc tctgcagtta gcatagaaga gggagcattc     500

cgagacagca actatctccg actgcttttc ctgtcccgta atcaccttag     550

cacaattccc tggggtttgc ccaggactat agaagaacta cgcttggatg     600

ataatcgcat atccactatt tcatcaccat ctcttcaagg tctcactagt     650

ctaaaacgcc tggttctaga tggaaacctg ttgaacaatc atggtttagg     700

tgacaaagtt ttcttcaacc tagttaattt gacagagctg tccctggtgc     750

ggaattccct gactgctgca ccagtaaacc ttccaggcac aaacctgagg     800

aagctttatc ttcaagataa ccacatcaat cgggtgcccc caaatgcttt     850

ttcttatcta aggcagctct atcgactgga tatgtccaat aataacctaa     900

gtaatttacc tcagggtatc tttgatgatt tggacaatat aacacaactg     950

attcttcgca acaatccctg gtattgcggg tgcaagatga aatgggtacg    1000

tgactggtta caatcactac ctgtgaaggt caacgtgcgt gggctcatgt    1050

gccaagcccc agaaaaggtt cgtgggatgg ctattaagga tctcaatgca    1100

gaactgtttg attgtaagga cagtgggatt gtaagcacca ttcagataac    1150

cactgcaata cccaacacag tgtatcctgc ccaaggacag tggccagctc    1200

cagtgaccaa acagccagat attaagaacc ccaagctcac taaggatcaa    1250

caaaccacag ggagtccctc aagaaaaaca attacaatta ctgtgaagtc    1300
```

-continued

```
tgtcacctct gataccattc atatctcttg gaaacttgct ctacctatga        1350

ctgctttgag actcagctgg cttaaactgg gccatagccc ggcatttgga        1400

tctataacag aaacaattgt aacaggggaa cgcagtgagt acttggtcac        1450

agccctggag cctgattcac cctataaagt atgcatggtt cccatggaaa        1500

ccagcaacct ctacctattt gatgaaactc ctgtttgtat tgagactgaa        1550

actgcacccc ttcgaatgta caaccctaca accaccctca atcgagagca        1600

agagaaagaa ccttacaaaa accccaattt acctttggct gccatcattg        1650

gtggggctgt ggccctggtt accattgccc ttcttgcttt agtgtgttgg        1700

tatgttcata ggaatggatc gctcttctca aggaactgtg catatagcaa        1750

agggaggaga agaaaggatg actatgcaga agctggcact aagaaggaca        1800

actctatcct ggaaatcagg gaaacttctt ttcagatgtt accaataagc        1850

aatgaaccca tctcgaagga ggagtttgta atacacacca tatttcctcc        1900

taatggaatg aatctgtaca aaaacaatca cagtgaaagc agtagtaacc        1950

gaagctacag agacagtggt attccagact cagatcactc acactcatga        2000

tgctgaagga ctcacagcag acttgtgttt tgggtttttt aaacctaagg        2050

gaggtgatgg t                                                  2061
```

<210> SEQ ID NO 132
<211> LENGTH: 649
<212> TYPE: PRT
<213> ORGANISM: Homo Sapien

<400> SEQUENCE: 132

```
Met Ile Ser Ala Ala Trp Ser Ile Phe Leu Ile Gly Thr Lys Ile
  1               5                  10                  15

Gly Leu Phe Leu Gln Val Ala Pro Leu Ser Val Met Ala Lys Ser
                 20                  25                  30

Cys Pro Ser Val Cys Arg Cys Asp Ala Gly Phe Ile Tyr Cys Asn
                 35                  40                  45

Asp Arg Phe Leu Thr Ser Ile Pro Thr Gly Ile Pro Glu Asp Ala
                 50                  55                  60

Thr Thr Leu Tyr Leu Gln Asn Asn Gln Ile Asn Asn Ala Gly Ile
                 65                  70                  75

Pro Ser Asp Leu Lys Asn Leu Leu Lys Val Glu Arg Ile Tyr Leu
                 80                  85                  90

Tyr His Asn Ser Leu Asp Glu Phe Pro Thr Asn Leu Pro Lys Tyr
                 95                 100                 105

Val Lys Glu Leu His Leu Gln Glu Asn Asn Ile Arg Thr Ile Thr
                110                 115                 120

Tyr Asp Ser Leu Ser Lys Ile Pro Tyr Leu Glu Glu Leu His Leu
                125                 130                 135

Asp Asp Asn Ser Val Ser Ala Val Ser Ile Glu Glu Gly Ala Phe
                140                 145                 150

Arg Asp Ser Asn Tyr Leu Arg Leu Leu Phe Leu Ser Arg Asn His
                155                 160                 165

Leu Ser Thr Ile Pro Trp Gly Leu Pro Arg Thr Ile Glu Glu Leu
                170                 175                 180

Arg Leu Asp Asp Asn Arg Ile Ser Thr Ile Ser Ser Pro Ser Leu
                185                 190                 195
```

-continued

```
Gln Gly Leu Thr Ser Leu Lys Arg Leu Val Leu Asp Gly Asn Leu
                200                 205                 210

Leu Asn Asn His Gly Leu Gly Asp Lys Val Phe Phe Asn Leu Val
                215                 220                 225

Asn Leu Thr Glu Leu Ser Leu Val Arg Asn Ser Leu Thr Ala Ala
                230                 235                 240

Pro Val Asn Leu Pro Gly Thr Asn Leu Arg Lys Leu Tyr Leu Gln
                245                 250                 255

Asp Asn His Ile Asn Arg Val Pro Pro Asn Ala Phe Ser Tyr Leu
                260                 265                 270

Arg Gln Leu Tyr Arg Leu Asp Met Ser Asn Asn Asn Leu Ser Asn
                275                 280                 285

Leu Pro Gln Gly Ile Phe Asp Asp Leu Asp Asn Ile Thr Gln Leu
                290                 295                 300

Ile Leu Arg Asn Asn Pro Trp Tyr Cys Gly Cys Lys Met Lys Trp
                305                 310                 315

Val Arg Asp Trp Leu Gln Ser Leu Pro Val Lys Val Asn Val Arg
                320                 325                 330

Gly Leu Met Cys Gln Ala Pro Glu Lys Val Arg Gly Met Ala Ile
                335                 340                 345

Lys Asp Leu Asn Ala Glu Leu Phe Asp Cys Lys Asp Ser Gly Ile
                350                 355                 360

Val Ser Thr Ile Gln Ile Thr Thr Ala Ile Pro Asn Thr Val Tyr
                365                 370                 375

Pro Ala Gln Gly Gln Trp Pro Ala Pro Val Thr Lys Gln Pro Asp
                380                 385                 390

Ile Lys Asn Pro Lys Leu Thr Lys Asp Gln Gln Thr Thr Gly Ser
                395                 400                 405

Pro Ser Arg Lys Thr Ile Thr Ile Thr Val Lys Ser Val Thr Ser
                410                 415                 420

Asp Thr Ile His Ile Ser Trp Lys Leu Ala Leu Pro Met Thr Ala
                425                 430                 435

Leu Arg Leu Ser Trp Leu Lys Leu Gly His Ser Pro Ala Phe Gly
                440                 445                 450

Ser Ile Thr Glu Thr Ile Val Thr Gly Glu Arg Ser Glu Tyr Leu
                455                 460                 465

Val Thr Ala Leu Glu Pro Asp Ser Pro Tyr Lys Val Cys Met Val
                470                 475                 480

Pro Met Glu Thr Ser Asn Leu Tyr Leu Phe Asp Glu Thr Pro Val
                485                 490                 495

Cys Ile Glu Thr Glu Thr Ala Pro Leu Arg Met Tyr Asn Pro Thr
                500                 505                 510

Thr Thr Leu Asn Arg Glu Gln Glu Lys Glu Pro Tyr Lys Asn Pro
                515                 520                 525

Asn Leu Pro Leu Ala Ala Ile Ile Gly Gly Ala Val Ala Leu Val
                530                 535                 540

Thr Ile Ala Leu Leu Ala Leu Val Cys Trp Tyr Val His Arg Asn
                545                 550                 555

Gly Ser Leu Phe Ser Arg Asn Cys Ala Tyr Ser Lys Gly Arg Arg
                560                 565                 570

Arg Lys Asp Asp Tyr Ala Glu Ala Gly Thr Lys Lys Asp Asn Ser
                575                 580                 585

Ile Leu Glu Ile Arg Glu Thr Ser Phe Gln Met Leu Pro Ile Ser
```

-continued 590 595 600

Asn Glu Pro Ile Ser Lys Glu Glu Phe Val Ile His Thr Ile Phe
605 610 615

Pro Pro Asn Gly Met Asn Leu Tyr Lys Asn Asn His Ser Glu Ser
620 625 630

Ser Ser Asn Arg Ser Tyr Arg Asp Ser Gly Ile Pro Asp Ser Asp
635 640 645

His Ser His Ser

<210> SEQ ID NO 133
<211> LENGTH: 1882
<212> TYPE: DNA
<213> ORGANISM: Homo Sapien

<400> SEQUENCE: 133
ccgtcatccc cctgcagcca cccttcccag agtcctttgc ccaggccacc 50
ccaggcttct tggcagccct gccgggccac ttgtcttcat gtctgccagg 100
gggaggtggg aaggaggtgg gaggagggcg tgcagaggca gtctgggctt 150
ggccagagct cagggtgctg agcgtgtgac cagcagtgag cagaggccgg 200
ccatggccag cctggggctg ctgctcctgc tcttactgac agcactgcca 250
ccgctgtggt cctcctcact gcctgggctg gacactgctg aaagtaaagc 300
caccattgca gacctgatcc tgtctgcgct ggagagagcc accgtcttcc 350
tagaacagag gctgcctgaa atcaacctgg atggcatggt gggggtccga 400
gtgctggaag agcagctaaa aagtgtccgg gagaagtggg cccaggagcc 450
cctgctgcag ccgctgagcc tgcgcgtggg gatgctgggg gagaagctgg 500
aggctgccat ccagagatcc ctccactacc tcaagctgag tgatcccaag 550
tacctaagag agttccagct gaccctccag cccgggtttt ggaagctccc 600
acatgcctgg atccacactg atgcctcctt ggtgtacccc acgttcgggc 650
cccaggactc attctcagag gagagaagtg acgtgtgcct ggtgcagctg 700
ctgggaaccg ggacggacag cagcgagccc tgcggcctct cagacctctg 750
caggagcctc atgaccaagc ccggctgctc aggctactgc ctgtcccacc 800
aactgctctt cttcctctgg gccagaatga ggggatgcac acagggacca 850
ctccaacaga gccaggacta tatcaacctc ttctgcgcca acatgatgga 900
cttgaaccgc agagctgagg ccatcggata cgcctaccct acccgggaca 950
tcttcatgga aaacatcatg ttctgtggaa tgggcggctt ctccgacttc 1000
tacaagctcc ggtggctgga ggccattctc agctggcaga aacagcagga 1050
aggatgcttc ggggagcctg atgctgaaga tgaagaatta tctaaagcta 1100
ttcaatatca gcagcatttt tcgaggagag tgaagaggcg agaaaaacaa 1150
tttccagatt ctcgctctgt tgctcaggct ggagtacagt ggcgcaatct 1200
cggctcactg caacctttgc ctcctgggtt caagcaattc tcttgcctca 1250
tcctcccgag tagctgggac tacaggagcg tgccaccata cctggctaat 1300
ttttatattt ttttagtaga gacagggttt catcatgttg ctcatgctgg 1350
tctcgaactc ctgatctcaa gagatccgcc cacctcaggc tcccaaagtg 1400
tgggattata ggtgtgagcc accgtgtctg gctgaaaagc actttcaaag 1450

-continued

```
agactgtgtt gaataaaggg ccaaggttct tgccacccag cactcatggg        1500

ggctctctcc cctagatggc tgctcctccc acaacacagc cacagcagtg        1550

gcagccctgg gtggcttcct atacatcctg gcagaatacc ccccagcaaa        1600

cagagagcca cacccatcca caccgccacc accaagcagc cgctgagacg        1650

gacggttcca tgccagctgc ctggaggagg aacagacccc tttagtcctc        1700

atcccttaga tcctggaggg cacggatcac atcctgggaa gaaggcatct        1750

ggaggataag caaagccacc ccgacaccca atcttggaag ccctgagtag        1800

gcagggccag ggtaggtggg ggccgggagg gacccaggtg tgaacggatg        1850

aataaagttc aactgcaact gaaaaaaaaa aa                           1882


<210> SEQ ID NO 134
<211> LENGTH: 440
<212> TYPE: PRT
<213> ORGANISM: Homo Sapien

<400> SEQUENCE: 134

Met Ser Ala Arg Gly Arg Trp Glu Gly Gly Gly Arg Arg Ala Cys
  1               5                  10                  15

Arg Gly Ser Leu Gly Leu Ala Arg Ala Gln Gly Ala Glu Arg Val
                 20                  25                  30

Thr Ser Ser Glu Gln Arg Pro Ala Met Ala Ser Leu Gly Leu Leu
                 35                  40                  45

Leu Leu Leu Leu Leu Thr Ala Leu Pro Pro Leu Trp Ser Ser Ser
                 50                  55                  60

Leu Pro Gly Leu Asp Thr Ala Glu Ser Lys Ala Thr Ile Ala Asp
                 65                  70                  75

Leu Ile Leu Ser Ala Leu Glu Arg Ala Thr Val Phe Leu Glu Gln
                 80                  85                  90

Arg Leu Pro Glu Ile Asn Leu Asp Gly Met Val Gly Val Arg Val
                 95                 100                 105

Leu Glu Glu Gln Leu Lys Ser Val Arg Glu Lys Trp Ala Gln Glu
                110                 115                 120

Pro Leu Leu Gln Pro Leu Ser Leu Arg Val Gly Met Leu Gly Glu
                125                 130                 135

Lys Leu Glu Ala Ala Ile Gln Arg Ser Leu His Tyr Leu Lys Leu
                140                 145                 150

Ser Asp Pro Lys Tyr Leu Arg Glu Phe Gln Leu Thr Leu Gln Pro
                155                 160                 165

Gly Phe Trp Lys Leu Pro His Ala Trp Ile His Thr Asp Ala Ser
                170                 175                 180

Leu Val Tyr Pro Thr Phe Gly Pro Gln Asp Ser Phe Ser Glu Glu
                185                 190                 195

Arg Ser Asp Val Cys Leu Val Gln Leu Leu Gly Thr Gly Thr Asp
                200                 205                 210

Ser Ser Glu Pro Cys Gly Leu Ser Asp Leu Cys Arg Ser Leu Met
                215                 220                 225

Thr Lys Pro Gly Cys Ser Gly Tyr Cys Leu Ser His Gln Leu Leu
                230                 235                 240

Phe Phe Leu Trp Ala Arg Met Arg Gly Cys Thr Gln Gly Pro Leu
                245                 250                 255

Gln Gln Ser Gln Asp Tyr Ile Asn Leu Phe Cys Ala Asn Met Met
                260                 265                 270
```

-continued

```
Asp Leu Asn Arg Arg Ala Glu Ala Ile Gly Tyr Ala Tyr Pro Thr
                275                 280                 285

Arg Asp Ile Phe Met Glu Asn Ile Met Phe Cys Gly Met Gly Gly
                290                 295                 300

Phe Ser Asp Phe Tyr Lys Leu Arg Trp Leu Glu Ala Ile Leu Ser
                305                 310                 315

Trp Gln Lys Gln Gln Glu Gly Cys Phe Gly Glu Pro Asp Ala Glu
                320                 325                 330

Asp Glu Glu Leu Ser Lys Ala Ile Gln Tyr Gln Gln His Phe Ser
                335                 340                 345

Arg Arg Val Lys Arg Arg Glu Lys Gln Phe Pro Asp Ser Arg Ser
                350                 355                 360

Val Ala Gln Ala Gly Val Gln Trp Arg Asn Leu Gly Ser Leu Gln
                365                 370                 375

Pro Leu Pro Pro Gly Phe Lys Gln Phe Ser Cys Leu Ile Leu Pro
                380                 385                 390

Ser Ser Trp Asp Tyr Arg Ser Val Pro Pro Tyr Leu Ala Asn Phe
                395                 400                 405

Tyr Ile Phe Leu Val Glu Thr Gly Phe His His Val Ala His Ala
                410                 415                 420

Gly Leu Glu Leu Leu Ile Ser Arg Asp Pro Pro Thr Ser Gly Ser
                425                 430                 435

Gln Ser Val Gly Leu
                440
```

<210> SEQ ID NO 135
<211> LENGTH: 884
<212> TYPE: DNA
<213> ORGANISM: Homo Sapien

<400> SEQUENCE: 135

```
ggtctgagtg cagagctgct gtcatggcgg ccgctctgtg gggcttcttt         50

cccgtcctgc tgctgctgct gctatcgggg gatgtccaga gctcggaggt        100

gcccggggct gctgctgagg gatcgggagg gagtggggtc ggcataggag        150

atcgcttcaa gattgagggg cgtgcagttg ttccaggggt gaagcctcag        200

gactggatct cggcggcccg agtgctggta gacggagaag agcacgtcgg        250

tttccttaag acagatggga gttttgtggt tcatgatata ccttctggat        300

cttatgtagt ggaagttgta tctccagctt acagatttga tcccgttcga        350

gtggatatca cttcgaaagg aaaaatgaga gcaagatatg tgaattacat        400

caaaacatca gaggttgtca gactgcccta tcctctccaa atgaaatctt        450

caggtccacc ttcttacttt attaaaaggg aatcgtgggg ctggacagac        500

tttctaatga acccaatggt tatgatgatg gttcttcctt tattgatatt        550

tgtgcttctg cctaaagtgg tcaacacaag tgatcctgac atgagacggg        600

aaatggagca gtcaatgaat atgctgaatt ccaaccatga gttgcctgat        650

gtttctgagt tcatgacaag actcttctct tcaaaatcat ctggcaaatc        700

tagcagcggc agcagtaaaa caggcaaaag tggggctggc aaaaggaggt        750

agtcaggccg tccagagctg gcatttgcac aaacacggca acactgggtg        800

gcatccaagt cttggaaaac cgtgtgaagc aactactata aacttgagtc        850
```

-continued atcccgacgt tgatctctta caactgtgta tgtt 884

<210> SEQ ID NO 136
<211> LENGTH: 242
<212> TYPE: PRT
<213> ORGANISM: Homo Sapien

<400> SEQUENCE: 136

Met Ala Ala Ala Leu Trp Gly Phe Phe Pro Val Leu Leu Leu Leu
1 5 10 15

Leu Leu Ser Gly Asp Val Gln Ser Ser Glu Val Pro Gly Ala Ala
20 25 30

Ala Glu Gly Ser Gly Gly Ser Gly Val Gly Ile Gly Asp Arg Phe
35 40 45

Lys Ile Glu Gly Arg Ala Val Val Pro Gly Val Lys Pro Gln Asp
50 55 60

Trp Ile Ser Ala Ala Arg Val Leu Val Asp Gly Glu Glu His Val
65 70 75

Gly Phe Leu Lys Thr Asp Gly Ser Phe Val Val His Asp Ile Pro
80 85 90

Ser Gly Ser Tyr Val Val Glu Val Val Ser Pro Ala Tyr Arg Phe
95 100 105

Asp Pro Val Arg Val Asp Ile Thr Ser Lys Gly Lys Met Arg Ala
110 115 120

Arg Tyr Val Asn Tyr Ile Lys Thr Ser Glu Val Val Arg Leu Pro
125 130 135

Tyr Pro Leu Gln Met Lys Ser Ser Gly Pro Pro Ser Tyr Phe Ile
140 145 150

Lys Arg Glu Ser Trp Gly Trp Thr Asp Phe Leu Met Asn Pro Met
155 160 165

Val Met Met Met Val Leu Pro Leu Leu Ile Phe Val Leu Leu Pro
170 175 180

Lys Val Val Asn Thr Ser Asp Pro Asp Met Arg Arg Glu Met Glu
185 190 195

Gln Ser Met Asn Met Leu Asn Ser Asn His Glu Leu Pro Asp Val
200 205 210

Ser Glu Phe Met Thr Arg Leu Phe Ser Ser Lys Ser Ser Gly Lys
215 220 225

Ser Ser Ser Gly Ser Ser Lys Thr Gly Lys Ser Gly Ala Gly Lys
230 235 240

Arg Arg

<210> SEQ ID NO 137
<211> LENGTH: 1571
<212> TYPE: DNA
<213> ORGANISM: Homo Sapien

<400> SEQUENCE: 137
gatggcgcag ccacagcttc tgtgagattc gatttctccc cagttcccct 50
gtgggtctga ggggaccaga agggtgagct acgttggctt tctggaaggg 100
gaggctatat gcgtcaattc cccaaaacaa gttttgacat ttcccctgaa 150
atgtcattct ctatctattc actgcaagtg cctgctgttc caggccttac 200
ctgctgggca ctaacggcgg agccaggatg gggacagaat aaaggagcca 250
cgacctgtgc caccaactcg cactcagact ctgaactcag acctgaaatc 300

-continued

```
ttctcttcac gggaggcttg gcagtttttc ttactcctgt ggtctccaga           350
tttcaggcct aagatgaaag cctctagtct tgccttcagc cttctctctg           400
ctgcgtttta tctcctatgg actccttcca ctggactgaa gacactcaat           450
ttgggaagct gtgtgatcgc cacaaacctt caggaaatac gaaatggatt           500
ttctgagata cggggcagtg tgcaagccaa agatggaaac attgacatca           550
gaatcttaag gaggactgag tctttgcaag acacaaagcc tgcgaatcga           600
tgctgcctcc tgcgccattt gctaagactc tatctggaca gggtatttaa           650
aaactaccag acccctgacc attatactct ccggaagatc agcagcctcg           700
ccaattcctt tcttaccatc aagaaggacc tccggctctc tcatgcccac           750
atgacatgcc attgtgggga ggaagcaatg aagaaataca gccagattct           800
gagtcacttt gaaaagctgg aacctcaggc agcagttgtg aaggctttgg           850
gggaactaga cattcttctg caatggatgg aggagacaga ataggaggaa           900
agtgatgctg ctgctaagaa tattcgaggt caagagctcc agtcttcaat           950
acctgcagag gaggcatgac ccaaaccac catctcttta ctgtactagt           1000
cttgtgctgg tcacagtgta tcttatttat gcattacttg cttccttgca          1050
tgattgtctt tatgcatccc caatcttaat tgagaccata cttgtataag          1100
atttttgtaa tatctttctg ctattggata tatttattag ttaatatatt          1150
tatttatttt ttgctattta atgtatttat ttttttactt ggacatgaaa          1200
ctttaaaaaa attcacagat tatatttata acctgactag agcaggtgat          1250
gtatttttat acagtaaaaa aaaaaaacct tgtaaattct agaagagtgg          1300
ctaggggggt tattcatttg tattcaacta aggacatatt tactcatgct          1350
gatgctctgt gagatatttg aaattgaacc aatgactact taggatgggt          1400
tgtggaataa gttttgatgt ggaattgcac atctacctta caattactga          1450
ccatccccag tagactcccc agtcccataa ttgtgtatct tccagccagg          1500
aatcctacac ggccagcatg tatttctaca aataaagttt tctttgcata          1550
ccaaaaaaaa aaaaaaaaaa a                                         1571
```

<210> SEQ ID NO 138
<211> LENGTH: 261
<212> TYPE: PRT
<213> ORGANISM: Homo Sapien

<400> SEQUENCE: 138

```
Met Arg Gln Phe Pro Lys Thr Ser Phe Asp Ile Ser Pro Glu Met
  1               5                  10                  15

Ser Phe Ser Ile Tyr Ser Leu Gln Val Pro Ala Val Pro Gly Leu
                 20                  25                  30

Thr Cys Trp Ala Leu Thr Ala Glu Pro Gly Trp Gly Gln Asn Lys
                 35                  40                  45

Gly Ala Thr Thr Cys Ala Thr Asn Ser His Ser Asp Ser Glu Leu
                 50                  55                  60

Arg Pro Glu Ile Phe Ser Ser Arg Glu Ala Trp Gln Phe Phe Leu
                 65                  70                  75

Leu Leu Trp Ser Pro Asp Phe Arg Pro Lys Met Lys Ala Ser Ser
                 80                  85                  90
```

-continued

```
Leu Ala Phe Ser Leu Leu Ser Ala Ala Phe Tyr Leu Leu Trp Thr
                95                  100                 105

Pro Ser Thr Gly Leu Lys Thr Leu Asn Leu Gly Ser Cys Val Ile
                110                 115                 120

Ala Thr Asn Leu Gln Glu Ile Arg Asn Gly Phe Ser Glu Ile Arg
                125                 130                 135

Gly Ser Val Gln Ala Lys Asp Gly Asn Ile Asp Ile Arg Ile Leu
                140                 145                 150

Arg Arg Thr Glu Ser Leu Gln Asp Thr Lys Pro Ala Asn Arg Cys
                155                 160                 165

Cys Leu Leu Arg His Leu Leu Arg Leu Tyr Leu Asp Arg Val Phe
                170                 175                 180

Lys Asn Tyr Gln Thr Pro Asp His Tyr Thr Leu Arg Lys Ile Ser
                185                 190                 195

Ser Leu Ala Asn Ser Phe Leu Thr Ile Lys Lys Asp Leu Arg Leu
                200                 205                 210

Ser His Ala His Met Thr Cys His Cys Gly Glu Glu Ala Met Lys
                215                 220                 225

Lys Tyr Ser Gln Ile Leu Ser His Phe Glu Lys Leu Glu Pro Gln
                230                 235                 240

Ala Ala Val Val Lys Ala Leu Gly Glu Leu Asp Ile Leu Leu Gln
                245                 250                 255

Trp Met Glu Glu Thr Glu
                260
```

<210> SEQ ID NO 139
<211> LENGTH: 2395
<212> TYPE: DNA
<213> ORGANISM: Homo Sapien

<400> SEQUENCE: 139

```
cctggagccg gaagcgcggc tgcagcaggg cgaggctcca ggtggggtcg        50

gttccgcatc cagcctagcg tgtccacgat gcggctgggc tccgggactt       100

tcgctacctg ttgcgtagcg atcgaggtgc tagggatcgc ggtcttcctt       150

cggggattct tcccggctcc cgttcgttcc tctgccagag cggaacacgg       200

agcggagccc ccagcgcccg aaccctcggc tggagccagt tctaactgga       250

ccacgctgcc accacctctc ttcagtaaag ttgttattgt tctgatagat       300

gccttgagag atgattttgt gtttgggtca aagggtgtga aatttatgcc       350

ctacacaact taccttgtgg aaaaaggagc atctcacagt tttgtggctg       400

aagcaaagcc acctacagtt actatgcctc gaatcaaggc attgatgacg       450

gggagccttc ctggctttgt cgacgtcatc aggaacctca attctcctgc       500

actgctggaa gacagtgtga taagacaagc aaaagcagct ggaaaaagaa       550

tagtctttta tggagatgaa acctgggtta aattattccc aaagcatttt       600

gtggaatatg atggaacaac ctcatttttc gtgtcagatt acacagaggt       650

ggataataat gtcacgaggc atttggataa agtattaaaa agaggagatt       700

gggacatatt aatcctccac tacctggggc tggaccacat tggccacatt       750

tcagggccca acagccccct gattgggcag aagctgagcg agatggacag       800

cgtgctgatg aagatccaca cctcactgca gtcgaaggag agagagacgc       850

ctttacccaa tttgctggtt ctttgtggtg accatggcat gtctgaaaca       900
```

-continued

```
ggaagtcacg gggcctcctc caccgaggag gtgaatacac ctctgatttt     950

aatcagttct gcgtttgaaa ggaaacccgg tgatatccga catccaaagc    1000

acgtccaata gacggatgtg gctgcgacac tggcgatagc acttggctta    1050

ccgattccaa aagacagtgt agggagcctc ctattcccag ttgtggaagg    1100

aagaccaatg agagagcagt tgagattttt acatttgaat acagtgcagc    1150

ttagtaaact gttgcaagag aatgtgccgt catatgaaaa agatcctggg    1200

tttgagcagt ttaaaatgtc agaaagattg catgggaact ggatcagact    1250

gtacttggag gaaaagcatt cagaagtcct attcaacctg ggctccaagg    1300

ttctcaggca gtacctggat gctctgaaga cgctgagctt gtccctgagt    1350

gcacaagtgg cccagttctc accctgctcc tgctcagcgt cccacaggca    1400

ctgcacagaa aggctgagct ggaagtccca ctgtcatctc ctgggttttc    1450

tctgctcttt tatttggtga tcctggttct ttcggccgtt cacgtcattg    1500

tgtgcacctc agctgaaagt tcgtgctact tctgtggcct ctcgtggctg    1550

gcggcaggct gcctttcgtt taccagactc tggttgaaca cctggtgtgt    1600

gccaagtgct ggcagtgccc tggacagggg gcctcaggga aggacgtgga    1650

gcagccttat cccaggcctc tgggtgtccc gacacaggtg ttcacatctg    1700

tgctgtcagg tcagatgcct cagttcttgg aaagctaggt tcctgcgact    1750

gttaccaagg tgattgtaaa gagctggcgg tcacagagga acaagccccc    1800

cagctgaggg ggtgtgtgaa tcggacagcc tcccagcaga ggtgtgggag    1850

ctgcagctga gggaagaaga gacaatcggc ctggacactc aggagggtca    1900

aaaggagact tggtcgcacc actcatcctg ccaccccag aatgcatcct     1950

gcctcatcag gtccagattt ctttccaagg cggacgtttt ctgttggaat    2000

tcttagtcct tggcctcgga caccttcatt cgttagctgg ggagtggtgg    2050

tgaggcagtg aagaagaggc ggatggtcac actcagatcc acagagccca    2100

ggatcaaggg acccactgca gtggcagcag gactgttggg cccccacccc    2150

aaccctgcac agccctcatc ccctcttggc ttgagccgtc agaggccctg    2200

tgctgagtgt ctgaccgaga cactcacagc tttgtcatca gggcacaggc    2250

ttcctcggag ccaggatgat ctgtgccacg cttgcacctc gggcccatct    2300

gggctcatgc tctctctcct gctattgaat tagtacctag ctgcacacag    2350

tatgtagtta ccaaaagaat aaacggcaat aattgagaaa aaaaa         2395
```

<210> SEQ ID NO 140
<211> LENGTH: 310
<212> TYPE: PRT
<213> ORGANISM: Homo Sapien

<400> SEQUENCE: 140

```
Met Arg Leu Gly Ser Gly Thr Phe Ala Thr Cys Cys Val Ala Ile
  1               5                  10                  15

Glu Val Leu Gly Ile Ala Val Phe Leu Arg Gly Phe Phe Pro Ala
                 20                  25                  30

Pro Val Arg Ser Ser Ala Arg Ala Glu His Gly Ala Glu Pro Pro
                 35                  40                  45

Ala Pro Glu Pro Ser Ala Gly Ala Ser Ser Asn Trp Thr Thr Leu
```

-continued

```
                50                  55                  60

Pro Pro Pro Leu Phe Ser Lys Val Val Ile Val Leu Ile Asp Ala
                65                  70                  75

Leu Arg Asp Asp Phe Val Phe Gly Ser Lys Gly Val Lys Phe Met
                80                  85                  90

Pro Tyr Thr Thr Tyr Leu Val Glu Lys Gly Ala Ser His Ser Phe
                95                  100                 105

Val Ala Glu Ala Lys Pro Pro Thr Val Thr Met Pro Arg Ile Lys
                110                 115                 120

Ala Leu Met Thr Gly Ser Leu Pro Gly Phe Val Asp Val Ile Arg
                125                 130                 135

Asn Leu Asn Ser Pro Ala Leu Leu Glu Asp Ser Val Ile Arg Gln
                140                 145                 150

Ala Lys Ala Ala Gly Lys Arg Ile Val Phe Tyr Gly Asp Glu Thr
                155                 160                 165

Trp Val Lys Leu Phe Pro Lys His Phe Val Glu Tyr Asp Gly Thr
                170                 175                 180

Thr Ser Phe Phe Val Ser Asp Tyr Thr Glu Val Asp Asn Asn Val
                185                 190                 195

Thr Arg His Leu Asp Lys Val Leu Lys Arg Gly Asp Trp Asp Ile
                200                 205                 210

Leu Ile Leu His Tyr Leu Gly Leu Asp His Ile Gly His Ile Ser
                215                 220                 225

Gly Pro Asn Ser Pro Leu Ile Gly Gln Lys Leu Ser Glu Met Asp
                230                 235                 240

Ser Val Leu Met Lys Ile His Thr Ser Leu Gln Ser Lys Glu Arg
                245                 250                 255

Glu Thr Pro Leu Pro Asn Leu Leu Val Leu Cys Gly Asp His Gly
                260                 265                 270

Met Ser Glu Thr Gly Ser His Gly Ala Ser Ser Thr Glu Glu Val
                275                 280                 285

Asn Thr Pro Leu Ile Leu Ile Ser Ser Ala Phe Glu Arg Lys Pro
                290                 295                 300

Gly Asp Ile Arg His Pro Lys His Val Gln
                305                 310


<210> SEQ ID NO 141
<211> LENGTH: 754
<212> TYPE: DNA
<213> ORGANISM: Homo Sapien

<400> SEQUENCE: 141

ggcacgaggc aagccttcca ggttatcgtg acgcaccttg aaagtctgag        50

agctactgcc ctacagaaag ttactagtgc cctaaagctg gcgctggcac       100

tgatgttact gctgctgttg gagtacaact tccctataga aaacaactgc       150

cagcacctta agaccactca caccttcaga gtgaagaact taaacccgaa       200

gaaattcagc attcatgacc aggatcacaa agtactggtc ctggactctg       250

ggaatctcat agcagttcca gataaaaact acatacgccc agagatcttc       300

tttgcattag cctcatcctt gagctcagcc tctgcggaga aaggaagtcc       350

gattctcctg ggggtctcta aaggggagtt ttgtctctac tgtgacaagg       400

ataaaggaca aagtcatcca tcccttcagc tgaagaagga gaaactgatg       450
```

-continued aagctggctg cccaaaagga atcagcacgc cggcccttca tcttttatag 500
ggctcaggtg ggctcctgga acatgctgga gtcggcggct caccccggat 550
ggttcatctg cacctcctgc aattgtaatg agcctgttgg ggtgacagat 600
aaatttgaga acaggaaaca cattgaattt tcatttcaac cagtttgcaa 650
agctgaaatg agccccagtg aggtcagcga ttaggaaact gccccattga 700
acgccttcct cgctaatttg aactaattgt ataaaaacac caaacctgct 750
cact 754

<210> SEQ ID NO 142
<211> LENGTH: 193
<212> TYPE: PRT
<213> ORGANISM: Homo Sapien

<400> SEQUENCE: 142

Met Leu Leu Leu Leu Leu Glu Tyr Asn Phe Pro Ile Glu Asn Asn
1 5 10 15

Cys Gln His Leu Lys Thr Thr His Thr Phe Arg Val Lys Asn Leu
20 25 30

Asn Pro Lys Lys Phe Ser Ile His Asp Gln Asp His Lys Val Leu
35 40 45

Val Leu Asp Ser Gly Asn Leu Ile Ala Val Pro Asp Lys Asn Tyr
50 55 60

Ile Arg Pro Glu Ile Phe Phe Ala Leu Ala Ser Ser Leu Ser Ser
65 70 75

Ala Ser Ala Glu Lys Gly Ser Pro Ile Leu Leu Gly Val Ser Lys
80 85 90

Gly Glu Phe Cys Leu Tyr Cys Asp Lys Asp Lys Gly Gln Ser His
95 100 105

Pro Ser Leu Gln Leu Lys Lys Glu Lys Leu Met Lys Leu Ala Ala
110 115 120

Gln Lys Glu Ser Ala Arg Arg Pro Phe Ile Phe Tyr Arg Ala Gln
125 130 135

Val Gly Ser Trp Asn Met Leu Glu Ser Ala Ala His Pro Gly Trp
140 145 150

Phe Ile Cys Thr Ser Cys Asn Cys Asn Glu Pro Val Gly Val Thr
155 160 165

Asp Lys Phe Glu Asn Arg Lys His Ile Glu Phe Ser Phe Gln Pro
170 175 180

Val Cys Lys Ala Glu Met Ser Pro Ser Glu Val Ser Asp
185 190

<210> SEQ ID NO 143
<211> LENGTH: 961
<212> TYPE: DNA
<213> ORGANISM: Homo Sapien

<400> SEQUENCE: 143
ctagagagta tagggcagaa ggatggcaga tgagtgactc cacatccaga 50
gctgcctccc tttaatccag gatcctgtcc ttcctgtcct gtaggagtgc 100
ctgttgccag tgtggggtga gacaagtttg tcccacaggg ctgtctgagc 150
agataagatt aagggctggg tctgtgctca attaactcct gtgggcacgg 200
gggctgggaa gagcaaagtc agcggtgcct acagtcagca ccatgctggg 250

-continued

```
cctgccgtgg aagggaggtc tgtcctgggc gctgctgctg cttctcttag          300

gctcccagat cctgctgatc tatgcctggc atttccacga gcaaagggac          350

tgtgatgaac acaatgtcat ggctcgttac ctccctgcca cagtggagtt          400

tgctgtccac acattcaacc aacagagcaa ggactactat gcctacagac          450

tggggcacat cttgaattcc tggaaggagc aggtggagtc caagactgta          500

ttctcaatgg agctactgct ggggagaact aggtgtggga aatttgaaga          550

cgacattgac aactgccatt tccaagaaag cacagagctg aacaatactt          600

tcacctgctt cttcaccatc agcaccaggc cctggatgac tcagttcagc          650

ctcctgaaca agacctgctt ggagggattc cactgagtga aacccactca          700

caggcttgtc catgtgctgc tcccacattc cgtggacatc agcactactc          750

tcctgaggac tcttcagtgg ctgagcagct ttggacttgt ttgttatcct          800

attttgcatg tgtttgagat ctcagatcag tgttttagaa aatccacaca          850

tcttgagcct aatcatgtag tgtagatcat taaacatcag cattttaaga          900

aaaaaaaaaa aaaaaaaaaa aaaaaaaaaa aaaaaaaaaa aaaaaaaaaa          950

aaaaaaaaaa a                                                    961
```

<210> SEQ ID NO 144
<211> LENGTH: 147
<212> TYPE: PRT
<213> ORGANISM: Homo Sapien

<400> SEQUENCE: 144

```
Met Leu Gly Leu Pro Trp Lys Gly Gly Leu Ser Trp Ala Leu Leu
  1               5                  10                  15

Leu Leu Leu Leu Gly Ser Gln Ile Leu Leu Ile Tyr Ala Trp His
                 20                  25                  30

Phe His Glu Gln Arg Asp Cys Asp Glu His Asn Val Met Ala Arg
                 35                  40                  45

Tyr Leu Pro Ala Thr Val Glu Phe Ala Val His Thr Phe Asn Gln
                 50                  55                  60

Gln Ser Lys Asp Tyr Tyr Ala Tyr Arg Leu Gly His Ile Leu Asn
                 65                  70                  75

Ser Trp Lys Glu Gln Val Glu Ser Lys Thr Val Phe Ser Met Glu
                 80                  85                  90

Leu Leu Leu Gly Arg Thr Arg Cys Gly Lys Phe Glu Asp Asp Ile
                 95                 100                 105

Asp Asn Cys His Phe Gln Glu Ser Thr Glu Leu Asn Asn Thr Phe
                110                 115                 120

Thr Cys Phe Phe Thr Ile Ser Thr Arg Pro Trp Met Thr Gln Phe
                125                 130                 135

Ser Leu Leu Asn Lys Thr Cys Leu Glu Gly Phe His
                140                 145
```

<210> SEQ ID NO 145
<211> LENGTH: 1157
<212> TYPE: DNA
<213> ORGANISM: Homo Sapien

<400> SEQUENCE: 145

```
ctgtgcagct cgaggctcca gaggcacact ccagagagag ccaaggttct           50

gacgcgatga ggaagcacct gagctggtgg tggctggcca ctgtctgcat          100
```

-continued

```
gctgctcttc agccacctct ctgcggtcca gacgaggggc atcaagcaca          150
gaatcaagtg gaaccggaag gccctgccca gcactgccca gatcactgag          200
gcccaggtgg ctgagaaccg cccgggagcc ttcatcaagc aaggccgcaa          250
gctcgacatt gacttcggag ccgagggcaa caggtactac gaggccaact          300
actggcagtt ccccgatggc atccactaca acggctgctc tgaggctaat          350
gtgaccaagg aggcatttgt caccggctgc atcaatgcca cccaggcggc          400
gaaccagggg gagttccaga agccagacaa caagctccac cagcaggtgc          450
tctggcggct ggtccaggag ctctgctccc tcaagcattg cgagttttgg          500
ttggagaggg gcgcaggact tcgggtcacc atgcaccagc cagtgctcct          550
ctgccttctg gctttgatct ggctcatggt gaaataagct tgccaggagg          600
ctggcagtac agagcgcagc agcgagcaaa tcctggcaag tgacccagct          650
cttctccccc aaacccacgc gtgttctgaa ggtgcccagg agcggcgatg          700
cactcgcact gcaaatgccg ctcccacgta tgcgccctgg tatgtgcctg          750
cgttctgata gatgggggac tgtggcttct ccgtcactcc attctcagcc          800
cctagcagag cgtctggcac actagattag tagtaaatgc ttgatgagaa          850
gaacacatca ggcactgcgc cacctgcttc acagtacttc ccaacaactc          900
ttagaggtag gtgtattccc gttttacaga taaggaaact gaggcccaga          950
gagctgaagt actgcaccca gcatcaccag ctagaaagtg gcagagccag         1000
gattcaaccc tggcttgtct aaccccaggt tttctgctct gtccaattcc         1050
agagctgtct ggtgatcact ttatgtctca cagggaccca catccaaaca         1100
tgtatctcta atgaaattgt gaaagctcca tgtttagaaa taaatgaaaa         1150
cacctga                                                        1157
```

<210> SEQ ID NO 146
<211> LENGTH: 176
<212> TYPE: PRT
<213> ORGANISM: Homo Sapien

<400> SEQUENCE: 146

```
Met Arg Lys His Leu Ser Trp Trp Trp Leu Ala Thr Val Cys Met
  1               5                  10                  15

Leu Leu Phe Ser His Leu Ser Ala Val Gln Thr Arg Gly Ile Lys
                 20                  25                  30

His Arg Ile Lys Trp Asn Arg Lys Ala Leu Pro Ser Thr Ala Gln
                 35                  40                  45

Ile Thr Glu Ala Gln Val Ala Glu Asn Arg Pro Gly Ala Phe Ile
                 50                  55                  60

Lys Gln Gly Arg Lys Leu Asp Ile Asp Phe Gly Ala Glu Gly Asn
                 65                  70                  75

Arg Tyr Tyr Glu Ala Asn Tyr Trp Gln Phe Pro Asp Gly Ile His
                 80                  85                  90

Tyr Asn Gly Cys Ser Glu Ala Asn Val Thr Lys Glu Ala Phe Val
                 95                 100                 105

Thr Gly Cys Ile Asn Ala Thr Gln Ala Ala Asn Gln Gly Glu Phe
                110                 115                 120

Gln Lys Pro Asp Asn Lys Leu His Gln Gln Val Leu Trp Arg Leu
                125                 130                 135
```

-continued

Val Gln Glu Leu Cys Ser Leu Lys His Cys Glu Phe Trp Leu Glu
140 145 150

Arg Gly Ala Gly Leu Arg Val Thr Met His Gln Pro Val Leu Leu
155 160 165

Cys Leu Leu Ala Leu Ile Trp Leu Met Val Lys
170 175

<210> SEQ ID NO 147
<211> LENGTH: 333
<212> TYPE: DNA
<213> ORGANISM: Homo Sapien

<400> SEQUENCE: 147
gccttggcct cccaaagggc tgggattata ggcgtgacca ccatgtctgg 50
tccagagtct catttcctga tgatttatag actcaaagaa aactcatgtt 100
cagaagctct cttctcttct ggcctcctct ctgtcttctt tccctctttc 150
ttcttatttt aattagtagc atctactcag agtcatgcaa gctggaaatc 200
tttcattttg cttgtcagtg gggtaggtca ctgagtctta gtttttattt 250
tttgaaattt caactttcag attcaggggg tacatgtgaa ggtttgtttt 300
atgagtatat tgcatgatgc tgaggtttgg ggt 333

<210> SEQ ID NO 148
<211> LENGTH: 73
<212> TYPE: PRT
<213> ORGANISM: Homo Sapien

<400> SEQUENCE: 148

Met Phe Arg Ser Ser Leu Leu Phe Trp Pro Pro Leu Cys Leu Leu
1 5 10 15

Ser Leu Phe Leu Leu Ile Leu Ile Ser Ser Ile Tyr Ser Glu Ser
20 25 30

Cys Lys Leu Glu Ile Phe His Phe Ala Cys Gln Trp Gly Arg Ser
35 40 45

Leu Ser Leu Ser Phe Tyr Phe Leu Lys Phe Gln Leu Ser Asp Ser
50 55 60

Gly Gly Thr Cys Glu Gly Leu Phe Tyr Glu Tyr Ile Ala
65 70

<210> SEQ ID NO 149
<211> LENGTH: 1893
<212> TYPE: DNA
<213> ORGANISM: Homo Sapien

<400> SEQUENCE: 149
gtctccgcgt cacaggaact tcagcaccca cagggcggac agcgctcccc 50
tctacctgga gacttgactc ccgcgcgccc caaccctgct tatcccttga 100
ccgtcgagtg tcagagatcc tgcagccgcc cagtcccggc ccctctcccg 150
ccccacaccc accctcctgg ctcttcctgt ttttactcct ccttttcatt 200
cataacaaaa gctacagctc caggagccca gcgccgggct gtgacccaag 250
ccgagcgtgg aagaatgggg ttcctcggga ccggcacttg gattctggtg 300
ttagtgctcc cgattcaagc tttccccaaa cctggaggaa gccaagacaa 350
atctctacat aatagagaat taagtgcaga aagacctttg aatgaacaga 400

-continued

```
ttgctgaagc agaagaagac aagattaaaa aaacatatcc tccagaaaac        450

aagccaggtc agagcaacta ttcttttgtt gataacttga acctgctaaa        500

ggcaataaca gaaaaggaaa aaattgagaa agaaagacaa tctataagaa        550

gctccccact tgataataag ttgaatgtgg aagatgttga ttcaaccaag        600

aatcgaaaac tgatcgatga ttatgactct actaagagtg gattggatca        650

taaatttcaa gatgatccag atggtcttca tcaactagac gggactcctt        700

taaccgctga agacattgtc cataaaatcg ctgccaggat ttatgaagaa        750

aatgacagag ccgtgtttga caagattgtt tctaaactac ttaatctcgg        800

ccttatcaca gaaagccaag cacatacact ggaagatgaa gtagcagagg        850

ttttacaaaa attaatctca aaggaagcca acaattatga ggaggatccc        900

aataagccca caagctggac tgagaatcag gctggaaaaa taccagagaa        950

agtgactcca atggcagcaa ttcaagatgg tcttgctaag ggagaaaacg       1000

atgaaacagt atctaacaca ttaaccttga caaatggctt ggaaaggaga       1050

actaaaacct acagtgaaga caactttgag gaactccaat atttcccaaa       1100

tttctatgcg ctactgaaaa gtattgattc agaaaaagaa gcaaaagaga       1150

aagaaacact gattactatc atgaaaacac tgattgactt tgtgaagatg       1200

atggtgaaat atggaacaat atctccagaa gaaggtgttt cctaccttga       1250

aaacttggat gaaatgattg ctcttcagac caaaaacaag ctagaaaaaa       1300

atgctactga caatataagc aagcttttcc cagcaccatc agagaagagt       1350

catgaagaaa cagacagtac caaggaagaa gcagctaaga tggaaaagga       1400

atatggaagc ttgaaggatt ccacaaaaga tgataactcc aacccaggag       1450

gaaagacaga tgaacccaaa ggaaaaacag aagcctattt ggaagccatc       1500

agaaaaaata ttgaatggtt gaagaaacat gacaaaaagg gaaataaaga       1550

agattatgac ctttcaaaga tgagagactt catcaataaa caagctgatg       1600

cttatgtgga gaaaggcatc cttgacaagg aagaagccga ggccatcaag       1650

cgcatttata gcagcctgta aaaatggcaa aagatccagg agtctttcaa       1700

ctgtttcaga aaacataata tagcttaaaa cacttctaat tctgtgatta       1750

aaattttttg acccaagggt tattagaaag tgctgaattt acagtagtta       1800

accttttaca agtggttaaa acatagcttt cttcccgtaa aaactatctg       1850

aaagtaaagt tgtatgtaag ctgaaaaaaa aaaaaaaaaa aaa              1893
```

<210> SEQ ID NO 150
<211> LENGTH: 468
<212> TYPE: PRT
<213> ORGANISM: Homo Sapien

<400> SEQUENCE: 150

```
Met Gly Phe Leu Gly Thr Gly Thr Trp Ile Leu Val Leu Val Leu
  1               5                  10                  15

Pro Ile Gln Ala Phe Pro Lys Pro Gly Gly Ser Gln Asp Lys Ser
                 20                  25                  30

Leu His Asn Arg Glu Leu Ser Ala Glu Arg Pro Leu Asn Glu Gln
                 35                  40                  45

Ile Ala Glu Ala Glu Glu Asp Lys Ile Lys Lys Thr Tyr Pro Pro
                 50                  55                  60
```

-continued

```
Glu Asn Lys Pro Gly Gln Ser Asn Tyr Ser Phe Val Asp Asn Leu
                65                  70                  75

Asn Leu Leu Lys Ala Ile Thr Glu Lys Glu Lys Ile Glu Lys Glu
                80                  85                  90

Arg Gln Ser Ile Arg Ser Ser Pro Leu Asp Asn Lys Leu Asn Val
                95                 100                 105

Glu Asp Val Asp Ser Thr Lys Asn Arg Lys Leu Ile Asp Asp Tyr
               110                 115                 120

Asp Ser Thr Lys Ser Gly Leu Asp His Lys Phe Gln Asp Asp Pro
               125                 130                 135

Asp Gly Leu His Gln Leu Asp Gly Thr Pro Leu Thr Ala Glu Asp
               140                 145                 150

Ile Val His Lys Ile Ala Ala Arg Ile Tyr Glu Glu Asn Asp Arg
               155                 160                 165

Ala Val Phe Asp Lys Ile Val Ser Lys Leu Leu Asn Leu Gly Leu
               170                 175                 180

Ile Thr Glu Ser Gln Ala His Thr Leu Glu Asp Glu Val Ala Glu
               185                 190                 195

Val Leu Gln Lys Leu Ile Ser Lys Glu Ala Asn Asn Tyr Glu Glu
               200                 205                 210

Asp Pro Asn Lys Pro Thr Ser Trp Thr Glu Asn Gln Ala Gly Lys
               215                 220                 225

Ile Pro Glu Lys Val Thr Pro Met Ala Ala Ile Gln Asp Gly Leu
               230                 235                 240

Ala Lys Gly Glu Asn Asp Glu Thr Val Ser Asn Thr Leu Thr Leu
               245                 250                 255

Thr Asn Gly Leu Glu Arg Arg Thr Lys Thr Tyr Ser Glu Asp Asn
               260                 265                 270

Phe Glu Glu Leu Gln Tyr Phe Pro Asn Phe Tyr Ala Leu Leu Lys
               275                 280                 285

Ser Ile Asp Ser Glu Lys Glu Ala Lys Glu Lys Glu Thr Leu Ile
               290                 295                 300

Thr Ile Met Lys Thr Leu Ile Asp Phe Val Lys Met Met Val Lys
               305                 310                 315

Tyr Gly Thr Ile Ser Pro Glu Glu Gly Val Ser Tyr Leu Glu Asn
               320                 325                 330

Leu Asp Glu Met Ile Ala Leu Gln Thr Lys Asn Lys Leu Glu Lys
               335                 340                 345

Asn Ala Thr Asp Asn Ile Ser Lys Leu Phe Pro Ala Pro Ser Glu
               350                 355                 360

Lys Ser His Glu Glu Thr Asp Ser Thr Lys Glu Glu Ala Ala Lys
               365                 370                 375

Met Glu Lys Glu Tyr Gly Ser Leu Lys Asp Ser Thr Lys Asp Asp
               380                 385                 390

Asn Ser Asn Pro Gly Gly Lys Thr Asp Glu Pro Lys Gly Lys Thr
               395                 400                 405

Glu Ala Tyr Leu Glu Ala Ile Arg Lys Asn Ile Glu Trp Leu Lys
               410                 415                 420

Lys His Asp Lys Lys Gly Asn Lys Glu Asp Tyr Asp Leu Ser Lys
               425                 430                 435

Met Arg Asp Phe Ile Asn Lys Gln Ala Asp Ala Tyr Val Glu Lys
               440                 445                 450
```

-continued

```
Gly Ile Leu Asp Lys Glu Glu Ala Glu Ala Ile Lys Arg Ile Tyr
                455                 460                 465

Ser Ser Leu
```

```
<210> SEQ ID NO 151
<211> LENGTH: 2598
<212> TYPE: DNA
<213> ORGANISM: Homo Sapien

<400> SEQUENCE: 151

cggctcgagg ctcccgccag gagaaaggaa cattctgagg ggagtctaca        50

ccctgtggag ctcaagatgg tcctgagtgg ggcgctgtgc ttccgaatga       100

aggactcggc attgaaggtg ctttatctgc ataataacca gcttctagct       150

ggagggctgc atgcagggaa ggtcattaaa ggtgaagaga tcagcgtggt       200

ccccaatcgg tggctggatg ccagcctgtc cccgtcatc ctgggtgtcc        250

agggtggaag ccagtgcctg tcatgtgggg tggggcagga gccgactcta       300

acactagagc cagtgaacat catggagctc tatcttggtg ccaaggaatc       350

caagagcttc accttctacc ggcgggacat ggggctcacc tccagcttcg       400

agtcggctgc ctacccgggc tggttcctgt gcacggtgcc tgaagccgat       450

cagcctgtca gactcaccca gcttcccgag aatggtggct ggaatgcccc       500

catcacagac ttctacttcc agcagtgtga ctagggcaac gtgcccccca       550

gaactccctg ggcagagcca gctcgggtga ggggtgagtg gaggagaccc       600

atggcggaca atcactctct ctgctctcag gacccccacg tctgacttag       650

tgggcacctg accactttgt cttctggttc ccagtttgga taaattctga       700

gatttggagc tcagtccacg gtcctccccc actggatggt gctactgctg       750

tggaaccttg taaaaaccat gtggggtaaa ctgggaataa catgaaaaga       800

tttctgtggg ggtggggtgg gggagtggtg ggaatcattc ctgcttaatg       850

gtaactgaca agtgttaccc tgagccccgc aggccaaccc atccccagtt       900

gagccttata gggtcagtag ctctccacat gaagtcctgt cactcaccac       950

tgtgcaggag agggaggtgg tcatagagtc agggatctat ggcccttggc      1000

ccagccccac cccttccct ttaatcctgc cactgtcata tgctaccttt       1050

cctatctctt ccctcatcat cttgttgtgg gcatgaggag gtggtgatgt      1100

cagaagaaat ggctcgagct cagaagataa aagataagta gggtatgctg      1150

atcctctttt aaaaacccaa gatacaatca aaatcccaga tgctggtctc      1200

tattcccatg aaaaagtgct catgacatat tgagaagacc tacttacaaa      1250

gtggcatata ttgcaattta ttttaattaa aagataccta tttatatatt      1300

tctttataga aaaaagtctg gaagagttta cttcaattgt agcaatgtca      1350

gggtggtggc agtataggtg atttttcttt taattctgtt aatttatctg      1400

tatttcctaa tttttctaca atgaagatga attccttgta taaaaataag      1450

aaaagaaatt aatcttgagg taagcagagc agacatcatc tctgattgtc      1500

ctcagcctcc acttccccag agtaaattca aattgaatcg agctctgctg      1550

ctctggttgg ttgtagtagt gatcaggaaa cagatctcag caaagccact      1600

gaggaggagg ctgtgctgag tttgtgtggc tggaatctct gggtaaggaa      1650
```

-continued

```
cttaaagaac aaaaatcatc tggtaattct ttcctagaag gatcacagcc          1700

cctgggattc caaggcattg gatccagtct ctaagaaggc tgctgtactg          1750

gttgaattgt gtccccctca aattcacatc cttcttggaa tctcagtctg          1800

tgagtttatt tggagataag gtctctgcag atgtagttag ttaagacaag          1850

gtcatgctgg atgaaggtag acctaaattc aatatgactg gtttccttgt          1900

atgaaaagga gaggacacag agacagagga gacgcgggga agactatgta          1950

aagatgaagg cagagatcgg agttttgcag ccacaagcta agaaacacca          2000

aggattgtgg caaccatcag aagcttggaa gaggcaaaga agaattcttc          2050

cctagaggct ttagagggat aacggctctg ctgaaacctt aatctcagac          2100

ttccagcctc ctgaacgaag aaagaataaa tttcggctgt tttaagccac          2150

caaggataat tggttacagc agctctagga aactaataca gctgctaaaa          2200

tgatccctgt ctcctcgtgt ttacattctg tgtgtgtccc ctcccacaat          2250

gtaccaaagt tgtctttgtg accaatagaa tatggcagaa gtgatggcat          2300

gccacttcca agattaggtt ataaaagaca ctgcagcttc tacttgagcc          2350

ctctctctct gccacccacc gcccccaatc tatcttggct cactcgctct          2400

gggggaagct agctgccatg ctatgagcag gcctataaag agacttacgt          2450

ggtaaaaaat gaagtctcct gcccacagcc acattagtga acctagaagc          2500

agagactctg tgagataatc gatgtttgtt gttttaagtt gctcagtttt          2550

ggtctaactt gttatgcagc aatagataaa taatatgcag agaaagag            2598
```

```
<210> SEQ ID NO 152
<211> LENGTH: 155
<212> TYPE: PRT
<213> ORGANISM: Homo Sapien

<400> SEQUENCE: 152

Met Val Leu Ser Gly Ala Leu Cys Phe Arg Met Lys Asp Ser Ala
  1               5                  10                  15

Leu Lys Val Leu Tyr Leu His Asn Asn Gln Leu Leu Ala Gly Gly
                 20                  25                  30

Leu His Ala Gly Lys Val Ile Lys Gly Glu Glu Ile Ser Val Val
                 35                  40                  45

Pro Asn Arg Trp Leu Asp Ala Ser Leu Ser Pro Val Ile Leu Gly
                 50                  55                  60

Val Gln Gly Gly Ser Gln Cys Leu Ser Cys Gly Val Gly Gln Glu
                 65                  70                  75

Pro Thr Leu Thr Leu Glu Pro Val Asn Ile Met Glu Leu Tyr Leu
                 80                  85                  90

Gly Ala Lys Glu Ser Lys Ser Phe Thr Phe Tyr Arg Arg Asp Met
                 95                 100                 105

Gly Leu Thr Ser Ser Phe Glu Ser Ala Ala Tyr Pro Gly Trp Phe
                110                 115                 120

Leu Cys Thr Val Pro Glu Ala Asp Gln Pro Val Arg Leu Thr Gln
                125                 130                 135

Leu Pro Glu Asn Gly Gly Trp Asn Ala Pro Ile Thr Asp Phe Tyr
                140                 145                 150

Phe Gln Gln Cys Asp
                155
```

-continued

<210> SEQ ID NO 153
<211> LENGTH: 1152
<212> TYPE: DNA
<213> ORGANISM: Homo Sapien

<400> SEQUENCE: 153
cttcagaaca ggttctcctt ccccagtcac cagttgctcg agttagaatt 50
gtctgcaatg gccgccctgc agaaatctgt gagctctttc cttatgggga 100
ccctggccac cagctgcctc cttctcttgg ccctcttggt acagggagga 150
gcagctgcgc ccatcagctc ccactgcagg cttgacaagt ccaacttcca 200
gcagccctat atcaccaacc gcaccttcat gctggctaag gaggctagct 250
tggctgataa caacacagac gttcgtctca ttggggagaa actgttccac 300
ggagtcagta tgagtgagcg ctgctatctg atgaagcagg tgctgaactt 350
cacccttgaa gaagtgctgt tccctcaatc tgataggttc cagccttata 400
tgcaggaggt ggtgcccttc ctggccaggc tcagcaacag gctaagcaca 450
tgtcatattg aaggtgatga cctgcatatc cagaggaatg tgcaaaagct 500
gaaggacaca gtgaaaaagc ttggagagag tggagagatc aaagcaattg 550
gagaactgga tttgctgttt atgtctctga gaaatgcctg catttgacca 600
gagcaaagct gaaaaatgaa taactaaccc cctttccctg ctagaaataa 650
caattagatg ccccaaagcg attttttta accaaaagga agatgggaag 700
ccaaactcca tcatgatggg tggattccaa atgaacccct gcgttagtta 750
caaaggaaac caatgccact tttgtttata agaccagaag gtagactttc 800
taagcataga tatttattga taacatttca ttgtaactgg tgttctatac 850
acagaaaaca atttattttt taaataattg tctttttcca taaaaaagat 900
tactttccat tcctttaggg gaaaaaaccc ctaaatagct tcatgtttcc 950
ataatcagta ctttatattt ataaatgtat ttattattat tataagactg 1000
cattttattt atatcatttt attaatatgg atttatttat agaaacatca 1050
ttcgatattg ctacttgagt gtaaggctaa tattgatatt tatgacaata 1100
attatagagc tataacatgt ttatttgacc tcaataaaca cttggatatc 1150
cc 1152

<210> SEQ ID NO 154
<211> LENGTH: 179
<212> TYPE: PRT
<213> ORGANISM: Homo Sapien

<400> SEQUENCE: 154

Met Ala Ala Leu Gln Lys Ser Val Ser Ser Phe Leu Met Gly Thr
1 5 10 15

Leu Ala Thr Ser Cys Leu Leu Leu Leu Ala Leu Leu Val Gln Gly
20 25 30

Gly Ala Ala Ala Pro Ile Ser Ser His Cys Arg Leu Asp Lys Ser
35 40 45

Asn Phe Gln Gln Pro Tyr Ile Thr Asn Arg Thr Phe Met Leu Ala
50 55 60

Lys Glu Ala Ser Leu Ala Asp Asn Asn Thr Asp Val Arg Leu Ile
65 70 75

-continued

Gly Glu Lys Leu Phe His Gly Val Ser Met Ser Glu Arg Cys Tyr
80 85 90

Leu Met Lys Gln Val Leu Asn Phe Thr Leu Glu Glu Val Leu Phe
95 100 105

Pro Gln Ser Asp Arg Phe Gln Pro Tyr Met Gln Glu Val Val Pro
110 115 120

Phe Leu Ala Arg Leu Ser Asn Arg Leu Ser Thr Cys His Ile Glu
125 130 135

Gly Asp Asp Leu His Ile Gln Arg Asn Val Gln Lys Leu Lys Asp
140 145 150

Thr Val Lys Lys Leu Gly Glu Ser Gly Glu Ile Lys Ala Ile Gly
155 160 165

Glu Leu Asp Leu Leu Phe Met Ser Leu Arg Asn Ala Cys Ile
170 175

<210> SEQ ID NO 155
<211> LENGTH: 1320
<212> TYPE: DNA
<213> ORGANISM: Homo Sapien

<400> SEQUENCE: 155
ggcttgctga aaataaaatc aggactccta acctgctcca gtcagcctgc 50
ttccacgagg cctgtcagtc agtgcccgac ttgtgactga gtgtgcagtg 100
cccagcatgt accaggtcag tgcagagggc tgcctgaggg ctgtgctgag 150
agggagagga gcagagatgc tgctgagggt ggagggaggc caagctgcca 200
ggtttggggc tgggggccaa gtggagtgag aaactgggat cccagggggga 250 gggtgcagat gagggagcga cccagattag gtgaggacag ttctctcatt 300
agccttttcc tacaggtggt tgcattcttg gcaatggtca tgggaaccca 350
cacctacagc cactggccca gctgctgccc cagcaaaggg caggacacct 400
ctgaggagct gctgaggtgg agcactgtgc ctgtgcctcc cctagagcct 450
gctaggccca accgccaccc agagtcctgt agggccagtg aagatggacc 500
cctcaacagc agggccatct ccccctggag atatgagttg gacagagact 550
tgaaccggct cccccaggac ctgtaccacg cccgttgcct gtgcccgcac 600
tgcgtcagcc tacagacagg ctcccacatg gacccccggg gcaactcgga 650
gctgctctac cacaaccaga ctgtcttcta caggcggcca tgccatggcg 700
agaagggcac ccacaagggc tactgcctgg agcgcaggct gtaccgtgtt 750
tccttagctt gtgtgtgtgt gcggccccgt gtgatgggct agccggacct 800
gctggaggct ggtccctttt tgggaaacct ggagccaggt gtacaaccac 850
ttgccatgaa gggccaggat gcccagatgc ttggcccctg tgaagtgctg 900
tctggagcag caggatcccg ggacaggatg gggggctttg ggggaaaacct 950 gcacttctgc acattttgaa aagagcagct gctgcttagg gccgccggaa 1000
gctggtgtcc tgtcattttc tctcaggaaa ggttttcaaa gttctgccca 1050
tttctggagg ccaccactcc tgtctcttcc tcttttccca tcccctgcta 1100
ccctggccca gcacaggcac tttctagata tttccccctt gctggagaag 1150
aaagagcccc tggttttatt tgtttgttta ctcatcactc agtgagcatc 1200
tactttgggt gcattctagt gtagttacta gtcttttgac atggatgatt 1250

-continued ctgaggagga agctgttatt gaatgtatag agatttatcc aaataaatat 1300
ctttatttaa aaatgaaaaa 1320

<210> SEQ ID NO 156
<211> LENGTH: 177
<212> TYPE: PRT
<213> ORGANISM: Homo Sapien

<400> SEQUENCE: 156

Met Arg Glu Arg Pro Arg Leu Gly Glu Asp Ser Ser Leu Ile Ser
1 5 10 15

Leu Phe Leu Gln Val Val Ala Phe Leu Ala Met Val Met Gly Thr
20 25 30

His Thr Tyr Ser His Trp Pro Ser Cys Cys Pro Ser Lys Gly Gln
35 40 45

Asp Thr Ser Glu Glu Leu Leu Arg Trp Ser Thr Val Pro Val Pro
50 55 60

Pro Leu Glu Pro Ala Arg Pro Asn Arg His Pro Glu Ser Cys Arg
65 70 75

Ala Ser Glu Asp Gly Pro Leu Asn Ser Arg Ala Ile Ser Pro Trp
80 85 90

Arg Tyr Glu Leu Asp Arg Asp Leu Asn Arg Leu Pro Gln Asp Leu
95 100 105

Tyr His Ala Arg Cys Leu Cys Pro His Cys Val Ser Leu Gln Thr
110 115 120

Gly Ser His Met Asp Pro Arg Gly Asn Ser Glu Leu Leu Tyr His
125 130 135

Asn Gln Thr Val Phe Tyr Arg Arg Pro Cys His Gly Glu Lys Gly
140 145 150

Thr His Lys Gly Tyr Cys Leu Glu Arg Arg Leu Tyr Arg Val Ser
155 160 165

Leu Ala Cys Val Cys Val Arg Pro Arg Val Met Gly
170 175

<210> SEQ ID NO 157
<211> LENGTH: 1515
<212> TYPE: DNA
<213> ORGANISM: Homo Sapien

<400> SEQUENCE: 157
ccggcgatgt cgctcgtgct gctaagcctg gccgcgctgt gcaggagcgc 50
cgtaccccga gagccgaccg ttcaatgtgg ctctgaaact gggccatctc 100
cagagtggat gctacaacat gatctaatcc ccggagactt gagggacctc 150
cgagtagaac ctgttacaac tagtgttgca acaggggact attcaatttt 200
gatgaatgta agctgggtac tccgggcaga tgccagcatc cgcttgttga 250
aggccaccaa gatttgtgtg acgggcaaaa gcaacttcca gtcctacagc 300
tgtgtgaggt gcaattacac agaggccttc cagactcaga ccagaccctc 350
tggtggtaaa tggacatttt cctacatcgg cttccctgta gagctgaaca 400
cagtctattt cattggggcc cataatattc ctaatgcaaa tatgaatgaa 450
gatggccctt ccatgtctgt gaatttcacc tcaccaggct gcctagacca 500
cataatgaaa tataaaaaaa agtgtgtcaa ggccggaagc ctgtgggatc 550
cgaacatcac tgcttgtaag aagaatgagg agacagtaga agtgaacttc 600

-continued

```
acaaccactc ccctgggaaa cagatacatg gctcttatcc aacacagcac      650

tatcatcggg ttttctcagg tgtttgagcc acaccagaag aaacaaacgc      700

gagcttcagt ggtgattcca gtgactgggg atagtgaagg tgctacggtg      750

cagctgactc catattttcc tacttgtggc agcgactgca tccgacataa      800

aggaacagtt gtgctctgcc cacaaacagg cgtccctttc cctctggata      850

acaacaaaag caagccggga ggctggctgc ctctcctcct gctgtctctg      900

ctggtggcca catgggtgct ggtggcaggg atctatctaa tgtggaggca      950

cgaaaggatc aagaagactt ccttttctac caccacacta ctgcccccca     1000

ttaaggttct tgtggtttac ccatctgaaa tatgtttcca tcacacaatt     1050

tgttacttca ctgaatttct tcaaaaccat tgcagaagtg aggtcatcct     1100

tgaaaagtgg cagaaaaaga aaatagcaga gatgggtcca gtgcagtggc     1150

ttgccactca aaagaaggca gcagacaaag tcgtcttcct tctttccaat     1200

gacgtcaaca gtgtgtgcga tggtacctgt ggcaagagcg agggcagtcc     1250

cagtgagaac tctcaagacc tcttccccct tgcctttaac cttttctgca     1300

gtgatctaag aagccagatt catctgcaca aatacgtggt ggtctacttt     1350

agagagattg atacaaaaga cgattacaat gctctcagtg tctgccccaa     1400

gtaccacctc atgaaggatg ccactgcttt ctgtgcagaa cttctccatg     1450

tcaagcagca ggtgtcagca ggaaaaagat cacaagcctg ccacgatggc     1500

tgctgctcct tgtag                                           1515
```

<210> SEQ ID NO 158
<211> LENGTH: 502
<212> TYPE: PRT
<213> ORGANISM: Homo Sapien

<400> SEQUENCE: 158

```
Met Ser Leu Val Leu Leu Ser Leu Ala Ala Leu Cys Arg Ser Ala
  1               5                  10                  15

Val Pro Arg Glu Pro Thr Val Gln Cys Gly Ser Glu Thr Gly Pro
                 20                  25                  30

Ser Pro Glu Trp Met Leu Gln His Asp Leu Ile Pro Gly Asp Leu
                 35                  40                  45

Arg Asp Leu Arg Val Glu Pro Val Thr Thr Ser Val Ala Thr Gly
                 50                  55                  60

Asp Tyr Ser Ile Leu Met Asn Val Ser Trp Val Leu Arg Ala Asp
                 65                  70                  75

Ala Ser Ile Arg Leu Leu Lys Ala Thr Lys Ile Cys Val Thr Gly
                 80                  85                  90

Lys Ser Asn Phe Gln Ser Tyr Ser Cys Val Arg Cys Asn Tyr Thr
                 95                 100                 105

Glu Ala Phe Gln Thr Gln Thr Arg Pro Ser Gly Gly Lys Trp Thr
                110                 115                 120

Phe Ser Tyr Ile Gly Phe Pro Val Glu Leu Asn Thr Val Tyr Phe
                125                 130                 135

Ile Gly Ala His Asn Ile Pro Asn Ala Asn Met Asn Glu Asp Gly
                140                 145                 150

Pro Ser Met Ser Val Asn Phe Thr Ser Pro Gly Cys Leu Asp His
                155                 160                 165
```

-continued

```
Ile Met Lys Tyr Lys Lys Lys Cys Val Lys Ala Gly Ser Leu Trp
                170                 175                 180

Asp Pro Asn Ile Thr Ala Cys Lys Lys Asn Glu Glu Thr Val Glu
                185                 190                 195

Val Asn Phe Thr Thr Thr Pro Leu Gly Asn Arg Tyr Met Ala Leu
                200                 205                 210

Ile Gln His Ser Thr Ile Ile Gly Phe Ser Gln Val Phe Glu Pro
                215                 220                 225

His Gln Lys Lys Gln Thr Arg Ala Ser Val Val Ile Pro Val Thr
                230                 235                 240

Gly Asp Ser Glu Gly Ala Thr Val Gln Leu Thr Pro Tyr Phe Pro
                245                 250                 255

Thr Cys Gly Ser Asp Cys Ile Arg His Lys Gly Thr Val Val Leu
                260                 265                 270

Cys Pro Gln Thr Gly Val Pro Phe Pro Leu Asp Asn Asn Lys Ser
                275                 280                 285

Lys Pro Gly Gly Trp Leu Pro Leu Leu Leu Leu Ser Leu Leu Val
                290                 295                 300

Ala Thr Trp Val Leu Val Ala Gly Ile Tyr Leu Met Trp Arg His
                305                 310                 315

Glu Arg Ile Lys Lys Thr Ser Phe Ser Thr Thr Thr Leu Leu Pro
                320                 325                 330

Pro Ile Lys Val Leu Val Val Tyr Pro Ser Glu Ile Cys Phe His
                335                 340                 345

His Thr Ile Cys Tyr Phe Thr Glu Phe Leu Gln Asn His Cys Arg
                350                 355                 360

Ser Glu Val Ile Leu Glu Lys Trp Gln Lys Lys Lys Ile Ala Glu
                365                 370                 375

Met Gly Pro Val Gln Trp Leu Ala Thr Gln Lys Lys Ala Ala Asp
                380                 385                 390

Lys Val Val Phe Leu Leu Ser Asn Asp Val Asn Ser Val Cys Asp
                395                 400                 405

Gly Thr Cys Gly Lys Ser Glu Gly Ser Pro Ser Glu Asn Ser Gln
                410                 415                 420

Asp Leu Phe Pro Leu Ala Phe Asn Leu Phe Cys Ser Asp Leu Arg
                425                 430                 435

Ser Gln Ile His Leu His Lys Tyr Val Val Val Tyr Phe Arg Glu
                440                 445                 450

Ile Asp Thr Lys Asp Asp Tyr Asn Ala Leu Ser Val Cys Pro Lys
                455                 460                 465

Tyr His Leu Met Lys Asp Ala Thr Ala Phe Cys Ala Glu Leu Leu
                470                 475                 480

His Val Lys Gln Gln Val Ser Ala Gly Lys Arg Ser Gln Ala Cys
                485                 490                 495

His Asp Gly Cys Cys Ser Leu
                500
```

<210> SEQ ID NO 159
<211> LENGTH: 535
<212> TYPE: DNA
<213> ORGANISM: Homo Sapien

<400> SEQUENCE: 159

```
agccaccagc gcaacatgac agtgaagacc ctgcatggcc cagccatggt             50
```

-continued

```
caagtacttg ctgctgtcga tattggggct tgcctttctg agtgaggcgg        100

cagctcggaa aatccccaaa gtaggacata ctttttttcca aaagcctgag        150

agttgcccgc ctgtgccagg aggtagtatg aagcttgaca ttggcatcat        200

caatgaaaac cagcgcgttt ccatgtcacg taacatcgag agccgctcca        250

cctccccctg gaattacact gtcacttggg accccaaccg gtacccctcg        300

gaagttgtac aggcccagtg taggaacttg ggctgcatca atgctcaagg        350

aaaggaagac atctccatga attccgttcc catccagcaa gagaccctgg        400

tcgtccggag gaagcaccaa ggctgctctg tttctttcca gttggagaag        450

gtgctggtga ctgttggctg cacctgcgtc acccctgtca tccaccatgt        500

gcagtaagag gtgcatatcc actcagctga agaag                        535
```

<210> SEQ ID NO 160
<211> LENGTH: 163
<212> TYPE: PRT
<213> ORGANISM: Homo Sapien

<400> SEQUENCE: 160

```
Met Thr Val Lys Thr Leu His Gly Pro Ala Met Val Lys Tyr Leu
  1               5                  10                  15

Leu Leu Ser Ile Leu Gly Leu Ala Phe Leu Ser Glu Ala Ala Ala
                 20                  25                  30

Arg Lys Ile Pro Lys Val Gly His Thr Phe Phe Gln Lys Pro Glu
                 35                  40                  45

Ser Cys Pro Pro Val Pro Gly Gly Ser Met Lys Leu Asp Ile Gly
                 50                  55                  60

Ile Ile Asn Glu Asn Gln Arg Val Ser Met Ser Arg Asn Ile Glu
                 65                  70                  75

Ser Arg Ser Thr Ser Pro Trp Asn Tyr Thr Val Thr Trp Asp Pro
                 80                  85                  90

Asn Arg Tyr Pro Ser Glu Val Val Gln Ala Gln Cys Arg Asn Leu
                 95                 100                 105

Gly Cys Ile Asn Ala Gln Gly Lys Glu Asp Ile Ser Met Asn Ser
                110                 115                 120

Val Pro Ile Gln Gln Glu Thr Leu Val Val Arg Arg Lys His Gln
                125                 130                 135

Gly Cys Ser Val Ser Phe Gln Leu Glu Lys Val Leu Val Thr Val
                140                 145                 150

Gly Cys Thr Cys Val Thr Pro Val Ile His His Val Gln
                155                 160
```

<210> SEQ ID NO 161
<211> LENGTH: 2380
<212> TYPE: DNA
<213> ORGANISM: Homo Sapien

<400> SEQUENCE: 161

```
acactggcca aacaaaaacg aaagcactcc gtgctggaag taggaggaga         50

gtcaggactc ccaggacaga gagtgcacaa actacccagc acagcccccct        100

ccgccccctc tggaggctga agagggattc cagcccctgc cacccacaga        150

cacgggctga ctggggtgtc tgcccccctt gggggggggc agcacagggc        200

ctcaggcctg ggtgccacct ggcacctaga agatgcctgt gccctggttc        250
```

-continued

```
ttgctgtcct tggcactggg ccgaagccca gtggtccttt ctctggagag      300
gcttgtgggg cctcaggacg ctacccactg ctctccgggc ctctcctgcc      350
gcctctggga cagtgacata ctctgcctgc ctggggacat cgtgcctgct      400
ccgggccccg tgctggcgcc tacgcacctg cagacagagc tggtgctgag      450
gtgccagaag gagaccgact gtgacctctg tctgcgtgtg gctgtccact      500
tggccgtgca tgggcactgg gaagagcctg aagatgagga aaagtttgga      550
ggagcagctg actcaggggt ggaggagcct aggaatgcct ctctccaggc      600
ccaagtcgtg ctctccttcc aggcctaccc tactgcccgc tgcgtcctgc      650
tggaggtgca agtgcctgct gcccttgtgc agtttggtca gtctgtgggc      700
tctgtggtat atgactgctt cgaggctgcc ctagggagtg aggtacgaat      750
ctggtcctat actcagccca ggtacgagaa ggaactcaac cacacacagc      800
agctgcctgc cctgccctgg ctcaacgtgt cagcagatgg tgacaacgtg      850
catctggttc tgaatgtctc tgaggagcag cacttcggcc tctccctgta      900
ctggaatcag gtccagggcc ccccaaaacc ccggtggcac aaaaacctga      950
ctggaccgca gatcattacc ttgaaccaca cagacctggt tccctgcctc     1000
tgtattcagg tgtggcctct ggaacctgac tccgttagga cgaacatctg     1050
ccccttcagg gaggaccccc gcgcacacca gaacctctgg caagccgccc     1100
gactgcgact gctgaccctg cagagctggc tgctggacgc accgtgctcg     1150
ctgcccgcag aagcggcact gtgctggcgg gctccgggtg gggacccctg     1200
ccagccactg gtcccaccgc tttcctggga gaacgtcact gtggacaagg     1250
ttctcgagtt cccattgctg aaaggccacc ctaacctctg tgttcaggtg     1300
aacagctcgg agaagctgca gctgcaggag tgcttgtggg ctgactccct     1350
ggggcctctc aaagacgatg tgctactgtt ggagacacga ggcccccagg     1400
acaacagatc cctctgtgcc ttggaaccca gtggctgtac ttcactaccc     1450
agcaaagcct ccacgagggc agctcgcctt ggagagtact tactacaaga     1500
cctgcagtca ggccagtgtc tgcagctatg ggacgatgac ttgggagcgc     1550
tatgggcctg ccccatggac aaatacatcc acaagcgctg ggccctcgtg     1600
tggctggcct gcctactctt tgccgctgcg ctttccctca tcctccttct     1650
caaaaaggat cacgcgaaag ggtggctgag gctcttgaaa caggacgtcc     1700
gctcgggggc ggccgccagg ggccgcgcgg ctctgctcct ctactcagcc     1750
gatgactcgg gtttcgagcg cctggtgggc gccctggcgt cggccctgtg     1800
ccagctgccg ctgcgcgtgg ccgtagacct gtggagccgt cgtgaactga     1850
gcgcgcaggg gcccgtggct tggtttcacg cgcagcggcg ccagaccctg     1900
caggagggcg gcgtggtggt cttgctcttc tctcccggtg cggtggcgct     1950
gtgcagcgag tggctacagg atggggtgtc cgggcccggg gcgcacggcc     2000
cgcacgacgc cttccgcgcc tcgctcagct gcgtgctgcc cgacttcttg     2050
cagggccggg cgcccggcag ctacgtgggg gcctgcttcg acaggctgct     2100
ccacccggac gccgtacccg cccttttccg caccgtgccc gtcttcacac     2150
tgccctccca actgccagac ttcctggggg ccctgcagca gcctcgcgcc     2200
```

-continued

```
ccgcgttccg ggcggctcca agagagagcg gagcaagtgt cccgggccct          2250

tcagccagcc ctggatagct acttccatcc cccggggact cccgcgccgg          2300

gacgcggggt gggaccaggg gcgggacctg gggcgggga cgggacttaa           2350

ataaaggcag acgctgtttt tctaaaaaaa                                2380
```

<210> SEQ ID NO 162
<211> LENGTH: 705
<212> TYPE: PRT
<213> ORGANISM: Homo Sapien

<400> SEQUENCE: 162

```
Met Pro Val Pro Trp Phe Leu Leu Ser Leu Ala Leu Gly Arg Ser
  1               5                  10                  15

Pro Val Val Leu Ser Leu Glu Arg Leu Val Gly Pro Gln Asp Ala
                 20                  25                  30

Thr His Cys Ser Pro Gly Leu Ser Cys Arg Leu Trp Asp Ser Asp
                 35                  40                  45

Ile Leu Cys Leu Pro Gly Asp Ile Val Pro Ala Pro Gly Pro Val
                 50                  55                  60

Leu Ala Pro Thr His Leu Gln Thr Glu Leu Val Leu Arg Cys Gln
                 65                  70                  75

Lys Glu Thr Asp Cys Asp Leu Cys Leu Arg Val Ala Val His Leu
                 80                  85                  90

Ala Val His Gly His Trp Glu Glu Pro Glu Asp Glu Glu Lys Phe
                 95                 100                 105

Gly Gly Ala Ala Asp Ser Gly Val Glu Glu Pro Arg Asn Ala Ser
                110                 115                 120

Leu Gln Ala Gln Val Val Leu Ser Phe Gln Ala Tyr Pro Thr Ala
                125                 130                 135

Arg Cys Val Leu Leu Glu Val Gln Val Pro Ala Ala Leu Val Gln
                140                 145                 150

Phe Gly Gln Ser Val Gly Ser Val Val Tyr Asp Cys Phe Glu Ala
                155                 160                 165

Ala Leu Gly Ser Glu Val Arg Ile Trp Ser Tyr Thr Gln Pro Arg
                170                 175                 180

Tyr Glu Lys Glu Leu Asn His Thr Gln Gln Leu Pro Ala Leu Pro
                185                 190                 195

Trp Leu Asn Val Ser Ala Asp Gly Asp Asn Val His Leu Val Leu
                200                 205                 210

Asn Val Ser Glu Glu Gln His Phe Gly Leu Ser Leu Tyr Trp Asn
                215                 220                 225

Gln Val Gln Gly Pro Pro Lys Pro Arg Trp His Lys Asn Leu Thr
                230                 235                 240

Gly Pro Gln Ile Ile Thr Leu Asn His Thr Asp Leu Val Pro Cys
                245                 250                 255

Leu Cys Ile Gln Val Trp Pro Leu Glu Pro Asp Ser Val Arg Thr
                260                 265                 270

Asn Ile Cys Pro Phe Arg Glu Asp Pro Arg Ala His Gln Asn Leu
                275                 280                 285

Trp Gln Ala Ala Arg Leu Arg Leu Leu Thr Leu Gln Ser Trp Leu
                290                 295                 300

Leu Asp Ala Pro Cys Ser Leu Pro Ala Glu Ala Ala Leu Cys Trp
                305                 310                 315
```

-continued

```
Arg Ala Pro Gly Gly Asp Pro Cys Gln Pro Leu Val Pro Pro Leu
                320                 325                 330

Ser Trp Glu Asn Val Thr Val Asp Lys Val Leu Glu Phe Pro Leu
                335                 340                 345

Leu Lys Gly His Pro Asn Leu Cys Val Gln Val Asn Ser Ser Glu
                350                 355                 360

Lys Leu Gln Leu Gln Glu Cys Leu Trp Ala Asp Ser Leu Gly Pro
                365                 370                 375

Leu Lys Asp Asp Val Leu Leu Leu Glu Thr Arg Gly Pro Gln Asp
                380                 385                 390

Asn Arg Ser Leu Cys Ala Leu Glu Pro Ser Gly Cys Thr Ser Leu
                395                 400                 405

Pro Ser Lys Ala Ser Thr Arg Ala Ala Arg Leu Gly Glu Tyr Leu
                410                 415                 420

Leu Gln Asp Leu Gln Ser Gly Gln Cys Leu Gln Leu Trp Asp Asp
                425                 430                 435

Asp Leu Gly Ala Leu Trp Ala Cys Pro Met Asp Lys Tyr Ile His
                440                 445                 450

Lys Arg Trp Ala Leu Val Trp Leu Ala Cys Leu Leu Phe Ala Ala
                455                 460                 465

Ala Leu Ser Leu Ile Leu Leu Leu Lys Lys Asp His Ala Lys Gly
                470                 475                 480

Trp Leu Arg Leu Leu Lys Gln Asp Val Arg Ser Gly Ala Ala Ala
                485                 490                 495

Arg Gly Arg Ala Ala Leu Leu Leu Tyr Ser Ala Asp Asp Ser Gly
                500                 505                 510

Phe Glu Arg Leu Val Gly Ala Leu Ala Ser Ala Leu Cys Gln Leu
                515                 520                 525

Pro Leu Arg Val Ala Val Asp Leu Trp Ser Arg Arg Glu Leu Ser
                530                 535                 540

Ala Gln Gly Pro Val Ala Trp Phe His Ala Gln Arg Arg Gln Thr
                545                 550                 555

Leu Gln Glu Gly Gly Val Val Val Leu Leu Phe Ser Pro Gly Ala
                560                 565                 570

Val Ala Leu Cys Ser Glu Trp Leu Gln Asp Gly Val Ser Gly Pro
                575                 580                 585

Gly Ala His Gly Pro His Asp Ala Phe Arg Ala Ser Leu Ser Cys
                590                 595                 600

Val Leu Pro Asp Phe Leu Gln Gly Arg Ala Pro Gly Ser Tyr Val
                605                 610                 615

Gly Ala Cys Phe Asp Arg Leu Leu His Pro Asp Ala Val Pro Ala
                620                 625                 630

Leu Phe Arg Thr Val Pro Val Phe Thr Leu Pro Ser Gln Leu Pro
                635                 640                 645

Asp Phe Leu Gly Ala Leu Gln Gln Pro Arg Ala Pro Arg Ser Gly
                650                 655                 660

Arg Leu Gln Glu Arg Ala Glu Gln Val Ser Arg Ala Leu Gln Pro
                665                 670                 675

Ala Leu Asp Ser Tyr Phe His Pro Pro Gly Thr Pro Ala Pro Gly
                680                 685                 690

Arg Gly Val Gly Pro Gly Ala Gly Pro Gly Ala Gly Asp Gly Thr
                695                 700                 705
```

-continued

<210> SEQ ID NO 163
<211> LENGTH: 2478
<212> TYPE: DNA
<213> ORGANISM: Homo Sapien

<400> SEQUENCE: 163

```
gtcagtgcgg gaggccggtc agccaccaag atgactgaca ggttcagctc      50
tctgcagcac actaccctca agccacctga tgtgacctgt atctccaaag     100
tgagatcgat tcagatgatt gttcatccta cccccacgcc aatccgtgca     150
ggcgatggcc accggctaac cctggaagac atcttccatg acctgttcta     200
ccacttagag ctccaggtca accgcaccta ccaaatgcac cttggaggga     250
agcagagaga atatgagttc ttcggcctga cccctgacac agagttcctt     300
ggcaccatca tgatttgcgt tcccacctgg gccaaggaga gtgcccccta     350
catgtgccga gtgaagacac tgccagaccg gacatggacc tactccttct     400
ccggagcctt cctgttctcc atgggcttcc tcgtcgcagt actctgctac     450
ctgagctaca gatatgtcac caagccgcct gcacctccca actccctgaa     500
cgtccagcga gtcctgactt tccagccgct gcgcttcatc caggagcacg     550
tcctgatccc tgtctttgac ctcagcggcc ccagcagtct ggcccagcct     600
gtccagtact cccagatcag ggtgtctgga cccagggagc ccgcaggagc     650
tccacagcgg catagcctgt ccgagatcac ctacttaggg cagccagaca     700
tctccatcct ccagccctcc aacgtgccac ctccccagat cctctcccca     750
ctgtcctatg ccccaaacgc tgcccctgag gtcgggcccc catcctatgc     800
acctcaggtg acccccgaag ctcaattccc attctacgcc ccacaggcca     850
tctctaaggt ccagccttcc tcctatgccc ctcaagccac tccggacagc     900
tggcctccct cctatggggt atgcatggaa ggttctggca aagactcccc     950
cactgggaca ctttctagtc ctaaacacct taggcctaaa ggtcagcttc    1000
agaaagagcc accagctgga agctgcatgt taggtggcct ttctctgcag    1050
gaggtgacct ccttggctat ggaggaatcc caagaagcaa aatcattgca    1100
ccagcccctg gggatttgca cagacagaac atctgaccca aatgtgctac    1150
acagtgggga ggaagggaca ccacagtacc taaagggcca gctcccccctc   1200
ctctcctcag tccagatcga gggccacccc atgtccctcc ctttgcaacc    1250
tccttccggt ccatgttccc cctcggacca aggtccaagt ccctggggcc    1300
tgctggagtc ccttgtgtgt cccaaggatg aagccaagag cccagcccct    1350
gagacctcag acctggagca gcccacagaa ctggattctc ttttcagagg    1400
cctggccctg actgtgcagt gggagtcctg aggggaatgg gaaaggcttg    1450
gtgcttcctc cctgtcccta cccagtgtca catccttggc tgtcaatccc    1500
atgcctgccc atgccacaca ctctgcgatc tggcctcaga cgggtgccct    1550
tgagagaagc agagggagtg gcatgcaggg cccctgccat gggtgcgctc    1600
ctcaccggaa caaagcagca tgataaggac tgcagcgggg gagctctggg    1650
gagcagcttg tgtagacaag cgcgtgctcg ctgagccctg caaggcagaa    1700
atgacagtgc aaggaggaaa tgcagggaaa ctcccgaggt ccagagcccc    1750
acctcctaac accatggatt caaagtgctc agggaatttg cctctccttg    1800
```

-continued

```
ccccattcct ggccagtttc acaatctagc tcgacagagc atgaggcccc          1850

tgcctcttct gtcattgttc aaaggtggga agagagcctg gaaaagaacc          1900

aggcctggaa aagaaccaga aggaggctgg gcagaaccag aacaacctgc          1950

acttctgcca aggccagggc cagcaggacg gcaggactct agggaggggt          2000

gtggcctgca gctcattccc agccagggca actgcctgac gttgcacgat          2050

ttcagcttca ttcctctgat agaacaaagc gaaatgcagg tccaccaggg          2100

agggagacac acaagccttt tctgcaggca ggagtttcag accctatcct          2150

gagaatgggg tttgaaagga aggtgagggc tgtggcccct ggacgggtac          2200

aataacacac tgtactgatg tcacaacttt gcaagctctg ccttgggttc          2250

agcccatctg ggctcaaatt ccagcctcac cactcacaag ctgtgtgact          2300

tcaaacaaat gaaatcagtg cccagaacct cggtttcctc atctgtaatg          2350

tggggatcat aacacctacc tcatggagtt gtggtgaaga tgaaatgaag          2400

tcatgtcttt aaagtgctta atagtgcctg gtacatgggc agtgcccaat          2450

aaacggtagc tatttaaaaa aaaaaaaa                                  2478


<210> SEQ ID NO 164
<211> LENGTH: 574
<212> TYPE: PRT
<213> ORGANISM: Homo Sapien

<400> SEQUENCE: 164

Met Arg Thr Leu Leu Thr Ile Leu Thr Val Gly Ser Leu Ala Ala
  1               5                  10                  15

His Ala Pro Glu Asp Pro Ser Asp Leu Leu Gln His Val Lys Phe
                 20                  25                  30

Gln Ser Ser Asn Phe Glu Asn Ile Leu Thr Trp Asp Ser Gly Pro
                 35                  40                  45

Glu Gly Thr Pro Asp Thr Val Tyr Ser Ile Glu Tyr Lys Thr Tyr
                 50                  55                  60

Gly Glu Arg Asp Trp Val Ala Lys Lys Gly Cys Gln Arg Ile Thr
                 65                  70                  75

Arg Lys Ser Cys Asn Leu Thr Val Glu Thr Gly Asn Leu Thr Glu
                 80                  85                  90

Leu Tyr Tyr Ala Arg Val Thr Ala Val Ser Ala Gly Gly Arg Ser
                 95                 100                 105

Ala Thr Lys Met Thr Asp Arg Phe Ser Ser Leu Gln His Thr Thr
                110                 115                 120

Leu Lys Pro Pro Asp Val Thr Cys Ile Ser Lys Val Arg Ser Ile
                125                 130                 135

Gln Met Ile Val His Pro Thr Pro Thr Pro Ile Arg Ala Gly Asp
                140                 145                 150

Gly His Arg Leu Thr Leu Glu Asp Ile Phe His Asp Leu Phe Tyr
                155                 160                 165

His Leu Glu Leu Gln Val Asn Arg Thr Tyr Gln Met His Leu Gly
                170                 175                 180

Gly Lys Gln Arg Glu Tyr Glu Phe Phe Gly Leu Thr Pro Asp Thr
                185                 190                 195

Glu Phe Leu Gly Thr Ile Met Ile Cys Val Pro Thr Trp Ala Lys
                200                 205                 210

Glu Ser Ala Pro Tyr Met Cys Arg Val Lys Thr Leu Pro Asp Arg
```

-continued

```
                215                 220                 225

Thr Trp Thr Tyr Ser Phe Ser Gly Ala Phe Leu Phe Ser Met Gly
                230                 235                 240

Phe Leu Val Ala Val Leu Cys Tyr Leu Ser Tyr Arg Tyr Val Thr
                245                 250                 255

Lys Pro Pro Ala Pro Pro Asn Ser Leu Asn Val Gln Arg Val Leu
                260                 265                 270

Thr Phe Gln Pro Leu Arg Phe Ile Gln Glu His Val Leu Ile Pro
                275                 280                 285

Val Phe Asp Leu Ser Gly Pro Ser Ser Leu Ala Gln Pro Val Gln
                290                 295                 300

Tyr Ser Gln Ile Arg Val Ser Gly Pro Arg Glu Pro Ala Gly Ala
                305                 310                 315

Pro Gln Arg His Ser Leu Ser Glu Ile Thr Tyr Leu Gly Gln Pro
                320                 325                 330

Asp Ile Ser Ile Leu Gln Pro Ser Asn Val Pro Pro Pro Gln Ile
                335                 340                 345

Leu Ser Pro Leu Ser Tyr Ala Pro Asn Ala Ala Pro Glu Val Gly
                350                 355                 360

Pro Pro Ser Tyr Ala Pro Gln Val Thr Pro Glu Ala Gln Phe Pro
                365                 370                 375

Phe Tyr Ala Pro Gln Ala Ile Ser Lys Val Gln Pro Ser Ser Tyr
                380                 385                 390

Ala Pro Gln Ala Thr Pro Asp Ser Trp Pro Pro Ser Tyr Gly Val
                395                 400                 405

Cys Met Glu Gly Ser Gly Lys Asp Ser Pro Thr Gly Thr Leu Ser
                410                 415                 420

Ser Pro Lys His Leu Arg Pro Lys Gly Gln Leu Gln Lys Glu Pro
                425                 430                 435

Pro Ala Gly Ser Cys Met Leu Gly Gly Leu Ser Leu Gln Glu Val
                440                 445                 450

Thr Ser Leu Ala Met Glu Glu Ser Gln Glu Ala Lys Ser Leu His
                455                 460                 465

Gln Pro Leu Gly Ile Cys Thr Asp Arg Thr Ser Asp Pro Asn Val
                470                 475                 480

Leu His Ser Gly Glu Glu Gly Thr Pro Gln Tyr Leu Lys Gly Gln
                485                 490                 495

Leu Pro Leu Leu Ser Ser Val Gln Ile Glu Gly His Pro Met Ser
                500                 505                 510

Leu Pro Leu Gln Pro Pro Ser Gly Pro Cys Ser Pro Ser Asp Gln
                515                 520                 525

Gly Pro Ser Pro Trp Gly Leu Leu Glu Ser Leu Val Cys Pro Lys
                530                 535                 540

Asp Glu Ala Lys Ser Pro Ala Pro Glu Thr Ser Asp Leu Glu Gln
                545                 550                 555

Pro Thr Glu Leu Asp Ser Leu Phe Arg Gly Leu Ala Leu Thr Val
                560                 565                 570

Gln Trp Glu Ser
```

<210> SEQ ID NO 165
<211> LENGTH: 1060
<212> TYPE: DNA
<213> ORGANISM: Homo Sapien -continued

<400> SEQUENCE: 165

```
tggcctactg gaaaaaaaaa aaaaaaaaaa aaaagtcacc cgggcccgcg          50
gtggccacaa catggctgcg gcgccggggc tgctcttctg gctgttcgtg         100
ctgggggcgc tctggtgggt cccgggccag tcggatctca gccacggacg         150
gcgtttctcg gacctcaaag tgtgcgggga cgaagagtgc agcatgttaa         200
tgtaccgtgg gaaagctctt gaagacttca cgggccctga ttgtcgtttt         250
gtgaatttta aaaaaggtga cgatgtatat gtctactaca aactggcagg         300
gggatccctt gaactttggg ctggaagtgt tgaacacagt tttggatatt         350
ttccaaaaga tttgatcaag gtacttcata aatacacgga agaagagcta         400
catattccag cagatgagac agactttgtc tgctttgaag gaggaagaga         450
tgattttaat agttataatg tagaagagct tttaggatct ttggaactgg         500
aggactctgt acctgaagag tcgaagaaag ctgaagaagt ttctcagcac         550
agagagaaat ctcctgagga gtctcggggg cgtgaacttg accctgtgcc         600
tgagcccgag gcattcagag ctgattcaga ggatggagaa ggtgctttct         650
cagagagcac cgaggggctg cagggacagc cctcagctca ggagagccac         700
cctcacacca gcggtcctgc ggctaacgct cagggagtgc agtcttcgtt         750
ggacactttt gaagaaattc tgcacgataa attgaaagtg ccgggaagcg         800
aaagcagaac tggcaatagt tctcctgcct cggtggagcg ggagaagaca         850
gatgcttaca aagtcctgaa aacagaaatg agtcagagag gaagtggaca         900
gtgcgttatt cattacagca aaggatttcg ttggcatcaa aatctaagtt         950
tgttttacaa agattgtttt tagtactaag ctgccttggc agtttgcatt        1000
tttgagccaa acaaaaatat attattttcc cttctaagta aaaaaaaaaa        1050
aaaaaaaaaa                                                    1060
```

<210> SEQ ID NO 166
<211> LENGTH: 303
<212> TYPE: PRT
<213> ORGANISM: Homo Sapien

<400> SEQUENCE: 166

```
Met Ala Ala Ala Pro Gly Leu Leu Phe Trp Leu Phe Val Leu Gly
  1               5                  10                  15

Ala Leu Trp Trp Val Pro Gly Gln Ser Asp Leu Ser His Gly Arg
                 20                  25                  30

Arg Phe Ser Asp Leu Lys Val Cys Gly Asp Glu Glu Cys Ser Met
                 35                  40                  45

Leu Met Tyr Arg Gly Lys Ala Leu Glu Asp Phe Thr Gly Pro Asp
                 50                  55                  60

Cys Arg Phe Val Asn Phe Lys Lys Gly Asp Asp Val Tyr Val Tyr
                 65                  70                  75

Tyr Lys Leu Ala Gly Gly Ser Leu Glu Leu Trp Ala Gly Ser Val
                 80                  85                  90

Glu His Ser Phe Gly Tyr Phe Pro Lys Asp Leu Ile Lys Val Leu
                 95                 100                 105

His Lys Tyr Thr Glu Glu Glu Leu His Ile Pro Ala Asp Glu Thr
                110                 115                 120

Asp Phe Val Cys Phe Glu Gly Gly Arg Asp Asp Phe Asn Ser Tyr
```

-continued

```
                125                 130                 135

Asn Val Glu Glu Leu Leu Gly Ser Leu Glu Leu Glu Asp Ser Val
                140                 145                 150

Pro Glu Glu Ser Lys Lys Ala Glu Glu Val Ser Gln His Arg Glu
                155                 160                 165

Lys Ser Pro Glu Glu Ser Arg Gly Arg Glu Leu Asp Pro Val Pro
                170                 175                 180

Glu Pro Glu Ala Phe Arg Ala Asp Ser Glu Asp Gly Glu Gly Ala
                185                 190                 195

Phe Ser Glu Ser Thr Glu Gly Leu Gln Gly Gln Pro Ser Ala Gln
                200                 205                 210

Glu Ser His Pro His Thr Ser Gly Pro Ala Ala Asn Ala Gln Gly
                215                 220                 225

Val Gln Ser Ser Leu Asp Thr Phe Glu Glu Ile Leu His Asp Lys
                230                 235                 240

Leu Lys Val Pro Gly Ser Glu Ser Arg Thr Gly Asn Ser Ser Pro
                245                 250                 255

Ala Ser Val Glu Arg Glu Lys Thr Asp Ala Tyr Lys Val Leu Lys
                260                 265                 270

Thr Glu Met Ser Gln Arg Gly Ser Gly Gln Cys Val Ile His Tyr
                275                 280                 285

Ser Lys Gly Phe Arg Trp His Gln Asn Leu Ser Leu Phe Tyr Lys
                290                 295                 300

Asp Cys Phe


<210> SEQ ID NO 167
<211> LENGTH: 2570
<212> TYPE: DNA
<213> ORGANISM: Homo Sapien

<400> SEQUENCE: 167

ccaggaccag ggcgcaccgg ctcagcctct cacttgtcag aggccgggga      50

agagaagcaa agcgcaacgg tgtggtccaa gccggggctt ctgcttcgcc     100

tctaggacat acacgggacc ccctaacttc agtcccccaa acgcgcaccc     150

tcgaagtctt gaactccagc cccgcacatc cacgcgcggc acaggcgcgg     200

caggcggcag gtcccggccg aaggcgatgc gcgcaggggg tcgggcagct     250

gggctcgggc ggcgggagta gggcccggca gggaggcagg gaggctgcat     300

attcagagtc gcgggctgcg ccctgggcag aggccgccct cgctccacgc     350

aacacctgct gctgccaccg cgccgcgatg agccgcgtgg tctcgctgct     400

gctgggcgcc gcgctgctct gcggccacgg agccttctgc cgccgcgtgg     450

tcagcggcca aaaggtgtgt tttgctgact tcaagcatcc ctgctacaaa     500

atggcctact tccatgaact gtccagccga gtgagctttc aggaggcacg     550

cctggcttgt gagagtgagg gaggagtcct cctcagcctt gagaatgaag     600

cagaacagaa gttaatagag agcatgttgc aaaacctgac aaaacccggg     650

acagggattt ctgatggtga tttctggata gggctttgga ggaatggaga     700

tgggcaaaca tctggtgcct gcccagatct ctaccagtgg tctgatggaa     750

gcaattccca gtaccgaaac tggtacacag atgaaccttc ctgcggaagt     800

gaaaagtgtg ttgtgatgta tcaccaacca actgccaatc ctggccttgg     850
```

-continued

```
gggtccctac ctttaccagt ggaatgatga caggtgtaac atgaagcaca          900

attatatttg caagtatgaa ccagagatta atccaacagc ccctgtagaa          950

aagccttatc ttacaaatca accaggagac acccatcaga atgtggttgt         1000

tactgaagca ggtataattc ccaatctaat ttatgttgtt ataccaacaa         1050

taccccctgct cttactgata ctggttgctt ttggaacctg ttgtttccag        1100

atgctgcata aaagtaaagg aagaacaaaa actagtccaa accagtctac         1150

actgtggatt tcaaagagta ccagaaaaga aagtggcatg gaagtataat         1200

aactcattga cttggttcca gaattttgta attctggatc tgtataagga         1250

atggcatcag aacaatagct tggaatggct tgaaatcaca aaggatctgc         1300

aagatgaact gtaagctccc ccttgaggca aatattaaag taatttttat         1350

atgtctatta tttcatttaa agaatatgct gtgctaataa tggagtgaga         1400

catgcttatt ttgctaaagg atgcacccaa acttcaaact tcaagcaaat         1450

gaaatggaca atgcagataa agttgttatc aacacgtcgg gagtatgtgt         1500

gttagaagca attcctttta tttctttcac ctttcataag ttgttatcta         1550

gtcaatgtaa tgtatattgt attgaaattt acagtgtgca aaagtatttt         1600

acctttgcat aagtgtttga taaaaatgaa ctgttctaat atttattttt         1650

atggcatctc atttttcaat acatgctctt ttgattaaag aaacttatta         1700

ctgttgtcaa ctgaattcac acacacacaa atatagtacc atagaaaaag         1750

tttgttttct cgaaataatt catctttcag cttctctgct tttggtcaat         1800

gtctaggaaa tctcttcaga aataagaagc tatttcatta agtgtgatat         1850

aaacctcctc aaacatttta cttagaggca aggattgtct aatttcaatt         1900

gtgcaagaca tgtgccttat aattattttt agcttaaaat taaacagatt         1950

ttgtaataat gtaactttgt taataggtgc ataaacacta atgcagtcaa         2000

tttgaacaaa agaagtgaca tacacaatat aaatcatatg tcttcacacg         2050

ttgcctatat aatgagaagc agctctctga gggttctgaa atcaatgtgg         2100

tccctctctt gcccactaaa caaagatggt tgttcggggt ttgggattga         2150

cactggaggc agatagttgc aaagttagtc taaggtttcc ctagctgtat         2200

ttagcctctg actatattag tatacaaaga ggtcatgtgg ttgagaccag         2250

gtgaatagtc actatcagtg tggagacaag cacagcacac agacatttta         2300

ggaaggaaag gaactacgaa atcgtgtgaa aatgggttgg aacccatcag         2350

tgatcgcata ttcattgatg agggtttgct tgagatagaa aatggtggct         2400

cctttctgtc ttatctccta gtttcttcaa tgcttacgcc ttgttcttct         2450

caagagaaag ttgtaactct ctggtcttca tatgtccctg tgctcctttt         2500

aaccaaataa agagttcttg tttctggggg aaaaaaaaaa aaaaaaaaaa         2550

aaaaaaaaaa aaaaaaaaaa                                          2570
```

<210> SEQ ID NO 168
<211> LENGTH: 273
<212> TYPE: PRT
<213> ORGANISM: Homo Sapien

<400> SEQUENCE: 168

Met Ser Arg Val Val Ser Leu Leu Leu Gly Ala Ala Leu Leu Cys

-continued

```
1               5                   10                  15

Gly His Gly Ala Phe Cys Arg Arg Val Val Ser Gly Gln Lys Val
                20                  25                  30

Cys Phe Ala Asp Phe Lys His Pro Cys Tyr Lys Met Ala Tyr Phe
                35                  40                  45

His Glu Leu Ser Ser Arg Val Ser Phe Gln Glu Ala Arg Leu Ala
                50                  55                  60

Cys Glu Ser Glu Gly Gly Val Leu Leu Ser Leu Glu Asn Glu Ala
                65                  70                  75

Glu Gln Lys Leu Ile Glu Ser Met Leu Gln Asn Leu Thr Lys Pro
                80                  85                  90

Gly Thr Gly Ile Ser Asp Gly Asp Phe Trp Ile Gly Leu Trp Arg
                95                  100                 105

Asn Gly Asp Gly Gln Thr Ser Gly Ala Cys Pro Asp Leu Tyr Gln
                110                 115                 120

Trp Ser Asp Gly Ser Asn Ser Gln Tyr Arg Asn Trp Tyr Thr Asp
                125                 130                 135

Glu Pro Ser Cys Gly Ser Glu Lys Cys Val Val Met Tyr His Gln
                140                 145                 150

Pro Thr Ala Asn Pro Gly Leu Gly Gly Pro Tyr Leu Tyr Gln Trp
                155                 160                 165

Asn Asp Asp Arg Cys Asn Met Lys His Asn Tyr Ile Cys Lys Tyr
                170                 175                 180

Glu Pro Glu Ile Asn Pro Thr Ala Pro Val Glu Lys Pro Tyr Leu
                185                 190                 195

Thr Asn Gln Pro Gly Asp Thr His Gln Asn Val Val Val Thr Glu
                200                 205                 210

Ala Gly Ile Ile Pro Asn Leu Ile Tyr Val Val Ile Pro Thr Ile
                215                 220                 225

Pro Leu Leu Leu Leu Ile Leu Val Ala Phe Gly Thr Cys Cys Phe
                230                 235                 240

Gln Met Leu His Lys Ser Lys Gly Arg Thr Lys Thr Ser Pro Asn
                245                 250                 255

Gln Ser Thr Leu Trp Ile Ser Lys Ser Thr Arg Lys Glu Ser Gly
                260                 265                 270

Met Glu Val


<210> SEQ ID NO 169
<211> LENGTH: 43
<212> TYPE: DNA
<213> ORGANISM: Artificial Sequence
<220> FEATURE:
<223> OTHER INFORMATION: Synthetic oligonucleotide probe

<400> SEQUENCE: 169

tgtaaaacga cggccagtta aatagacctg caattattaa tct                       43


<210> SEQ ID NO 170
<211> LENGTH: 41
<212> TYPE: DNA
<213> ORGANISM: Artificial Sequence
<220> FEATURE:
<223> OTHER INFORMATION: Synthetic oligonucleotide probe

<400> SEQUENCE: 170

caggaaacag ctatgaccac ctgcacacct gcaaatccat t                         41
```

SECRETED AND TRANSMEMBRANE POLYPEPTIDES AND NUCLEIC ACIDS ENCODING THE SAME

RELATED APPLICATIONS

This application is a continuation of, and claims priority under 35 USC §120 to, U.S. application Ser. No. 10/006,867 filed Dec. 6, 2001, which is a continuation of, and priority under 35 USC §120 to, PCT Application PCT/US00/23328 filed Aug. 24, 2000, which is a continuation-in-part of, and claims priority under 35 USC §120 to, U.S. application Ser. No. 09/403,297 filed Oct. 18, 1999, now abandoned, which is the National Stage filed under 35 USC §371 of PCT Application PCT/US99/20111 filed Sep. 1, 1999, which claims priority under 35 USC §119 U.S. Provisional Application 60/100,683 filed Sep. 17, 1998.

BACKGROUND OF THE INVENTION

The present invention relates generally to the identification and isolation of novel DNA and to the recombinant production of novel polypeptides.

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., Proc. Natl. Acad. Sci. 93:7108–7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

SUMMARY OF INVENTION

In one embodiment, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which binds, preferably specifically, to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In yet other embodiments, the present invention is directed to methods of using the PRO polypeptides of the present invention for a variety of uses based upon the functional biological assay data presented in the Examples below.

BRIEF DESCRIPTION OF DRAWINGS

FIG. 1 shows a nucleotide sequence (SEQ ID NO:1) of a native sequence PRO180 cDNA, wherein SEQ ID NO:1 is a clone designated herein as "DNA26843-1389".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO218 cDNA, wherein SEQ ID NO:3 is a clone designated herein as "DNA30867-1335".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO263 cDNA, wherein SEQ ID NO:5 is a clone designated herein as "DNA34431-1177".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO295 cDNA, wherein SEQ ID NO:7 is a clone designated herein as "DNA38268-1188".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO874 cDNA, wherein SEQ ID NO:9 is a clone designated herein as "DNA40621-1440".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO300 cDNA, wherein SEQ ID NO:11 is a clone designated herein as "DNA40625-1189".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO1864 cDNA, wherein SEQ ID NO:13 is a clone designated herein as "DNA45409-2511".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO1282 cDNA, wherein SEQ ID NO:15 is a clone designated herein as "DNA45495-1550".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO1063 cDNA, wherein SEQ ID NO:17 is a clone designated herein as "DNA49820-1427".

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO1773 cDNA, wherein SEQ ID NO:19 is a clone designated herein as "DNA56406-1704".

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO1013 cDNA, wherein SEQ ID NO:21 is a clone designated herein as "DNA56410-1414".

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO937 cDNA, wherein SEQ ID NO:23 is a clone designated herein as "DNA56436-1448".

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO842 cDNA, wherein SEQ ID NO:25 is a clone designated herein as "DNA56855-1447".

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO1180 cDNA, wherein SEQ ID NO:27 is a clone designated herein as "DNA56860-1510".

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO831 cDNA, wherein SEQ ID NO:29 is a clone designated herein as "DNA56862-1343".

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO1115 cDNA, wherein SEQ ID NO:31 is a clone designated herein as "DNA56868-1478".

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO1277 cDNA, wherein SEQ ID NO:33 is a clone designated herein as "DNA56869-1545".

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO1074 cDNA, wherein SEQ ID NO:35 is a clone designated herein as "DNA57704-1452".

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO1344 cDNA, wherein SEQ ID NO:37 is a clone designated herein as "DNA58723-1588".

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO1136 cDNA, wherein SEQ ID NO:39 is a clone designated herein as "DNA57827-1493".

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO1109 cDNA, wherein SEQ ID NO:41 is a clone designated herein as "DNA58737-1473".

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO1003 cDNA, wherein SEQ ID NO:43 is a clone designated herein as "DNA58846-1409".

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO1138 cDNA, wherein SEQ ID NO:45 is a clone designated herein as "DNA58850-1495".

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO994 cDNA, wherein SEQ ID NO:47 is a clone designated herein as "DNA58855-1422".

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO1069 cDNA, wherein SEQ ID NO:49 is a clone designated herein as "DNA59211-1450".

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO1411 cDNA, wherein SEQ ID NO:51 is a clone designated herein as "DNA59212-1627".

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO1129 cDNA, wherein SEQ ID NO:53 is a clone designated herein as "DNA59213-1487".

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO1027 cDNA, wherein SEQ ID NO:55 is a clone designated herein as "DNA59605-1418".

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO1106 cDNA, wherein SEQ ID NO:57 is a clone designated herein as "DNA59609-1470".

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO1291 cDNA, wherein SEQ ID NO:59 is a clone designated herein as "DNA59610-1556".

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO3573 cDNA, wherein SEQ ID NO:61 is a clone designated herein as "DNA59837-2545".

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO3566 cDNA, wherein SEQ ID NO:63 is a clone designated herein as "DNA59844-2542".

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO1098 cDNA, wherein SEQ ID NO:65 is a clone designated herein as "DNA59854-1459".

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO1158 cDNA, wherein SEQ ID NO:67 is a clone designated herein as "DNA60625-1507".

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO1124 cDNA, wherein SEQ ID NO:69 is a clone designated herein as "DNA60629-1481".

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO1287 cDNA, wherein SEQ ID NO:71 is a clone designated herein as "DNA61755-1554".

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO1335 cDNA, wherein SEQ ID NO:73 is a clone designated herein as "DNA62812-1594".

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO1315 cDNA, wherein SEQ ID NO:75 is a clone designated herein as "DNA62815-1576".

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO1357 cDNA, wherein SEQ ID NO:77 is a clone designated herein as "DNA64881-1602".

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO1356 cDNA, wherein SEQ ID NO:79 is a clone designated herein as "DNA64886-1601".

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO1557 cDNA, wherein SEQ ID NO:81 is a clone designated herein as "DNA64902-1667".

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO1347 cDNA, wherein SEQ ID NO:83 is a clone designated herein as "DNA64950-1590".

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO1302 cDNA, wherein SEQ ID NO:85 is a clone designated herein as "DNA65403-1565".

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO1270 cDNA, wherein SEQ ID NO:87 is a clone designated herein as "DNA66308-1537".

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO1268 cDNA, wherein SEQ ID NO:89 is a clone designated herein as "DNA66519-1535".

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO1327 cDNA, wherein SEQ ID NO:91 is a clone designated herein as "DNA66521-1583".

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO1328 cDNA, wherein SEQ ID NO:93 is a clone designated herein as "DNA66658-1584".

FIG. 94 shows the amino acid sequence (SEQ ID NO:94) derived from the coding sequence of SEQ ID NO:93 shown in FIG. 93.

FIG. 95 shows a nucleotide sequence (SEQ ID NO:95) of a native sequence PRO1329 cDNA, wherein SEQ ID NO:95 is a clone designated herein as "DNA66660-1585".

FIG. 96 shows the amino acid sequence (SEQ ID NO:96) derived from the coding sequence of SEQ ID NO:95 shown in FIG. 95.

FIG. 97 shows a nucleotide sequence (SEQ ID NO:97) of a native sequence PRO1340 cDNA, wherein SEQ ID NO:97 is a clone designated herein as "DNA66663-1598".

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO1342 cDNA, wherein SEQ ID NO:99 is a clone designated herein as "DNA66674-1599".

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO3579 cDNA, wherein SEQ ID NO:101 is a clone designated herein as "DNA68862-2546".

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO1472 cDNA, wherein SEQ ID NO:103 is a clone designated herein as "DNA68866-1644".

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO1461 cDNA, wherein SEQ ID NO:105 is a clone designated herein as "DNA68871-1638".

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO1568 cDNA, wherein SEQ ID NO:107 is a clone designated herein as "DNA68880-1676".

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO1753 cDNA, wherein SEQ ID NO:109 is a clone designated herein as "DNA68883-1691".

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO1570 cDNA, wherein SEQ ID NO:111 is a clone designated herein as "DNA68885-1678".

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO1446 cDNA, wherein SEQ ID NO:113 is a clone designated herein as "DNA71277-1636".

FIG. 114 shows the amino acid sequence (SEQ ID NO:114) derived from the coding sequence of SEQ ID NO:113 shown in FIG. 113.

FIG. 115 shows a nucleotide sequence (SEQ ID NO:115) of a native sequence PRO1565 cDNA, wherein SEQ ID NO:115 is a clone designated herein as "DNA73727-1673".

FIG. 116 shows the amino acid sequence (SEQ ID NO:116) derived from the coding sequence of SEQ ID NO:115 shown in FIG. 115.

FIG. 117 shows a nucleotide sequence (SEQ ID NO:117) of a native sequence PRO1572 cDNA, wherein SEQ ID NO:117 is a clone designated herein as "DNA73734-1680".

FIG. 118 shows the amino acid sequence (SEQ ID NO:118) derived from the coding sequence of SEQ ID NO:117 shown in FIG. 117.

FIG. 119 shows a nucleotide sequence (SEQ ID NO:119) of a native sequence PRO1573 cDNA, wherein SEQ ID NO:119 is a clone designated herein as "DNA73735-1681".

FIG. 120 shows the amino acid sequence (SEQ ID NO:120) derived from the coding sequence of SEQ ID NO:119 shown in FIG. 119.

FIG. 121 shows a nucleotide sequence (SEQ ID NO:121) of a native sequence PRO1550 cDNA, wherein SEQ ID NO:121 is a clone designated herein as "DNA76393-1664".

FIG. 122 shows the amino acid sequence (SEQ ID NO:122) derived from the coding sequence of SEQ ID NO:121 shown in FIG. 121.

FIG. 123 shows a nucleotide sequence (SEQ ID NO:123) of a native sequence PRO1693 cDNA, wherein SEQ ID NO:123 is a clone designated herein as "DNA77301-1708".

FIG. 124 shows the amino acid sequence (SEQ ID NO:124) derived from the coding sequence of SEQ ID NO:123 shown in FIG. 123.

FIG. 125 shows a nucleotide sequence (SEQ ID NO:125) of a native sequence PRO1566 cDNA, wherein SEQ ID NO:125 is a clone designated herein as "DNA77568-1626".

FIG. 126 shows the amino acid sequence (SEQ ID NO:126) derived from the coding sequence of SEQ ID NO:125 shown in FIG. 125.

FIG. 127 shows a nucleotide sequence (SEQ ID NO:127) of a native sequence PRO1774 cDNA, wherein SEQ ID NO:127 is a clone designated herein as "DNA77626-1705".

FIG. 128 shows the amino acid sequence (SEQ ID NO:128) derived from the coding sequence of SEQ ID NO:127 shown in FIG. 127.

FIG. 129 shows a nucleotide sequence (SEQ ID NO:129) of a native sequence PRO1928 cDNA, wherein SEQ ID NO:129 is a clone designated herein as "DNA81754-2532".

FIG. 130 shows the amino acid sequence (SEQ ID NO:130) derived from the coding sequence of SEQ ID NO:129 shown in FIG. 129.

FIG. 131 shows a nucleotide sequence (SEQ ID NO:131) of a native sequence PRO1865 cDNA, wherein SEQ ID NO:131 is a clone designated herein as "DNA81757-2512".

FIG. 132 shows the amino acid sequence (SEQ ID NO:132) derived from the coding sequence of SEQ ID NO:131 shown in FIG. 131.

FIG. 133 shows a nucleotide sequence (SEQ ID NO:133) of a native sequence PRO1925 cDNA, wherein SEQ ID NO:133 is a clone designated herein as "DNA82302-2529".

FIG. 134 shows the amino acid sequence (SEQ ID NO:134) derived from the coding sequence of SEQ ID NO:133 shown in FIG. 133.

FIG. 135 shows a nucleotide sequence (SEQ ID NO:135) of a native sequence PRO1926 cDNA, wherein SEQ ID NO:135 is a clone designated herein as "DNA82340-2530".

FIG. 136 shows the amino acid sequence (SEQ ID NO:136) derived from the coding sequence of SEQ ID NO:135 shown in FIG. 135.

FIG. 137 shows a nucleotide sequence (SEQ ID NO:137) of a native sequence PRO1801 cDNA, wherein SEQ ID NO:137 is a clone designated herein as "DNA83500-2506".

FIG. 138 shows the amino acid sequence (SEQ ID NO:138) derived from the coding sequence of SEQ ID NO:137 shown in FIG. 137.

FIG. 139 shows a nucleotide sequence (SEQ ID NO:139) of a native sequence PRO4405 cDNA, wherein SEQ ID NO:139 is a clone designated herein as "DNA84920-2614".

FIG. 140 shows the amino acid sequence (SEQ ID NO:140) derived from the coding sequence of SEQ ID NO:139 shown in FIG. 139.

FIG. 141 shows a nucleotide sequence (SEQ ID NO:141) of a native sequence PRO3435 cDNA, wherein SEQ ID NO:141 is a clone designated herein as "DNA85066-2534".

FIG. 142 shows the amino acid sequence (SEQ ID NO:142) derived from the coding sequence of SEQ ID NO:141 shown in FIG. 141.

FIG. 143 shows a nucleotide sequence (SEQ ID NO:143) of a native sequence PRO3543 cDNA, wherein SEQ ID NO:143 is a clone designated herein as "DNA86571-2551".

FIG. 144 shows the amino acid sequence (SEQ ID NO:144) derived from the coding sequence of SEQ ID NO:143 shown in FIG. 143.

FIG. 145 shows a nucleotide sequence (SEQ ID NO:145) of a native sequence PRO3443 cDNA, wherein SEQ ID NO:145 is a clone designated herein as "DNA87991-2540".

FIG. 146 shows the amino acid sequence (SEQ ID NO:146) derived from the coding sequence of SEQ ID NO:145 shown in FIG. 145.

FIG. 147 shows a nucleotide sequence (SEQ ID NO:147) of a native sequence PRO3442 cDNA, wherein SEQ ID NO:147 is a clone designated herein as "DNA92238-2539".

FIG. 148 shows the amino acid sequence (SEQ ID NO:148) derived from the coding sequence of SEQ ID NO:147 shown in FIG. 147.

FIG. 149 shows a nucleotide sequence (SEQ ID NO:149) of a native sequence PRO5990 cDNA, wherein SEQ ID NO:149 is a clone designated herein as "DNA96042-2682".

FIG. 150 shows the amino acid sequence (SEQ ID NO:150) derived from the coding sequence of SEQ ID NO:149 shown in FIG. 149.

FIG. 151 shows a nucleotide sequence (SEQ ID NO:151) of a native sequence PRO4342 cDNA, wherein SEQ ID NO:151 is a clone designated herein as "DNA96787-2534".

FIG. 152 shows the amino acid sequence (SEQ ID NO:152) derived from the coding sequence of SEQ ID NO:151 shown in FIG. 151.

FIG. 153 shows a nucleotide sequence (SEQ ID NO:153) of a native sequence PRO10096 cDNA, wherein SEQ ID NO:153 is a clone designated herein as "DNA125185-2806".

FIG. 154 shows the amino acid sequence (SEQ ID NO:154) derived from the coding sequence of SEQ ID NO:153 shown in FIG. 153.

FIG. 155 shows a nucleotide sequence (SEQ ID NO:155) of a native sequence PRO10272 cDNA, wherein SEQ ID NO:155 is a clone designated herein as "DNA147531-2821".

FIG. 156 shows the amino acid sequence (SEQ ID NO:156) derived from the coding sequence of SEQ ID NO:155 shown in FIG. 155.

FIG. 157 shows a nucleotide sequence (SEQ ID NO:157) of a native sequence PRO5801 cDNA, wherein SEQ ID NO:157 is a clone designated herein as "DNA115291-2681".

FIG. 158 shows the amino acid sequence (SEQ ID NO:158) derived from the coding sequence of SEQ ID NO:157 shown in FIG. 157.

FIG. 159 shows a nucleotide sequence (SEQ ID NO:159) of a native sequence PRO20110 cDNA, wherein SEQ ID NO:159 is a clone designated herein as "DNA166819".

FIG. 160 shows the amino acid sequence (SEQ ID NO:160) derived from the coding sequence of SEQ ID NO:159 shown in FIG. 159.

FIG. 161 shows a nucleotide sequence (SEQ ID NO:161) of a native sequence PRO20040 cDNA, wherein SEQ ID NO:161 is a clone designated herein as "DNA164625-2890".

FIG. 162 shows the amino acid sequence (SEQ ID NO:162) derived from the coding sequence of SEQ ID NO:161 shown in FIG. 161.

FIG. 163 shows a nucleotide sequence (SEQ ID NO:163) of a native sequence PRO20233 cDNA, wherein SEQ ID NO:163 is a clone designated herein as "DNA165608".

FIG. 164 shows the amino acid sequence (SEQ ID NO:164) derived from the coding sequence of SEQ ID NO:163 shown in FIG. 163.

FIG. 165 shows a nucleotide sequence (SEQ ID NO:165) of a native sequence PRO19670 cDNA, wherein SEQ ID NO:165 is a clone designated herein as "DNA131639-2874".

FIG. 166 shows the amino acid sequence (SEQ ID NO:166) derived from the coding sequence of SEQ ID NO:165 shown in FIG. 165.

FIG. 167 shows a nucleotide sequence (SEQ ID NO:167) of a native sequence PRO1890 cDNA, wherein SEQ ID NO:167 is a clone designated herein as "DNA79230-2525".

FIG. 168 shows the amino acid sequence (SEQ ID NO:168) derived from the coding sequence of SEQ ID NO:167 shown in FIG. 167.

DETAILED DESCRIPTION

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng. 10:1–6 (1997) and von Heinje et al., Nucl. Acids. Res. 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X", "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., Methods in Enzymology 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., Methods in Enzymology 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term “immunoadhesin” designates antibody-like molecules which combine the binding specificity of a heterologous protein (an “adhesin”) with the effector functions of immunoglobulin constant domains. Structurally, the immunoadhesins comprise a fusion of an amino acid sequence with the desired binding specificity which is other than the antigen recognition and binding site of an antibody (i.e., is “heterologous”), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

“Active” or “activity” for the purposes herein refers to form(s) of a PRO polypeptide which retain a biological and/or an immunological activity of native or naturally-occurring PRO, wherein “biological” activity refers to a biological function (either inhibitory or stimulatory) caused by a native or naturally-occurring PRO other than the ability to induce the production of an antibody against an antigenic epitope possessed by a native or naturally-occurring PRO and an “immunological” activity refers to the ability to induce the production of an antibody against an antigenic epitope possessed by a native or naturally-occurring PRO.

The term “antagonist” is used in the broadest sense, and includes any molecule that partially or fully blocks, inhibits, or neutralizes a biological activity of a native PRO polypeptide disclosed herein. In a similar manner, the term “agonist” is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

“Treatment” refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

“Chronic” administration refers to administration of the agent(s) in a continuous mode as opposed to an acute mode, so as to maintain the initial therapeutic effect (activity) for an extended period of time. “Intermittent” administration is treatment that is not consecutively done without interruption, but rather is cyclic in nature.

“Mammal” for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration “in combination with” one or more further therapeutic agents includes simultaneous (concurrent) and consecutive administration in any order.

“Carriers” as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

“Antibody fragments” comprise a portion of an intact antibody, preferably the antigen binding or variable region of the intact antibody. Examples of antibody fragments include Fab, Fab', $F(ab')_2$, and Fv fragments; diabodies; linear antibodies (Zapata et al., Protein Eng. 8(10): 1057–1062 [1995]); single-chain antibody molecules; and multispecific antibodies formed from antibody fragments.

Papain digestion of antibodies produces two identical antigen-binding fragments, called “Fab” fragments, each with a single antigen-binding site, and a residual “Fc” fragment, a designation reflecting the ability to crystallize readily. Pepsin treatment yields an $F(ab')_2$ fragment that has two antigen-combining sites and is still capable of cross-linking antigen.

“Fv” is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The “light chains” of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

“Single-chain Fv” or “sFv” antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol.113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons

Table 1

```
/*
 *
 * C-C increased from 12 to 15
 * Z is average of EQ
 * B Is average of ND
 * match with stop is _M; stop-stop = 0; J (joker) match = 0
 */
#define   _M      -8        /* value of a match with a stop */

int       _day[26][26] = {
/*     A B C D E F G H I J K L M N O P Q R S T U V W X Y Z */
/* A */   { 2, 0,-2, 0, 0,-4, 1,-1,-1, 0,-1,-2,-1, 0,_M, 1, 0,-2, 1, 1, 0, 0,-6, 0,-3, 0},
/* B */   { 0, 3,-4, 3, 2,-5, 0, 1,-2, 0, 0,-3,-2, 2,_M,-1, 1, 0, 0, 0, 0,-2,-5, 0,-3, 1},
/* C */   {-2,-4,15,-5,-5,-4,-3,-3,-2, 0,-5,-6,-5,-4,_M,-3,-5,-4, 0,-2, 0,-2,-8, 0, 0,-5},
/* D */   { 0, 3,-5, 4, 3,-6, 1, 1,-2, 0, 0,-4,-3, 2,_M,-1, 2,-1, 0, 0, 0,-2,-7, 0,-4, 2},
/* E */   { 0, 2,-5, 3, 4,-5, 0, 1,-2, 0, 0,-3,-2, 1,_M,-1, 2,-1, 0, 0, 0,-2,-7, 0,-4, 3},
/* F */   {-4,-5,-4,-6,-5, 9,-5,-2, 1, 0,-5, 2, 0,-4,_M,-5,-5,-4,-3,-3, 0,-1, 0, 0, 7,-5},
/* G */   { 1, 0,-3, 1, 0,-5, 5,-2,-3, 0,-2,-4,-3, 0,_M,-1,-1,-3, 1, 0, 0,-1,-7, 0,-5, 0},
/* H */   {-1, 1,-3, 1, 1,-2,-2, 6,-2, 0, 0,-2,-2, 2,_M, 0, 3, 2,-1,-1, 0,-2,-3, 0, 0, 2},
/* I */   {-1,-2,-2,-2,-2, 1,-3,-2, 5, 0,-2, 2, 2,-2,_M,-2,-2,-2,-1, 0, 0, 4,-5, 0,-1,-2},
/* J */   { 0, 0, 0, 0, 0, 0, 0, 0, 0, 0, 0, 0, 0, 0,_M, 0, 0, 0, 0, 0, 0, 0, 0, 0, 0, 0},
/* K */   {-1, 0,-5, 0, 0,-5,-2, 0,-2, 0, 5,-3, 0, 1,_M,-1, 1, 3, 0, 0, 0,-2,-3, 0,-4, 0},
/* L */   {-2,-3,-6,-4,-3, 2,-4,-2, 2, 0,-3, 6, 4,-3,_M,-3,-2,-3,-3,-1, 0, 2,-2, 0,-1,-2},
/* M */   {-1,-2,-5,-3,-2, 0,-3,-2, 2, 0, 0, 4, 6,-2,_M,-2,-1, 0,-2,-1, 0, 2,-4, 0,-2,-1},
/* N */   { 0, 2,-4, 2, 1,-4, 0, 2,-2, 0, 1,-3,-2, 2,_M,-1, 1, 0, 1, 0, 0,-2,-4, 0,-2, 1},
/* O */   {_M,_M,_M,_M,_M,_M,_M,_M,_M,_M,_M,_M,_M,_M, 0,_M,_M,_M,_M,_M,_M,_M,_M,_M,_M,_M},
/* P */   { 1,-1,-3,-1,-1,-5,-1, 0,-2, 0,-1,-3,-2,-1,_M, 6, 0, 0, 1, 0, 0,-1,-6, 0,-5, 0},
/* Q */   { 0, 1,-5, 2, 2,-5,-1, 3,-2, 0, 1,-2,-1, 1,_M, 0, 4, 1,-1,-1, 0,-2,-5, 0,-4, 3},
/* R */   {-2, 0,-4,-1,-1,-4,-3, 2,-2, 0, 3,-3, 0, 0,_M, 0, 1, 6, 0,-1, 0,-2, 2, 0,-4, 0},
/* S */   { 1, 0, 0, 0, 0,-3, 1,-1,-1, 0, 0,-3,-2, 1,_M, 1,-1, 0, 2, 1, 0,-1,-2, 0,-3, 0},
/* T */   { 1, 0,-2, 0, 0,-3, 0,-1, 0, 0, 0,-1,-1, 0,_M, 0,-1,-1, 1, 3, 0, 0,-5, 0,-3, 0},
/* U */   { 0, 0, 0, 0, 0, 0, 0, 0, 0, 0, 0, 0, 0, 0,_M, 0, 0, 0, 0, 0, 0, 0, 0, 0, 0, 0},
/* V */   { 0,-2,-2,-2,-2,-1,-1,-2, 4, 0,-2, 2, 2,-2,_M,-1,-2,-2,-1, 0, 0, 4,-6, 0,-2,-2},
/* W */   {-6,-5,-8,-7,-7, 0,-7,-3,-5, 0,-3,-2,-4,-4,_M,-6,-5, 2,-2,-5, 0,-6,17, 0, 0,-6},
/* X */   { 0, 0, 0, 0, 0, 0, 0, 0, 0, 0, 0, 0, 0, 0,_M, 0, 0, 0, 0, 0, 0, 0, 0, 0, 0, 0},
/* Y */   {-3,-3, 0,-4,-4, 7,-5, 0,-1, 0,-4,-1,-2,-2,_M,-5,-4,-4,-3,-3, 0,-2, 0, 0,10,-4},
/* Z */   { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
 */
#include <stdio.h>
#include <ctype.h>

#define  MAXJMP 16      /* max jumps in a diag */
#define  MAXGAP         24      /* don't continue to penalize gaps larger than this */
#define  JMPS           1024    /* max jmps in an path */
#define  MX             4       /* save if there's at least MX-1 bases since last jmp */

#define  DMAT           3       /* value of matching bases */
#define  DMIS           0       /* penalty for mismatched bases */
#define  DINS0          8       /* penalty for a gap */
#define  DINS1          1       /* penalty per base */
#define  PINS0          8       /* penalty for a gap */
#define  PINS1          4       /* penalty per residue */

struct jmp {
        short           n[MAXJMP];      /* size of jmp (neg for dely) */
        unsigned short  x[MAXJMP];      /* base no. of jmp in seq x */
};                                      /* limits seq to 2^16 -1 */

struct diag {
        int             score;          /* score at last jmp */
        long            offset;         /* offset of prev block */
        short           ijmp;           /* current jmp index */
        struct jmp      jp;             /* list of jmps */
};

struct path {
        int     spc;            /* number of leading spaces */
        short   n[JMPS]; /* size of jmp (gap) */
        int     x[JMPS]; /* loc of jmp (last elem before gap) */
};

char            *ofile;                 /* output file name */
char            *namex[2];              /* seq names: getseqs() */
char            *prog;                  /* prog name for err msgs */
char            *seqx[2];               /* seqs: getseqs() */
int             dmax;                   /* best diag: nw() */
int             dmax0;                  /* final diag */
int             dna;                    /* set if dna: main() */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw() */
int             *xbm;                   /* bitmap for matching */
long            offset;                 /* current offset in jmp file */
struct  diag    *dx;                    /* holds diagonals */
struct  path    pp[2];                  /* holds path for seqs */

char            *calloc(), *malloc(), *index(), *strcpy();
char            *getseq(), *g_calloc();
```

Table 1 (cont')

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)                                                                main
          int       ac;
          char      *av[ ];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lowercase\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;

          endgaps = 0;                    /* 1 to penalize endgaps */
          ofile = "align.out";            /* output file */

          nw();                 /* fill in the matrix, get the possible jmps */
          readjmps();           /* get the actual jmps */
          print();              /* print stats, alignment */

          cleanup(0);           /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                    nw
{
        char            *px, *py;           /* seqs and ptrs */
        int             *ndely, *dely;      /* keep track of dely */
        int             ndelx, delx;        /* keep track of delx */
        int             *tmp;               /* for swapping row0, row1 */
        int             mis;                /* score for each type */
        int             ins0, ins1;         /* insertion penalties */
        register        id;                 /* diagonal index */
        register        ij;                 /* jmp index */
        register        *col0, *col1;       /* score for curr, last row */
        register        xx, yy;             /* index into seqs */

        dx = (struct diag *)g_calloc("to get diags", len0+len1+1, sizeof(struct diag));

        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;

        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;            /* Waterman Bull Math Biol 84 */
        }
        else
                for (yy = 1; yy <= len1; yy++)
                        dely[yy] = -ins0;

        /* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

        /* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

        /* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

        /* pick the maximum score; we're favoring
         * mis over any del and delx over dely
         */
```

Table 1 (cont')

...nw

```
			id = xx - yy + len1 - 1;
			if (mis >= delx && mis >= dely[yy])
				col1[yy] = mis;
			else if (delx >= dely[yy]) {
				col1[yy] = delx;
				ij = dx[id].ijmp;
				if (dx[id].jp.n[0] && (!dna || (ndelx >= MAXJMP
				&& xx > dx[id].jp.x[ij]+MX) || mis > dx[id].score+DINS0)) {
					dx[id].ijmp++;
					if (++ij >= MAXJMP) {
						writejmps(id);
						ij = dx[id].ijmp = 0;
						dx[id].offset = offset;
						offset += sizeof(struct jmp) + sizeof(offset);
					}
				}
				dx[id].jp.n[ij] = ndelx;
				dx[id].jp.x[ij] = xx;
				dx[id].score = delx;
			}
			else {
				col1[yy] = dely[yy];
				ij = dx[id].ijmp;
if (dx[id].jp.n[0] && (!dna || (ndely[yy] >= MAXJMP
				&& xx > dx[id].jp.x[ij]+MX) || mis > dx[id].score+DINS0)) {
					dx[id].ijmp++;
					if (++ij >= MAXJMP) {
						writejmps(id);
						ij = dx[id].ijmp = 0;
						dx[id].offset = offset;
						offset += sizeof(struct jmp) + sizeof(offset);
					}
				}
				dx[id].jp.n[ij] = -ndely[yy];
				dx[id].jp.x[ij] = xx;
				dx[id].score = dely[yy];
			}
			if (xx == len0 && yy < len1) {
				/* last col
				 */
				if (endgaps)
					col1[yy] -= ins0+ins1*(len1-yy);
				if (col1[yy] > smax) {
					smax = col1[yy];
					dmax = id;
				}
			}
		}
		if (endgaps && xx < len0)
			col1[yy-1] -= ins0+ins1*(len0-xx);
		if (col1[yy-1] > smax) {
			smax = col1[yy-1];
			dmax = id;
		}
		tmp = col0; col0 = col1; col1 = tmp;
}
(void) free((char *)ndely);
(void) free((char *)dely);
```

```
(void) free((char *)col0);
(void) free((char *)col1);
}
```

Table 1 (cont')

```
/*
 *
 * print() -- only routine visible outside this module
 *
 * static:
 * getmat() -- trace back best path, count matches: print()
 * pr_align() -- print alignment of described in array p[ ]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() --put a line of stars: dumpblock()
 * stripname() -- strip any path and prefix from a seqname
 */

#include "nw.h"

#define SPC        3
#define P_LINE     256     /* maximum output line */
#define P_SPC      3       /* space between name or num and seq */

extern     _day[26][26];
int        olen;           /* set output line length */
FILE       *fx;            /* output file */

print()                                                            print
{
        int     lx, ly, firstgap, lastgap;      /* overlap */

        if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();
}
```

Table 1 (cont')

getmat

```
/*
 * trace back the best path, count matches
 */
static
getmat(lx, ly, firstgap, lastgap)
	int	lx, ly;			/* "core" (minus endgaps) */
	int	firstgap, lastgap;	/* leading trailing overlap */
{
	int		nm, i0, i1, siz0, siz1;
	char		outx[32];
	double		pct;
	register	n0, n1;
	register char	*p0, *p1;

	/* get total matches, score
	 */
	i0 = i1 = siz0 = siz1 = 0;
	p0 = seqx[0] + pp[1].spc;
	p1 = seqx[1] + pp[0].spc;
	n0 = pp[1].spc + 1;
	n1 = pp[0].spc + 1;

	nm = 0;
	while ( *p0 && *p1 ) {
		if (siz0) {
			p1++;
			n1++;
			siz0--;
		}
		else if (siz1) {
			p0++;
			n0++;
			siz1--;
		}
		else {
			if (xbm[*p0-'A']&xbm[*p1-'A'])
				nm++;
			if (n0++ == pp[0].x[i0])
				siz0 = pp[0].n[i0++];
			if (n1++ == pp[1].x[i1])
				siz1 = pp[1].n[i1++];
			p0++;
			p1++;
		}
	}

	/* pct homology:
	 * if penalizing endgaps, base is the shorter seq
	 * else, knock off overhangs and take shorter core
	 */
	if (endgaps)
		lx = (len0 < len1)? len0 : len1;
	else
		lx = (lx < ly)? lx : ly;
	pct = 100.*(double)nm/(double)lx;
	fprintf(fx, "\n");
	fprintf(fx, "<%d match%s in an overlap of %d: %.2f percent similarity\n",
		nm, (nm == 1)? "" : "es", lx, pct);
```

Table 1 (cont')

...getmat

```
        fprintf(fx, "<gaps in first sequence: %d", gapx);
        if (gapx) {
                (void) sprintf(outx, " (%d %s%s)",
                        ngapx, (dna)? "base":"residue", (ngapx == 1)? "":"s");
                fprintf(fx,"%s", outx);

        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
}

static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
 * print alignment of described in struct path pp[ ]
 */
static
pr_align()
{
        int             nn;     /* char count */
        int             more;
        register        i;

        for (i = 0, lmax = 0; i < 2; i++) {
                nn = stripname(namex[i]);
                if (nn > lmax)
                        lmax = nn;

                nc[i] = 1;
                ni[i] = 1;
                siz[i] = ij[i] = 0;
```

pr_align

```
ps[i] = seqx[i];
po[i] = out[i];
}
```

Table 1 (cont')

...pr_align

```
	for (nn = nm = 0, more = 1; more; ) {
		for (i = more = 0; i < 2; i++) {
			/*
			 * do we have more of this sequence?
			 */
			if (!*ps[i])
				continue;

			more++;

			if (pp[i].spc) {	/* leading space */
				*po[i]++ = ' ';
				pp[i].spc--;
			}
			else if (siz[i]) {	/* in a gap */
				*po[i]++ = '-';
				siz[i]--;
			}
			else {			/* we're putting a seq element
						 */
				*po[i] = *ps[i];
				if (islower(*ps[i]))
					*ps[i] = toupper(*ps[i]);
				po[i]++;
				ps[i]++;

				/*
				 * are we at next gap for this seq?
				 */
				if (ni[i] == pp[i].x[ij[i]]) {
					/*
					 * we need to merge all gaps
					 * at this location
					 */
					siz[i] = pp[i].n[ij[i]++];
					while (ni[i] == pp[i].x[ij[i]])
						siz[i] += pp[i].n[ij[i]++];
				}
				ni[i]++;
			}
		}
		if (++nn == olen || !more && nn) {
			dumpblock();
			for (i = 0; i < 2; i++)
				po[i] = out[i];
			nn = 0;
		}
	}
}

/*
 * dump a block of lines, including numbers, stars: pr_align()
 */
static
dumpblock()
{
	register	i;
```

dumpblock

```
for (i = 0; i < 2; i++)
        *po[i]- = '\0';
```

Table 1 (cont')

...dumpblock

```
		(void) putc('\n', fx);
		for (i = 0; i < 2; i++) {
			if (*out[i] && (*out[i] != ' ' || *(po[i]) != ' ')) {
				if (i == 0)
					nums(i);
				if (i == 0 && *out[1])
					stars();
				putline(i);
				if (i == 0 && *out[1])
					fprintf(fx, star);
				if (i == 1)
					nums(i);
			}
		}
}

/*
 * put out a number line: dumpblock()
 */
static
nums(ix)
		int		ix;		/* index in out[] holding seq line */
{
		char			nline[P_LINE];
		register		i, j;
		register char		*pn, *px, *py;

		for (pn = nline, i = 0; i < lmax+P_SPC; i++, pn++)
			*pn = ' ';
		for (i = nc[ix], py = out[ix]; *py; py++, pn++) {
			if (*py == ' ' || *py == '-')
				*pn = ' ';
			else {
				if (i%10 == 0 || (i == 1 && nc[ix] != 1)) {
					j = (i < 0)? -i : i;
					for (px = pn; j; j /= 10, px--)
						*px = j%10 + '0';
					if (i < 0)
						*px = '-';
				}
				else
					*pn = ' ';
				i++;
			}
		}
		*pn = '\0';
		nc[ix] = i;
		for (pn = nline; *pn; pn++)
			(void) putc(*pn, fx);
		(void) putc('\n', fx);
}

/*
 * put out a line (name, [num], seq, [num]): dumpblock()
 */
static
```

nums

```
putline(ix)
int ix; {                                                putline
```

Table 1 (cont')

...putline

```
	int		i;
	register char	*px;

	for (px = namex[ix], i = 0; *px && *px != ':'; px++, i++)
		(void) putc(*px, fx);
	for (; i < lmax+P_SPC; i++)
		(void) putc(' ', fx);

	/* these count from 1:
	 * ni[] is current element (from 1)
	 * nc[] is number at start of current line
	 */
	for (px = out[ix]; *px; px++)
		(void) putc(*px&0x7F, fx);
	(void) putc('\n', fx);
}


/*
 * put a line of stars (seqs always in out[0], out[1]): dumpblock()
 */
static
stars()
{
	int		i;
	register char	*p0, *p1, cx, *px;

	if (!*out[0] || (*out[0] == ' ' && *(po[0]) == ' ') ||
	    !*out[1] || (*out[1] == ' ' && *(po[1]) == ' '))
		return;
	px = star;
	for (i = lmax+P_SPC; i; i--)
		*px++ = ' ';

	for (p0 = out[0], p1 = out[1]; *p0 && *p1; p0++, p1++) {
		if (isalpha(*p0) && isalpha(*p1)) {

			if (xbm[*p0-'A']&xbm[*p1-'A']) {
				cx = '*';
				nm++;
			}
			else if (!dna && _day[*p0-'A'][*p1-'A'] > 0)
				cx = '.';
			else
				cx = ' ';
		}
		else
			cx = ' ';
		*px++ = cx;
	}
	*px++ = '\n';
	*px = '\0';
}
```

stars

Table 1 (cont')

```
/*
 * strip path or prefix from pn, return len: pr_align()
 */
static
stripname(pn)
        char        *pn;        /* file name (may be path) */
{
        register char        *px, *py;

        py = 0;
        for (px = pn; *px; px++)
                if (*px == '/')
                        py = px + 1;
        if (py)
                (void) strcpy(pn, py);
        return(strlen(pn));

}
```

stripname

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
#include "nw.h"
#include <sys/file.h>

char    *jname = "/tmp/homgXXXXXX";          /* tmp file for jmps */
FILE    *fj;

int     cleanup();                    /* cleanup tmp file */
long    lseek();

/*
 * remove any tmp file if we blow
 */
cleanup(i)                                                          cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)                                                   getseq
        char    *file;  /* file name */
        int     *len;   /* seq len */
{
        char            line[1024], *pseq;
        register char   *px, *py;
        int             natgc, tlen;
        FILE            *fp;

        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
        py = pseq + 4;
        *len = tlen;
        rewind(fp);

        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
```

g_calloc

```
char    *
g_calloc(msg, nx, sz)
        char    *msg;           /* program, calling routine */
        int     nx, sz;         /* number and size of elements */
{
        char            *px, *calloc();

        if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}
```

readjmps

```
/*
 * get final jmps from dx[] or tmp file, set pp[], reset dmax: main()
 */
readjmps()
{
        int             fd = -1;
        int             siz, i0, i1;
        register        i, j, xx;

        if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
```

```
for (j = dx[dmax].ijmp; j >= 0 && dx[dmax].jp.x[j] >= xx; j--)
        ;
```

Table 1 (cont')

...readjmps

```
			if (j < 0 && dx[dmax].offset && fj) {
				(void) lseek(fd, dx[dmax].offset, 0);
				(void) read(fd, (char *)&dx[dmax].jp, sizeof(struct jmp));
				(void) read(fd, (char *)&dx[dmax].offset, sizeof(dx[dmax].offset));
				dx[dmax].ijmp = MAXJMP-1;
			}
			else
				break;
		}
		if (i >= JMPS) {
			fprintf(stderr, "%s: too many gaps in alignment\n", prog);
			cleanup(1);
		}
		if (j >= 0) {
			siz = dx[dmax].jp.n[j];
			xx = dx[dmax].jp.x[j];
			dmax += siz;
			if (siz < 0) {			/* gap in second seq */
				pp[1].n[i1] = -siz;
				xx += siz;
				/* id = xx - yy + len1 - 1
				 */
				pp[1].x[i1] = xx - dmax + len1 - 1;
				gapy++;
				ngapy -= siz;
/* ignore MAXGAP when doing endgaps */
				siz = (-siz < MAXGAP || endgaps)? -siz : MAXGAP;
				i1++;
			}
			else if (siz > 0) {	/* gap in first seq */
				pp[0].n[i0] = siz;
				pp[0].x[i0] = xx;
				gapx++;
				ngapx += siz;
/* ignore MAXGAP when doing endgaps */
				siz = (siz < MAXGAP || endgaps)? siz : MAXGAP;
				i0++;
			}
		}
		else
			break;
	}

	/* reverse the order of jmps
	 */
	for (j = 0, i0--; j < i0; j++, i0--) {
		i = pp[0].n[j]; pp[0].n[j] = pp[0].n[i0]; pp[0].n[i0] = i;
		i = pp[0].x[j]; pp[0].x[j] = pp[0].x[i0]; pp[0].x[i0] = i;
	}
	for (j = 0, i1--; j < i1; j++, i1--) {
		i = pp[1].n[j]; pp[1].n[j] = pp[1].n[i1]; pp[1].n[i1] = i;
		i = pp[1].x[j]; pp[1].x[j] = pp[1].x[i1]; pp[1].x[i1] = i;
	}
	if (fd >= 0)
		(void) close(fd);
	if (fj) {
		(void) unlink(jname);
		fj = 0;
```

```
        offset = 0;
    }
}
```

Table 1 (cont')

writejmps

```
/*
 * write a filled jmp struct offset of the prev one (if any): nw()
 */
writejmps(ix)
        int     ix;
{
        char    *mktemp();

        if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as “PRO/number”, regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244: 1081–1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol., 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal.

Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; an α-tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

In an alternative embodiment, the chimeric molecule may comprise a fusion of the PRO with an immunoglobulin or a particular region of an immunoglobulin. For a bivalent form of the chimeric molecule (also referred to as an “immunoadhesin”), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., Solid-Phase Peptide Synthesis, W. H. Freeman Co., San Francisco, Calif. (1969); Merrifield, J. Am. Chem. Soc., 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer’s instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding PRO is to use PCR methodology [Sambrook et al., supra; Dieffenbach et al., PCR Primer: A Laboratory Manual (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456–457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527–537 (1990) and Mansour et al., Nature, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT $kan^r$; *E. coli* W3110 strain 37D6, which has the complete genotype tonA ptr3 phoA E15 (argF-lac)169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, Nature, 290: 140 [1981]; EP 139,383 published May 2, 1985); *Kluyveromyces* hosts (U.S. Pat. No. 4,943,529; Fleer et al., Bio/Technology, 9:968–975 (1991)) such as, e.g., *K. lactis* (MW98-8C, CBS683, CBS4574; Louvencourt et al., J. Bacteriol., 154(2):737–742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265–278 [1988]); *Candida; Trichoderma reesia* (EP 244,234); *Neurospora crassa* (Case et al., Proc. Natl. Acad. Sci. USA, 76:5259–5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/000357 published 10 Jan. 1991), and *Aspergillus* hosts such as *A. nidulans* (Ballance et al., Biochem. Biophys. Res. Commun., 112:284–289 [1983]; Tilburn et al., Gene, 26:205–221 [1983]; Yelton et al., Proc. Natl. Acad. Sci. USA, 81: 1470–1474 [1984]) and *A. niger* (Kelly and Hynes, EMBO J., 4:475–479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated PRO are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp 1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp 1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21–25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., Nature, 293:620–625 (1981); Mantei et al., Nature, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143–4146

[1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429–4432 (1987); and Wagner et al., Proc. Natl. Acad. Sci. USA 87, 3410–3414 (1990). For review of gene marking and gene therapy protocols see Anderson et al., Science 256, 808–813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a PRO polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon- (rhIFN-), interleukin-2, and MN rgp120. Johnson et al., Nat. Med., 2:795–799 (1996); Yasuda, Biomed. Ther., 27:1221–1223 (1993); Hora et al., Bio/Technology, 8:755–758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using polylactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245–246 (1989); Chien et al., Proc. Natl. Acad. Sci. USA, 88:9578–9582 (1991)) as disclosed by Chevray and Nathans, Proc. Natl. Acad. Sci. USA, 89: 5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Current Protocols in Immun., 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al., Science, 241: 456 (1988); Dervan et al., Science, 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, Neurochem., 56:560 (1991); Oligodeoxynucleotides as Antisense Inhibitors of Gene Expression (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology, 4:469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779–783 (1992); Lonberg et al., Nature 368 856–859 (1994); Morrison, Nature 368, 812–13 (1994); Fishwild et al., Nature Biotechnology 14, 845–51 (1996); Neuberger, Nature Biotechnology 14, 826 (1996); Lonberg and Huszar, Intern. Rev. Immunol. 13 65–93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., J. Exp. Med. 175:217 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148 (5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (Fc γ R), such as Fc γ RI (CD64), Fc γ RII (CD32) and Fc γ RIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity may also be prepared using heterobifunctional cross-linkers as described in Wolff et al. Cancer Research, 53: 2560–2565 (1993). Alternatively, an antibody can be engineered that has dual Fc regions and may thereby have enhanced complement lysis and ADCC capabilities. See Stevenson et al., Anti-Cancer Drug Design, 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286–288 (1982) via a disulfide-interchange reaction. A chemotherapeutic agent (such as Doxorubicin) is optionally contained within the liposome. See Gabizon et al., J. National Cancer Inst., 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889–7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

C. Uses for Anti-PRO Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, Monoclonal Antibodies: A Manual of Techniques, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Anti-PRO antibodies also are useful for the affinity purification of PRO from recombinant cell culture or natural sources. In this process, the antibodies against PRO are immobilized on a suitable support, such as Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., Methods in Enzymology 266:460–480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., Current Protocols in Molecular Biology, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278–1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500–1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3–52, leu2–3, leu2–112, his3–11, his3–15, $MAL^+$, $SUC^+$, $GAL^+$. Preferably, yeast mutants can be employed that have deficient post-translational pathways. Such mutants may have translocation deficient alleles in sec 71, sec 72, sec 62, with truncated sec 71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., Nucl. Acid. Res., 20:1425 (1992). Transformed cells were then inoculated from agar into YEPD complex media broth (100 ml) and grown overnight at 30° C. The YEPD broth was prepared as described in Kaiser et al., Methods in Yeast Genetics, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4–0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol.<10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5–10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., Methods in Yeast Genetics, Cold Spring Harbor Press, Cold Spring Harbor, N.Y., p. 208–210 (1994). Transformants were grown at 30° C. for 2–3 days.

The detection of colonies secreting amylase was performed by including red starch in the selective growth media. Starch was coupled to the red dye (Reactive Red-120, Sigma) as per the procedure described by Biely et al., Anal. Biochem., 172:176–179 (1988). The coupled starch was incorporated into the SCD-Ura agar plates at a final concentration of 0.15% (w/v), and was buffered with potassium phosphate to a pH of 7.0 (50–100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

5'-TGTAAAACGACGGCCAGTTAAATAGACCTGCAATTATTAATCT-3' (SEQ ID NO:169)

The sequence of reverse oligonucleotide 2 was:

5'-CAGGAAACAGCTATGACCACCTGCACACCTGCAAATCCATT-3' (SEQ ID NO:170)

PCR was then performed as follows:

| | | | | |
|---|---|---|---|---|
| a. | | Denature | 92° C., | 5 minutes |
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |
| d. | 25 cycles of: | Denature | 92° C., | 30 seconds |
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA Clones Encoding Human PRO Polypeptides

Using the techniques described in Examples 1 to 3 above, numerous full-length cDNA clones were identified as encoding PRO polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below.

TABLE 7

| Material | ATCC Dep. No. | Deposit Date |
|---|---|---|
| DNA26843-1389 | 203099 | Aug. 4, 1998 |
| DNA30867-1335 | 209807 | Apr. 28, 1998 |
| DNA34431-1177 | 209399 | Oct. 17, 1997 |
| DNA38268-1188 | 209421 | Oct. 28, 1997 |
| DNA40621-1440 | 209922 | Jun. 2, 1998 |
| DNA40625-1189 | 209788 | Apr. 21, 1998 |
| DNA45409-2511 | 203579 | Jan. 12,1999 |
| DNA45495-1550 | 203156 | Aug. 25, 1998 |
| DNA49820-1427 | 209932 | Jun. 2, 1998 |
| DNA56406-1704 | 203478 | Nov. 17, 1998 |
| DNA56410-1414 | 209923 | Jun. 2, 1998 |
| DNA56436-1448 | 209902 | May 27, 1998 |
| DNA56855-1447 | 203004 | Jun. 23, 1998 |
| DNA56860-1510 | 209952 | Jun. 9, 1998 |

TABLE 7-continued

| Material | ATCC Dep. No. | Deposit Date |
|---|---|---|
| DNA56862-1343 | 203174 | Sep. 1, 1998 |
| DNA56868-1478 | 203024 | Jun. 23, 1998 |
| DNA56869-1545 | 203161 | Aug. 25, 1998 |
| DNA57704-1452 | 209953 | Jun. 9, 1998 |
| DNA58723-1588 | 203133 | Aug. 18, 1998 |
| DNA57827-1493 | 203045 | Jul. 1, 1998 |
| DNA58737-1473 | 203136 | Aug. 18, 1998 |
| DNA58846-1409 | 209957 | Jun. 9, 1998 |
| DNA58850-1495 | 209956 | Jun. 9, 1998 |
| DNA58855-1422 | 203018 | Jun. 23, 1998 |
| DNA59211-1450 | 209960 | Jun. 9, 1998 |
| DNA59212-1627 | 203245 | Sep. 9, 1998 |
| DNA59213-1487 | 209959 | Jun. 9, 1998 |
| DNA59605-1418 | 203005 | Jun. 23, 1998 |
| DNA59609-1470 | 209963 | Jun. 9, 1998 |
| DNA59610-1556 | 209990 | Jun. 16, 1998 |
| DNA59837-2545 | 203658 | Feb. 9, 1999 |
| DNA59844-2542 | 203650 | Feb. 9, 1999 |
| DNA59854-1459 | 209974 | Jun. 16, 1998 |
| DNA60625-1507 | 209975 | Jun. 16, 1998 |
| DNA60629-1481 | 209979 | Jun. 16, 1998 |
| DNA61755-1554 | 203112 | Aug. 11, 1998 |
| DNA62812-1594 | 203248 | Sep. 9, 1998 |
| DNA62815-1576 | 203247 | Sep. 9, 1998 |
| DNA64881-1602 | 203240 | Sep. 9, 1998 |
| DNA64886-1601 | 203241 | Sep. 9, 1998 |
| DNA64902-1667 | 203317 | Oct. 6, 1998 |
| DNA64950-1590 | 203224 | Sep. 15, 1998 |
| DNA65403-1565 | 203230 | Sep. 15, 1998 |
| DNA66308-1537 | 203159 | Aug. 25, 1998 |
| DNA66519-1535 | 203236 | Sep. 15, 1998 |
| DNA66521-1583 | 203225 | Sep. 15, 1998 |
| DNA66658-1584 | 203229 | Sep. 15, 1998 |
| DNA66660-1585 | 203279 | Sep. 22, 1998 |
| DNA66663-1598 | 203268 | Sep. 22, 1998 |
| DNA66674-1599 | 203281 | Sep. 22, 1998 |
| DNA68862-2546 | 203652 | Feb. 9, 1999 |
| DNA68866-1644 | 203283 | Sep. 22, 1998 |
| DNA68871-1638 | 203280 | Sep. 22, 1998 |
| DNA68880-1676 | 203319 | Oct. 6, 1998 |
| DNA68883-1691 | 203535 | Dec. 15, 1998 |
| DNA68885-1678 | 203311 | Oct. 6, 1998 |
| DNA71277-1636 | 203285 | Sep. 22, 1998 |
| DNA73727-1673 | 203459 | Nov. 3, 1998 |
| DNA73734-1680 | 203363 | Oct. 20, 1998 |
| DNA73735-1681 | 203356 | Oct. 20, 1998 |
| DNA76393-1664 | 203323 | Oct. 6, 1998 |
| DNA77301-1708 | 203407 | Oct. 27, 1998 |
| DNA77568-1626 | 203134 | Aug. 18, 1998 |
| DNA77626-1705 | 203536 | Dec. 15, 1998 |
| DNA81754-2532 | 203542 | Dec. 15, 1998 |
| DNA81757-2512 | 203543 | Dec. 15, 1998 |
| DNA82302-2529 | 203534 | Dec. 15, 1998 |
| DNA82340-2530 | 203547 | Dec. 22, 1998 |
| DNA83500-2506 | 203391 | Oct. 29, 1998 |
| DNA84920-2614 | 203966 | Apr. 27, 1999 |
| DNA85066-2534 | 203588 | Jan. 12, 1999 |
| DNA86571-2551 | 203660 | Feb. 9, 1999 |
| DNA87991-2540 | 203656 | Feb. 9, 1999 |
| DNA92238-2539 | 203602 | Jan. 20, 1999 |
| DNA96042-2682 | PTA-382 | Jul. 20, 1999 |
| DNA96787-2534 | 203589 | Jan. 12, 1999 |
| DNA125185-2806 | PTA-1031 | Dec. 7, 1999 |
| DNA147531-2821 | PTA-1185 | Jan. 11, 2000 |
| DNA115291-2681 | PTA-202 | Jun. 8, 1999 |
| DNA164625-28890 | PTA-1535 | Mar. 21, 2000 |
| DNA131639-2874 | PTA-1784 | Apr. 25, 2000 |
| DNA79230-2525 | 203549 | Dec. 22, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 5

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 6

Expression of PRO in *E. Coli*

This example illustrates preparation of an unglycosylated form of PRO by recombinant expression in *E. coli.*

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in *E. coli* in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) Ion galE rpoHts (htpRts) clpP(laclq). Transformants are first grown in LB containing 50 mg/ml carbenicillin at 30° C. with shaking until an O.D.600 of 3–5 is reached. Cultures are then diluted 50–100 fold into CRAP media (prepared by mixing 3.57 g $(NH_4)_2SO_4$, 0.71 g sodium citrate-2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-page analysis, and the bulk culture is centrifuged to pellet the cells. Cell pellets are frozen until purification and refolding.

*E. coli* paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 7

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}S$-cysteine and 200 μCi/ml $^{35}S$-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., Proc. Natl. Acad. Sci., 12:7575 (1981). 293 cells are grown to maximal density in a spinner flask and 700 μg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3\times10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2\times10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 8

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 9

Expression of PRO in Baculovirus—Infected Insect Cells

The following method describes recombinant expression of PRO in Baculovirus—infected insect cells.

The sequence coding for PRO is fused upstream of an epitope tag contained a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., Baculovirus expression vectors: A Laboratory Manual, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., Nature, 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 10

Preparation of Antibodies That Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 11

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 12

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with a PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 13

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c.f., Hodgson, Bio/Technology, 9: 19–21(1991)).

In one approach, the three-dimensional structure of the PRO polypeptide, or of a PRO polypeptide-inhibitor complex, is determined by X-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, Biochemistry, 31:7796–7801 (1992) or which act as inhibitors, agonists, or antagonists of native peptides as shown by Athauda et al., J. Biochem., 113: 742–746(1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to X-ray crystallography.

Example 14

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Induction of c-fos expression in pericytes is also indicative of the induction of angiogenesis and, as such, PRO polypeptides capable of inducing the expression of c-fos would be expected to be useful for the treatment of conditions where induced angiogenesis would be beneficial including, for example, wound healing, and the like. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 μl of PRO polypeptide test samples and controls (positive control=DME+5% serum+/−PDGF at 500 ng/ml; negative control=protein 32). Replicates are averaged and SD/CV are determined. Fold increase over Protein 32 (buffer control) value indicated by chemiluminescence units (RLU) luminometer reading verses frequency is plotted on a histogram. Two-fold above Protein 32 value is considered positive for the assay. ASY Matrix: Growth media=low glucose DMEM=20% FBS+1× pen strep+1× fungizone. Assay Media=low glucose DMEM+5% FBS.

The following polypeptides tested positive in this assay: PRO1347 and PRO1340.

Example 15

Ability of PRO Polypeptides to Stimulate the Release of Proteoglycans from Cartilage (Assay 97)

The ability of various PRO polypeptides to stimulate the release of proteoglycans from cartilage tissue was tested as follows.

The metacarphophalangeal joint of 4–6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) with 0.1% BSA and 100 U/ml penicillin and 100 μg/ml streptomycin. After washing three times, approximately 100 mg of articular cartilage was aliquoted into micronics tubes and incubated for an additional 24 hours in the above SF media. PRO polypeptides were then added at 1% either alone or in combination with 18 ng/ml interleukin-1α, a known stimulator of proteoglycan release from cartilage tissue. The supernatant was then harvested and assayed for the amount of proteoglycans using the 1,9-dimethyl-methylene blue (DMB) colorimetric assay (Farndale and Buttle, Biochem. Biophys. Acta 883:173–177 (1985)). A positive result in this assay indicates that the test polypeptide will find use, for example, in the treatment of sports-related joint problems, articular cartilage defects, osteoarthritis or rheumatoid arthritis.

When various PRO polypeptides were tested in the above assay, the polypeptides demonstrated a marked ability to stimulate release of proteoglycans from cartilage tissue both basally and after stimulation with interleukin-1α and at 24 and 72 hours after treatment, thereby indicating that these PRO polypeptides are useful for stimulating proteoglycan release from cartilage tissue. As such, these PRO polypeptides are useful for the treatment of sports-related joint problems, articular cartilage defects, osteoarthritis or rheumatoid arthritis. The polypeptides testing positive in this assay are: PRO1565, PRO1693, PRO1801 and PRO10096.

Example 16

Detection of Polypeptides That Affect Glucose or FFA Uptake in Skeletal Muscle (Assay 106)

This assay is designed to determine whether PRO polypeptides show the ability to affect glucose or FFA uptake by skeletal muscle cells. PRO polypeptides testing positive in this assay would be expected to be useful for the therapeutic treatment of disorders where either the stimulation or inhibition of glucose uptake by skeletal muscle would be beneficial including, for example, diabetes or hyper- or hypo-insulinemia.

In a 96 well format, PRO polypeptides to be assayed are added to primary rat differentiated skeletal muscle, and allowed to incubate overnight. Then fresh media with the PRO polypeptide and +/− insulin are added to the wells. The sample media is then monitored to determine glucose and FFA uptake by the skeletal muscle cells. The insulin will stimulate glucose and FFA uptake by the skeletal muscle, and insulin in media without the PRO polypeptide is used as a positive control, and a limit for scoring. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: PRO4405.

Example 17

Identification of PRO Polypeptides That Stimulate TNF-α Release in Human Blood (Assay 128)

This assay shows that certain PRO polypeptides of the present invention act to stimulate the release of TNF-α in human blood. PRO polypeptides testing positive in this assay are useful for, among other things, research purposes where stimulation of the release of TNF-α would be desired and for the therapeutic treatment of conditions wherein enhanced TNF-α release would be beneficial. Specifically, 200 μl of human blood supplemented with 50 mM Hepes buffer (pH 7.2) is aliquotted per well in a 96 well test plate. To each well is then added 300 μl of either the test PRO polypeptide in 50 mM Hepes buffer (at various concentrations) or 50 mM Hepes buffer alone (negative control) and the plates are incubated at 37° C. for 6 hours. The samples are then centrifuged and 50 μl of plasma is collected from each well and tested for the presence of TNF-α by ELISA assay. A positive in the assay is a higher amount of TNF-α in the PRO polypeptide treated samples as compared to the negative control samples.

The following PRO polypeptides tested positive in this assay: PRO263, PRO295, PRO1282, PRO1063, PRO1356, PRO3543, and PRO5990.

Example 18

Tumor Versus Normal Differential Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200–600 base pair amplified fragment from the 3' end of its associated template in a standard PCR reaction. The oligonucleotide probes were employed in standard quantitative PCR amplification reactions with cDNA libraries isolated from different human tumor and normal human tissue samples and analyzed by agarose gel electrophoresis so as to obtain a quantitative determination of the level of expression of the PRO polypeptide-encoding nucleic acid in the various tumor and normal tissues tested. β-actin was used as a control to assure that equivalent amounts of nucleic acid was used in each reaction. Identification of the differential expression of the PRO polypeptide-encoding nucleic acid in one or more tumor tissues as compared to one or more normal tissues of the same tissue type renders the molecule useful diagnostically for the determination of the presence or absence of tumor in a subject suspected of possessing a tumor as well as therapeutically as a target for the treatment of a tumor in a subject possessing such a tumor. These assays provided the following results.

| Molecule | is more highly expressed in: | as compared to: |
|---|---|---|
| DNA26843-1389 | normal lung | lung tumor |
| | rectum tumor | normal rectum |
| DNA30867-1335 | normal kidney | kidney tumor |

-continued

| Molecule | is more highly expressed in: | as compared to: |
|---|---|---|
| DNA40621-1440 | normal lung | lung tumor |
| DNA40625-1189 | normal lung | lung tumor |
| DNA45409-2511 | melanoma tumor | normal akin |
| DNA56406-1704 | kidney tumor | normal kidney |
| | normal skin | melanoma tumor |
| DNA56410-1414 | normal stomach | stomach tumor |
| DNA56436-1448 | normal skin | melanoma tumor |
| DNA56855-1447 | normal esophagus | esophageal tumor |
| | rectum tumor | normal rectum |
| DNA56860-1510 | normal kidney | kidney tumor |
| | rectum tumor | normal rectum |
| DNA56862-1343 | kidney tumor | normal kidney |
| | normal lung | lung tumor |
| DNA56868-1478 | normal stomach | stomach tumor |
| | normal lung | lung tumor |
| DNA56869-1545 | normal esophagus | esophageal tumor |
| | normal skin | melanoma tumor |
| DNA57704-1452 | normal stomach | stomach tumor |
| | rectum tumor | normal rectum |
| DNA58723-1588 | normal stomach | stomach tumor |
| | kidney tumor | normal kidney |
| | normal akin | melanoma tumor |
| DNA57827-1493 | normal stomach | stomach tumor |
| | normal skin | melanoma tumor |
| DNA58737-1473 | esophageal tumor | normal esophagus |
| | normal stomach | stomach tumor |
| DNA58846-1409 | lung tumor | normal lung |
| DNA58850-1495 | esophageal tumor | normal esophagus |
| | kidney tumor | normal kidney |
| DNA58855-1422 | normal stomach | stomach tumor |
| | rectum tumor | normal rectum |
| DNA59211-1450 | normal kidney | kidney tumor |
| DNA59212-1627 | normal skin | melanoma tumor |
| DNA59213-1487 | normal stomach | stomach tumor |
| | normal skin | melanoma tumor |
| DNA59605-1418 | melanoma tumor | normal skin |
| DNA59609-1470 | esophageal tumor | normal esophagus |
| DNA59610-1556 | esophageal tumor | normal esophagus |
| | lung tumor | normal lung |
| | normal skin | melanoma tumor |
| DNA59837-2545 | normal skin | melanoma tumor |
| DNA59844-2542 | normal skin | melanoma tumor |
| | esophageal tumor | normal esophagus |
| DNA59854-1459 | normal esophagus | esophageal tumor |
| | stomach tumor | normal stomach |
| | normal lung | lung tumor |
| DNA60625-1507 | normal lung | lung tumor |
| DNA60629-1481 | normal esophagus | esophageal tumor |
| | normal rectum | rectum tumor |
| DNA61755-1554 | normal stomach | stomach tumor |
| | kidney tumor | normal kidney |
| DNA62812-1594 | normal stomach | stomach tumor |
| | normal lung | lung tumor |
| | normal rectum | rectum tumor |
| | normal skin | melanoma tumor |
| DNA62815-1576 | esophageal tumor | normal esophagus |
| DNA64881-1602 | normal stomach | stomach tumor |
| | normal lung | lung tumor |
| DNA64902-1667 | esophageal tumor | normal esophagus |
| | kidney tumor | normal kidney |
| DNA65403-1565 | normal esophagus | esophageal tumor |
| DNA66308-1537 | normal lung | lung tumor |
| DNA66519-1535 | kidney tumor | normal kidney |
| DNA66521-1583 | normal esophagus | esophageal tumor |
| | normal stomach | stomach tumor |
| | normal lung | lung tumor |
| | normal rectum | rectum tumor |
| | normal skin | melanoma tumor |
| DNA66658-1584 | normal lung | lung tumor |
| | melanoma tumor | normal skin |
| DNA66660-1585 | lung tumor | normal lung |
| DNA66674-1599 | kidney tumor | normal kidney |
| | normal lung | lung tumor |
| DNA68862-2546 | melanoma tumor | normal skin |
| DNA68866-1644 | normal stomach | stomach tumor |
| DNA68871-1638 | lung tumor | normal lung |
| | normal skin | melanoma tumor |

-continued

| Molecule | is more highly expressed in: | as compared to: |
|---|---|---|
| DNA68880-1676 | normal lung | lung tumor |
| | normal skin | melanoma tumor |
| DNA68883-1691 | esophageal tumor | normal esophagus |
| DNA68885-1678 | lung tumor | normal lung |
| DNA71277-1636 | normal stomach | stomach tumor |
| DNA73734-1680 | normal lung | lung tumor |
| DNA73735-1681 | esophageal tumor | normal esophagus |
| | normal kidney | kidney tumor |
| | lung tumor | normal lung |
| | normal skin | melanoma tumor |
| DNA76393-1664 | esophageal tumor | normal esophagus |
| | stomach tumor | normal stomach |
| | lung tumor | normal lung |
| | rectum tumor | normal rectum |
| DNA77568-1626 | normal stomach | stomach tumor |
| | lung tumor | normal lung |
| DNA77626-1705 | normal rectum | rectum tumor |
| DNA81754-2532 | normal skin | melanoma tumor |
| DNA81757-2512 | esophageal tumor | normal esophagus |
| | normal stomach | stomach tumor |
| | melanoma tumor | normal skin |
| DNA82302-2529 | normal stomach | stomach tumor |
| | normal lung | lung tumor |
| DNA82340-2530 | normal esophagus | esophageal tumor |
| DNA85066-2534 | lung tumor | normal lung |
| | normal skin | melanoma tumor |
| DNA87991-2540 | esophageal tumor | normal esophagus |
| DNA92238-2539 | normal skin | melanoma tumor |
| DNA96787-2534 | normal kidney | kidney tumor |

Example 19

Identification of Receptor/Ligand Interactions

In this assay, various PRO polypeptides are tested for ability to bind to a panel of potential receptor or ligand molecules for the purpose of identifying receptor/ligand interactions. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparation of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

The assay is performed as follows. A PRO polypeptide of the present invention suspected of being a ligand for a receptor is expressed as a fusion protein containing the Fc domain of human IgG (an immunoadhesin). Receptor-ligand binding is detected by allowing interaction of the immunoadhesin polypeptide with cells (e.g. Cos cells) expressing candidate PRO polypeptide receptors and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors encoding PRO polypeptides that may function as receptor molecules. Cells are then incubated for 1 hour in the presence of the PRO polypeptide immunoadhesin being tested for possible receptor binding. The cells are then washed and fixed with paraformaldehyde. The cells are then incubated with fluorescent conjugated antibody directed against the Fc portion of the PRO polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO polypeptide immunoadhesin, the individual cDNA species that comprise the pool are tested individually (the pool is "broken down") to determine the specific cDNA that encodes a receptor able to interact with the PRO polypeptide immunoadhesin.

In another embodiment of this assay, an epitope-tagged potential ligand PRO polypeptide (e.g. 8 histidine "His" tag) is allowed to interact with a panel of potential receptor PRO polypeptide molecules that have been expressed as fusions with the Fc domain of human IgG (immunoadhesins). Following a 1 hour co-incubation with the epitope tagged PRO polypeptide, the candidate receptors are each immunoprecipitated with protein A beads and the beads are washed. Potential ligand interaction is determined by western blot analysis of the immunoprecipitated complexes with antibody directed towards the epitope tag. An interaction is judged to occur if a band of the anticipated molecular weight of the epitope tagged protein is observed in the western blot analysis with a candidate receptor, but is not observed to occur with the other members of the panel of potential receptors.

Using these assays, the following receptor/ligand interactions have been herein identified:

(1) PRO10272 binds to PRO5801.

(2) PRO20110 binds to the human IL-17 receptor (Yao et al., *Cytokine* 9(11):794–800 (1997); also herein designated as PRO1) and to PRO20040.

(3) PRO10096 binds to PRO20233.

(4) PRO19670 binds to PRO1890.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

The invention claimed is:

1. An isolated polypeptide comprising:

(a) the amino acid sequence of the polypeptide of SEQ ID NO:94;

(b) the amino acid sequence of the polypeptide of SEQ ID NO:94, lacking its associated signal peptide;

(c) the amino acid sequence of the extracellular domain of the polypeptide of SEQ ID NO:94, wherein the extracellular domain is amino acids 20–31, 139–151, or 236–257;

(d) the amino acid sequence of the extracellular domain of the polypeptide of SEQ ID NO:94, lacking its associated signal peptide, wherein the extracellular domain is amino acids acids 20–31, 139–151, or 236–257; or (e) the amino acid sequence of the polypeptide encoded by the full-length coding sequence of the cDNA deposited under ATCC accession number 203229.

2. The isolated polypeptide of claim 1 comprising the amino acid sequence of the polypeptide of SEQ ID NO:94.

3. The isolated polypeptide of claim 1 comprising the amino acid sequence of the polypeptide of SEQ ID NO: 94, lacking its associated signal peptide.

4. The isolated polypeptide of claim 1 comprising the amino acid sequence of the extracellular domain of the polypeptide of SEQ ID NO:94, wherein the extracellular domain is amino acids 20–31, 139–151, or 236–257.

5. The isolated polypeptide of claim 1 comprising the amino acid sequence of the extracellular domain of the polypeptide of SEQ ID NO:94, lacking its associated signal peptide, wherein the extracellular domain is amino acids 20–31, 139–151, or 236–257.

6. The isolated polypeptide of claim 1 comprising the amino acid sequence of the polypeptide encoded by the full-length coding sequence of the cDNA deposited under ATCC accession number 203229.

7. A chimeric polypeptide comprising a polypeptide according to claim 1 fused to a heterologous polypeptide.

8. The chimeric polypeptide of claim 7, wherein said heterologous polypeptide is a tag polypeptide or an Fc region of an immunoglobulin.

9. An isolated polypeptide having at least 95% amino acid sequence identity to:

(a) the amino acid sequence of the polypeptide of SEQ ID NO:94;

(b) the amino acid sequence of the polypeptide of SEQ ID NO:94, lacking its associated signal peptide;

(c) the amino acid sequence of the extracellular domain of the polypeptide of SEQ ID NO:94, wherein the extracellular domain is amino acids 20–31, 139–151, or 236–257;

(d) the amino acid sequence of the extracellular domain of the polypeptide of SEQ ID NO:94, lacking its associated signal peptide, wherein the extracellular domain is amino acids 20–31, 139–151, or 236–257; or (e) the amino acid sequence of the polypeptide encoded by the frill-length coding sequence of the cDNA deposited under ATCC accession number 203229;

wherein said isolated polypeptide or a fragment thereof can be used to generate an antibody which can be used to specifically detect the polypeptide of SEQ ID NO: 94 in lung or skin tissue samples.

10. The isolated polypeptide of claim 9 having at least 99% amino acid sequence identity to:

(a) the amino acid sequence of the polypeptide of SEQ ID NO:94;

(b) the amino acid sequence of the polypeptide of SEQ ID NO:94, lacking its associated signal peptide;

(c) the amino acid sequence of the extracellular domain of the polypeptide of SEQ ID NO:94, wherein the extracellular domain is amino acids 20–31, 139–151, or 236–257;

(d) the amino acid sequence of the extracellular domain of the polypeptide of SEQ ID NO:94, lacking its associated signal peptide, wherein the extracellular domain is amino acids acids 20–31, 139–151, or 236–257; or (e) the amino acid sequence of the polypeptide encoded by the full-length coding sequence of the cDNA deposited under ATCC accession number 203229;

wherein said isolated polypeptide or a fragment thereof can be used to generate an antibody which can be used to specifically detect the polypeptide of SEQ ID NO: 94 in lung or skin tissue samples.

11. A chimeric polypeptide comprising a polypeptide according to claim 9 fused to a heterologous polypeptide.

12. The chimeric polypeptide of claim 11, wherein said heterologous polypeptide is a tag polypeptide or an Fc region of an immunoglobulin.

* * * * *

UNITED STATES PATENT AND TRADEMARK OFFICE
CERTIFICATE OF CORRECTION

PATENT NO. : 7,230,076 B2 
APPLICATION NO. : 10/063600
DATED : June 12, 2007
INVENTOR(S) : Audrey Goddard et al.

It is certified that error appears in the above-identified patent and that said Letters Patent is hereby corrected as shown below:

Title Page;

On Page 2, at Column 1, Line 1, in Other Publications section, please delete "predicitive" and insert --predictive--, therefor.

On Page 2, at Column 1, Line 22, in Other Publications section, please delete "oncogene," and insert --oncogene.--, therefor.

On Page 2, at Column 1, Line 22, in Other Publications section, please delete "1(27)L" and insert --1(27):--, therefor.

On Page 2, at Column 1, Line 59, in Other Publications section, please delete "regultation" and insert --regulation--, therefor.

On Page 2, at Column 1, Line 70, in Other Publications section, please delete "Chemistry277" and insert --Chemistry, 277--, therefor.

On Page 2, at Column 2, Line 11, in Other Publications section, please delete "regualation" and insert --regulation--, therefor.

On Page 2, at Column 2, Line 13, in Other Publications section, please delete "ThyroidOct." and insert --Thyroid. Oct.--, therefor.

On Page 2, at Column 2, Line 69, in Other Publications section, please delete "Eqwuagu," and insert --Egwuagu,--, therefor.

On Page 3, at Column 1, Line 57, in Other Publications section, after "non-invasive" please insert --and invasive--.

On Page 3, at Column 2, Line 7, in Other Publications section, please delete "Hasset," and insert --Hassett,--, therefor.

On Page 3, at Column 2, Line 29, in Other Publications section, please delete "messanger" and insert --messenger--, therefor.

UNITED STATES PATENT AND TRADEMARK OFFICE
CERTIFICATE OF CORRECTION

PATENT NO. : 7,230,076 B2

APPLICATION NO. : 10/063600
DATED : June 12, 2007
INVENTOR(S) : Audrey Goddard et al.

It is certified that error appears in the above-identified patent and that said Letters Patent is hereby corrected as shown below:

On Page 3, at Column 2, Line 38, in Other Publications section, please delete "is" and insert --in--, therefor.

On Page 3, at Column 2, Line 59, in Other Publications section, please delete "Expression" and insert --"Expression--, therefor.

On Page 3, at Column 2, Line 62, in Other Publications section, please delete "chemotherapy.38" and insert --chemotherapy."--, therefor.

On Page 4, at Column 1, Line 2, in Other Publications section, please delete "Gyenecol" and insert --Gynecol--, therefor.

On Page 4, at Column 2, Line 5, in Other Publications section, after "subunit of" please insert --the--.

On Page 4, at Column 2, Line 37, in Other Publications section, please delete "regultion" and insert --regulation--, therefor.

On Page 5, at Column 1, Line 12, in Other Publications section, please delete "cells"" and insert --cells."--, therefor.

On Page 5, at Column 1, Line 24, in Other Publications section, please delete "identify" and insert --identity--, therefor.

On Page 5, at Column 1, Line 35, in Other Publications section, please delete "interferring" and insert --interfering--, therefor.

On Page 5, at Column 1, Line 53, in Other Publications section, please delete "et al:" and insert --et al.--, therefor.

On Page 5, at Column 2, Line 55, in Other Publications section, please delete "Clincopathological" and insert --Clinicopathological--, therefor.

UNITED STATES PATENT AND TRADEMARK OFFICE
CERTIFICATE OF CORRECTION

| | | |
|---|---|---|
| PATENT NO. | : 7,230,076 B2 | |
| APPLICATION NO. | : 10/063600 | |
| DATED | : June 12, 2007 | |
| INVENTOR(S) | : Audrey Goddard et al. | |

It is certified that error appears in the above-identified patent and that said Letters Patent is hereby corrected as shown below:

On Page 5, at Column 2, Line 56, in Other Publications section, after "expression" please delete "expression".

On Page 5, at Column 2, Line 64, in Other Publications section, please delete "proteinand" and insert --protein and--, therefor.

On Page 6, at Column 1, Line 10, in Other Publications section, please delete "Immunology28" and insert --Immunology, 28--, therefor.

On Page 6, at Column 2, Line 5, in Other Publications section, please delete "throid" and insert --thyroid--, therefor.

On Page 6, at Column 2, Line 8, in Other Publications section, please delete "Obstertrics" and insert --Obstetrics--, therefor.

At Column 1, Line 9, after "and" please insert --claims--.

At Column 1, Line 16, after "119" please insert --to--.

At Column 1, Lines 16-17, please delete "Applcation" and insert --Application--, therefor.

At Column 1, Line 19 (approximately), after "OF" please delete "THE".

At Column 2, Line 13, after "employed" please insert --for--.

At Column 5, Line 6, after "without the" please insert --signal--.

At Column 6, Line 24, after "sequence or" please delete "a" and insert --an--, therefor.

At Column 15, Line 26, please delete "comtemplated" and insert --contemplated--, therefor.

UNITED STATES PATENT AND TRADEMARK OFFICE

CERTIFICATE OF CORRECTION

PATENT NO. : 7,230,076 B2
APPLICATION NO. : 10/063600
DATED : June 12, 2007
INVENTOR(S) : Audrey Goddard et al.

It is certified that error appears in the above-identified patent and that said Letters Patent is hereby corrected as shown below:

At Column 26, Line 33 (approximately), after “Daltons” please insert --.--.

At Column 73, Line 34 (approximately), below “Comparison DNA” please delete “DNA”.

At Column 80, Line 17, please delete “91/000357” and insert --91/00357--, therefor.

At Column 84, Line 44, after “metal” please insert --complexes--.

At Column 85, Line 7, after “into a” please insert --cell--.

At Column 86, Line 33, after “line” please insert --(e.g.,--.

At Column 91, Line 38 (approximately), after “used to” please insert --control--.

At Column 95, Line 64, after “have” please insert --the--.

At Column 98, Lines 16-17, please delete “glutareldehyde),” and insert --glutaraldehyde),--, therefor.

At Column 98, Line 40, please delete “Natl” and insert --Natl.--, therefor.

At Column 103, Line 67, after “343” please insert --bp--.

At Column 104, Line 24 (approximately), after “optionally” please insert --the--.

At Column 107, Line 33, please delete “2H2O,” and insert --$2H_2O$,--, therefor.

At Column 107, Line 48, please delete “Ultracentifuge” and insert --Ultracentrifuge--, therefor.

At Column 108, Line 16, after “of” please insert --proteins--.

At Column 111, Line 24 (approximately), after “removing the” please insert --yeast--.

At Column 111, Line 39, after “contained” please insert --within--.

UNITED STATES PATENT AND TRADEMARK OFFICE

CERTIFICATE OF CORRECTION

PATENT NO. : 7,230,076 B2
APPLICATION NO. : 10/063600
DATED : June 12, 2007
INVENTOR(S) : Audrey Goddard et al.

It is certified that error appears in the above-identified patent and that said Letters Patent is hereby corrected as shown below:

At Column 115, Line 59, please delete "serum+/-PDGF" and insert --serum +/- PDGF--, therefor.

At Column 118, Line 7 (approximately), please delete "akin" and insert --skin--, therefor.

At Column 118, Line 23 (approximately), please delete "akin" and insert --skin--, therefor.

At Column 455, Line 14, in Claim 1, after "acids" please delete "acids".

At Column 456, Line 11 (approximately), in Claim 9, please delete "frill" and insert --full--, therefor.

At Column 456, Line 31, in Claim 10, after "acids" please delete "acids".

Signed and Sealed this

Third Day of March, 2009

JOHN DOLL
*Acting Director of the United States Patent and Trademark Office*